US012573481B2

(12) United States Patent
Ginsburg et al.

(10) Patent No.: US 12,573,481 B2
(45) Date of Patent: Mar. 10, 2026

(54) DYNAMIC HEALTH RECORDS

(71) Applicant: DHRpro, LLC, Merion Station, PA (US)

(72) Inventors: Leonard H. Ginsburg, Merion, PA (US); Nancy Wilson Crawford, Glen Mills, PA (US); Ryan Twomey-Allaire, Orlando, WV (US)

(73) Assignee: DHRPRO, LLC, Merion Station, PA (US)

( * ) Notice: Subject to any disclaimer, the term of this patent is extended or adjusted under 35 U.S.C. 154(b) by 573 days.

(21) Appl. No.: 17/940,908

(22) Filed: Sep. 8, 2022

(65) Prior Publication Data

US 2023/0073347 A1 Mar. 9, 2023

Related U.S. Application Data

(63) Continuation of application No. PCT/US2021/020751, filed on Mar. 3, 2021, and a
(Continued)

(51) Int. Cl.
*G16H 15/00* (2018.01)
*G16H 10/60* (2018.01)
(Continued)

(52) U.S. Cl.
CPC .............. *G16H 15/00* (2018.01); *G16H 10/60* (2018.01); *G16H 40/20* (2018.01); *G16H 40/63* (2018.01); *G06F 3/04842* (2013.01)

(58) Field of Classification Search
None
See application file for complete search history.

(56) References Cited

U.S. PATENT DOCUMENTS 7,039,878 B2    5/2006   Auer et al.
7,171,277 B2    1/2007   Engleson et al.
(Continued)

FOREIGN PATENT DOCUMENTS

CA        2887622 A1      4/2014
EP        2937799 A1 * 10/2015    ............. G16H 15/00
(Continued)

OTHER PUBLICATIONS

Zhu et al. "Using Timeline Displays to Improve Medication Reconciliation" 2009 International Conference on eHealth, Telemedicine, and Social Medicine, Cancun, Mexico, 2009, pp. 1—(Year: 2009).*
(Continued)

*Primary Examiner* — Jonathan Ng
(74) *Attorney, Agent, or Firm* — SCHWEGMAN LUNDBERG & WOESSNER, P.A.

(57) ABSTRACT
A computer implemented method of creating medical orders includes generating a dashboard display comprising one or multiple visible panels having data corresponding to different respective medical services, receiving a request to create an order in response to user interaction with a first one of the multiple panels, retrieving first medical information as a function of information associated with the panel from which the request was received, and populating a place order panel with the retrieved first medical information.

40 Claims, 144 Drawing Sheets

Related U.S. Application Data continuation of application No. 17/187,843, filed on Feb. 28, 2021, and a continuation of application No. 17/035,648, filed on Sep. 28, 2020, now abandoned, and a continuation of application No. 17/008,631, filed on Aug. 31, 2020, now abandoned, and a continuation of application No. 17/008,586, filed on Aug. 31, 2020, now Pat. No. 11,837,334, and a continuation of application No. 16/802,547, filed on Feb. 26, 2020.

(60) Provisional application No. 63/127,840, filed on Dec. 18, 2020, provisional application No. 63/116,684, filed on Nov. 20, 2020, provisional application No. 63/026,547, filed on May 18, 2020, provisional application No. 62/987,165, filed on Mar. 9, 2020.

(51) Int. Cl.
| | |
|---|---|
| *G16H 40/20* | (2018.01) |
| *G16H 40/63* | (2018.01) |
| *G06F 3/04842* | (2022.01) |

(56) References Cited

U.S. PATENT DOCUMENTS

| | | | |
|---|---|---|---|
| 7,987,428 B2 | 7/2011 | Handy et al. | |
| 8,321,383 B2 | 11/2012 | Schumacher et al. | |
| 9,104,789 B2 | 8/2015 | Gross et al. | |
| 9,483,614 B2 | 11/2016 | Ash et al. | |
| 9,626,479 B2 | 4/2017 | Zaleski | |
| 10,622,105 B2 | 4/2020 | Von Reden | |
| 10,685,743 B2 | 6/2020 | Ginsburg et al. | |
| 11,205,505 B2 | 12/2021 | Ginsburg | |
| 11,387,000 B2 | 7/2022 | Saliman et al. | |
| 11,666,702 B2 | 6/2023 | Morawiec et al. | |
| 11,837,334 B2 | 12/2023 | Ginsburg et al. | |
| 2001/0032100 A1 | 10/2001 | Mahmud et al. | |
| 2002/0002473 A1 | 1/2002 | Schrier et al. | |
| 2006/0064020 A1 | 3/2006 | Burnes et al. | |
| 2006/0080620 A1 | 4/2006 | Dvorak et al. | |
| 2006/0085223 A1 | 4/2006 | Anderson et al. | |
| 2006/0265249 A1* | 11/2006 | Follis | G16H 10/60 |
| | | | 715/254 |
| 2006/0294092 A1 | 12/2006 | Giang et al. | |
| 2008/0033754 A1 | 2/2008 | Smith et al. | |
| 2008/0086332 A1* | 4/2008 | Hertel | G06Q 10/10 |
| | | | 705/2 |
| 2008/0086333 A1* | 4/2008 | Hertel | G06Q 10/10 |
| | | | 705/2 |
| 2008/0195422 A1 | 8/2008 | Nessinger et al. | |
| 2008/0243548 A1* | 10/2008 | Cafer | G16H 40/67 |
| | | | 705/3 |
| 2009/0070136 A1* | 3/2009 | Morita | G16H 40/63 |
| | | | 705/2 |
| 2009/0192823 A1 | 7/2009 | Hawkins et al. | |
| 2009/0204421 A1 | 8/2009 | Guimaraes | |
| 2009/0217189 A1 | 8/2009 | Martin et al. | |
| 2009/0222286 A1 | 9/2009 | Elsholz | |
| 2009/0265188 A1 | 10/2009 | Lamy et al. | |
| 2010/0057646 A1 | 3/2010 | Martin et al. | |
| 2010/0094649 A1 | 4/2010 | White | |
| 2010/0131293 A1 | 5/2010 | Linthicum et al. | |
| 2010/0131482 A1* | 5/2010 | Linthicum | G16H 40/63 |
| | | | 707/706 |
| 2010/0131883 A1 | 5/2010 | Linthicum et al. | |
| 2010/0280846 A1* | 11/2010 | Clements | G16H 50/50 |
| | | | 705/2 |
| 2011/0004494 A1 | 1/2011 | Denny, Jr. et al. | |
| 2011/0071464 A1 | 3/2011 | Palerm | |
| 2011/0202370 A1 | 8/2011 | Green, III et al. | |
| 2011/0276348 A1 | 11/2011 | Ahn et al. | |
| 2011/0295618 A1 | 12/2011 | Naipaul et al. | |
| 2012/0029303 A1 | 2/2012 | Shaya | |

| | | | |
|---|---|---|---|
| 2012/0078664 A1 | 3/2012 | Hasan et al. | |
| 2012/0130197 A1 | 5/2012 | Kugler et al. | |
| 2012/0130741 A1 | 5/2012 | Sparandara et al. | |
| 2012/0131498 A1 | 5/2012 | Gross et al. | |
| 2012/0131507 A1 | 5/2012 | Sparandara et al. | |
| 2012/0232918 A1 | 9/2012 | Mack et al. | |
| 2012/0253841 A1 | 10/2012 | Erlandsen et al. | |
| 2012/0286955 A1* | 11/2012 | Welch | G16H 40/63 |
| | | | 340/573.1 |
| 2013/0024206 A1 | 1/2013 | Hughes et al. | |
| 2013/0027411 A1 | 1/2013 | Hebler et al. | |
| 2013/0041677 A1 | 2/2013 | Nusimow et al. | |
| 2013/0080192 A1 | 3/2013 | Bucur et al. | |
| 2013/0083185 A1 | 4/2013 | Coleman, III | |
| 2013/0159022 A1 | 6/2013 | Verbeek et al. | |
| 2013/0191161 A1 | 7/2013 | Churchwell et al. | |
| 2013/0290005 A1 | 10/2013 | Vesto et al. | |
| 2014/0012597 A1 | 1/2014 | Nolte et al. | |
| 2014/0068489 A1* | 3/2014 | Wyland | G16H 10/60 |
| | | | 715/771 |
| 2014/0074509 A1 | 3/2014 | Amarasingham et al. | |
| 2014/0181128 A1* | 6/2014 | Riskin | G06F 16/3344 |
| | | | 707/756 |
| 2014/0207486 A1 | 7/2014 | Carty et al. | |
| 2014/0236627 A1 | 8/2014 | Odessky et al. | |
| 2014/0236631 A1 | 8/2014 | Perrin et al. | |
| 2014/0236635 A1 | 8/2014 | Liberty et al. | |
| 2014/0249833 A1 | 9/2014 | Conti et al. | |
| 2014/0304005 A1 | 10/2014 | Hughes et al. | |
| 2015/0052032 A1 | 2/2015 | Aharoni | |
| 2015/0185972 A1 | 7/2015 | Ash et al. | |
| 2015/0254403 A1 | 9/2015 | Laperna | |
| 2015/0269323 A1 | 9/2015 | Ginsburg | |
| 2015/0317435 A1* | 11/2015 | Klocek | G16H 10/60 |
| | | | 705/3 |
| 2016/0063212 A1 | 3/2016 | Monier et al. | |
| 2016/0125137 A1 | 5/2016 | Ott | |
| 2016/0125149 A1 | 5/2016 | Abramowitz | |
| 2016/0147978 A1 | 5/2016 | Adams et al. | |
| 2016/0162638 A1 | 6/2016 | Albro et al. | |
| 2016/0198996 A1 | 7/2016 | Dullen | |
| 2016/0283664 A1* | 9/2016 | Tubman | G16H 10/60 |
| 2016/0321399 A1 | 11/2016 | Ramachandran | |
| 2016/0321404 A1* | 11/2016 | Ginsburg | G16H 10/60 |
| 2016/0328526 A1 | 11/2016 | Park et al. | |
| 2016/0357914 A1 | 12/2016 | Morris et al. | |
| 2017/0068780 A1* | 3/2017 | Dobrean | G16H 30/40 |
| 2017/0116373 A1 | 4/2017 | Ginsburg et al. | |
| 2018/0121605 A1* | 5/2018 | Allen | G16H 20/10 |
| 2018/0261306 A1* | 9/2018 | Naito | G06F 3/048 |
| 2018/0330457 A1 | 11/2018 | Hawkins et al. | |
| 2018/0336457 A1 | 11/2018 | Pal et al. | |
| 2019/0259479 A1 | 8/2019 | Ginsburg | |
| 2020/0005916 A1* | 1/2020 | Brooks | G16H 15/00 |
| 2020/0185100 A1 | 6/2020 | Francois | |
| 2020/0185103 A1* | 6/2020 | Allen | G06N 5/04 |
| 2020/0265932 A1 | 8/2020 | Ginsburg et al. | |
| 2020/0294640 A1 | 9/2020 | Ginsburg | |
| 2021/0110897 A1 | 4/2021 | Ginsburg et al. | |
| 2021/0174916 A1 | 6/2021 | Ginsburg et al. | |
| 2022/0084641 A1 | 3/2022 | Ginsburg | |
| 2022/0084645 A1 | 3/2022 | Ginsburg et al. | |
| 2022/0084664 A1 | 3/2022 | Ginsburg | |
| 2022/0215919 A9 | 7/2022 | Ginsburg et al. | |
| 2022/0367016 A1 | 11/2022 | Ginsburg | |
| 2024/0257931 A1 | 8/2024 | Ginsburg et al. | |

FOREIGN PATENT DOCUMENTS

| | | |
|---|---|---|
| IN | 202217055674 A | 7/2023 |
| JP | 2017510015 | 4/2017 |
| KR | 20030095691 A | 12/2003 |
| KR | 20110021370 A | 3/2011 |
| WO | WO-2015143455 | 9/2015 |
| WO | WO-2015191562 A1 | 12/2015 |
| WO | WO-2018017927 A1 | 1/2018 |
| WO | WO-2018057918 A1 | 3/2018 |

(56)                References Cited

FOREIGN PATENT DOCUMENTS

WO      WO-2021042077 A1      3/2021
WO      WO-2021174169 A1      9/2021
WO      WO-2021183347 A1      9/2021

OTHER PUBLICATIONS

Ledesma A, Bidargaddi N, Strobel J, Schrader G, Nieminen H, Korhonen I, Ermes M. Health timeline: an insight-based study of a timeline visualization of clinical data. BMC Med Inform Decis Mak. Aug. 22, 2019;19(1):170 (Year: 2019).*

U.S. Appl. No. 16/802,547, filed Feb. 26, 2020, Data Command Center Visual Display System.

U.S. Appl. No. 17/035,648, filed Sep. 28, 2020, Intelligent, Individualized Medical and Image Management System.

U.S. Appl. No. 17/008,586 now U.S. Pat. No. 11,837,337, filed Aug. 31, 2020, Whole-Life, Medication Management, and Ordering Display System.

U.S. Appl. No. 18/490,466, filed Oct. 19, 2023, Whole-Life, Medication Management, and Ordering Display System.

U.S. Appl. No. 17/187,843, filed Feb. 28, 2021, Dynamic Health Records.

U.S. Appl. No. 17/008,631, filed Aug. 31, 2020, Dynamic Health Records Visual Display System.

U.S. Appl. No. 17/686,194, filed Mar. 3, 2022, Dynamic Health Records.

"U.S. Appl. No. 14/666,278, Non Final Office Action mailed Jan. 9, 2018", 22 pgs.

"U.S. Appl. No. 14/666,278, Non Final Office Action mailed Dec. 21, 2017", 20 pgs.

"U.S. Appl. No. 14/666,278, Response filed Jun. 11, 2018 to Non Final Office Action mailed Jan. 9, 2018", 33 pgs.

"U.S. Appl. No. 15/204,900, Non Final Office Action mailed Jan. 9, 2018", 32 pgs.

"U.S. Appl. No. 15/275,223, Corrected Notice of Allowability mailed Mar. 24, 2020", 2 pgs.

"U.S. Appl. No. 15/275,223, Notice of Allowance mailed Feb. 3, 2020", 21 pgs.

"U.S. Appl. No. 15/275,223, Preliminary Amendment filed Mar. 16, 2017", 11 pgs.

"U.S. Appl. No. 15/275,223, Supplementary Preliminary Amendment Filed May 1, 2019", 14 pgs.

"U.S. Appl. No. 16/399,974, 312 Amendment filed Nov. 15, 2021", 23 pgs.

"U.S. Appl. No. 16/399,974, Examiner Interview Summary mailed Nov. 4, 2021", 3 pgs.

"U.S. Appl. No. 16/399,974, Notice of Allowance mailed Nov. 15, 2021", 31 pgs.

"U.S. Appl. No. 16/399,974, Preliminary Amendment filed Mar. 3, 2020", 15 pgs.

"U.S. Appl. No. 16/399,974, Preliminary Amendment filed Mar. 25, 2021", 13 pgs.

"U.S. Appl. No. 16/802,547, Advisory Action mailed Apr. 25, 2024", 3 pgs.

"U.S. Appl. No. 16/802,547, Examiner Interview Summary mailed Jan. 31, 2024", 2 pgs.

"U.S. Appl. No. 16/802,547, Examiner Interview Summary mailed Apr. 15, 2024", 2 pgs.

"U.S. Appl. No. 16/802,547, Examiner Interview Summary mailed Apr. 25, 2023", 2 pgs.

"U.S. Appl. No. 16/802,547, Examiner Interview Summary mailed Oct. 7, 2022", 2 pgs.

"U.S. Appl. No. 16/802,547, Final Office Action mailed Jan. 31, 2023", 37 pgs.

"U.S. Appl. No. 16/802,547, Final Office Action mailed Feb. 12, 2024", 34 pgs.

"U.S. Appl. No. 16/802,547, Non Final Office Action mailed May 2, 2022", 39 pgs.

"U.S. Appl. No. 16/802,547, Non Final Office Action mailed Jun. 27, 2024", 37 pgs.

"U.S. Appl. No. 16/802,547, Non Final Office Action mailed Aug. 17, 2023", 36 pgs.

"U.S. Appl. No. 16/802,547, Preliminary Amendment filed Jan. 11, 2022", 11 pgs.

"U.S. Appl. No. 16/802,547, Response filed Jan. 17, 2024 to Non Final Office Action mailed Aug. 17, 2023", 24 pgs.

"U.S. Appl. No. 16/802,547, Response filed Mar. 31, 2022 to Restriction Requirement mailed Feb. 24, 2022", 10 pgs.

"U.S. Appl. No. 16/802,547, Response filed Apr. 12, 2024 to Final Office Action mailed Feb. 12, 2024", 27 pgs.

"U.S. Appl. No. 16/802,547, Response filed May 13, 2024 to Advisory Action mailed Apr. 25, 2024", 28 pgs.

"U.S. Appl. No. 16/802,547, Response filed May 31, 2023 to Final Office Action mailed Jan. 31, 2023", 22 pgs.

"U.S. Appl. No. 16/802,547, Response filed Oct. 3, 2022 to Non Final Office Action mailed May 2, 2022", 12 pgs.

"U.S. Appl. No. 16/802,547, Restriction Requirement mailed Feb. 24, 2022", 6 pgs.

"U.S. Appl. No. 16/865,859, Preliminary Amendment filed Dec. 23, 2021", 21 pgs.

"U.S. Appl. No. 16/865,859, Supplemental Preliminary Amendment Filed Jul. 25, 2022", 23 pgs.

"U.S. Appl. No. 17/008,586, Examiner Interview Summary mailed May 5, 2023", 2 pgs.

"U.S. Appl. No. 17/008,586, Final Office Action mailed Mar. 9, 2023", 23 pgs.

"U.S. Appl. No. 17/008,586, Non Final Office Action mailed Jun. 23, 2022", 16 pgs.

"U.S. Appl. No. 17/008,586, Non Final Office Action mailed Aug. 8, 2023", 19 pgs.

"U.S. Appl. No. 17/008,586, Notice of Allowability mailed Sep. 24, 2023", 2 pgs.

"U.S. Appl. No. 17/008,586, Notice of Allowance mailed Sep. 14, 2023", 11 pgs.

"U.S. Appl. No. 17/008,586, Preliminary Amendment filed Feb. 16, 2021", 4 pgs.

"U.S. Appl. No. 17/008,586, Preliminary Amendment filed Dec. 30, 2020", 3 pgs.

"U.S. Appl. No. 17/008,586, Response filed Jun. 9, 2023 to Final Office Action mailed Mar. 9, 2023", 22 pgs.

"U.S. Appl. No. 17/008,586, Response filed Aug. 31, 2023 to Non Final Office Action mailed Aug. 8, 2023", 19 pgs.

"U.S. Appl. No. 17/008,586, Response filed Dec. 19, 2022 to Non Final Office Action mailed Jun. 23, 2022", 14 pgs.

"U.S. Appl. No. 17/008,631, Final Office Action mailed Aug. 16, 2023", 16 pgs.

"U.S. Appl. No. 17/008,631, Non Final Office Action mailed Feb. 2, 2023", 16 pgs.

"U.S. Appl. No. 17/008,631, Preliminary Amendment filed Dec. 30, 2020", 3 pgs.

"U.S. Appl. No. 17/008,631, Response filed Jan. 12, 2023 to Restriction Requirement mailed Aug. 12, 2022", 9 pgs.

"U.S. Appl. No. 17/008,631, Response filed Aug. 2, 2023 to Non Final Office Action mailed Feb. 2, 2023", 11 pgs.

"U.S. Appl. No. 17/008,631, Restriction Requirement mailed Aug. 12, 2022", 6 pgs.

"U.S. Appl. No. 17/035,648, Advisory Action mailed Jun. 13, 2023", 4 pgs.

"U.S. Appl. No. 17/035,648, Examiner Interview Summary mailed May 30, 2023", 2 pgs.

"U.S. Appl. No. 17/035,648, Final Office Action mailed Jan. 18, 2024", 19 pgs.

"U.S. Appl. No. 17/035,648, Final Office Action mailed Mar. 23, 2023", 29 pgs.

"U.S. Appl. No. 17/035,648, Non Final Office Action mailed Aug. 16, 2023", 17 pgs.

"U.S. Appl. No. 17/035,648, Non Final Office Action mailed Sep. 1, 2022", 17 pgs.

"U.S. Appl. No. 17/035,648, Response filed Feb. 1, 2023 to Non Final Office Action mailed Sep. 1, 2022", 15 pgs.

(56)                References Cited

OTHER PUBLICATIONS

"U.S. Appl. No. 17/035,648, Response filed May 23, 2023 to Final Office Action mailed Mar. 23, 2023", 17 pgs.
"U.S. Appl. No. 17/035,648, Response filed Dec. 18, 2023 to Non Final Office Action mailed Aug. 16, 2023", 10 pgs.
"U.S. Appl. No. 17/187,843, Final Office Action mailed Sep. 28, 2024", 17 pgs.
"U.S. Appl. No. 17/187,843, Non Final Office Action mailed Mar. 13, 2024", 15 pgs.
"U.S. Appl. No. 17/187,843, Response filed Sep. 13, 2024 to Non Final Office Action mailed Mar. 13, 2024", 7 pgs.
"U.S. Appl. No. 17/456,286, Examiner Interview Summary mailed Apr. 22, 2022", 2 pgs.
"U.S. Appl. No. 17/456,286, Examiner Interview Summary mailed May 11, 2022", 2 pgs.
"U.S. Appl. No. 17/456,286, Examiner Interview Summary mailed Jun. 29, 2022", 2 pgs.
"U.S. Appl. No. 17/456,286, Non Final Office Action mailed Feb. 16, 2022", 35 pages.
"U.S. Appl. No. 17/456,286, Notice of Allowance mailed Jul. 25, 2022", 9 pgs.
"U.S. Appl. No. 17/456,286, Response filed Jun. 16, 2022 to Non Final Office Action mailed Feb. 16, 2022", 17 pgs.
"U.S. Appl. No. 17/686,194, Non Final Office Action mailed Jul. 16, 2024", 18 pgs.
"U.S. Appl. No. 18/490,466, Examiner Interview Summary mailed Aug. 23, 2024", 2 pgs.
"U.S. Appl. No. 18/490,466, Final Office Action mailed Sep. 6, 2024", 22 pgs.
"U.S. Appl. No. 18/490,466, Non Final Office Action mailed May 23, 2024", 18 pgs.
"U.S. Appl. No. 18/490,466, Response filed Aug. 23, 2024 to Non Final Office Action mailed May 23, 2024", 16 pgs.
"Australian Application Serial No. 2015230980, First Examination Report mailed Dec. 24, 2019", 3 pgs.
"Australian Application Serial No. 2015230980, Subsequent Examiners Report mailed Jul. 23, 2020", 3 pgs.
"Canadian Application Serial No. 2,942,566, Office Action mailed May 18, 2021", 6 pgs.
"Canadian Application Serial No. 2,942,566, Office Action mailed Jul. 4, 2022", With English translation, 1 pg.
"Canadian Application Serial No. 2,942,566, Response filed Sep. 18, 2021 to Office Action mailed May 18, 2021", 43 pgs.
"Canadian Application Serial No. 3,076,349, Office Action mailed May 26, 2021", 6 pgs.
"Canadian Application Serial No. 3,076,349, Office Action mailed Jul. 4, 2022", With English translation, 1 pg.
"European Application Serial No. 21760037.8, Extended European Search Report mailed Oct. 23, 2023", 12 pgs.
"International Application Serial No. PCT/US2015/022091, International Preliminary Report on Patentability mailed Sep. 29, 2016", 7 pgs.
"International Application Serial No. PCT/US2015/022091, International Search Report mailed Jun. 29, 2015", 3 pgs.
"International Application Serial No. PCT/US2015/022091, Written Opinion mailed Jun. 29, 2015", 5 pgs.
"International Application Serial No. PCT/US2017/052993, International Preliminary Report on Patentability mailed Apr. 4, 2019", 11 pgs.
"International Application Serial No. PCT/US2017/052993, International Search Report mailed Dec. 1, 2017", 2 pgs.
"International Application Serial No. PCT/US2017/052993, Written Opinion mailed Dec. 1, 2017", 9 pgs.

"International Application Serial No. PCT/US2020/048849, International Preliminary Report on Patentability mailed Mar. 10, 2022", 9 pgs.
"International Application Serial No. PCT/US2020/048849, International Search Report mailed Feb. 2, 2021", 6 pgs.
"International Application Serial No. PCT/US2020/048849, Written Opinion mailed Feb. 2, 2021", 7 pgs.
"International Application Serial No. PCT/US2020/052964, International Search Report mailed Dec. 22, 2020", 2 pgs.
"International Application Serial No. PCT/US2020/052964, Written Opinion mailed Dec. 22, 2020", 7 pgs.
"International Application Serial No. PCT/US2021/020159, International Preliminary Report on Patentability mailed Sep. 9, 2022", 14 pgs.
"International Application Serial No. PCT/US2021/020159, International Search Report mailed Aug. 3, 2021", 6 pgs.
"International Application Serial No. PCT/US2021/020159, Invitation to Pay Additional Fees mailed Jun. 4, 2021", 7 pgs.
"International Application Serial No. PCT/US2021/020159, Written Opinion mailed Aug. 3, 2021", 12 pgs.
"International Application Serial No. PCT/US2021/020751, International Preliminary Report on Patentability mailed Sep. 22, 2022", 12 pgs.
"International Application Serial No. PCT/US2021/020751, International Search Report mailed Jul. 2, 2021", 3 pgs.
"International Application Serial No. PCT/US2021/020751, Written Opinion mailed Jul. 2, 2021", 10 pgs.
"Israel Application Serial No. 265575, Notification of Defects in Patent Application mailed Dec. 31, 2020", with English translation, 10 pages.
"Korean Application Serial No. 1020167029340, Notice of Preliminary Rejection mailed Aug. 27, 2021", with English translation, 26 pages.
"Korean Application Serial No. 1020167029340, Response Filed Jan. 24, 2022 to Notice of Preliminary Rejection mailed Aug. 27, 2021", with English claims, 22 pages.
"Medication Ordering Screenshots 1A, 1B, 1C", MDoffice EHR, (Jan. 22, 2020), 3 pgs.
"Placement of Inventor work by MD Office in EyeNet Extra", distributed as a Supplement to an EyeNet magazine available in Oct. 2014 at the American Academy of Ophthalmology AAO 2014 Conference, (Oct. 18-21, 2014), 2 pages.
"Scheduling Screenshots 2A, 2B, 2C", MDoffice EHR, (Jan. 22, 2020), 3 pgs.
"Test Ordering Screenshots 3A, 3B, 3C, 3D, 3E", MDoffice EHR, (Jan. 22, 2020), 5 pgs.
Fogerty, Kevin, "In the Cloud, Distance Matters for Compute Efficiency", Network Computing, [Online]. Retrieved from the Internet: <URL: https://www.networkcomputing.com/cloud-networking/in-the-cloud-distance-matters-for-compute-efficiency>, (2013), 12 pages.
"U.S. Appl. No. 16/802,547, Response filed Nov. 26, 2024 to Non Final Office Action mailed Jun. 27, 2024", 25 pgs.
"U.S. Appl. No. 16/802,547, Examiner Interview Summary mailed Nov. 26, 2024", 2 pgs.
"U.S. Appl. No. 17/686,194, Response filed Dec. 16, 2024 to Non Final Office Action mailed Jul. 16, 2024", 14 pgs.
"U.S. Appl. No. 17/686,194, Examiner Interview Summary mailed Dec. 17, 2024", 2 pgs.
"U.S. Appl. No. 16/802,547, Final Office Action mailed Jan. 13, 2025", 41 pgs.
"U.S. Appl. No. 17/686,194, Final Office Action mailed Mar. 31, 2025", 22 pgs.

* cited by examiner

| DATA TYPE | EXAMPLE |
|---|---|
| FREE TEXT | NOTES / COMMENTS |
| CODIFIED TEXT | ICD-10 / CPT / RXNORM |
| LIST | ACTIVE MEDICATIONS / ALLERGIES |
| CONCATENATION OF TEXT | CODE PLUS CODE DESCRIPTION |
| DOCUMENTS | PDF / REPORT / LETTER |
| IMAGES | DIAGNOSTIC TEST / PATIENT PHOTO |

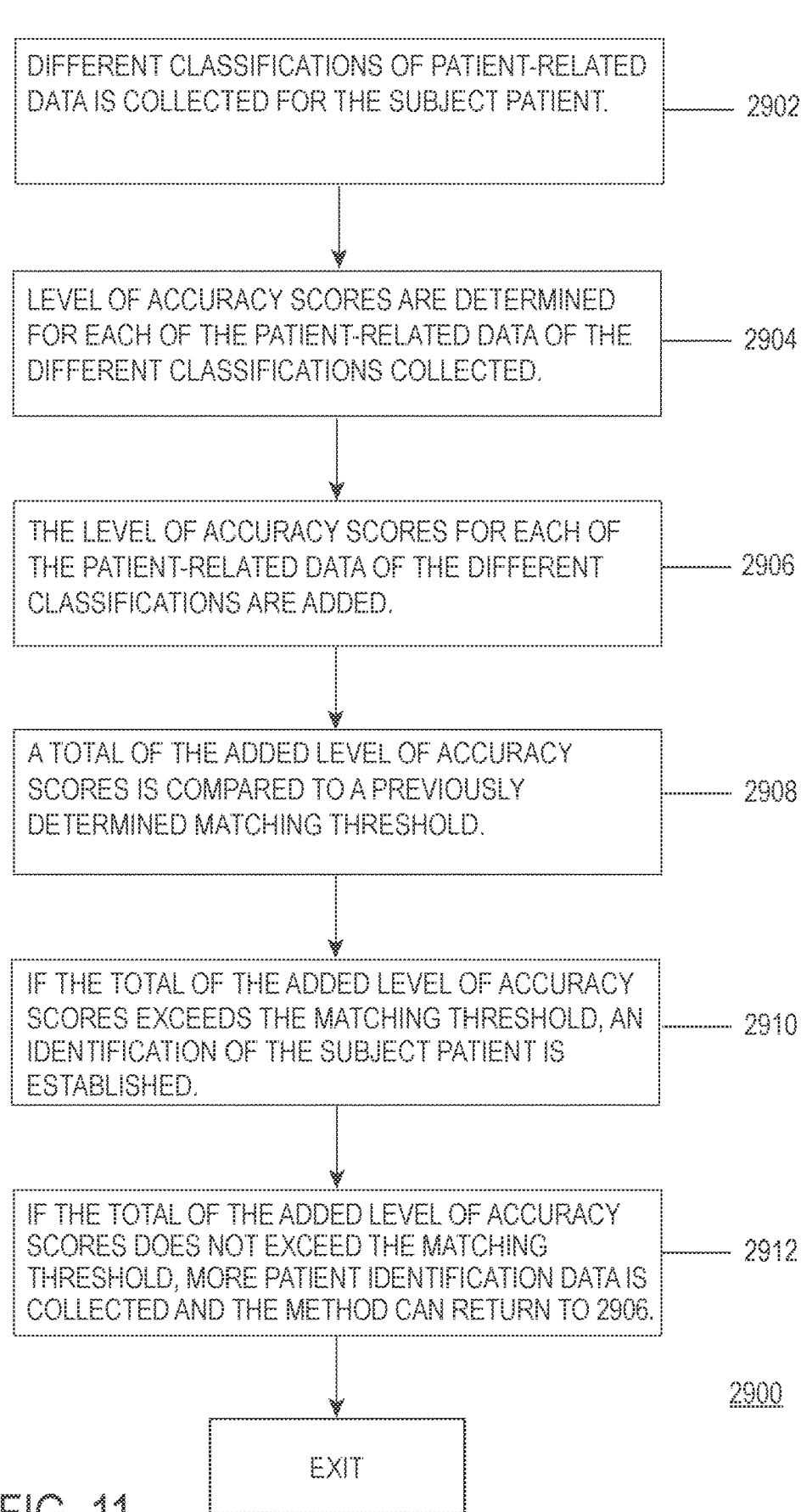

DIFFERENT CLASSIFICATIONS OF PATIENT-RELATED DATA IS COLLECTED FOR THE SUBJECT PATIENT. — 2902

LEVEL OF ACCURACY SCORES ARE DETERMINED FOR EACH OF THE PATIENT-RELATED DATA OF THE DIFFERENT CLASSIFICATIONS COLLECTED. — 2904

THE LEVEL OF ACCURACY SCORES FOR EACH OF THE PATIENT-RELATED DATA OF THE DIFFERENT CLASSIFICATIONS ARE ADDED. — 2906

A TOTAL OF THE ADDED LEVEL OF ACCURACY SCORES IS COMPARED TO A PREVIOUSLY DETERMINED MATCHING THRESHOLD. — 2908

IF THE TOTAL OF THE ADDED LEVEL OF ACCURACY SCORES EXCEEDS THE MATCHING THRESHOLD, AN IDENTIFICATION OF THE SUBJECT PATIENT IS ESTABLISHED. — 2910

IF THE TOTAL OF THE ADDED LEVEL OF ACCURACY SCORES DOES NOT EXCEED THE MATCHING THRESHOLD, MORE PATIENT IDENTIFICATION DATA IS COLLECTED AND THE METHOD CAN RETURN TO 2906. — 2912

2900

EXIT

FIG. 11

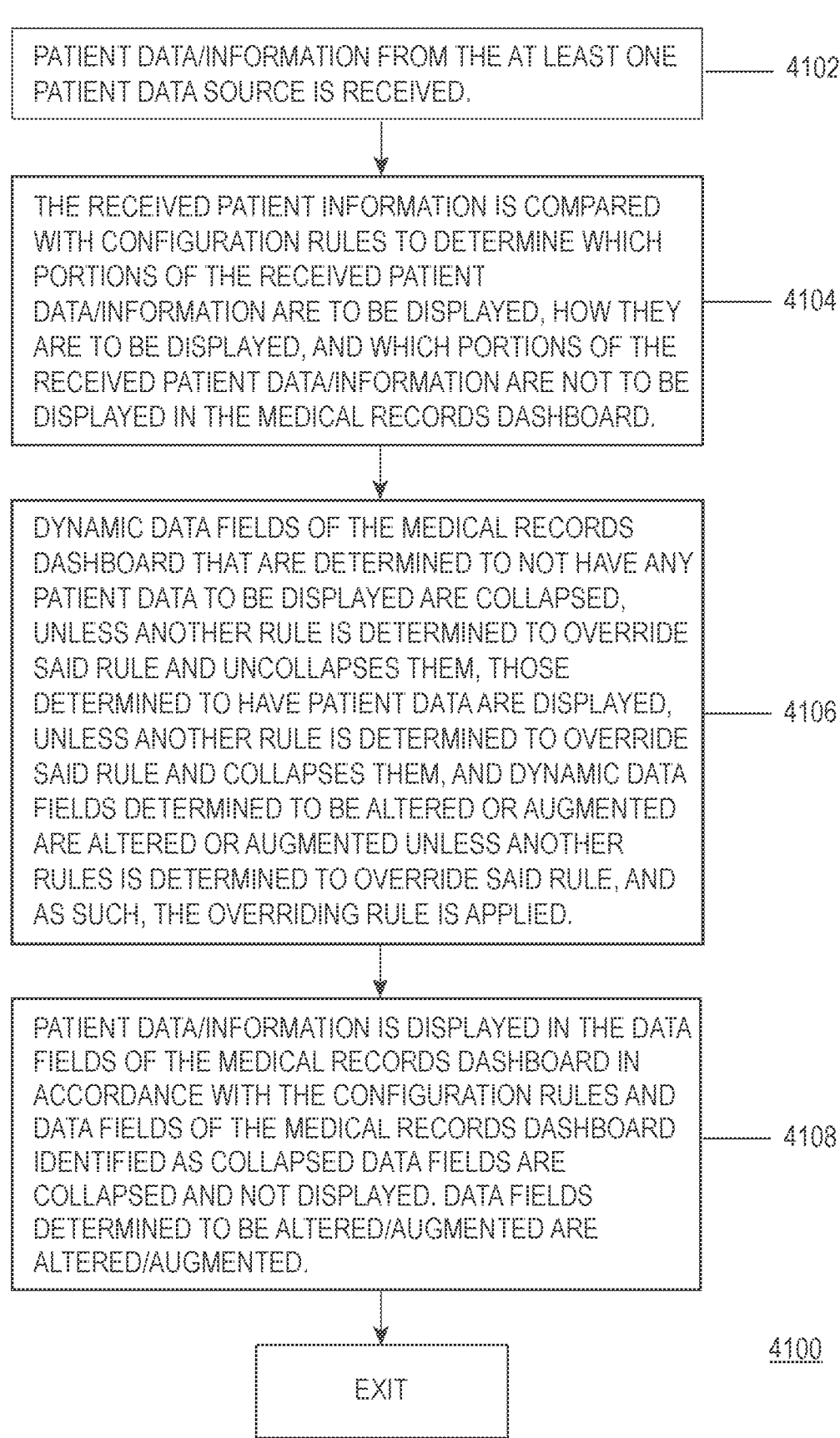

PATIENT DATA/INFORMATION FROM THE AT LEAST ONE PATIENT DATA SOURCE IS RECEIVED. — 4102

THE RECEIVED PATIENT INFORMATION IS COMPARED WITH CONFIGURATION RULES TO DETERMINE WHICH PORTIONS OF THE RECEIVED PATIENT DATA/INFORMATION ARE TO BE DISPLAYED, HOW THEY ARE TO BE DISPLAYED, AND WHICH PORTIONS OF THE RECEIVED PATIENT DATA/INFORMATION ARE NOT TO BE DISPLAYED IN THE MEDICAL RECORDS DASHBOARD. — 4104

DYNAMIC DATA FIELDS OF THE MEDICAL RECORDS DASHBOARD THAT ARE DETERMINED TO NOT HAVE ANY PATIENT DATA TO BE DISPLAYED ARE COLLAPSED, UNLESS ANOTHER RULE IS DETERMINED TO OVERRIDE SAID RULE AND UNCOLLAPSES THEM, THOSE DETERMINED TO HAVE PATIENT DATA ARE DISPLAYED, UNLESS ANOTHER RULE IS DETERMINED TO OVERRIDE SAID RULE AND COLLAPSES THEM, AND DYNAMIC DATA FIELDS DETERMINED TO BE ALTERED OR AUGMENTED ARE ALTERED OR AUGMENTED UNLESS ANOTHER RULES IS DETERMINED TO OVERRIDE SAID RULE, AND AS SUCH, THE OVERRIDING RULE IS APPLIED. — 4106

PATIENT DATA/INFORMATION IS DISPLAYED IN THE DATA FIELDS OF THE MEDICAL RECORDS DASHBOARD IN ACCORDANCE WITH THE CONFIGURATION RULES AND DATA FIELDS OF THE MEDICAL RECORDS DASHBOARD IDENTIFIED AS COLLAPSED DATA FIELDS ARE COLLAPSED AND NOT DISPLAYED. DATA FIELDS DETERMINED TO BE ALTERED/AUGMENTED ARE ALTERED/AUGMENTED. — 4108

4100

EXIT

FIG. 13D

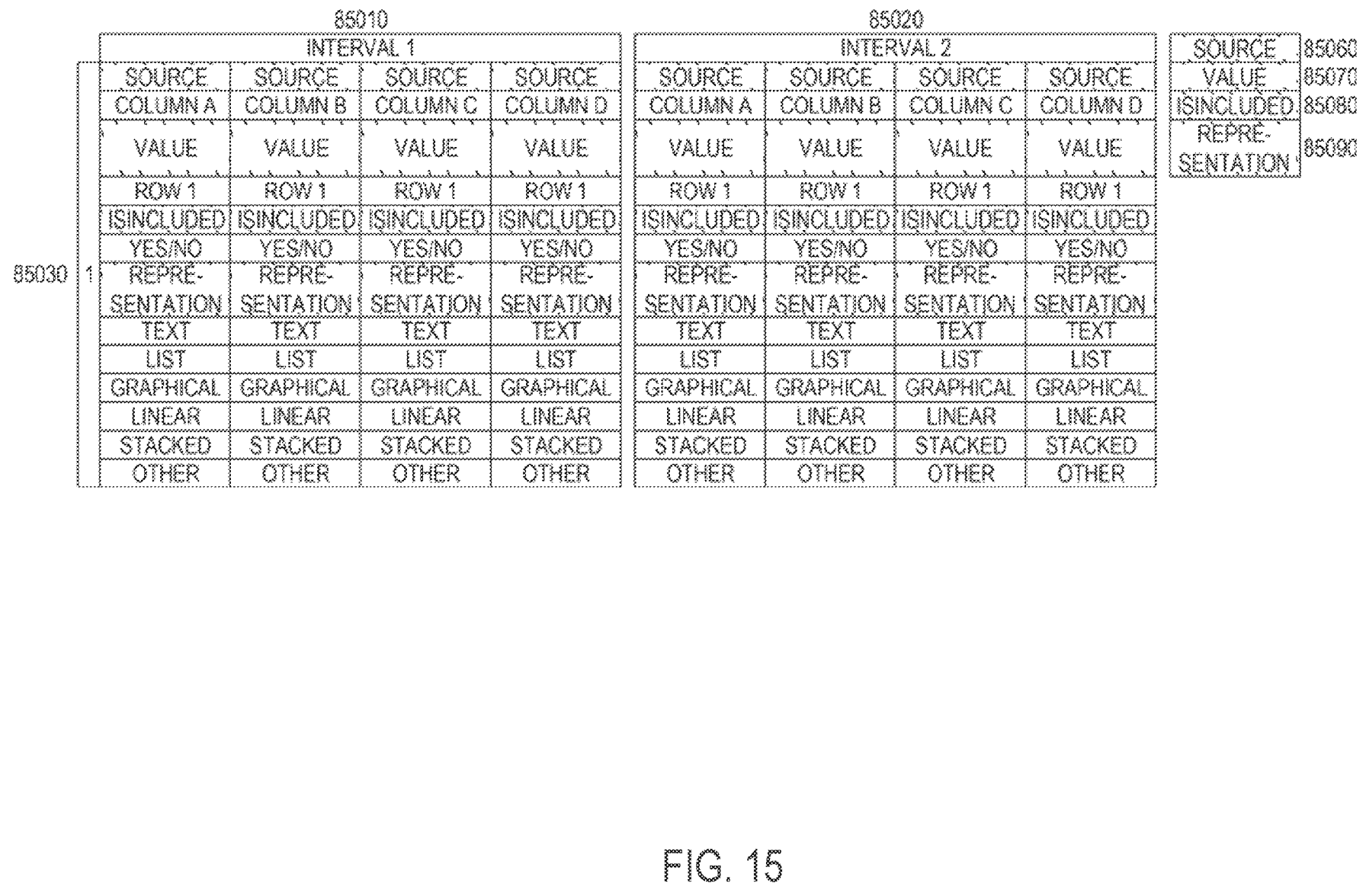

| | 85060 | 85070 | 85080 | 85090 |
|---|---|---|---|---|
| | SOURCE | VALUE | ISINCLUDED | REPRE-SENTATION |

INTERVAL 2   85020

| | SOURCE COLUMN A | SOURCE COLUMN B | SOURCE COLUMN C | SOURCE COLUMN D |
|---|---|---|---|---|
| VALUE | ROW 1 | ROW 1 | ROW 1 | ROW 1 |
| ISINCLUDED | YES/NO | YES/NO | YES/NO | YES/NO |
| REPRE-SENTATION | TEXT | TEXT | TEXT | TEXT |
| | LIST | LIST | LIST | LIST |
| | GRAPHICAL | GRAPHICAL | GRAPHICAL | GRAPHICAL |
| | LINEAR | LINEAR | LINEAR | LINEAR |
| | STACKED | STACKED | STACKED | STACKED |
| | OTHER | OTHER | OTHER | OTHER |

INTERVAL 1   85010   85030

| | SOURCE COLUMN A | SOURCE COLUMN B | SOURCE COLUMN C | SOURCE COLUMN D |
|---|---|---|---|---|
| VALUE | ROW 1 | ROW 1 | ROW 1 | ROW 1 |
| ISINCLUDED | YES/NO | YES/NO | YES/NO | YES/NO |
| REPRE-SENTATION | TEXT | TEXT | TEXT | TEXT |
| | LIST | LIST | LIST | LIST |
| | GRAPHICAL | GRAPHICAL | GRAPHICAL | GRAPHICAL |
| | LINEAR | LINEAR | LINEAR | LINEAR |
| | STACKED | STACKED | STACKED | STACKED |
| | OTHER | OTHER | OTHER | OTHER |

FIG. 15

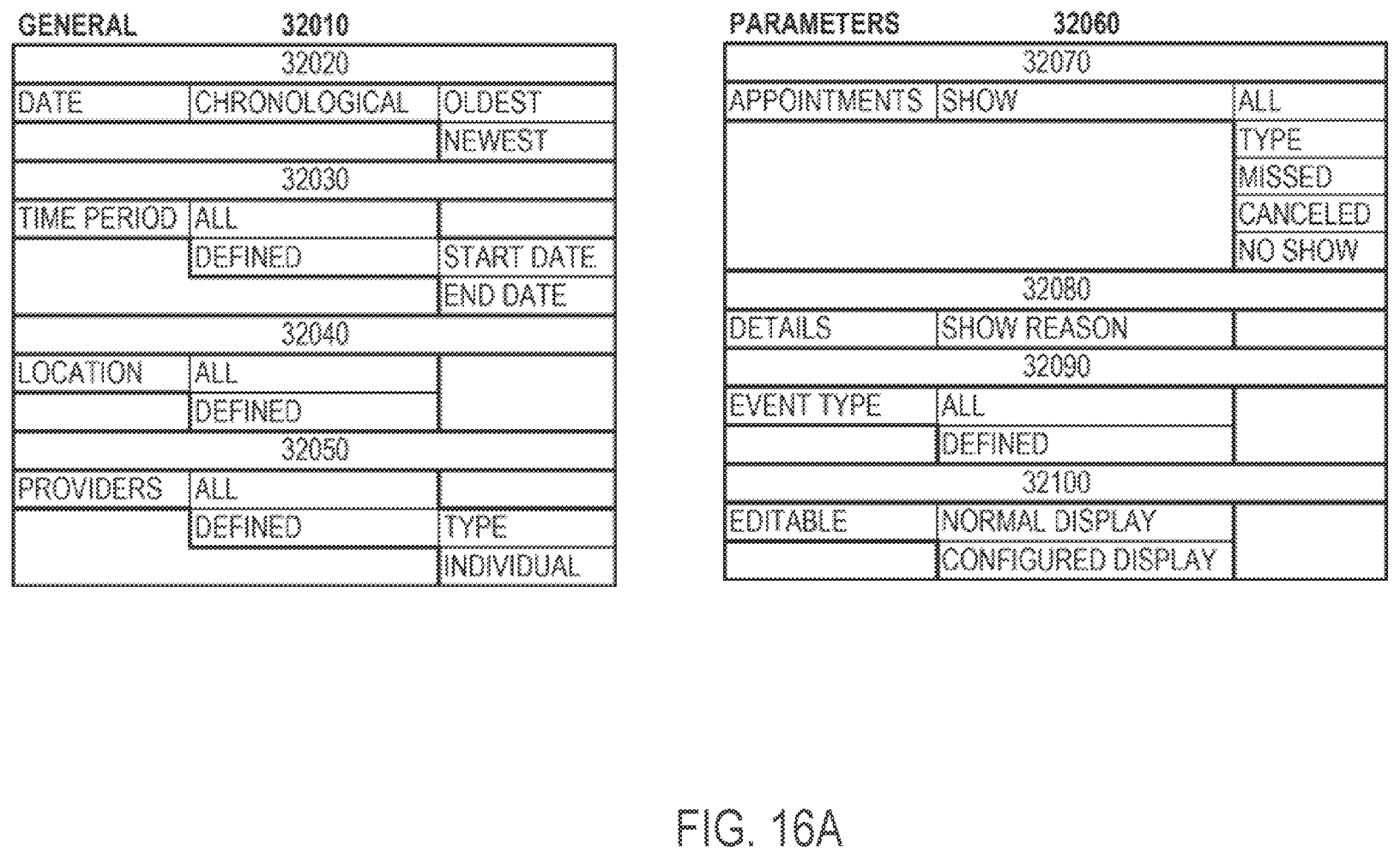

GENERAL 32010

| | 32020 | | | | |
|---|---|---|---|---|---|
| DATE | CHRONOLOGICAL | OLDEST | | | |
| | | NEWEST | | | |
| | 32030 | | | START DATE | |
| TIME PERIOD | ALL | | | | |
| | DEFINED | | | END DATE | |
| | 32040 | | | | |
| LOCATION | ALL | | | | |
| | DEFINED | | | | |
| | 32050 | | | | |
| PROVIDERS | ALL | | | TYPE | |
| | DEFINED | | | INDIVIDUAL | |

PARAMETERS 32060

| | 32070 | | ALL | |
|---|---|---|---|---|
| APPOINTMENTS | SHOW | | TYPE | MISSED |
| | | | | CANCELED |
| | | | | NO SHOW |
| | 32080 | | | |
| DETAILS | SHOW REASON | | | |
| | 32090 | | | |
| EVENT TYPE | ALL | | | |
| | DEFINED | | | |
| | 32100 | | | |
| EDITABLE | NORMAL DISPLAY | | | |
| | CONFIGURED DISPLAY | | | |

FIG. 16A

CONFIGURATION                    32110

| 32120 | | |
|---|---|---|
| DATE CONFIGURATION | MM/DD/YYYY | |
| 32130 | | |
| DISPLAY DURATION | EVENT TRIGGER | |
| | TIME PERIOD | START DATE |
| | | END DATE |
| 32140 | | |
| SIZE | NORMAL | |
| | SMALLER | |
| | LARGER | |
| 32150 | | |
| DISPLAY TYPE | FONT | |
| | COLOR | |
| | TYPOGRAPHY | |
| | HIDE | |
| | HOVER FOR DETAILS | |
| 32160 | | |
| MOVE | LOCATION | |
| 32170 | | |
| DIRECT ACCESS | IMAGE | |
| | TEXT | |
| | ORDERING | |
| | CO-MANAGEMENT | |
| 32180 | | |
| OVERRIDE | OVERRIDE RULES | RULE |

FIG. 16B

INTERVAL 1 (10010)

| | SOURCE COLUMN A | SOURCE COLUMN B | SOURCE COLUMN C | SOURCE COLUMN D |
|---|---|---|---|---|
| SOURCE (10030) | COLUMN A | COLUMN B | COLUMN C | COLUMN D |
| VALUE (10040) | ROW 1 | ROW 1 | ROW 1 | ROW 1 |
| ISINCLUDED (10050) | YES | YES | YES | YES |
| REPRESENTATION (10060) | TEXT | GRAPHICAL | TEXT | LINEAR |
| RULES (10070) | LIMIT EXCEEDED | N/A | LIMIT EXCEEDED | ADD IF PRESENT |
| RULES (10080) | N/A | N/A | RELATION TRIGGER | LIMIT EXCEEDED |
| ACTION (10090) | NONE | NONE | NONE | NONE |

INTERVAL 2 (10020)

| | SOURCE COLUMN A | SOURCE COLUMN B | SOURCE COLUMN C | SOURCE COLUMN D |
|---|---|---|---|---|
| SOURCE | COLUMN A | COLUMN B | COLUMN C | COLUMN D |
| VALUE | ROW 1 | ROW 1 | ROW 1 | ROW 1 |
| ISINCLUDED | YES | YES | YES | YES |
| REPRESENTATION | TEXT | GRAPHICAL | TEXT | LINEAR |
| RULES | LIMIT EXCEEDED | RELATION TRIGGER | LIMIT EXCEEDED | LIMIT EXCEEDED |
| RULES | N/A | N/A | 3X LARGER | RELATION TRIGGER |
| ACTION | NONE | MESSAGE | NONE | RELATION EFFECT |

FIG. 19

| DATE | PROV/LOC | VA | | IOP | | OD | | | OS | | | PHOTO (2Y3M1D) |
|---|---|---|---|---|---|---|---|---|---|---|---|---|
| | | OD | OS | OD | OS | PROC | INJECTIONS | AiS | PROC | INJECTIONS | AiS | |
| 10/13/2020 | LHG/SPH | 20/30-2 | 20/50-1 | 20 | 22 | | LUCENTIS 0.5MG (1M24D) <br> INJECT/IONS (21D) | | | INJECT-IONS (1M24D) | | |
| 08/10/2020 | LHG/SPH | 20/30-2 | 20/50-1 | | | | | | | LUCENTIS 0.5MG (2M5D) | | |
| 08/20/2020 | LHG/SPH | 20/30-2 | 20/50-2 | | | | LUCENTIS 0.5MG (2M5D) | | | | | |
| 08/16/2020 | LHG/SPH | 20/30-2 | 20/50+2 | 20 | 22 | | LUCENTIS 0.5MG (1M13D) | | | | | |
| 03/19/2020 | LHG/SPH | 20/30 | 20/40 | 18 | 22 | | | | | LUCENTIS 0.5MG (1M7D) | | |
| | | 20/25-3 <br> 20/70-1 | 20/16 <br> 10/60+2 | 22 | 24 | Y:1, C:1 | L:28, E:24 | | C:1, F:1 | L:25, E:23 | | 5 |

Reference numerals: 90010, 90020, 90030, 90035, 90040, 90045, 90050, 90060, 90065, 90070, 90080, 90100, 90110, 90120, 90130, 90140, 90150.

FIG. 23

| | | | Appointments: | All |
|---|---|---|---|---|
| 1/24/19 | Dr. C | Dallas | Details: | In informational alert |
| 6/23/18 | Dr. A | Houston | Event type: | Over 8.0 |
| 11/1/17 | Dr. B | Boston | Editable: | No |
| | | | Display duration: | Indefinite |
| 5/22/15 | Dr. A | Houston | Size: | Unchanged |
| | | | Display type: | Red alert |
| 4/12/13 | Dr. A | Houston | Move: | Unchanged |
| | | | Direct access: | N/A |
| Summary | A:2 B:2 C:1 D:1 | H:2 B:2 D:2 | Override: | Manual |

| Problems | Medications | Allergies |
|---|---|---|
| Diabetes mellitus | | Active |
| Melanoma | | Active |
| Appendicitis | | Inactive |

Assessment and plan

10/22/2020

Follow diabetes. advised patient to check blood sugar regularly.

Schedule follow up in 2-3 weeks

FIG. 29B

| Primary care | | | Speciality 1 | Speciality 2 | | | |
|---|---|---|---|---|---|---|---|
| Date | Provider | Location | Proc | HbA1c | X-ray | Meds | |
| 12/2/22 | Dr. C | | | | | | |
| Next visit | | | | | X | | |
| Today's visit | Dr. E | Springfield | Shave biopsy | 8.5 | | | |
| 10/22/20 | Dr. B | Boston | Minor sutures | 7.85 | | | |
| 5/12/20 | Dr. D | Springfield | | | | | |
| 8/2/19 | Dr. C | Dallas | Appendix removal | 6.5 | | | |
| 1/24/19 | Dr. C | Dallas | | | | | |
| 6/23/18 | Dr. A | Houston | ----- | ----- | | | |
| 11/1/17 | Dr. B | Boston | | 6.5 | | | |
| 5/22/15 | Dr. A | Houston | | | | | |
| 4/12/13 | Dr. A | Houston | Fracture repair | 7.0 | | | |
| Summary | A:2 B:2 C:1 D:1 | H:2 B:2 D:2 | S:1 M:1 A:1 F:1 | 6./8.5 | 2 | 1 | |

| Date | Code | Medication |
|---|---|---|
| 05/22/2019 | VF/Sph | |
| 05/13/2019 | LHG/Sph | Eylea (4m27d) |
| 04/15/2019 | LHG/Sph | |
| 03/28/2019 | NWC/Sph | |
| 02/14/2019 | LHG/Sph | |
| 12/17/2018 | LHG/Sph | Eylea (2m10d) |
| 12/06/2018 | LHG/Sph | |
| 10/08/2018 | LHG/Sph | Eylea (1m24d) 2373 |
| 09/19/2018 | LHG/Sph | Eylea (15days) 2332 |
| 07/13/2018 | LHG/Sph | Lucentis 0.5 (1m29d) |
| 06/28/2018 | LHG/Sph | |
| 05/23/2018 | NWC/Sph | |
| 05/21/2018 | NWC/Sph | |
| 04/30/2018 | LHG/Sph | Lucentis 0.5 (1m29d) |
| 04/12/2018 | LHG/Sph | |
| 02/22/2018 | LHG/Sph | Lucentis 0.5 (2m7d) |
| 02/15/2018 | LHG/Sph | Lucentis 0.5 |
| 12/28/2017 | DM/Sph | |

| | | H | | (1m26d) |
|---|---|---|---|---|
| 12/21/2017 | GC/Sph | | | --- |
| 12/13/2017 | GC/Sph | | | --- |
| 11/10/2017 | GC/Sph | | | |
| 10/23/2017 | LHG/Sph | | | Lucentis 0.5 (1m9d) |
| 09/25/2017 | VF/Sph | | | --- |
| 09/18/2017 | LHG/Sph | | | --- |
| 09/15/2017 | LHG/Sph | | | --- |
| 09/14/2017 | LHG/Sph | | | Lucentis 0.5 (1m5d) |
| Summary | | L:9, E:5 | | L:26, E:7 |

2375  2376                    2378              2380

2374

Figure 43A:
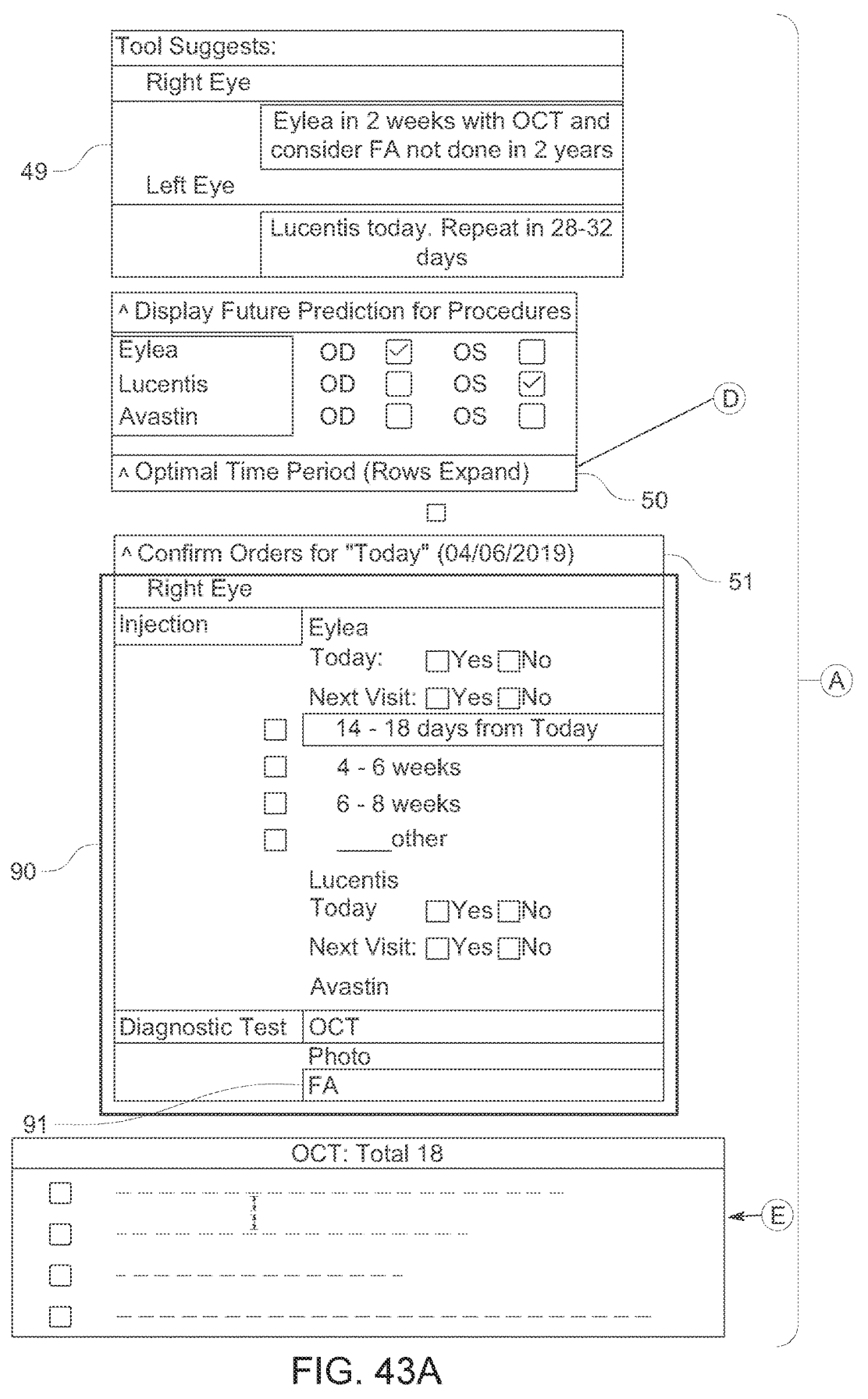

| Tool Suggests: | |
|---|---|
| Right Eye | |
| | Eylea in 2 weeks with OCT and consider FA not done in 2 years |
| Left Eye | |
| | Lucentis today. Repeat in 28-32 days |

49

50

D

A

| ∧ Display Future Prediction for Procedures | | | | |
|---|---|---|---|---|
| Eylea | OD | ☑ | OS | ☐ |
| Lucentis | OD | ☐ | OS | ☑ |
| Avastin | OD | ☐ | OS | ☐ |
| ∧ Optimal Time Period (Rows Expand) | | | | |

☐

∧ Confirm Orders for "Today" (04/06/2019)

51

90

| Right Eye | |
|---|---|
| Injection | Eylea |
| | Today:    ☐Yes☐No |
| | Next Visit: ☐Yes☐No |
| ☐ | 14 - 18 days from Today |
| ☐ | 4 - 6 weeks |
| ☐ | 6 - 8 weeks |
| ☐ | ____other |
| | Lucentis |
| | Today    ☐Yes☐No |
| | Next Visit: ☐Yes☐No |
| | Avastin |
| Diagnostic Test | OCT |
| | Photo |
| | FA |

91

| OCT: Total 18 |
|---|
| ☐  - - - - - - - - I - - - - - - - - - |
| ☐  - - - - - - - - - - - - - - - - - - - |
| ☐  - - - - - - - - - - - - - - - - - - - |
| ☐  - - - - - - - - - - - - - - - - - - - |

| Display Future Prediction if: |
|---|
| Left Eye |
| Not follow AI advice and on 04/06/19 inject Eylea instead of Lucentis in left eye |
| Right Eye |
| Switch to Avastin since cost savings of $ |

FIG. 46A

Patient Search

Retina | Glaucoma | Comprehensive

| Date | OD | | | OS | | | Date |
|---|---|---|---|---|---|---|---|
| | Injections ☐ | OCT CMT | VA | Injections ☐ | OCT CMT | VA | |
| 11/21/2020 | Eylea (60) | 280 | 20/30 | Lucentis (28) | 395 | 20/150 | 12/06/2019 |
| 10/21/2019 | Eylea (30) | 295 | 20/50 | Lucentis (28) | 440 | 20/200 | 11/06/2019 |
| 09/21/2019 | Eylea (29) | 320 | 20/70 | Lucentis (29) | 450 | 20/400 | 10/06/2019 |
| 08/21/2019 | Eylea (28) | 330 | 20/100 | Lucentis (28) | 500 | CF | 09/06/2019 |
| 07/21/2019 | Eylea (29) | 370 | 20/100 | Eylea (29) | 475 | 20/400 | 08/06/2019 |
| 06/21/2019 | Avastin (28) | 360 | 20/70 | Eylea (30) | 450 | 20/400 | 07/06/2019 |
| 05/21/2019 | Avastin (29) | 350 | 20/60 | Eylea (28) | 420 | 20/400 | 06/06/2019 |
| 04/21/2019 | Avastin (28) | 320 | 20/60 | Eylea (29) | 410 | 20/400 | 05/06/2019 |
| Today's Visit 04/06/2019 | | 295 | 20/60+2 | Eylea 0.3 (29) | 408 | 20/400 | 04/06/2019 |

Mandatory Switch

Mandatory Switch

| Date | Type | | | Weight 1 | Weight 2 |
|---|---|---|---|---|---|
| 03/08/2018 | NWC/Ext | | | 17g | 22g |
| 02/02/2018 | NWC/Ext | | | 18g | 22g |
| 01/19/2018 | NWC/Ext | | | | |
| 12/14/2017 | NWC/Ext | | | 16g | 18g |
| 11/09/2017 | NWC/Ext | | | 16g | 24g |
| 08/04/2017 | NWC/Ext | | | 12g | 14g |
| 07/21/2017 | NWC/Ext | | SLT | 17g | 21g |
| 06/08/2017 | NWC/Ext | | | | |
| 03/17/2017 | NWC/Ext | SLT | | | |
| 03/03/2017 | NWC/Ext | | | | |
| 02/09/2017 | NWC/Ext | | | | |
| 01/12/2017 | NWC/Ext | | | 24g | 26g |
| 01/06/2017 | NWC/Ext | | | 18g | 18g |
| 08/05/2016 | NWC/Ext | S:1 | S:1 | 26 | 26 |

FIG. 50B

| Start date | Stop date | Last used | Medication | Dosage | Eye |
|---|---|---|---|---|---|
| 11/9/2017 | 8/29/2018 | | | | |
| 11/9/2017 | 8/29/2018 | | Azopt 1% drop,suspension | 1 % | OU |
| 11/9/2017 | 1/14/2018 | | Timolol maleate 0.5% eye drops | 1 | OU |
| 1/12/2017 | 8/29/2018 | | Brimonidine 0.15% eye drops | 0.15 % | OU |
| 5/1/2015 | 9/10/2015 | | Lumigan | 1 drop | OD |
| 5/21/2014 | 11/9/2017 | | Dorzolamide-timolol 2%-0.5% eye drops | 22.3-6.8 mg/ml | OU |

Patient summary note | Problems | Glaucoma meds | Ocular meds | Systemic meds

3050

Figure 50E:
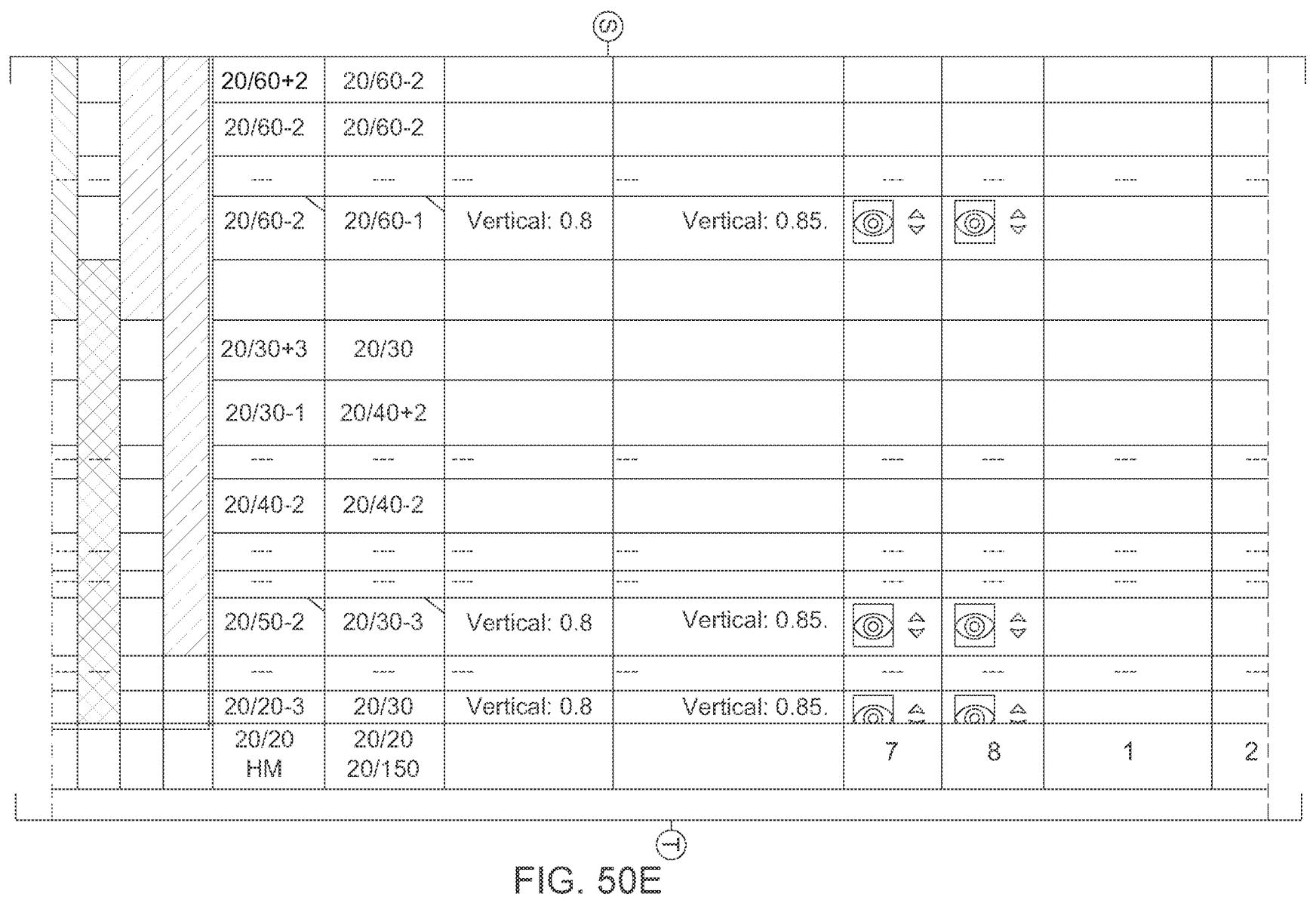

| | | | | | | | | 8 | 7 | | | 1 | 2 |
|---|---|---|---|---|---|---|---|---|---|---|---|---|---|

20/60+2 | 20/60-2

20/60-2 | 20/60-2

20/60-2 | —

20/60-2 | 20/60-1

Vertical: 0.8 | Vertical: 0.85

20/30+3 | 20/30

20/30-1 | 20/40+2

20/40-2 | —

20/40-2 | 20/40-2

20/50-2 | 20/30-3

Vertical: 0.8 | Vertical: 0.85

— | —

20/20-3 | 20/30

Vertical: 0.8 | Vertical: 0.85

Figure 50H:
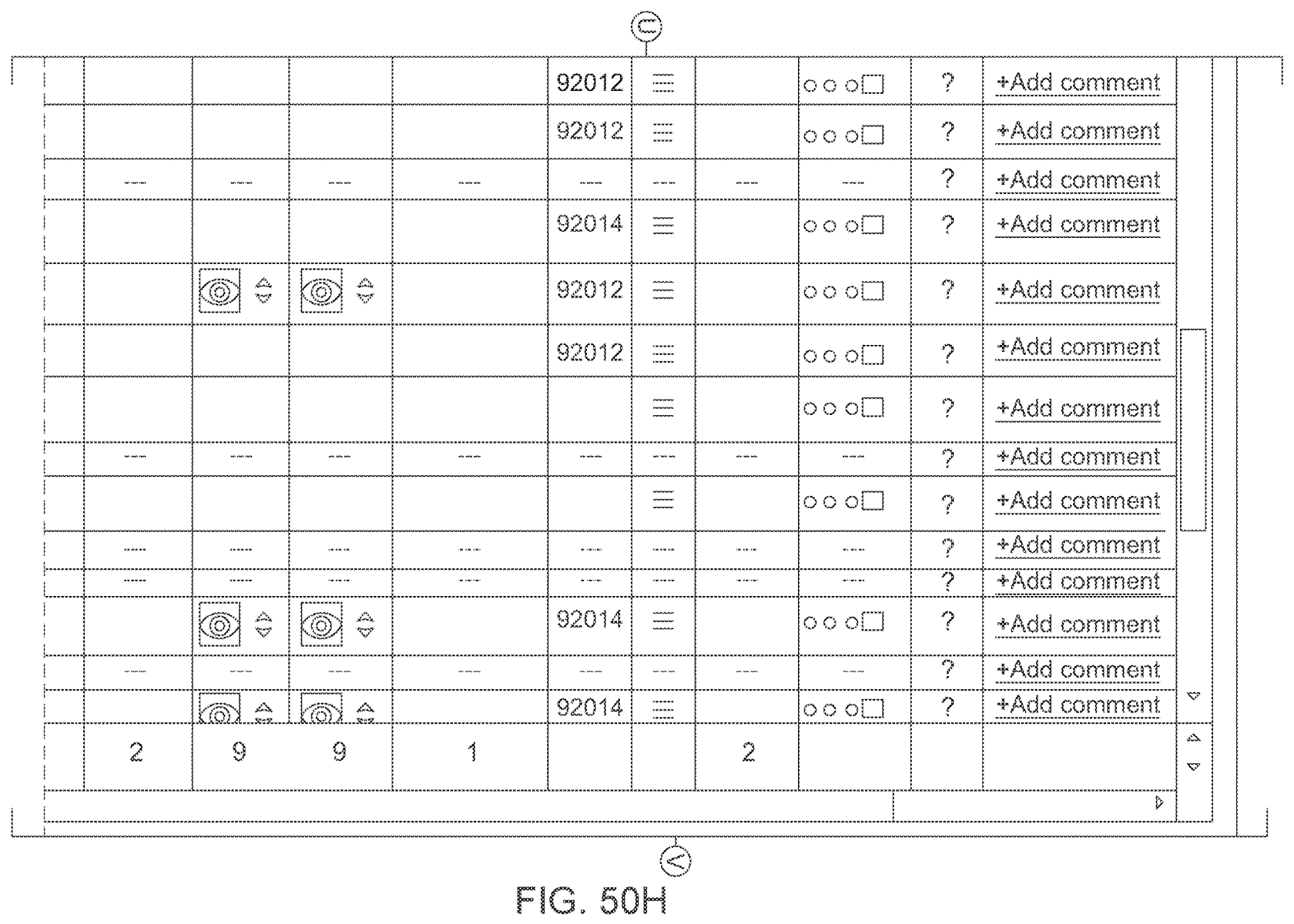

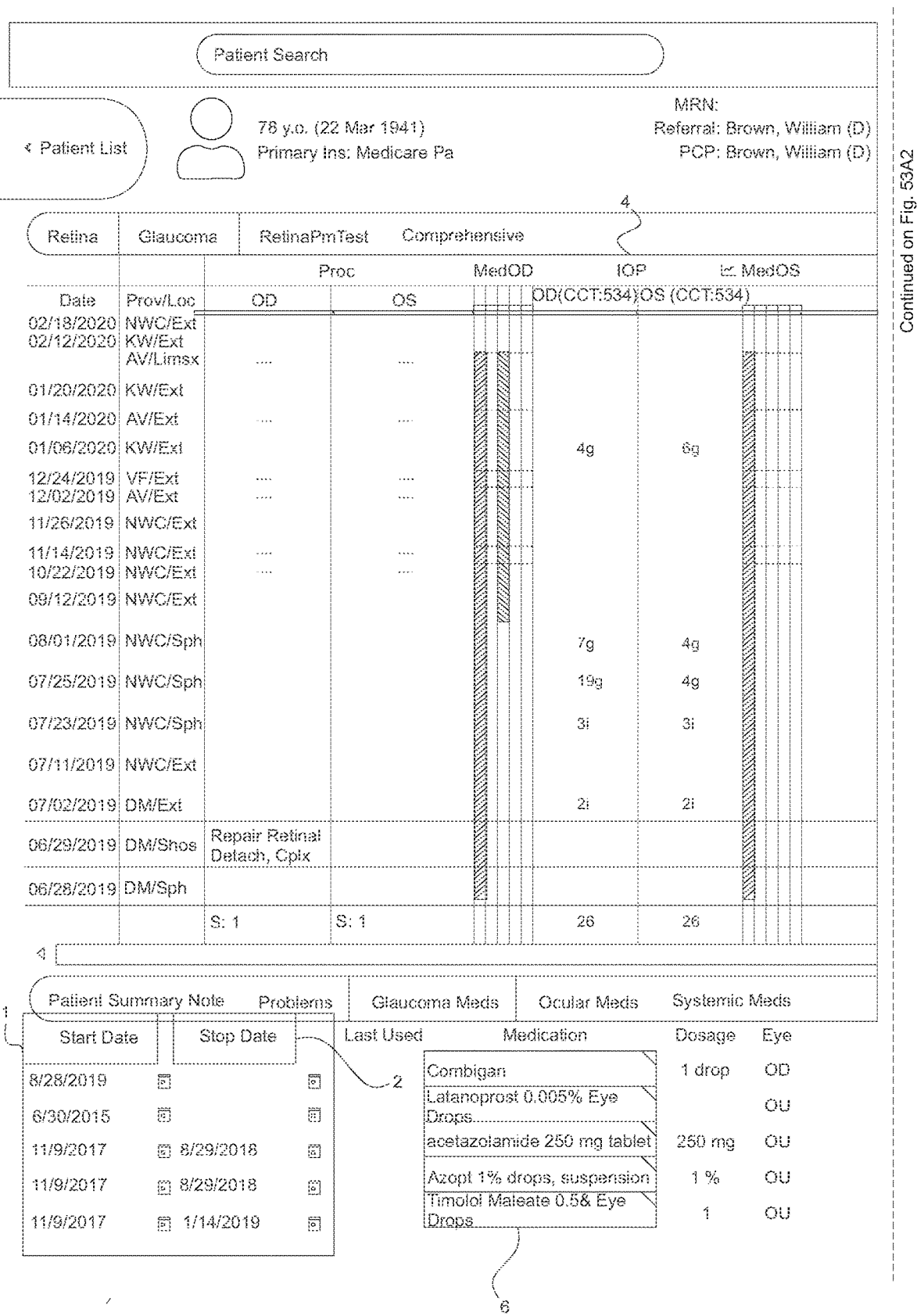
FIG. 53A1

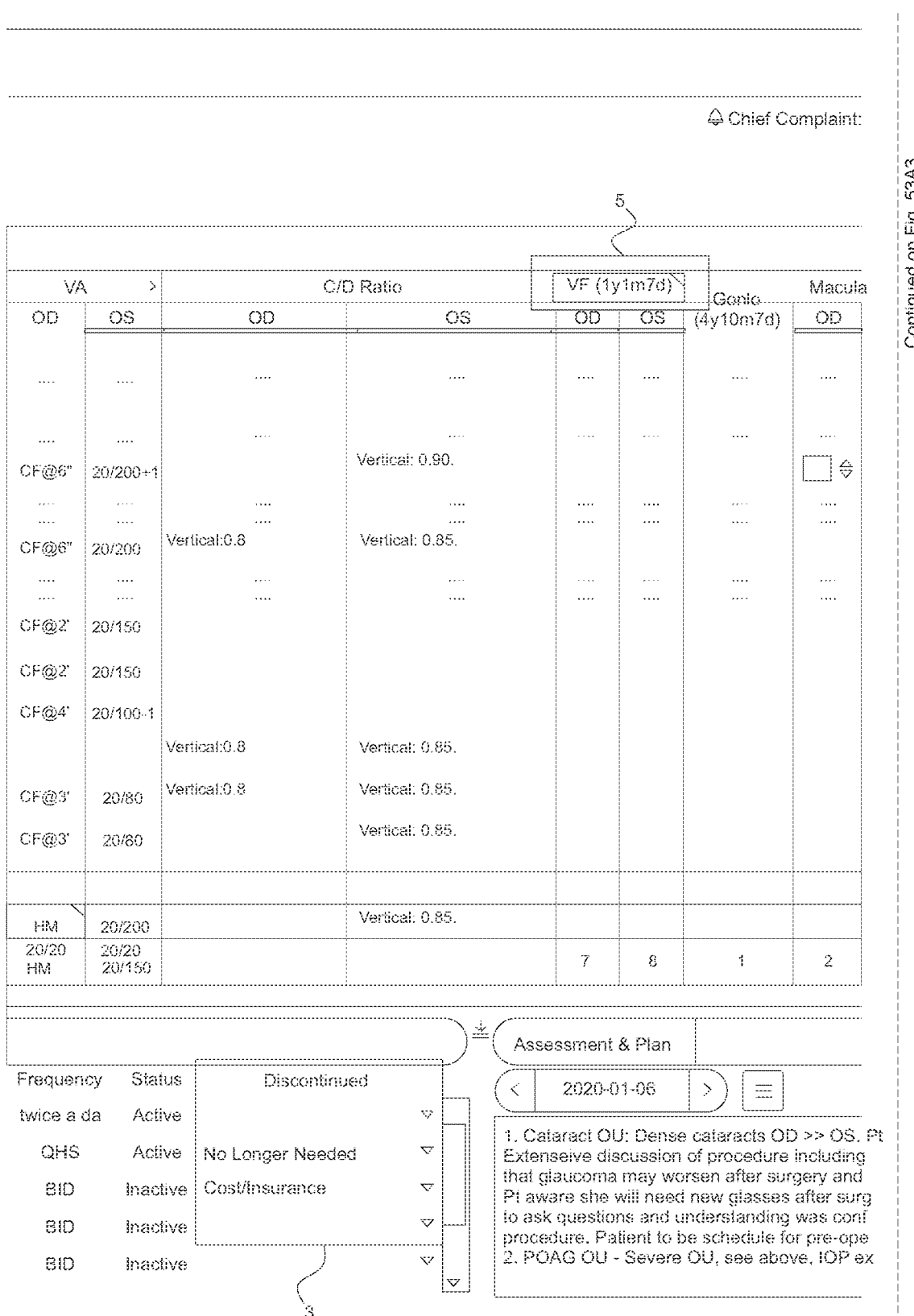
FIG. 53A2

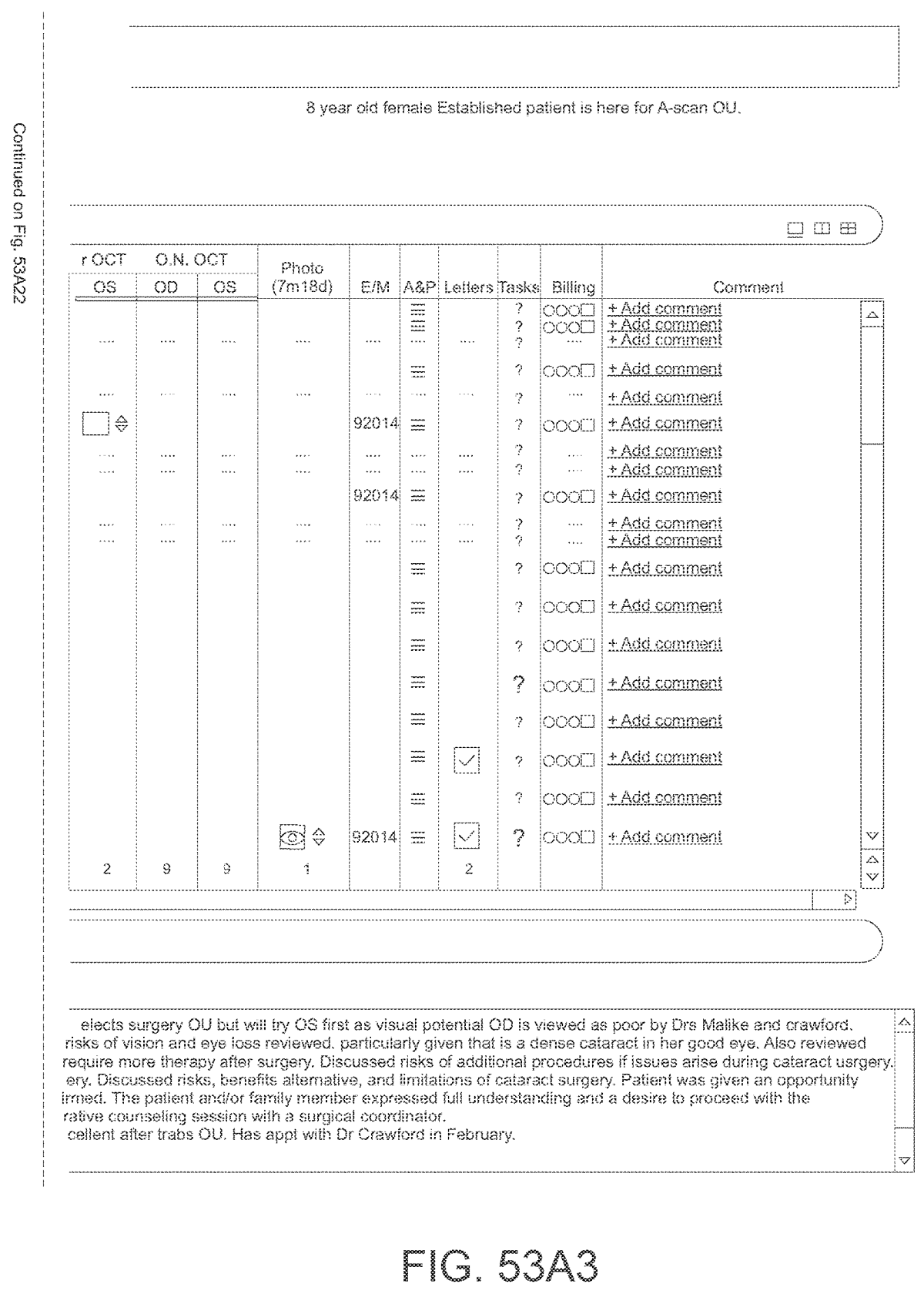

Continued on Fig. 53A22

8 year old female Established patient is here for A-scan OU.

| r OCT | O.N. OCT | | Photo (7m18d) | E/M | A&P | Letters | Tasks | Billing | Comment |
|---|---|---|---|---|---|---|---|---|---|
| OS | OD | OS | | | | | | | |
| | | | | | ≡ | | ? | OOO☐ | + Add comment |
| | | | | | ≡ | | ? | OOO☐ | + Add comment |
| .... | .... | .... | .... | .... | .... | .... | ? | .... | + Add comment |
| | | | | | ≡ | | ? | OOO☐ | + Add comment |
| .... | .... | .... | .... | .... | .... | .... | ? | .... | + Add comment |
| ☐ ⇕ | | | | 92014 | ≡ | | ? | OOO☐ | + Add comment |
| .... | .... | .... | .... | .... | .... | .... | ? | .... | + Add comment |
| .... | .... | .... | .... | .... | .... | .... | ? | .... | + Add comment |
| | | | | 92014 | ≡ | | ? | OOO☐ | + Add comment |
| .... | .... | .... | .... | .... | .... | .... | ? | .... | + Add comment |
| .... | .... | .... | .... | .... | .... | .... | ? | .... | + Add comment |
| | | | | | ≡ | | ? | OOO☐ | + Add comment |
| | | | | | ≡ | | ? | OOO☐ | + Add comment |
| | | | | | ≡ | | ? | OOO☐ | + Add comment |
| | | | | | ≡ | | ? | OOO☐ | + Add comment |
| | | | | | ≡ | | ? | OOO☐ | + Add comment |
| | | | | | ≡ | ✓ | ? | OOO☐ | + Add comment |
| | | | | | ≡ | | ? | OOO☐ | + Add comment |
| | | | ⊙ ⇕ | 92014 | ≡ | ✓ | ? | OOO☐ | + Add comment |
| 2 | 9 | 9 | 1 | | | 2 | | | | elects surgery OU but will try OS first as visual potential OD is viewed as poor by Drs Malike and crawford. risks of vision and eye loss reviewed. particularly given that is a dense cataract in her good eye. Also reviewed require more therapy after surgery. Discussed risks of additional procedures if issues arise during cataract usrgery. ery. Discussed risks, benefits alternative, and limitations of cataract surgery. Patient was given an opportunity irmed. The patient and/or family member expressed full understanding and a desire to proceed with the rative counseling session with a surgical coordinator. cellent after trabs OU. Has appt with Dr Crawford in February.

FIG. 53A3

PatientSearch

< Patient list    Primary Ins: Medicare Pa

Re:

◁

| Retina | Glaucoma | RetinaPmTest | Comprehensive | 5 |

| | | Proc | | MedOD | IOP | MedOS |
|---|---|---|---|---|---|---|
| Date | Prov/Loc | (PO:70 Cataract! | (OS:42 Cataract! | | OD (CCT:534) | OD (CCT:534) |
| 04/23/2019 | NWC/Ext | | | | 10g | 8g |
| 04/11/2019 | NWC/Ext | | | | | |
| 04/10/2019 | NWC/Sph | | | | 10g | |
| 04/09/2019 | NWC/Brin | Trabeculectomy | | | | |
| 03/26/2019 | NWC/Ext | | | | 21g | 7g |
| 01/10/2019 | NWC/Ext | | | | 20i | 8i |
| 12/13/2018 | VF/Ext | ---- | ---- | | | |
| 11/27/2018 | VF/Ext | ---- | ---- | | | |
| 10/05/2018 | NWC/Ext | | | | 23g | |
| 09/20/2018 | NWC/Sph | | | | 18g | 8g |
| 09/17/2018 | NWC/Sph | | | | | |
| 09/13/2018 | NWC/Ext | | | | 16g | 16g |
| 09/12/2018 | NWC/Sph | | | | 26g | 24g |
| 09/11/2018 | NWC/Brin | | Trabeculectomy | | | |
| 08/28/2018 | NWC/Ext | | | | 21g | 24g |
| 07/24/2018 | VF/Ext | ---- | ---- | | | |
| 06/14/2018 | NWC/Ext | | | | 18g | 21g |
| 03/08/2018 | NWC/Ext | | | | 17g | 22g |
| 02/02/2018 | NWC/Ext | ---- | ---- | | 18g | 22g |
| 01/19/2018 | NWC/Ext | | | | | |
| 12/14/2017 | NWC/Ext | | | | 16g | 18g |
| 11/09/2017 | NWC/Ext | | | | 16g | 24g |
| 08/04/2017 | NWC/Ext | | | | 12g | 14g |
| 08/04/2017 | NWC/Ext | | SLT | | 17g | 21g |
| 06/08/2017 | NWC/Ext | ---- | ---- | | | |
| 03/17/2017 | NWC/Ext | SLT | | | | |
| 03/03/2017 | NWC/Ext | ---- | ---- | | | |
| 02/09/2017 | NWC/Ext | ---- | ---- | | | |
| 01/12/2017 | NWC/Ext | | | | 24g | 26g |

FIG. 53B1

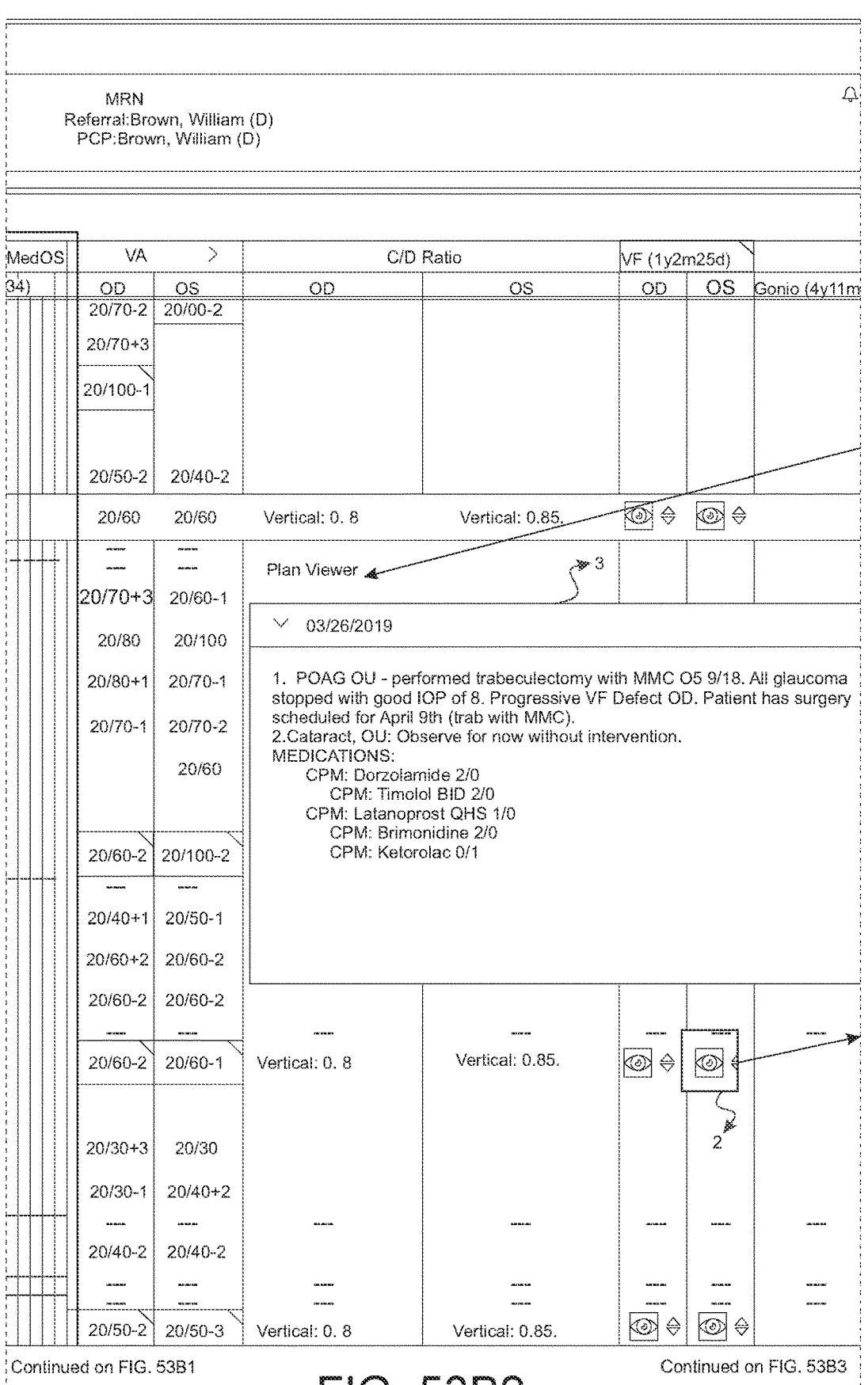

FIG. 53B2

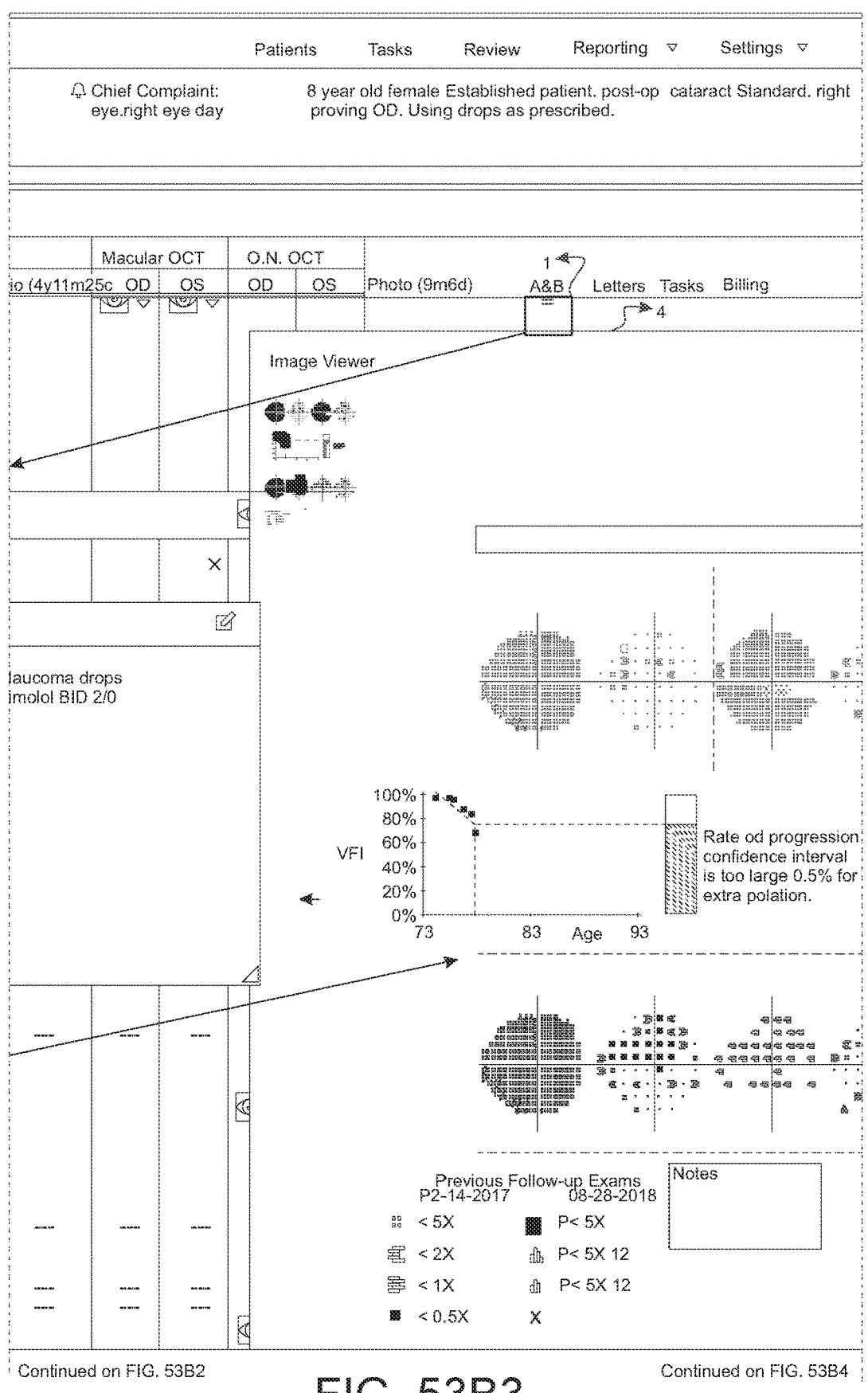
FIG. 53B3

∇ ard. right

Comment

FIG. 53B4

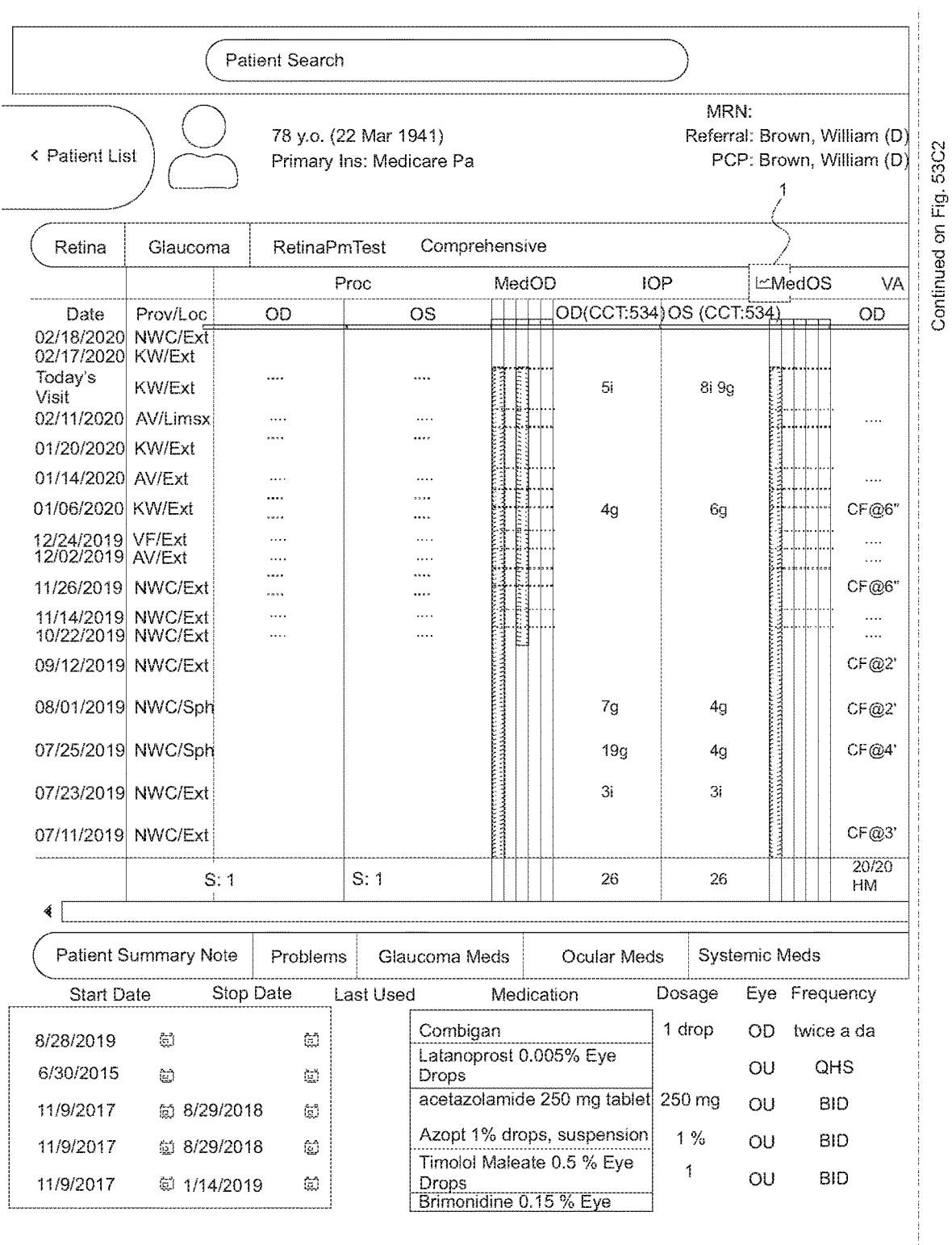
FIG. 53C1

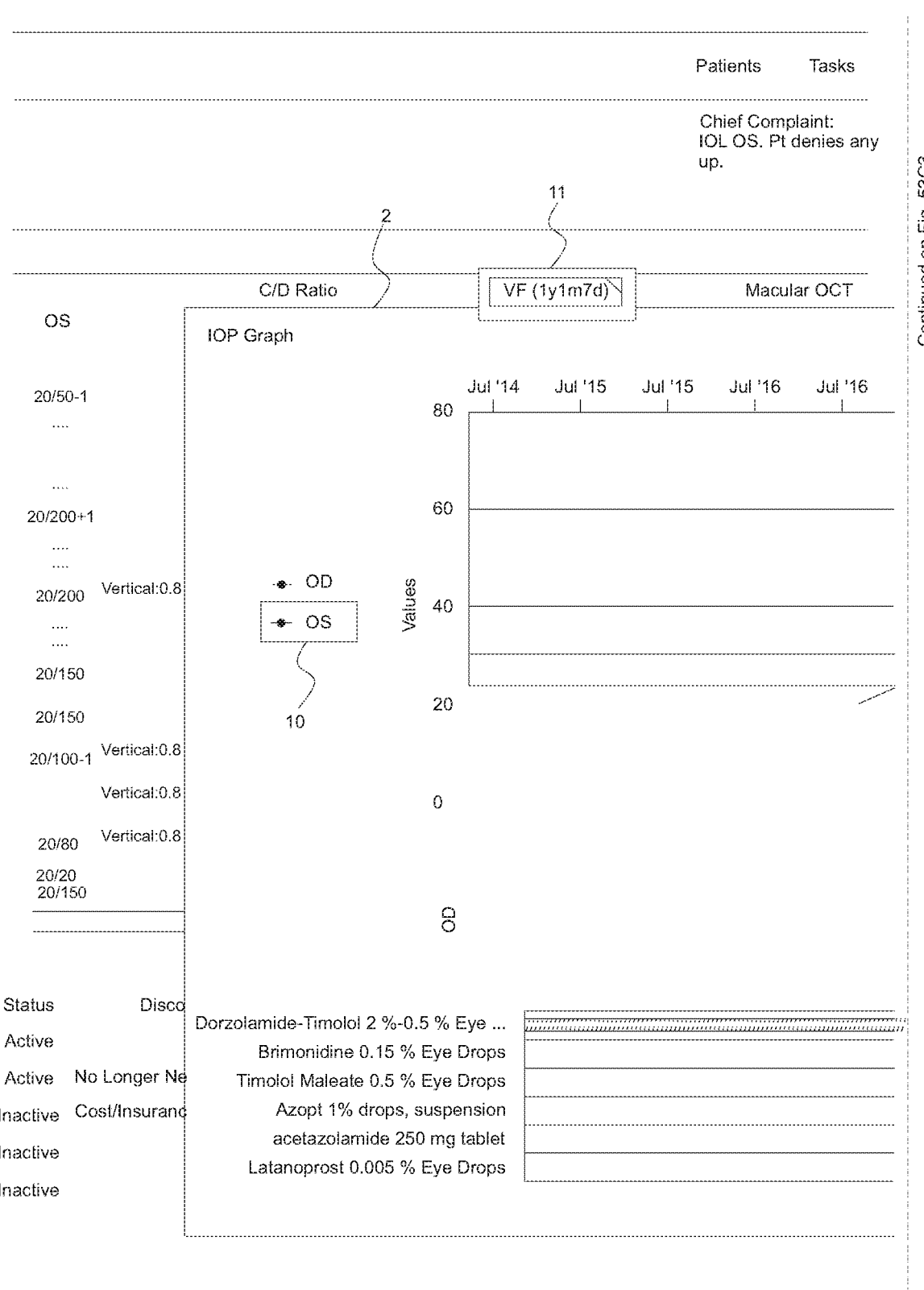
FIG. 53C2

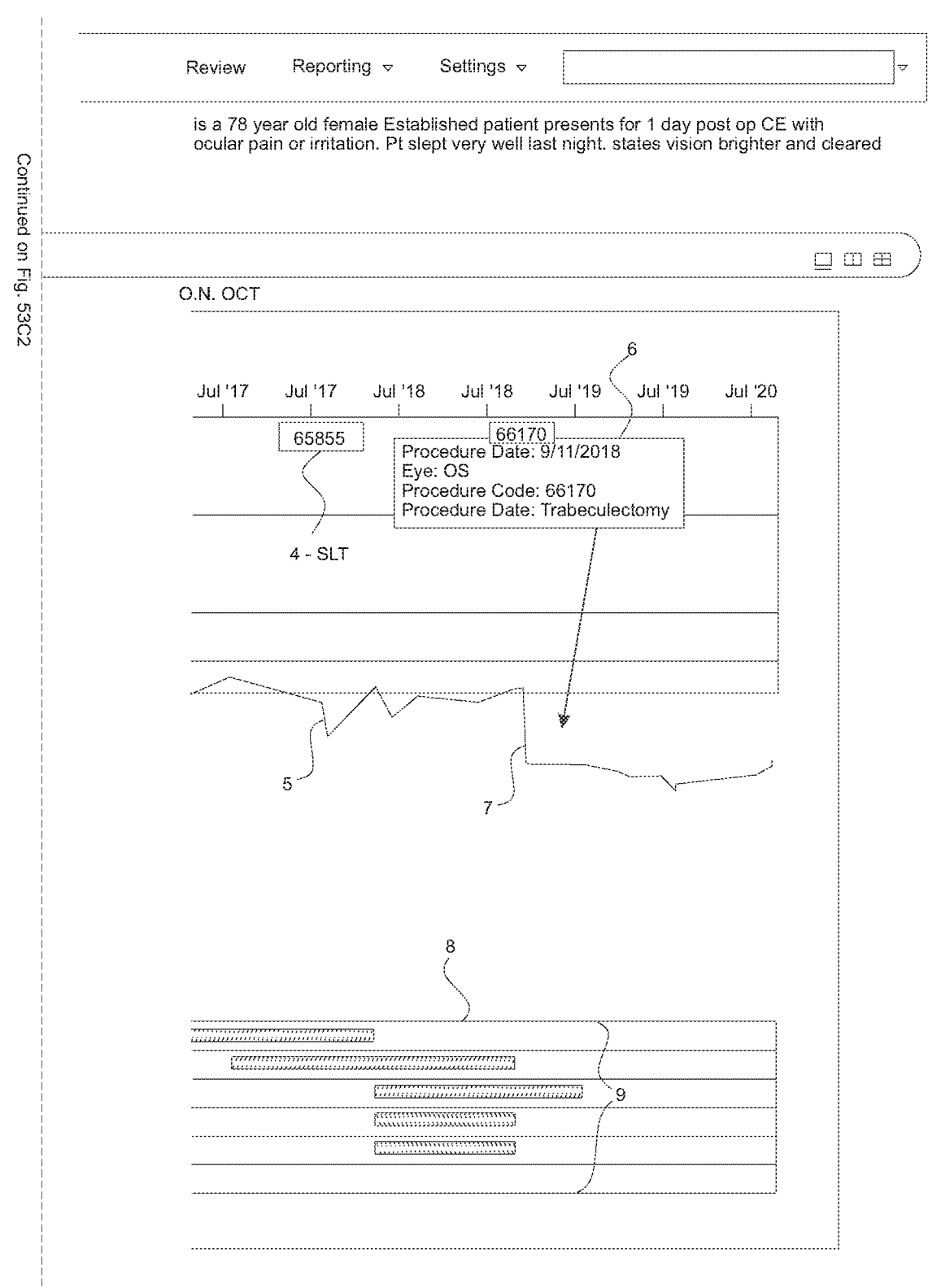
FIG. 53C3

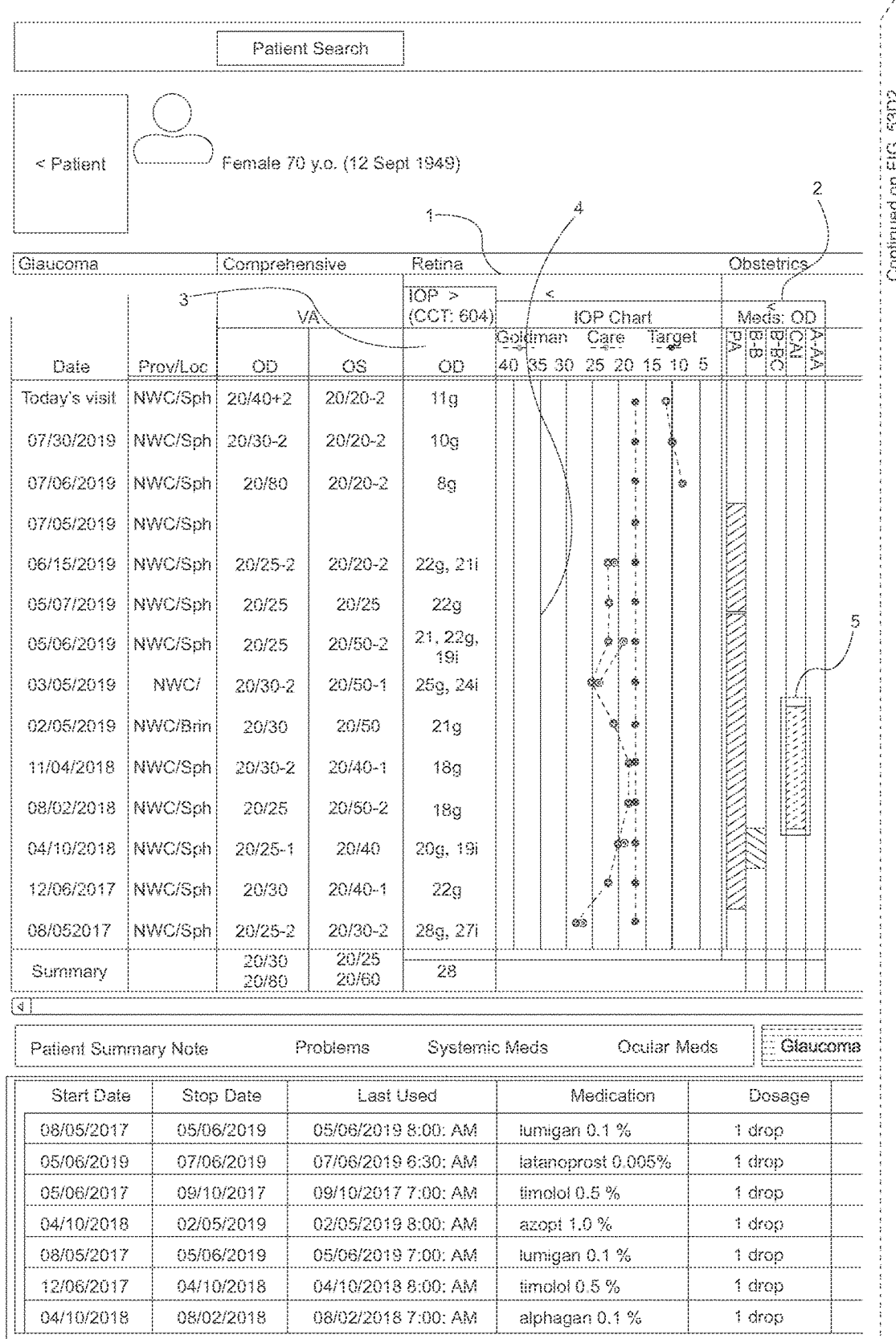
FIG. 53D1

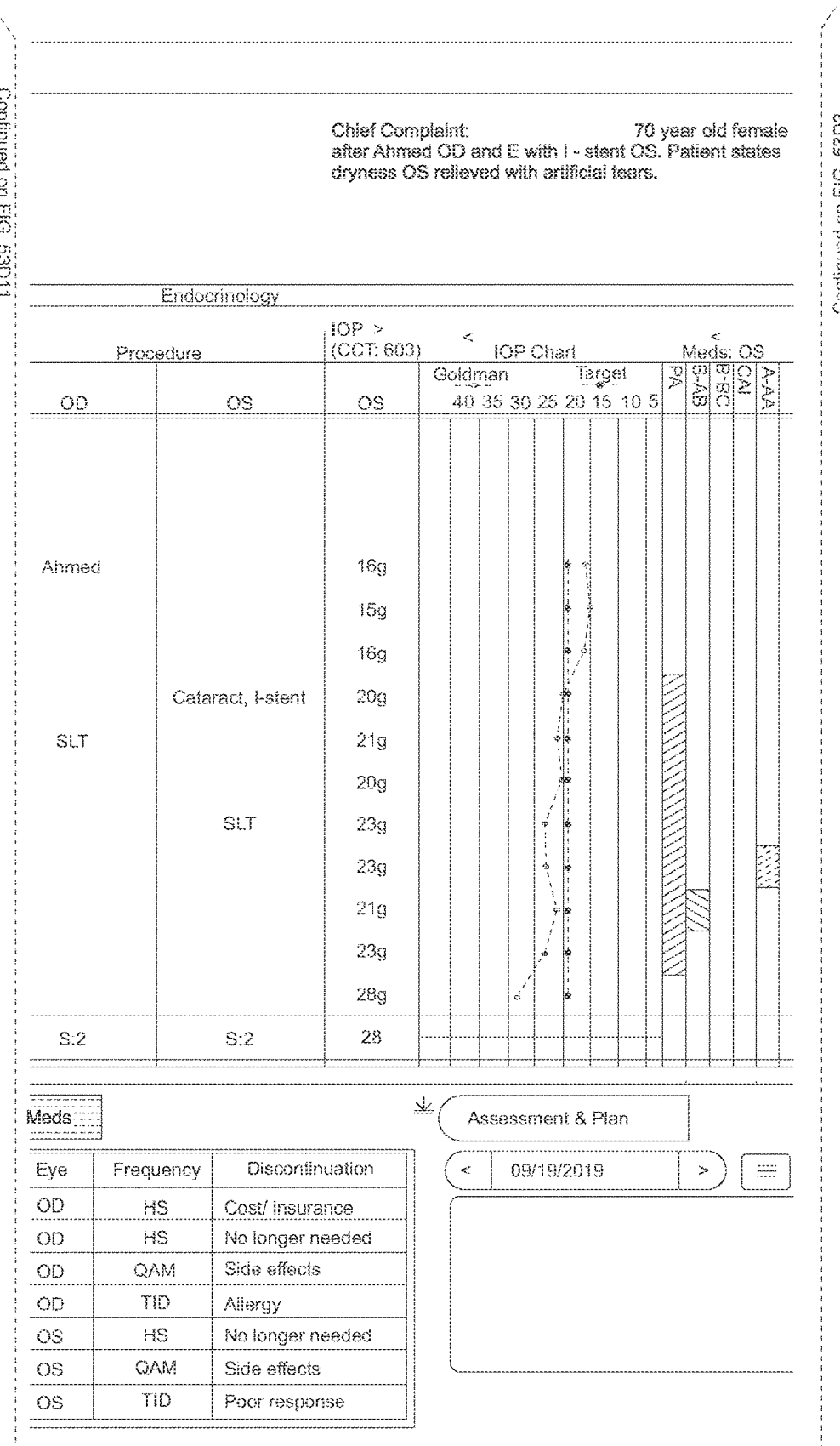
FIG. 53D2 patient. F/U for POAG. Patient on no meds
very happy with vision but gets occasional

| C/D Ratio | | VF (127) | | O.N. OCT | | Photo (23) | Gonio (246) | A&P | Comment |
|---|---|---|---|---|---|---|---|---|---|
| OD | OS | OD | OS | OD | OS | | | | |
| | | | | | | | | ≡ | + Add comment |
| | | | | | | | | ≡ | + Add comment |
| | | | | | | | | ≡ | + Add comment |
| | | | | | | | | ≡ | + Add comment |
| | | | | | | ⊙ | ⊙ | ≡ | + Add comment |
| | | | | | | | | ≡ | + Add comment |
| Vertical: 0.85 | Vertical: 0.65 | ⊙ | ⊙ | ⊙ | ⊙ | | | ≡ | + Add comment |
| | | | | | | | | ≡ | + Add comment |
| | | | | | | | | ≡ | + Add comment |
| | | ⊙ | ⊙ | ⊙ | ⊙ | | | ≡ | + Add comment |
| Vertical: 0.80 | Vertical: 0.65 | | | | | | | ≡ | + Add comment |
| | | ⊙ | ⊙ | | | | | ≡ | + Add comment |
| | | | | | | ⊙ | | ≡ | + Add comment |
| Vertical: 0.80 | Vertical: 0.65 | ⊙ | ⊙ | ⊙ | ⊙ | | ⊙ | ≡ | + Add comment |
| 3 | 3 | 4 | 4 | 3 | 3 | 2 | 2 | | ○ ◉ ○ □ l |

FIG. 53D3

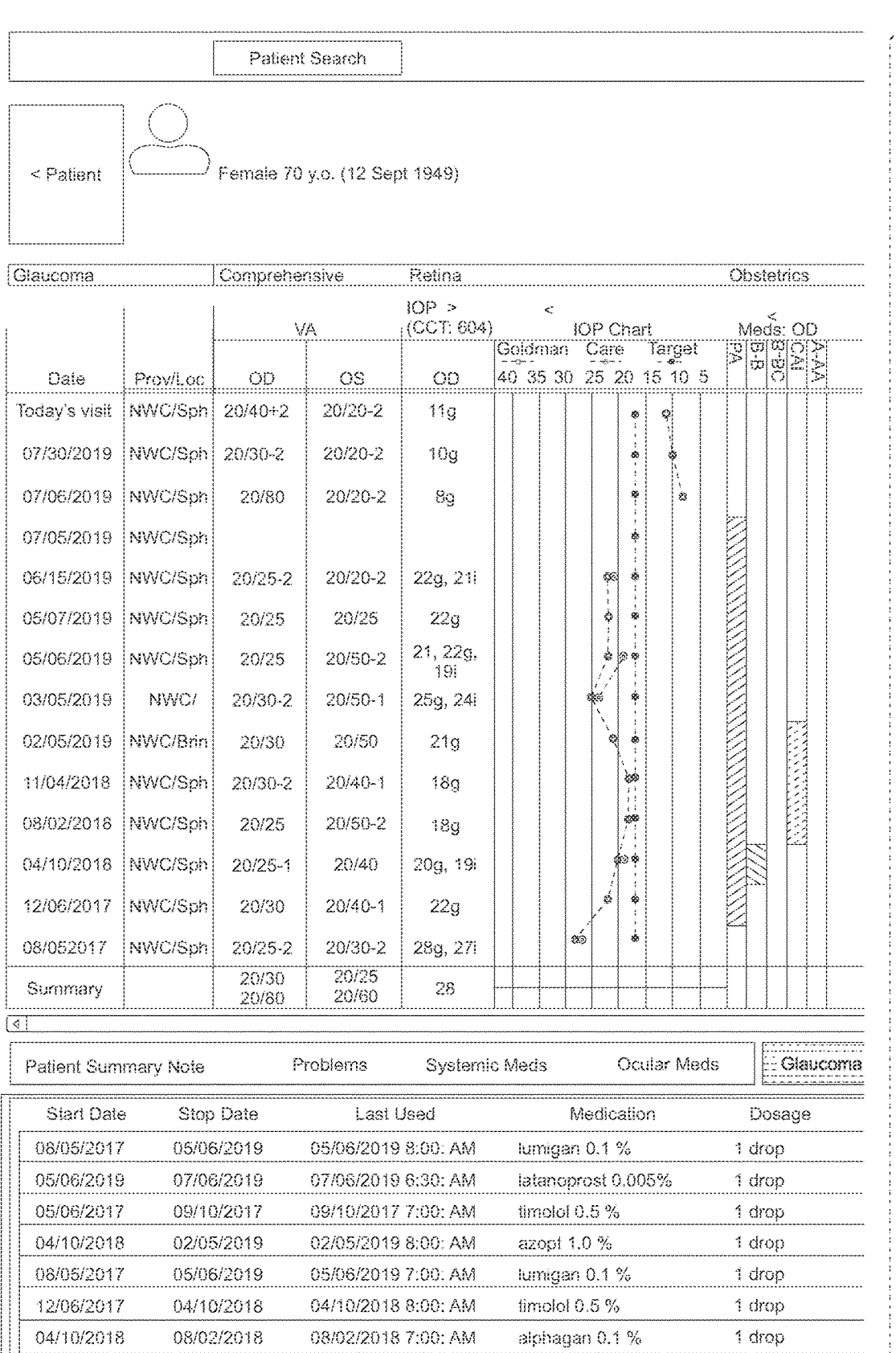

Patient Search

< Patient    Female 70 y.o. (12 Sept 1949)

Glaucoma          Comprehensive          Retina                    Obstetrics

| Date | Prov/Loc | VA OD | VA OS | IOP > (CCT: 604) OD | Goldman Care Target 40 35 30 25 20 15 10 5 | Meds: OD |
|---|---|---|---|---|---|---|
| Today's visit | NWC/Sph | 20/40+2 | 20/20-2 | 11g | | |
| 07/30/2019 | NWC/Sph | 20/30-2 | 20/20-2 | 10g | | |
| 07/06/2019 | NWC/Sph | 20/80 | 20/20-2 | 8g | | |
| 07/05/2019 | NWC/Sph | | | | | |
| 06/15/2019 | NWC/Sph | 20/25-2 | 20/20-2 | 22g, 21i | | |
| 05/07/2019 | NWC/Sph | 20/25 | 20/25 | 22g | | |
| 05/06/2019 | NWC/Sph | 20/25 | 20/50-2 | 21, 22g, 19i | | |
| 03/05/2019 | NWC/ | 20/30-2 | 20/50-1 | 25g, 24i | | |
| 02/05/2019 | NWC/Brin | 20/30 | 20/50 | 21g | | |
| 11/04/2018 | NWC/Sph | 20/30-2 | 20/40-1 | 18g | | |
| 08/02/2018 | NWC/Sph | 20/25 | 20/50-2 | 18g | | |
| 04/10/2018 | NWC/Sph | 20/25-1 | 20/40 | 20g, 19i | | |
| 12/06/2017 | NWC/Sph | 20/30 | 20/40-1 | 22g | | |
| 08/05/2017 | NWC/Sph | 20/25-2 | 20/30-2 | 28g, 27i | | |
| Summary | | 20/30 20/80 | 20/25 20/60 | 28 | | |

Patient Summary Note     Problems     Systemic Meds     Ocular Meds     Glaucoma

| Start Date | Stop Date | Last Used | Medication | Dosage |
|---|---|---|---|---|
| 08/05/2017 | 05/06/2019 | 05/06/2019 8:00 AM | lumigan 0.1 % | 1 drop |
| 05/06/2019 | 07/06/2019 | 07/06/2019 6:30 AM | latanoprost 0.005% | 1 drop |
| 05/06/2017 | 09/10/2017 | 09/10/2017 7:00 AM | timolol 0.5 % | 1 drop |
| 04/10/2018 | 02/05/2019 | 02/05/2019 8:00 AM | azopt 1.0 % | 1 drop |
| 08/05/2017 | 05/06/2019 | 05/06/2019 7:00 AM | lumigan 0.1 % | 1 drop |
| 12/06/2017 | 04/10/2018 | 04/10/2018 8:00 AM | timolol 0.5 % | 1 drop |
| 04/10/2018 | 08/02/2018 | 08/02/2018 7:00 AM | alphagan 0.1 % | 1 drop |

FIG. 53E1

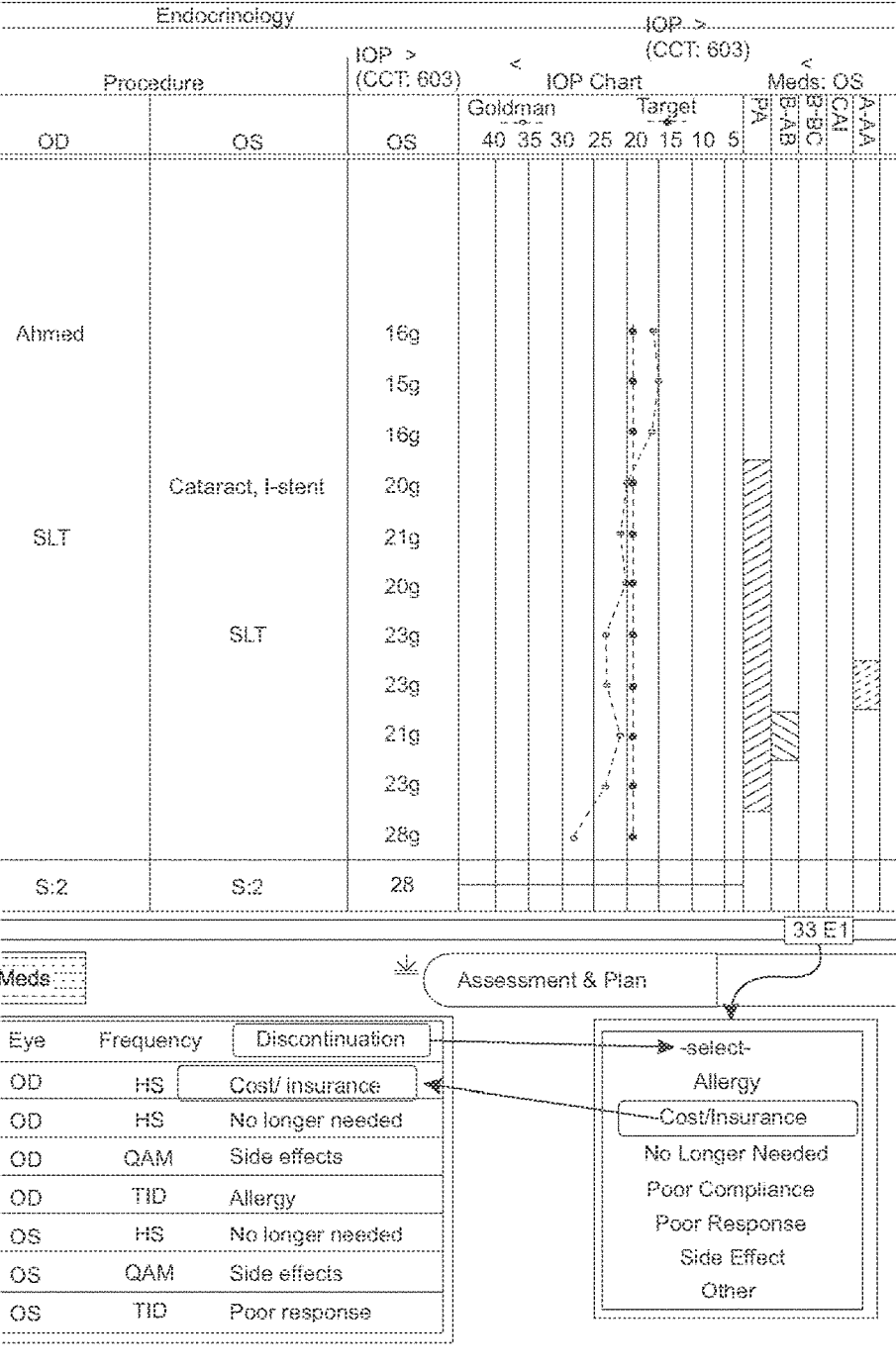
Chief Complaint:                    70 year old female
after Ahmed OD and E with I - stent OS. Patient states
dryness OS relieved with artificial tears.
FIG. 53E2 patient. F/U for POAG. Patient on no meds
very happy with vision but gets occasional

| C/D Ratio | | VF (127) | | O.N. OCT | | Photo (23) | Gonio (246) | A&P | Comment |
|---|---|---|---|---|---|---|---|---|---|
| OD | OS | OD | OS | OD | OS | | | | |
| | | | | | | | | ≡ | + Add comment |
| | | | | | | | | ≡ | + Add comment |
| | | | | | | | | ≡ | + Add comment |
| | | | | | | | | ≡ | + Add comment |
| | | | | | | | 👁⇕ | 👁⇕ | ≡ | + Add comment |
| | | | | | | | | ≡ | + Add comment |
| Vertical: 0.85 | Vertical: 0.65 | 👁⇕ | 👁⇕ | 👁⇕ | 👁⇕ | | | ≡ | + Add comment |
| | | | | | | | | ≡ | + Add comment |
| | | | | | | | | ≡ | + Add comment |
| | | 👁⇕ | 👁⇕ | 👁⇕ | 👁⇕ | | | ≡ | + Add comment |
| Vertical: 0.80 | Vertical: 0.65 | | | | | | | ≡ | + Add comment |
| | | 👁⇕ | 👁⇕ | | | | | ≡ | + Add comment |
| | | | | | | 👁⇕ | | ≡ | + Add comment |
| Vertical: 0.80 | Vertical: 0.65 | 👁⇕ | 👁⇕ | 👁⇕ | 👁⇕ | | 👁⇕ | ≡ | + Add comment |
| 3 | 3 | 4 | 4 | 3 | 3 | 2 | 2 | | ○⦿○□▯ |

FIG. 53E3

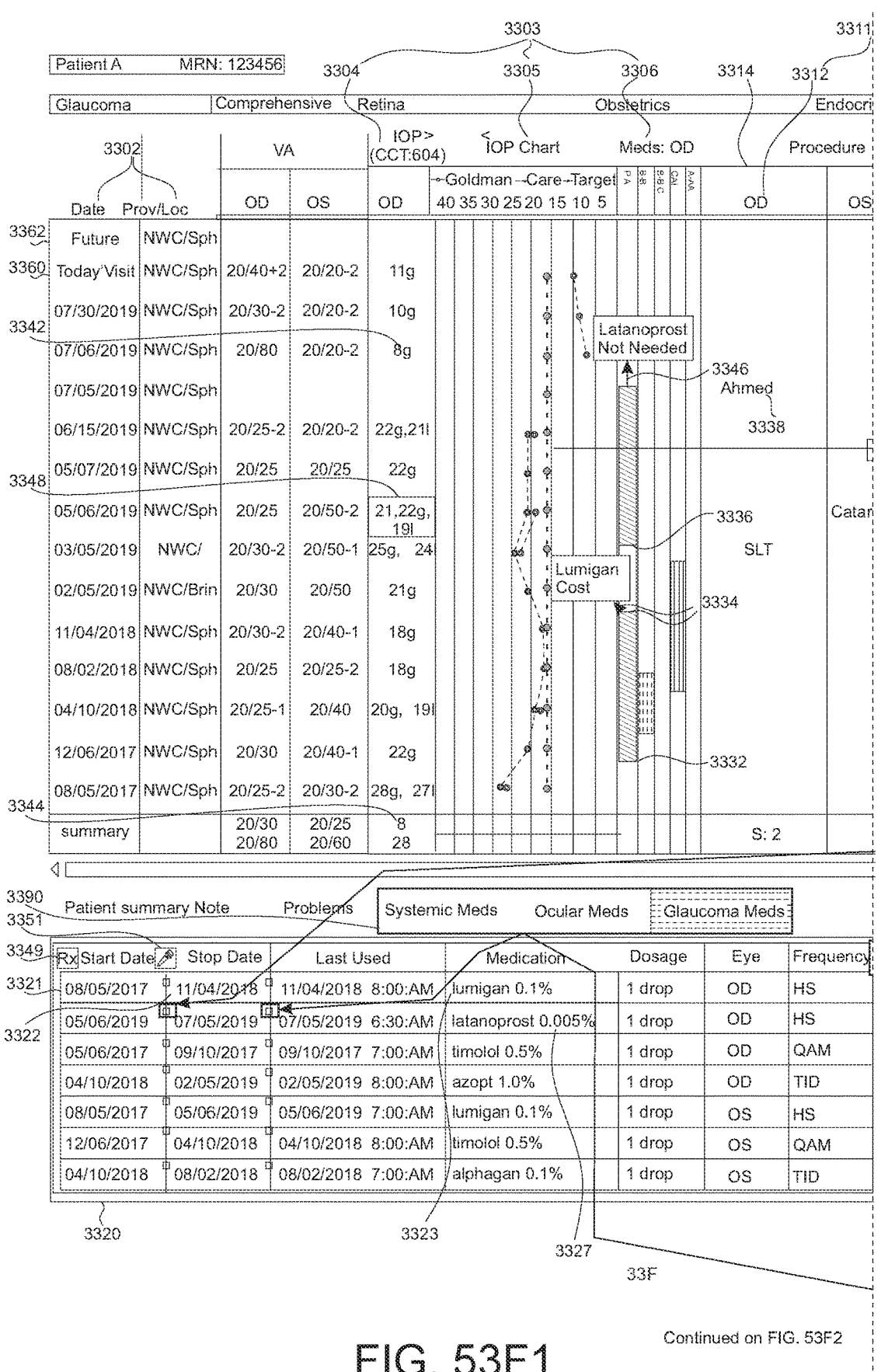
FIG. 53F1

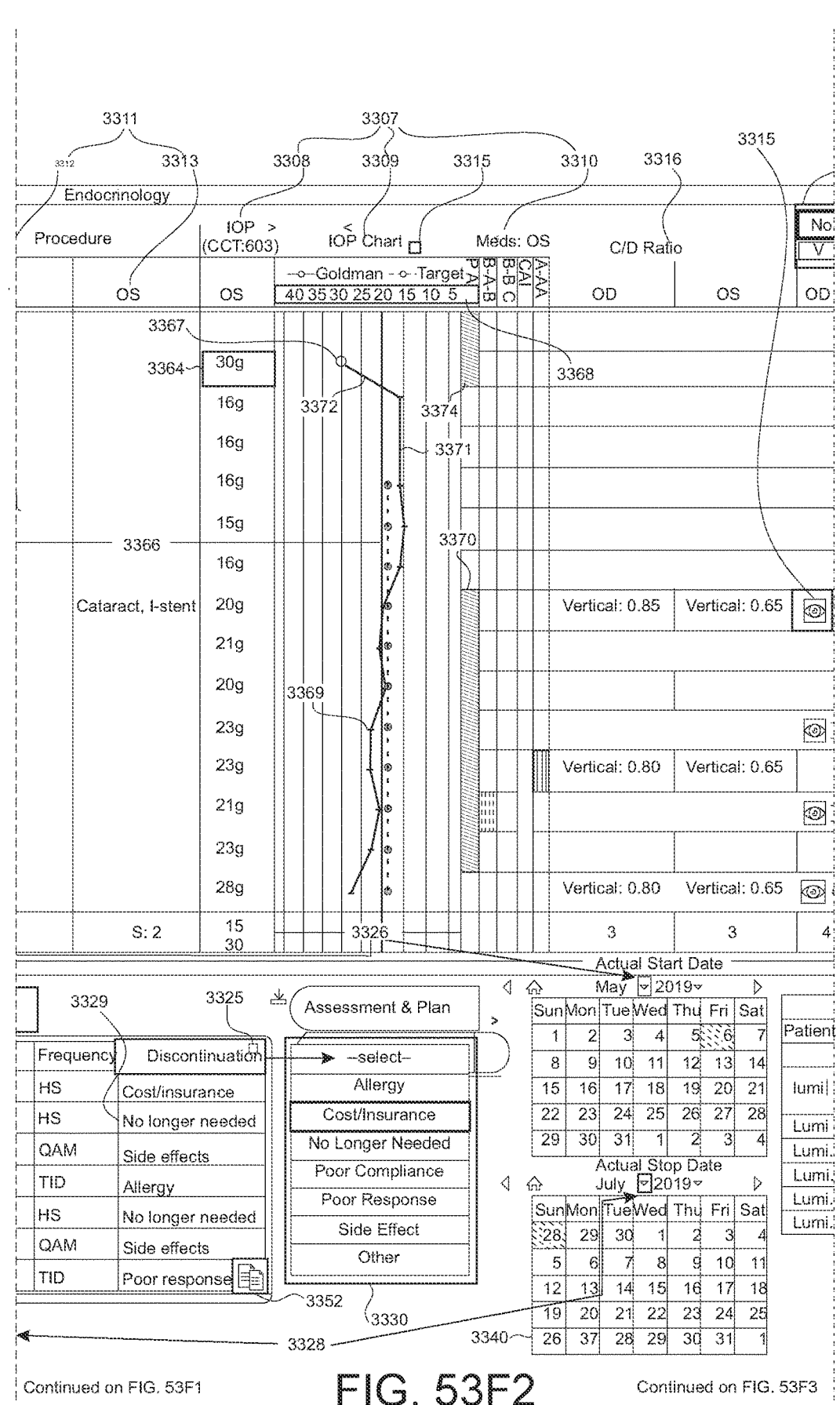
FIG. 53F2

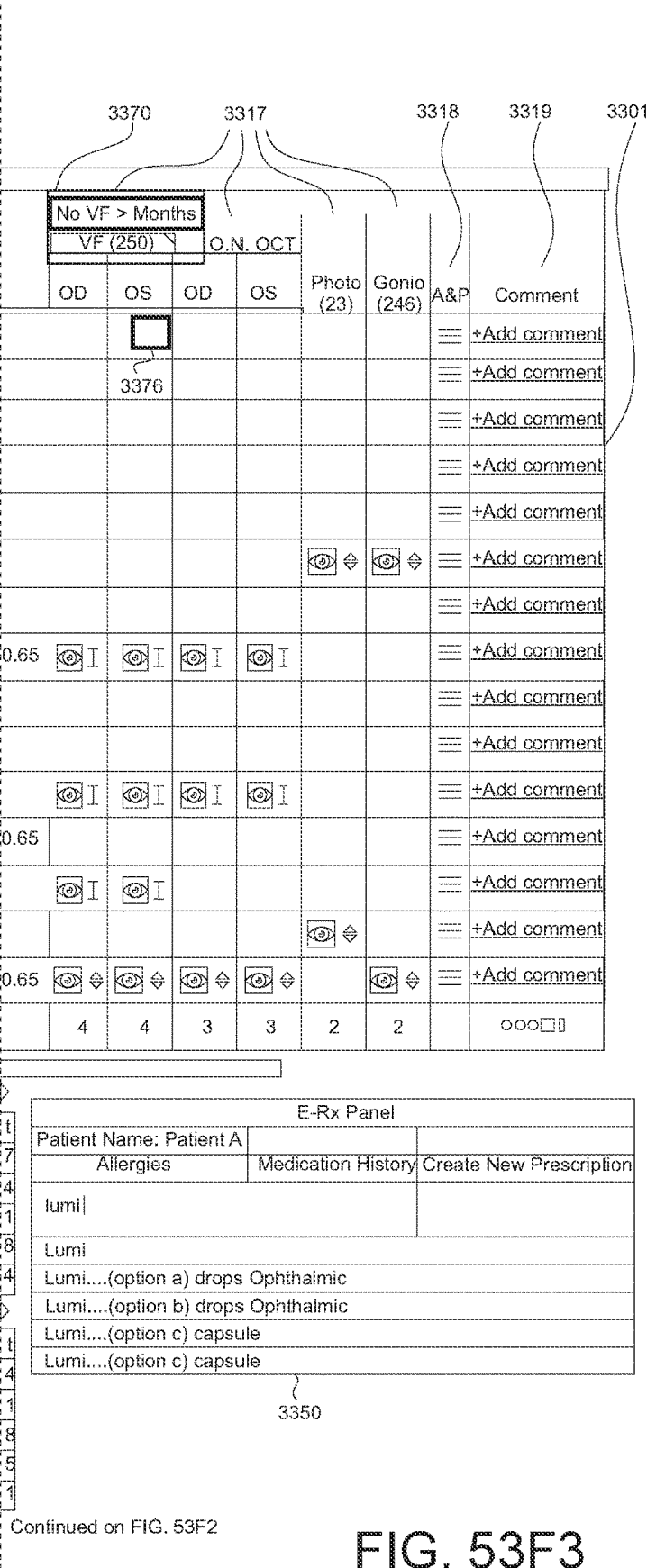
FIG. 53F3

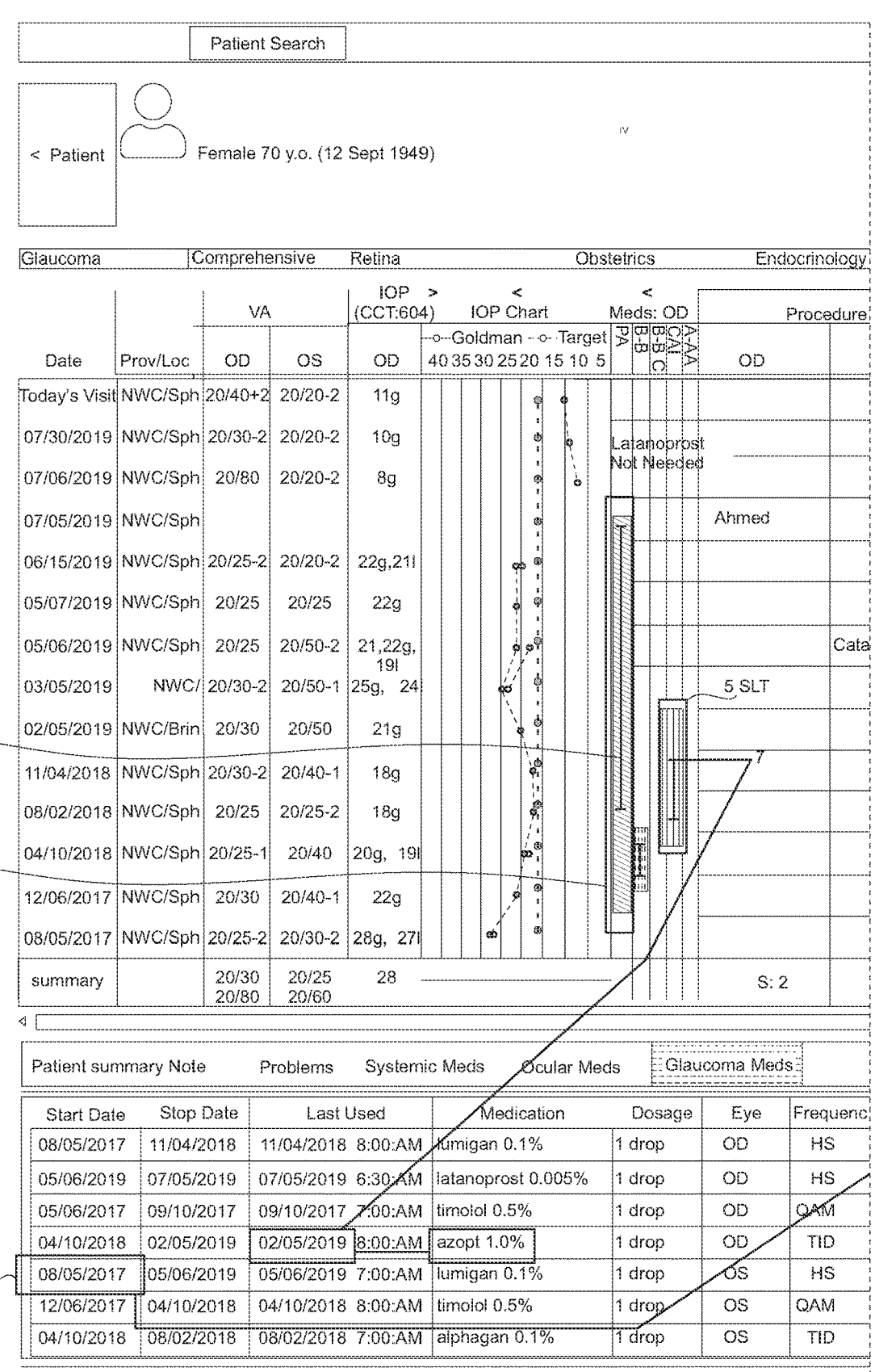
FIG. 53G1

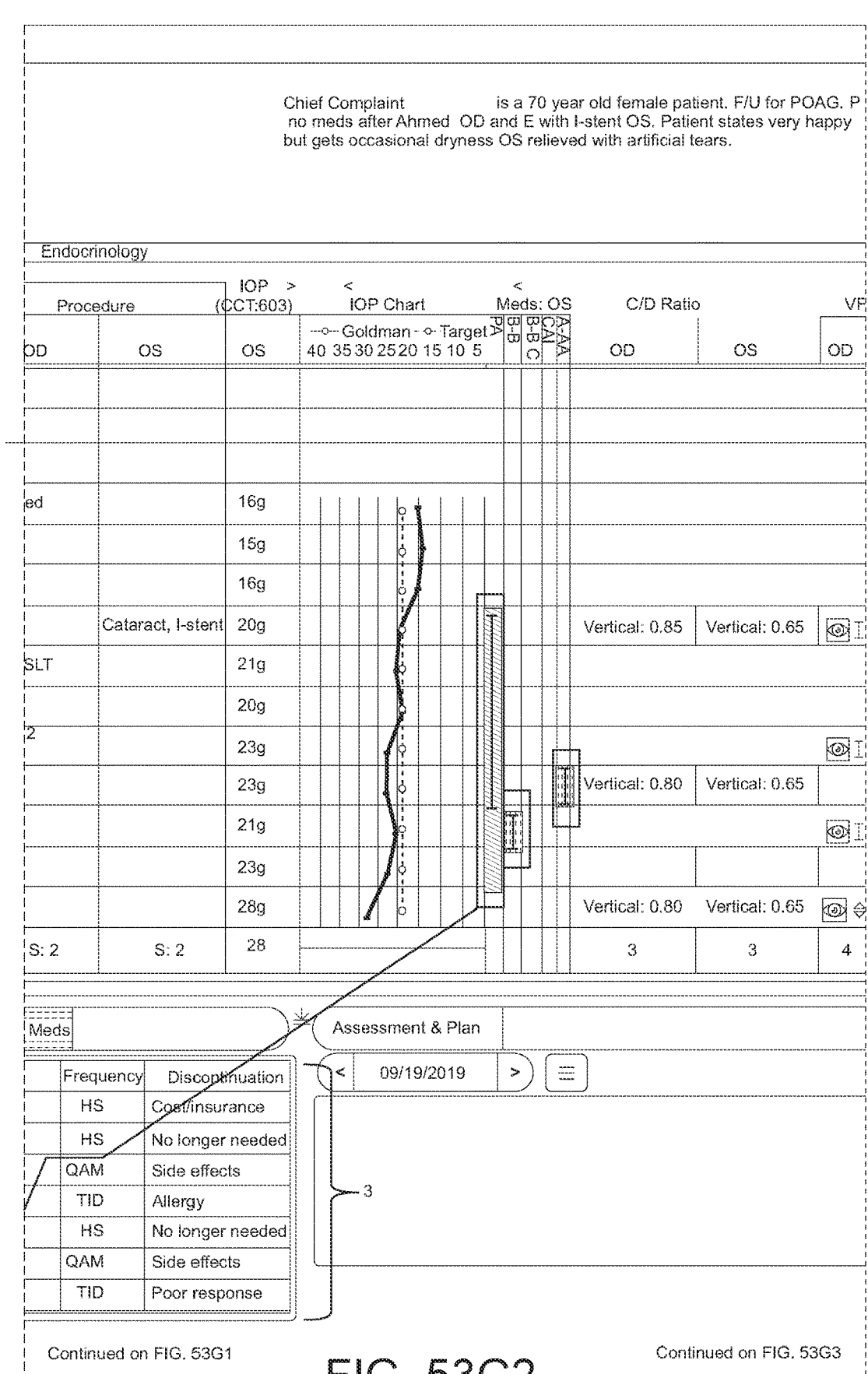
Chief Complaint          is a 70 year old female patient. F/U for POAG. P
no meds after Ahmed  OD and E with I-stent OS. Patient states very happy
but gets occasional dryness OS relieved with artificial tears.
FIG. 53G2

U for POAG. Patient on
s very happy with vision

| | VF (250) O.N. OCT | | | | | | | |
| | OD | OS | OD | OS | Photo (23) | Gonio (246) | A&P | Comment |
|---|---|---|---|---|---|---|---|---|
| | | | | | | | ≡ | +Add comment |
| | | | | | | | ≡ | +Add comment |
| | | | | | | | ≡ | +Add comment |
| | | | | | | | ≡ | +Add comment |
| | | | | | ◉ ◈ | ◉ ◈ | ≡ | +Add comment |
| | | | | | | | ≡ | +Add comment |
| : 0.65 | ◉ I | ◉ I | ◉ I | ◉ I | | | ≡ | +Add comment |
| | | | | | | | ≡ | +Add comment |
| | | | | | | | ≡ | +Add comment |
| | ◉ I | ◉ I | ◉ I | ◉ I | | | ≡ | +Add comment |
| : 0.65 | | | | | | | ≡ | +Add comment |
| | ◉ I | ◉ I | | | | | ≡ | +Add comment |
| | | | | | ◉ ◈ | | ≡ | +Add comment |
| : 0.65 | ◉ ◈ | ◉ ◈ | ◉ ◈ | ◉ ◈ | | ◉ ◈ | ≡ | +Add comment |
| 3 | 4 | 4 | 3 | 3 | 2 | 2 | | ○○○□▯ |

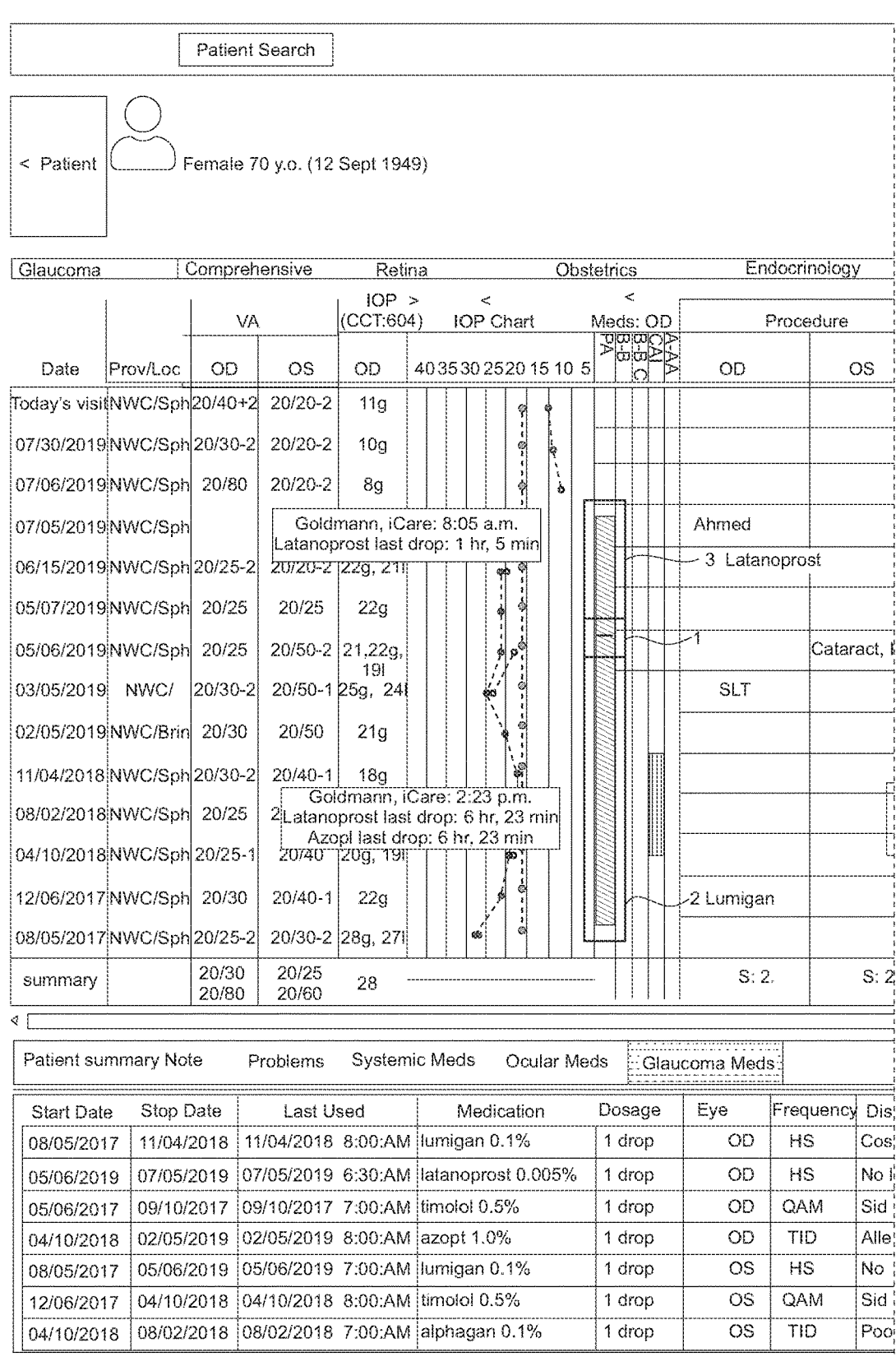
FIG. 53H1

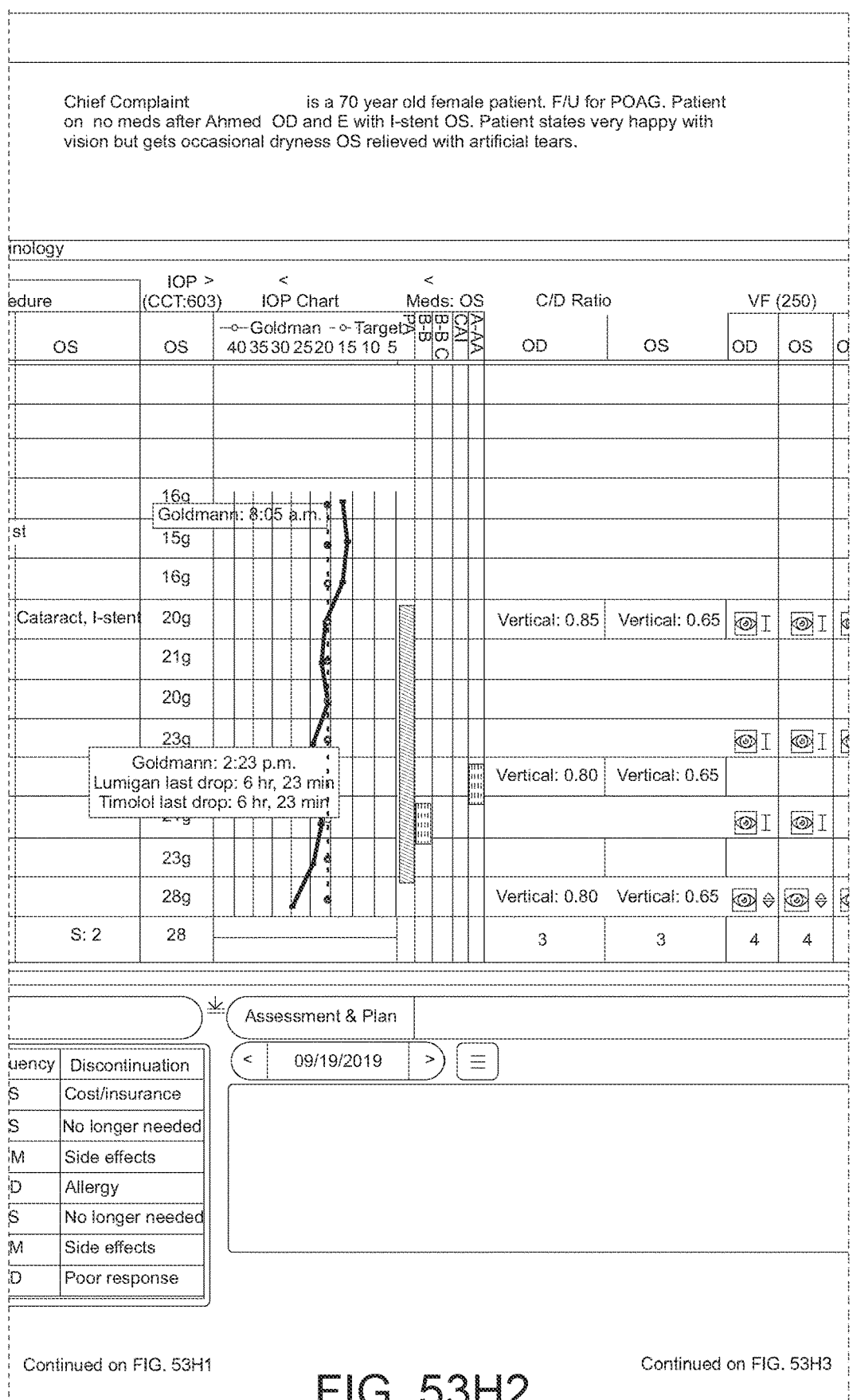
Chief Complaint        is a 70 year old female patient. F/U for POAG. Patient on no meds after Ahmed OD and E with I-stent OS. Patient states very happy with vision but gets occasional dryness OS relieved with artificial tears.
FIG. 53H2

| F (250) O.N. OCT | | | | Photo (23) | Gonio (246) | A&P | Comment |
|---|---|---|---|---|---|---|---|
| | OS | OD | OS | | | | |
| | | | | | | ≡ | +Add comment |
| | | | | | | ≡ | +Add comment |
| | | | | | | ≡ | +Add comment |
| | | | | | | ≡ | +Add comment |
| | | | | 👁 ⇕ | 👁 ⇕ | ≡ | +Add comment |
| | | | | | | ≡ | +Add comment |
| I | 👁 I | 👁 I | 👁 I | | | ≡ | +Add comment |
| | | | | | | ≡ | +Add comment |
| | | | | | | ≡ | +Add comment |
| I | 👁 I | 👁 I | 👁 I | | | ≡ | +Add comment |
| | | | | | | ≡ | +Add comment |
| I | 👁 I | | | | | ≡ | +Add comment |
| | | | | 👁 ⇕ | | ≡ | +Add comment |
| ⇕ | 👁 ⇕ | 👁 ⇕ | 👁 ⇕ | | 👁 ⇕ | ≡ | +Add comment |
| | 4 | 3 | 3 | 2 | 2 | | ○○○□▯ |

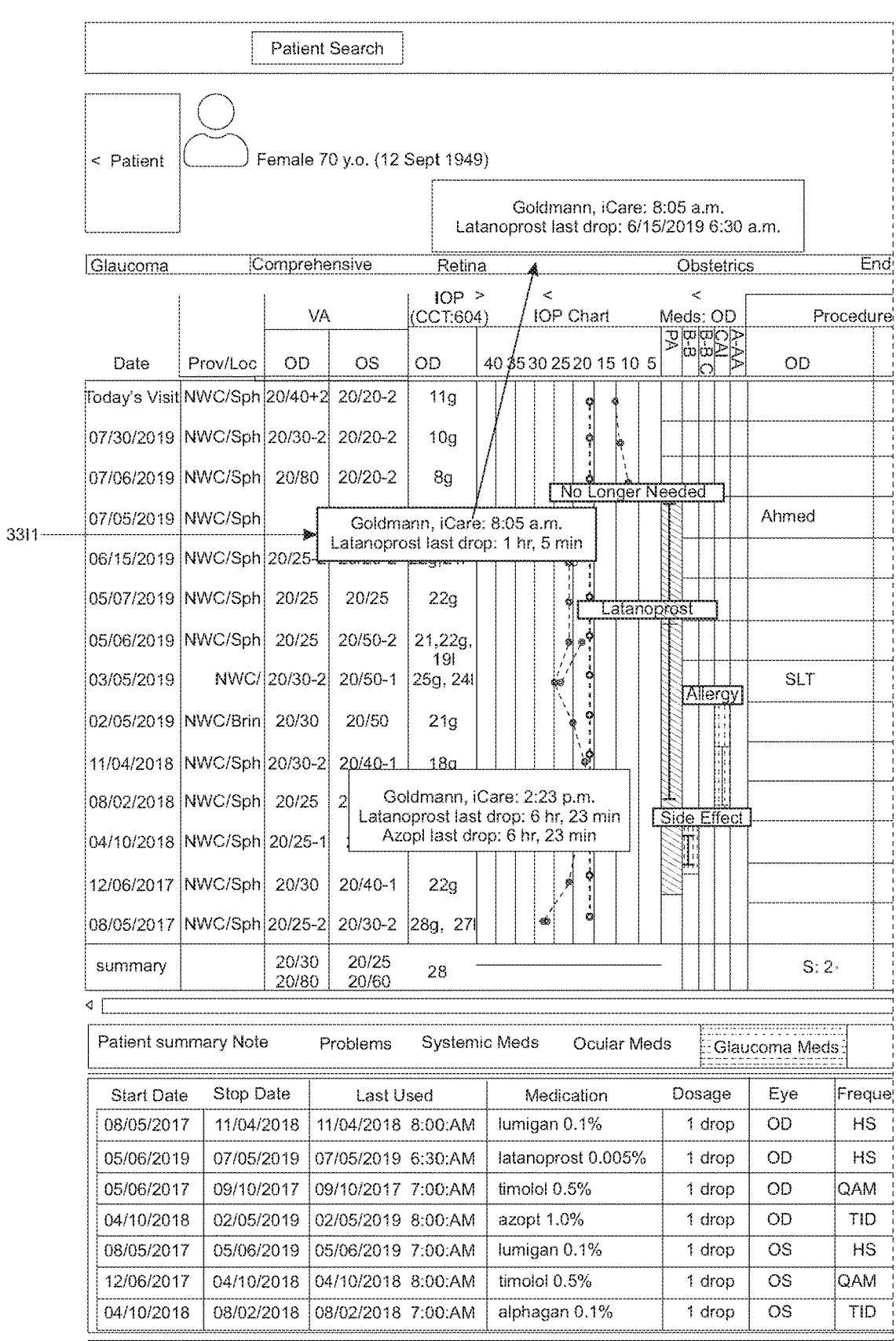
FIG. 53I1

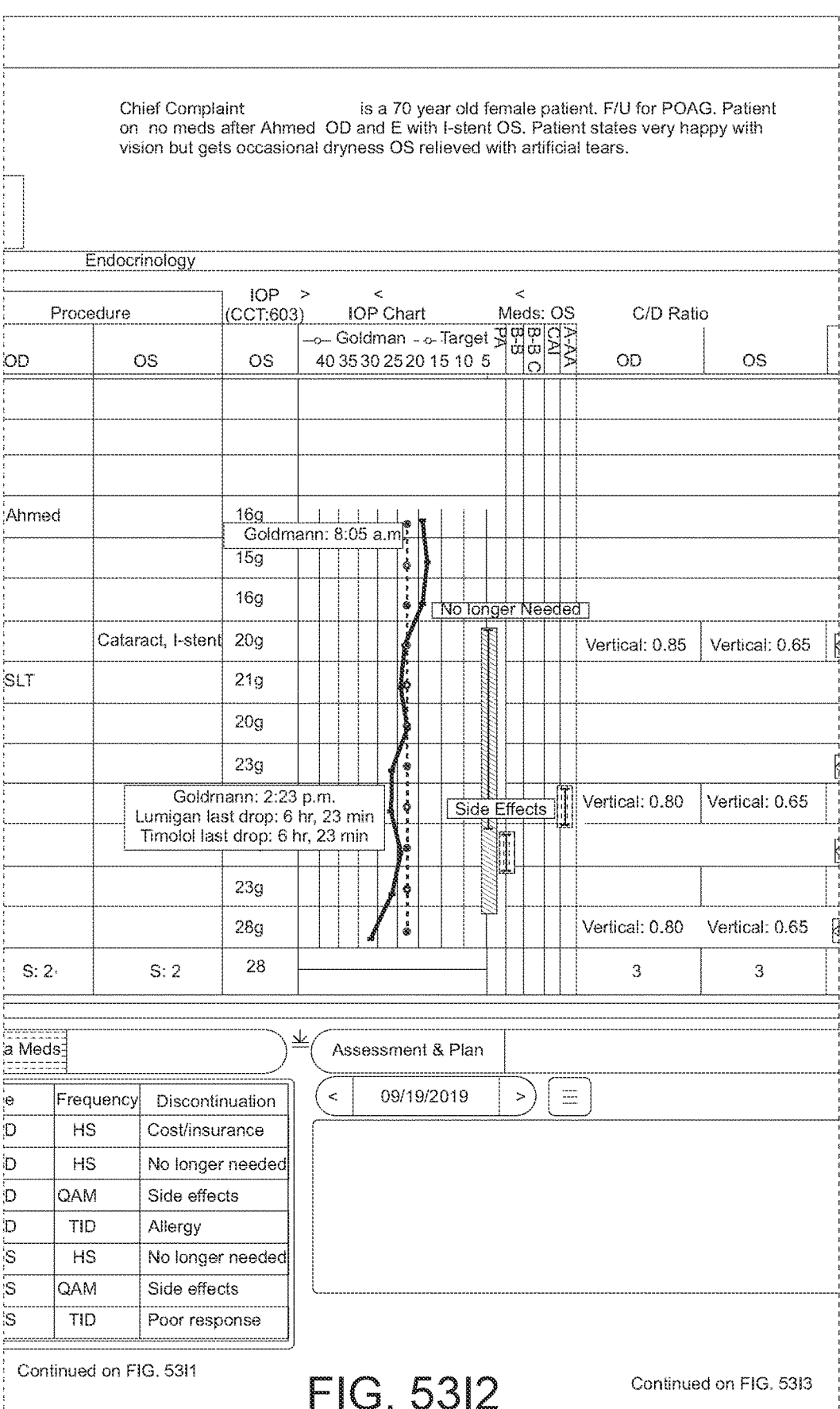

Chief Complaint        is a 70 year old female patient. F/U for POAG. Patient on no meds after Ahmed OD and E with I-stent OS. Patient states very happy with vision but gets occasional dryness OS relieved with artificial tears.

Endocrinology

| Procedure | | IOP (CCT:603) | IOP Chart | Meds: OS | C/D Ratio | |
|---|---|---|---|---|---|---|
| OD | OS | OS | —o— Goldman  –o– Target  40 35 30 25 20 15 10 5 | PA B-B B-B CAI A-A | OD | OS |
| Ahmed | | 16g | Goldmann: 8:05 a.m | | | |
| | | 15g | | | | |
| | | 16g | No longer Needed | | | |
| | Cataract, I-stent | 20g | | | Vertical: 0.85 | Vertical: 0.65 |
| SLT | | 21g | | | | |
| | | 20g | | | | |
| | | 23g | | | | |
| | | | Goldmann: 2:23 p.m. Lumigan last drop: 6 hr, 23 min Timolol last drop: 6 hr, 23 min | Side Effects | Vertical: 0.80 | Vertical: 0.65 |
| | | 23g | | | | |
| | | 28g | | | Vertical: 0.80 | Vertical: 0.65 |
| S: 2· | S: 2 | 28 | | | 3 | 3 | a Meds

Assessment & Plan

| e | Frequency | Discontinuation | < | 09/19/2019 | > | ≡ |
|---|---|---|---|---|---|---|
| D | HS | Cost/insurance | | | | |
| D | HS | No longer needed | | | | |
| D | QAM | Side effects | | | | |
| D | TID | Allergy | | | | |
| S | HS | No longer needed | | | | |
| S | QAM | Side effects | | | | |
| S | TID | Poor response | | | | |

FIG. 53I2

| | VF (127) | O.N. OCT | | | Photo (23) | Gonio (246) | A&P | Comment |
|---|---|---|---|---|---|---|---|---|
| OS | OD | OS | OD | OS | | | | |
| | | | | | | | ≡ | +Add comment |
| | | | | | | | ≡ | +Add comment |
| | | | | | | | ≡ | +Add comment |
| | | | | | | | ≡ | +Add comment |
| | | | | | 👁 ⇕ | 👁 ⇕ | ≡ | +Add comment |
| | | | | | | | ≡ | +Add comment |
| rtical: 0.65 | 👁 I | 👁 I | 👁 I | 👁 I | | | ≡ | +Add comment |
| | | | | | | | ≡ | +Add comment |
| | | | | | | | ≡ | +Add comment |
| | 👁 I | 👁 I | 👁 I | 👁 I | | | ≡ | +Add comment |
| tical: 0.65 | | | | | | | ≡ | +Add comment |
| | 👁 I | 👁 I | | | | | ≡ | +Add comment |
| | | | | | 👁 ⇕ | | ≡ | +Add comment |
| tical: 0.65 | 👁 ⇕ | 👁 ⇕ | 👁 ⇕ | 👁 ⇕ | | 👁 ⇕ | ≡ | +Add comment |
| 3 | 4 | 4 | 3 | 3 | 2 | 2 | | ooo□🛈 |

FIG. 53I3

| Visit Date | Prov/Loc | Next visit | Referring |
|---|---|---|---|
| 3502 | 3504 | 3506 | 3508 |
| 08/07/2020 | DM/Sph | Next visit: 12/09/2020 NWC/Sph | Nagaraj,Ravi Joseph |
| 08/07/2020 | DM/Sph | Next visit: 12/09/2020 NWC/Sph | Nagaraj,Ravi Joseph |
| 08/07/2020 | DM/Sph | Next visit: 12/09/2020 NWC/Sph | Nagaraj,Ravi Joseph |
| 08/07/2020 | DM/Sph | Next visit: 12/09/2020 NWC/Sph | Nagaraj,Ravi Joseph |
|  |  |  |  |
| 08/07/2020 | DM/Sph | Next visit: 09/04/2020 NWC/Sph | Coco, Lisa |
| 08/07/2020 | DM/Sph | Next visit: 09/04/2020 NWC/Sph | Coco, Lisa |
| 08/07/2020 | DM/Sph | Next visit: 09/04/2020 NWC/Sph | Coco, Lisa |
| 08/07/2020 | DM/Sph | Next visit: 09/04/2020 NWC/Sph | Coco, Lisa |
|  |  |  |  |
| 08/06/2020 | DM/Ext | Next visit: 12/15/2020 NWC/Ext | Weber, Patrick |
| 08/06/2020 | DM/Ext | Next visit: 12/15/2020 NWC/Ext | Weber, Patrick |
| 08/06/2020 | DM/Ext | Next visit: 12/15/2020 NWC/Ext | Weber, Patrick |

FIG. 55A 3511    3510    3512      3515    3514    3516

| Diagnosis | | OD | |
|---|---|---|---|
| OD | OS | Proc | Injections |
| Age-related nuclear cataract, | Age-related nuclear cataract, | | |
| Age-related nuclear cataract, | Age-related nuclear cataract, | | |
| Age-related nuclear cataract, | Age-related nuclear cataract, | | |
| Age-related nuclear cataract, | Age-related nuclear cataract, | | |
| | | F:7, S: 1 | E:33, L: 1 |
| Type 1 diabetes mellitus with | Type 1 diabetes mellitus with | | Eylea (1m12d) |
| Type 1 diabetes mellitus with | Type 1 diabetes mellitus with | | Eylea (1m12d) |
| Type 1 diabetes mellitus with | Type 1 diabetes mellitus with | | Eylea (1m12d) |
| Type 1 diabetes mellitus with | Type 1 diabetes mellitus with | | Eylea (1m12d) |
| | | P: 2, F: 2 | E:18 |
| VMT retinal edema | VMT retinal edema | Focal mac edema | |
| VMT retinal edema | VMT retinal edema | Focal mac edema | |
| VMT retinal edema | VMT retinal edema | Focal mac edema | |

3830
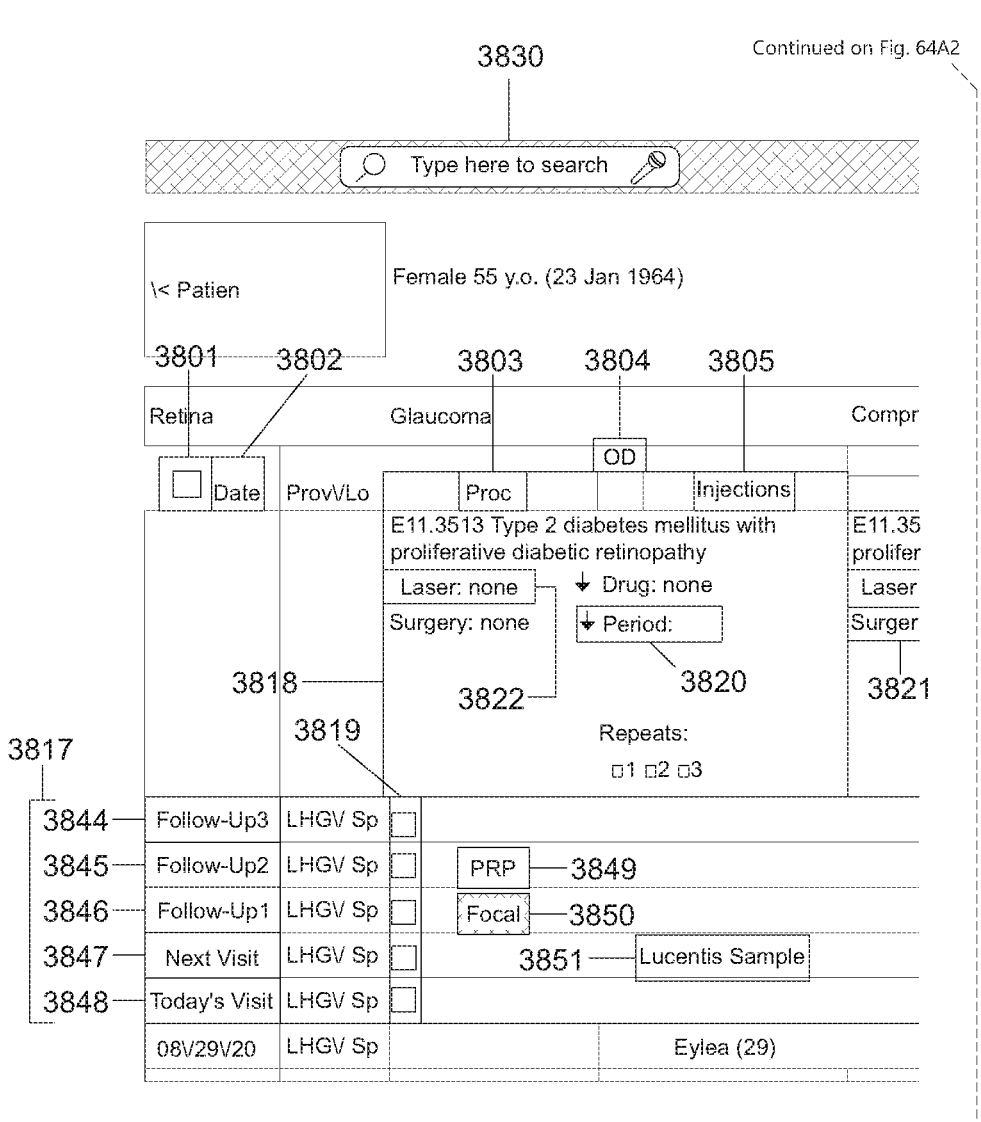
Fig. 64A1

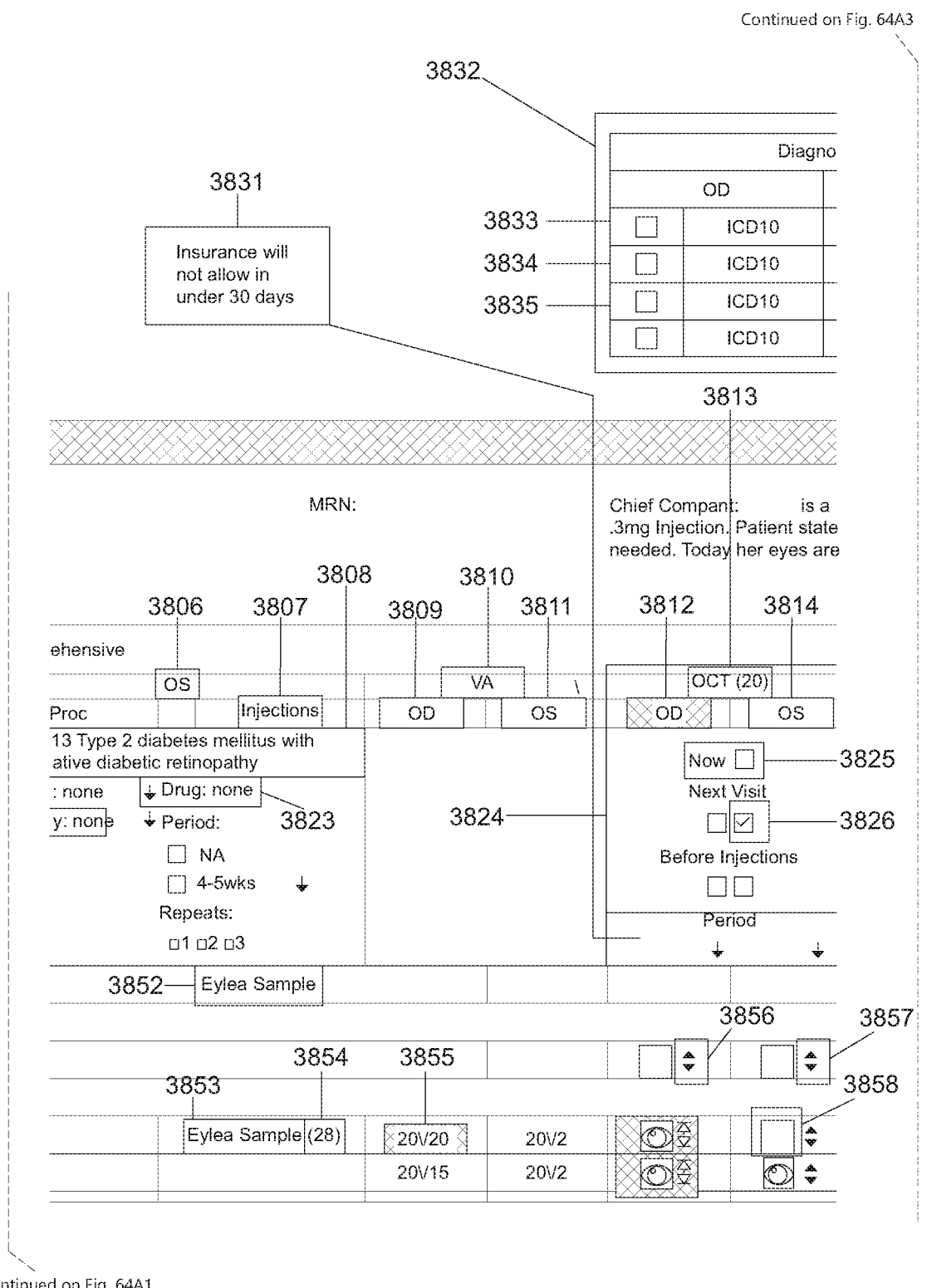
Fig. 64A2

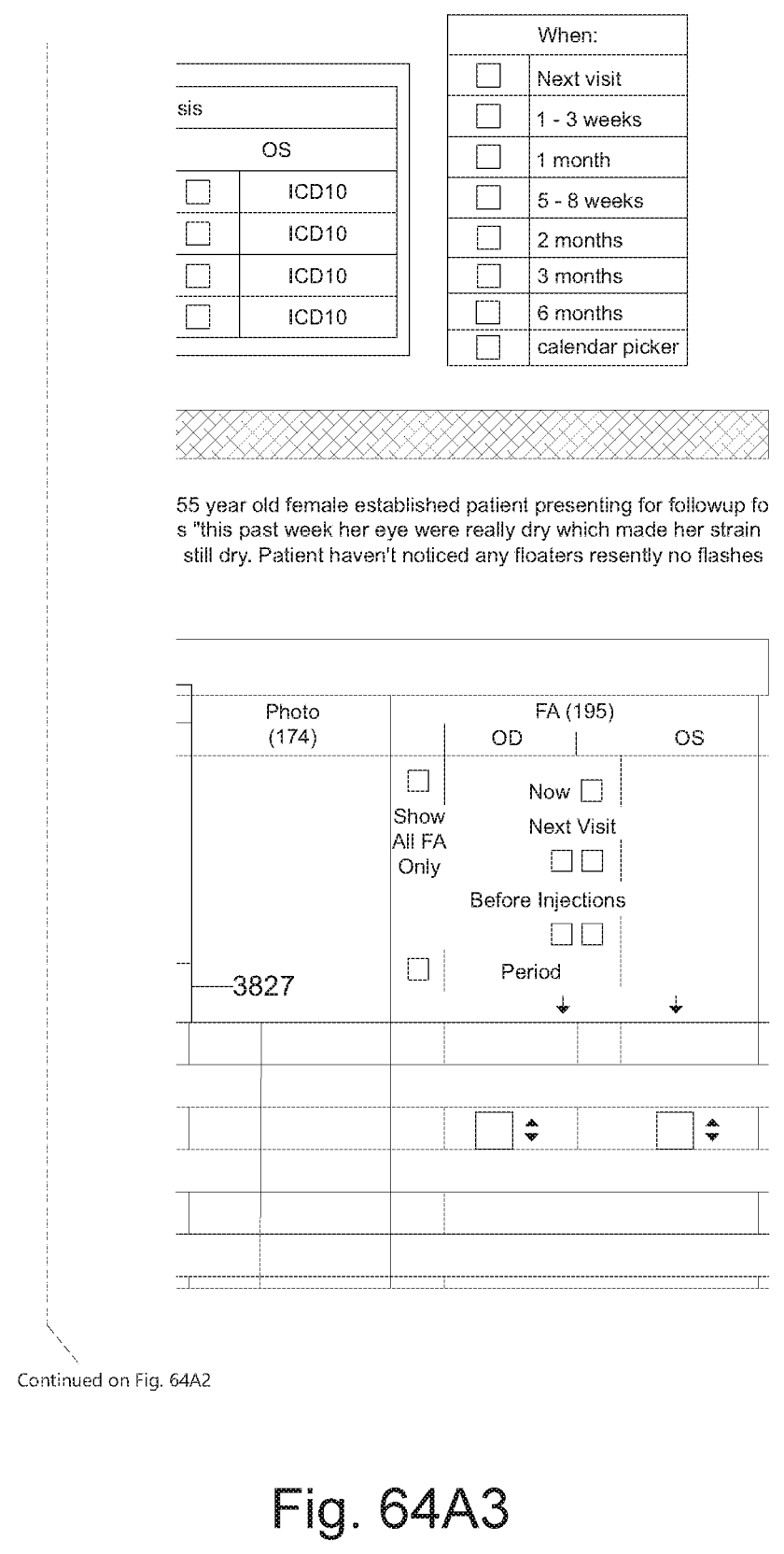

| | When: |
|---|---|
| ☐ | Next visit |
| ☐ | 1 - 3 weeks |
| ☐ | 1 month |
| ☐ | 5 - 8 weeks |
| ☐ | 2 months |
| ☐ | 3 months |
| ☐ | 6 months |
| ☐ | calendar picker |

| sis | |
|---|---|
| OS | |
| ☐ | ICD10 |
| ☐ | ICD10 |
| ☐ | ICD10 |
| ☐ | ICD10 |

55 year old female established patient presenting for followup fo
s "this past week her eye were really dry which made her strain
still dry. Patient haven't noticed any floaters resently no flashes

| Photo (174) | FA (195) | |
|---|---|---|
| | OD | OS |
| ☐ Show All FA Only | Now ☐ Next Visit ☐ ☐ Before Injections ☐ ☐ | |
| ☐ ——3827 | Period ↓ | ↓ |
| | | |
| | ☐ ↕ | ☐ ↕ |
| | | |
| | | |

Fig. 64A3

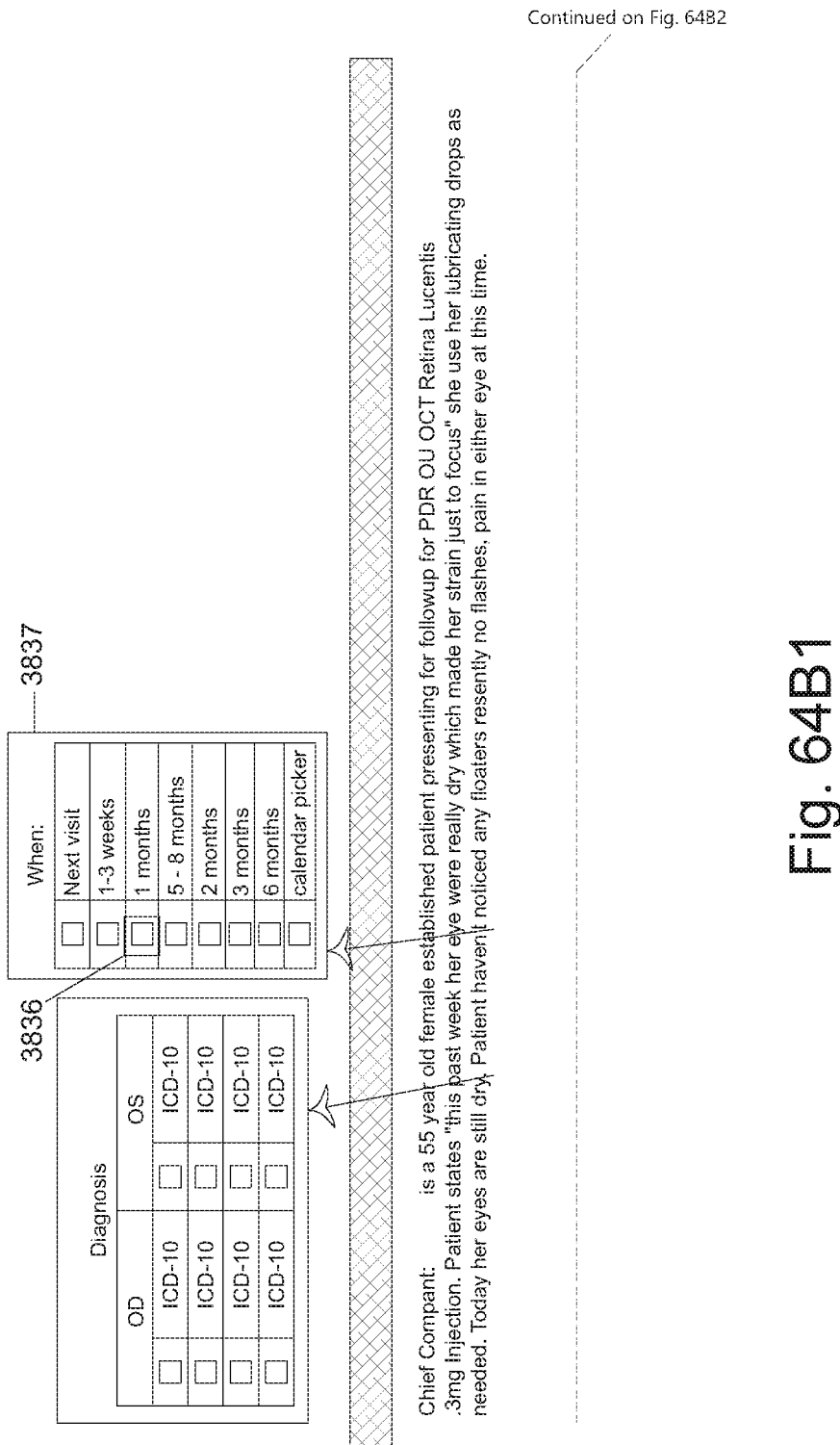
Fig. 64B1

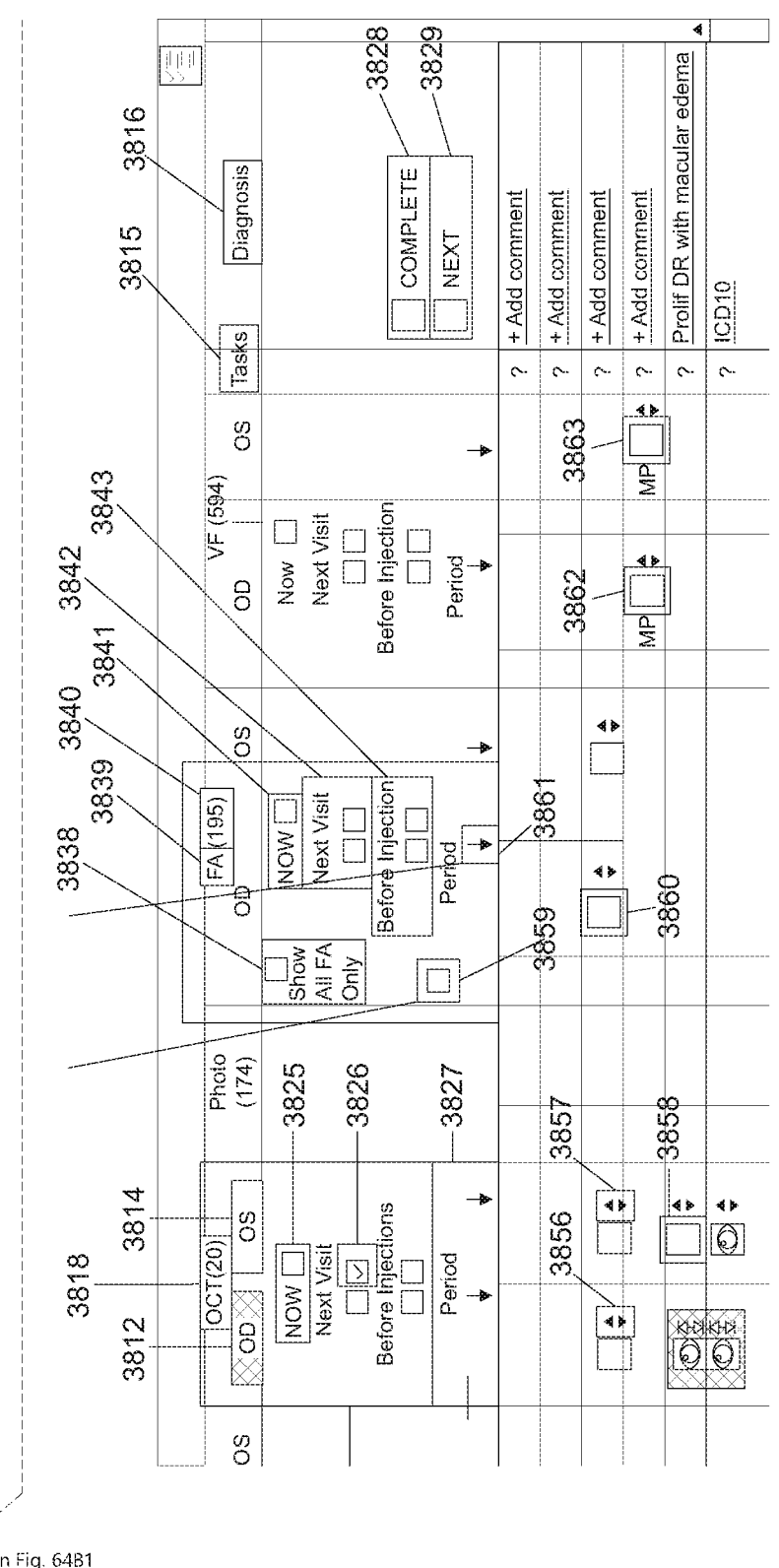
Fig. 64B2

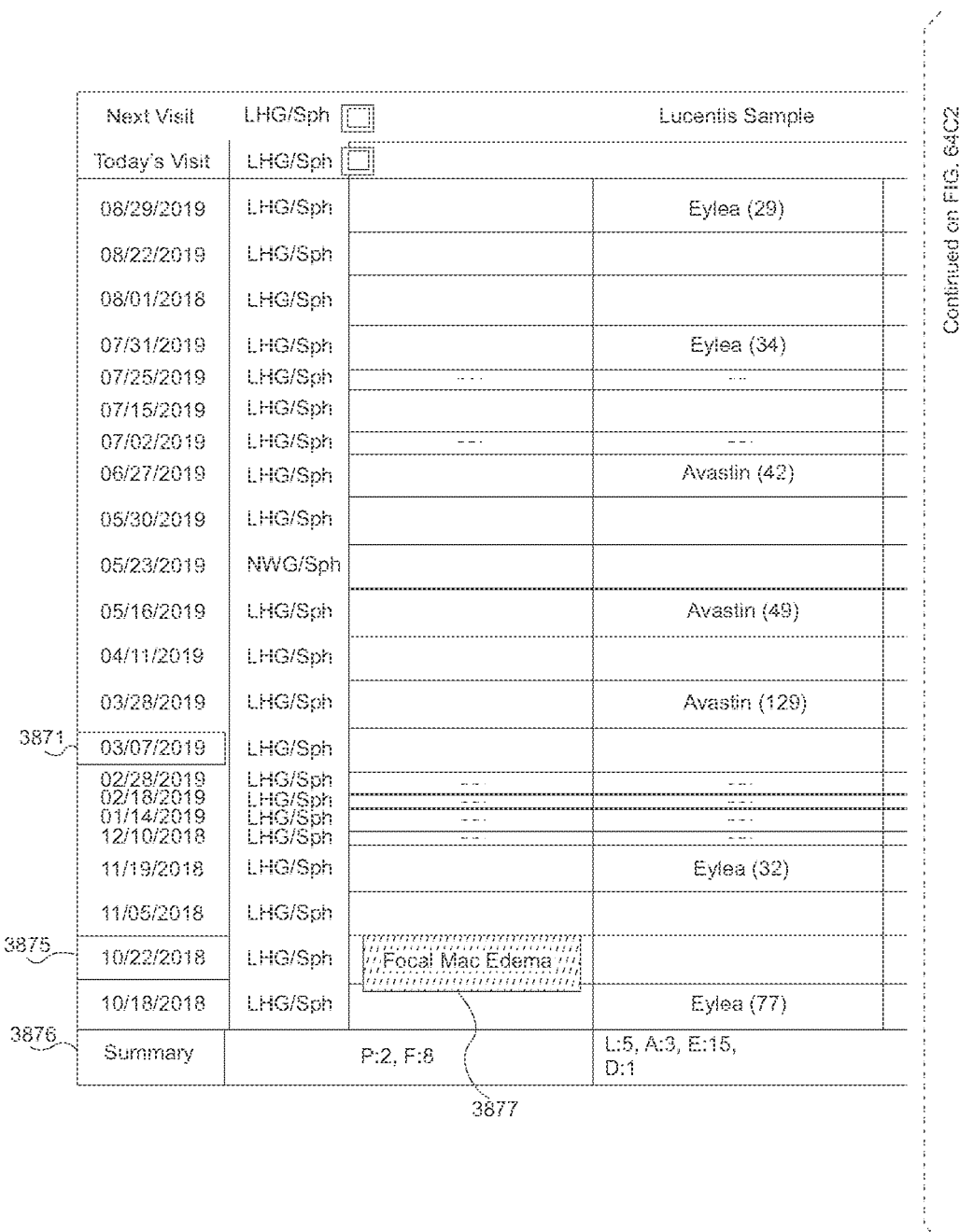
FIG. 64C1

3864

| | | | | |
|---|---|---|---|---|
| Eylea Sample (28) | | 20/200 | 20/25 | |
| | | 20/150 | 20/20 | |
| Eylea (38) | | 20/150 | 20/20-1 | |
| Focal Mac Edema | | 20/150 | 20/25 | |
| | | 20/150 | 20/25+1 | |
| - - - | - - - | - - - | - - - | - - - |
| Eylea (46) | | 20/80 | 20/25+2 | |
| - - - | - - - | - - - | - - - | - - - |
| | | 20/400 | 20/25 | |
| Avastin (49) | | 20/400+1 | 20/25-1 | |
| | | 20/400 | 20/25-2 | |
| 20/25 | | 20/400 | 20/25 | |
| Avastin (157) | | CF@6" | 20/25-1 | |
| | | 20/400 | 20/25-2 | |
| | | 20/400 | 20/25 | |
| - - - | - - - | - - - | - - - | - - - |
| - - - | - - - | - - - | - - - | - - - |
| - - - | - - - | - - - | - - - | - - - |
| | | 20/200 | 20/25 | |
| Eylea (585) | | 20/200 | 20/30 | |
| | | 20/150-2 | 20/30-1 | |
| | | 20/100+1 | 20/30-2 | |
| | | 20/25-1 CF@6" | 20/20+2 20/40 | |

3865

3879

3880

When ordering consider the following:  ~3878
3884~ Test today:        Allergy:  ~3888
3885~ Clinical today:    Interaction:  ~3889
3886~ Last done:
3887~ Insurance issue:

FIG. 64C2

DYNAMIC HEALTH RECORDS

CLAIM OF PRIORITY

This patent application is a continuation of International Application No. PCT/US2021/020751, filed Mar. 3, 2021, which application claims the benefit of priority to U.S. Provisional Application Ser. No. 62/987,165, filed Mar. 9, 2020; U.S. Provisional Application Ser. No. 63/026,547, filed May 18, 2020; U.S. Provisional Application Ser. No. 63/116,684, filed Nov. 20, 2020; U.S. Provisional Application Ser. No. 63/127,840, filed Dec. 18, 2020, which are incorporated by reference herein in their entireties. This patent application is also a continuation of U.S. application Ser. No. 16/802,547, filed Feb. 26, 2020; U.S. application Ser. No. 17/008,586, filed Aug. 31, 2020; U.S. application Ser. No. 17/008,631, filed Aug. 31, 2020; U.S. application Ser. No. 17/035,648, filed Sep. 28, 2020; and U.S. application Ser. No. 17/187,843, filed Feb. 28, 2021, which are incorporated by reference herein in their entireties.

BACKGROUND

The third most common cause of death in the United States is medical error. Needed is a mechanism to help assist doctors when placing orders to allow them to see relevant data, medical services, guidelines, and what is most important to consider emphasized and displayed., Important data relevant to placing an order should be visible at the time of creation of the order. When Doctors prescribe or create orders, they do so in a vacuum, not certain what the order they placed actually looks like against other relevant data, and cannot identify an order placed immediately or in the future is in fact for example is the correct body part in relation to other relevant information that may impact decision making. If the order could be seen in context, medical errors could be reduced. The importance of also displaying relevant data when a medical professional is viewing and interpreting diagnostic tests as well documenting and creating assessment and plans for care of the patient, is also vital in the delivery of efficient, accurate care and preventing errors. Among the most common reasons for malpractice claims are patients missing appointments or scheduled medical services. Medical professionals have no efficient way of knowing or prioritizing those patients most at risk or knowing when future appointments are scheduled and with which provider or medical service. What is needed is an intuitive display system that helps the doctor identify patients at risk with missed medical services and a system that automatically notifies the correct user and even the patient, so important medical services are not delayed and performed.

Caregivers are often called upon to make rapid life and death decisions based on a patient's condition in the context of a medical history as presented, for example, in an Electronic Health Record's ("EHR"). However, the visual display systems for EHR's are difficult to understand and require the user to move through multiple screens, interfaces, and menus to obtain the disparate information needed to make a medical decision. This creates great difficulties when caring for multiple patients in a busy practice and is compounded when different doctors provide care for the same patient. Moreover, the complex interfaces associated with EMRs are particularly problematic at the point of care as they slow caregivers down and distract them from meaningful face-time, caring for patients. Communication and sharing care for a particular patient between multiple health care providers has become more difficult. Now, rather than a fax or short dictated medical summary, caregivers are sending voluminous amounts of information often filled with error from click mistakes, right, left confusion and cut and paste functionality. EHR also has no organized way to correlate associated data over time nor share information across different EHR's, and non-integrated systems.

Furthermore, no system displays clinical and examination findings, medications actually taken by the patient, procedures, and diagnostic tests in a way that a user can discover at a glance if treatment is effective. No system, provides the ability for the user to visualize in context to allow them to double check that the orders and medications they are placing, are in fact the exact correct ones they intend to order. There is no system that displays, correlates, and highlights interrelated data points that can make a difference in the life of each patient. When information is displayed in a flow chart in an EHR, the presentations are not able to be adjusted manually and dynamically for an individual patient. Now that former paper medical records have been digitalized, data is very difficult to find. Medical care and the associated data dispersed in the computer has become so complex that what is needed is the type of intelligent, actionable visual display system that in context automatically adjusts the presentation, sorts, compresses and highlights the data the user needs to be able to make a medical decision and visualize the cause-and-effect of treatment.

In health care, EHR systems, and practice and image management systems borrow dashboards and displays from other fields. These displays often have time or date in one direction, with width or height consistent and variable factors that are being shown or measured in the other direction. The importance of certain occurrences in time may deserve more or less emphasis. Time spent does not always equate with work effort, impact of findings, or results.

While these traditional methods of evaluating data may work for some fields, these displays are sorely lacking in the medical field, which demands an entire new approach to all existing displays, flow charts, spreadsheets, and dashboards. In medicine a particular date of service could have an occurrence with much greater significance than another date. One date might be a routine office examination and another cancer discovered. An encounter with one provider, can be much more impactful than another. Both dates of service may have common features such as a particular clinical measurement. However, what is needed is a way to express the intensely different occurrences, so that at a glance with limited space and time, the critical information for a particular patient is conveyed. Unfortunately, EMR's, if they have a flow chart, it Is borrowed from displays in other fields, and simply displays data in similar ways used outside of medicine. Existing spreadsheets such as excel, may work for assisting accountants or even building an airplane. Once one plane is built, the next can be built the exact same way. Replicating even one human being has never been accomplished and no two people are the same nor react to disease and medical care in the exact same way.

What is needed is an entirely new display approach to presenting, organizing, and measuring data tailored for the human being. A simple, elegant solution that enables caregivers to synthesize information and populate and document a chart and even display orders as created when seeing a patient. A single presentation that enables a caregiver to identify medical problems and errors through data visualization, where data is presented and displayed in an intuitive, easy to view manner.

SUMMARY

The above and other needs in the art are addressed by a data command center visual display system and associated methods for displaying data on a display from multiple data sources and allowing navigation amongst the data without leaving the display of the visual display system. Numerous technical issues rooted in computer technology must be solved for the data to be presented to the visual display system so that the data may be displayed in the command center using a single display interface. For example, the visual display system must provide access to the requisite health information systems and third-party support services whereby the data may be accessed, processed, and presented without unacceptable delay. Also, the display data must be collected and ordered to facilitate the various combinations of the data into respective display panels that may be navigated on the interface. For example, it is desirable for the data to be configured in a task-based or specialty-specific display configuration for use by physicians, for example. To do this, various features in prior art systems needed to be acquired and combined in a new way to facilitate access to the features without having to navigate away from the display. For example, conventional EMR systems provide interfaces to third party prescription ordering systems but require the user the navigate to another system and away from the EMR interface. Accessing ordering panels without leaving the display becomes particularly difficult where the display space is limited as is the case for many physicians who use portable display devices and mobile computers. The structural embodiments described herein address these technical issues to generate the Dynamic health Records actionable display system embodiments described herein.

In exemplary embodiments, such a data command center visual display system in accordance with the present principles includes a patient database that stores patient identification information, patient insurance information, patient medical history information, a computer readable storage medium having stored thereon instructions thereon, and a processor that executes the instructions to perform operations including creating a plurality of adjustable display panels configured to display predetermined combinations of the patient identification information, patient insurance information, patient medical history information, and creating a patient flowsheet that integrates the patient medical history information into a table that presents the patient's medical history by visit to at least one physician with respective procedures or actions performed during each visit represented as first icons identifying the procedure or action performed and second icons enabling selection of a new procedure or action, where the first and second icons provide links to associated patient medical information and ordering display panels that may be accessed without leaving the display. In response to selection of the second icon by a user of the visual display system, an ordering display panel is presented to the display in addition to the adjustable display panels and patient flowsheet. The desired procedures or actions may be ordered from the ordering display panels while relevant portions of the patient's medical history are still visible on the display screen. The scope of the claims also contemplates corresponding methods performed by the visual display system and users thereof.

In exemplary embodiments, the ordering display panel comprises an ePrescribing panel for ordering medication or a medical procedure ordering panel for ordering a medical procedure. By way of example, the medical procedure ordering panel for ordering a medical procedure may further provide a link to the quality reporting panel that displays quality reporting metrics and/or peer data related to the procedure that is being ordered. All of such ordering display panels are configured in the context of the display to conserve display space so that the ordering display panel may be displayed while still being able to view the medical history data, for example.

In other exemplary embodiments, the ordering display panel comprises an imaging order panel for ordering a medical image of the patient or a lab order panel for ordering a lab test of the patient. In still other embodiments, instructions are provided that when executed create an image icon in an adjustable display panel and/or the patient flowsheet that, when selected by the user of the visual data system, opens a display window for viewing of one or more images without leaving the display.

In other exemplary embodiments, the visual display system incorporates financial data with the patient medical history data into the display panels. Such a visual display system includes a patient database that stores patient identification information, patient insurance information, patient medical history information, and patient payment information, a computer readable storage medium having stores thereon instructions thereon, and a processor that executes the instructions to perform operations including creating a plurality of adjustable display panels configured to display predetermined combinations of the patient identification information, patient insurance information, patient medical history information, and patient payment information, and creating a patient flowsheet that integrates the patient medical history information and patient payment information into a table that presents the patient's medical history by visit to at least one physician with respective procedures or actions performed during each visit represented as first icons identifying the procedure or action performed and second icons indicating whether the procedure or action has been paid for in part or in full, the first and second icons providing links to associated patient medical history information and/or patient payment information. In response to selection by a user of the visual display system, the adjustable display panels and patient flowsheet are moved into a task-based or specialty-specific display configuration such that the patient identification information, patient insurance information, patient medical history information, and patient payment information may be accessed without leaving the display. The task-based or specialty-specific display configuration is then presented to the display. In exemplary embodiments, selection of the first icons or second icons open display windows to associated medical history data and/or financial data and overlay a portion of the display with the display windows whereby the associated medical history data and/or financial data may be viewed by the user of the visual display system while the adjustable display panels and the patient flowsheet are displayed in a background on the display. Throughout this description, it will be appreciated that all financial data in the system, including costs to patient, is compartmentalized such that no user may see financial details for users or organizations not authorized in accordance with applicable policies and law. Also, the scope of the claims also contemplates corresponding methods performed by the visual display system and users thereof.

The visual display system includes a number of features that enable accessing information on the display. For example, third icons are provided in the patient flowsheet or display panels that include links to compliance information about compliance with insurance guidelines and/or good clinical practice guidelines for a procedure or action associated with each third icon. In exemplary embodiments, the compliance information includes aggregated medical treatment guidelines and an overview outlining similarities and differences amongst different medical treatment guidelines making up the aggregated medical treatment guidelines. The aggregated medical treatment guidelines may include information related to recommended follow-up with the patient, information related to procedures permitted or prevented by the patient's insurance or contra-indications, and information relating to proper billing for the procedure or action associated with a third icon selected from the patient flowsheet or display panels. In exemplary embodiments, the visual display system provides access to a clinical decision support system that uses a rules engine and/or natural language processing to aggregate the medical treatment guidelines and to generate the overview outlining similarities and differences amongst different medical treatment guidelines making up the aggregated medical treatment guidelines. The clinical decision support system and/or natural language processing system may further compare medical data to notice patterns, errors and anomalies in different entries or notes, find discrepancies in payments, alert the user of the visual display system about inconsistent medical documentation or improper orders, speed up the process of complying with regulations, alert the user of the visual display system that a plan or order is inconsistent with a preferred practice plan for a patient, or warn the user of the visual display system that billing certain procedures might not be covered. The natural language processing system may also be accessed parse notes in the patient flowsheet or display panels for potential ICD10 codes or alternative diagnosis.

The visual display system also includes a display configuration that enables users of the visual display system to order medications, diagnostic tests, images, procedures, and the like directly from the patient flowsheet or display panel. For example, an icon or link in the patient flowsheet or display panel may include an ePrescribing panel for ordering medication or a medical procedure ordering panel for ordering a medical procedure. The medical procedure ordering panel may further include a link to a quality reporting panel that displays quality reporting metrics and/or peer data related to the procedure that is being ordered. In other embodiments, an icon or link in the patient flowsheet or display panel may include an imaging order panel for ordering a medical image of the patient or a lab order panel for ordering a lab test of the patient. In still other embodiments, an image icon is provided in an adjustable display panel and/or the patient flowsheet that, when selected by the user of the visual data system, opens a display window for viewing of one or more images without leaving the display screen. In other embodiments, an alert icon is provided in an adjustable display panel and/or the patient flowsheet that, when selected by the user of the visual data system, opens an alert message without leaving the display. In still other embodiments, one of the display panels may be configured to accept today's visit notes from the user of the visual display system in connection with a patient visit for storage for access with other data of the one display panel.

In still other embodiments, data input by the user of the visual display system may trigger auto-population of information in the adjustable display panels and patient flowsheet and auto-population of the patient's medical record in an electronic medical record system. In the exemplary embodiments, the auto-population occurs without the user of the video display system leaving the display.

In other embodiments, new clinical information for the patient is provided to a diagnosis evaluation algorithm for comparison of the new clinical information with previous corresponding clinical information for the patient to determine whether the new clinical information is indicative of an improvement or worsening of the patient's medical condition. The visual display system further generates diagnosis indicators providing a visual representation of an improvement of a medical problem, disease, or symptom, or a worsening of a medical problem, disease, or symptom as a result of taking a particular medication or undergoing a particular medical procedure and displays the diagnosis indicators in the adjustable display panels and/or the patient flowsheet.

Other embodiments of the visual display system allows for increased speed of data presentation by a local database that stores a subset of patient identification information, patient insurance information, patient medical history information, and patient payment information, where the subset includes the patient identification information, patient insurance information, patient medical history information, and patient payment information for patients having an appointment within a predetermined time window.

The visual display system in exemplary embodiments includes interfaces to an external health information system and third party service systems. In exemplary embodiments, the external health information system includes at least one of an electronic health records system, Electronic Medical records, a practice management system, a health information exchange, a picture archive and communications system, a clearing house/billing system, Image management systems, diagnostic equipment, and a laboratory system. On the other hand, the third party service systems may include one or more of an ePrescribing system, an insurance verification/referral/pre-authorization system, a system for establishing medical necessity by verifying that a procedure or medication is associated with a correct diagnostic code such as an ICD10 code or other current code supporting its use, a clinical services pricing and location system, a claim status checking system, services in support of the National Correct Coding Initiative, services to proactively ensure claims are coded correctly to prevent issues in billing, claims compliance services that evaluate claims against National Coverage Determination (NCD) and Local Coverage Determination (LCD) guidelines as well as local insurance regulations to establish and document medical necessity, a natural language processing system, and artificial intelligence/cognitive systems that provide clinical decision support.

In exemplary embodiments, the patient identification information, patient insurance information, patient medical history information, and patient payment information is stored in the patient database in transactional tables that capture clinical and billing data and reporting tables where data is aggregated for a particular physician, practice, health system or other entity. Each table uses a surrogate primary key that is a unique value within the table used to identify a row that is not directly tied to data in that row. In the exemplary embodiments, XML code moves and stores different display panel and flowsheet views. The XML code further identifies a collection of panels and tabs, wherein within each panel is a panel ID that links the panel to a tab, the panel's position, and whether or not the panel is stacked with another panel. The XML code may also set up the display panels and patient flowsheet on the display by, for example, identifying a collection of columns and, for each column, a name of the column along with a data source. The display panels so configured are presented to the display for selection and display panel frames on the display screen are manipulated for receiving selected display panels.

In other exemplary embodiments, the patient flowsheet is organized around patient medical information corresponding to a particular disease state and/or procedures and/or insurance coverage and/or actions for treating the particular disease state.

The patient database may also be adapted to include patient medical history information from a plurality of medical care providers whereby the patient flowsheet may be adapted to include medical history information from more than one medical care provider in order to provide shared treatment of the patient in the patient flowsheet. In other embodiments, a summary table may be provided that illustrates everything the user of the visual display system has done for each patient in a particular time frame or for each patient having a particular disease state in a particular time frame. The summary table may also include information from other medical care providers who are providing shared treatment of the patient. If financial data, cost, charge, payment is on the summary table with the medical data, this data is compartmentalized such that no user may see financial details for users or organizations not authorized in accordance with applicable policies and law.

In yet other embodiments, a data command center visual display system is provided that presents dynamic data to a display. The command center visual display system includes a plurality of adjustable display panels configured to display predetermined combinations of patient identification information and patient medical information. A patient flowsheet is created that includes a table that presents the patient's medical information by medical service, medical procedure, diagnostic test, medication, and diagnosis that is prescribed, ordered, performed, or selected during respective encounters with at least one medical care provider. In response to selection by a user, at least two adjustable display panels containing medical information relating to one or more patients in the patient flowsheet are presented to the display in a single view. The user may edit or move the medical information or the patient identification information within the display panels while the display panels are simultaneously open.

In some embodiments, a method for rules-based data display in a data command center including a medical records dashboard including one or more windows including information received or derived from at least one patient database, the medical records dashboard comprising a display, using the one or more windows, of at least one of medical services, clinical data, examination findings, diagnostic tests, and the procedures performed on one or more patients, the one or more windows comprising a plurality of data fields, including at least one dynamic data field, for displaying the information received or derived from the at least one patient database, wherein the at least one of the medical services, the clinical data, the examination findings, the diagnostic tests, and the procedures are arranged in rows or columns on the display according to at least one of a time and a date that the medical services, the clinical data, the examination findings, the diagnostic tests and the procedures were performed on the one or more patients, the method includes receiving patient-related data from the at least one patient database, comparing the received patient-related data with configuration rules to determine which portions of the received patient-related data are to be displayed in data fields of the medical records dashboard, identifying dynamic data fields of the at least one dynamic data field of the medical records dashboard that are determined to not have any patient-related data to display as collapsed data fields, displaying patient-related data in the data fields of the medical records dashboard in accordance with the configuration rules and dynamic data fields of the medical records dashboard identified as collapsed data fields.

In some embodiments, a data command center visual display system that displays data on a display includes a computing device comprising at least one processor, a non-transitory computer-readable medium, having stored thereon, software instructions that when executed by the at least one processor of the computing device, cause the computing device to perform operations comprising at least, linking to and receiving patient related medical records including patient data from at least one patient data source, and displaying a medical records dashboard including one or more windows, the medical record dashboard capable of displaying, using the one or more windows, patient data from at least one patient data source including at least one of medical services, clinical data, examination findings, diagnostic tests, and the procedures performed on one or more patients, the one or more windows comprising a plurality of data fields, including at least one dynamic data field, for displaying the information received or derived from the at least one patient database, wherein the at least one of the medical services, the clinical data, the examination findings, the diagnostic tests, and the procedures are arranged in rows or columns on the one or more windows according to at least one of a time and a date that the medical services, the clinical data, the examination findings, the diagnostic tests and the procedures were performed on the one or more patients, wherein a display of patient data in the medical records dashboard is determined by: comparing the patient data with configuration rules to determine which portions of the patient data are to be displayed in the data fields of the medical records dashboard, identifying dynamic data fields of the at least one dynamic data field of the medical records dashboard that are determined to not have patient data to display as collapsed data fields, and displaying patient data in the data fields of the medical records dashboard in accordance with the configuration rules and dynamic data fields of the medical records dashboard identified as collapsed data fields. The terms computer-readable medium, machine readable medium, and storage device do not include carrier waves to the extent carrier waves are deemed too transitory. Storage can also include networked storage, such as a storage area network (SAN).

In some embodiments, a method for unique patient identification of a subject patient in a data command center including patient-related data received or derived from at least one patient database includes collecting patient-related data having different data classifications from the at least one patient database, assigning a level of accuracy score for each of the patient-related data of the different classifications, adding, the level of accuracy scores for each of the patient-related data of the different classifications, comparing a total of the added level of accuracy scores to a previously determined matching threshold, if the total of the added level of accuracy scores exceeds the matching threshold, establishing an identification of the subject patient, and if the total of the added level of accuracy scores does not exceed the matching threshold, collecting additional patient-related data and returning to the assigning phase.

In some embodiments, a data command center visual display system for determining a unique patient identification includes a computing device comprising at least one processor, a non-transitory computer-readable medium, having stored thereon, software instructions that when executed by the at least one processor of the computing device, cause the computing device to perform operations comprising at least: linking to and receiving patient related medical records including patient data from at least one patient data source, collecting patient-related data having different data classifications from the at least one patient database, assigning a level of accuracy score for each of the patient-related data of the different classifications, adding, the level of accuracy scores for each of the patient-related data of the different classifications, comparing a total of the added level of accuracy scores to a previously determined matching threshold, if the total of the added level of accuracy scores exceeds the matching threshold, establishing an identification of the subject patient, and if the total of the added level of accuracy scores does not exceed the matching threshold, collecting additional patient-related data and returning to the assigning.

In some embodiments, a method for medication management and display in a data command center comprising one or more windows for display and including information received or derived from at least one patient database, the data command center displaying, using the one or more windows, at least one of medical services, clinical data, examination findings, diagnostic tests, and procedures performed on one or more patients, the one or more windows comprising a plurality of data fields for displaying the information received or derived from the at least one patient database, wherein the at least one of the medical services, the clinical data, the examination findings, the diagnostic tests, and the procedures are arranged in on the one or more windows according to at least one of a time and a date that the medical services, the clinical data, the examination findings, the diagnostic tests and the procedures were performed on the one or more patients, includes determining, from at least one of the information received or derived from the at least one patient database and the at least one of the medical services, the clinical data, the examination findings, the diagnostic tests, and the procedures, medications prescribed or administered to the one or more patients, generating a respective graphical representation for each of the determined prescribed or medications prescribed or administered to the one or more patients, and displaying at least one generated, respective graphical representation of at least one medication administered to a patient in the at least one or more windows in context with at least one of the information received or derived from the at least one patient database and the at least one of the medical services, the clinical data, the examination findings, the diagnostic tests, and the procedures, wherein the at least one generated, respective graphical representation of the at least one medication administered to the patient is arranged in on the one or more windows according to at least one of the times and the dates that the at least one medication was being administered to the patient.

In some embodiments, a data command center visual display system that displays data on a display includes a computing device comprising at least one processor, a non-transitory computer-readable medium, having stored thereon, software instructions that when executed by the at least one processor of the computing device, cause the computing device to perform operations including at least, linking to and receiving patient related medical records including patient data from at least one patient data source, wherein the patient data includes at least one of medical services, clinical data, examination findings, diagnostic tests, and procedures performed on one or more patients, determining, from at least one of the patient data and the at least one of the medical services, the clinical data, the examination findings, the diagnostic tests, and the procedures, prescribed or medications prescribed or administered to the one or more patients, generating a respective graphical representation for each of the determined medications prescribed or administered to the one or more patients, and displaying using the one or more windows, at least one of medical services, clinical data, examination findings, diagnostic tests, and procedures performed on one or more patients and at least one generated, respective graphical representation of at least one medication administered to a patient in context with at least one of the patient data and the at least one of the medical services, the clinical data, the examination findings, the diagnostic tests, and the procedures, wherein the at least one of the medical services, the clinical data, the examination findings, the diagnostic tests, and the procedures are arranged on the display according to at least one of a time and a date that the medical services, the clinical data, the examination findings, the diagnostic tests and the procedures were performed on the one or more patients, and wherein the at least one generated, respective graphical representation of the at least one medication administered to the patient is arranged on the display according to at least one of the times and the dates that the at least one medication was being administered to the patient.

In some embodiments, a method for a display of a graphical representation of complete medical history of a patient in a data command center comprising one or more windows for display and including patient-related data received or derived from at least one patient database, the method includes determining, from the patient-related data, a complete medical history of at least one patient including at least one of medical services, clinical data, examination findings, diagnostic tests, medications prescribed or administered to and procedures performed on a patient, as well as cancelled or missed visits, generating a graphical representation of the determined complete medical history of the patient including the at least one of medical services, clinical data, examination findings, diagnostic tests, identified or prescribed medications, and procedures performed on the patient, and displaying the generated graphical representation in the at least one or more windows according to at least one of a time and a date that the at least one of the medical services, the clinical data, the examination findings, the diagnostic tests, and the procedures the medical services, the clinical data, the examination findings, the diagnostic tests and the procedures were performed on the one or more patients and at least one of the times and the dates that the medications were being administered to the patient, wherein a user is enabled to select a location in the displayed graphical representation and details regarding the at least one of medical services, clinical data, examination findings, diagnostic tests, medications prescribed or administered to and procedures performed on the patient related to that selected location are presented to the user. In one embodiments, the system allows connecting to home monitoring devices, systems such as I phone watches that monitor constantly Blood pressure and pulse and can discover if patient may be having a heart attack and can display one of a time or date that no medical service was performed by the Doctor but a clinical measurement by the patient or outside entity can be displayed including time and date medications were actually taken by the patient or physical therapy was performed by the patient. In some embodiments this information can be displayed along with time and dates medical services were provided or can be selected to be separate. The system can monitor these times and dates that measurements by the patient or outside entity performed the clinical measurement for instance blood pressure, pulse, reading, blood sugar readings and when critical new data that exceeds a threshold occurs, alerts and expandable fields can be inserted within the data fields of the time and dates of medical services even if the user chooses an option not to comingle home monitoring for instance with measurement's during time and dates that a medical service occurs. In some embodiment cancelled or missed appointments and future appointments and any medical service or action to have been or to be performed are displayed so the user can identify the impact, necessity, and correctness of what was or is to be performed and which may have an impact on any date of service.

In some embodiments, multiple aspects of this invention may be displayed and correlated against each other, or groups of embodiments, or as a whole, such as representing summary groupings of results for specific disease states alongside graphical representations of relevant results, contributing factors, life events, medical procedures, medications, and all other data represented herein. Correlation may be automated in accordance with principles defined herein, and may employ clinical decision support in determining which aspects to display.

Other and further embodiments in accordance with the present principles are described below.

DESCRIPTION OF THE DRAWINGS

FIG. 11 depicts a flow diagram of a method for Unique Patient Identification in a Data Command Center in accordance with an embodiment of the present principles.

FIG. 13D depicts a flow diagram of a method for rules-based data display in a data command center comprising a medical records dashboard in accordance with an embodiment of the present principles.

FIG. 15 depicts a series of data points associated with the determination of how and when to display data fields.

FIG. 16 depicts configuration options associated with dynamic data representation.

FIG. 19 illustrates a series of configurations in accordance with an embodiment of the present principles.

FIG. 23 illustrates dynamic, interactive header and summary rows in accordance with an embodiment of the present principles.

FIG. 53A depicts an example of how the Control Panel #1 of FIG. 50 can be implemented by a user to identify start and stop dates for the various medications taken by a user in accordance with an embodiment of the present principles.

FIG. 53B depicts an embodiment of a Medication Management Chart in which icons can be activated to bring up additional information in accordance with an embodiment of the present principles.

FIG. 53C depicts another embodiment of a Medication Management Chart in which icons can be activated to bring up additional information in accordance with another embodiment of the present principles.

FIG. 53D depicts an embodiment of the Medication Management Chart in which intraocular pressure, in addition to being listed by number, is also displayed as a vertical line graph, for example as depicted by element 1 in accordance with an embodiment of the present principles.

FIG. 53E depicts an embodiment of the Medication Management Chart of FIG. 53D in which the control panel can be used to input a reason that a medication has been started or stopped in accordance with an embodiment of the present principles.

FIG. 53F depicts an embodiment of the Medication Management Chart of FIG. 53D in which the control panel can be used to correct start and stop dates for a medication in accordance with an embodiment of the present principles.

FIG. 53G depicts an embodiment of the Medication Management Chart of FIG. 53D in which both corrected start and stop dates for a medication taken by a patient and incorrect start and stop dates for a medication taken by a patient and listed for example by a $3^{rd}$ party data provider such as an EMR can be displayed simultaneously in accordance with an embodiment of the present principles.

FIG. 53H depicts an embodiment of the Medication Management Chart of FIG. 53D in which a user is alerted that a medication being taken by a patient has changed, even if medications are being listed by class and the new medication is of the same class as the old medication in accordance with an embodiment of the present principles.

FIG. 53I depicts an embodiment of the Medication Management Chart of FIG. 53H in which a user is able to select a portion of a graph to bring up additional information associated with the graph in accordance with an embodiment of the present principles.

FIG. 64 depicts a whole view of an embodiment of a medical records dashboard of a Data Command Center in which a user/medical care provider is enabled to place orders and view orders in context with other relevant patient data/information.

FIG. 64A depicts a first enlarged portion of the Data Command Center of FIG. 64.

FIG. 64B depicts a second enlarged portion of the Data Command Center of FIG. 64.

FIG. 64C depicts a third enlarged portion of the Data Command Center of FIG. 64.

Figure 1:
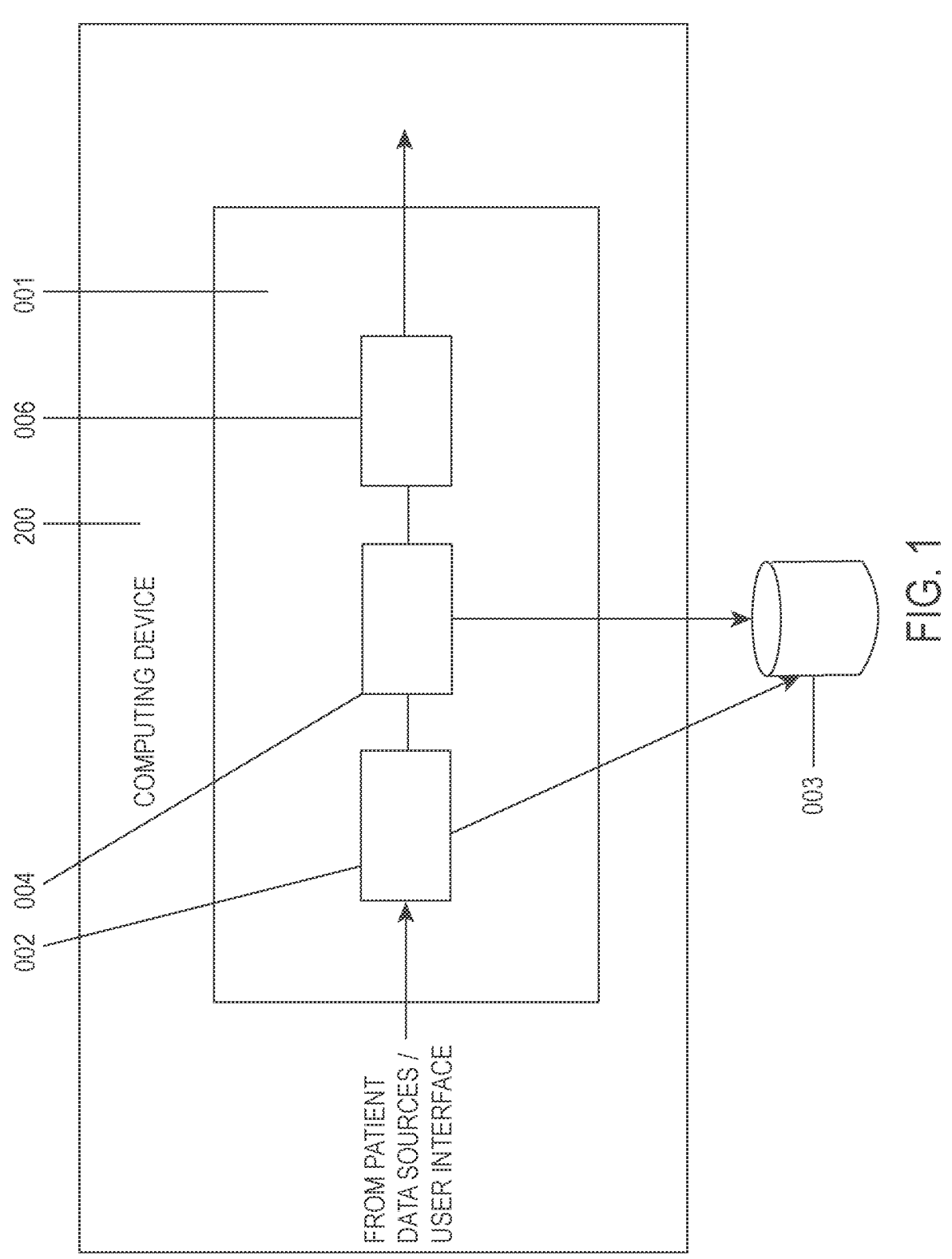
FIG. 1 depicts a high-level block diagram of a Data Command Center in accordance with an embodiment of the present principles.

Dynamic Health Records The figures are not drawn to scale and may be simplified for clarity. It is contemplated that elements and features of one embodiment may be beneficially incorporated in other embodiments without further recitation.

DETAILED DESCRIPTION

Embodiments of the present principles generally relate to a Data Command Center, also referred to as dynamic health record system or dynamic health record for displaying data on a display screen from multiple data sources and enabling navigation amongst the data on a single display. While the concepts of the present principles are susceptible to various modifications and alternative forms, specific embodiments thereof are shown by way of example in the drawings and are described in detail below. It should be understood that there is no intent to limit the concepts of the present principles to the particular forms disclosed. On the contrary, the intent is to cover all modifications, equivalents, and alternatives consistent with the present principles and the appended claims. For example, although embodiments of the present principles will be described primarily with respect to inter-function with an EMR system, such teachings should not be considered limiting. Embodiments in accordance with the present principles can inter-function with other informational systems such as Health Information Exchanges (HIEs), Billing Clearinghouses, Insurance Companies, Picture Archiving and Communication Systems (PACS) as well as third party services and the like.

In addition, the tool embodiments of the present principles are not limited in application to the details of construction and the arrangement of components set forth in the following description or illustrated in the following drawings. Embodiments of the present principles are capable of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, the term "medical care provider" is intended to represent any healthcare provider/clinical professional such as a doctor, physician, podiatrist, chiropractor, dentist, veterinarian, ancillary staff, nurses, physician's assistant, medical care provider, physical therapist, all allied health professionals, and/or hospital staff member. All such healthcare providers/clinical professional can implement embodiments of the present principles the tool as interchangeable users.

As used herein a row, column, or line of items (even a diagonal line) is intended to represent a sequencing or evaluation of information in any direction. In the embodiments depicted herein, information does not have to be depicted as having a visual or physical separation in the vertical or horizontal direction to be defined as being a row or column. In accordance with the present principles, items next to each other horizontally, lined up in such a way that straight lines above and below can be drawn, and items fall between those two horizontal lines, can be considered as being in a row. Items in rows can be related by similar time or other common or same denominator, such as a medical service, procedure, image, or financial number, so that a user can quickly visualize trends or changes in those items. Similarly, items next to each other vertically, lined up in such a way that straight lines to the left and to the right can be drawn can be considered as being in a column. In some embodiments, items can be arranged diagonally and be considered to be in a row or a column.

As used herein, Practice Management Systems (PMs) are programs that perform the billing collection and reconciliation of payments as well as scheduling patients. PMs can also be referred to as Revenue Cycle Management (RCM) and have associated billing companies that use software to help practices and medical care providers get the bills out and collect money from insurance companies. In some embodiment, these entities can integrate with and work through clearing houses.

In the embodiments described herein, the terms window screen, scrolling screen, display. view, snapshot, and the like can be used interchangeably and are intended to represent a single instance of the presentation of medical information associated with at least one patient. In the described embodiments, the single instance can be presented on one or more windows, in a single or multiple screens, a scrolling screen, in one or more views and using one or more snapshots. For example, in some embodiments in accordance with the present principles a user can access different panels from a scrolling screen and converge the panels into a single view or snapshot. That is, in accordance with the present principles, a user is able to compile data/information from various windows, screens, scrolling screens, displays, snapshots and the like and create a single instance presentation including the data/information of interest to the user for at least one patient. In accordance with the present principles, a single instance presentation can be presented on more than one monitor at a time. As used herein, the term single instance presentation is intended to describe a single display interface that is not limited to a single monitor. That is, in some embodiments, what defines a single instance presentation is the fact that there is a single interface, a single control that controls the presentation of the date/information, which can be then be viewed on one or more monitors or other means.

The term medical tests as described herein is intended to describe medical procedures performed for or on patients including but not limited to image or imaging, diagnostic tests, radiological tests or procedures, laboratories, chemistry and hematological tests, photography, genetic testing, nuclear scans, ultrasounds, x-rays, optical coherent tomography photographs and angiographies, assessments and plans, letters, examination findings and any medical testing or medical services that tests or screens patients for a medical condition, which in some instance can be identified by CPT codes. It should be further noted that in some instances, terms like diagnosis can be reflected by ICD 9 or 10 or similar identifying factors, and medications can be interchangeable.

As used herein, the terms icon, symbol, and indicator are all interchangeable and are intended to describe a visual element enabling the access of additional underlying information and having the ability to convey additional information simply by their presentation. That is, such visual elements can convey information by their display which can include such visual presentations including but not limited to words, numbers, blinking elements, flashing elements, color changing elements, elements in italics, underlined elements, and the like or any means that draws the attention of a user.

The reference to a medical records dashboard of the present principles described throughout the teachings herein is intended to refer to any embodiment of a medical records dashboard according to the present principles that is applicable to a currently described embodiment.

FIG. 1 depicts a high-level block diagram of a Data Command Center (DCC) 001 in accordance with an embodiment of the present principles. In the embodiment of FIG. 1, the Data Command Center 001 illustratively comprises an integration module 002 (i.e., to interface data between an EMR and the DCC), a Rules module 004 (i.e., to determine where and how the data is to be displayed), and a display module 006 (i.e., to display the data in the appropriate place). In the embodiment of FIG. 1, the integration module 002 and the rules module 004 can be in communication with a data storage 003. For example, the integration module 002 can store data from patient data sources in the data storage 003 and the rules module 004 can access the data storage 003 to retrieve data and/or information stored therein.

Figure 2:
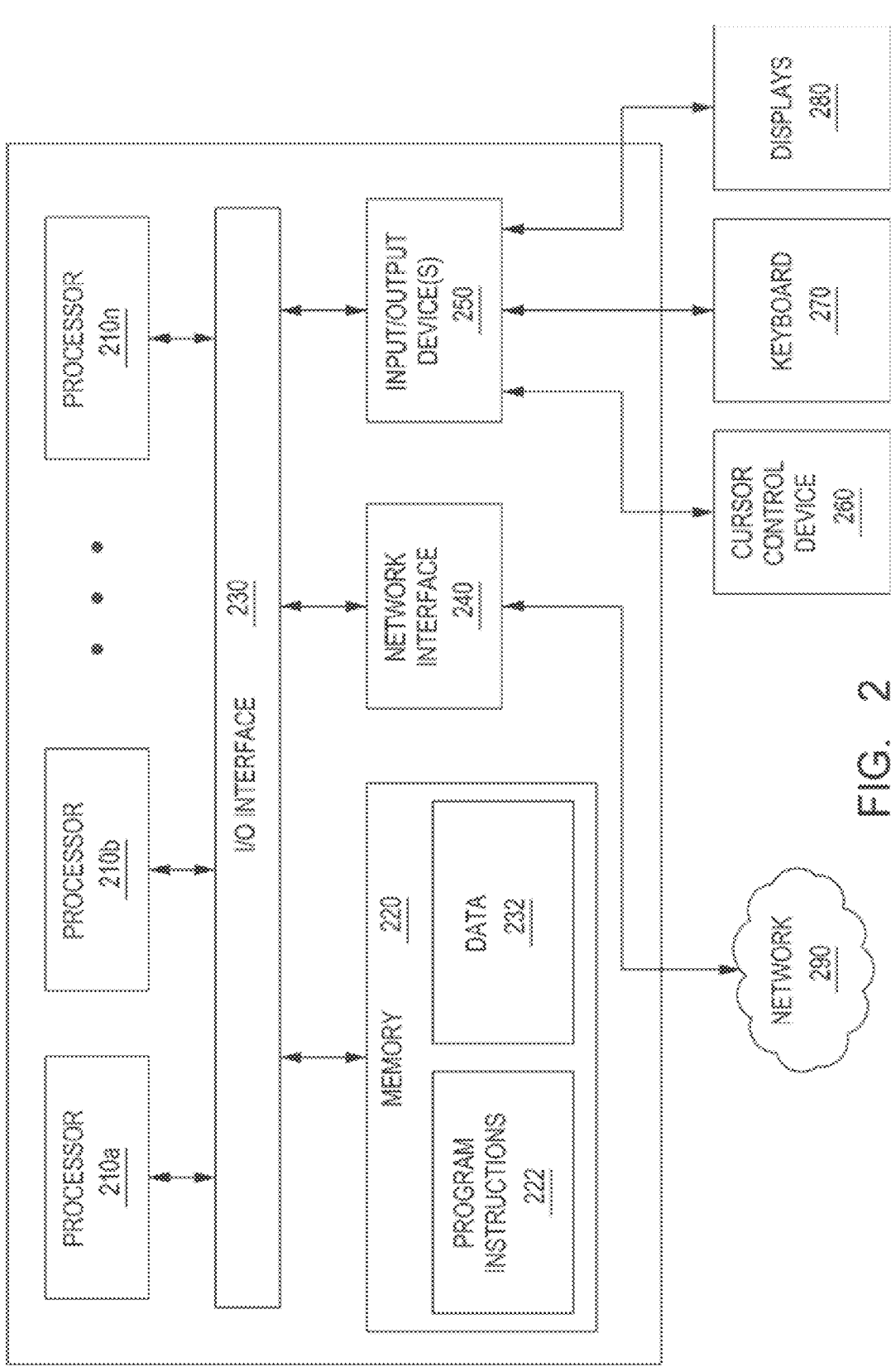
FIG. 2 depicts a high-level block diagram of a computing device 200 suitable for use with embodiments of a Data Command Center in accordance with the present principles.

As depicted in FIG. 1, embodiments of a Data Command Center in accordance with the present principles, such as the Data Command Center 001 of FIG. 1, can be implemented in a computing device 200. FIG. 2 depicts a high-level block diagram of a computing device 200 suitable for use with embodiments of a Data Command Center in accordance with the present principles such as the user Data Command center 001 of FIG. 1. In some embodiments, the computing device 200 can be configured to implement methods of the present as processor-executable executable program instructions 222 (e.g., program instructions executable by processor(s) 210) in various embodiments.

In the embodiment of FIG. 2, the computing device 200 includes one or more processors 210a-210n coupled to a system memory 220 via an input/output (I/O) interface 230. The computing device 200 further includes a network interface 240 coupled to I/O interface 230, and one or more input/output devices 250, such as cursor control device 260, keyboard 270, and display(s) 280. In various embodiments, a user interface can be generated and displayed on display 280. In some cases, it is contemplated that embodiments can be implemented using a single instance of computing device 200, while in other embodiments multiple such systems, or multiple nodes making up the computing device 200, can be configured to host different portions or instances of various embodiments. For example, in one embodiment some elements can be implemented via one or more nodes of the computing device 200 that are distinct from those nodes implementing other elements. In another example, multiple nodes may implement the computing device 200 in a distributed manner.

In different embodiments, the computing device 200 can be any of various types of devices, including, but not limited to, a personal computer system, desktop computer, laptop, notebook, tablet or netbook computer, mainframe computer system, handheld computer, workstation, network computer, a camera, a set top box, a mobile device, a consumer device, video game console, handheld video game device, application server, storage device, a peripheral device such as a switch, modem, router, or in general any type of computing or electronic device.

In various embodiments, the computing device 200 can be a uniprocessor system including one processor 210, or a multiprocessor system including several processors 210 (e.g., two, four, eight, or another suitable number). Processors 210 can be any suitable processor capable of executing instructions. For example, in various embodiments processors 210 may be general-purpose or embedded processors implementing any of a variety of instruction set architectures (ISAs). In multiprocessor systems, each of processors 210 may commonly, but not necessarily, implement the same ISA.

System memory 220 can be configured to store program instructions 222 and/or data 232 accessible by processor 210. In various embodiments, system memory 220 can be implemented using any suitable memory technology, such as static random-access memory (SRAM), synchronous dynamic RAM (SDRAM), nonvolatile/Flash-type memory, or any other type of memory. In the illustrated embodiment, program instructions and data implementing any of the elements of the embodiments described above can be stored within system memory 220. In other embodiments, program instructions and/or data can be received, sent, or stored upon different types of computer-accessible media or on similar media separate from system memory 220 or computing device 200.

In one embodiment, I/O interface 230 can be configured to coordinate I/O traffic between processor 210, system memory 220, and any peripheral devices in the device, including network interface 240 or other peripheral interfaces, such as input/output devices 250. In some embodiments, I/O interface 230 can perform any necessary protocol, timing, or other data transformations to convert data signals from one component (e.g., system memory 220) into a format suitable for use by another component (e.g., processor 210). In some embodiments, I/O interface 230 can include support for devices attached through various types of peripheral buses, such as a variant of the Peripheral Component Interconnect (PCI) bus standard or the Universal Serial Bus (USB) standard, for example. In some embodiments, the function of I/O interface 230 can be split into two or more separate components, such as a north bridge and a south bridge, for example. Also, in some embodiments some or all of the functionality of I/O interface 230, such as an interface to system memory 220, can be incorporated directly into processor 210.

Network interface 240 can be configured to allow data to be exchanged between the computing device 200 and other devices attached to a network (e.g., network 290), such as one or more external systems or between nodes of the computing device 200. In various embodiments, network 290 can include one or more networks including but not limited to Local Area Networks (LANs) (e.g., an Ethernet or corporate network), Wide Area Networks (WANs) (e.g., the Internet), wireless data networks, some other electronic data network, or some combination thereof. In various embodiments, network interface 240 can support communication via wired or wireless general data networks, such as any suitable type of Ethernet network, for example, via digital fiber communications networks; via storage area networks such as Fiber Channel SANs, or via any other suitable type of network and/or protocol.

Input/output devices 250 can, in some embodiments, include one or more display terminals, keyboards, keypads, touchpads, scanning devices, voice or optical recognition devices, or any other devices suitable for entering or accessing data by one or more computer systems. Multiple input/output devices 250 can be present in computer system or can be distributed on various nodes of the computing device 200. In some embodiments, similar input/output devices can be separate from the computing device 200 and can interact with one or more nodes of the computing device 200 through a wired or wireless connection, such as over network interface 240.

Those skilled in the art will appreciate that the computing device 200 is merely illustrative and is not intended to limit the scope of embodiments. In particular, the computer system and devices can include any combination of hardware or software that can perform the indicated functions of various embodiments, including computers, network devices, Internet appliances, PDAs, wireless phones, pagers, and the like. The computing device 200 can also be connected to other devices that are not illustrated, or instead can operate as a stand-alone system. In addition, the functionality provided by the illustrated components can in some embodiments be combined in fewer components or distributed in additional components. Similarly, in some embodiments, the functionality of some of the illustrated components may not be provided and/or other additional functionality can be available.

The computing device 200 can communicate with other computing devices based on various computer communication protocols such a Wi-Fi, Bluetooth RTM. (and/or other standards for exchanging data over short distances includes protocols using short-wavelength radio transmissions), USB, Ethernet, cellular, an ultrasonic local area communication protocol, etc. The computing device 200 can further include a web browser.

Although the computing device 200 is depicted as a general purpose computer, the computing device 200 is programmed to perform various specialized control functions and is configured to act as a specialized, specific computer in accordance with the present principles, and embodiments can be implemented in hardware, for example, as an application specified integrated circuit (ASIC). As such, the process steps described herein are intended to be broadly interpreted as being equivalently performed by software, hardware, or a combination thereof.

Those skilled in the art will also appreciate that, while various items are illustrated as being stored in memory or on storage while being used, these items or portions of them can be transferred between memory and other storage devices for purposes of memory management and data integrity. Alternatively, in other embodiments some or all of the software components can execute in memory on another device and communicate with the illustrated computer system via inter-computer communication. Some or all of the system components or data structures can also be stored (e.g., as instructions or structured data) on a computer-accessible medium or a portable article to be read by an appropriate drive, various examples of which are described above. In some embodiments, instructions stored on a computer-accessible medium separate from the computing device 200 can be transmitted to the computing device 200 via transmission media or signals such as electrical, electromagnetic, or digital signals, conveyed via a communication medium such as a network and/or a wireless link. Various embodiments can further include receiving, sending, or storing instructions and/or data implemented in accordance with the foregoing description upon a computer-accessible medium or via a communication medium such as cloud based storage. In general, a computer-accessible medium can include a storage medium or memory medium such as magnetic or optical media, e.g., disk or DVD/CD-ROM, volatile or non-volatile media such as RAM (e.g., SDRAM, DDR, RDRAM, SRAM, and the like), ROM, and the like.

When a patient record is shared with another medical professional, if the professional does not have access to the D a t a Command Center of the present principles, the other medical professional can receive an email to register for access to the Data Command Center. In some embodiments, if the professional does have an account but a new patient is being shared, the physician can receive an email notification. The new external user will only have access to the specific patients that are shared. Such sharing of patient medical records amongst the patient's physicians better enables the physicians to work together to follow preferred practice patterns for patient treatment as may be required by insurance companies and/or the government. This process is particularly helpful for managing patients with certain chronic diseases like diabetes in which a nephrologist, podiatrist, ophthalmologist, endocrinologist, and family physician need to see each other's results. Another example is shared care before and after cataract surgery where optometrists and ophthalmologist need to see each other's results.

Figure 3:
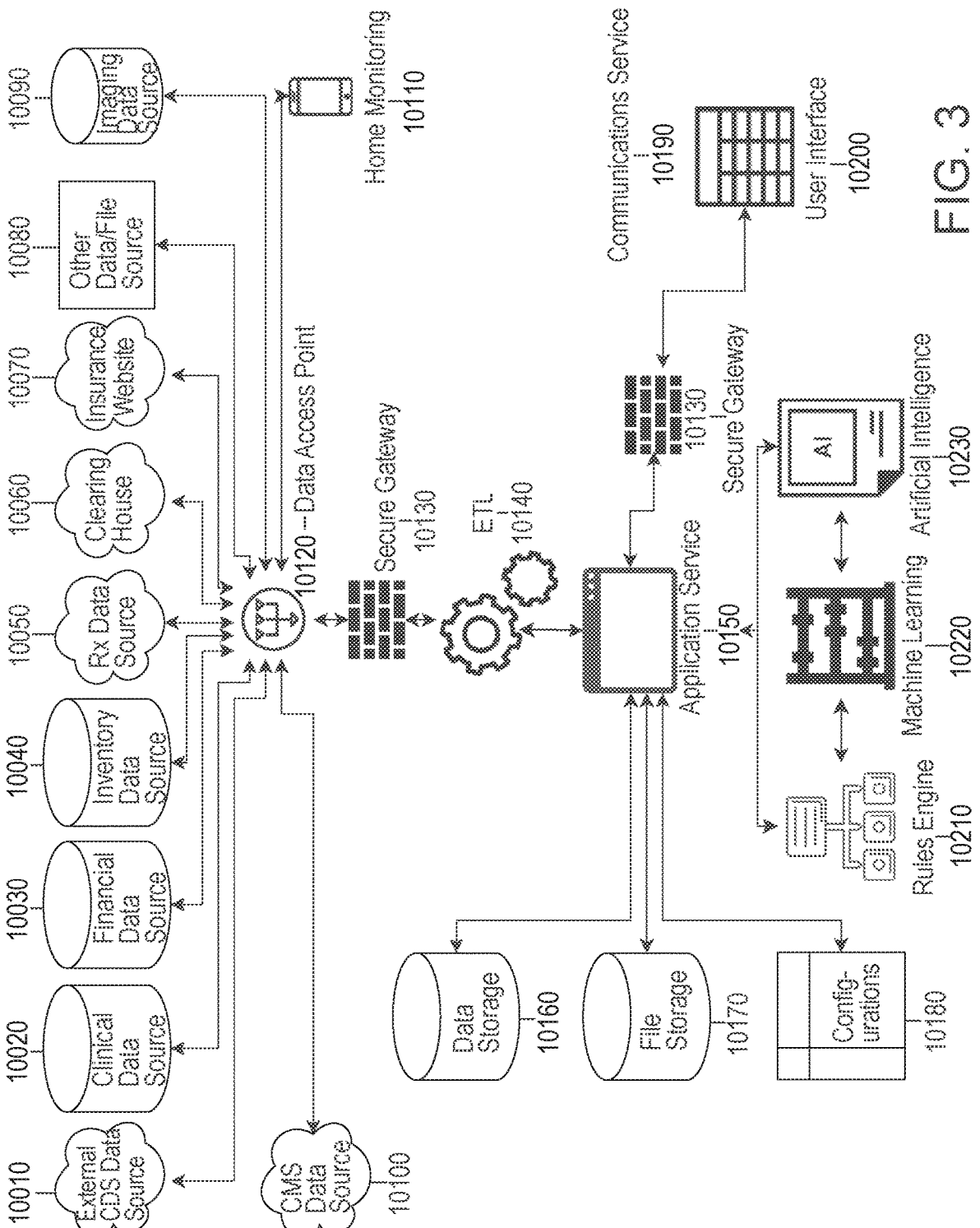
FIG. 3 depicts a high-level infrastructure diagram of a Data Command Center in accordance with an embodiment of the present principles.

FIG. 3 depicts an embodiment of a Data Command Center architecture in accordance with an alternate embodiment of the present principles. FIG. 3 further depicts how the Data Command Center connects to external Health Information Technology systems and third party services 10010-10110. The Data Command Center architecture of FIG. 3 is a multi-tenant cloud-based web application. Multi-tenant infers that the application is deployed once, and all customers access the same server or farm. In the embodiment of FIG. 3, data is segregated by the application so that customers can only access their own data. The Data Command Center is accessible over the Internet via a user interface 10200 through a Secure Gateway 10130.

The Data Command Center architecture illustrated in FIG. 3 is one embodiment of how the system can be configured to access data from multiple sources, compile and evaluate the data, take action, and display the data to the end user. In FIG. 3, for security purposes, access to the cloud platform containing the Data Command Center is governed by a Secure Gateway 10130, whether a connection exists between the Data Command Center and the end user or the Data Command Center and external data sources. Additionally, end to end encryption can be an inherent part of the Data Command Center architecture of FIG. 3 as the Data Command Center architecture is optimized to meet the highest privacy and security expectations. Each component allows for both the application of current high strength encryption (ex. AES 256) as well as continuous implementation of evolving data protection and security best practices.

In the embodiment of FIG. 3, the exchange of information between multiple external health information technology (HIT) systems 10010-10110 and the Application Service 10150 is routed through an external Data Access Point 10120. Exchange of data may occur in a monodirectional or bidirectional manner, dependent upon access and scenario. In such embodiments, external data sources can include, but are not limited to:

External CDS Data Sources: External Clinical Decision Support Data Sources 10010 may include Registries, Societies, Industry Resources, Insurance Companies, and other sources make available relevant rules and data to evaluate against.

Clinical Data Sources: Clinical Data Sources 10020 may include EHR/EHRs, available anonymized Clinical Data Sources, Referral Management Data Sources, and other available clinical data repositories. Clinical data may be read and/or written back to the data source.

Financial Data Sources: Financial Data Sources 10030 may include banks, Clearing Houses, Insurance Data Sources, Center for Medicare and Medicaid Services Data Sources, and other repositories of financial data. Financial Data may be read and/or written back to the data source.

Inventory Data Sources: Inventory Data Sources 10040 may include internal and/or external Inventory Management Systems. Inventory Data may be read and/or written back to the data source.

Rx Data Sources: Rx Data Sources 10050 may include available e-Prescribing Data Sources, Pharmacy Data Sources, and other external Prescription Data Sources. Rx Data may be read and/or written back to the data source.

Clearing House: Clearing Houses 10060 contain large amounts of Financial and Insurance Data, access to Insurance Data Sources, and Claims Scrubbing Mechanisms. Clearing House data may be read and/or written back to the data source.

Insurance Websites: Insurance Websites 10070 offer direct interaction with Insurance Data Sources beyond standardized Clearing House access. Insurance Website data may be read and/or written back to the data source.

Other Data/File Sources: A key benefit of the Command Center is the ability to pull relevant data from various, disparate data sources. Other Data/File Sources 10080 may include any repository of relevant data, Clinical, Insurance, Financial, CDS, or otherwise. Other data sources may comprise non-standard data repositories, smartphone apps, or even a Google or Excel spreadsheet that a practice records relevant data in. Other Data/File Sources may be read and/or written back to the data source.

Imaging Data Source: Imaging Data Sources 10090 may consist of locally hosted image repositories, diagnostic testing systems, cloud-based image repositories, or other sources of medically relevant imaging.

CMS Data Source: The Center for Medicare and Medicaid Services (CMS) 10100 make available patient data for Medicare and Medicaid patients for research and development.

Home Monitoring Devices: With the advent of the IoT, more and more home-based monitoring devices 10110 are being used to track important health information from a patient's home. Such information may be relevant to patient care, and as such, the Command Center reads, compiles, and evaluates said data.

In the embodiment of the Data Command Center of FIG. 3, data can be posted and/or retrieved from External Data Sources 10010-10110, routed through a Data Access Point 10120, validated by a Secure Gateway 10130, and then may be processed through an ETL (Extract Transform Load) service 10140. The ETL service 10140 is utilized by the Data Command Center to perform necessary transformation of data from proprietary or non-standard formats into industry standard formats that are universal, manageable, and portable. It should be appreciated that an inverse ETL process can be utilized to take previously transformed data and return said data in its initial format.

Utilizing such a technique, no one data source need be solely responsible for any given data point. Where accessible, data which can be missing from one system can be imported from a different system if such data exists. Employing the same logic, missing data which may not be found elsewhere can be flagged as missing to inform a user such data is not present in any relevant data source.

A service or group of services, referred to as the Application Service 10150, manage the routing of data between storage 10160-10170, rules engine 10210-10230 services, configuration services 10180, and the user interface 10200 and/or communications service 10190. The Application Service 10150 is responsible for the overall management of data and other services. Data, after transformed into industry standard formats, can be stored in a Data Storage repository 10160, in one or multiple formats dependent upon use case. Data may also not be stored, and directly posted to the User Interface 10200 through a Secure Gateway 10130. Data can also be converted to files and stored within the File Storage repository 10170. Files received can be stored in the File Storage repository 10170, can be reformatted into industry standard formats by the ETL service 10140 and stored in the File Storage repository 10170, or can be transformed into data and stored in the Data Storage repository 10160. Files may also not be stored and directed posted to the User Interface 10200 through a Secure Gateway 10130. Data and Files, stored or not stored, can be posted to the User Interface 10200 through a Secure Gateway 10130 with additional information and/or edits/enhancements/augmentation to their content.

Data and Files can, dependent upon use case, be processed through a Rules Engine 10210 responsible for evaluating a set of rules against the Data and Files. Rules can be predefined, retrieved from external data sources 10010-10110, generated at runtime, and/or generated based on Machine Learning 10220 and/or Artificial Intelligence 10230. Machine Learning 10220 can employ a number of techniques, to adapt to new information, and Artificial Intelligence 10230 may compile, coordinate, and evaluate data for trends to further define new rules.

All relevant data can then be processed through the Application Service 10150 and can be returned to the User Interface 10200 through a Secure Gateway 10130, ensuring proper security and encryption is in place to protect sensitive information. The Configurations service 10180 can store predefined lists used to determine which data can be displayed and can work alone or in conjunction with the Rules services 10210-10230 to make the determinations. The Rules services 10210-10230 can also utilize the Application Service 10150 to access the Communications service 10190 for external automated communications, where appropriate. It should be appreciated that best practices, and evolving technology, can be used to determine the best approach for data retrieval, transformation, storage, and transmittal in accordance with the present principles.

Figure 4:
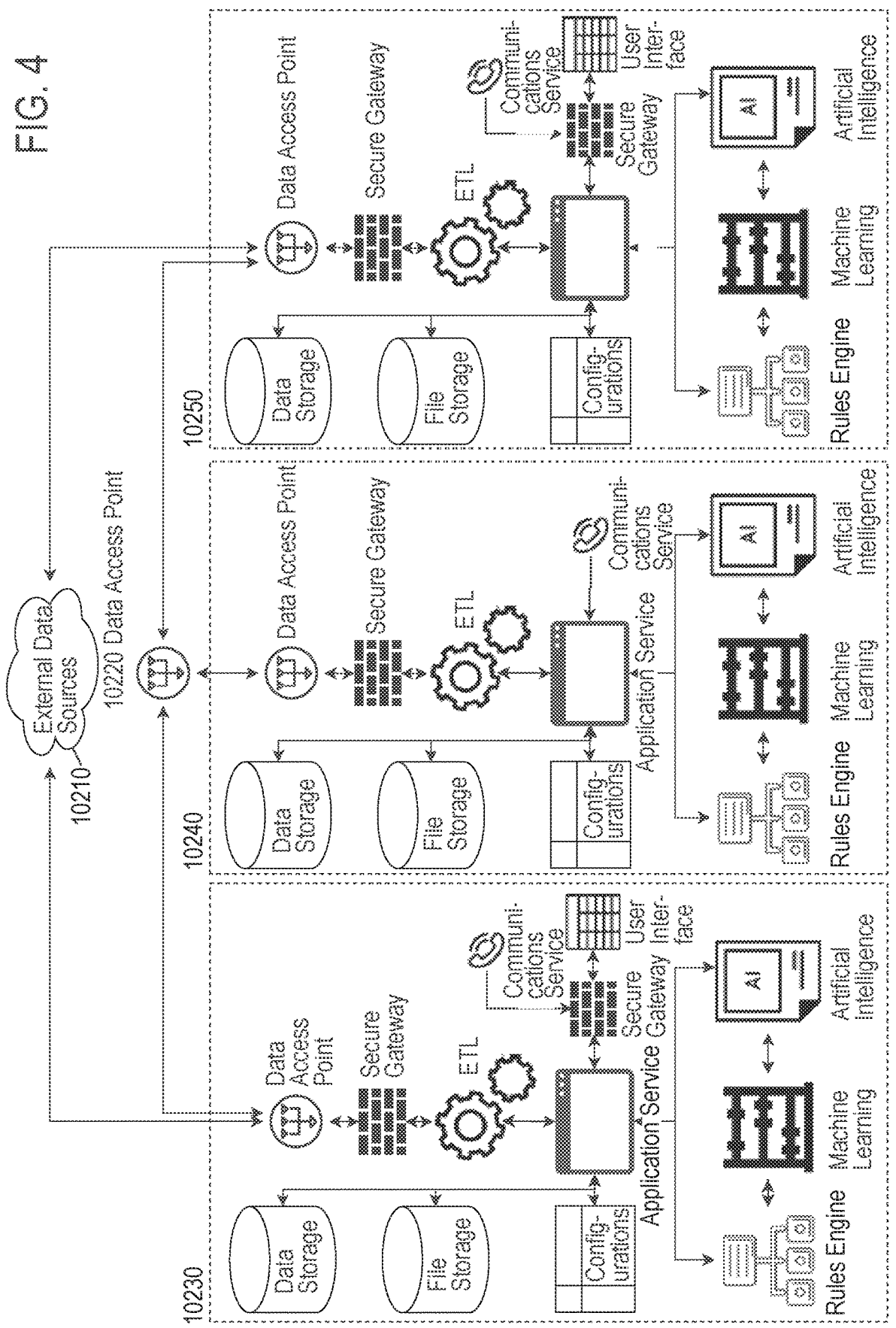
FIG. 4 illustrates a logical implementation of a multi-tenant example of Dynamic Health Records with a Co-Management Connection to allow for sharing of data.

FIG. 4 depicts an implementation diagram of the ability of the Data Command Center of the present principles to connect several instances of the application to each other, as well as to external data sources, such that all can function as a single, logical application. As depicted in FIG. 4, utilizing a multi-tenant architecture, all data can be centralized, and managed by the Application service 10150 of, for example, FIG. 3. Logical separation of data occurs at the software level. That is, FIG. 4 is an example of an implementation diagram whereby multiple tenants 10230, 10240 can subscribe to multiple external data sources 10210, which can consist of both unique and shared resources. In this example, the first Client 10230 and second Client 10240 can exist within a single server or farm, yet the logical separation of data still exists. A third instance of the application 10240 can be used to connect the Clients to each other through use of an external or internal Data Access Point 10220. As such, each Client functions as its own entity, yet sharing of data between clients can be achieved.

Figure 5:
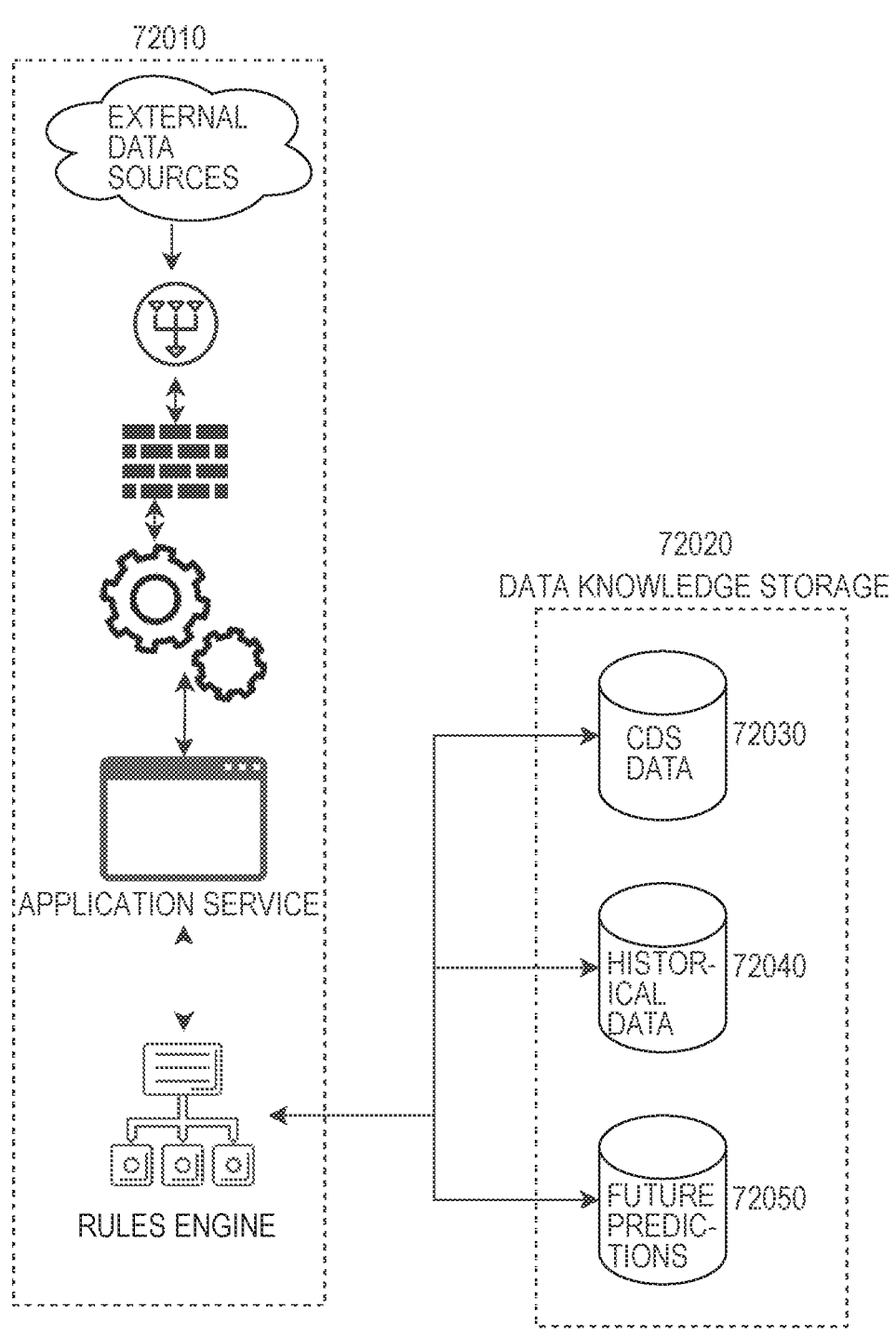
FIG. 5 illustrates a high-level data knowledge storage system in accordance with an embodiment of the present principles.

FIG. 5 illustrates a high-level data knowledge storage system in accordance with an embodiment of the present principles. The process for interaction between external data sources 10010-10110 of FIG. 3 and the Rules Engine 10210 of FIG. 3 is summarized in 72010 of FIG. 5. As such, interaction with all available data is accessible to the Rules Engine. Subsequently, the Rules Engine can implement various storage mechanisms to maintain an accurate account of transformations and states of data. This can be achieved using, as shown in the example, Data Knowledge Storage 72020. Data Knowledge Storage can consist of separate repositories, or a single repository logically divided. Such data can be categorized, as in this example, as Clinical Decision Support data 72030, Historical Data 72040, and Future Predictions 72050. Clinical Decision Support data can be comprised of data directly accessed from External CDS Data Sources 10010 of FIG. 3, or any of the other relevant data sources, and can also be derived or compiled by the application, itself. Historical Data 72040 maintains an active record of augmentation and alteration performed by the Command Center to allow for the application to reference prior states of data at any given time. Future Prediction Data 72050 maintains an active record of predictions made for validation as well as to maintain a record of options available to correlate with actions other than those predicted for.

Figure 6:
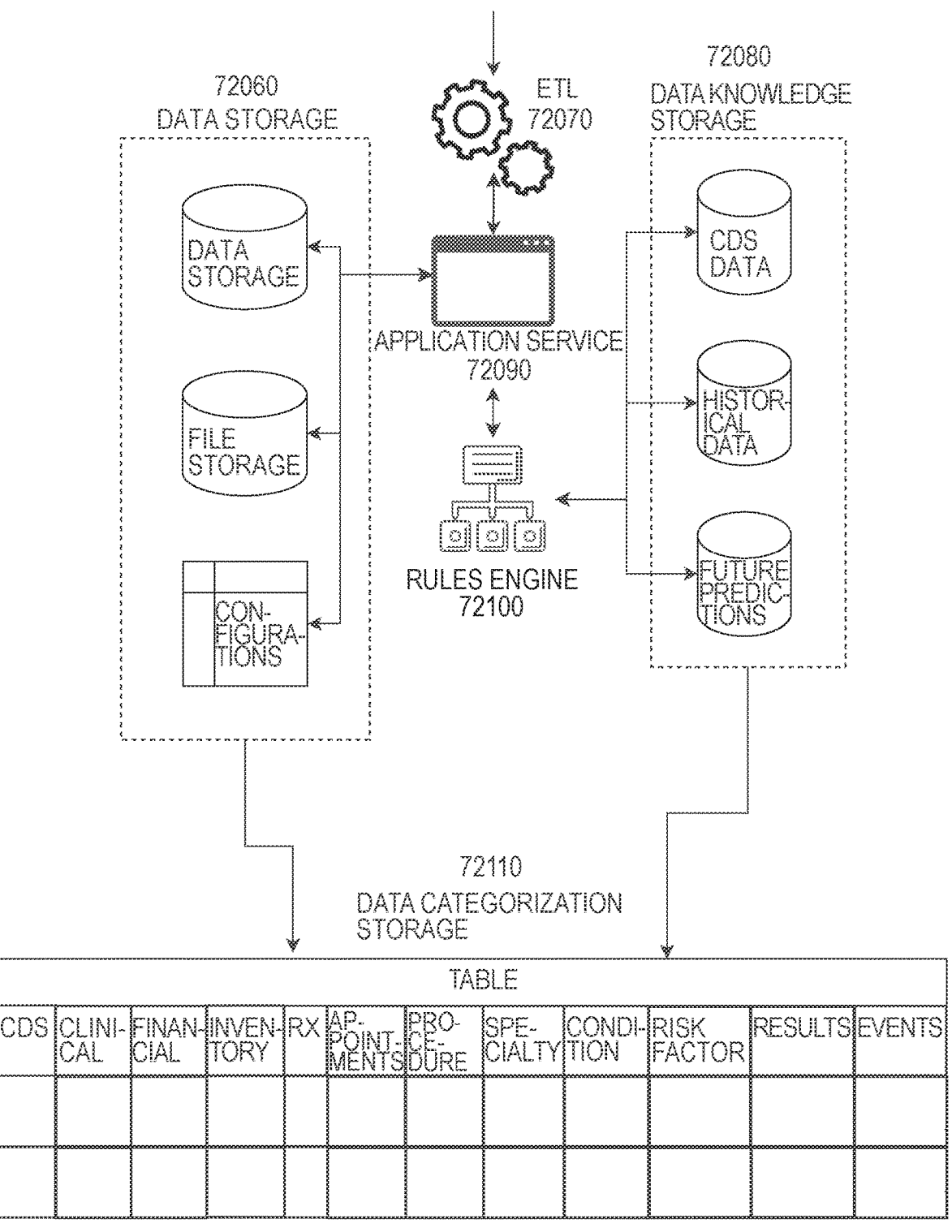
FIG. 6 illustrates a high-level data categorization system in accordance with an embodiment of the present principles.

FIG. 6 illustrates a high-level data categorization system in accordance with an embodiment of the present principles. As previously described, data received from External Data Sources 10010-10110 of FIG. 3 is processed through an ETL process. Illustrated in FIG. 6 as 72070, this ETL process converts data received to standardized formats, which enables data of a similar category to be received from multiple sources. External data received is generally stored in the Data Storage 72060. Such data storage is managed through the Application Service 72090. Data generated by the application is generally stored in the Data Knowledge Storage 72080. Such data storage is managed through the Rules Engine 72100. All data storage is subsequently categorized for easy searchability and reporting purposes in the Data Categorization Storage 72110. Data is categorized into topics derived by requirements described herein. It should be noted that data is not limited to existing in a single category, and all data associated with a category can be stored or associated with its respective category.

Figure 7:
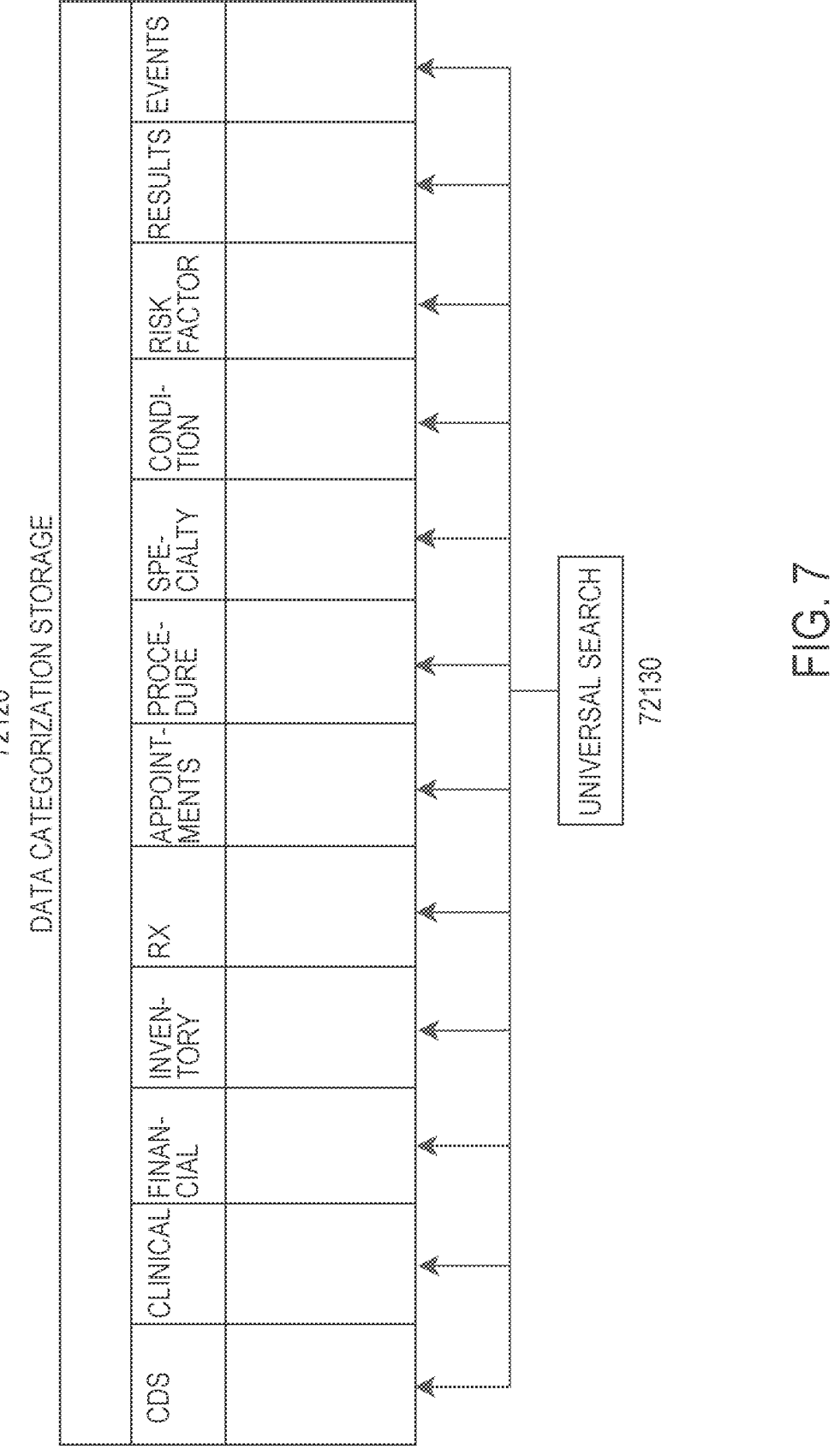
FIG. 7 illustrates a high-level data category search system in accordance with an embodiment of the present principles.

FIG. 7 illustrates a high-level data category search system in accordance with an embodiment of the present principles. In embodiments of the Data Command Center of the present principles, search boxes appear to query relevant data. Each search box can be individually configured to return data only related to a specific section of the application, but all search boxes can conform to a standardized Universal Search, as illustrated in FIG. 7. As data is received, transformed, and categorized, it is this final result of categorization by which a search is performed. The categorized information can reside in data storage such as Data Categorization Storage 72120, in a search-friendly format such as a star schema.

The Universal Search box 72130 queries against this precategorized data, granting the ability to search data that may have originated from a variety of data sources through a single, universal search mechanism.

Figure 8:
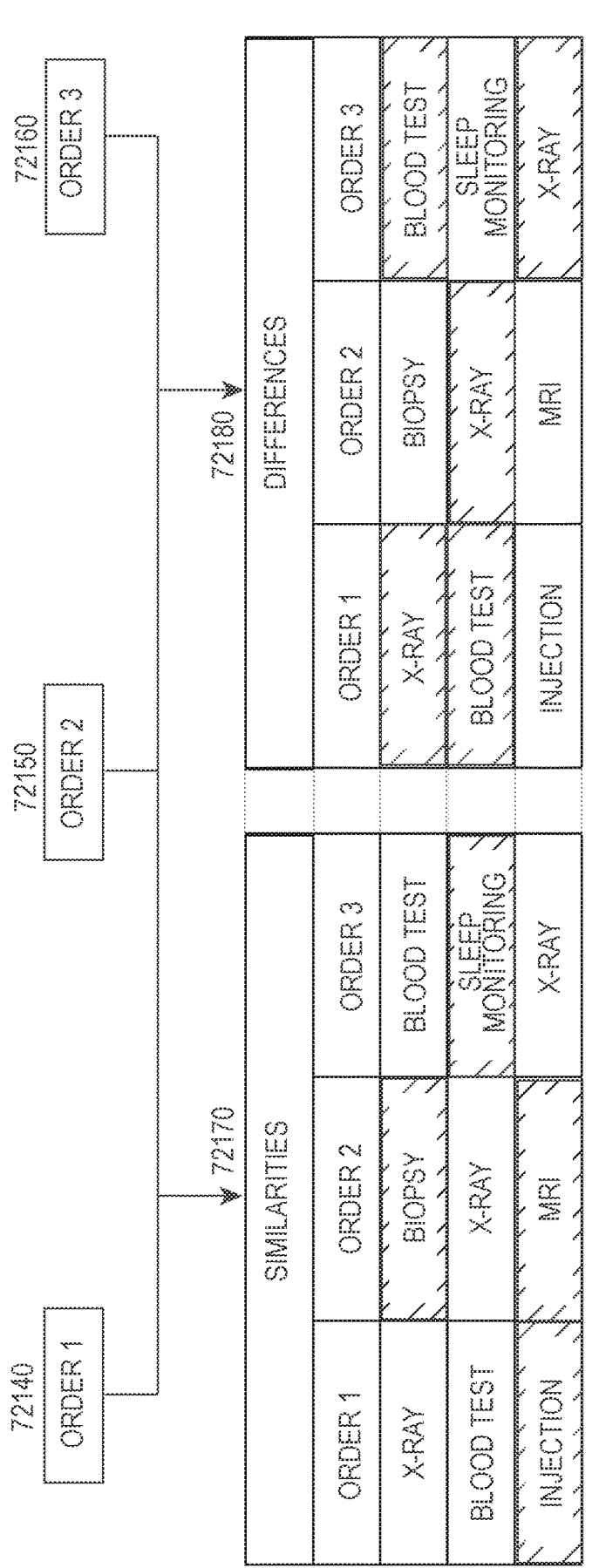
FIG. 8 illustrates a high-level data correlation system in accordance with an embodiment of the present principles.

FIG. 8 illustrates a high-level data correlation system in accordance with an embodiment of the present principles. In embodiments of the present principles, as data is received from multiple sources, and collated from multiple practices, overlap becomes apparent. One doctor in one office may be attempting to schedule the same test or treatment as another doctor in another office. Or, perhaps, one doctor is scheduling a test or treatment that another has already completed. Such instances lead to wasted time and effort, while increasing cost. As such, when an event occurs, the Command Center searches all relevant data in the category to see if there is an existing record which would suffice the requirement. In the embodiment of FIG. 8, three orders 72140-72160 are being placed. The Data Command Center of the present principles reviews the orders for Similarities 72170 and Differences 72180. Identified Similarities, in this example, include X-Rays and Blood Tests. It is possible the same X-Ray is required by all requestors, and as such, the Data Command Center can suggest a single order to satisfy all requirements. It is also possible that each Blood Test requires the same or slightly different requirements. The Data Command Center can suggest multiple tests be run on a single sample to reduce redundancy. In the case of the differences, 72180, the Biopsy, Sleep Monitoring, Injection, and MRI are unique. The Data Command Center can still suggest utilization of a single resource, such as one lab, for all diagnostics.

Figure 9:
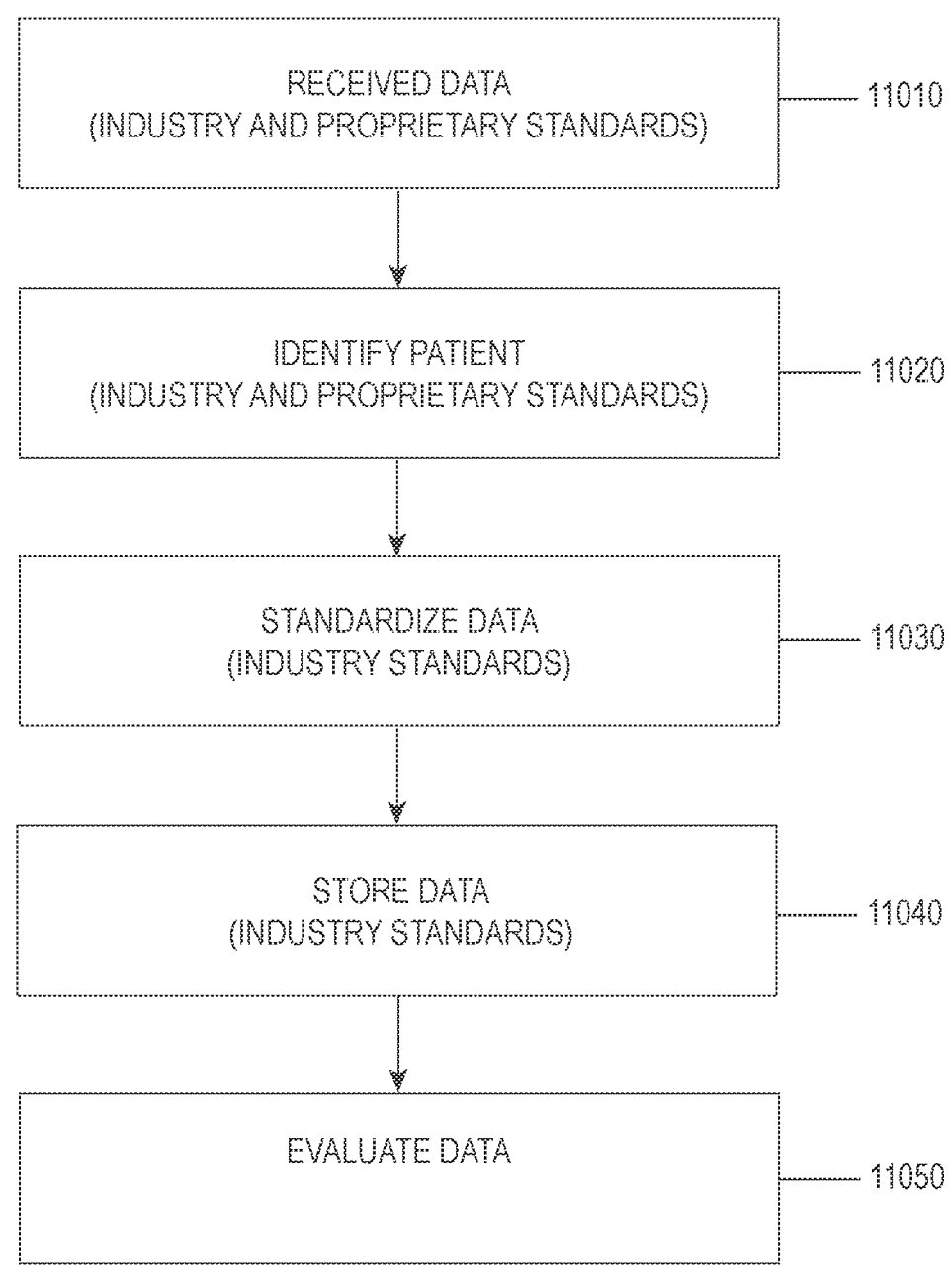
FIG. 9 Illustrates a standard workflow when data is received from an external system through any of the messaging standards or API methods in accordance with the tool described herein.

FIG. 9 depicts a high-level workflow diagram of the receipt, storage, and evaluation of data associated with a Data Command Center of the present principles. In the embodiment of FIG. 9, the Data Command Center can use constant poling at interval or monitoring for change to determine when new data is available. When data is received from an external system 10010-10100 through any of the messaging standards or API methods, a standard workflow can be followed as depicted in the embodiment of FIG. 9. The first step (11010) is to receive data using the previously discussed methods. The message is parsed and the patient identifying information is extracted so the correct Patient can be identified (11020). Once the patient is identified, the data is standardized (11030) so that the data can be effectively used in the Data Command Center and then can be stored (11040). The last step in the process is to evaluate the data (11050) using a variety of mechanisms using advanced analytics as will be described in greater detail below.

In accordance with the present principles, there exist multiple criteria which affect the display and augmentation of data fields, considered by the inventors as Dynamic Data Fields, for a Data Command Center of the present principles. In some embodiments, the Data Command Center enables the medical records dashboard to intelligently alert by any means, gray out, expand, collapse, display, and/or hide columns, rows, fields, and/or any other portion of the medical records dashboard to show precisely what a user wishes to display, or can alert by any means, gray out, expand, collapse, display, and/or hide columns, rows, fields, and/or any other portion of the medical records dashboard based on rules or triggers overriding the user's pre-determined display to show important details which the user should be made aware of. For example, in one embodiment, a Flowsheet including patient treatment and health information can be accessed from an EHR system using, in some embodiments, an icon/button, keystroke, or series of keystrokes, gesture, voice command, or other means, associated with at least one of the Data Command Center and the medical records dashboard. Upon accessing the Flowsheet, a set of Rules and Configurations associated with, for example, a Rules Engine, for example the Rules Engine 10180 of FIG. 3, can be evaluated to determine which data from the Flowsheet is to be displayed in a medical records dashboard of the present principles. For example, in some embodiments, the Rules Engine 10180 of FIG. 3 can include information on what data to display, and in turn what portions of the medical records dashboard to display, based on, including but not limited to, at least one of an identity of a medical care provider, an identity of a patient, a patient's medical history, a medical care provider's specialty, a user's custom configurations, patient appointment type, conditions of a patient, patient procedures, risk factors, diagnostic tests and/or results, future orders, future appointments, co-management status, predefined triggers, triggers generated in real time, values recorded, values not recorded, calculated values, and absolute values for display.

For example, in some embodiments in accordance with the present principles, Rules and Configurations can be predetermined and stored, for example, in the Rules Engine 10180 of FIG. 3, for determining which data of a Flowsheet and, as such, which portions of the medical records dashboard to alert by any means, gray out, expand, collapse, display, and/or hide based on known rules. Alternatively, or in addition, in some embodiments, a user can self-configure the medical records dashboard to display only certain portions or to hide certain data of a Flowsheet and, as such, which portions of the medical records dashboard to display or to hide using, for example, a user interface associated with the medical records dashboard. Alternatively, or in addition, data of the Flowsheet can contain an indicator (e.g., a flag) that can be identified by, for example, the Rules Engine 10180 of FIG. 3, for determining when and if a piece of data should be displayed, or can alert by any means, gray out, expand, collapse, display, and/or hide.

Figure 10:
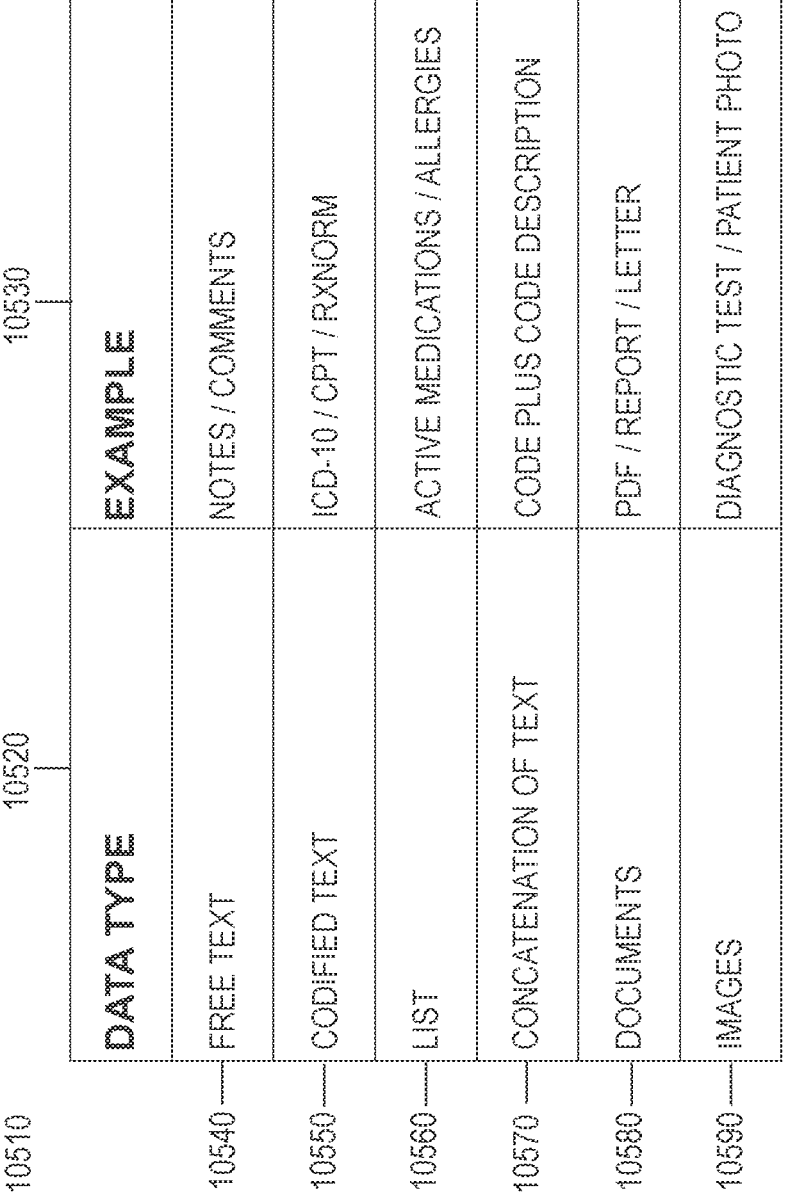
FIG. 10 illustrates examples of different data being accessed.

FIG. 10 depicts a Table listing of examples of different data types able to be accessed by a Data Command Center of the present principles such as the Data Command Center of FIG. 3. Data takes many forms, and is an overarching term for information, in general, regardless of format. In the case of Healthcare IT, certain standards exist, and data types which are common to the development of digital solutions. For the purpose of this document, several examples 10510 of data being accessed are listed below.

These data are listed by type 10520 and Example 10530. For example, such data can include but is not limited to:

Free Text 10540: Generally, any text that is entered free-hand without pertaining to a selectable list of options or industry standard. Notes and Comments fall into this category.

Codified Text 10550: Certain text within Healthcare IT applications are directly connected to industry standard code lists, such as ICD-10, CPT Codes, and RxNorm codes.

List 10560: Data elements can be comprised of lists of Problems, Medications, Allergies, or the like, and are stored and transported as such.

Concatenation of Text 10570: Not all data is maintained in normalized and standardized formats. As such, the ability to read and parse sections of text is important. In the case of data strings which can contain several elements, such as a code and a description, or a date and a doctor or location, certain elements can be important, while others can be ignored.

Documents 10580: Some data is simply stored in a precompiled format, such as a PDF or Word document. As such, the document can be stored and transported or can be parsed and data elements pulled out to populate discrete data fields.

Images 10590: Images can contain nothing more than the image, itself, and as such can be stored and transported in native format or converted to a different format. Images can also contain metadata and/or data elements within the image. As such, they can be parted, and data elements pulled out to populate discrete data fields.

In co-management, where different practices share information about the same patient, it is critical to identify that the patient that is being shared is in fact the same person. There can be dozens of John Smiths and systems cross-reference by looking at the last name, the age, the gender, the zip code and perhaps the home address. But still, there can be confusion between patients. In medicine you can take no chances that you confuse one patient with the other and when patients travel from different offices or different EMRs and computer systems, the possibility of confusion is present.

In some embodiments, the Data Command Center of the present principles, such as the Data Command center 001 of FIG. 1, enables unique patient identification by incorporating patient medical history information. Current methods for identifying patients include matching Social Security Numbers (SSN) and Driver's License Numbers, where available. However, as privacy became more of a concern in the modern digital age, such data is becoming less available to medical care providers and their Practices. In addition, other methods for identifying patients can include identifying patients via First Name, Middle Name or Initial, Last Name, Age, Sex, Address, City, State, and Zip Code. Such information, however, is subject to flaws of human error, such as typos, human choice, such as a patient offering a nickname instead of the accurate name on a birth certificate or other identification. In addition, even having accurate patient information, it can still be difficult to distinguish between two people having the same name. Using such current methods, multiple systems are only able to match patients whose information is listed exactly the same in the multiple systems, a limitation which requires human intervention and prevents full automation of the process.

A subset of data exists within the Medical Community, as mandated by Meaningful Use 2014 and 2015 EHR Certification requirements specified in 45 CFR § 170.102, known as the Common Clinical Data Set (CCDS). The CCDS consists of patient information including, Patient Name, Sex, Date of birth, Race, Ethnicity, Preferred language, Smoking status, Medical Problems, Medications being taken, Medication allergies, Laboratory test(s) having been performed on the patient, values of the Laboratory result(s), Vital signs, Procedures, Care team member(s), Immunizations, Unique device identifier(s) for a patient's implantable device(s), Assessment and plan of treatment, Treatment Goals, Health concerns and the like.

CCDS was developed to encourage interoperability through the exchange of a common data set and is routinely shared between practices by means of the Direct Messaging Exchange, a secure messaging system by which Continuity of Care Document (CCD) or other document conforming to the Clinical Document Architecture (CDA) as defined in the 2014 and 2015 Certified EHR requirements. This is the current standard for Clinical Data transport between EHRs, thus between practices. The future requirement, Fast Healthcare Interoperability Resources (FHIR), expands on the clinical data set to include more discrete data points.

In accordance the present principles, the inventors propose to incorporate such additional data, such as the data supplied through the CCDS, to accurately identify unique patients using a combination of techniques including but not limited to a Common PII Matching technique, a Problems, Allergies, and Medications technique, a Doctors, Locations, and Procedures technique, and CCDS data technique.

In a Common PII Matching technique, none of the PII data may be valid given name changes, nicknames, and misspellings, as well as marriage and legal name changes, addresses and phone numbers change overtime, and the increasing reluctance of patient and practice alike to maintain or share key identification numbers. At best, every data point would need to match exactly to ensure the closest match but can still fall short in the cases of same names such as in the case of George Forman's eight sons all named George Edward Foreman, if date of birth and suffix data was not present. Twins could make identification even more difficult. As evident, the Common PII Matching technique may not be reliable on its own for identifying unique patients.

In a Problems, Allergies, and Medications technique, a commonly shared data set which includes key conditions (Problems), allergies to certain medicines (Allergies), and specific medications (Medications), is compared to determine a profile of a patient which offers an additional level of accuracy by taking a loose match from PII and determining if that patient also has the same list of Medical Problems, Allergies, and Medications in a system for comparison. The likelihood that two people within similar PII, or lacking key aspects of PII, would also share the same Problems, Allergies, and Medications is a significant reduction in ambiguity. For instance, George Foreman's 3rd son may share certain genetic predispositions to Medical Problems and even share Allergies with a $1^{st}$ son, but the likelihood that George Foreman's two sons would have been prescribed the same exact Medications for these and any other Problems they have is minimal.

In a Doctors, Locations, and Procedures technique, information from a document complying with the CCDA can be used for identifying a unique patient. For example, each CCD, or document complying with the CCDA, is required to have specific information in the Header of the document denoting the Care Provider, Date, and Location. The body of the document contains Procedures and relative Dates. The high accuracy enabled when comparing patients' Doctors, Locations, and Procedures is a product of the inability for a Doctor to see more than one patient at the exact same time, the unlikelihood of that even if the doctor saw more than one patient at the same time, and at the same location, the Doctor still would have little ability to perform the same procedure at the same time on more than one patient.

In a CCDS data technique, additional Data from the CCDS, when available, offers increased accuracy in patient identification and matching. That is, comparing patient information including at least Patient Name, Sex, Date of birth, Race, Ethnicity, Preferred language, Smoking status, Medical Problems, Medications being taken, Medication allergies, Laboratory test(s) having been performed on the patient, values of the Laboratory result(s), Vital signs, Procedures, Care team member(s), Immunizations, Unique device identifier(s) for a patient's implantable device(s), Assessment and plan of treatment, Treatment Goals, Health concerns and the like, among different patients, greatly increases the accuracy of unique patient identification.

In some embodiments of a Unique Patient Identification method of a Data Command Center in accordance with the present principles, a Unique Patient Identification algorithm collects every available Identification Point, validates the points for presence of data, and assigns each Identification point a level of accuracy as it pertains to Patient Matching. Presence of data points with High Accuracy are prioritized and validated. Each Exact match is scored for accuracy. Each Likely Match is appropriately scored for accuracy. Each data point with no matching counterpart is negatively scored. Presence of data points with Moderate Accuracy are then prioritized and validated. Each Exact match is scored for accuracy. Each Likely Match is appropriately scored for accuracy. Each data point with no matching counterpart is negatively scored. Moderate accuracy data points are scored lower than High accuracy data points. Presence of data points with Low Accuracy are then prioritized and validated. Each Exact match is scored for accuracy. Each Likely Match is appropriately scored for accuracy. Each data point with no matching counterpart is negatively scored. Low accuracy data points are score lower than Moderate accuracy data points.

Upon gathering and analyzing all available data for Unique Patient Identification, scores are tallied and compared to an acceptable Matching Threshold. In some embodiments of the present principles, the Matching Threshold is configured to clearly exceed a matching accuracy of current patient identification techniques with the inclusion of far more points of identification to compare. In some embodiments, the matching of the present principles can occur without the requirement of matching on current PII data. For example, George Edward Foreman IV may have been staying with a friend in Florida when he visited a doctor. Not wanting to be identified as the son of the famous boxer, he purposely listed his name as G. Foreman and address as the place he was staying. Date of birth may have been left blank. A positive identification can still be made, in accordance with the present principles, if the clinical data supplied matches with a high enough degree of accuracy clinical data stored for George Edward Foreman IV, such as the unique identifier on his knee replacement or the fact that a large number of Doctors, Locations, Procedures, Problems, Allergies, Medications, and Lab Results are found to be matching, while the name, address, and date of birth have non-matching counterparts.

A Unique Patient Identification algorithm of the present principles can reach a logical end when a positive match is determined, or no positive match can be made. In some embodiments, should no positive match be made, the patient and possible matches can be flagged for human intervention.

FIG. 11 depicts a flow diagram of a method for Unique Patient Identification for a subject patient in a Data Command Center including patient-related data received or derived from at least one patient database in accordance with an embodiment of the present principles. The method 2900 of FIG. 11 illustratively begins at 2902 during which different classifications of patient-related data is collected for the subject patient. For example, and as described above, in some embodiments, data from the Common Clinical Data Set and other sources can be collected to be used in patient identification techniques of the present principles. The method 2900 can proceed to 2904.

At 2904, level of accuracy scores are given for each of the patient-related data of the different classifications collected. The method 2900 can proceed to 2906.

At 2906, the level of accuracy scores for each of the patient-related data of the different classifications are added. The method 2900 can proceed to 2908.

At 2908, a total of the added level of accuracy scores is compared to a previously determined matching threshold. The method 2900 can proceed to 2910.

At 2910, if the total of the added level of accuracy scores exceeds the matching threshold, an identification of the subject patient is established. The method 2900 can proceed to 2912.

At 2912, if the total of the added level of accuracy scores does not exceed the matching threshold, more patient identification data is collected and the method 2900 can return to 2906. The method 2900 can then be exited.

The Command Center clinical decision support logic is implemented in a variety of methods. Pre-authorization, referral management, claims scrubbing, medical necessity checking for compliance with governmental and insurance regulations, and similar rules are embodied in the system through the use of third party systems. Internally, the Rules Engine (10180 of FIG. 3) is an implementation of the if-then style of clinical decision support.

Figure 12:
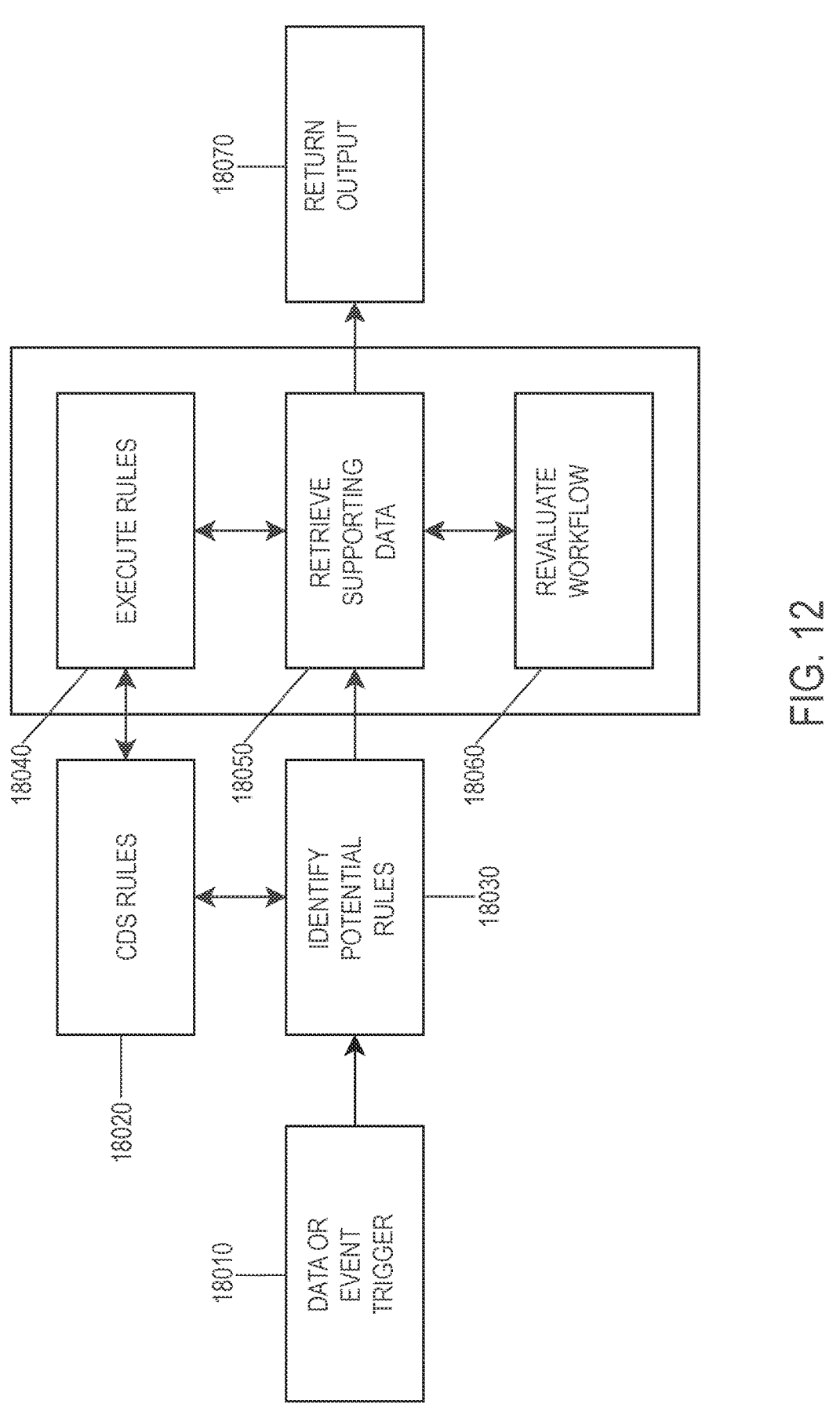
FIG. 12 illustrates an exemplary clinical decision support system in accordance with the tool described herein.

More complex clinical decision support is illustrated in FIG. 12. In FIG. 12, the support is handled through the use of a RETE style (pattern matching, rules-based) algorithm. A RETE rules engine or inference engine embodies a set of rules built around a data model whereby when an event is triggered 18010 (data input or a new day starts) potential rules 18020 are identified (18030) that relate to the data/event. If rules are identified, they are executed (18040) along with the evaluation of workflow rules 18050 using supporting data retrieved (18060) as needed from the patient, insurance, clinical, financial, and imaging data repositories. Once complete, the outcome is returned (18070) to the requesting system for processing. Typically, the output is displayed on the screen for the user to consume or for storage in the designated database in the Command Center. In exemplary embodiments, the Command Center CDS illustrated in FIG. 12 is based on the Health Level (HL7) and Object Management Group (OMG) Decision Support Standards making it flexible and compatible with other similar systems. Those skilled in the art will appreciate that the inference engine may implement conventional artificial intelligence techniques such as those provided commercially by Watson Health and Truven Health Analytics, Inc. to process received data in connection with data repositories to provide diagnostic feedback and the like.

Figure 13A:
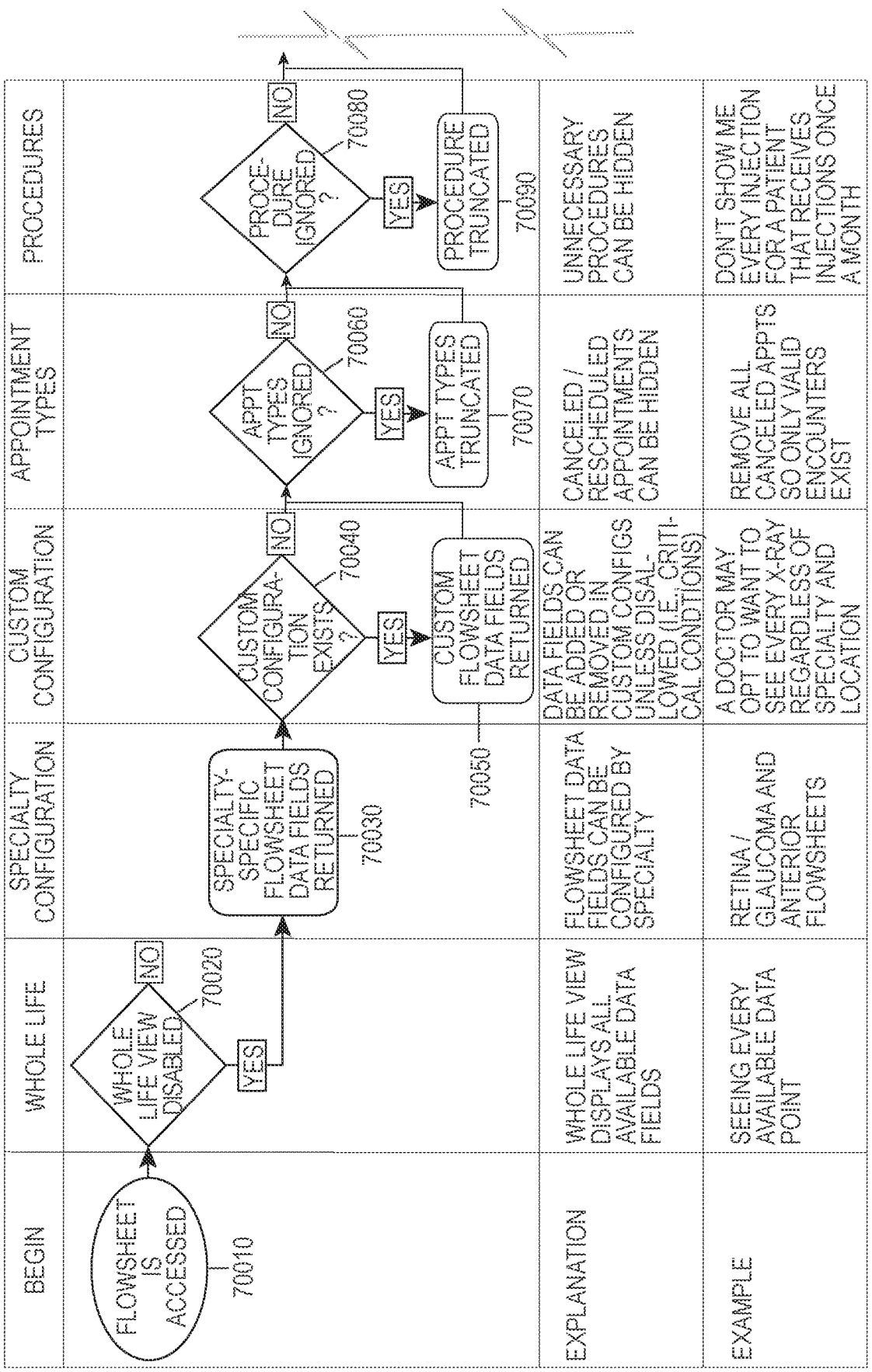
FIG. 13A depicts a first portion of a workflow diagram of a process for intelligently expanding, collapsing, highlighting, emphasizing, graying, displaying, and/or hiding columns, rows and/or any other portion of the medical records dashboard in accordance with an embodiment of the present principles.
Figure 13B:
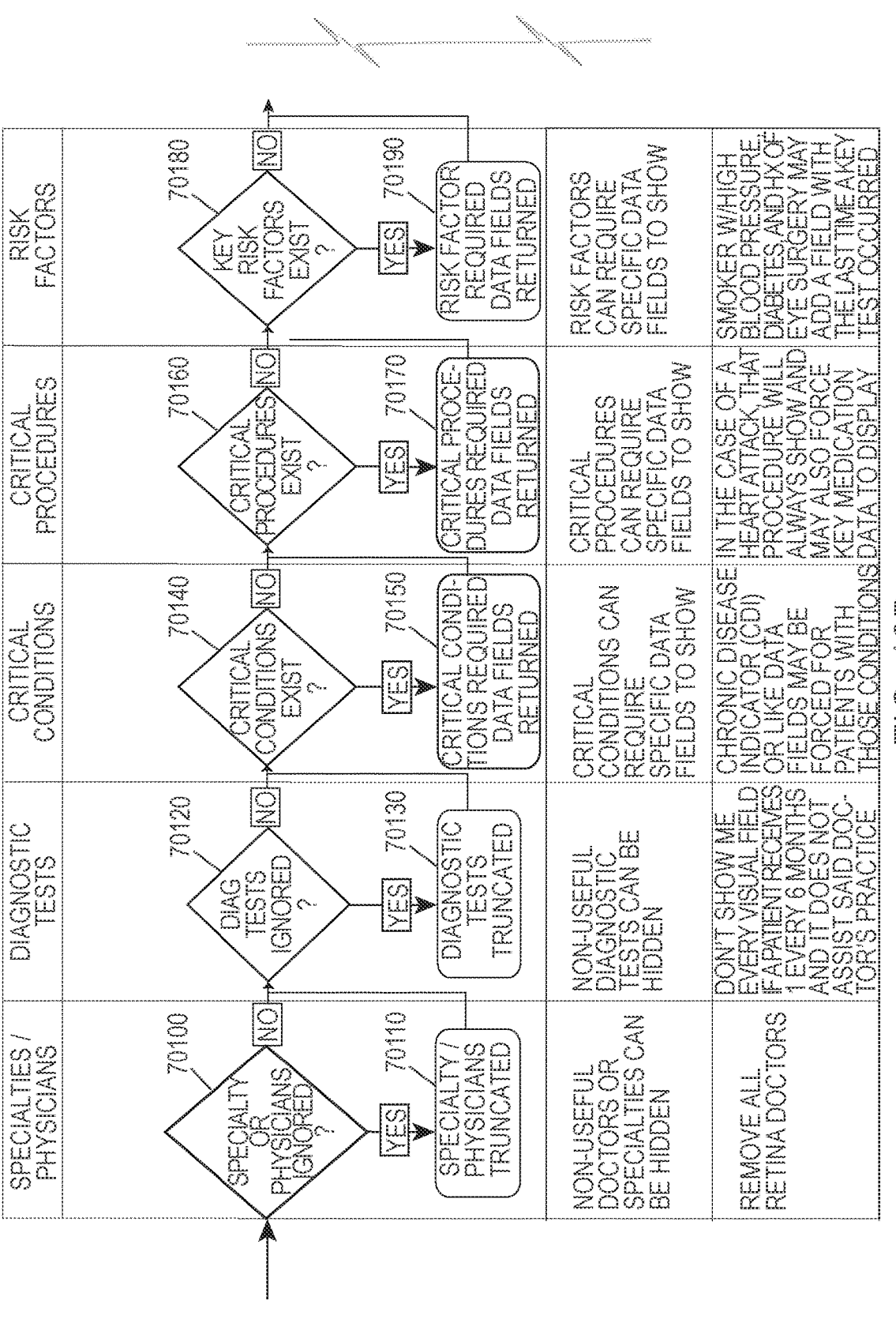
FIG. 13B depicts a second portion of the workflow diagram of a process of FIG. 48A for intelligently expanding, collapsing, highlighting, graying, displaying, and/or hiding columns, rows and/or any other portion of the medical records dashboard in accordance with an embodiment of the present principles.
Figure 13C:
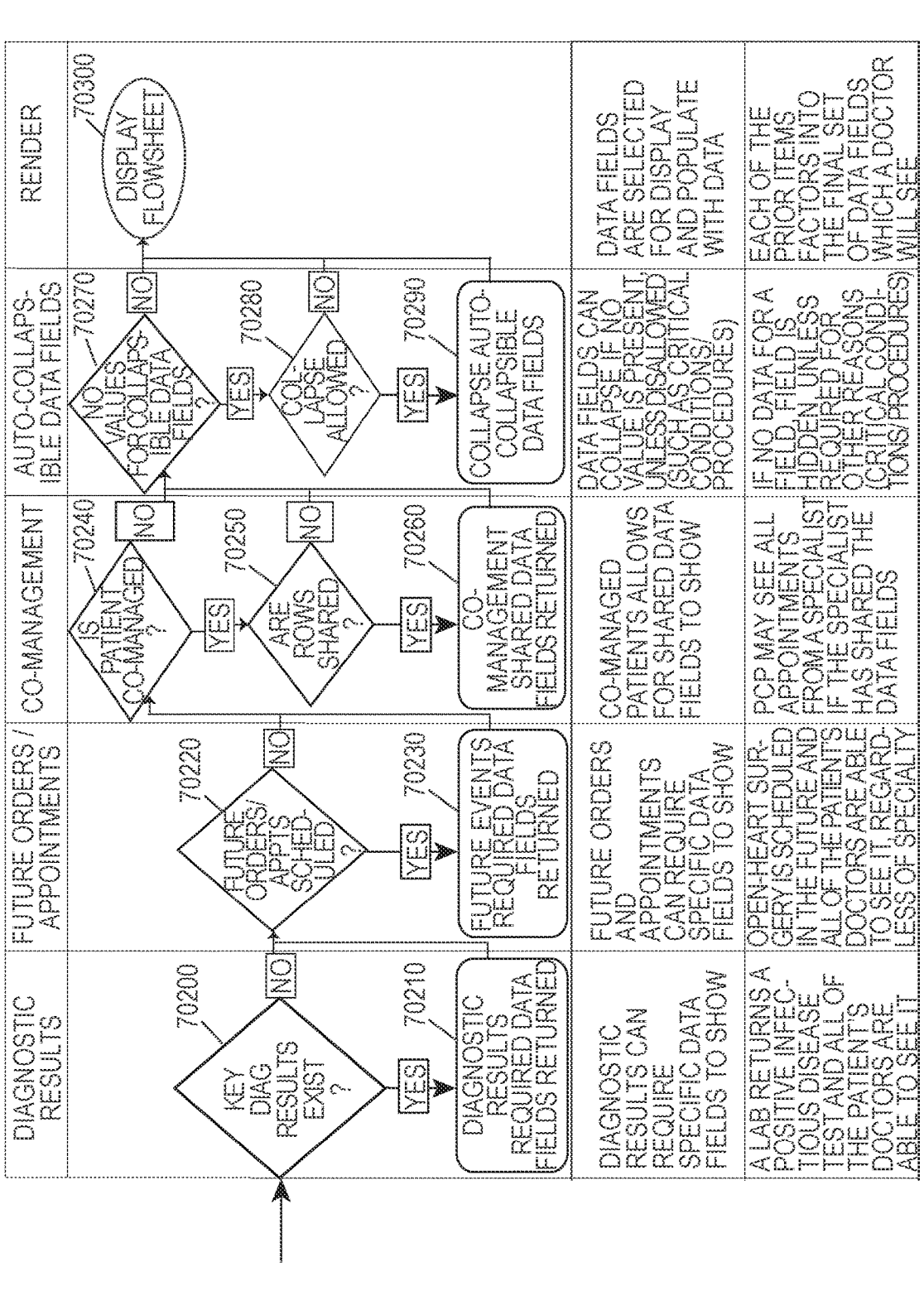
FIG. 13C depicts a third portion of the workflow diagram of a process of FIG. 48A for intelligently expanding, collapsing, highlighting, graying, displaying, and/or hiding columns, rows and/or any other portion of the medical records dashboard in accordance with an embodiment of the present principles.

FIGS. 13A, 13B, and 13C, collectively referred to as FIG. 13 herein, depict a workflow diagram of an alternate embodiment of a process for intelligently alerting by any means, graying out, expanding, collapsing, displaying, and/or hiding columns, rows, fields, and/or any other portion of the medical records dashboard based on rules. In the embodiment depicted in FIG. 13, the process begins at 70010 during which a Flowsheet including patient treatment and health information is accessed from, for example, an EHR system. The process illustratively proceeds to 70020. At 70020, it is determined if, what the inventors refer to as a "Whole Life View", is disabled. More specifically, at 70020 it is determined if all the data in the Flowsheet should be displayed in the medical records dashboard. If Whole Life View is disabled, the process proceeds to 70240 during which all of the data from the Flowsheet is displayed in the medical records dashboard. If not, the process illustratively proceeds to 70030.

At 70030, it is determined if at least one Specialty Configuration exists. For example, in some embodiments a Specialty Configuration can include a configuration based on the specialty of a medical care provider. If so, the process proceeds through 70030 during which all Specialty Configurations are identified such that the data from the Flowsheet can be filtered to only display data associated with identified Specialty Configurations. For example, as previously described, in some embodiments, information associated with medical care provider specialties and data to be displayed and hidden in the medical records dashboard dependent on the specialties can be predetermined and stored in the Rules Engine 10180 of FIG. 3. In accordance with the present principles, Specialty Configurations can require certain portions, columns, and/or rows of the medical records dashboard to be displayed or hidden. After the Specialty Configurations are identified and/or if it is determined that a Specialty Configuration does not exist, the process illustratively proceeds to 70040. In accordance with the present principles, data from the Flowsheet to be displayed in or hidden from the medical records dashboard can be filtered using the identified Specialty Configurations.

At 70040, it is determined if at least one Custom Configuration exists. If so, the process proceeds to 70050 during which all Custom Configurations are identified such that the data from the Flowsheet is filtered to only display or hide, collapse or expand, gray out or alert by any means, data associated with the identified Custom Configurations. For example, in some embodiments custom configurations and data to be displayed in, hidden from, or alerted by any means, the medical records dashboard dependent on the custom configurations can be predetermined and stored in the Rules Engine 10180 of FIG. 3. Alternatively, or in addition, in some embodiments, a user can use a user interface associated with the medical records dashboard to create and/or identify custom configurations. In accordance with the present principles, Custom Configurations can require certain portions, columns, and/or rows of the medical records dashboard to be displayed or hidden. After the Custom Configurations are identified and/or if it is determined that a Custom Configuration does not exist, the process illustratively proceeds to 70060. In accordance with the present principles, data from the Flowsheet to be displayed in or hidden, collapsed or expanded, grayed out or alerted by any means, from the medical records dashboard can be filtered using the identified Custom Configurations.

At 70060, it is determined if at least one predefined Appointment Type exists. That is, in some embodiments, appointment types can be identified that, no matter what rules indicate that certain data should not be displayed or hidden, collapsed or expanded, grayed out or alerted by any means, the identified appointment types are to be displayed or hidden, collapsed or expanded, grayed out or alerted by any means, in at least one location of a medical records dashboard of the present principles. In some embodiments, appointment types can be identified and stored in, for example, a storage accessible by the Rules Engine 10180 of FIG. 3. Alternatively, or in addition, a user can identify appointment types using a user interface associated with a medical records dashboard of the present principles. If it is determined that at least one specified appointment type exists, the process proceeds to 70070 during which the appointment types are identified such that any data from the Flowsheet identified as a specified appointment type can be displayed or hidden, collapsed or expanded, grayed out or alerted by any means, in at least one portion of a medical records dashboard of the present principles. In accordance with the present principles, appointment types can require certain portions, columns, and/or rows of the medical records dashboard to be displayed or hidden, collapsed or expanded, grayed out or alerted by any means. After the appointment types are identified or if it is determined that a specified appointment type does not exist, the process illustratively proceeds to 70080.

At 70080, it is determined if at least one predefined Procedure exists. That is, in some embodiments, procedures can be identified that, no matter what rules indicate that certain data should not be displayed or hidden, collapsed or expanded, grayed out or alerted by any means, the identified procedures are to be displayed or hidden, collapsed or expanded, grayed out or alerted by any means, in at least one location of a medical records dashboard of the present principles. In some embodiments, procedures can be identified and stored in, for example, a storage accessible by the Rules Engine 10180 of FIG. 3. Alternatively, or in addition, a user can identify procedures using a user interface associated with a Data Command Center of the present principles. If it is determined that at least one specified procedure exists, the process proceeds to 70090 during which the procedures are identified such that any data from the Flowsheet identified as a specified procedure can be displayed or hidden, collapsed or expanded, grayed out or alerted by any means, in at least one portion of a medical records dashboard of the present principles. In accordance with the present principles, procedures can require certain portions, columns, and/or rows of the medical records dashboard to be displayed or hidden, collapsed or expanded, grayed out or alerted by any means. After the procedures are identified or if it is determined that a specified procedure does not exist, the process illustratively proceeds to 70100.

At 70100, it is determined if at least one predefined Specialty or Physician exists. That is, in some embodiments, specialties or physicians can be identified that, no matter what rules indicate that certain data should not be displayed or hidden, collapsed or expanded, grayed out or alerted by any means, the identified specialties or physicians are to be displayed or hidden, collapsed or expanded, grayed out or alerted by any means, in at least one location of the medical records dashboard. In some embodiments, specialties or physicians can be identified and stored in, for example, a storage accessible by the Rules Engine 10180 of FIG. 3. Alternatively, or in addition, a user can identify specialties or physicians using a user interface associated with a medical records dashboard of the present principles. If it is determined that at least one specified specialty or physician exists, the process proceeds to 70110 during which the specialties or physicians are identified such that any data from the Flowsheet identified as a specified specialty or physician can be displayed or hidden, collapsed or expanded, grayed out or alerted by any means. In accordance with the present principles, specialties or physicians can require certain portions, columns, and/or rows of the medical records dashboard to be displayed or hidden, collapsed or expanded, grayed out or alerted by any means. After the specialties and physicians are identified or if it is determined that a specified specialty or physician does not exist, the process illustratively proceeds to 70120.

At 70120, it is determined if at least one predefined Diagnostic Test exists. That is, in some embodiments, diagnostic tests can be identified that, no matter what rules indicate that certain data should not be displayed or hidden, collapsed or expanded, grayed out or alerted by any means, the identified diagnostic tests are to be displayed or hidden, collapsed or expanded, grayed out or alerted by any means, in at least one location of a medical records dashboard of the present principles. In some embodiments, diagnostic tests can be identified and stored in, for example, a storage accessible by the Rules Engine 10180 of FIG. 3. Alternatively, or in addition, a user can identify diagnostic tests using a user interface associated with a medical records dashboard of the present principles. If it is determined that at least one specified diagnostic test exists, the process proceeds to 70130 during which the diagnostic tests are identified such that any data from the Flowsheet identified as a specified diagnostic test can be displayed or hidden, collapsed or expanded, grayed out or alerted by any means, in at least one portion of a medical records dashboard of the present principles. In accordance with the present principles, diagnostic tests can require certain portions, columns, and/or rows of the medical records dashboard to be displayed or hidden, collapsed or expanded, grayed out or alerted by any means. After the diagnostic tests are identified or if it is determined that a specified diagnostic test does not exist, the process illustratively proceeds to 70140.

At 70140, it is determined if at least one Critical Condition exists. That is, in some embodiments, critical conditions can be identified that, no matter what rules indicate that certain data should not be displayed or hidden, the identified critical conditions are to be displayed in at least one location of a medical records dashboard of the present principles. In some embodiments, Critical Conditions can be identified and stored in the Rules Engine 10180 of FIG. 3. Alternatively, or in addition, a user can identify Critical Conditions using a user interface associated with the medical records dashboard 400. If it is determined that at least one Critical Condition exists, the process proceeds to 70150 during which the Critical Conditions are identified such that any data from the Flowsheet identified as a Critical Condition can be displayed. In accordance with the present principles, Critical Conditions can require certain portions, columns, and/or rows of the medical records dashboard to be displayed or hidden. After the Critical Conditions are identified or if it is determined that a Critical Condition does not exist, the process illustratively proceeds to 70160.

At 70160, it is determined if at least one Critical Procedure exists. That is, in some embodiments, critical procedures can be identified that, no matter what rules indicate that certain data should not be displayed or hidden, data associated with the identified critical procedures are to be displayed in at least one location of the medical records dashboard 400. In some embodiments, Critical Procedures can be identified and stored in the Rules Engine 10180 of FIG. 3. Alternatively, or in addition, a user can identify Critical Procedures using a user interface associated with the medical records dashboard 400. If it is determined that at least one Critical Procedure exists, the process proceeds to 70170 during which data associated the Critical Procedures are identified such that any data from the Flowsheet identified as being associated with a Critical Procedure can be displayed in at least one portion of the medical records dashboard 400. In accordance with the present principles, Critical Procedures can require certain portions, columns, and/or rows of the medical records dashboard to be displayed or hidden. After the Critical Procedures are identified or if it is determined that a Critical Procedure does not exist, the process illustratively proceeds to 70180.

At 70180, it is determined if at least one Risk Factor exists. That is, in some embodiments, Risk Factors can be identified that, no matter what rules indicate that certain data should not be displayed or hidden, the identified Risk Factors are to be displayed in at least one location of a medical records dashboard of the present principles. In accordance with the present principles, Risk Factors can require certain portions, columns, and/or rows of the medical records dashboard to be displayed or hidden. For example, a smoker with high blood pressure, and diabetes having an identified Risk Factor for a heart attack can require a visual field column with an alert to be displayed in at least a portion of the medical records dashboard 400. In some embodiments, Risk Factors can be identified and stored in, for example, a storage accessible by the Rules Engine 10180 of FIG. 3. Alternatively, or in addition, a user can identify Risk Factors using a user interface associated with the medical records dashboard. If it is determined that at least one Risk Factor exists, the process proceeds to 70190 during which the Risk Factors are identified such that any data from the Flowsheet identified as identifying a Risk Factor can be displayed in at least one portion of the medical records dashboard. After the Risk Factors are identified or if it is determined that a Risk Factor does not exist, the process illustratively proceeds to 70200.

At 70200, it is determined if at least one Key Diagnostic Result exists. That is, in some embodiments, Diagnostic Results that are considered Key can be identified that, no matter what rules indicate that certain data should not be displayed or should be hidden, data associated with the identified Key Diagnostic Results are to be displayed in at least one location of a medical records dashboard of the present principles. In accordance with the present principles, Key Diagnostic Results can require certain portions, columns, and/or rows of the medical records dashboard to be displayed or hidden. For example, if a lab returns a positive infectious disease test, data associated with that Key Diagnostic Result can be caused to be displayed in at least a portion of the medical records dashboard. In some embodiments, Key Diagnostic Results can be identified and stored in, for example, a storage accessible by the Rules Engine 10180 of FIG. 3. Alternatively, or in addition, a user can identify Key Diagnostic Results using a user interface associated with the medical records dashboard. If it is determined that at least one Key Diagnostic Results exists, the process proceeds to 70210 during which the Key Diagnostic Results are identified such that any data from the Flowsheet identified as being associated with a Key Diagnostic Results can be displayed in at least one portion of the medical records dashboard 400. After the Key Diagnostic Results are identified or if it is determined that a Key Diagnostic Results does not exist, the process illustratively proceeds to 70220.

At 70220 of the embodiment of FIG. 13, it is determined if at least one Future Order/Appointment exists. That is, in some embodiments, Future Orders/Appointments can be identified that, no matter what rules indicate that certain data should not be displayed or should be hidden, data associated with the identified Future Order/Appointment are to be displayed in at least one location of a medical records dashboard of the present principles. In accordance with the present principles, Future Orders/Appointments can require certain portions, columns, and/or rows of the medical records dashboard to be displayed or hidden. For example, if an Open-heart surgery is scheduled for the future, it can be desirable for all medical care providers to see the scheduled Open-heart surgery in at least a portion of the medical records dashboard regardless of a medical care provider's specialty. In some embodiments, Future Orders/Appointments can be identified and stored in, for example, a storage accessible by the Rules Engine 10180 of FIG. 3. Alternatively, or in addition, a user can identify Future Orders/Appointments using a user interface associated with the medical records dashboard. If it is determined that at least one Future Order/Appointment exists, the process proceeds to 70230 during which the Future Orders/Appointments are identified such that any data from the Flowsheet identified as being associated with a Future Order/Appointment can be displayed in at least one portion of the medical records dashboard. After the Future Orders/Appointments are identified or if it is determined that a Future Order/Appointment does not exist, the process illustratively proceeds to 70240.

At 70240, it is determined if Co-Management of at least one patient is allowed and if patient information sharing is allowed. That is, in some embodiments, Co-Management of patients can require certain portions, columns, and/or rows of the medical records dashboard to be shared or hidden amongst different users/medical care providers. For example, at 70250, if a medical records dashboard in accordance with the present principles is being used by multiple medical care providers to care for a patient, the patient's primary care physician is able to see lab results from a specialist if the specialist has shared at least the relevant portions of a medical records dashboard. In some embodiments, patient data/information to be shared and, as such, portions of a medical records dashboard to be shared can be identified and stored in, for example, a storage accessible by the Rules Engine 10180 of FIG. 3. Alternatively, or in addition, a user can identify patient data/information to be shared and, as such, portions of a medical records dashboard to be shared using a user interface associated with the medical records dashboard. If it is determined that Co-Management of at least one patient exists and if patient information sharing is allowed, the process proceeds to 70260 during which the existence of Co-Management of at least one patient and patient information sharing is identified such that any data from the Flowsheet identified as being associated with Co-Management and patient information sharing can be displayed in at least one portion of the medical records dashboard 400. After the Co-Management and patient information sharing is identified or if it is determined that Co-Management and patient information sharing does not exist, the process illustratively proceeds to 70270.

In the embodiment of FIG. 13, at 70270, it is determined if any of the collapsible portions, columns, and/or rows of the medical records dashboard contain no respective values (i.e., are empty). If it is determined that collapsible portions, columns, and/or rows of the medical records dashboard contain no respective values, the process proceeds to 70280 during which it is determined if there are any overriding rules to disallow collapsing or hiding portions, columns, and/or rows of the medical records dashboard. If it is determined that collapsible portions, columns, and/or rows of the medical records dashboard contain no respective values, and there are no overriding rules, the collapsible portions, columns, and/or rows of a medical records dashboard of the present principles containing no respective values proceed to 70290 and can be collapsed or hidden from display on a least a portion of the medical records dashboard. After all of the display configurations have been determined as described above, at 70300 the data of the Flowsheet to be displayed, as determined by the process of FIG. 13 described above, is displayed in the medical records dashboard. The process can then be exited.

In accordance with the present principles and as described above, in some embodiments, rules determine portions, columns, and/or rows of the medical records dashboard to expand or display based on predefined criteria, and also determine portions, columns, and/or rows of the medical records dashboard to collapse or hide based on the predefined criteria, and can also determine portions, columns, and/or rows of the medical records dashboard to flag or emphasize such as by highlighting, bolding or otherwise calling attention to records based on the predefined criteria. For example, in some embodiments, the entirety of a patient's accessible records can be viewed. In some embodiments, the entirety of a patient's accessible records is evaluated against specialty and user-specific configuration criteria (e.g., Rules), actively collapsing or hiding portions, columns, and/or rows of the medical records dashboard deemed unnecessary for a user or specialty and actively enabling the display of portions, columns, and/or rows of the medical records dashboard deemed relevant to the user or specialty. In some embodiments, an intelligent Rules system actively determines which portions, columns, and/or rows of the medical records dashboard to display based on a user, a user's specialty, a patient, a patient conditions, a patient procedures, risk factors, diagnostic results, future orders, future appointments, values recorded, values not recorded, calculated values, and absolute values for display. In another embodiment, shared portions, columns, and/or rows of the medical records dashboard between medical care providers and facilities can be added or expanded based on preconfigured or point-of-sharing decisions made by the sharing medical care providers.

Although the embodiment of the process for intelligently expanding, collapsing, displaying, hiding, graying out, and/or alerting columns, rows and/or any other portion of the medical records dashboard of the present principles described with reference to FIG. 13 illustratively comprises specific Rules-based configurations, other embodiments of the process in accordance with the present principles can comprise any combination of some or all of the described Rules-based configurations and can also comprise other Rules-based configurations. Even further, those skilled in the art will appreciate that the order of operations denoted in the process above with reference to FIG. 13 can be non-linear and optimized based on usage and workflow. That is, order, inclusion, and omission can be intelligently determined based on accessibility of data, predefined configurations, real-time user selection, custom configurations, preferred practice patterns, and/or workflow.

In addition, although in the embodiment of the process for intelligently expanding, collapsing, displaying, hiding, graying out, and/or alerting columns, rows and/or any other portion of the medical records dashboard of the present principles described with reference to FIG. 13, the Rules are described as being stored in a storage accessible to the Rules Engine 10180 of FIG. 3, those skilled in the art will appreciate that rules and configurations of a process of the present principles can be stored in tables, accessed remotely via API or other digital communications technology, or generated on-the-fly as the result of calculations during the operations. Rules and configurations can be stored within the application or reference outside data sources. Rules and configurations can be altered by the user, in some embodiments, by the application, in some embodiments, and/or by outside resources.

In addition, although in the embodiment of the process for intelligently expanding, collapsing, displaying, hiding, graying out, or alerting columns, rows and/or any other portion of the medical records dashboard of the present principles described with reference to FIG. 13, it is described that upon rendering the Flowsheet, data populates within the columns specified, in some embodiments, further rules and configurations can apply post-rendering, based on data returned and/or calculated within columns. In addition, in some embodiments, manual manipulation allows for human interaction with the finally determined dataset. As such, a user can acknowledge and remove portions, columns, and/or rows of the medical records dashboard once they have been rendered. Removal of such portions, columns, and/or rows of the medical records dashboard can be one-time, or permanent unless a subsequent event retriggers the rendering of those portions, columns, and/or rows of the medical records dashboard, and such rendering can be patient-specific, provider-specific, location-specific, or otherwise tied to an event, condition, or trigger.

In one example of the process of the present principles, a dentist can access a Flowsheet for a patient with a rare blood disorder. As a dentist, the returned set of data to be displayed in accordance with a process of the present principles would ordinarily include data germane to dentistry, collapsing or hiding certain portions, columns, and/or rows of the medical records dashboard with no values present and/or deemed unnecessary. The dentist can have also chosen not to view certain portions, columns, and/or rows of the medical records dashboard as a matter of practice. In accordance with embodiments of the present principles, as a patient with a rare blood disorder, additional portions, columns, and/or rows of the medical records dashboard could be added to the display to reflect the patient's condition of the rare blood disorder and such information could be emphasized such as by highlighting/flagging to alert a user as to the importance of the information being displayed.

In another example, an ophthalmologist sees a diabetic patient with no diagnostic testing for a chronic illness. As an ophthalmologist, the patient data ordinarily returned for display by a process of the present principles would ordinarily include data germane to ophthalmology, collapsing or hiding certain portions, columns, and/or rows of the medical records dashboard with no values present or data deemed unnecessary for display by the process. In some embodiments, the ophthalmologist can have also chosen not to view certain columns as a matter of practice. As a patient with a lapse in testing and underlying condition requiring testing, portions, columns, and/or rows of the medical records dashboard having no value present which would normally be collapsed/hidden, could now be expanded/displayed, and highlighted or flagged or otherwise emphasized to draw the attention of a user to the lack of testing having been performed on the patient.

In a third example, a primary care physician (PCP) may wish to view an entire patient history. The patient history can consist of patient care provided by the PCP, patient care provided by doctors in the same office as the PCP, and patient care provided by specialists outside the practice that co-manage the patient and have shared data with the PCP. In this arrangement, the entire dataset is provided for viewing on the medical records dashboard for care provided by the PCP and doctors within the same practice, and a shared dataset can be provided for viewing on the medical records dashboard for care provided by the specialists. Columns with no values can be collapsed or hidden if no value exists as described above.

FIG. 13D depicts a flow diagram of a method for rules-based data display in a data command center comprising a medical records dashboard including one or more windows including information received or derived from at least one patient database, the medical records dashboard comprising a display on a screen, using the one or more windows, of at least one of medical services, clinical data, examination findings, diagnostic tests, and the procedures performed on one or more patients, the one or more windows comprising a plurality of dynamic data fields for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, the method beginning at 6602 during which patient data/information from the at least one patient database is received. The method can proceed to 6604.

At 6604, the received patient information is compared with configuration rules to determine which portions of the received patient data/information are to be displayed and which portions of the received patient data/information is not to be displayed in the medical records dashboard. The method can proceed to 6606.

At 6606, dynamic data fields of the medical records dashboard that are determined to not have any patient data to display are identified as collapsed data fields, unless another rule is determined to override said rule and uncollapses/expands them. Those determined to have patient data are displayed, unless another rule is determined to override said rule and collapses them. Those determined to be altered, augmented, and/or emphasized are altered or augmented, unless another rule is determined to override said rule, and as such, the overriding rule is applied. The method can proceed to 6608.

At 6608, Patient data/information is displayed in the data fields of the medical records dashboard in accordance with the configuration rules and data fields of the medical records dashboard identified as collapsed data fields are collapsed and not displayed. Data fields determined to be altered/augmented are altered/augmented. The method can then be exited.

In some embodiments the dynamic data fields identified as intelligently alerted by any means, grayed out, expanded, collapsed, displayed, and/or hidden columns, rows, fields, and/or any other portion of the medical records dashboard comprise at least one of a column, row, or panel of a medical records dashboard of the present principles.

Figure 14:
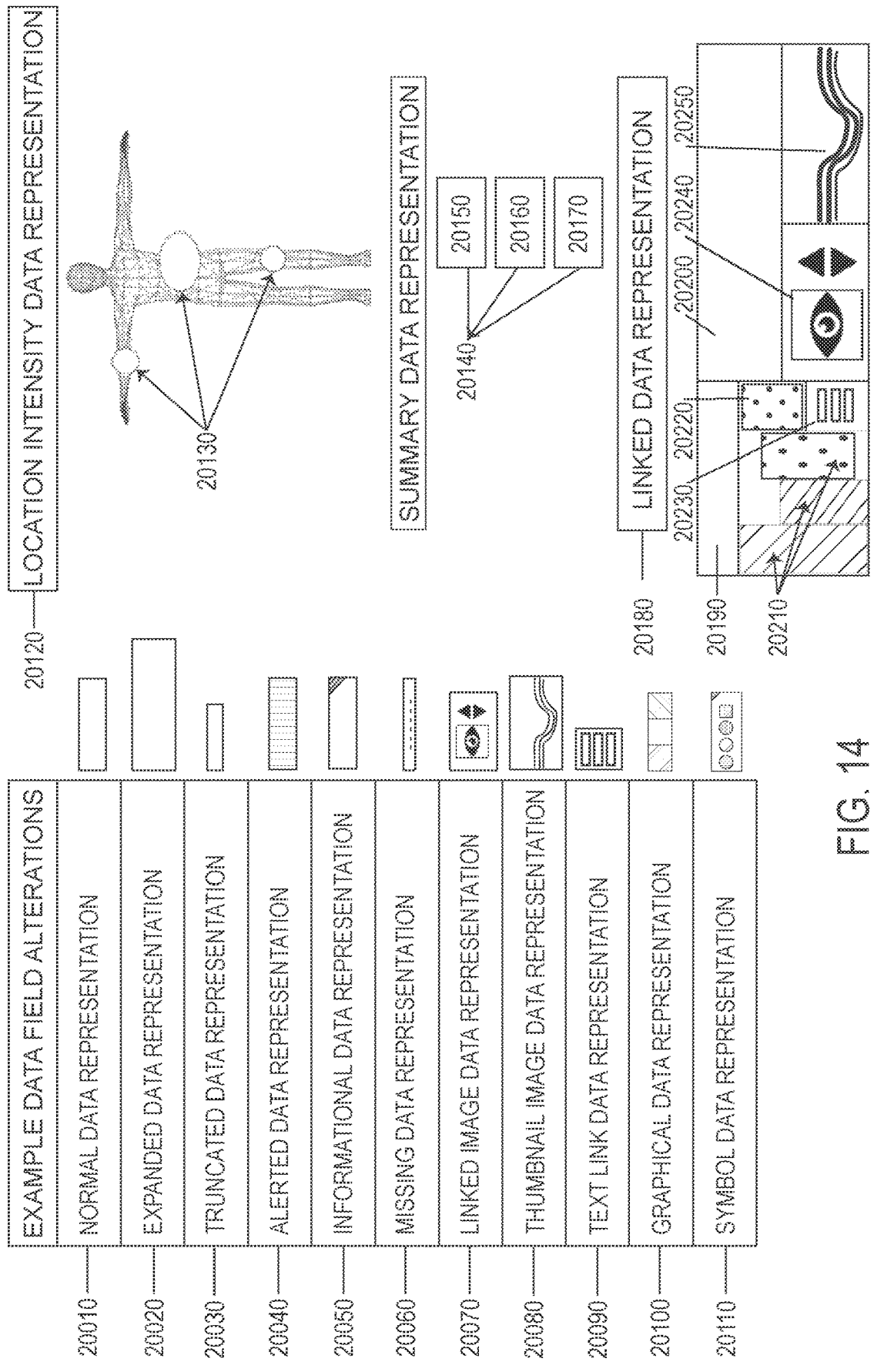
FIG. 14 illustrates examples of different ways data fields may be dynamically updated in accordance with an embodiment of the present principles.

FIG. 14 depicts a graphical representation of examples of altered/augmented data representation in accordance with Dynamic Data Representation in accordance with an embodiment of the present principles. Dynamic Data Representation in accordance with the present principles can include but are not limited to:

Normal Data Representation 20010: As an example, a normal data field can simply exist as a box to contain data. It can also be represented as an icon, image, diagram, or any other means by which the data could be displayed without any alteration or augmentation.

Expanded Data Representation 20020: A data field can be expanded to show more data, or to draw attention to data contained within.

Truncated Data Representation 20030: A data field can be shrunken to hide less important data or to show the lack of data present.

Alerted Data Representation 20040: A data field can be highlighted by, for example, color, to draw attention to or otherwise emphasize incorrect data, data exceeding a threshold, or critically important data.

Informational Data Representation 20050: An highlighted or otherwise emphasized notification, such as the corner notification of FIG. 14, can be displayed and an associated note can identify more information as to why the notification is present.

Missing Data Representation 20060: A data field can have a series of dashes to indicate that although the data field was expected, the field is not filled to indicate missing data such as canceled or missed appointment data.

Linked Image Data Representation 20070: A data field can contain an icon and even a grading system to show that the field enables direct access to an underlying image, and can also indicate whether the image indicates whether there is an improvement or degradation from a prior image.

Thumbnail Image Data Representation 20080: A thumbnail of an image can be present within a data field offering a quick snapshot of, and direct access to, an underlying image.

Text Link Data Representation 20090: A data field can contain an icon to show direct access to text via the data field.

Graphical Data Representation 20100: A data field can represent underlying information as a graphical representation of the data.

Symbol or Icon Data Representation 20110: A data field can use a series of symbols or icons to represent underlying data in a way that the end user can interpret the symbols or icons to understand the underlying data.

Location Intensity Data Representation 20120: Data Representation is a general term to describe how to display an area which represents data. As such, representing the importance of key events in a graphical representation of a human body is also relevant. Differing representations can show location and intensity or importance of key areas being called out. In 20130, three different size and color data representations are depicted, which illustratively implement size and color to denote a relative intensity or importance of the data.

Summary Data Representation 20140-20170: Summary Data Representation illustrates a single data representation 20140 comprised of multiple data sources 20150-20160, with the ability to collate and summarize more than a single data source in a single representation. Summary data representations can offer total counts, highest and lowest values, best/worst values, and interaction within underlying data.

Linked Data Representation 20180: Linked Data Representation comprises multiple data representations in a combined representation. The example of Linked Data Representation 20180 as illustrated shows a Normal data representation 20190, next to an Expanded data representation 20200, above multiple Graphical data representations 20210, an Alerted data representation 20220, Linked Text data representation 20230, Linked Image data representation 20240, and a Thumbnail Image data representation 20250. Each individual data representation may affect the representation of any other, such that an alert 20220 can enlarge based on changes to the source data represented graphically 20210.

FIG. 15 depicts a Table depicting example configurations (data visualizations) of dynamic data fields in accordance with an embodiment of the present principles. In the embodiment of FIG. 15, data visualization is achieved with a series of configurations to determine what and how to display. For example, in one embodiment, Source Data (85060) consists of a Value (85070), an Inclusion/Exclusion Rule (85080), and a Visual Representation Configuration (85090). The data can consist of one type (85030), a series of data points collected, values captured, validated for inclusion, and visualized across 2 intervals (85010, 85020), correlated against additional types, a series of separate data points collected, values captured, validated for inclusion, and visualized across the same 2 intervals (85010, 85020).

FIG. 16 depicts a graphical representation of Dynamic Data Field Example Configurations. In some embodiments, in order to accomplish dynamic data representation, a series of configuration rules must be employed. An example of such rules are illustrated with respect to the embodiment of FIG. 16. In this example, configuration has been shown with three panels, General Configuration 32010, denoting high-level choices as to what will be displayed, Parameters 32060, denoting when to augment display of data, and Configuration 32110, describing how to augment display of data. It should be noted that in some embodiments such configuration can include more or less sections or options within sections, based on use case and requirements.

Under General Configuration 32010, Date Configuration 32020 is displayed with options for Chronological ordering from Oldest to Newest or Newest to Oldest. Time Period 32030 enables the configuration to show all available data, or just data within a defined start and end date. Location 32040 enables refinement of which data will be displayed for example, for a specific medical provider practice/specialty. Providers 32050 enables specification of individual or types of providers.

Parameters 32060 address reasons to show, hide, or augment data. Appointments 32070 enables user defined types of appointments to be configured. Details 32080 determines if more information should be displayed about the underlying data. Event Type 32090 enables augmentation to be defined based on important, or any, event. Editable 32100 determines if such data should be accessible for alteration, insertion, deletion, or other modifications.

Configuration 32110 addresses how to augment underlying data. Date Configuration 32120 enables for date format to be specified, when date is present. Display Duration 32130 can be used to define a time period within which data will display or the tying of the duration of display to an event or action. Size 32140 enables the ability to make data appear larger or smaller than standard display. Display Type 32150 enables for augmentation of underlying data by enabling the data to have visual and/or typographic alterations. Move 32160 enables data to appear in a different location. Direct Access 32170 enables data to link to other data, images, or access panels. Override 32180 enables configurations to override other, predefined configurations.

Figure 25A:
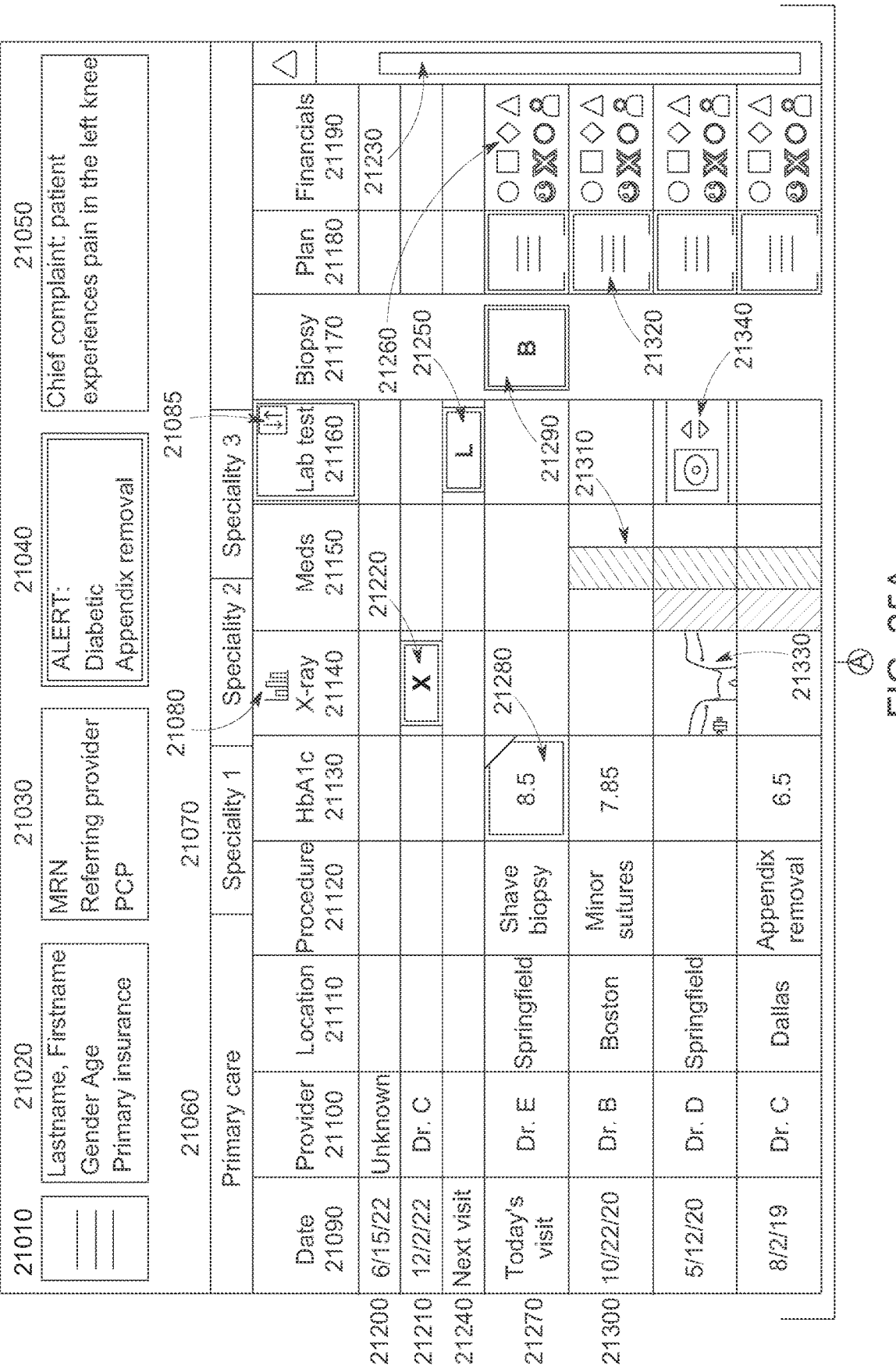
FIG. 25 depicts a patient specific dashboard in accordance with an embodiment of present principals.
Figure 25B:
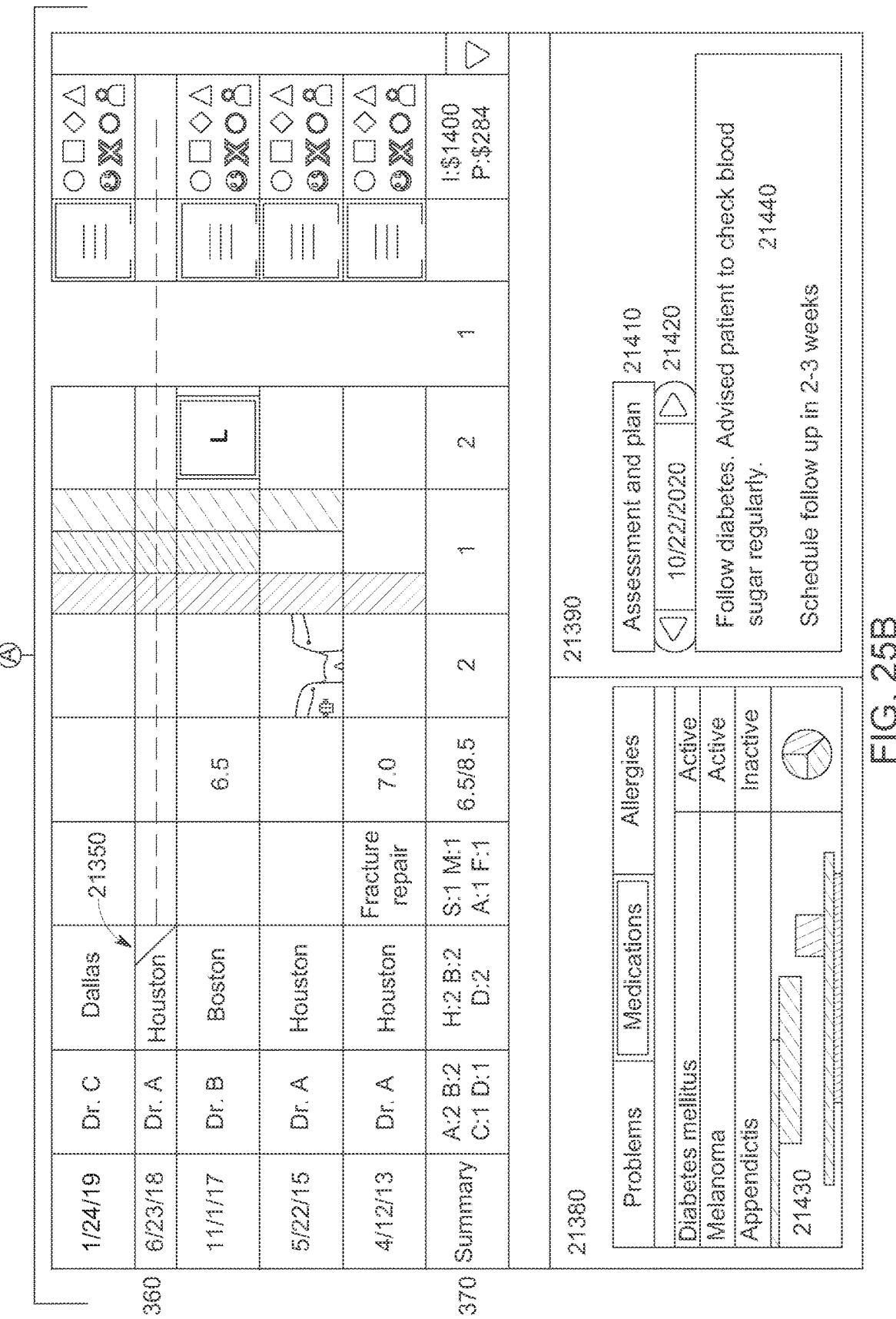

The representation of Dynamic Data of the present principles can take several forms, and exist within several different configurations, as is the nature of dynamic data representation. For example, FIG. 25 depicts a Patient-Specific Dashboard display of Dynamic Data in accordance with an embodiment of the present principles. In the embodiment of FIG. 25, a Master Header Row is represented by 21060-21070, a Flowsheet Header Row is represented by 21090-21190, a Flowsheet is represented by 21200-21360, a Flowsheet Summary Row is represented by 21370, and two separate modules are represented by 21380 and 21390.

Embodiments of a Data Command Center of the present principles can be configured for providing a Patient Evaluation Methodology included as, in at least some embodiments, an Electronic Critical Patient Reactivation (e-CPR) technique. That is, embodiments of the present principles can be configured to provide an adaptive, intelligent system for determining which patients are in critical need of care, utilizing a hybrid user-defined/automated Patient Evaluation Methodology, that can automatically take action to rectify identified issues of concern.

For example, in the ever-changing world of healthcare and healthcare IT, sorting through and identifying which data is truly of importance is key to identifying which patients are in the most urgent need of care. In order to accomplish this task, governments have mandated key data elements be recorded, stored, and shared, with the end goal of improved patient care. The downside to recording all of this data is that no human alive is capable of parsing every detail in a timely manner to make the determination as to which patients are of highest concern, and no human is capable of consuming all data points to establish unforeseen patterns of importance. Only through advancements in computing and artificial intelligence can the mass amounts of data be parsed, sorted, prioritized, and acted upon with any level of efficiency. With recent changes requiring the sharing of medical data between EHRs, there still exists no mechanism for alerting doctors or patients as to key factors which may exist in one system, but not within another. No position has ever been defined that requires a person to oversee this interrelationship of medical data, nor would a single person, or even large groups of people, be capable, in an efficient manner, to act upon such vast amounts of information quickly enough to truly manage patient care.

Electronic Critical Patient Reactivation (e-CPR) in accordance with the present principles brings to bear the full power of technological advancement and artificial intelligence to manage a task that existing Patient Reactivation Systems were previously incapable of accomplishing on their own. Through the utilization of established datasets, machine learning, and interoperability, a solution has been realized that can truly accomplish this Herculean task. A system capable of, but not limited to, identifying patients which meet the following criteria, as well as identifying previously unknown criteria, is now possible:

Meet similar Demographic criteria, even with Medical Records in disparate systems or care provided by other providers, that may also meet other key indicators for criticality.

Exhibit Risk Factors, even with Medical Records in disparate systems or care provided by other providers, that may also meet other key indicators for criticality.

Exhibit Conditions, even with Medical Records in disparate systems or care provided by other providers, that may also meet other key indicators for criticality.

Exhibit Critical Conditions, even with Medical Records in disparate systems or care provided by other providers, that may also meet other key indicators for criticality.

Have undergone Procedures, even with Medical Records in disparate systems or care provided by other providers, that may also meet other key indicators for criticality.

Have undergone Critical Procedures, even with Medical Records in disparate systems or care provided by other providers, that may also meet other key indicators for criticality.

Have Diagnostic Test Results, even with Medical Records in disparate systems or care provided by other providers, that may also meet other key indicators for criticality.

Have Critical Diagnostic Test Results, even with Medical Records in disparate systems or care provided by other providers, that may also meet other key indicators for criticality.

Are being seen by specific Specialties or Physicians, even with Medical Records in disparate systems or care provided by other providers, that may also meet other key indicators for criticality.

Have specific Appointment Types, even with Medical Records in disparate systems or care provided by other providers, that may also meet other key indicators for criticality.

Have Future Events Scheduled, even with Medical Records in disparate systems or care provided by other providers, that may also meet other key indicators for criticality.

Have a history of Canceled or Missed Appointments, even with Medical Records in disparate systems or care provided by other providers, that may also meet other key indicators for criticality.

Additionally, with the advent of machine learning, even events or categories of events not previously known can be identified utilizing an algorithm that not only identifies cause and effect but can also deduce cause by effect. In existing patient reactivation algorithms, if key factors are identified beforehand, patients may be identified which meet the criteria. e-CPR New Category Identification accounts for, but is not limited to, evaluating:

Pre-Identified Factors

Existing Data

Historical Event Factors

Current Event Factors

Future Scheduled Event Factors

Key Events

Key Results

In each of the areas described above, the evaluation is not limited to a linear parsing of data. Each step may be accounted for, but e-CPR utilizes machine learning to identify when patterns exist that were not previously identified, and automatically begins accounting for the newly acquired data. As an example, a doctor or patient reactivation system can know that a patient with diabetes needs to be seen every 1-2 years, and a patient with diabetes and heart disease may need to be seen every 6-12 months, but can be completely unaware that patients within 50 miles of a specific zip code are exhibiting complications requiring them to be seen every 3-6 months. The complications may not have yet been identified or correlated to this location, but utilizing advanced pattern analysis, e-CPR can parse all patient records and identify a pattern of worsening outcomes linked by locality. The root cause can be a factory with faulty filtration, environmental conditions, or even a localized outbreak. Such contributing factors would not have been identifiable without first connecting the data that patients with specific conditions have worsening outcomes, and that the patients exist within a certain locality. With the local population seeking healthcare at several different facilities, each facility may not notice the increased pathology due to the small sample size and focus on individual patient care. Only through correlating several factors from all locations in the area do such issues come to light.

In another example, a specific patient can have a history of relatively minor risk factors, conditions, and/or procedures, but poor compliance with maintaining a proper schedule of doctor visits. Such a patient can see 4-5 different providers, all at different locations, or can only visit a hospital for emergency care when conditions become unbearable. No one provider may be aware of the history of missed appointments because they are only missing a few appointments at each provider. In such an example, the reason for the missed appointments now becomes a higher priority. If the patient is missing key appointments with specialists they have been referred to see, such a patient is in danger of becoming critical. As mentioned, this can lead the patient to visit the emergency room for conditions that would have best been addressed through routine care. Identifying such a patient is critical, not just for individual patient care, but also for determining factors to identify similar patients before they reach this critical state, such as socio-economic conditions, language barriers, lack of transportation, and the like.

Identification is only the first step in electronic Critical Patient Reactivation. After proper identification, the most important factor is ensuring patient compliance. Existing patient reactivation systems implement many established means of communication to send a reminder to the patient to come in, by mail, email, text, and/or automated or manual phone call. In some more advanced patient reactivation systems, responses to communications may be tracked and accounted for, such as a missed phone call may be followed up on x more times, and a report can even be generated to show non-compliant patients. With e-CPR's advanced communication management, method of communication with a given patient is not limited to patient or practice preference. Similar to identifying critical patients for reactivation, an algorithm is used to determine the most effective means of communication. Historical data is compiled and analyzed, not just for the individual patient, but also correlated against other patient with similar age, conditions, locality, and other key factors, to determine that a certain patient can prefer a text message between the hours of 8 AM and 5 PM Monday through Friday, a cellular phone call between 5 and 6 PM on the same days, and 10 AM through 8 PM on weekend, but desires a home phone call outside of those times. Historical data may also point to a dramatic inability to contact a patient through established methods, thus determining a certified letter or even an in-person visit may be required to ensure said notification is delivered and received. By compiling and correlating all available data, e-CPR's AI can determine not only the most effective means of communication, but the most effective times to communicate via a specific method.

e-CPR is not limited to a single action or set of actions in response to an attempt to contact and bring a patient back in. Several steps may be predefined, but, as is the strength of e-CPR, additional steps may be defined or redefined based on current or future responses. E-CPR is also not limited to patient communication in an attempt to reactivate a critical patient. With connections throughout the care process, e-CPR has the ability to send tasks to schedulers, visually notify doctors at point of care, and even reach out directly to all of the patient's doctors, to immediately make them aware of the need for the patient to be seen for a specified reason. A process of the present principles can implement several conditions, steps, requirements, and triggers to ensure that the patient is never lost within the system. FIG. 13 depicts a Table having example parameters of a process for e-CPR in accordance with the present principles.

Figure 17:
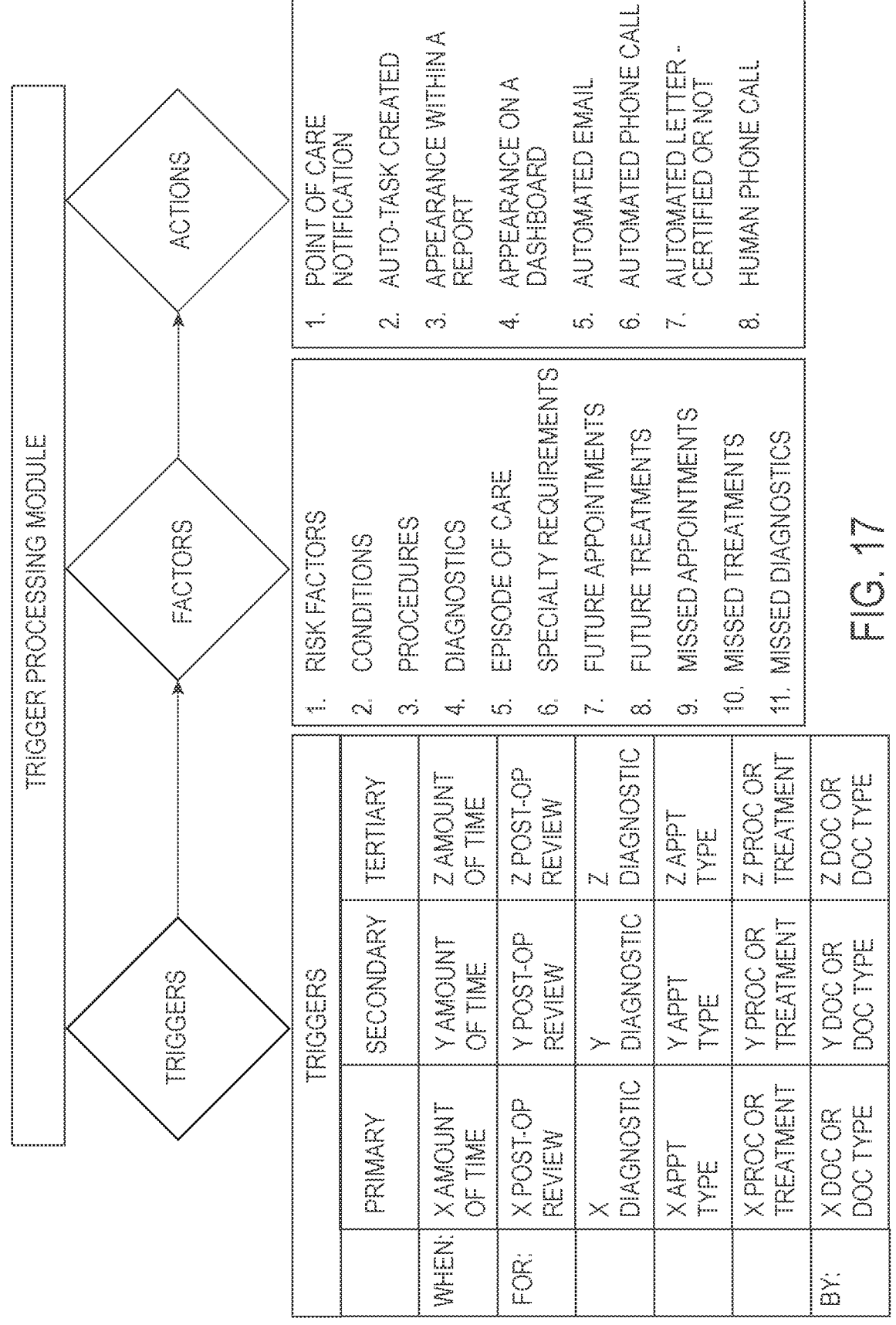
FIG. 17 depicts a trigger processing module in accordance with principals denoted in FIG. 16.

An example of such a process is depicted in FIG. 17. While the example of FIG. 17 depicts a total of three triggers, triggers are not limited by number, nor are the steps or information contained within meant to express a limitation or linear process. Multiple and complex arrangements of triggers, counter-triggers, and multi-dimensional triggers can be implemented as needed to accomplish the requirements of electronic Critical Patient Reactivation of the present principles. It should also be noted that, in FIG. 17, the Y-Axis display listing When, For, and By, is not limited to these values or this number of values. Pre-defined criteria, as well as criteria determined at time of execution, can add, remove, or otherwise alter this criteria list.

In the process of FIG. 17, actions to be taken can include, but are not limited to:

Point of care notification to a Provider

Auto-Task created to a Scheduler or Doctor with enough information to make a medically relevant decision Appearance within a report with enough information to make a medically relevant decision Appearance on a dashboard Automated email to Patient, Practice, Provider, Scheduler Automated phone call to Patient, Practice, Provider, Scheduler Automate letter, Certified or not, to Patient, Practice, Provider, Scheduler Human phone call to Patient, Practice, Provider, Scheduler Human visit to Patient, Practice, Provider, Scheduler As noted above, in embodiments of the present principles several key factors are compared and can affect the outcome of the critical patient reactivation workflow, either by triggering an action, or satisfying a requirement. Triggering an action occurs when a requirement is met for a trigger. For example, if a requirement for a patient with specified risk factors and conditions is not met, as in an obese diabetic patient with glaucoma not receiving a diagnostic test to track their condition within 6 months, and action may trigger a point of care notification to the specialist tracking the disease. If the requirement is not met, and a second threshold occurs, such as not receiving the diagnostic test in 18 months, an auto-task and alert on a dashboard can trigger to the schedulers to ensure the patient is scheduled for the diagnostic. A third requirement can occur if the first and second requirements are not met, which can trigger a series of notifications to the assigned specialist, and possibly all users providing care for the patient, the schedulers, and the patient, to ensure the patient is receiving proper care.

In accordance with the present principles, should additional data become available during the course of the above described process, such as a new procedure or condition being recorded, the algorithm can be reinitiated or refactored as required based on the newly acquired information. Should a patient commit to a future event, such as scheduling an appointment, which satisfies existing criteria, an additional step can be created to ensure the future commitment is met. If it is not, the patient can reenter the previous workflow, or newly defined requirements can be established.

Figure 18:
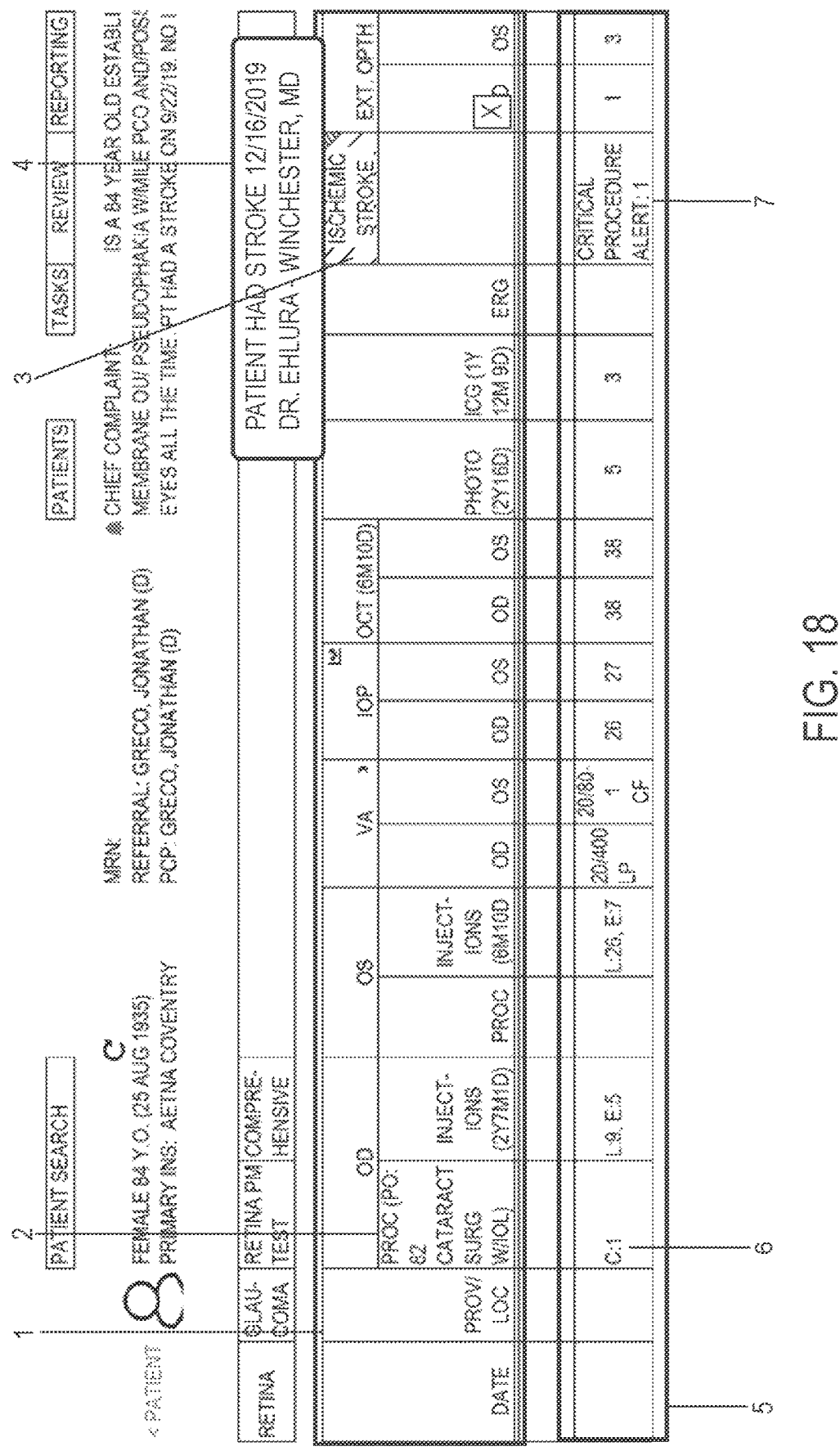
FIG. 18 illustrates an example of a critical patient indicator.

Critical Patient Indicators of the present principles can directly interact with Dynamic Health Records. For example, FIG. 17 depicts a flow diagram of a trigger processing method in accordance with an embodiment of the present principles. As illustrated in FIG. 18, at element 1, the Dynamic Health Records Header Row is displayed. Such a row denotes column names as well as key indicators regarding the contents of said column. At element 2, an indicator for a Cataract Surgery Post-Operative Period is clearly denoted. This indicator states that the patient is in the 82nd day of a 90-day Post-Operative Period. As such, an Ophthalmologist would clearly recognize the criticality of said patient. A column which would not normally be displayed, element 3, Ischemic Stroke, is automatically added to the Ophthalmologist's dashboard by way of Patient Evaluation Methodology, to show that said patient has had a Critical Procedure. By way of hovering over, selecting, or otherwise interacting with said column, more information may be displayed as shown in element 4, denoting the procedure, date, physician, and location where the stroke was recorded.

In FIG. 18, element 5 denotes a Dynamic Health Records Summary Row. Such a row denotes counts, totals, min/max, assessments, best/worse, et al values based on the contents of said column. At element 6, a Count of procedures is displayed, in this case, C: 1 to denote one cataract procedure has been performed in the right eye. Finally, at element 7, a summary for the newly added column, Ischemic Stroke, is displayed denoting that a Critical Procedure Alert exists in the column. This is an example of the display of a Point of Care notification to a Provider.

Indicators can also exist within columns, within rows, outside of rows or columns, attached to modules, panels, in popups, pop outs, pop overs, and by other methods used to notify a provider. Indicators are not limited to visual indicators and may employ sound, voice recordings, and other audio methods of notification. Indicators may also include vibrational feedback and other means of notification available based on the media used to access e-CPR and/or Dynamic Health Records.

FIG. 19 illustrates a series of Data Visualization Storage configurations in accordance with an embodiment of the present principles. In the embodiment of FIG. 19, data visualization is achieved with a series of configurations to determine what and how to display. In some embodiments, Source Data (10010) consists of at least one of a Value (10030), of at least one of an Inclusion/Exclusion Rule (10050), of at least one of a Visual Representation Configuration (10060), of at least one of a set of governing Rules (10070, 10080), and of at least one of a set of Actions to be taken (10090). The data can be visualized across multiple intervals (10010, 10020).

Figure 20:
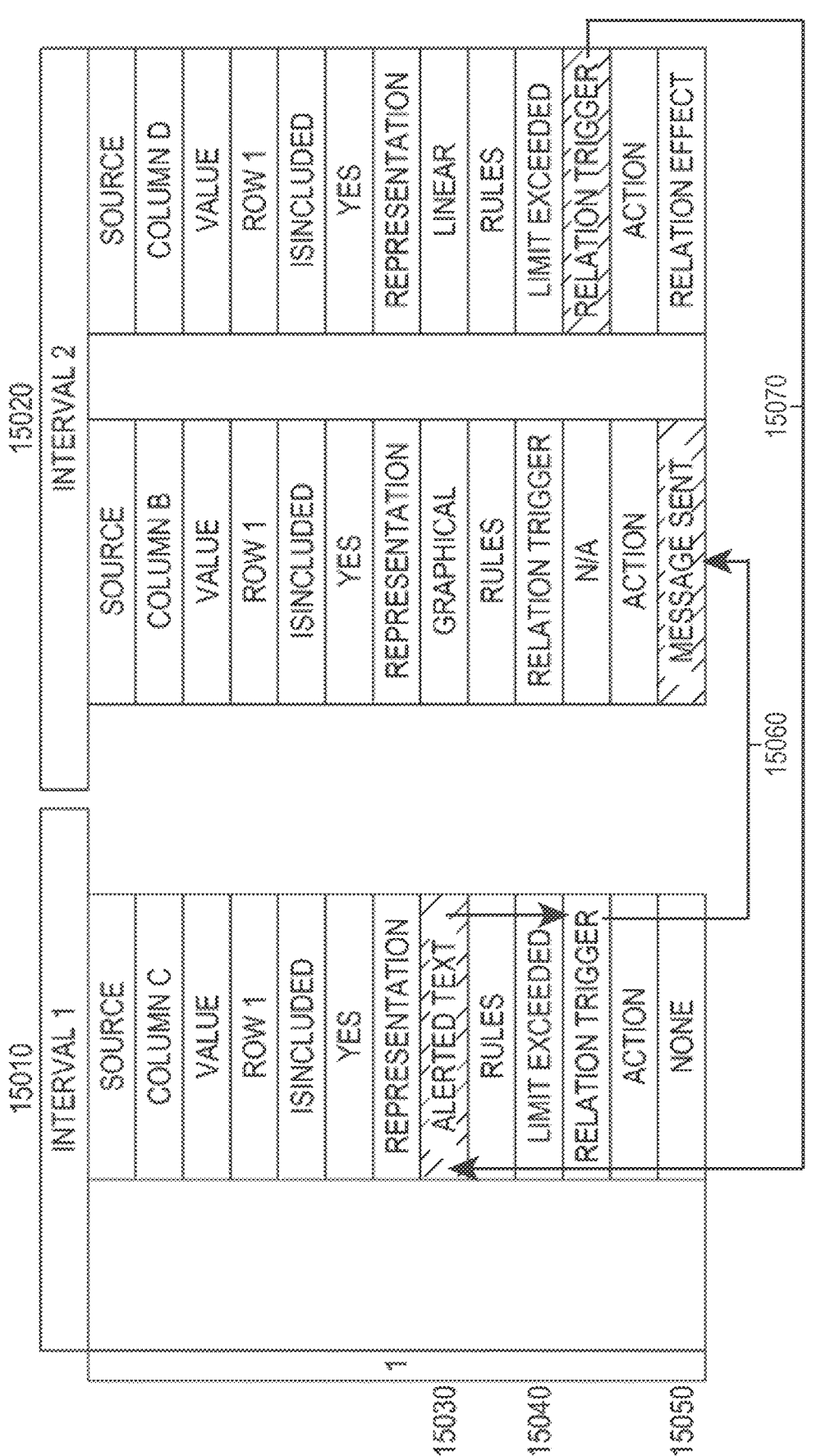
FIG. 20 illustrates interactions between data sets in accordance with an embodiment of the present principles.

FIG. 20 illustrates interactions between data sets in accordance with an embodiment of the present principles. In the embodiment of FIG. 20, data stored or generated at runtime can be correlated and evaluated against other data stored or generated at runtime, reinitiating the process until no further changes occur. In such a process, data recorded for interval 1, as illustrated in 15010 of FIG. 20, can be correlated and evaluated against data recorded for interval 2 (15020). At 15030, Alerted Text in column C is displayed, which was previously listed as Text in column C 10050 of FIG. 19. This can be triggered by a series of actions occurring, such as a Limit Exceeded Rule invoking a Relation Trigger 15040. Such a Relation Trigger directly affects 15070 the field specified in the Relation Trigger, in this case, reevaluation of the Representation in Column C 15030 of Interval 1 15010. Subsequently, the text of Column C 15030, now invokes a Relation Trigger 15040 of its own, which directly affects 15060 the field specified in the Relation Trigger, in this case, reevaluation of the rules for Column B of Interval 2 15020. As such, a Message is now sent.

Configurations stored can be correlated between intervals, within the same interval, from different source data, and between separate categorizations of visualized data. Utilizing the methodology, one can assume any change in source data may initiate refactoring of the evaluation process, as well as any change, addition, or deletion in displayed data can initiate refactoring of the evaluation process. Furthermore, data added for future consideration, such as future appointments or orders, can be evaluated, displayed, and reevaluated.

Figure 21:
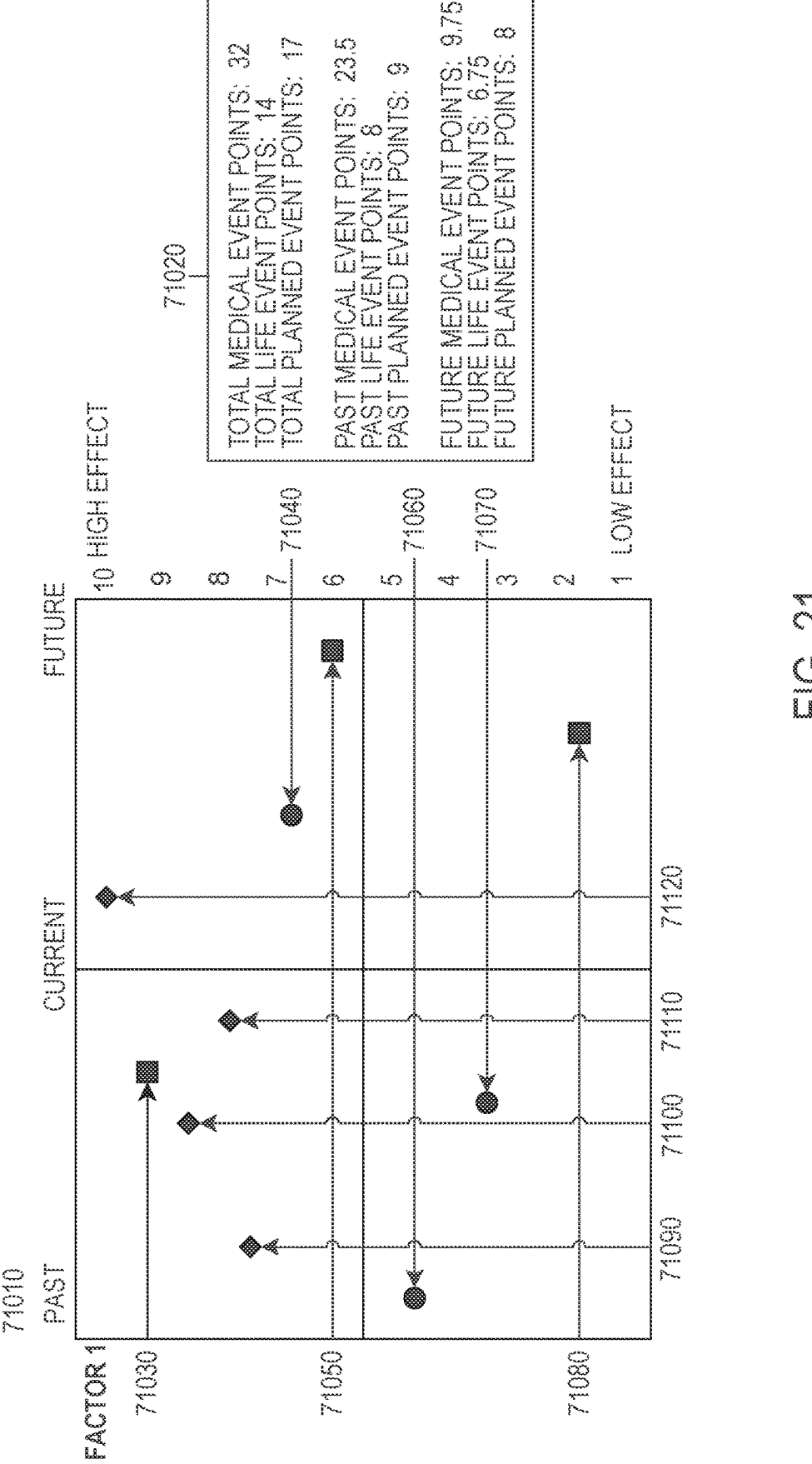
FIG. 21 illustrates a weighting system in accordance with an embodiment of the present principles.

FIG. 21 illustrates a weighting system in accordance with an embodiment of the present principles. In FIG. 21, 71010 displays a correlation between Effect (importance) and Occurrence (represented in time). 71020 illustrates an overall total of different categories of events, as well as past and future event totals. In the embodiment of FIG. 21, weighting can occur at an overall level with a full Whole Life View displayed, or in past or present as required by zoom level, and weighting can change based on relevance of events to other events. In this example, a planned event is displayed at 71030. The planned event can be representative of a planned appointment or treatment that was not met, or the planned event can be representative of a medical event. At 71050 and 71080 future planned events are displays. Future planned events could be representative of appointments or orders scheduled for future dates. Past, present, and future planned events can interact such that a missed planned event 71030 can increase the importance of a future planned event, or medical or life events.

In FIG. 21, at 71040, a view for a future life event is generated. This could be representative of events such as a wedding or important anniversary, which can have an effect on the weight of prior or subsequent events. 71060 and 71070 represent past life events, such as a divorce or loss of a loved one. Life events can affect the overall health and compliance of a patient, and as such are weighted and accounted for. In FIG. 21, 71090-71110 represent past medical events, procedures, injections, surgeries, diagnostic tests, or any other medical event in the past. Each medical event is weighted and correlated with each other and other events. 71120 represents a future medical event, not a planned event, because a medical professional may know, with increased certainty, of the occurrence of this future event. Such an event can include a transplant or other major procedure for which there is little to no option for the event to not occur.

With such representations of weighting 71010 in accordance with the present principles, an axis for effect ranging from low to high, as well as past to future is enabled. This is only one example of a correlation, although many correlations work together for ultimate determination of the weight, as mentioned by the zoom level refactoring the weight of events. Total event points 71020 rise and fall based on such factors, until a final result for the specified view is determined. Results can be refactored based on changes to source data or actions taken to alter displayed data.

Figure 22:
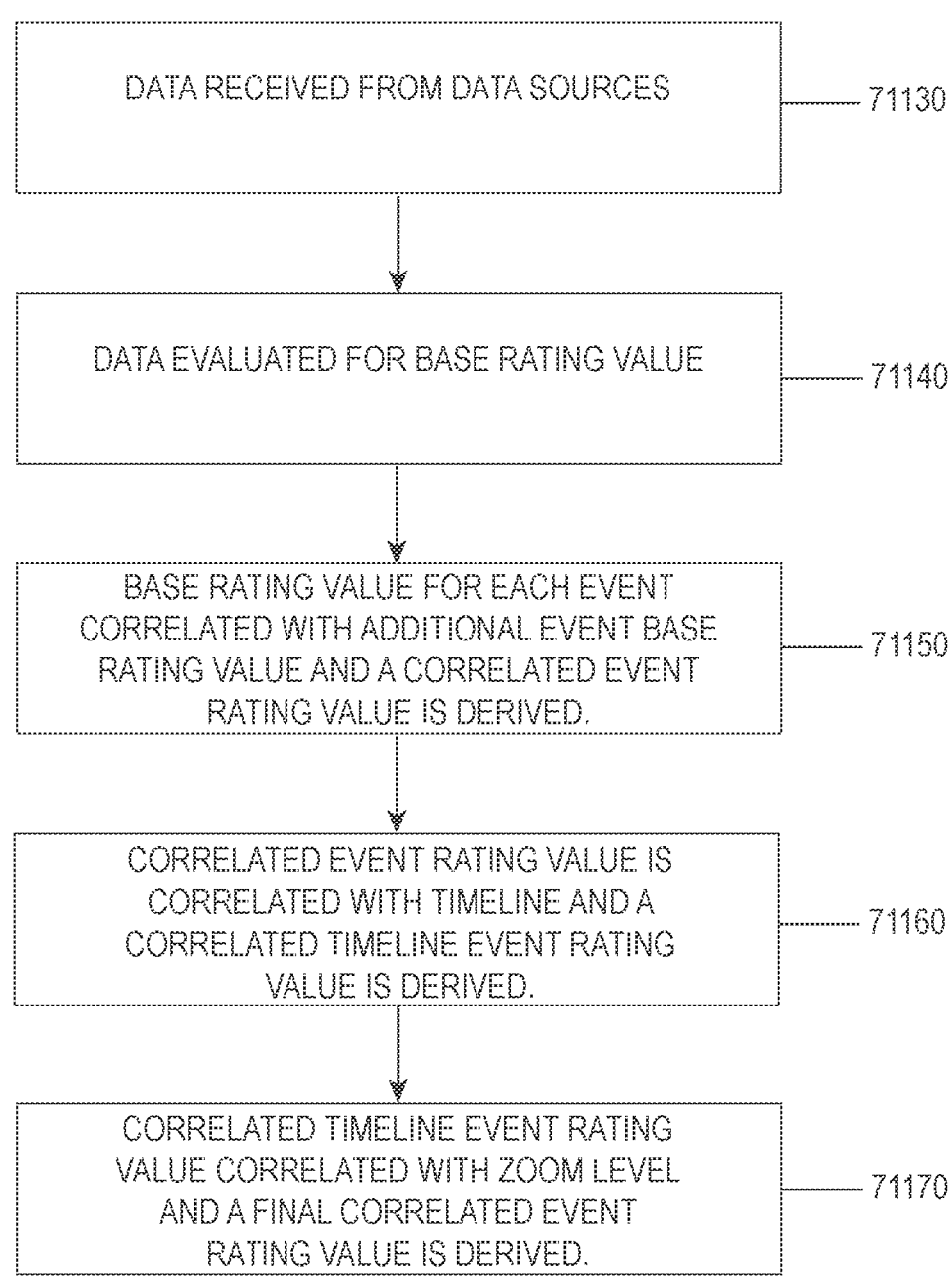
FIG. 22 illustrates a weighting system flow diagram in accordance with an embodiment of the present principles.

FIG. 22 illustrates a flow diagram of a weighting method in accordance with an embodiment of the present principles. In the embodiment of FIG. 22, data is received from data source 71130, either external 10010-10110 of FIG. 3, internal from application storage 10160-10180 of FIG. 3 or the Rules Engine 10210 of FIG. 3. Initial data evaluation occurs, and a Base Rating Value is assigned based on type and contents of data received 71140. Data evaluation ratings can be stored. Once Base Rating Values are assigned to events, all events are evaluated against each other to determine a Correlated Event Rating Value 71150. This Correlated Event Rating Value accounts for the interactions of key events and can weight one event higher or lower based on the existence of another event. Once all events are evaluated and Correlated Event Rating Values are assigned, each is then reevaluated based on when the event occurred, resulting in a Timeline Event Rating Value 71160. At each step, resulting values can be stored in volatile memory until no longer needed. Once all evaluations of and between data and timeline occur, the view is then accounted for. At 71170, the specified zoom level is factored in, and a Final Correlated Event Rating Value is used to determine the final weight of the values to display.

FIG. 23 depicts a Flowsheet depicting Header and Summary Row functionality as it pertains to Dynamic Data Sets in accordance with an embodiment of the present principles. A key feature of the Data Command Center is the ability for Flowsheet Header and Summary data representations to be programmed, or intelligently adapted based on rules defined in the Rules Engine 10180 of, for example, FIG. 3, to display notifications and allow interaction with the data that lies between them as describe in Summary Data Representation 20140 of FIG. 14. In the embodiment of FIG. 23, the Flowsheet Header consists of a Date 90010, Doctor and Location 90020, Visual Acuity 90030, Intraocular Pressure 90040, Procedures 90050, Injections 90060, Medications 90070, and an array of Diagnostic Tests 90080. Each header can behave differently based on the data contained within the represented data set, data contained within other data sets, data displayed, and/or data not displayed.

For the purposes of the embodiment of FIG. 23, Date 90010 is the date of an appointment, encounter, occurrence, or event which pertains to the treatment and care of a patient. Doctor and Location 90020 is comprised of any doctor or caregiver, and the location at which they interacted with the patient. Also displayable within this data set may be diagnostic testing equipment, equipment which can exist outside of the practice such as remote monitoring systems or take-home testing equipment, and/or anything that may provide a result or measurement which pertains to patient healthcare.

In the embodiment of FIG. 23, Visual Acuity 90030 depicts a summary of multiple Visual Acuity test results. Within the VA header, there are OD and OS column headers to accurately display the Right Eye (OD) and Left Eye (OS), yet any column can be set to a single group, multiple subgroups, and the subgroups can also contain multiple subgroups. At 90035, an expander is available within the header which will expand to show several data sets with distinct Visual Acuity results based on a number of methods for testing. It should be noted that the expander can be implemented to depict, or in the inverse, to hide, a number of data sets. The Expander may be set to Expanded—True, and all data sets will show unless the icon is selected to collapse them. The Expander can also be set to Expanded—False, in which case, all specified data sets will be collapsed unless the icon is selected to expand them. As seen in this example, one data set, VA, is set to expanded, while several other related data sets are set to collapsed. In another embodiment, the Expander can expand to show all or collapse to hide all, or any combination of showing and hiding data sets as denoted in configuration.

In the embodiment of FIG. 23, VA 90030 also contains a summary field 90100 denoting the best and worst values within the data set. Best VA is denoted in a first color (e.g., green), while Worst VA is denoted in second color (e.g., red). It should be noted that a series of configurations can be set to determine color, size, position, and purpose of any summary row. Summary Row data fields are interactive. In the summary field 90100, selecting the Best or Worst value may collapse all other fields to show only the value selected, as demonstrated in FIG. 28. Fields can be expanded to show when a user deselects the summary field value.

Intraocular Pressure 90040 contains two sub data sets, OD and OS, to represent the right and left eye. Within the parent group, results of IOP testing are displayed. At 90045, one will note an icon of a graph. The icon can initiate a correlative graph of several key factors, including but not limited to, Date, IOP, Medications, and Procedures. An icon, such as in 21080 of FIG. 25, can exist anywhere within a header, and on any portion of the application, to launch a different representation of the data.

In the embodiment of FIG. 23, IOP 90040 contains a Summary Data Representation 90110 displaying the highest recorded value in the column. It should be appreciated that the field has been configured differently than the VA summary field, and a series of configurations can be set to determine color, size, position, and purpose of any summary data representation.

In FIG. 23, Procedures 90050 can display any or all medical procedures performed on a patient. Procedures has a summary field 90120 which denotes a count of each type of procedure which was performed on a patient. Injections 90060 is a segregated group of procedures. It should be noted that any portion of the Data Command Center of the present principles can be configured to display any record, group of records, and calculations based on records. At 90065, a Header denotes the number of days since the last occurrence of an event in that data set. As with Procedures 90050, Injections 90060 also has a summary field 90130 showing the total count for each type of injection procedure within that data set.

In the embodiment of FIG. 23, Medications 90700 display in a graphical data representation. A single bar exists in the example because the patient is only on one medication. All other medications are hidden in accordance with dynamic data representation describe herein. A medication, in this example, displays as a bar beneath said header, originating at the start date and concluding at the end date. The summary field, unlike in previous examples, will display as many events as the medication takes up from the start date through the end date. All events which do not contain an instance of the medication bar will be collapsed until such time as the user deselects the summary field.

In 90080, a data set containing Fundus Photos displays a header denoting the amount of time that has elapsed since the last Fundus Photo occurred. At 2 years 3 months and 1 day, an alert is triggered by a rule which states the diagnostic test should occur within a specified timeframe, highlighting or otherwise emphasizing the header field in a different color. A corner informational data representation in the header allows for the user to view the precise reason for the alert. As no Fundus Photos have been performed in over 2 years, and with the display only showing the current year, the importance of the summary field 90140 becomes apparent. The summary field denotes a total of 5 Fundus Photos have occurred within the time of patient care, and the column header denotes there has been over 2 years since the diagnostic was performed. In FIG. 23, Summary fields 90100 through 90150 act and interact differently with the displayed data. Each serves a purpose, and while the purpose can differ, it should be noted that singularly, or in conjunction, all summary fields can be used to alter the display of data, and return said display to its original state.

Figure 24A:
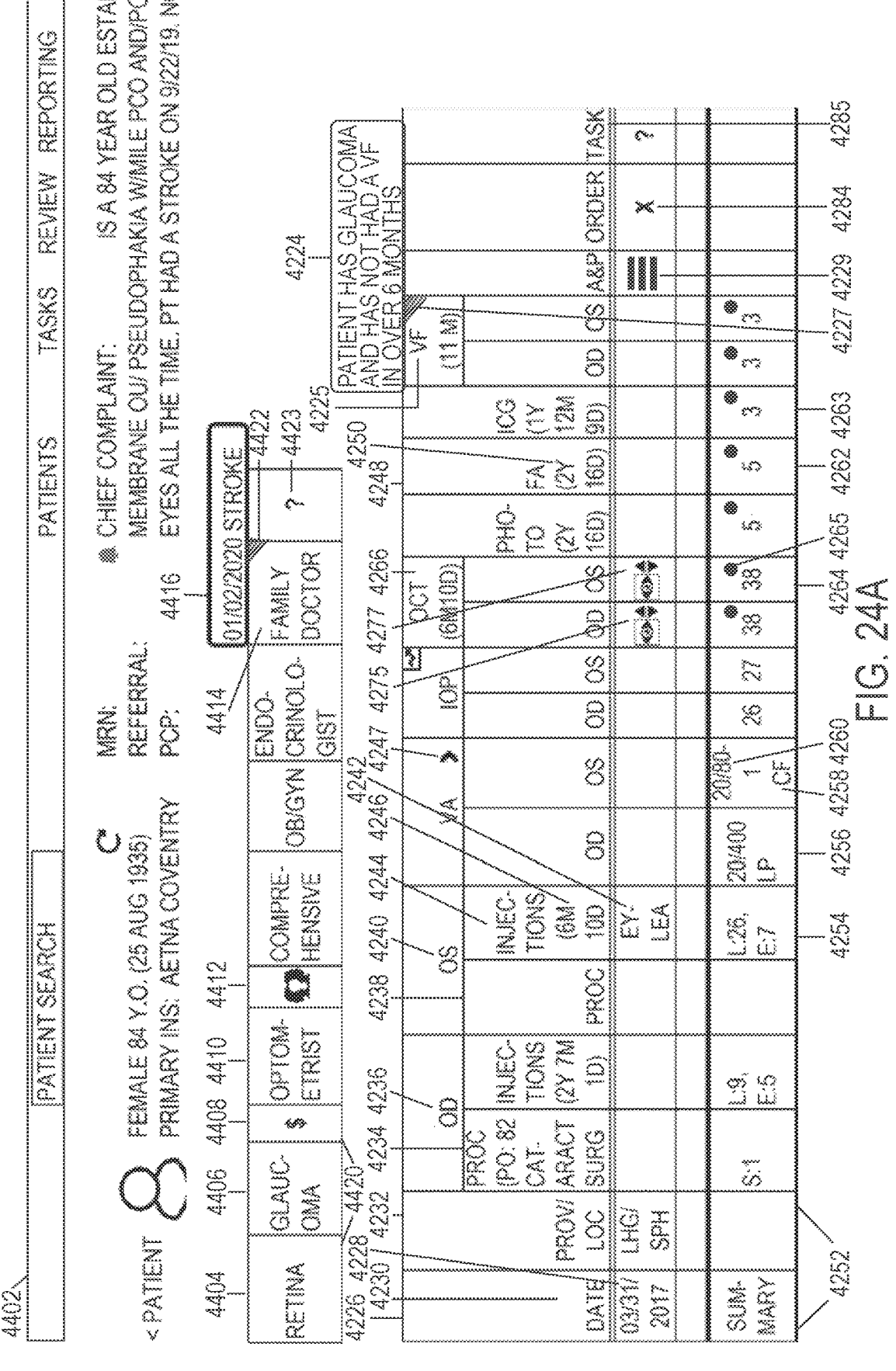
FIG. 24 further illustrates dynamic, interactive header and summary rows in accordance with an embodiment of the present principles.
Figure 24B:
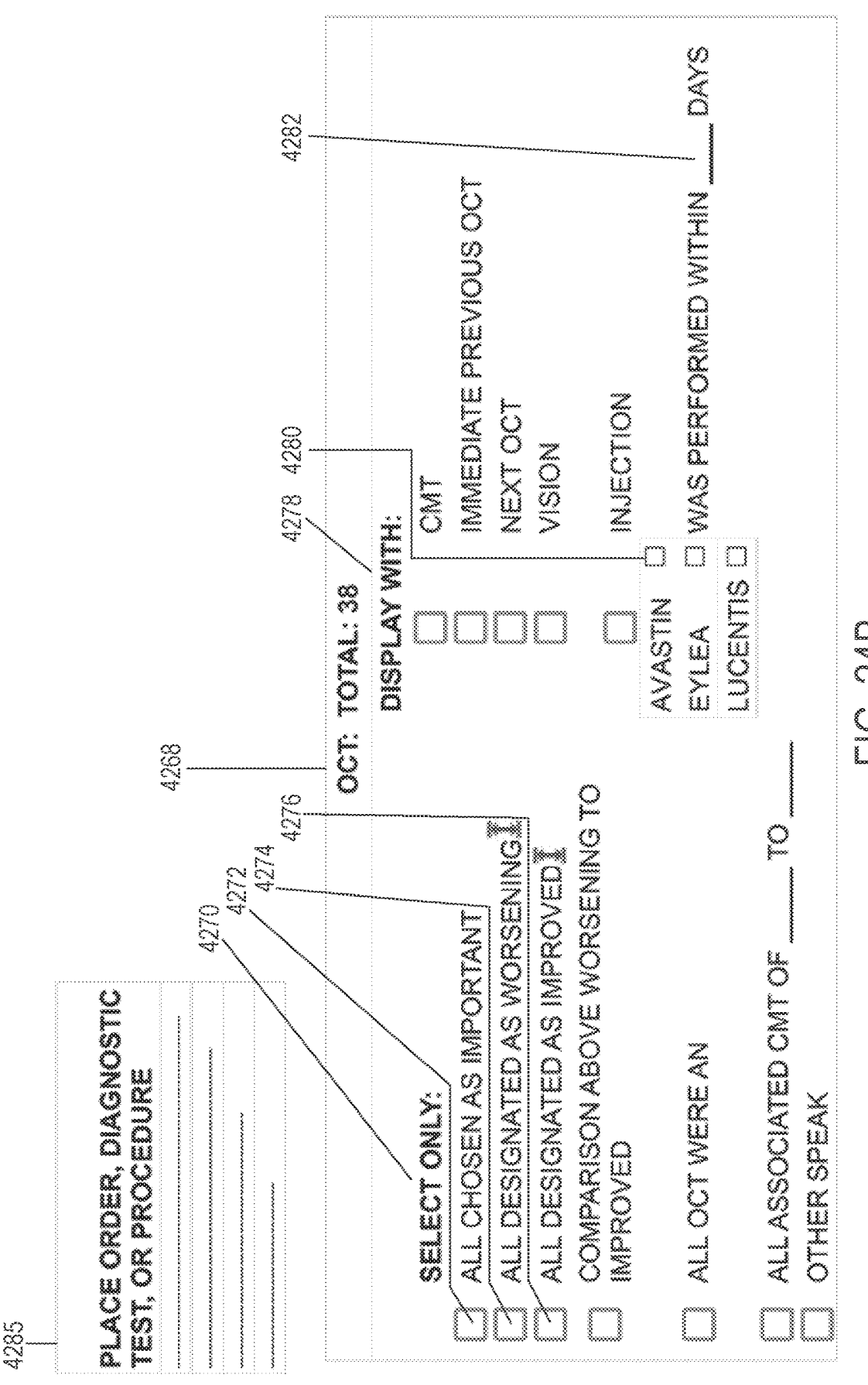

FIG. 24 depicts an alternate embodiment of a Flowsheet depicting Header and Summary Row functionality as it pertains to Dynamic Data Sets in accordance with an embodiment of the present principles. The embodiment of FIG. 24 depicts the functionality of three specific rows in the user interface in accordance with an embodiment of the present principles. That is, FIG. 24 illustrates how three rows or panels in the user interface 4218 can convey a plethora of information for a healthcare professional in some embodiments. Header 4226 is an example of a header that can appear on each individualized specialty-based provider's actionable dashboard. As illustrated at 4220, different actionable dashboards that have been particularly designed for different providers of different specialties can be accessed. In the embodiment of FIG. 24, a summary row

4252 can be provided on each individualized dashboard for each doctor, specialist, or other user and can be specialized for each user. In the header 4226, the date is represented at 4230. The date can include a time, day, and/or date of a patient visit or the visit of a group of patients. 4232 can include the initials or name of the provider who cared for the patient or if just a location of testing, can include an indication of the location of the test performed. That is, in some embodiments, a medical care provider's initials can be presented at 232, which can also include a location, as providers can have multiple offices. In some embodiments, the information in 4232 can include an abbreviation, description, or identifying factor of which office a patient visited. In FIG. 24, 4228 shows an example of one of many patient encounters overtime.

In FIG. 24, 4236 depicts an example of a column that includes a procedure and, in the embodiment of FIG. 24, is divided into two different sides of a patient's body. In 4236 OD is displayed, which in eye care refers to a patient's right eye. In the case of orthopedics, 4236 could reference a patient's right knee. Similarly, an OS in 4240 represents the left column or in the case of eye care, the left eye, and in the case of orthopedics can refer to a left knee. As illustrated, the OS or left column of the header can be a procedure 4238. Under the column of the left eye is listed, by encounter, identifying procedures such as injections 4244. Item 4242 depicts an injection that has been performed (e.g., injection of Eylea is listed but can represent any data related to the column and row it is under.), while 4228 shows the date of the medical encounter which by way of example shows Mar. 21, 2017.

As illustrated at 4234, the header 4226 is able to display that a cataract surgery has been performed and that a postoperative period is counting down. The header 4226 can also display that injections 4246 were last performed six months and ten days ago. 4224 can display a last time this test or item was performed on a patient or any kind of alert for instance if patient is allergic to the item or a condition impacts this test or procedure and 4224 can be on any column or row. Cell 4225 can have any highlights or otherwise emphasis that can inform additional information such as an alert that something has not been done but should be in one year, such as orange, or if not done in two years that can be a severe warning so cell could be red. 4227 is a mechanism for user to learn more details and more information can come up for example 4227. In the embodiment of FIG. 24, 4224 depicts that a test was performed 2 years and 16 days ago. Header 4226 also includes a pop-up 4224 of underlying information. In the embodiment of FIG. 24, the patient has a diagnosis of glaucoma and has not had a visual field in over six months. 4247 shows an expanding mechanism where many more columns can suddenly appear. In this case, it appears in VA (vision) cell and there are many ways to test a vision, which can have different data. To save space on the display, the other methods are hidden until the user clicks on 4247 and then other columns are displayed. Clicking again on 4247 reverses the process and the columns are hidden again.

The summary row 4252 of FIG. 24 depicts how not only is the total number of something that had occurred in the rows above counted, but it can be divided according to what was performed. That is, in the embodiment of FIG. 24, summary row 4252 is a smart summary column. In the embodiment of FIG. 24,4254 demonstrates that there were twenty-six Ls and seven Es of which one E (Eylea) is shown at 4242. The embodiment of FIG. 24 depicts an example of a retina doctor who performs injections in the right eye in this case, and used "L," which stands for Lucentis times and "E," which stands for Eylea. 4256 similarly demonstrates the summary cell in a column of the left eye. 4260 shows the vision in the left eye is 20/80-1 and could also reflect the best number or event that occurred in the entire row overall of dates of service, and can be highlighted or otherwise emphasized to inform the user that it is the best value. 4258 shows CF. In this illustration of a retina surgeon, CF means count fingers, which is very bad vision and is, therefore, red. For the first time in this illustration, a retina surgeon can know, over the time that the doctor has been delivering services, or any doctor, what is being reflected in encounters and rows above. The best vision was 20/80 (4260). The worst was count fingers (4258). This can also be the best blood pressure and the worst blood pressure. Every different specialty in medicine has different ways that it would like to measure the highs and lows in a column. 4262 simply shows the counting of the number that had occurred in all of the encounters. In this case five FAs 4248. Patients may be seen over a hundred times and many medical services are provided. 4252 can be implemented to first show the doctor summary and identify critical items for the doctor to consider and for the first time the user can instantly view whatever is critical. In some embodiments, the user simply clicks on any of the information in 4252 and instantly all the encounters related to that data clicked is displayed in the number of rows 4228 that are needed to show the data. If a user engages by any method 4262, five rows of 4248 (in this case FA), are displayed in 4228 with five rows of 4228, since there are five listed in 4262. If user also wants to view simultaneously 4263 (3 ICG listed), then three additional 4228 will be displayed. So, if 4262 and 4263 are clicked, a total of eight rows of 4228 will be revealed unless some of those two (2) tests were done at the same visit. Clicking again on 4262 and 4263 can reverse the process. 4202 provides another way for the user to sort information and display in 7126.

It is important to note that the Data Command Center of the present principles can measure anything in the row and display it in multiple different ways. The choice could be just to see the high and low as in 4260 and 4258 over a short period of one year or over as many years as there have been encounters. It can also be set to show percentage changes over time. In any case, this summary provides a tremendous amount of information to the provider for enabling rapid decisions.

A panel 4220 can be located at the top, side, or bottom of the display and can provide access for each specialist to different types of healthcare providers or different doctors who want to customize the display. Any type of doctor or dentist or other health care provider of any specialty can be listed. As few or as many as have actionable dashboards that can be accessed immediately with direct access by simply clicking on the specialist's name. For instance, the specialists can be retina 4220, glaucoma doctors 4206, or an optometrist 4210. All three happen to be types of eye doctors. All three could be in the same practice, separate practices, or even in different countries. Each, when clicked on, pulls up an actionable dashboard specially designed for them or their practice in that specialty. 4214 provides an example of a non-eye doctor, in this case, the family doctor.

It is important to note that any health care provider, if given permission by the patient, and each specialty noted in FIG. 24 could see the actionable dashboard of the other specialists for as little or as much as each would allow. There is some information in an actionable dashboard to each specialist, practice, or doctor that they might not want others to see, which can be hidden (e.g., payments and costs). In addition, next to each actionable dashboard can also be additional information that can also be pulled up instead of the actionable dashboard itself. For instance, a dollar sign 4208 could be for providing for each practice or actionable dashboard, payments, costs, or any financial matter that can pop-up to show a different type of financial dashboard. 4212 shows an example that can pull up any type of additional information, such as a shared care dashboard between different providers.

4222 illustrates that an entire cell can alert all of the other providers of something important. It can be a color change, or flash, or blink. When activated, it represents that there is some type of important event, for instance, that all providers should know. A pop-up 4216 also can be shown at all times or by hovering over 4222. The popup could represent whatever the important item is to be alerted, for instance, a new diagnosis like that the patient had a stroke on 1/2/20, which all providers would like to know. It can also inform all providers that the patient missed an appointment that was particularly important with that doctor. So, that all specialists would know that and be able to remind the patient. The critical information in 4216 can also be inputted by creating a row 4228 in time order or as the first row that every provider views when they open their personalized flowsheet.

It will be further appreciated that the actionable dashboard can further include a communication center where users can send messages to each other in a HIPAA compliant way. A physician, while seeing a patient, can send a message in one of many ways for instance, by clicking 4223 and a mechanism to send a message to any other doctors caring for the patient, even if not in their own practice but another practice such as 4214 or 4210 and a message sent and added to that patient's actionable dashboard in the other practice. This mechanism can also set an alert, as seen in 4216 or allow any doctor when they believe something is so important for all providers to know to set a row in all providers tools and creating a row inserted. Doctors can also send messages within their own practice such as to their chief technician or the office manager to talk about following up on a patient or also to the billing office that there is a billing problem. Then, staff can report back to the doctor and this message can be imbedded into the smart actionable dashboard so that the next time a doctor sees the patient through icons and columns of correspondence of communication within the practice, the doctor can pull up what was the response to a message they had sent earlier. This response can be read live while treating the patient so that the doctor can take it into perspective while making decisions. The messaging system, attachments, or anything else can be sent to the doctor or health care provider in any way that they would want. Whether through email or the internal messaging system or as a tickler system within the EMR system that automatically toggles back and forth to the actionable dashboard, so the doctors can see their messages at the end of the day or the end of the week, or while seeing the patient. It really helps organize the doctor's life, so this actionable dashboard becomes the communication hub, the switchboard, for the entire practice, while communicating with the health care provider.

FIG. 24 further depicts an embodiment of how the interaction with a header and summary row can work. When a doctor interacts with the Flowsheet of the embodiment of FIG. 24 and element number 4252 and clicks on the numbers. In another embodiment, colored dots can be depicted to enable a doctor to refine further exactly what they would want to see. Clicking on 4264 for instance on the summary row Element 4252 brings up just those encounters when that particular test was done and the 38 OCTs performed would come up and be displayed in 4228 where one such OCT encounter is depicted. If the user wants to sort further, then in one embodiment an example would be clicking on a colored dot in 4265 which enables a user to refine exactly what data the user needs to visualize to make decisions. For instance, upon activation a display panel can display on the screen when 4265 is activated. As such, a user can select 4270 and now many options can be selected to precisely sort and search what the user wants to find from the data. For instance, the user can choose all OCT's 4272 or just choose the OCTs that show worsening with the colored (e.g., red) arrows, 4274 which would select diagnostic tests with colored identification 4275 which could mean many things such as diagnostic tests with worsening result. The user can select to see only tests that are as designated as improved perhaps in this case as another colored (e.g., green) icon 4276. Only the OCTs that have that designation and the time of those encounters would be displayed. As can be seen, many different options on exactly how to refine which OCT can be selected.

In addition, other encounters can be selected to also be displayed along with the initial data encounters selected in 4270 of FIG. 24. Patients can have hundreds of visits and if a user wants to refine what they're looking for, the user can choose and pick out any particular diagnostic tests that share a common features as seen on FIG. 24, 4268, and the user can ask for other encounter dates and rows to be also sorted and displayed such as also showing if injections of Avastin, 4280, were performed within a certain time period 4282 of the OCT's, where criteria was selected to be displayed in 4270.

In FIG. 24, 4266 can be implemented to bring up an ordering panel 4285 or to expand other areas for ordering but always though one user interface and one display. Now the user is enabled to place an order while visualizing relevant data.

The Patient-Specific Dashboard of FIG. 25 can be accessed by direct login to an application, launched from a separate application, either within the context of an existing patient from the application or generally through a patient search, or from within other aspects of a Command Center. A Master Header, in this example, is used to represent general data and information about a patient. A Navigation icon 21010 can be utilized to exit the Patient-Specific Dashboard, navigate to other aspect of a Command Center, or return to an initiating application. Patient Demographic and Insurance information can be represented in 21020. Medical Record Number and Associated Providers can be represented in 21030. Critical Patient Alerts can be represented in 21040, highlighted or otherwise emphasized, such as in color, to draw attention to them. The Chief Complaint, or purpose for a visit, can be represented in 21050. In the embodiment of FIG. 25, the key purpose of a Master Header is to denote the context within which all subsequent data representations exist.

The Master Header Row 21060-21070 can be utilized to differentiate different personas. In the embodiment of FIG. 25, Primary Care 21060 is the selected Persona, and as such, data is represented in accordance with requirements of and for the Primary Care Persona. Beyond this persona, distinctions can be made per user or per other configurations, but the general governing persona remains Primary Care. Other Personas, such as Specialty 1, Specialty 2, and Specialty 3, collectively 21070, can be accessed through their respective fields, and can be highlighted or otherwise emphasized to draw attention to important aspects of patient information which may not be represented within the selected Persona's view, such as Specialty 3 being highlighted. Personas can include, but are not limited to, user-or specialty-defined personas, practice defined personas, or any logical or geographical representation, not limited to a single user or practice, and inclusive of outside practice patient information.

The Flowsheet Header Row 21090-21190 denotes, in this example, column headers. Said Flowsheet Header Row is not limited to columnar data, and may exist vertically, or along any axis, or exist outside the context of an array of data. The Flowsheet Header Row, in this example, is comprised of Summary Data Representations 20140 of FIG. 14, accounting for all data in the underlying column or logical grouping to be represented by Summary Data Representations.

In the embodiment of FIG. 25, the Flowsheet Header Row begins with Date 21090 representing the date of occurrence of key events. Provider 21100 represents an associated provider for such an event. Location 21110 represents the geographical location of the event. Procedure 21120 represents the occurrence of a medical procedure. HbA1c 21130 represents results from a medical test. X-Ray 21140 represents a diagnostic test. Within the X-Ray data field, an icon 21080 exists by which a user can launch a different representation of the presented data. Meds 21150 represents patient medications. Lab Test 21160 represents a laboratory test. In this example, the Lab Test data field is highlighted, for example in color, to denote an alert based on key data within the column, or logical grouping of information. Within the Lab Test field, an icon 21085 exists by which a user is enabled to launch a different interface, in this example, an Order Interface. Biopsy 21170, highlighted, for example in gray, represents a Flowsheet Header Row from a different Persona, in this example, Specialty 3, also highlighted, as this is important information which may not be normally viewable under the Primary Care Persona. Plan 21180 represents a provider's Assessment and Plan of Treatment for a patient. Financials 21190 represents the financial circumstances regarding the patient, patient's insurance, and other relevant financial information.

In FIG. 25, the Flowsheet 21200-21360 is an array of patient information graphically represented in accordance with the Date 21090 column. At 21200, a Future Appointment is depicted, scheduled for a date, but not yet with a specific Provider. Such future appointments inform a provider as to future plans for either the provider, or any persona, to see the patient again. At 21210, we see a Future Order. Said order is scheduled for a Date, with a Provider, for an X-Ray 21220. At 21240, a Next Visit is depicted. In this example, the Next Visit is not scheduled for a Date, Provider, or Location. What has been specified for the Next Visit is a Lab Test 21250, which can occur at any Next Visit. Each of these three events, Future Appointment, Future Order, and Next Visit are all exemplified as Truncated Data Representations 20030 of FIG. 14. The Future Order of an X-Ray 21220 and Next Visit Lab Test 21250 are Linked Image Data Representations 20070 of FIG. 14, yet without the relevant data to link to, as they have not yet occurred. At 21230, a Scroll Bar is presented, denoting that there may be more information below the viewable portion, and provides access to the information.

Today's Visit 21270 is specific to an event occurring on the present Date and lists a Provider and Location. Also denoted for Today's Visit is a Procedure, a Shave Biopsy, which has occurred with Specialty 3 and has been added to the Flowsheet at 21290. An HbA1c result 21280 is an Alerted Data Representation 20040 of FIG. 14, as well as an Informational Data Representation 20050 of FIG. 14. As such, the field is Alerted by highlighting in red, and offers a colored (e.g. green) corner notification which can be interacted with to see more information. The Financial information 21260 is a Symbol Data Representation 20110 of FIG. 14. In this example, symbols may represent payment status of different categories, such as Office Visits, Procedures, and Diagnostic Tests, General Financial Status for the patient, Percentage of Deductible Paid, Likelihood of Insurance Denial, and Patient Responsible Balance. Symbols are configurable, and as such can be used to represent any data which may be relevant to a logical grouping of data represented.

Past Visits 21300 are shown below Today's Visit 21270. In this Past Visit, a Medication 21310 is denoted by a Graphical Data Representation 20100 of FIG. 14. In the embodiment of FIG. 25, a colored bar (e.g., magenta bar) exists denoting the start and stop dates of the medication, between a first color represented (e.g. teal) medication and a second color represented (e.g., yellow) medication. Graphical representations of medications can conform to existing color specifications or custom configurations. The Plan 21320 is denoted by a Text Link Data Representation 20090 of FIG. 14. As such, interacting with the data will provide more information, such as the ability to read the full Plan.

At 21330, a Thumbnail Image Representation 20080 of FIG. 14 is depicted. A smaller view of an image is displayed to convey a quick overview of the underlying image. 21340 is a Linked Image Data Representation 20070 of FIG. 14. This provides enough information to inform the user that there is an underlying image, which can be directly accessed through interaction with the data representation.

At 21360, a Canceled Visit is depicted. Such a visit is shown as a Missing Data Representation 20060 of FIG. 14, to depict that there was an expectation of data, but it was not present. There was enough information to show a date, provider, and location, but because the patient did not arrive, nothing further is available. An Informational Data Representation 20050 of FIG. 14 shows in the Location logical grouping, which can convey whether the appointment was canceled by the practice or patient, missed, or rescheduled.

A Flowsheet Summary Row 21370 at the bottom of the Flowsheet is comprised of Summary Data Representations 20140 of FIG. 14, and can contain values such as how many visits occurred with each provider, at each location, how many of each type of procedure occurred, highest/lowest HbA1c results, total count of diagnostic tests, a summary of insurance patient balances, and the like. As a Summary Data Representation, each representation can be implemented to interact with data representations within the logical grouping of data associated with the field, such as filtering or placing an order.

A separate module 21380 exists in the bottom right, in the embodiment of FIG. 25 to display Problems, Medications, and Allergies, 21400, a common subset of medical data. Problems is the selected tab, yet Medications is highlighted, for example in color, and as such, a representation of medications 21430 exists within the Problems tab, utilizing Linked Data Representation 20180 of FIG. 14. Such a module is a Linked Data Representation, as is the Module at 21390. Assessment and Plan 21410 denotes a main function of the module of FIG. 25, yet it can be interacted with to change the function of the module, or rules can automatically determine the most important information to be represented. A Date Selector 21420 enables the context of this module to change to a selected date or can represent a date the user interacts with on the flowsheet. This exact information from the Assessment and Plan for the selected date is shown at 21440.

Figure 26A:
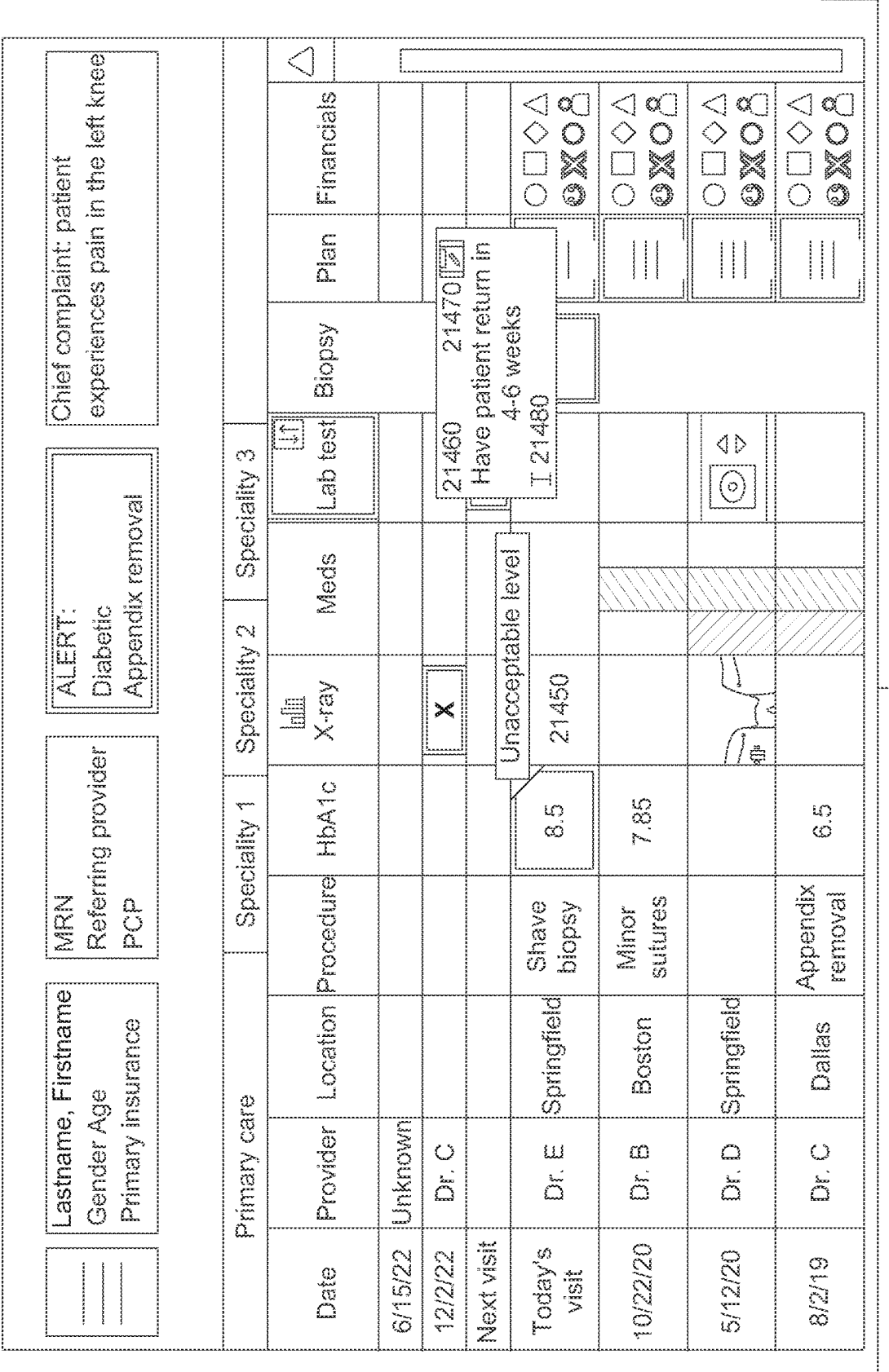
FIG. 26 depicts additional data display within a patient specific dashboard in accordance with an embodiment of present principals.
Figure 26B:
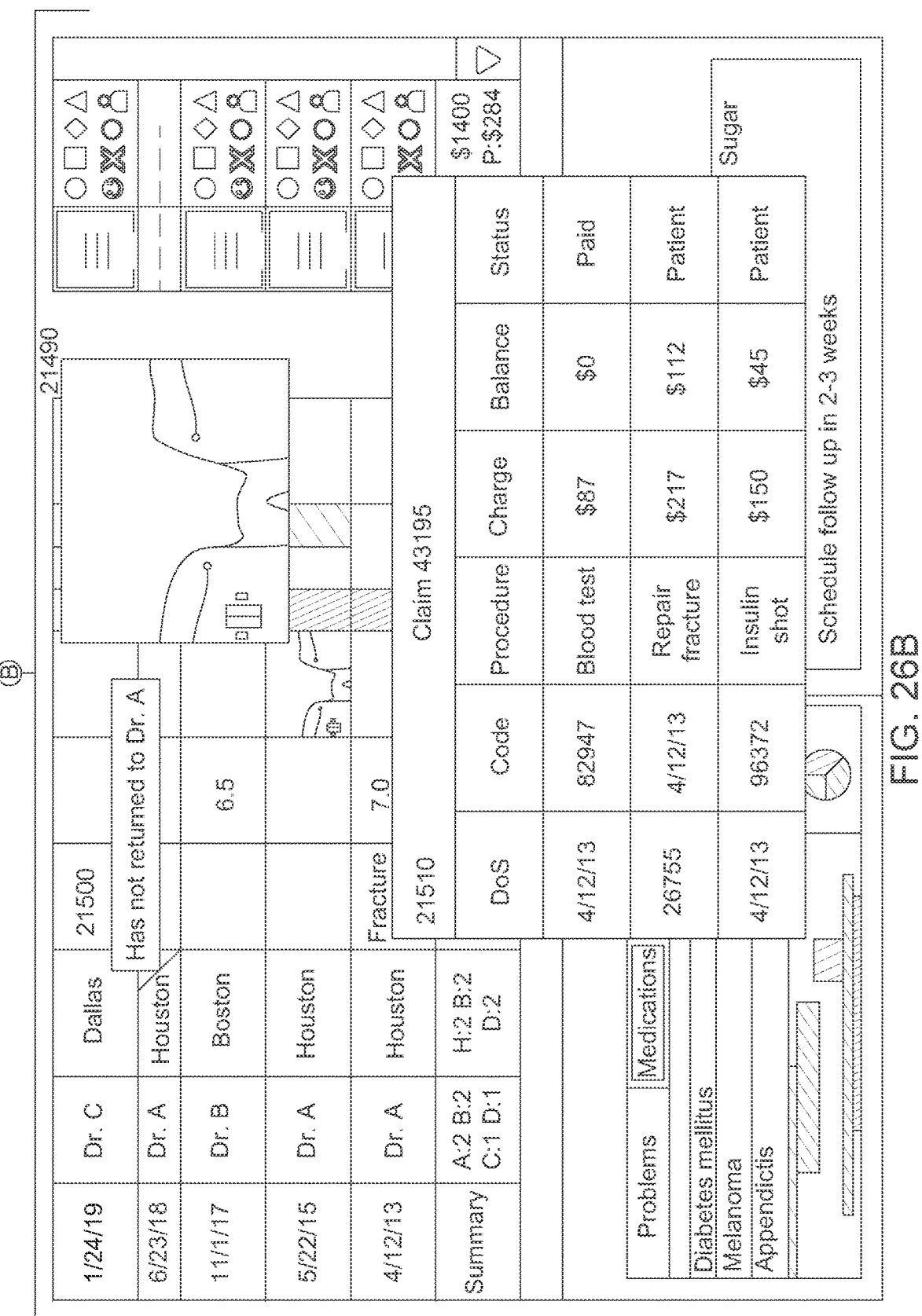

Several Dynamic Data Representations enable access to further information. For example, FIG. 26 depicts a Dashboard display of Dynamic Data enabling access to additional data in accordance with an embodiment of the present principles. The HbA1C Informational Data Representation at 21450 can be shown upon interaction using a hover, select, or other operation to select the relevant data. At 21450 of FIG. 26, it is depicted that the HbA1c is at an unacceptable level. The Plan Text Link Data Representation interacted with at 21460 displays the full Assessment and Plan. In FIG. 26, an icon at 21470 denotes the field is editable. As such, a text cursor is displayed at 21480 and the user can edit the plan. An Image Thumbnail Representation interacted with can display the full-sized image as seen at 21490. The Missed Appointment Informational Data Representation interacted with denotes the patient has not returned to see the provider their last appointment was scheduled with at 21500. The Financial information Symbol Data Representation interacted with shows a patient's charge status for the respective visit date at 21510. Each representation provides more information, as well as direct access and the ability to edit information.

Figure 27A:
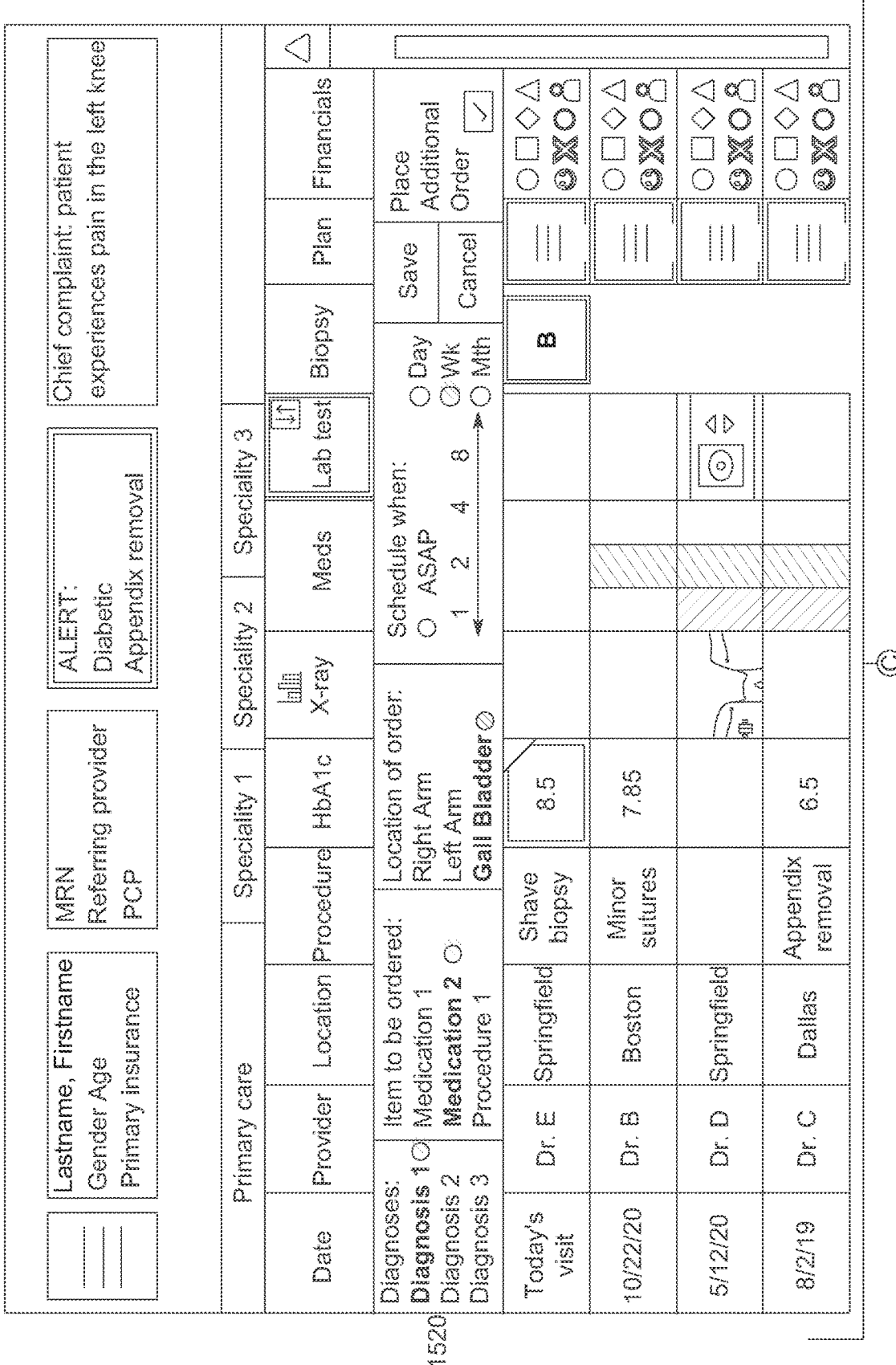
FIG. 27 depicts an ordering module within a patient specific dashboard in accordance with an embodiment of present principals.
Figure 27B:
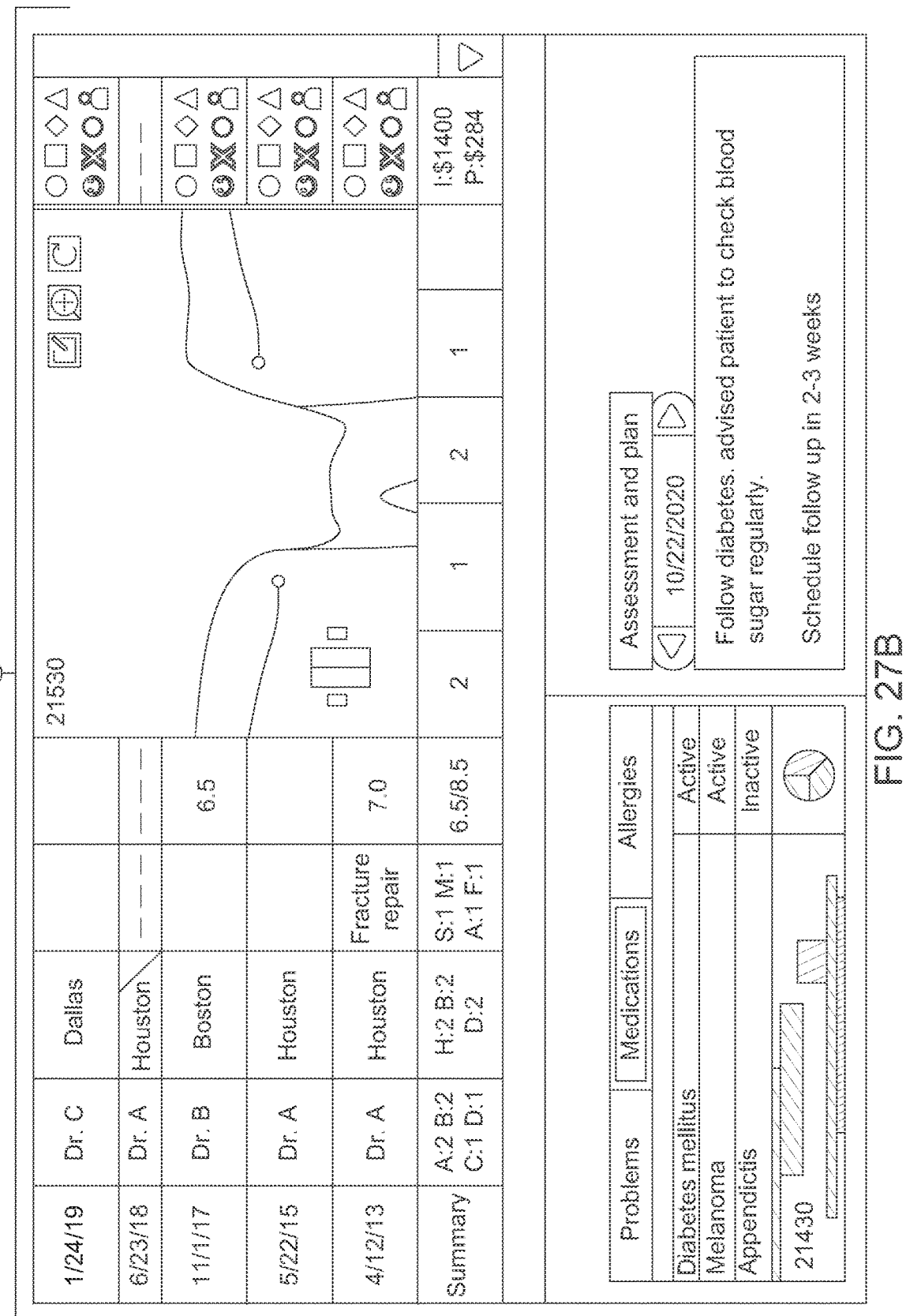

FIG. 27 depicts an embodiment of a Dynamic Data Flowsheet in which the actual Flowsheet is being altered to allow for additional and/or different sized representations. At 21520, a full ordering panel is depicted as will be described in greater detail below. In the embodiment of FIG. 27, however, future visits have been removed to make room for the ordering panel. Also represented within the ordering panel are colored alerts for Procedure, Medication, and Gall Bladder, to inform the user if there is a discrepancy in their selections. At 21540, a Thumbnail Image Representation is depicted expanded to take up several adjoining data representations to show the full image within the data representations.

Figure 28A:
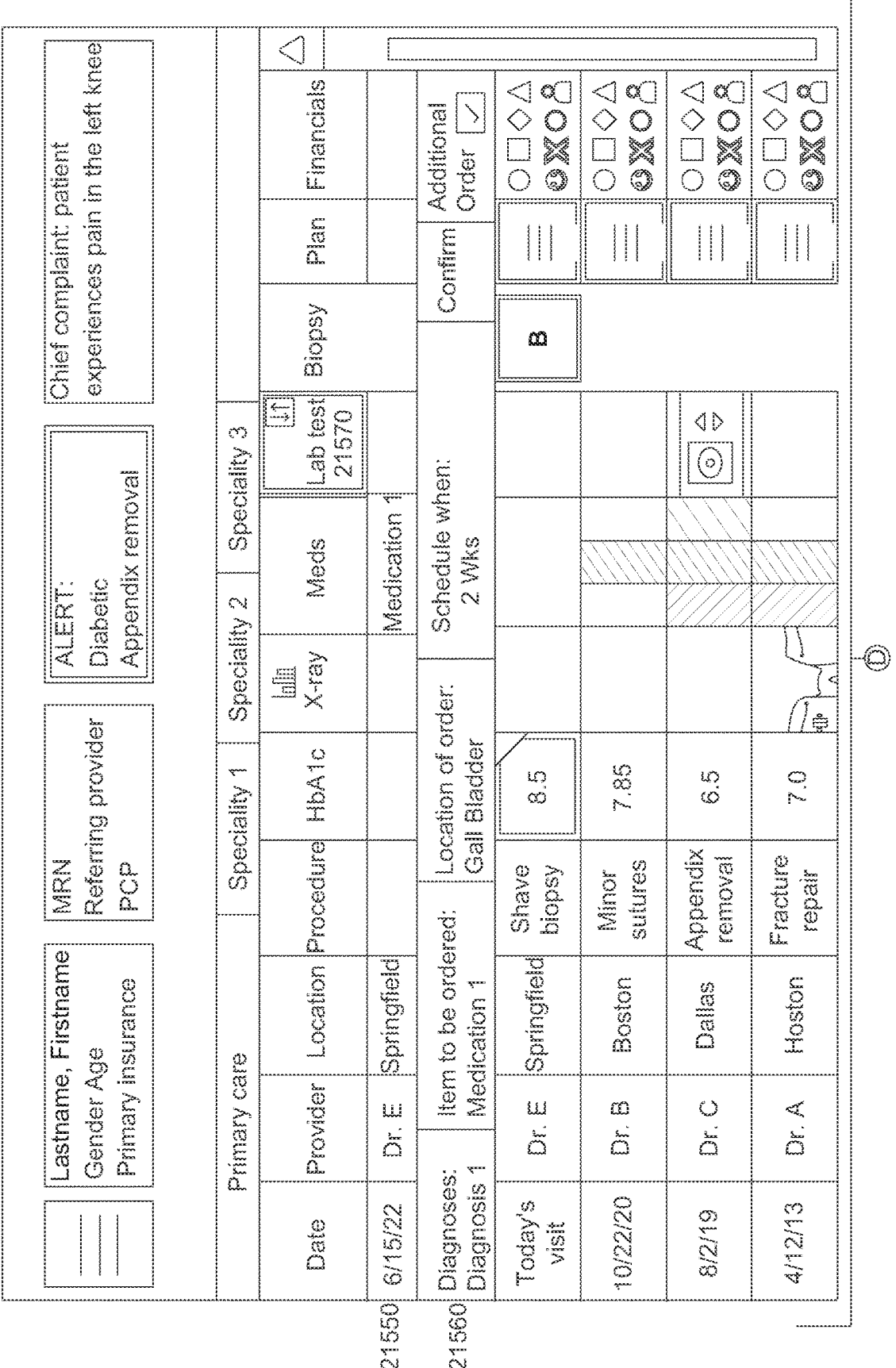
FIG. 28 depicts a future order and filtering within patient specific dashboard in accordance with an embodiment of present principals.
Figure 28B:
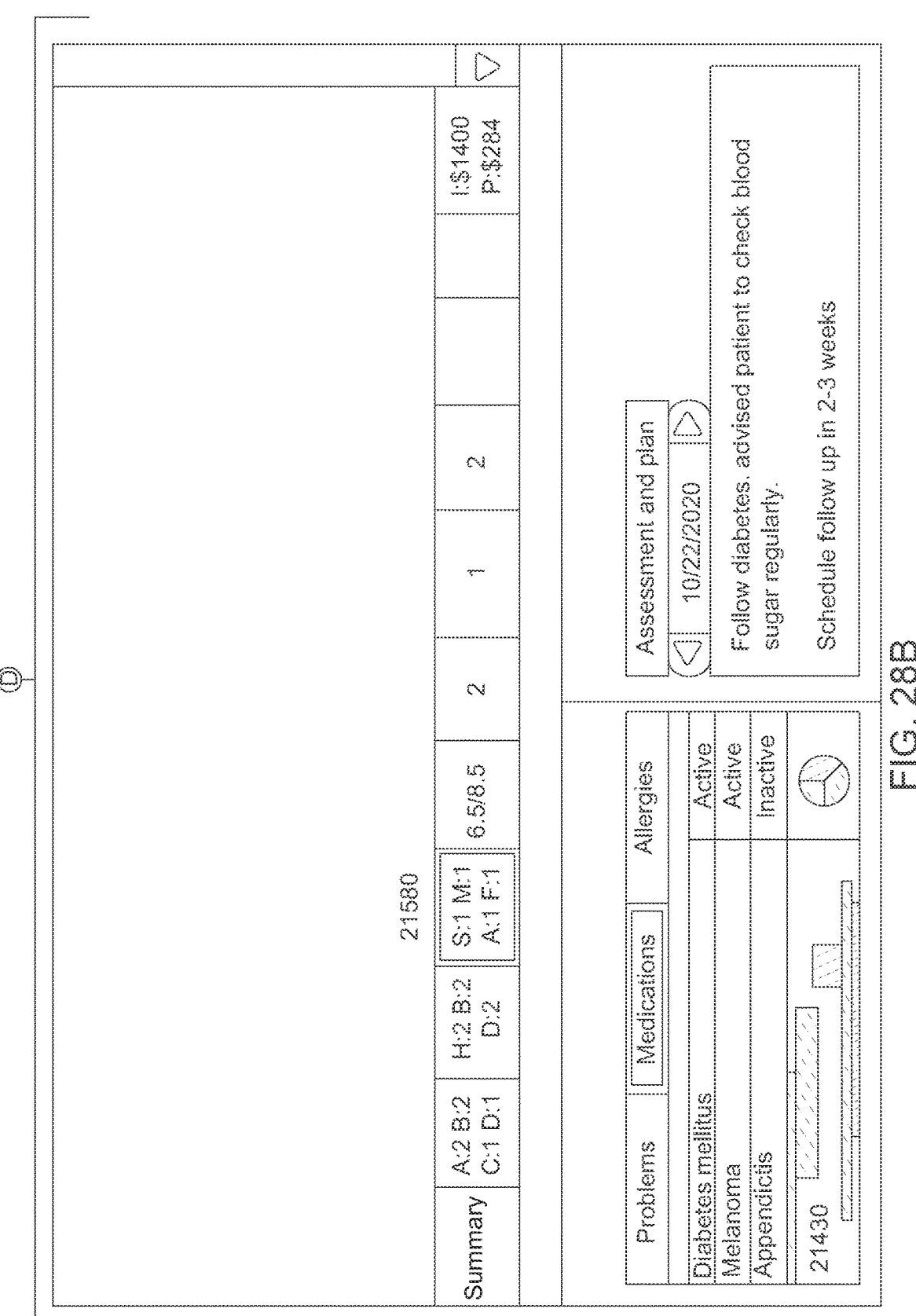

FIG. 28 depicts an embodiment of a Dynamic Data Flowsheet including an order in the process of being placed. In the embodiment of FIG. 28 space is made for a new row to be added at 21550, showing that Medication 1 is set to be ordered in accordance with the specified parameters. A colored notification exists at 21570 to inform the provider that the patient has an issue related to a Lab Test, such as one being indicated based on prior conditions and risk factors. At 21560, the intended order details are depicted, no longer alerted because the provider has properly selected compatible Procedure, Medication, and Location. The provider can now review the order, ensure that they have selected what they intended, and can confirm the order using the Confirm button. Additional orders can subsequently be placed by leaving the Additional Order check box checked.

In the embodiment of FIG. 28, below the order, several events have now been hidden. Interacting with Summary Data Representation 21580, relevant data can be filtered. A single interaction can only display those rows with relevant values. For demonstrative purposes, a context menu 21590 is displayed to illustrate complex filtering functionality. In this case, Value of Procedures is selected, and as such, only events containing Procedures are now displayed. Several Summary Data Representation filters can be implemented at the same time, and can be configured to work based on user selection, such as instantiating the Order Process, which can automatically hide or show portions of the application relevant to the process.

Figure 29A:
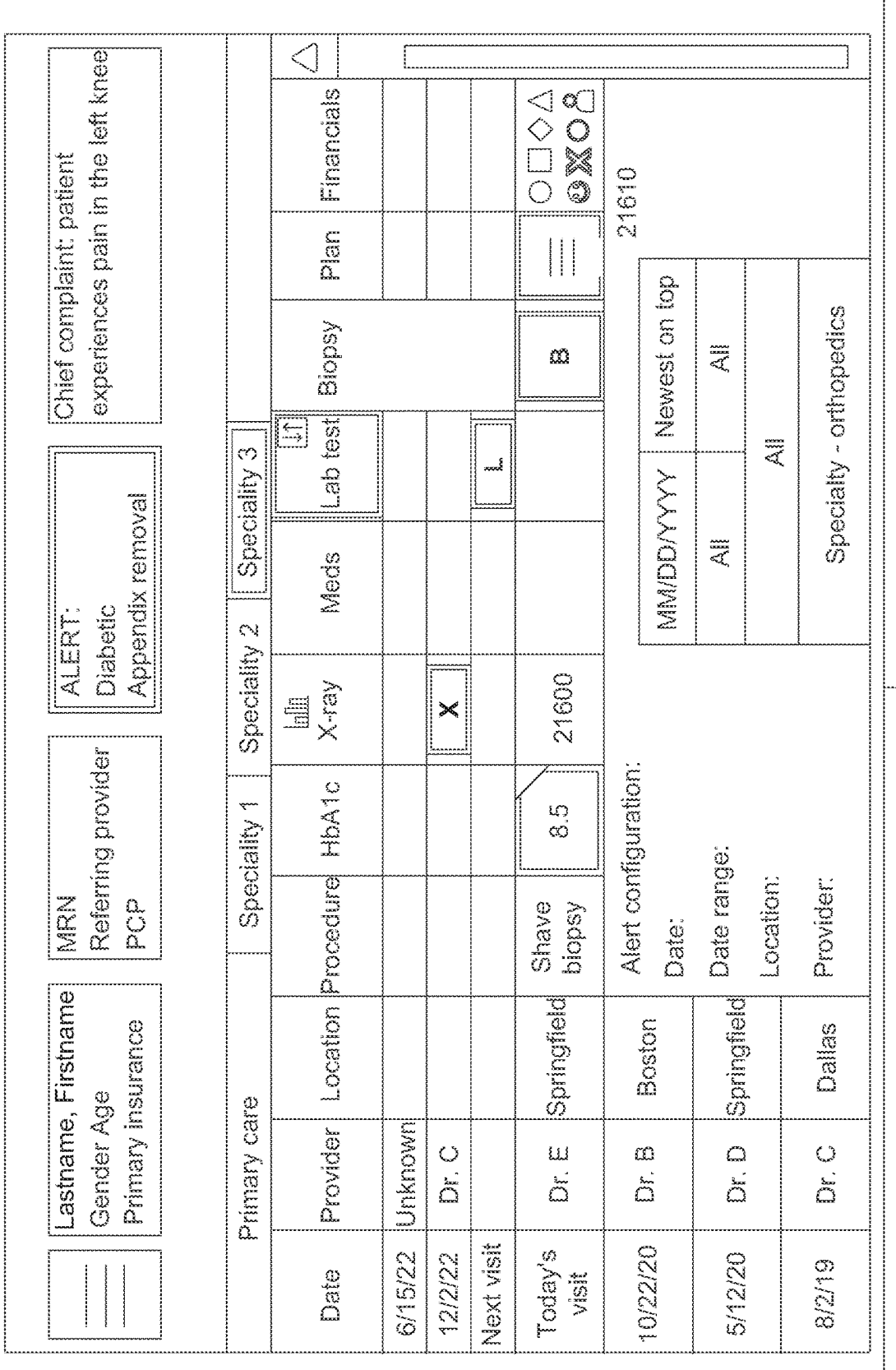
FIG. 29 depicts in-context alert configuration within a patient specific dashboard in accordance with an embodiment of present principals.

FIG. 29 depicts an embodiment of a Dynamic Data Flowsheet including an Alerted Informational Data representation at 21600. That is, configuration of Dynamic Data Representations can occur within the context of the underlying data so as to ensure proper configuration is being entered. In the embodiment of FIG. 29, an Alerted Informational Data representation is depicted at 21600. In some embodiments, such a representation can be configured by interaction directly with the field. Instantiating the Alert Configuration module 21610, parameters can be set in accordance with FIG. 15. Specific selections within this example show that for an Event Type of Over 8.0, a colored alert will display, and Details will show in an Informational Data Representation.

Figure 30A:
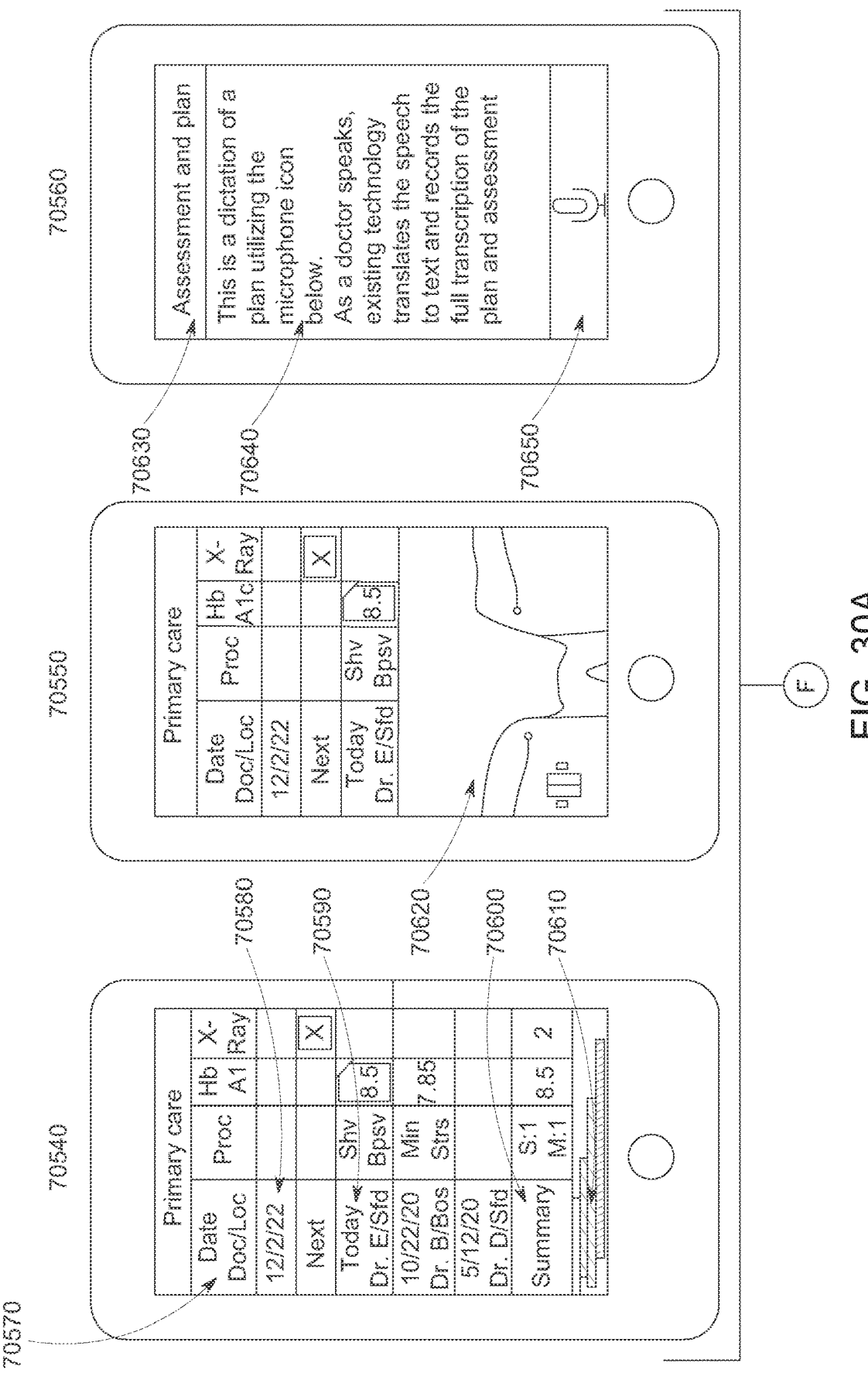
FIG. 30 illustrates several views of limited area displays in accordance with an embodiment of the present principles.
Figure 30B:
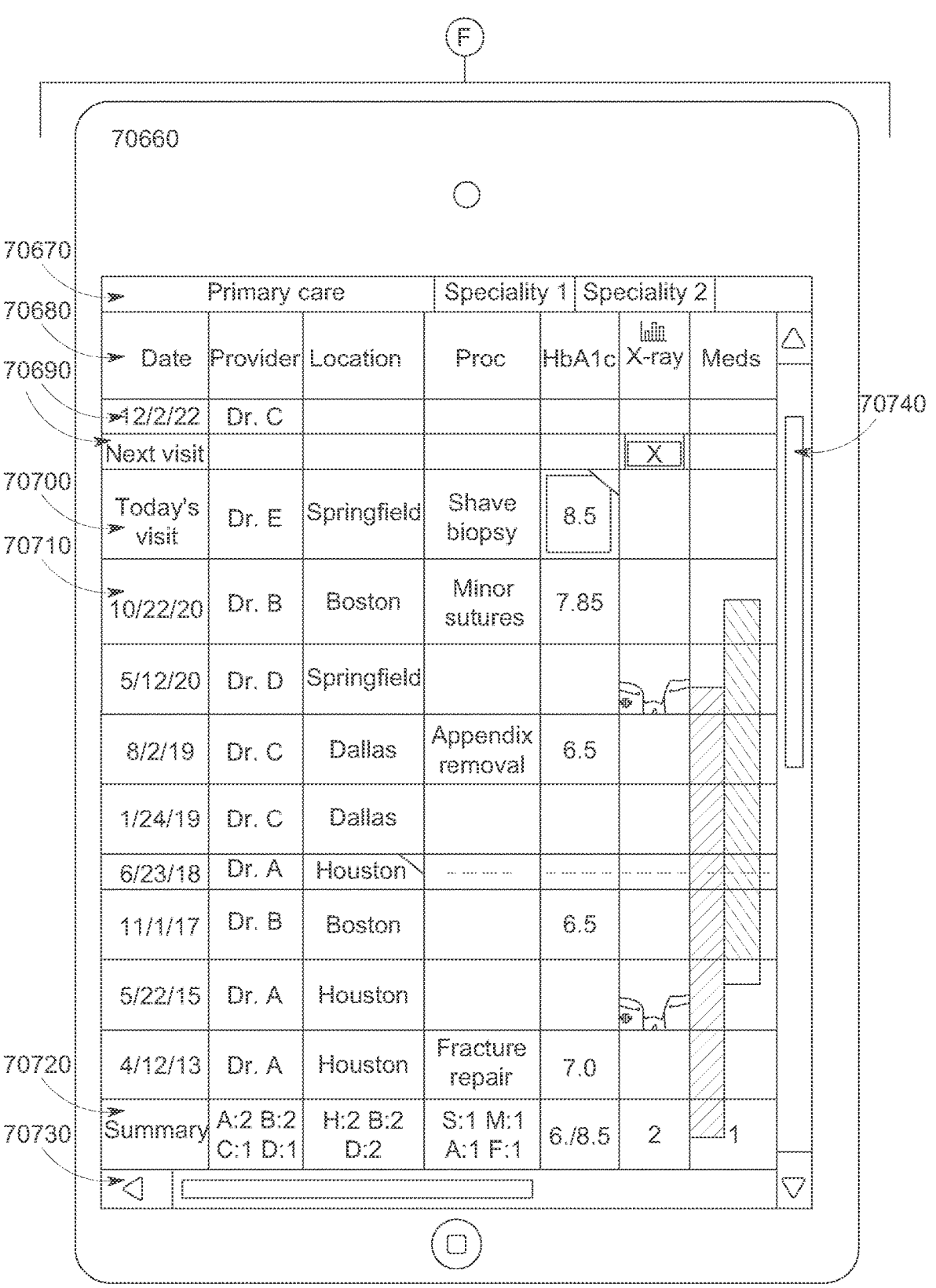

FIG. 30 illustrates Screen Resizing including several views of limited area displays in accordance with an embodiment of the present principles. Useful for maximizing screen space, these same principals can be applied to smaller devices such as smartphones and tables. 70540-70560 depicts how the Command Center can implement different described functionality to generate different views based on an available screen size. At 70570, concatenated text is displayed in a field to show Date, Doctor, and Location. At 70580, future events are displayed. At 70590, a Today's Visit is displayed. 70600 illustrates the Summary Row, and 70610 can be used to display medications. At 70620 of 70550, an enlarged image is displayed, while the rest of the screen shows relevant data. Direct access to edit a plan, as described herein, displays in 70560. At 70630, the type of information being edited is displayed. At 70640, text that was dictated using existing smartphone capabilities is displayed, and at 70650, the microphone icon common to most smartphones associated with text-to-speech functionality is displayed.

In FIG. 30, 70660 represents a tablet, such as an iPad. 70670 displays specialties, 70680 is the flowsheet header row, 70690 displays future events, 70700 is Today's Visit, 70710 represents past visits, and 70720 is the summary row. In FIGS. 30, 70730 and 70740 are scrollbars used to view more information, in some embodiments off screen.

Figure 31:
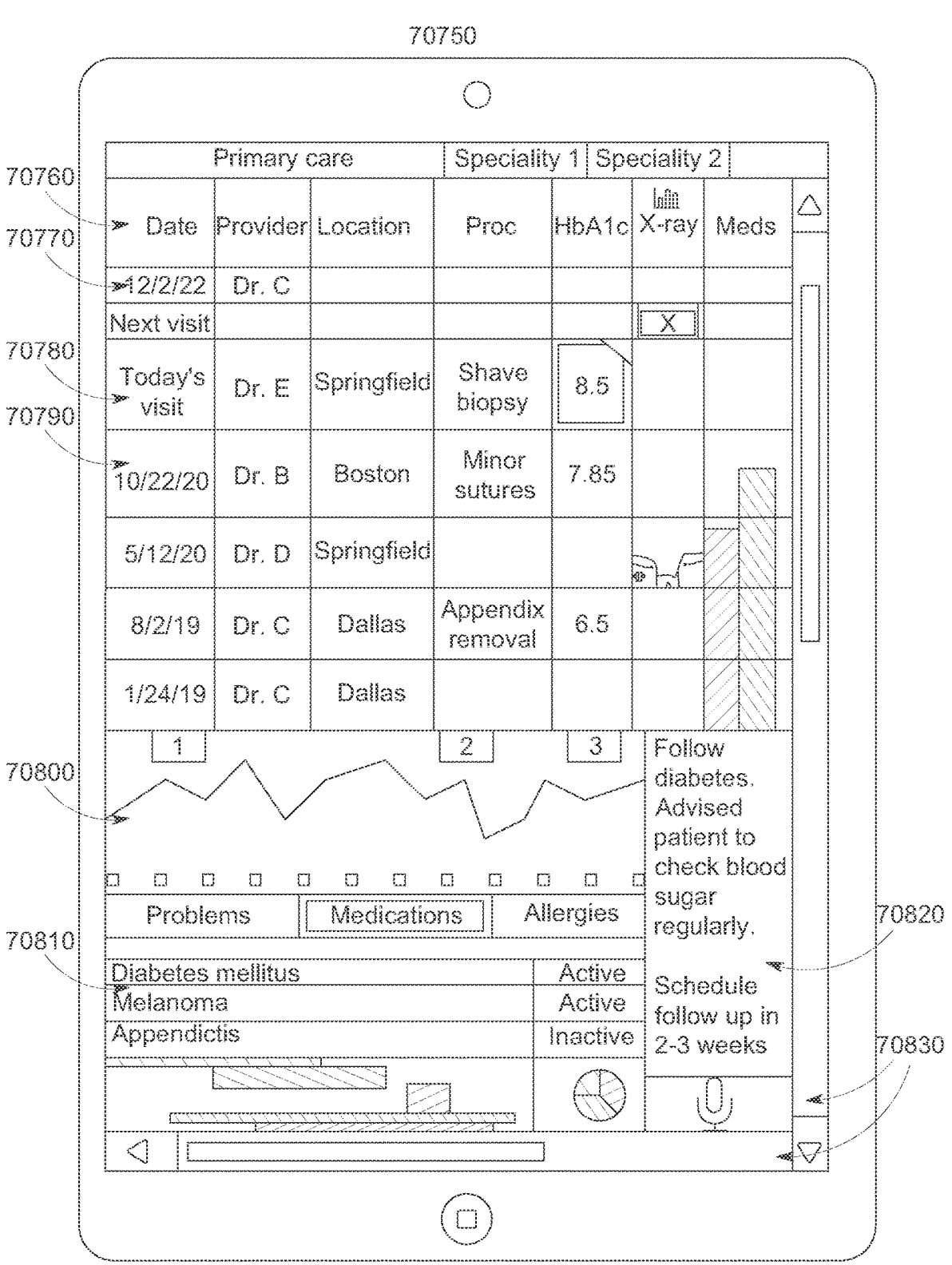
FIG. 31 illustrates another view of limited area display in accordance with an embodiment of the present principles.
Figure 32A:
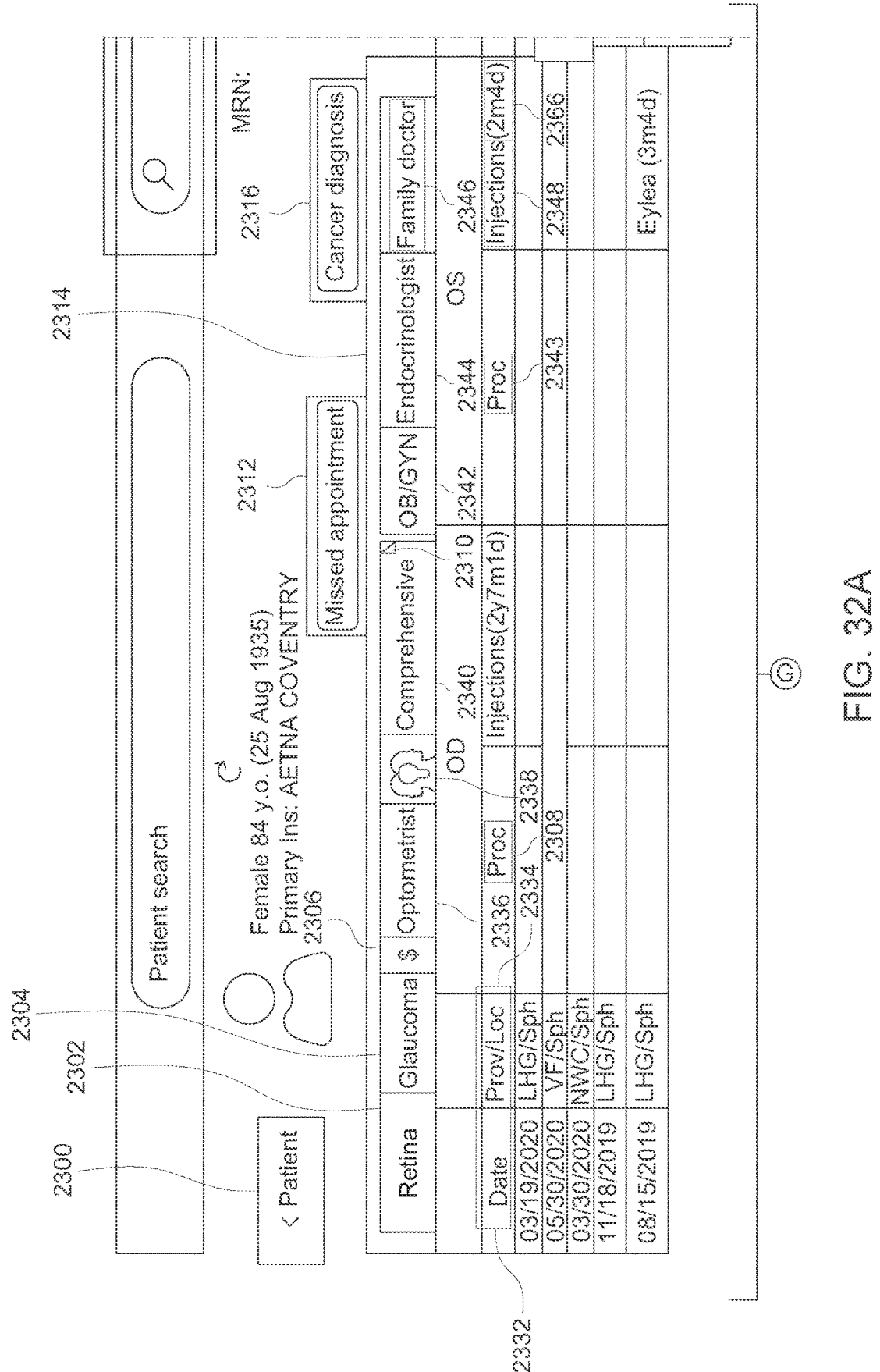
FIG. 32 depicts an embodiment of a medical records dashboard in accordance with another embodiment of the present principles.
Figure 32C:
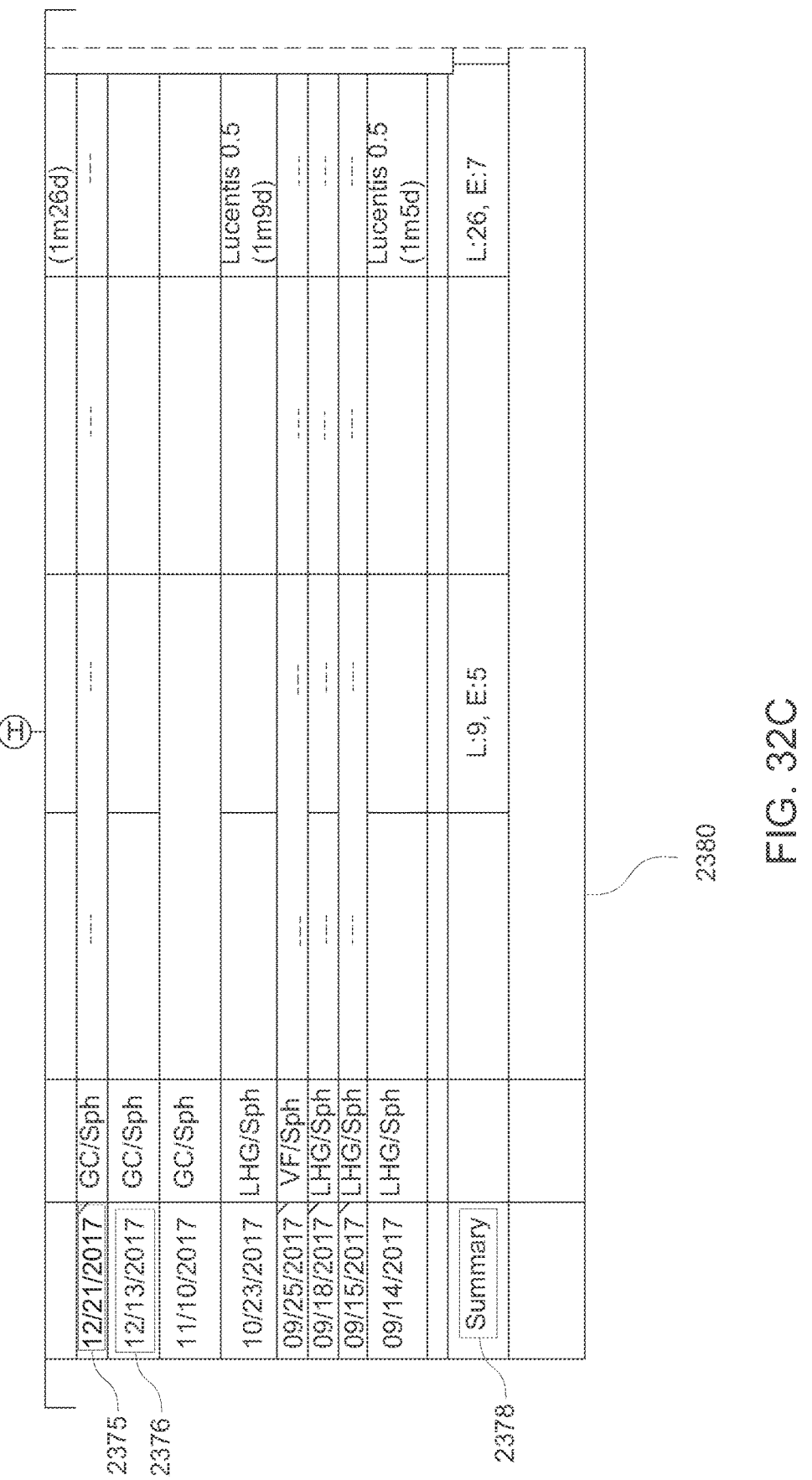
Figure 32D:
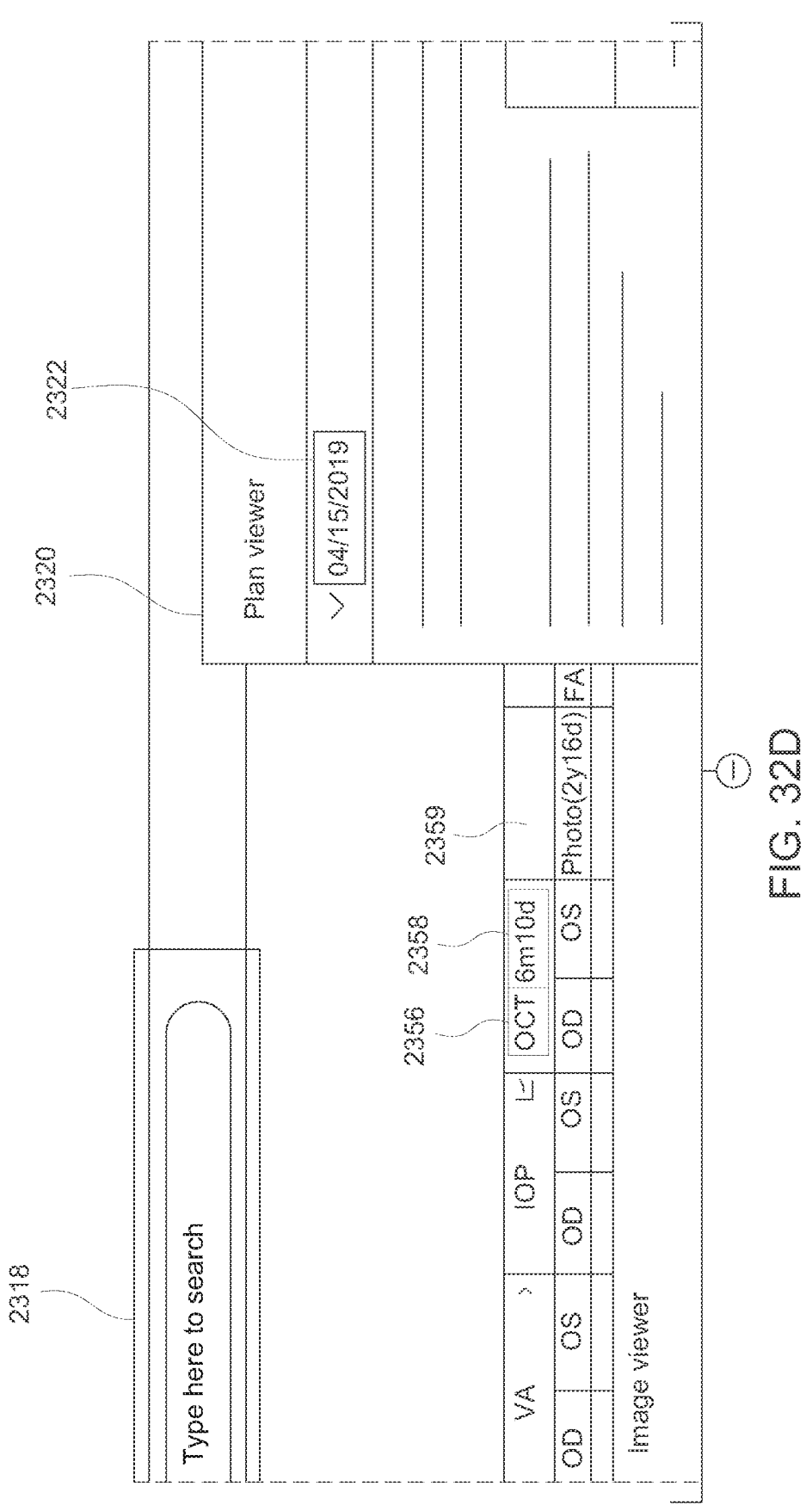
Figure 32E:
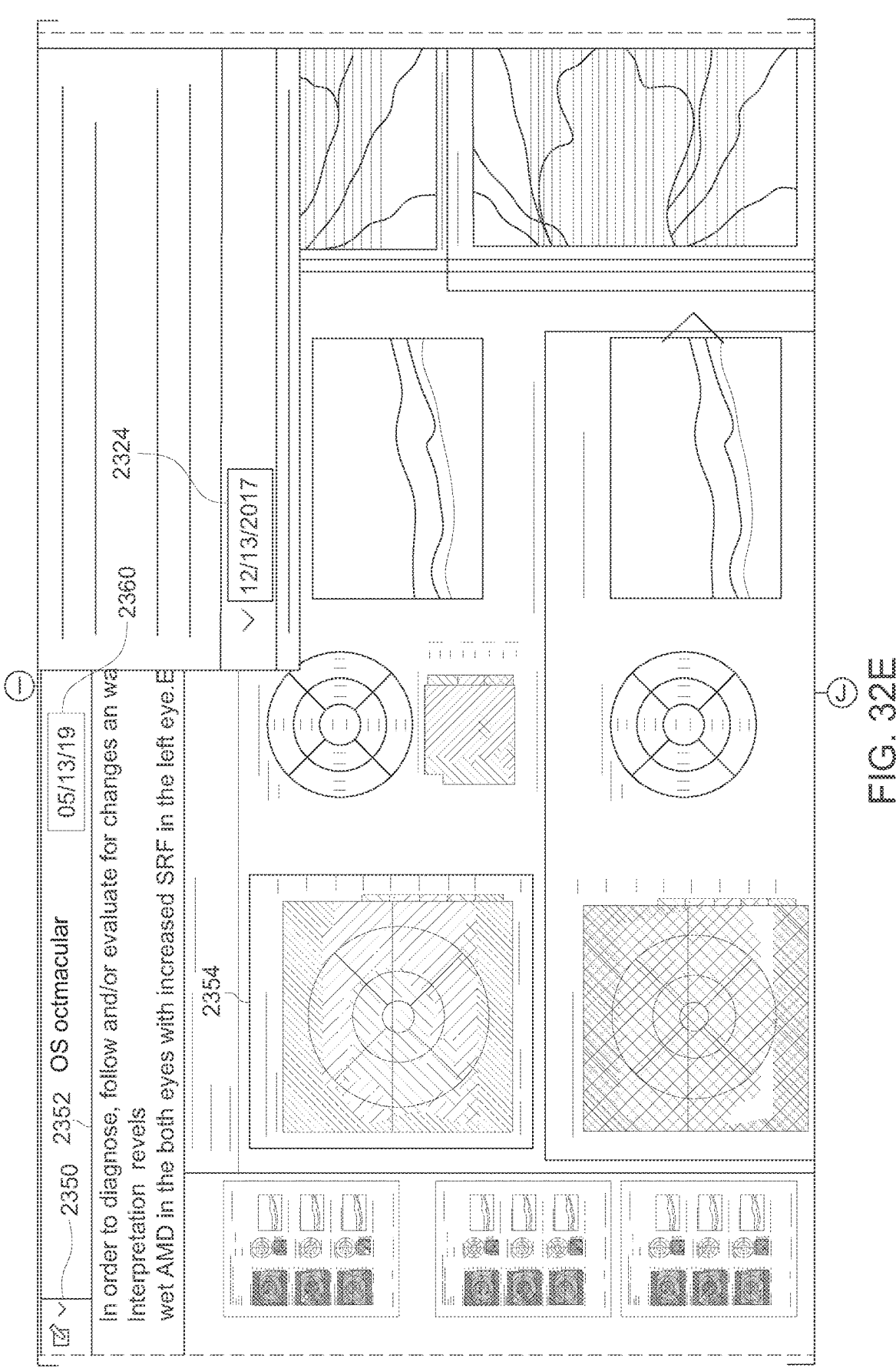
Figure 32F:
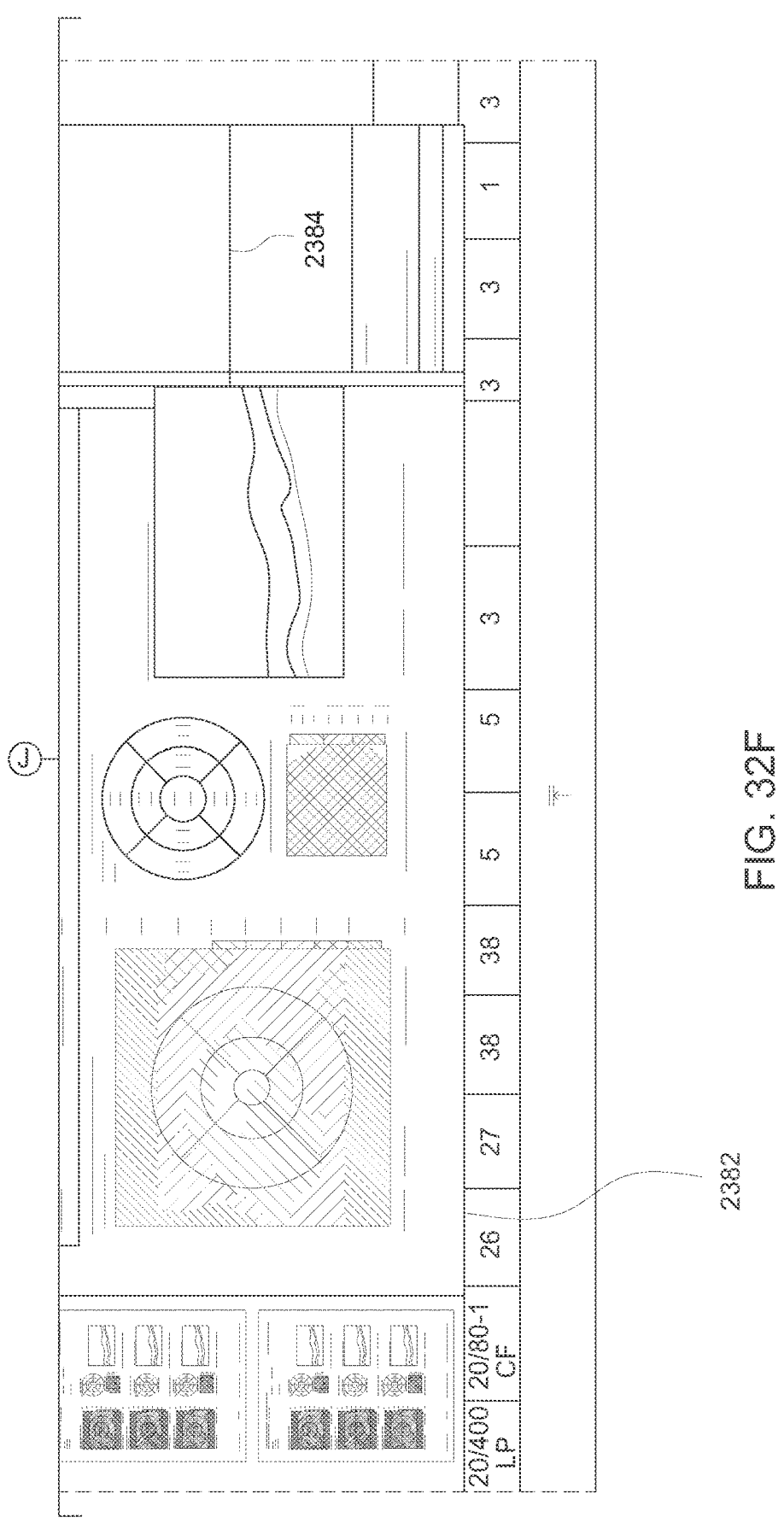
Figure 32G:
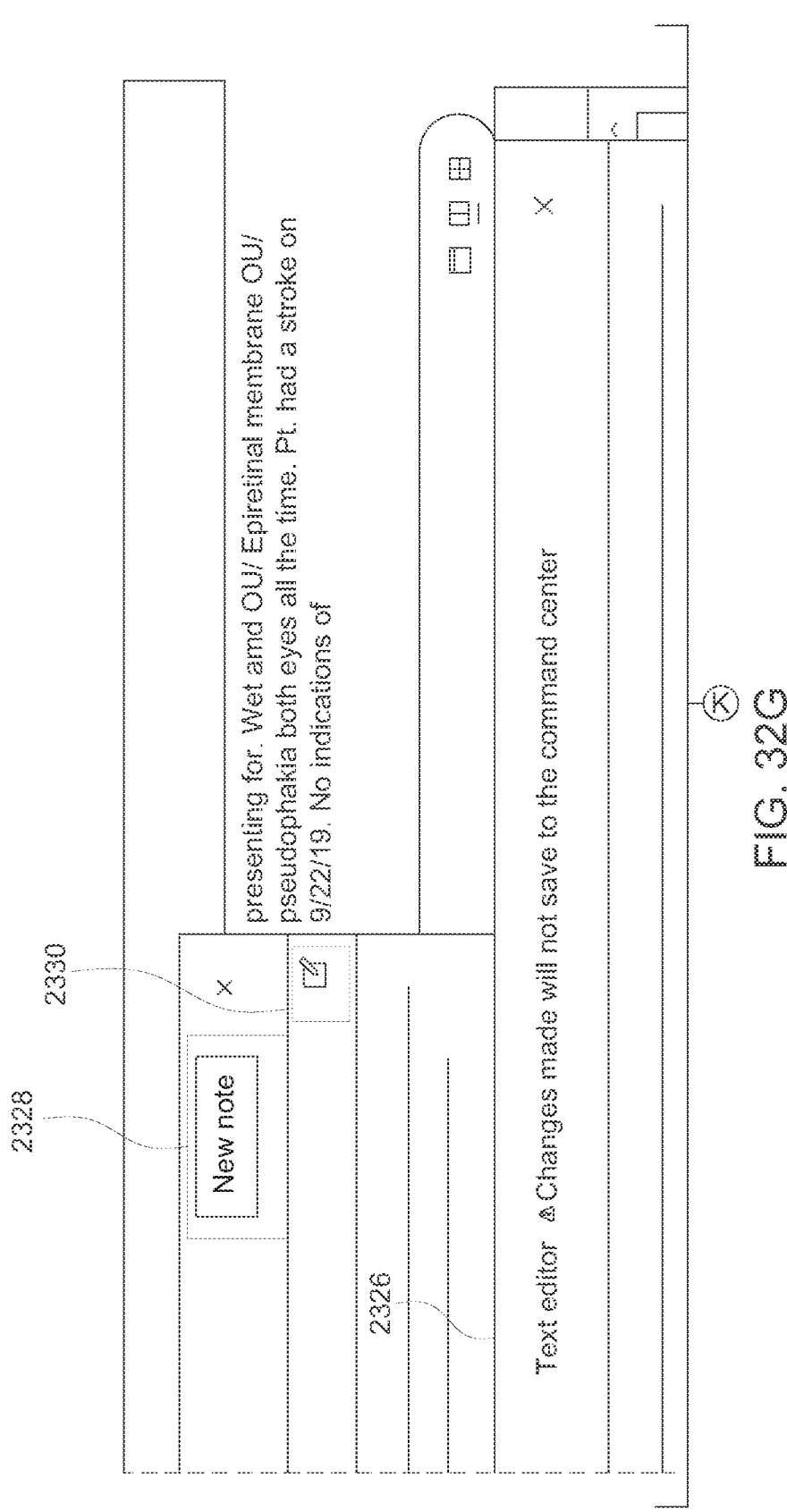
Figure 32H:
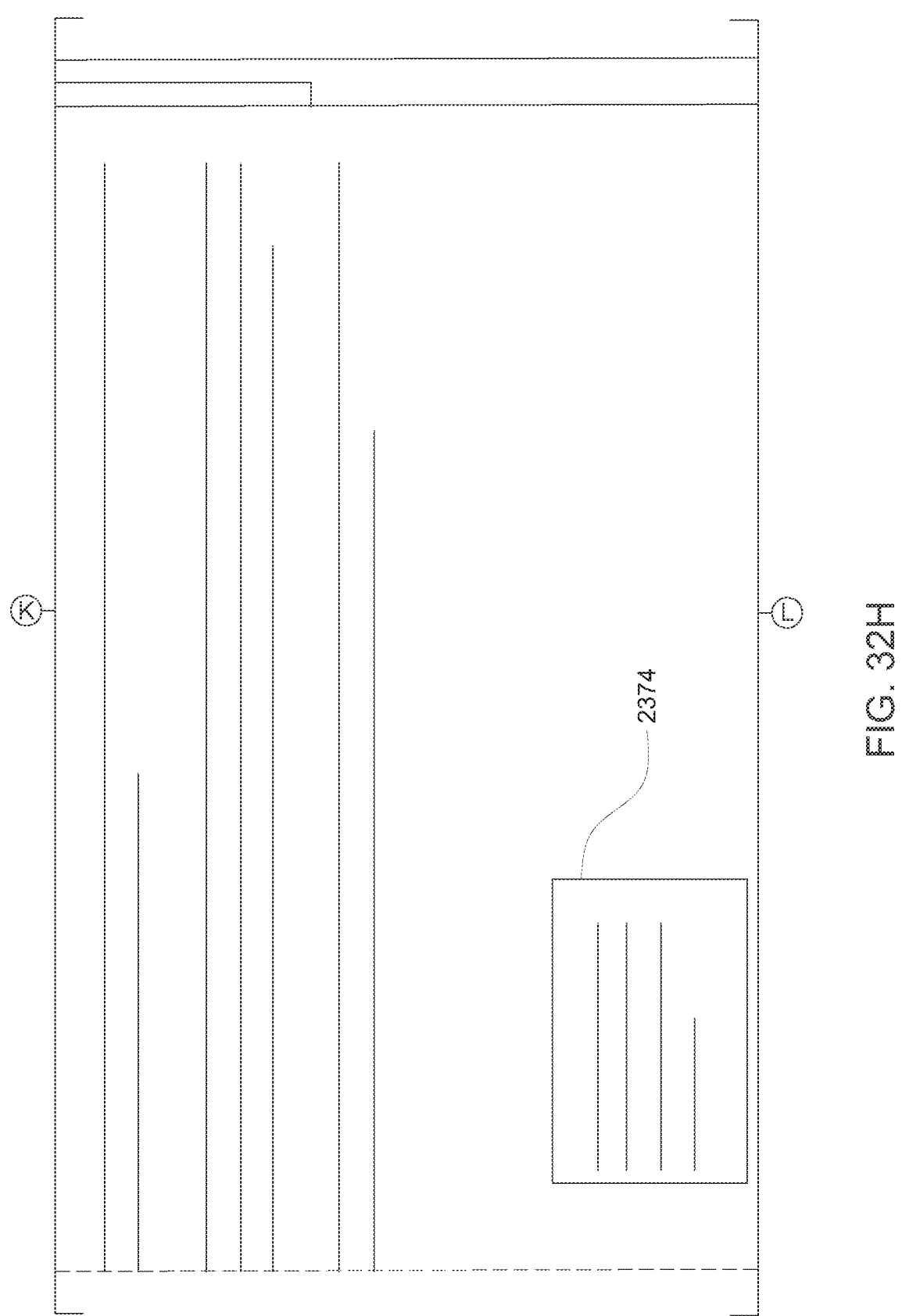
Figure 32I:
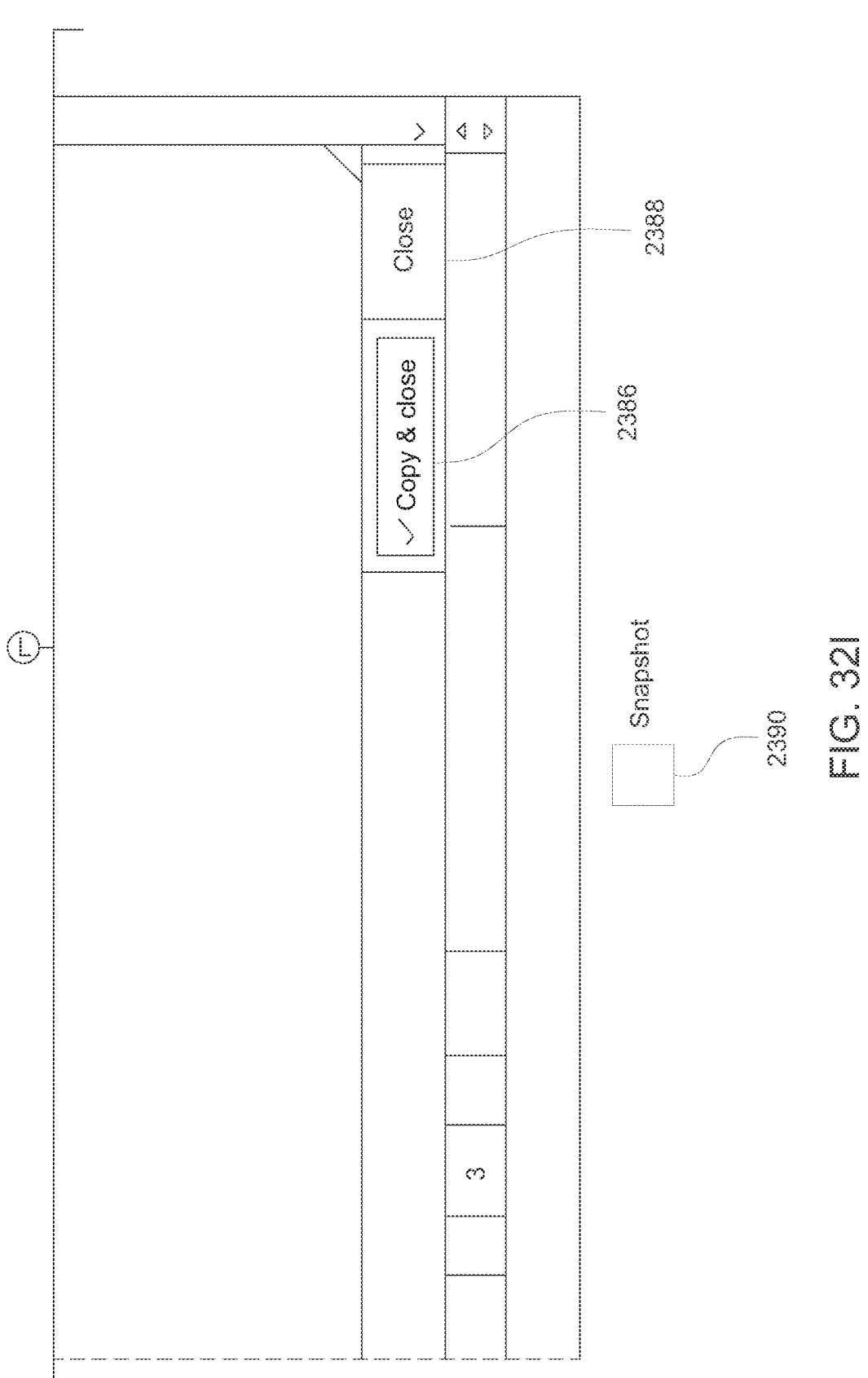

FIG. 31 illustrates another view of limited area display in accordance with an embodiment of the present principles. In FIG. 31, a second view of a tablet 70750 is depicted. In the embodiment of FIG. 31, data representations have been resized to display more important information. At 70760, the header row is still displayed, 70770 displays future events, 70780 displays Today's Visit, 70790 displays past visits, and now 70800 displays the horizontal graph described herein. 70810 displays the problems, medications, and allergies data representation described herein. 70820 displays the Assessment and Plan described herein. 70830 displays scroll bars to access more information, in some embodiments off screen.

FIG. 32 depicts an embodiment of a medical records dashboard in accordance with another embodiment of the present principles. In accordance with the present principles, the medical records dashboard of FIG. 32 is intended to provide and display to a user/medical care provider with all patient data/information necessary to perform accurate and efficient patient care using a single display. In the embodiment of the medical records dashboard of FIG. 32, panels 2380, 2382, 2326, 2320, and 2314 are some examples of different panels that can be moved around, toggled, simultaneously active (i.e., information from each panel can be assessed interchangeably without changing views) and displayed while critical information is viewed. In each column, what is an important data element over time can be followed as noted in column 2332. This enables a user to view the information vital to evaluation of their patients. In addition, in some embodiments, the medical records dashboard of FIG. 32 enables, direct access to patient data/information (no more than one click, one hover or selected directly in any manner). Some embodiments enable toggling by a mechanism such as alt-tab to gain access to underlying patient data/information or associated screen, tab, or window. A user/medical care provider is able to decide what is important to pull up, directly to view, and can move the separate windows or other pop-ups out of the way to view important patient data/information underneath. In one embodiment, a Rules module, such as the Rules module 004 of the Data Command center 001 of FIG. 1, can be configured to know what information for the patient is important, what information must not be blocked, and when information is directly clicked and displayed, enables the movement of a needed columns into a set area on the screen where critical information remains in view. In the embodiment of FIG. 32, an example of two data sets that remain in view is depicted by column 2332, which includes the date of service when an encounter occurred with a patient, and column 2334, which displays the provider and location of encounter. In the embodiment of the medical records dashboard of FIG. 32, all of the other columns, such as column 2348, which depicts injections performed on a patient and/or procedures column 2308 can be moved or at least partially covered from display.

Alternatively, or in addition, in some embodiments none of the patient data/information is completely blocked from view through the use of transparency viewing. In FIG. 32, block 2354 displays an image of an OCT that displays to a user/medical care provider if injections of the left eye are working. In the embodiment of the medical records dashboard of FIG. 32, column 2348 is viewed, not blocked, so the user can correlate when the injection (or any procedure of clinical information or diagnostic test) was performed and how it relates to the information that was pulled up, with direct access to any additional information. In some embodiments of a medical records dashboard of the present principles, columns/windows/pop-ups of interest to a user can be moved to another portion of the medical records dashboard where no patient data/information or patient data/information of little or no interest to a user, exists. For example, if the user would also like to compare OCT data 2356 and in particular the left eye, as this example shows injections of certain medications (i.e. Eylea, Lucentis) and column 2348 over time, the user could simply drag 2356 or just 2358 (left eye) over to column 2308, because no data is present in that area of the medical records dashboard. Now all in one view and in a particular section of the medical records dashboard, exists all information that user would need to compare OCTs 2356 over time with injections 2348. In another example, when a photo 2359 is being compared to when an injection is done in the left eye 2348, then 2359, can be moved, dragged, or automatically be placed in location for example next to or in place of 2343. A user remains in control and able to move items out of view and by activating icon 2390 can take a snapshot (record) of a current arrangement of the medical records dashboard such that a record of the arrangement can be stored.

Simultaneously, a medical records dashboard of the present principles enables a user/medical care provider to recall and view plans of the past by activating a plan or A&P column or a particular plan in a column. The medical records dashboard of FIG. 32 enables current and past plans to be simultaneously displayed. As such, in context, a new note could be created in block 2328. A medical records dashboard of the present principles, such as the medical records dashboard of FIG. 32, enables images, procedures, dates of service, plan, or any other patient-related data/information, such as clinical measurement, i.e. VA (vision OD 3005—right or OS 3006—left), to be compared in context. By way of example, how a treatment is working as measured by an image, clinical parameter, or any other related data set can be interpreted and noted in the medical records dashboard in at least block 2352, which can be a new interpretation and can be edited by activating icon 2350. In one embodiment a plan viewer can be accessed by activating block 2328 and a new note or the editing of an old exiting note 2330 can be accomplished via a text editor window 2326. In the embodiment of the medical records dashboard of FIG. 32, a user/medical record provider is enabled to type or dictate a note 2374 accurately while relevant information is viewed in for example a window. Although in the embodiment of FIG. 32 the medical records dashboard only provides a user/medical care provider one means for editing notes, in some embodiments, a medical records dashboard of the present principles can provide a user/medical care provider many ways to edit notes.

In the medical records dashboard of FIG. 32, panel 2314 enables a user/medical care provider to select to view patient-related data/information from a number of different health care providers, such that patient-related data/information from every medical care provider that has ever cared for a patient can be viewed by, for example, all other specialties who provide care for that patient. For example, in FIG. 32, a user/medical care provider can select to see patient care data/information related to a retina specialist 2302 and/or a glaucoma specialist 2304. In some embodiments, sharing of patient-related data/information from other users/medical care providers can require permission from at least one of the patient and the other user/medical care provider.

In the medical records dashboard of FIG. 32, the panel, arranges patient data/information displayed in rows and columns. Users/medical care providers can have dashboards that are similar in display because the users/medical care providers charge, order, or perform similar CPT codes and often treat similar ICD diagnostic codes. Type of eye doctors are listed in order in this example #2302 (retina), 2304 (glaucoma), 2336 (optometrist), and 2340 comprehensive eye doctor.

In the embodiment of the medical records dashboard of FIG. 32, the different users/medical care providers can let all the other providers know something is important by highlighting the tab 2302, 2304, 2342, 2344, and 2346 in the medical records dashboard view of other users/medical care providers. In such embodiments, a user/medical care provider is able to hover or otherwise active the highlighted tab to bring into view a message 2312 that can detail an important aspect of patient care for the corresponding other user/medical care provider. As depicted in FIG. 32, a current user/medical care provider is alerted that a patient has missed appointments with a corresponding user/medical care provider. In another example, a tab to a family doctor 2346 could light up or blink or in any way get a user's attention to indicate that an event is particularly important. In another example and as depicted in FIG. 32, when activated by a user/medical care provider, over a blinking endocrinologists tab 2344 can appear an alert window 2316 that can inform a user/medical care provider that a patient has received a diagnosis of cancer. In some embodiments, such important messages can be caused to display without requiring a user to activate or hover over a blinking or colored specialist tab.

There are situations where doctors, even if in separate practices and separate specialties, what they do can impact what another doctor does. By way of example, a retina surgeon injects many times in an eye, up to 12 times a year. But, clearly, if a family doctor discovers cancer that might change the frequency a retina doctor may want to inject. If a patient has a stroke, there are some research studies that suggest the medication that one doctor is using, in this case displayed 2348 injections in the eye, by a retina surgeon might increase the risk of another stroke. In some embodiments, a Rules module of the present principles, such as the Rules module 004 of the Data Command center 001 of FIG. 1, is configured to recognize such situations in which treatment by one doctor can affect a treatment by another doctor and, in such instances, the Rules module 004 is configured to generate an alert to be displayed to all users/medical care providers of such situations.

There are many different ways that embodiments of a medical records dashboard of the present principles can display important information. By way of another example, at any time, if an important event occurs in any encounter of any provider, the information can be inserted into a row in chronological order, where it makes sense, to show on a timeline that the event occurred. So, if it was discovered that the patient had a stroke on May 25, 2019, as depicted by number 2362 in FIG. 32 the initials of a caring provider can be displayed under the provider instead of a current provider as depicted in FIG. 32 by 2362 marked as 2364. The difference between providers can be highlighted in many different ways. If it's a provider that is not normally on a row on clinical panel 2380 or for example in this case, illustrated as an example of a retina doctor provider, then this new provider with a row can be highlighted or be a smaller row or a larger row. Also, instead of having the normal information in columns, because the other provider might not perform similar CPTs, instead in some embodiments there can be displayed, at the end of the row in a specially designated area for outside attachments or notes, information and it can be identified if the information is from a different provider.

In the embodiment of the medical records dashboard of FIG. 32, 2306 can include financial data, and in this example shows '$' sign. In such embodiments, access to financial data can be limited to only user/medical care providers credentialed to have access for instance only the users/medical care providers and colleagues in their practice can have access. In the embodiment of FIG. 32, icon 2338 can be activated to enable access to financial data to different users/medical care providers. For example, in FIG. 32 2336 is an example of an optometrist and 2338 depicts an icon with appearance of two faces which can represent sharing access.

In the embodiment of the medical records dashboard of FIG. 32, the glaucoma specialists 2304 has entry 2306 next to it, which can be used to launch a revenue cycle management (RCM), which is just one mechanism that any user/medical care provider can use to get more information in regard to their own practice's billing or any other information. By way of example, in the embodiment of FIG. 32, activating icon 2306 can enable access to a user/medical care provider to cost, charges, any financial information payments, rejections, to which the user/medical care provider has access. In one embodiment, the financial information can comprise a mirror-image of the clinical dashboard, so a doctor, by toggling back and forth, a transparency or overlay can be used to determine what was charged, paid, rejected, or authorized for every service performed. Alternatively, or in addition, clicking on RCM 2306 on the same view or on the same scanning screen the information that is financial in nature can be displayed under, over, above, or superimposed, similar to transparent paper, with one embodiment, the billing function, being behind or lighter and clinical being darker or vice versa. In some embodiments, each row of panel 2314 can have 2306 or 2338 next to every one of the tabs (actionable dashboards of different providers).

In some embodiments of the present principles, a user of a medical records dashboard is identified upon use. For example, in some embodiments, a user/medical care provider is required to provide identifying information when the user/medical care provider wants to use a medical records dashboard of the present principles. In some embodiments, a user/medical care provider can provide predetermined configuration information to identify how a medical records dashboard should be displayed for that particular user. For example, in some embodiments a Rules module, such as the Rules module 004 of the Data Command center 001 of FIG. 1 can have access to configuration information for a medical records dashboard provided by a user. In such embodiments, the Rules module 004 can be configured to arrange and cause a display of the medical records dashboard in accordance with the predetermined configuration information provided by the user, for example, upon initiation of the medical records dashboard by the user.

Alternatively, or in addition, in some embodiments, a user/medical care provider can drag and drop portions of a medical records dashboard to arrange the medical records dashboard into an arrangement that is best for the user and/or the user's practice or in some embodiments, into an arrangement that is best for a particular patient. For example, an eye doctors might care more about a condition like diabetes, so any doctor that takes care of diabetes, endocrinologists, family doctors, kidney specialists, urologists tend to have more patients and procedures related to diabetes than other specialists, like a radiologist.

In the embodiment of the medical records dashboard of FIG. 32, when a user selects entry 2330, window 2374 is displayed for inserting notes, which can then be saved and closed by selecting 2386, or just closed by selecting entry 2388.

Tab 2348 of FIG. 32 is a tab for providing a user information regarding injections given to a patient, and tab 2366 of FIG. 32 can provide quick information about the injections including a number of injection or a type of the injections. In FIG. 32, 2372 depicts the identification of an example of an Eylea injection having been performed on Jul. 13, 2018, and it is red but can be highlighted in many different ways. In 2372 adjacent to Eylea it says 15 days which in this example count from the last time an injection in the eye was done. In the embodiment of FIG. 32, the medical records dashboard depicts that Lucentis was injected 6/28/18 which is only days earlier from a 7/13/18 injection of Eylea and the column counts in the embodiment from one to the other. In some instances, procedures of Eylea or Lucentis injections are allowed only every 28 days from each other. In embodiments of the present principles, a Rules module, such as the Rules module 004 of the Data Command center 001 of FIG. 1, can be configured to have access to information, including but not limited to, rules regarding how frequent or far apart medications can be given, and in some embodiments, the Rules module 004 is configured to cause the display of an alert if a user/medical care provider is attempting to order a procedure improperly or if procedures have already been performed improperly.

In the embodiment of FIG. 32, the panel can be used to display diagnostic test and images. In the embodiment of FIG. 32, when tab 2350 is selected an interpretation panel 2352 is opened, which can display notes of an interpretation of patient care that could be actually written on the day of treatment. Element 3254 of FIG. 32 is an image of a test performed on the patient.

In some embodiments, image icons, representative of results of test performed on a patient, can be selected to cause a display of an underlying corresponding image, such that a user/medical care provider can, in context, make a determination of the test and see the actual test while knowing whether there was a procedure or in this example a medication injection done, as depicted in 2366.

The embodiment of the medical records dashboard of the present principles of FIG. 32 illustratively includes a search box 2318. The search box of the medical records dashboard of FIG. 32 can be used to search for a doctor, a date, an image, particular procedures, a particular diagnosis, payment rejections and payments and substantially any other patient related data/information related to the medical records dashboard. In some embodiment, the medical records dashboard can instantly reconfigure based on what is searched and can be configured to display only the portions of the medical records dashboard for which search results are returned. Combinations of queries can be searched. For instance, show only the rows and dates of service with the diagnosis of diabetes that had injections of a particular medication, column 2348. Instantly, only the rows with injections with the patient having a diagnosis of a certain ICD like diabetes or if comparing a particular diagnostic test with a procedure and trying to correlate it, along with a clinical finding, the user could search "show me only the rows and dates of service where the vision was between 20/20 and 20/80" or "the pressure of 16 to 20 that also had the same date of service, a procedure in 2348 of Eylea and also had an OCT. The patient data/information associated with the medical records dashboard can then be searched and in some embodiments, only rows and columns of the medical records dashboard related to the search can be searched.

In some embodiments, a Data Command Center of the present principles is enabled to provide a Customizable, Correlative Graph (CCG). That is, the Data Command Center is able to collate data and visualize correlation between different, related datapoints, each with their own distinct visualizations. Novel to customizable visualizations is to display an array of customized visualizations correlated on a comparative axis or axes. This customized, correlative display consists of one or more visualizations of Command Center data, horizontally, vertically, on a Z axis, or on multiple axes displaying multiple events, results, and/or calculations. In some embodiments, the Customizable, Correlative Line Graph display can be launched from within a Patient Flowsheet using a button, keystroke, or series of keystrokes such as the icon shown in 21080 of FIG. 25. Upon launch, the Customizable, Correlative Line Graph generates a view and can display as a popup, popover, pop out, or otherwise in relation to, but not limited by the launch point. The Graph can overlay or adjoin the underlying Flowsheet in opaque or transparent states, be pinned to the Flowsheet, and/or may hover over or aside said Flowsheet.

Upon initiating the Customizable, Correlative Graph, a series of actions are performed to determine data and format of data displayed. Preconfigured CCG displays can be stored in tables or generated at runtime based on key considerations such as those laid out in Dynamic Data Representations described above.

Figure 33:
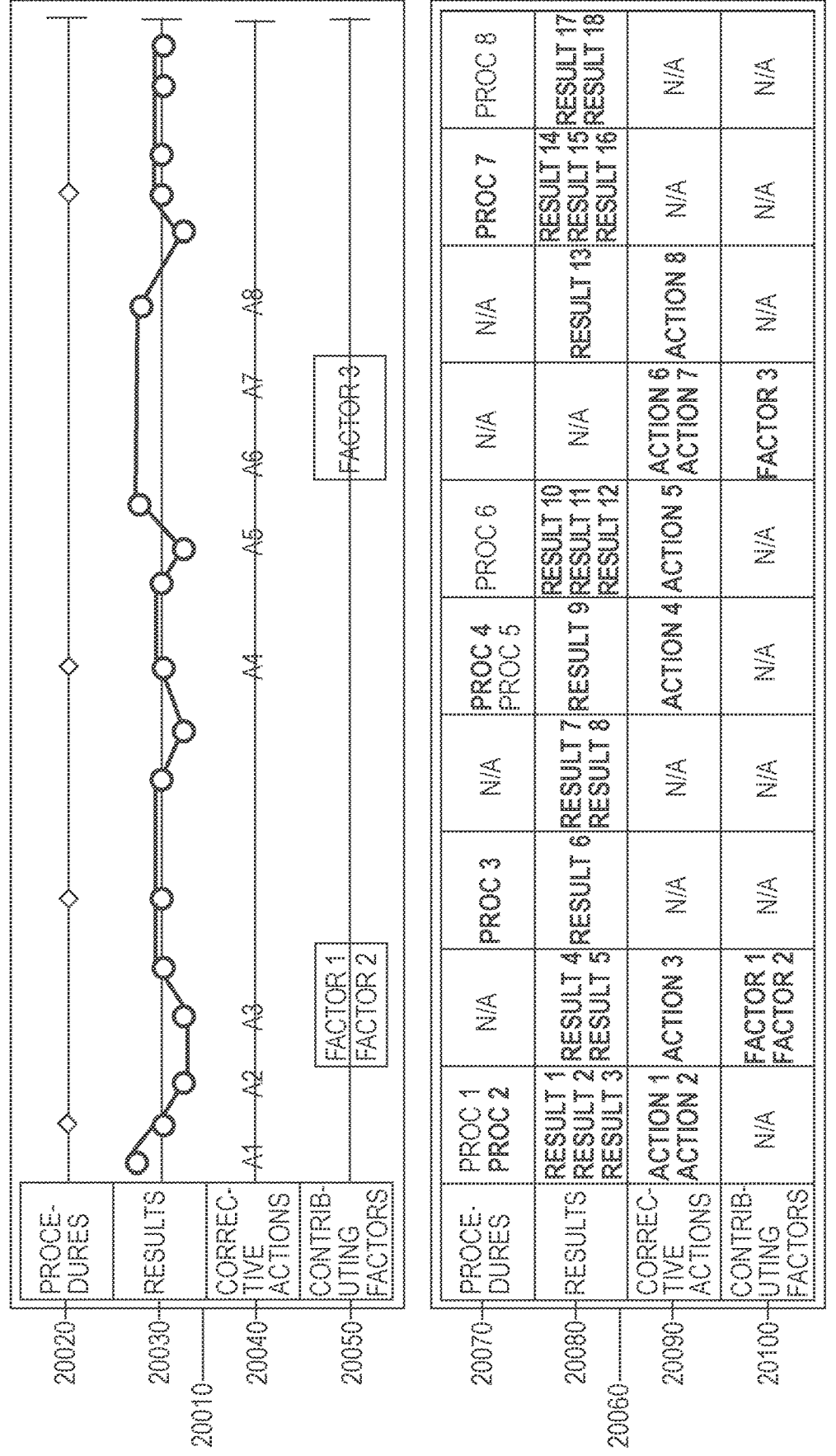
FIG. 33 illustrates a horizontal correlative graph in accordance with an embodiment of the present principles.

FIG. 33 illustrates a horizontal correlative graph in accordance with an embodiment of the present principles. In the embodiment of FIG. 33, available data (20060) is visualized graphically (20010), as a series of events (20070) graphed against a timeline (20020), correlated with a series of results (20080, 20030), a series of actions (20090, 20040), and a series of contributing factors (20100, 20050). Any number of relevant details and categories of data can be correlated as needed.

Rendered Customizable, Correlative Graphs can be interacted with in such ways as to turn on or off represented values in a similar manner to expanding/collapsing/filtering of Dynamic Data Representations, i.e. turning on or off subsections of data, individual visualizations categorized by logical grouping, selecting only specific elements to display. Selecting data representations within the display, and/or moving elements between positions to achieve a different view, can also be affected based on principals described in FIG. 13 and throughout the teachings herein. It should be noted that additional visualizations can be added, additional flags derived, and a series of rules explained throughout the teachings herein to manifest in the final rendering.

It should be noted that the single axis representation of the CSG of the present principles described above and represented in the Figures does not preclude multi-dimensional representations with multiple parallel representations as well as multiple perpendicular, or otherwise non-parallel representations.

The Customizable, Correlative Graph of the present principles reaches its logical end at which point all data is rendered, processing of rendered data has occurred, and any/all necessary actions have been taken based on the processed data, including, but not limited to, Flags, Alerts, Clinical Decision Support, and Auto-Tasks. Auto-updates to patient data can initiate refactoring of the Customizable, Correlative Graph.

Figure 34A:
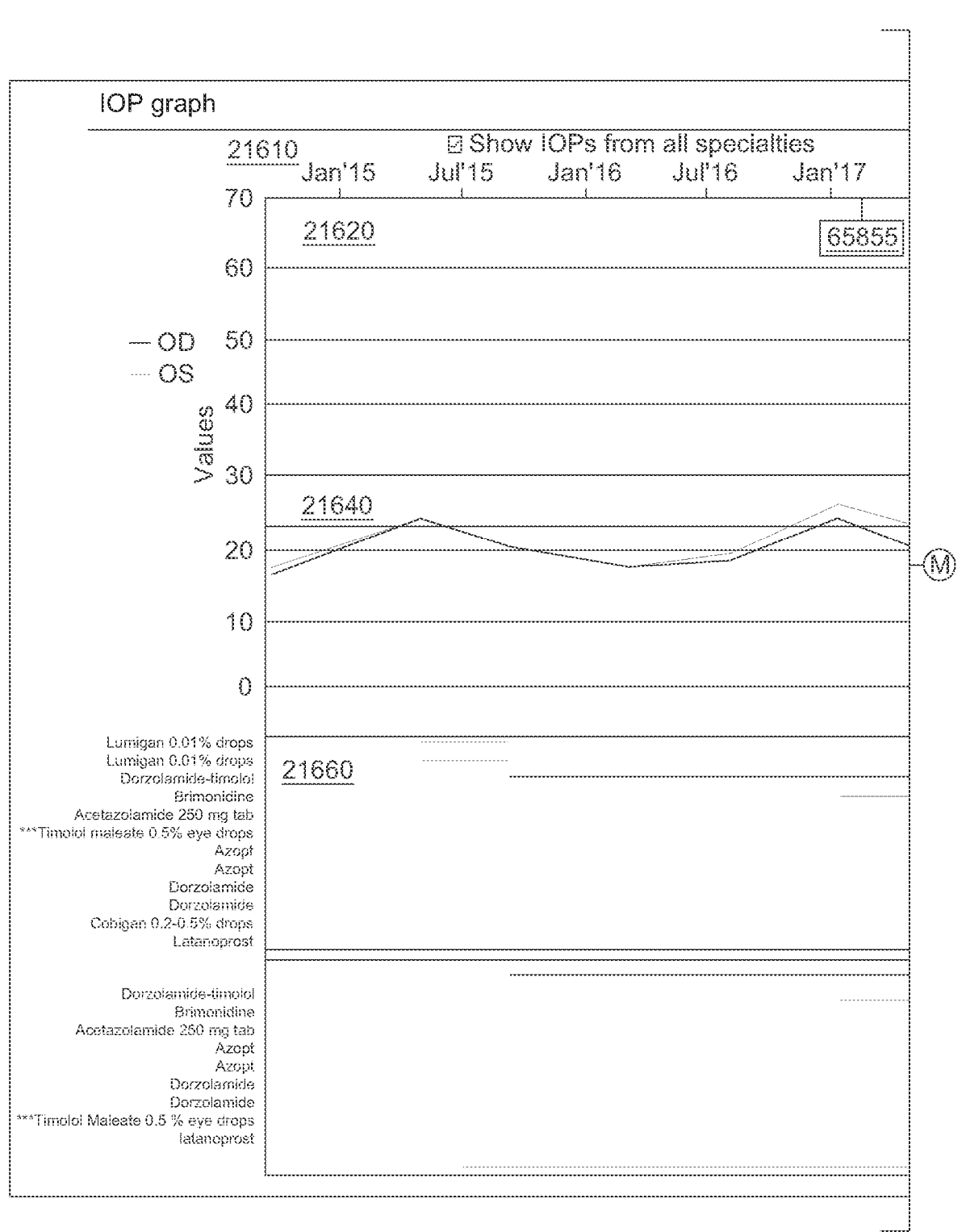
FIG. 34 depicts a correlative line graph in accordance with an embodiment of present principals.
Figure 34B:
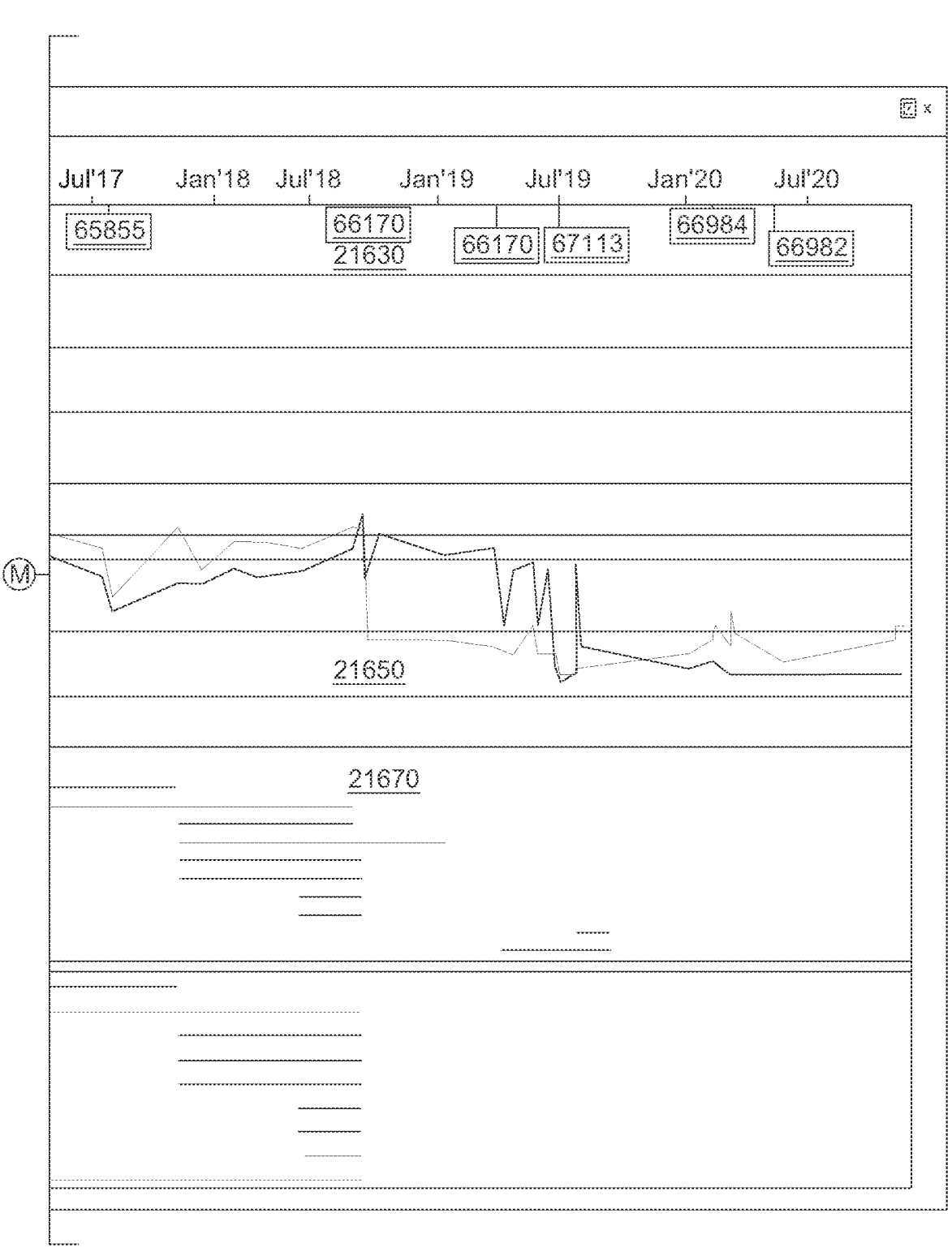

FIG. 34 depicts a diagram of a correlative graphical representation of patient data able to be displayed by a Data Command Center in accordance with an embodiment of the present principles. That is, a Data Command Center of the present principles can collate, evaluate, and correlate multiple data sets to represent them in a correlative graph, such as illustrated in FIG. 34. In this embodiment, the correlative graph 21610 is comprised of three sections. The first section 21620 represents procedures by a code such as seen at 21630. The second section 21640 represents pressure, exemplified as a line graph which tracks with the pressure. A large drop in pressure is illustrated at 21650. The third section 21660 represents medications as graphical lines corresponding to each medication. A clear stop of multiple medications is shown at 21670. In the embodiment of FIG. 34, these three factors, procedures, pressure, and medications, are depicted as inherently tied together in treatment.

Figure 35A:
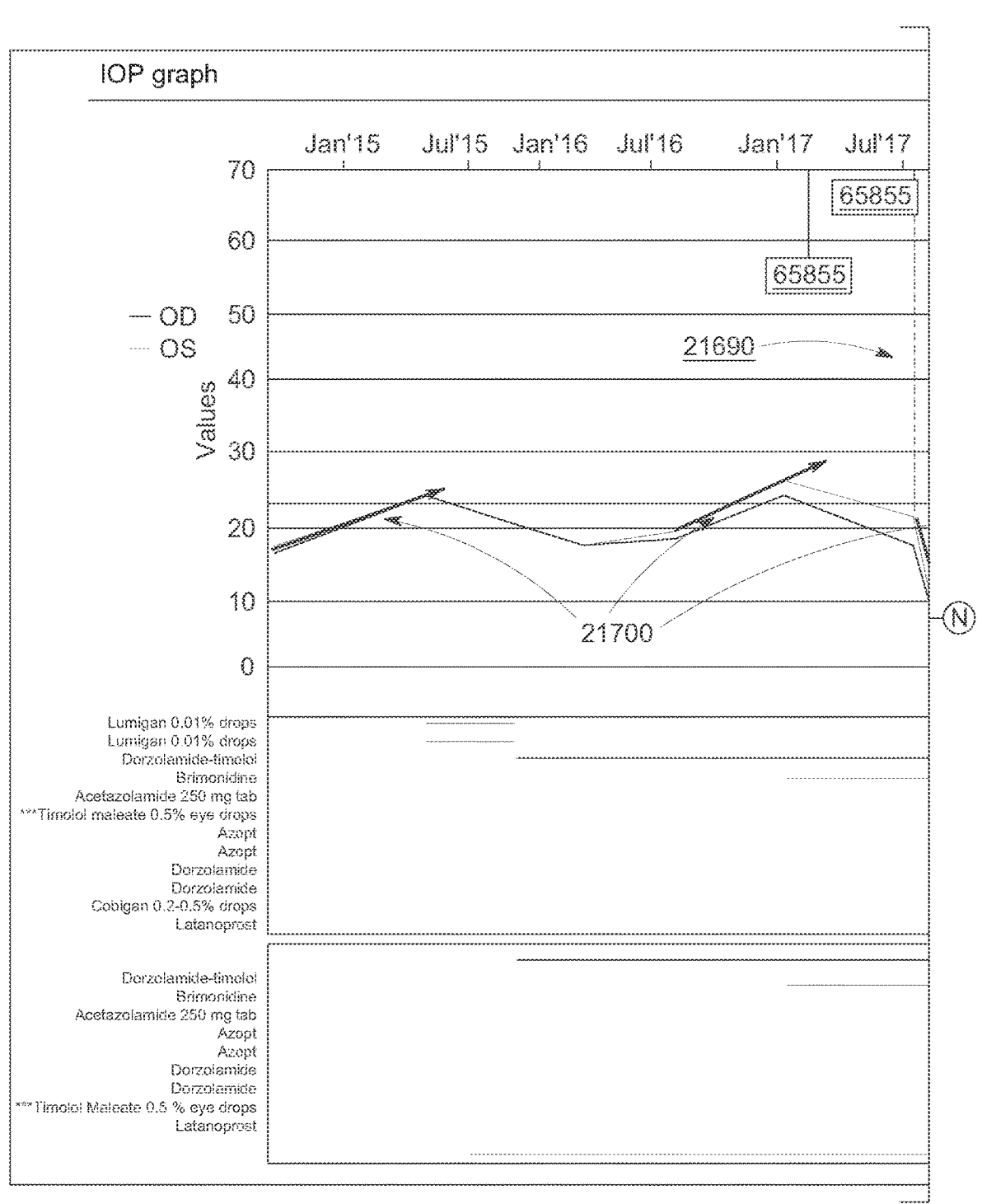
FIG. 35 depicts an augmented correlative line graph in accordance with an embodiment of present principals.
Figure 35B:
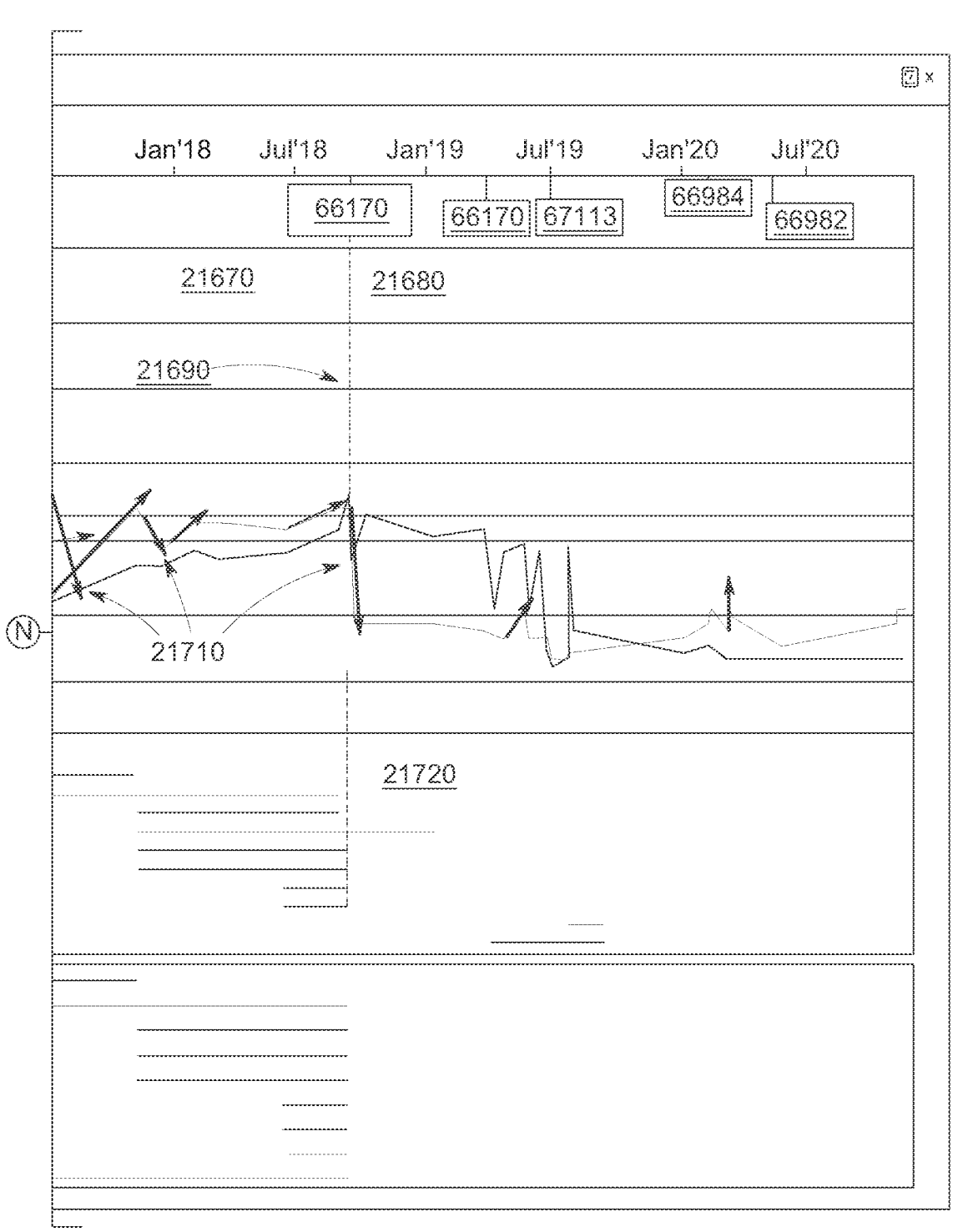

FIG. 35 depicts correlations made for the diagram of the correlative graphical representation of patient data of FIG. 34 in accordance with an embodiment of the present principles. More specifically, in FIG. 34, at 21670, a procedure is depicted, now larger and highlighted, which correlates to a drop in pressure. A second, larger procedure 21680, now highlighted, for example in color, correlates to an even larger drop in pressure. These correlations are illustrated by the lines at 21690. Arrows of increasing size and differing color now represent notable rises and falls in pressure. At 21700, the first 2 arrows comprise a first color (e.g., yellow) and denote a moderate rise in pressure, while the third arrow comprises a second color (e.g., orange) and is thicker, denoting a significant increase. At 21710, colored arrows denote drops in pressure. The third arrow is clearly thicker, denoting a significant drop in pressure. It becomes clear that the procedure at 21690 is the significant factor in this drop. Another correlation is made at this point. At 21720, a connection to the cessation of several medications is depicted. In the past, such information would have existed in separate areas and associations would need to be made outside of the present application. In accordance with the present principles, in the embodiment of FIG. 34 and FIG. 35 everything is clearly delineated, correlated, and displayed in such a manner as to reduce the amount of information needed to make connections, and as such, informed treatment decisions.

Figure 36A:
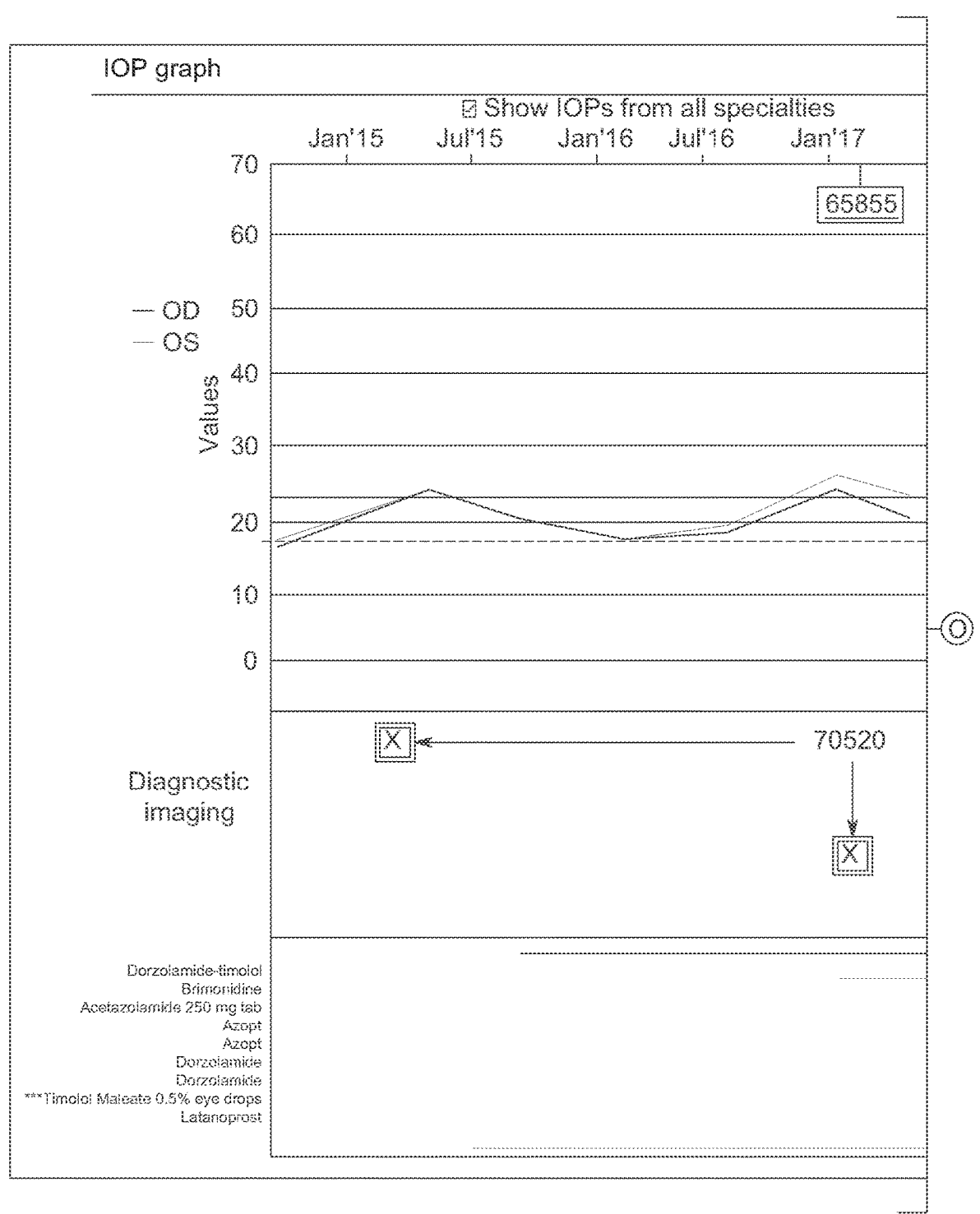
FIG. 36 illustrates direct access and parameter setting on a horizontal graph in accordance with an embodiment of the present principles.
Figure 36B:
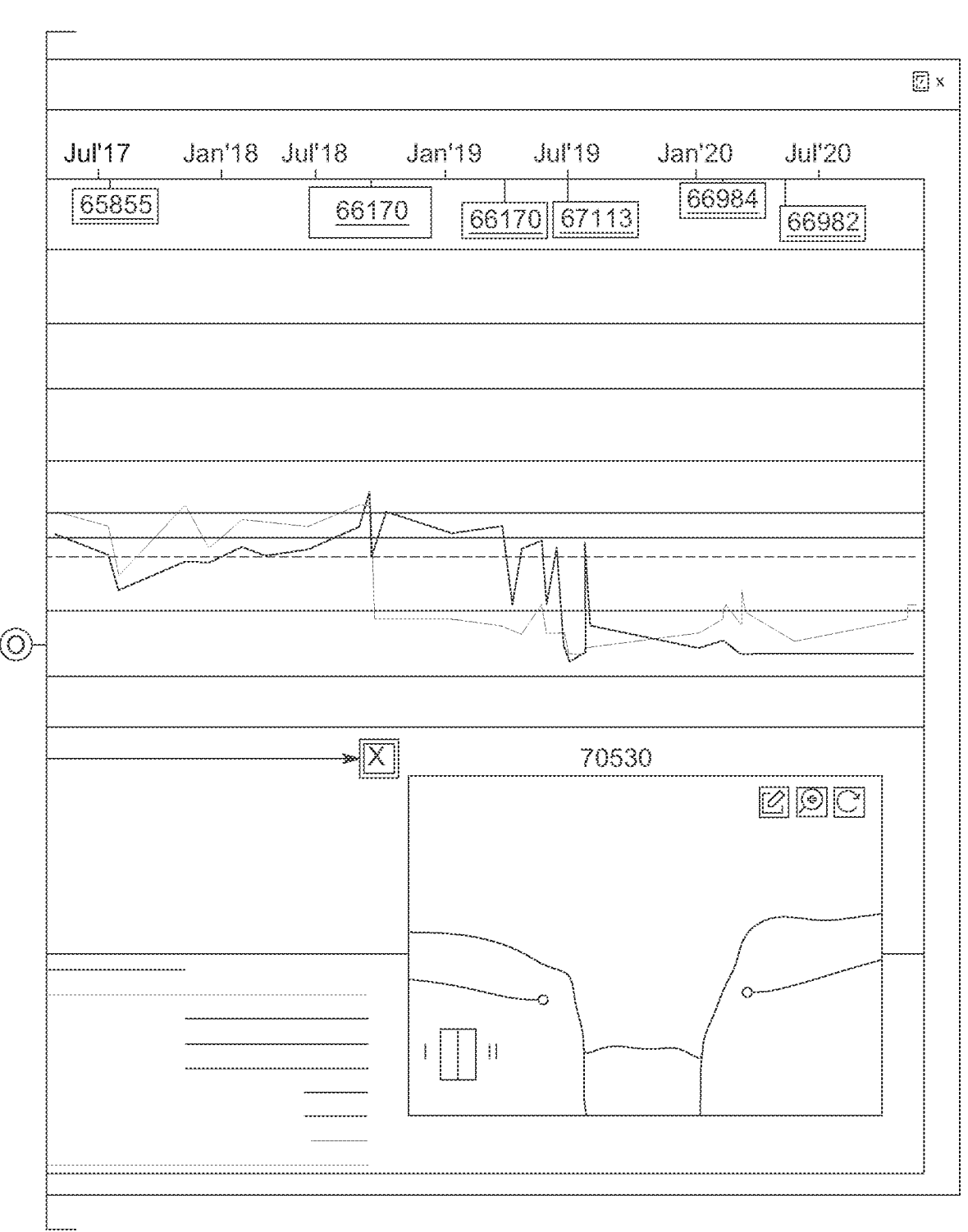

FIG. 36 illustrates direct access and parameter setting on a horizontal graph in accordance with an embodiment of the present principles. In the embodiment of FIG. 36, at 70510, a dotted line is displayed denoting a threshold for pressure. Such a line defines the limit at which this patient, or any patient if configured globally, may reach a point at which action is required. Above this line, an event is triggered. This can result in an alert, message, task, or other notification. As the data is interactive, one can drag this line higher or lower to adjust the threshold, updating respective rules to now account for the new threshold set. Illustrated at 70520 are several Diagnostic Images. Each is positioned according to the governing timeline. At 70530, an image is shown being directly accessed from a respective icon, which generates a view of an in-context image viewer. As all data representations can be set to interactive, actions such as generating an image viewer/editor, order panel, bidirectional text editing, or other interface can be accessed.

In some embodiments, if a patient misses an appointment, an auto task can be generated to alert a user/medical care provider schedule that the patient missed the appointment so that another appointment can be scheduled. or to the Clinical trial coordinator if it is part of a research protocol. Even parameters of when to create the task such as two missed appointments in a row can be set. This enables automatic tracking and a user/medical care provider can set it knowing the unique individual issues with a patient and can determine how important a missed appointment might be for a particular patient at a glance by showing previous data projected in the background or through one user interface on another monitor the user/medical care provider can cross check and individualize the alerts and tasks since a single missed appointment may be serious for one patient, but not so serious for another. Even parameters of when to create the task such as two missed appointments in a row can be set.

Figure 37A:
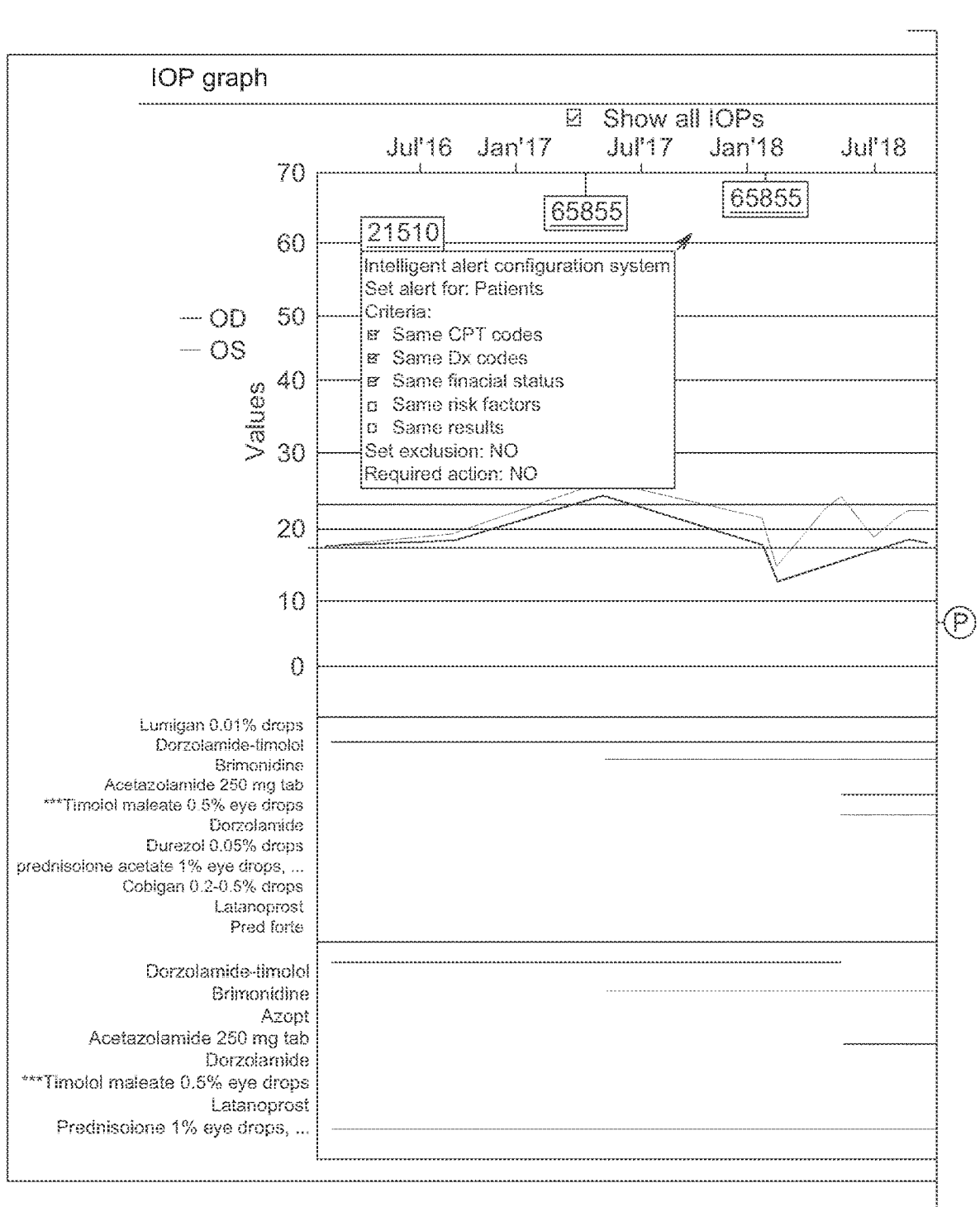
FIG. 37 depicts three different representations of an intelligent alert configuration system overlayed upon several different aspects of an application in accordance with an embodiment of the present principles.
Figure 37B:
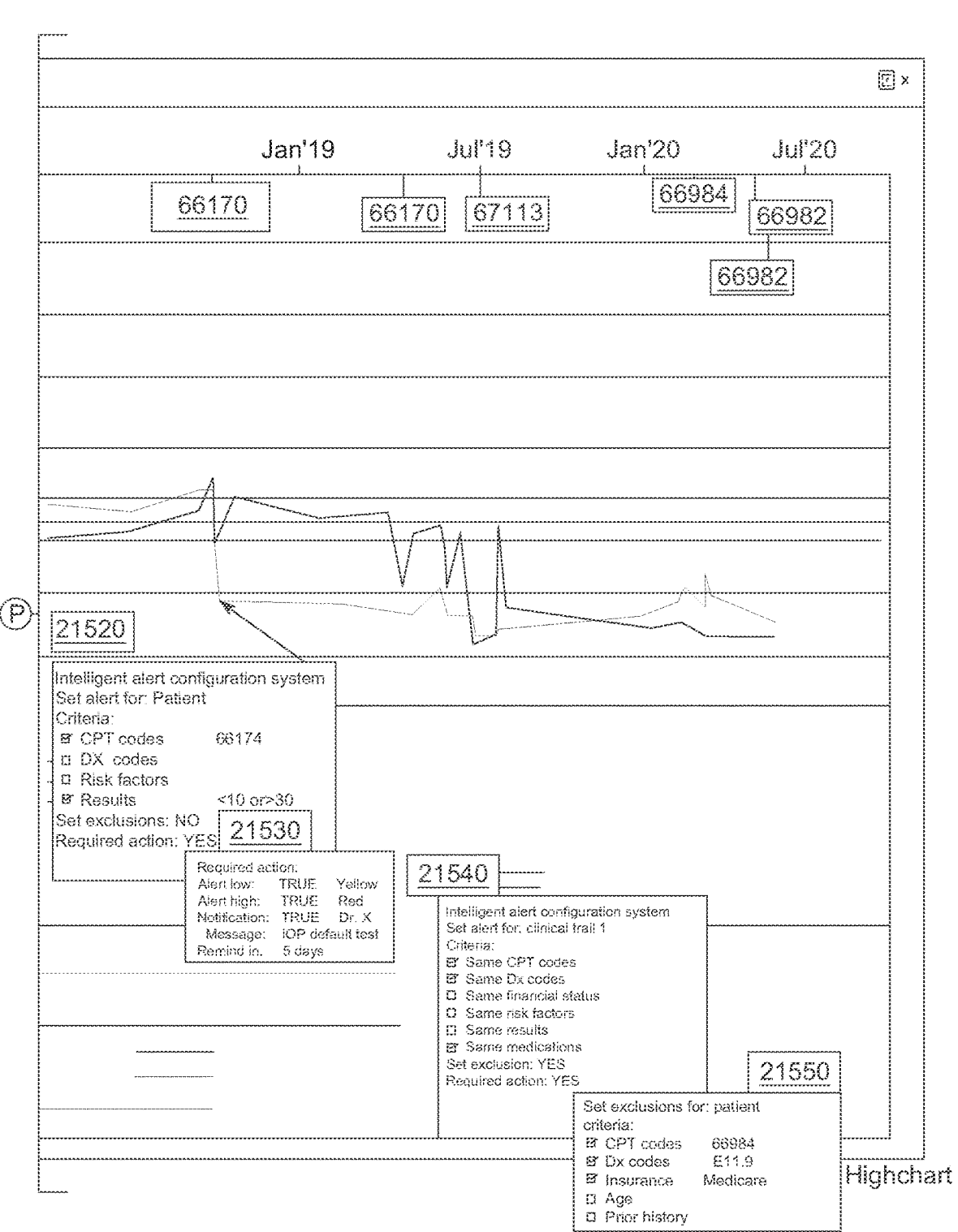

An intelligent alert configuration system, in one embodiment, can be represented in multiple ways, based on several criteria. For example, FIG. 37 depicts three different representations of an intelligent alert configuration system overlayed upon several different aspects of an application in accordance with an embodiment of the present principles. The alert configuration system of FIG. 37 can, in the case of a procedure 21510, display parameters associated with procedures, patients with like procedures, correlations to diagnoses, financial status, risk factors, results, or other relevant criteria, while enabling for exclusion criteria and actions to be taken, while also being able to be assigned to a patient, group of patients, all patients, or a patient or group of patients with specified criteria. In the case of launching the intelligent alert configuration from a result 21520, a different set of parameters can be specified relevant to that result, patients with similar results, correlations to diagnoses, financial status, risk factors, results, or other relevant criteria, while enabling for exclusion criteria and actions to be taken, while also being able to be assigned to a patient, group of patients, all patients, or a patient or group of patients with specified criteria. An example of required actions 21530 denotes several key actions which can occur upon triggering the alert. These include, but are not limited to, a visual or audio alert, tiers of alerts based on values, notifications to be sent and to whom, reminders are to be sent. In the case of launching the intelligent alert configuration from a medication 21540, a different set of parameters can be specified relevant to medications, patients with similar medications, correlations to diagnoses, financial status, risk factors, results, or other relevant criteria, while allowing for exclusion criteria and actions to be taken, while also being able to be assigned to a patient, group of patients, all patients, or a patient or group of patients with specified criteria. An example of exclusions 21550 denotes several key actions which can exclude a patient or patients from an alert.

In the Whole-Life View of the present principles, all pre-described functionality is aggregated into a single, intelligent view of a patient's whole life. All relevant data underlies the Whole-Life View, but zoom levels add an additional dimension to what is displayed. At its highest zoom level, only the most important factors are displayed. And its lowest zoom level, flowsheet-level access can be achieved. At each zoom interval, reprocessing of rules can occur to include additional data, differing representations of data, and notifications of key events.

Whole-Life View can be accessed from within the context of a Flowsheet, report, or patient list, utilizing a button, keystroke, or series of keystrokes, to initiate the Whole-Life View, such as the icon shown in 21080 of FIG. 25. Whole-Life View can display at a preconfigured zoom level, a preferred zoom level, or can utilize rules to determine the required zoom level based on key factors that can be stored in tables or generated on-the-fly based on key considerations such as those laid out in Dynamic Data Representations, and those laid out in the Customizable, Correlative Line Graph FIG. 33, FIG. 19, and FIG. 20. While within Whole-Life View, zooming can be achieved by selecting a button, keystroke, series of keystrokes, utilizing the mouse, hand gestures, touchscreen, or other logical means of interface. Zooming can also be automated based on rules as defined by the Rules Engine 10180 of FIG. 3, whereby important events can directly affect starting zoom level.

The determination of the importance of data to display in a Whole Life View must account for point-in-time refactoring of data displayed. While a heart attack can be hugely important, overall, if the zoom level is achieved which does not account for when the event occurred, only the events of the specified timeframe will be accounted for in the general view. Critical patient indicators can be implemented to account for events outside of the viewable display. This does not mean that events outside of the viewable timeframe are not of importance and can still affect the display of events in the view, such as the heart attack increasing the importance of a stent procedure within the view. In some embodiments, a weighting system can be implemented to make such determinations.

Figure 38:
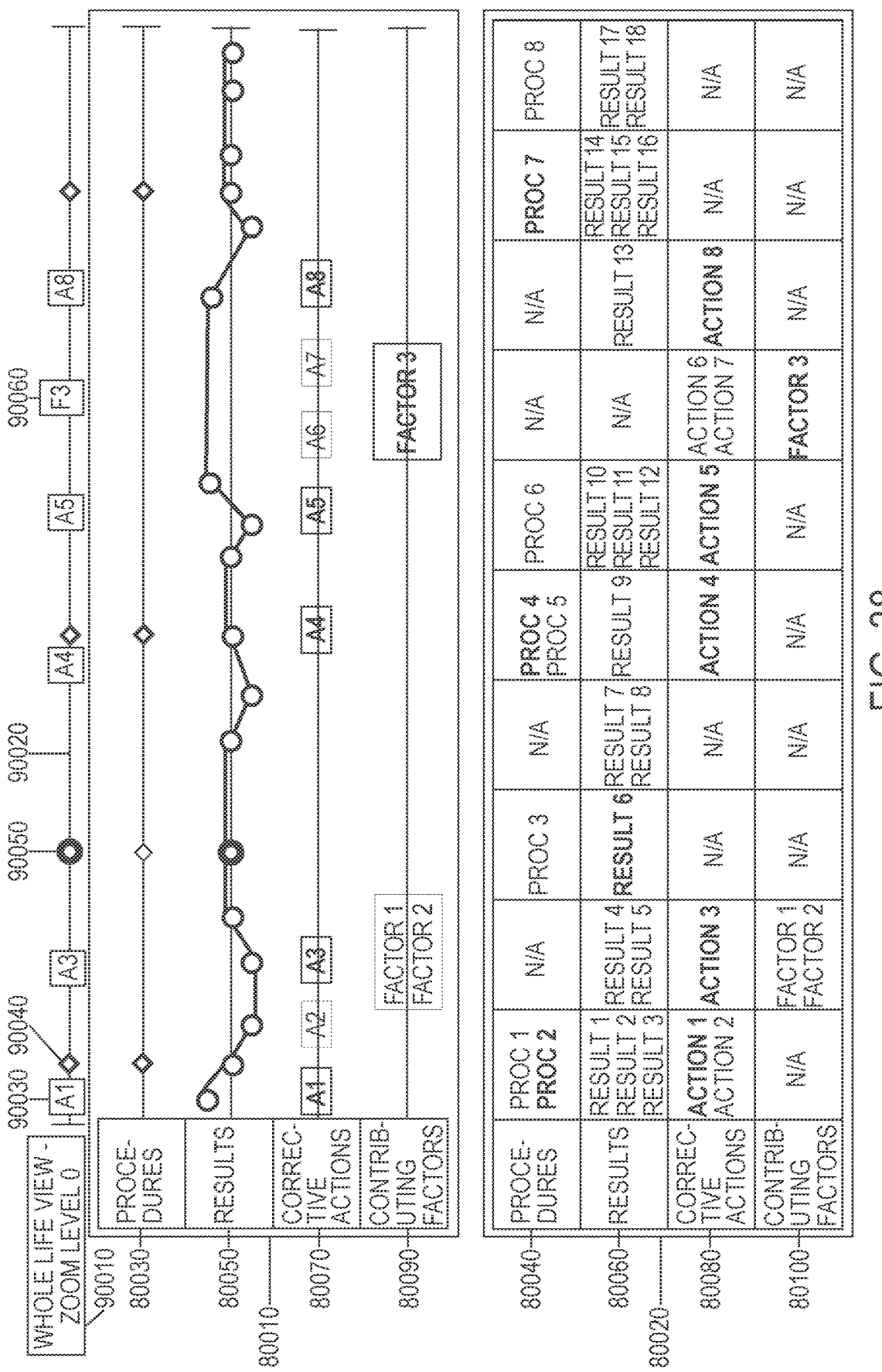
FIG. 38 illustrates a whole life view zoomed out in accordance with an embodiment of the present principles.

FIG. 38 illustrates a whole life view zoomed out in accordance with an embodiment of the present principles. In the embodiment of FIG. 38, Zoom Level 0 (90010) is achieved, and the entire timeline of the patient's life is displayed (90020). Underlying data (80010-80020) is processed and key datapoints are intelligently determined for display. Configurations then apply to intelligently determine how to represent the datapoints. As an example, these datapoints can include all corrective actions (90030), procedures (90040), results (90050), contributing factors (90060), and any other correlated dataset display deemed necessary for display at this zoom level. Additional items of each type can also be included based on importance determined by the Rules Engine 10180 of FIG. 3, and by implementing the weighting system of FIG. 21.

Figure 39:
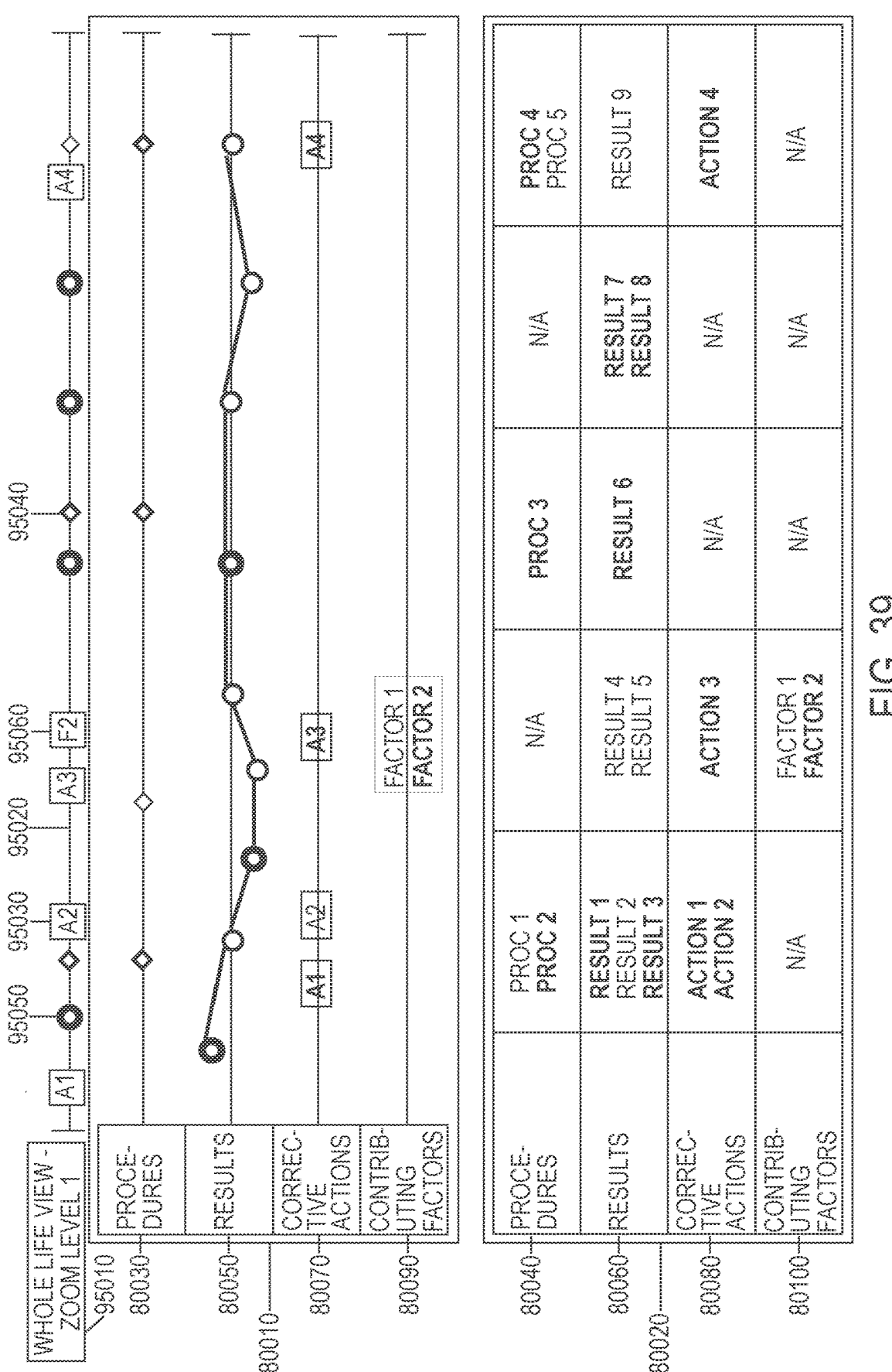
FIG. 39 illustrates a whole life view zoomed in to a first level in accordance with an embodiment of the present principles.

FIG. 39 illustrates a whole life view zoomed in to a first level in accordance with an embodiment of the present principles. In the embodiment of FIG. 39, Zoom Level 1 (95010) is achieved and a subsection of the entire timeline of the patient's life (95020) is displayed in more detail. This higher level of detail can be implemented when viewing any section of the Whole Life View. Underlying data (80000-80020) is reprocessed and additional key datapoints are intelligently determined for display. Configurations then apply to intelligently determine how to represent the datapoints (80000-80010). These datapoints can include additional corrective actions (95030), procedures (95040), results (95050), contributing factors (95060), and any other correlated dataset display determined for display at this zoom level.

Figure 40:
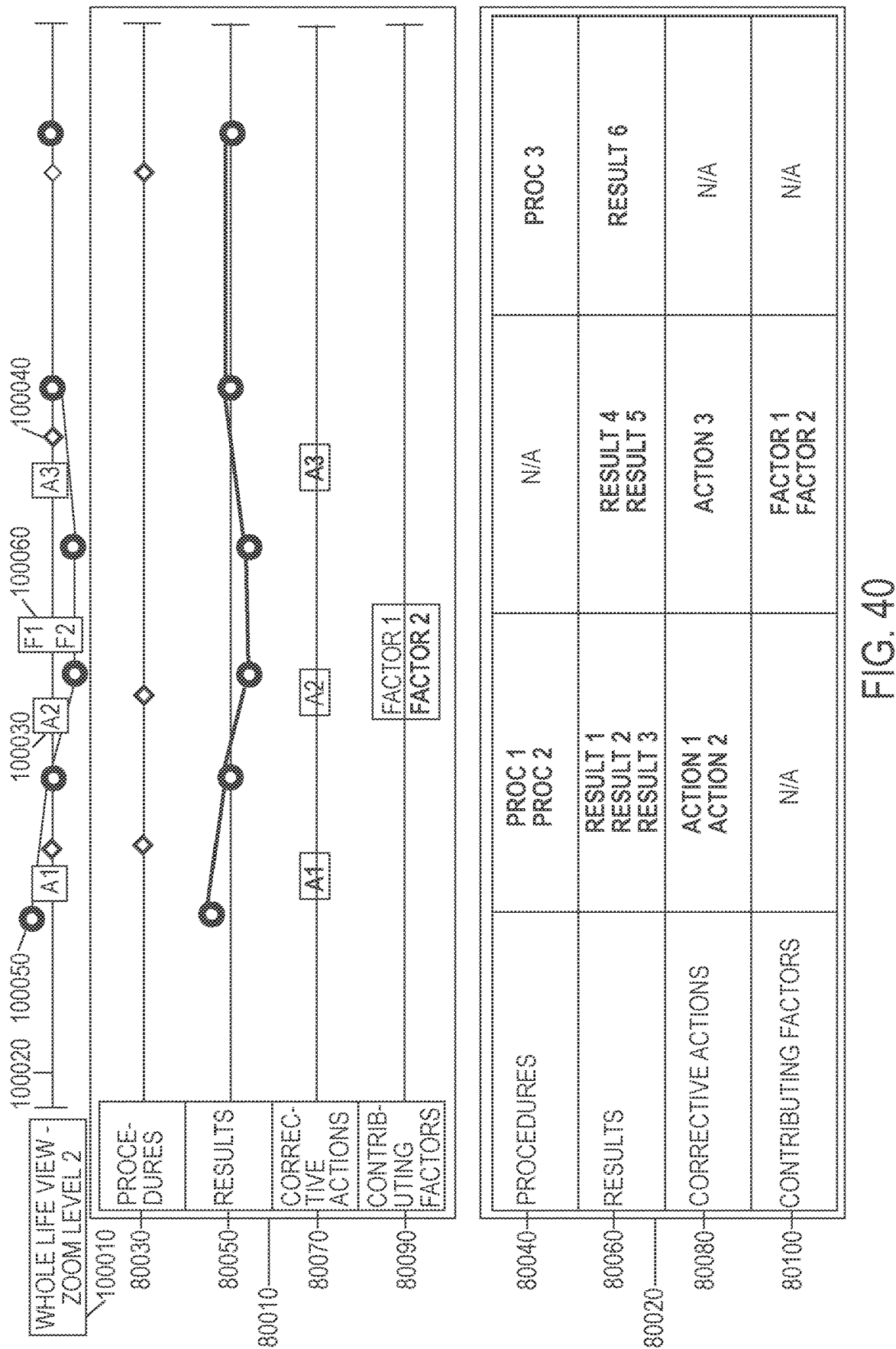
FIG. 40 illustrates a whole life view fully zoomed in in accordance with an embodiment of the present principles.

FIG. 40 illustrates a whole life view fully zoomed in in accordance with an embodiment of the present principles. In the embodiment of FIG. 40, Zoom Level 2 (100010) is achieved and a more highly zoomed subsection of the entire timeline of the patient's life (100020) is displayed in far more detail. Underlying data (80000-80020) is reprocessed and all datapoints are determined for display. Configurations then apply to intelligently determine how to represent the datapoints. These datapoints can include all corrective actions (100030), procedures (100040), results (100050), contributing factors (100060), and any other correlated dataset display determined for display at this zoom level, as mentioned before, or a new set of data can be defined based on the increased zoom level affecting weighting as defined in FIG. 21. Graphical representations can take on higher levels of resolution and accuracy (100050), include predefined colors and alerts, and may allow more discrete interaction. All predefined manner of graphical and textual formatting can be displayed.

In some embodiments, a further level of Zoom can bring a user directly into a patient-specific flowsheet. Zoom can be refocused at any time, in or out, and/or on different areas of the timeline. Events on the timeline can be interacted with in such manner as would within a flowsheet, including, but not limited to, viewing images, updating plans, viewing billing data, sending a task, setting a configuration, or any other means of interaction with which that object has been defined to accept.

Embodiments of Corelative Graphs and Whole Life Displays of the present principles provide aggregating datasets into multiple modules, intelligently correlating the modules along a common axis, each with their own, unique configurations and rules, with the ability to be independently or collectively interacted with, within the context of a patient's entire lifetime of healthcare. In embodiments of the present principles, zoom levels are not limited to a set number and can accommodate all degrees of zoom levels and multidimensional representations with multiple parallel representations as well as multiple perpendicular, or otherwise non-parallel representations.

Figure 41A:
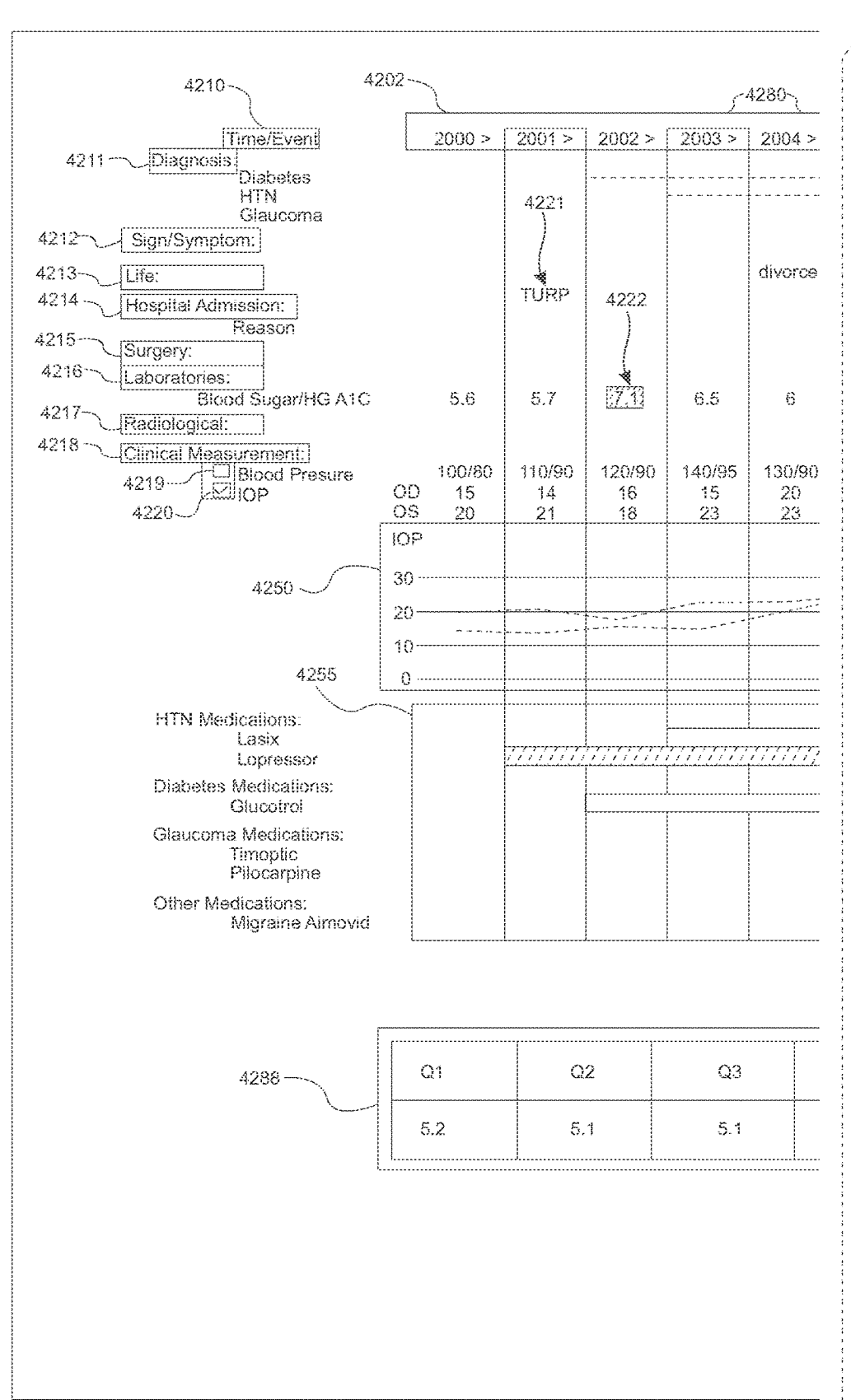
FIG. 41 depicts a graphical view of the entire medical history of a patient as a Whole Life tool in accordance with an embodiment of the present principles.
Figure 41B:
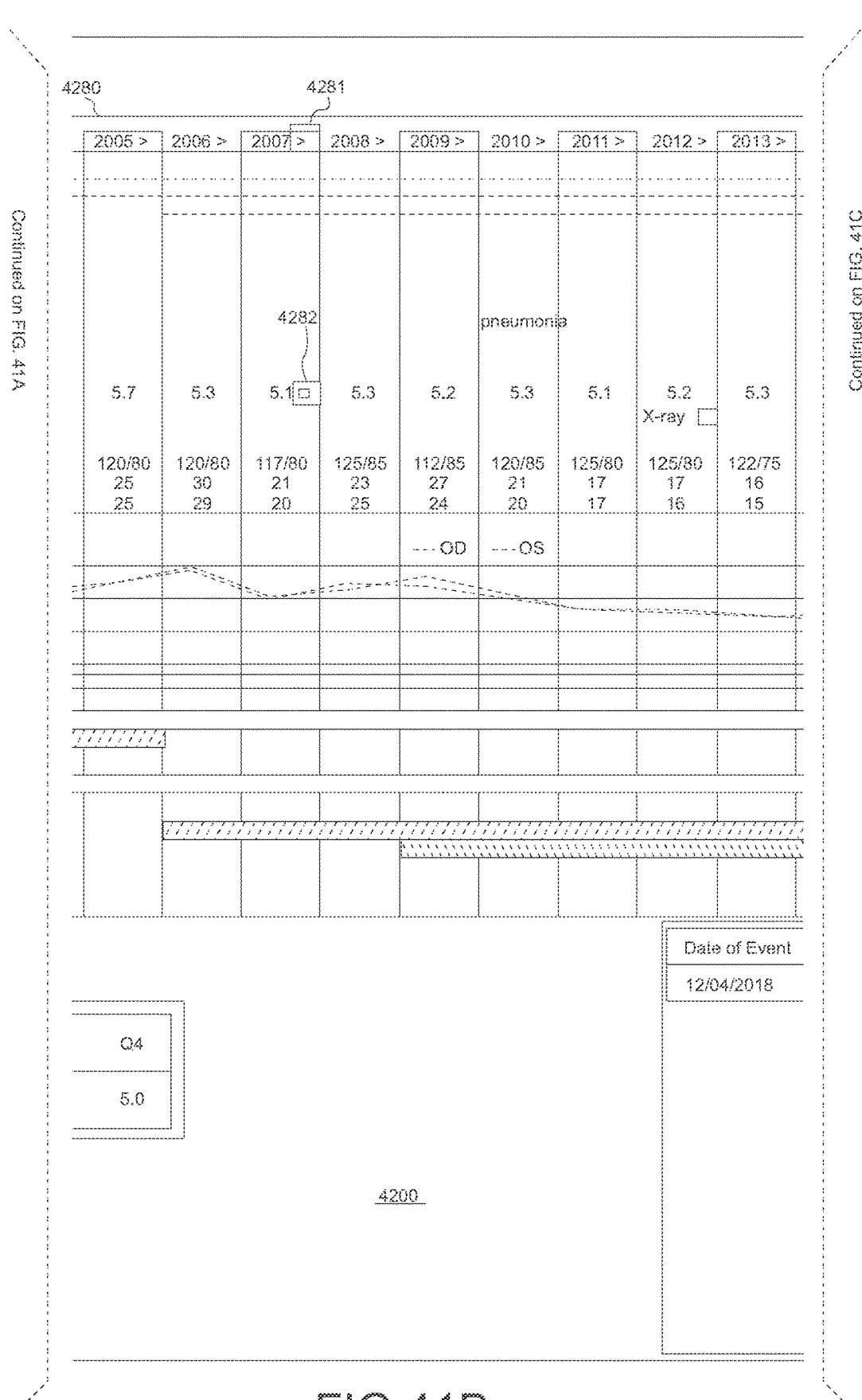
Figure 41C:
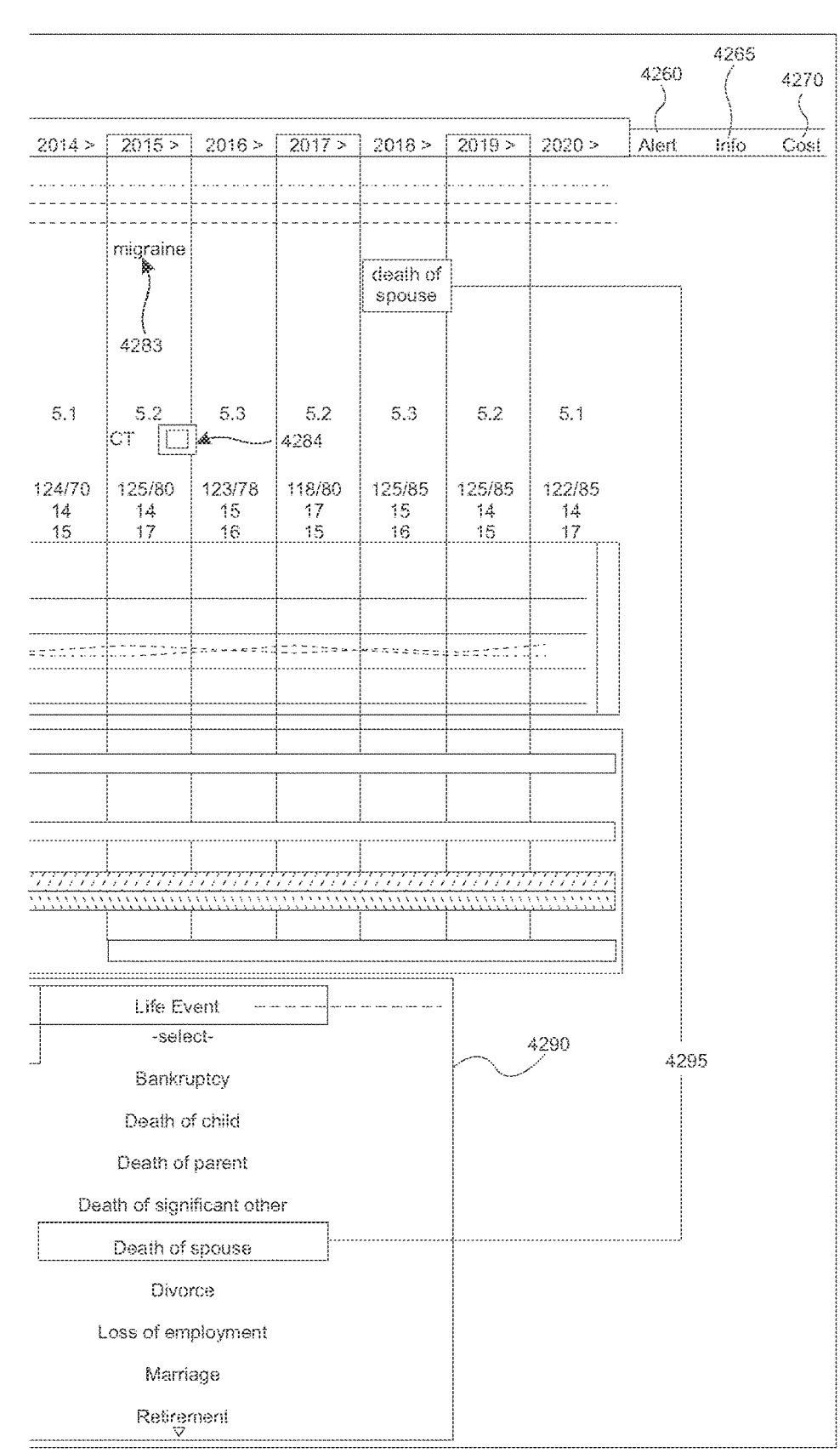

In some embodiments, the Data Command Center of the present principles, such as the Data Command center 001 of FIG. 1 enables, either as part of a medical records dashboard of the present principles or individually as a Whole Life tool, a user/medical care provider to graphically view, in a single display, a patient's entire medical history. For example, FIG. 41 depicts a graphical view of the entire medical history of a patient as a Whole Life tool in accordance with an embodiment of the present principles. In the embodiment of FIG. 41, the Whole Life tool 4200 illustratively lists dates, in one year incremented columns, across a top row 4202 of the Whole Life tool for a period of 20 years from 2000 through 2020. Although in the embodiment of FIG. 41 the time increments are illustratively one year increments, in other embodiments the time increments can be substantially any time increments chosen by the user/medical care provider.

In the embodiment of FIG. 41, the Whole Life tool 4200 in a first column 4210 lists a series of life events that occurred in a patient's life including diagnosis 4211 given to the patient, signs and symptoms 4212 the patient has had, major life events 4213 of the patient, hospital admissions 4214, surgeries 4215 the patient has had, laboratories 4216 performed on the patient, radiological procedures 4217 performed on the patient, and clinical measurements 4218 made on the patient. The Whole Life tool 4200 of FIG. 41 further illustratively includes an IOP section 4250 graphically displaying the intraocular pressure of a patient's right eye (OD) and the patient's left eye (OS) as a line graph spanning the 20 depicted years of the patient's medical history. In the embodiment of FIG. 41, the line graph of the IOP of a patient's right eye (OD) is color-coded red and the line graph of the IOP of the patient's left eye is color-coded blue for easier distinction. In the embodiment of the Whole Life tool 4200 of FIG. 41, a lower section 4260 graphically displays a medication history for the patient. In FIG. 41, horizontal bar graphs depict a history of the medication taken by and/or prescribed to a patient spanning the 20 depicted years of the patient's medical history. In the embodiment of FIG. 41, the various medication bar graphs can be color-coded to more easily distinguish between medications. In some embodiments, color standards, such as defined by the American Academy of Ophthalmology, can be used for color coding the medications. Alternatively, or in addition, in some embodiment custom colors can be used.

In the Whole Life tool 4200 of FIG. 41 any column, 4281, can be selected 4280 and expanded to take up the entire page, or a partial part of the page, or a navigation template 4290 may be used to navigate the timeline by date range or to zoom in on specific results for that time increment 4282. For example, if a user/medical provider selects the year 2007, that particular year can expand so that instead of displaying one full year as depicted in FIG. 41, the Whole Life tool 4200 can display 12 months in the year in one month increments or quarterly or in any other increments, for example, for every medical encounter the patient has had. In some embodiments, a user/medical care provider is enabled to select whether to display all the encounters that the patient has had with any medical care providers or just particular medical care providers. In some embodiments, a zoom view of a particular time span can be displayed on another monitor such that a user/medical care provider is able to view the zoomed time increment simultaneously with the whole life view.

In the embodiment of the Whole Life tool 4200 of FIG. 41, the patient illustratively had three major disease states, diabetes, hypertension, and glaucoma, as listed in the diagnosis row 4211. The Whole Life tool 4200 enables a user/medical care provider to select any of the identified major disease states to find out more detailed data regarding the selected disease state and update start/stop dates or activate/inactive a diagnosis. As depicted in FIG. 41, a user/medical care provider is able to determine when the disease exactly occurred by referring to the Whole Life tool 4200. In the embodiment of FIG. 41, the diabetes occurred in 2002, 2003 was hypertension, and 2006 was glaucoma. These are chronic diseases, and these are the dates of onset. In some embodiments, the Whole Life tool can include a bar graph that can continue along a horizontal date line displaying the time period that the patient had that diagnosis, and if for some reason they no longer had that diagnosis, the bar graph could stop.

The Whole Life tool 4200 of FIG. 41 displays for a user/medical care provider in row 4212 when a patient developed a symptom and identify the symptom 4283. Similarly, the Whole Life tool 4200 of FIG. 41 is able to display for a user/medical care provider in row 4213 when a major life event that can affect the well-being of a patient occurred such as a divorce or the loss of a loved one, etc. As previously described, in row 4214, the Life tool 4200 of FIG. 41 is able to display for a user/medical care provider hospital admissions the patient had over the 20 years spanning the patient's recorded medical history. In the embodiment of FIG. 41, in 2010, the patient was hospitalized for pneumonia. As depicted in row 4215 of the Whole Life tool 4200 of FIG. 41, the patient had a surgery, transurethral resection of the prostate, in 2001. In addition, row 4216 of the Whole Life tool 4200 of FIG. 41 depicts that the patient has had laboratories, illustratively, blood sugars labs were performed, like hemoglobin A1C and update start/stop dates or activate/inactive a diagnosis. It should be noted that in the embodiment of the Whole Life tool 4200 of FIG. 41, a valued displayed in some rows and/or columns can be an average value of a measured parameter for the time increment depicted by the column. That is, in some embodiments each row and/or column can be a smart row or column and if a laboratory was taken four times in a year, the Whole Life tool 4200 can be configured to display an average of all values measured during the time increment. In some embodiments, by selecting a value in a row, patient data/information can be displayed in a window or other display means depicting all of the values measured and/or laboratories for the time increment. Even further, by selecting a particular measured value or laboratory, further detailed information for that particular value or laboratory can be displayed to a user/medical provider. Although the embodiment of FIG. 41 is described as displaying an average value, in some embodiments a high, low, or other particular value can be selected by a user to be displayed 4222 represents an alert for an abnormal result.

In row 4217 of the Whole Life tool 4200 of FIG. 41, radiological procedures performed on the patient are displayed. For example, in FIG. 41, a CT scan was performed on the patient in 2015. In accordance with the present principles, by selectin the indicator in row 4217 of the year 2105, the image of the CT scan can be displayed to the user/medical care provider. In row 4217 of the Whole Life tool 4200 of FIG. 41, clinical measurement taken on the patient can be displayed. Such clinical measurement can include blood pressures taken at each doctor's visit. In some embodiments, the results can be displayed as a number. Alternative or in addition, in some embodiments, by selecting an icon associated with the clinical measurements, a graph representing the clinical measurements over time can be displayed. 4219 and 4220 represent radiological procedures and show how they may be toggled between one, many, or all. Images may be directly accessed and viewed within context by selecting them 4284.

In accordance with the present principles, in the Whole Life tool 4200 of FIG. 41, substantially any portion of a time increment, or presentation of patient-related data/information can be selected to cause a display of a more detailed view of the selected time period/value.

In the Medications section (4255) of the Whole Life tool 4200 of FIG. 41, start dates and stop dates for each of the medications are displayed and may be interacted with in accordance with Medication Management protocols described herein.

The Whole Life tool 4200 of FIG. 41 illustratively comprises three optional columns: an alert column 4260, an info column 4265 and a cost column 4270. The alert column 4260 can be used to alert a user/medical care provider of an issue that requires further attention. In some embodiment alerts are automatically created by, for example a Rules module (described in greater detail below), and alternatively or in addition, alerts can be input by the user/medical providers with access to the Whole Life tool 4200.

Whole Life view may be interacted with whereby a doctor may choose to update an event, such as a life event (4290) by selecting said event and the event will auto-populate on the whole life view (4295).

The info column 4265 of the Whole Life tool 4200 of FIG. 41 can be used to provide information for a user/medical care provider. For example, in some embodiments, links can be provided to direct a user/medical care provider to sources of additional information, such as PUBMED, if the user/medical care provider is interested in learning about medications. Alternatively, or in addition, the info column 4265 can be used by users/medical care providers to provide information to other users/medical care providers.

The cost column 4270 of the Whole Life tool 4200 of FIG. 41 can be used to display to a user/medical care provider information associated with cost in providing medical care a patient. For example, in some embodiments, the cost column 4270 can be used to provide to a user/medical care provider information regarding what a patient's insurance company will authorize. Alternatively, or in addition, in some embodiments that cost column 4270 of the Whole Life tool 4200 can display to a user/medical care provider information regarding bills, paid or unpaid, associated with a patient.

In some embodiments, a user/medical care provider can input patient-related data/information into a Whole Life tool of the present principles. Alternatively, or in addition, a Rules module can auto-populate patient-related data/information into a Whole Life tool of the present principles. For example, in some embodiments, an integration module of the present principles, such as the integration module 002 of the Data Command Center 001 of FIG. 1, can collect patient data/information from outside sources (e.g., an EMR system). The patient data/information is made accessible, for example via a storage means, to a Rules module of the present principles, such as the Rules module 004 of the Data Command Center of FIG. 1. In addition to having access to the data/information collected by the Integration module 002, the Rules module 004 can have access to all information input by a user/medical care provider via, for example, a medical records dashboard or any other user interface. Alternatively, or in addition, in some embodiments, the Rules module 004 is configured to further have access to patient related information and general medical knowledge including but not limited to medical information regarding health conditions and treatments, symptoms and side effects, procedures, images and diagnosis, and other related medical information. As such, in some embodiments, the Rules module 004 can auto-populate at least portions of a Whole Life tool of the present principles. The Rules module 004 can then, via for example a Display module, such as the Display module 006 of the Data Command center 001 of FIG. 1, can cause the display of any portion or zoomed-in portion of a Whole Life tool of the present principles.

Embodiments of a Data Command Center convert and generate a display/view that efficiently translates clinical decision support (CDS) into a visual display. For instance, an OCT can be correlated in a display with injections, along with the measurements in microns of the OCT, graphing results on a timeline. The application renders efficient representations to effectively assist a user/medical care provider in determining the best course of action for a patient.

In embodiments of the present principles, once individual practice patterns are learned using AI/machine learning techniques, decisions can be customized. All users may not perform their practice in a similar manner, however, there are nationally set guidelines of preferred practice patterns based on condition. Based on these and other relevant information, sets of preferred practices can be programmed to guide users/medical care providers. Through evaluating local, regional, and national practice patterns, best practice can be identified and disseminated among users of embodiments of the present principles.

Although embodiments of the present principles can be applied to all fields of medicine where there are different medications and procedure options for treating any medical condition, described below is an example of a retina surgeon using embodiments of the present principles to treat Diabetic Macular Edema. Information always considered important to the treatment of Diabetic Macular Edema include, but is not limited to:

1. Type of injected medication in an eye
2. Frequency and time interval between injections
3. Impact on the swelling of the very center of the retina, called the fovea, as measured by an OCT; this center thickening measurement is called central macular thickness (CMT)
4. Clinical findings and how this impacts the patient's vision.

Figure 42:
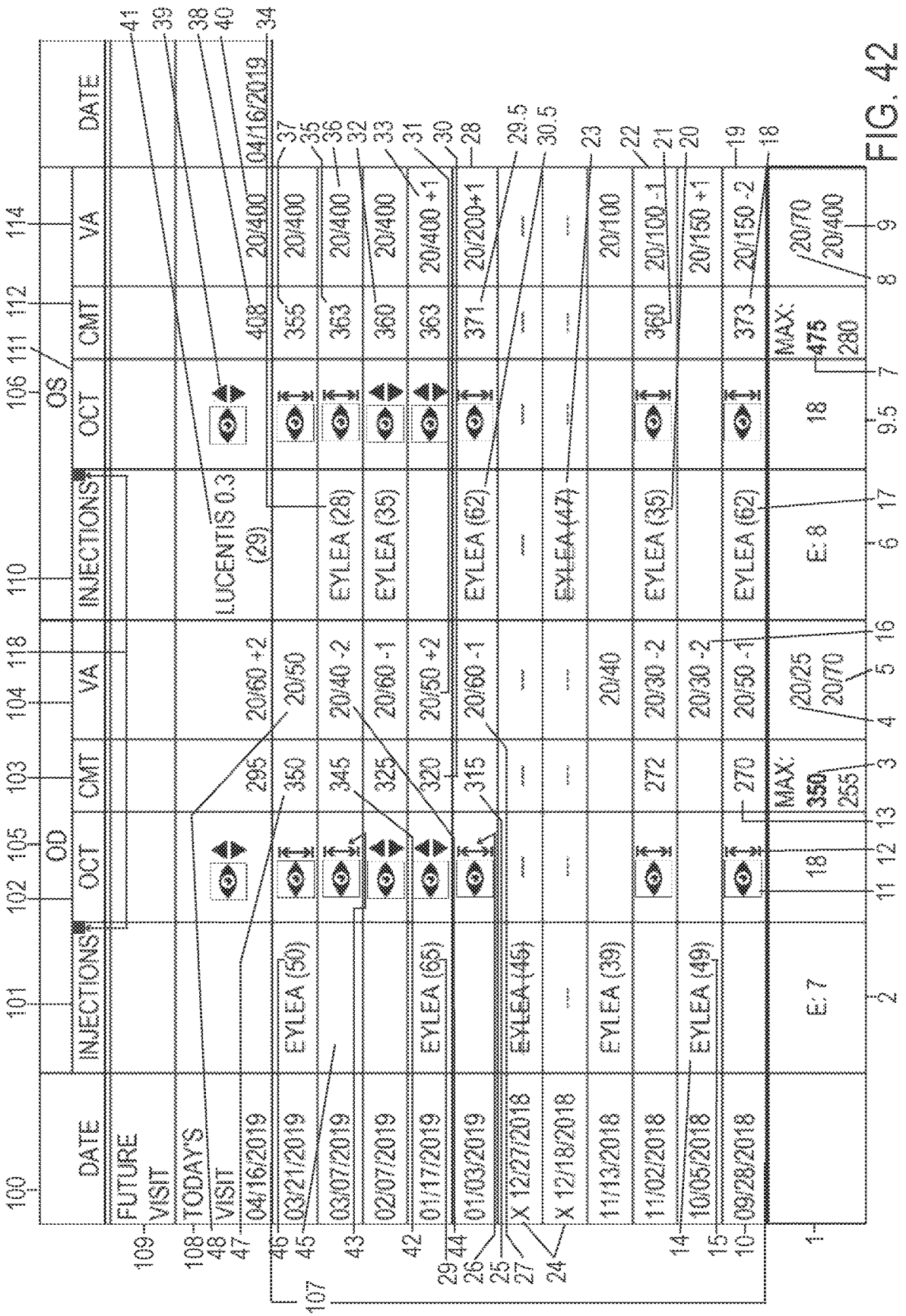
FIG. 42 illustrates a first Flowsheet that can be used in predictive analytics in accordance with an embodiment of the present principles.
Figure 43B:
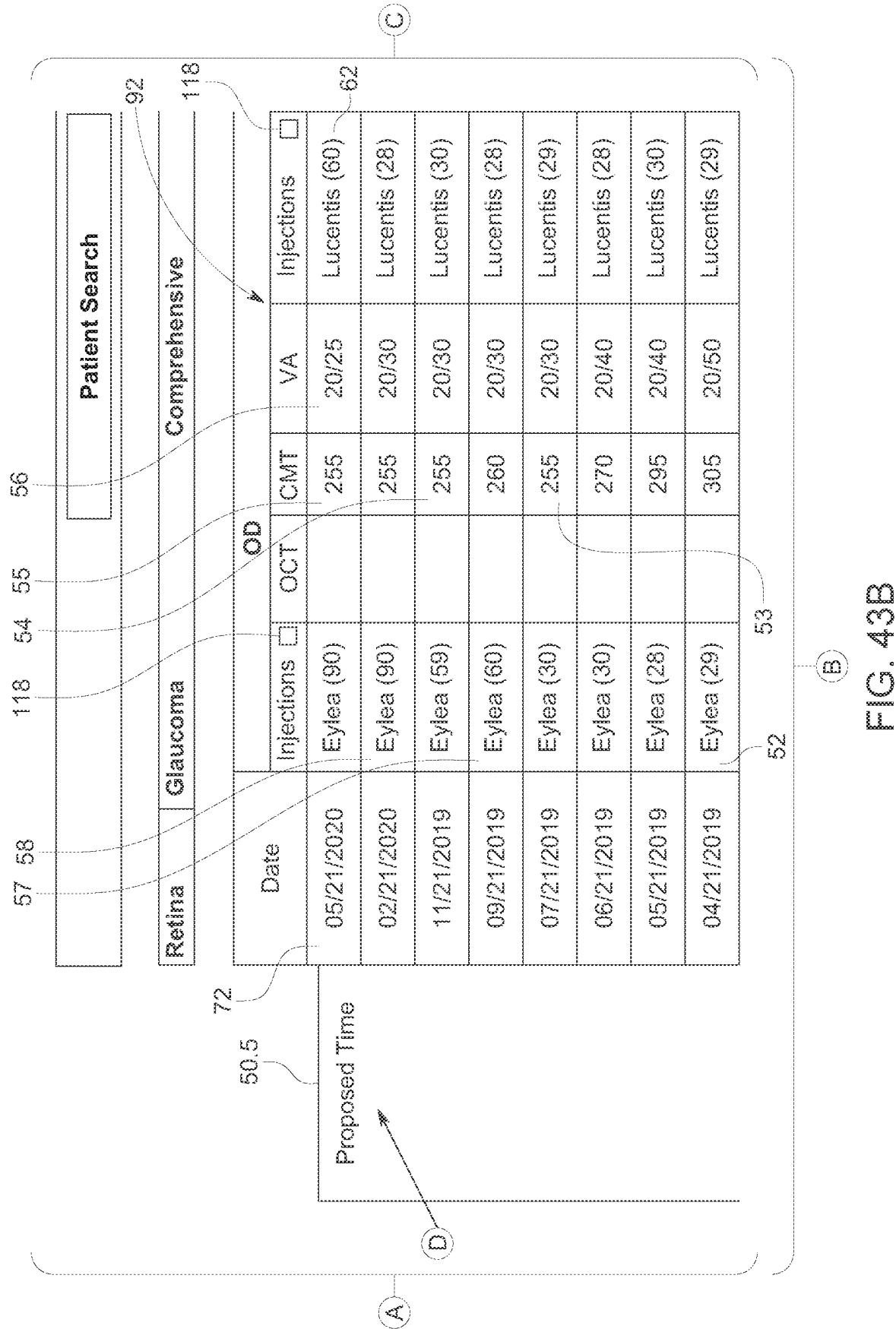
FIG. 43 illustrates a second Flowsheet that can be used in predictive analytics in accordance with an embodiment of the present principles.
Figure 43C:
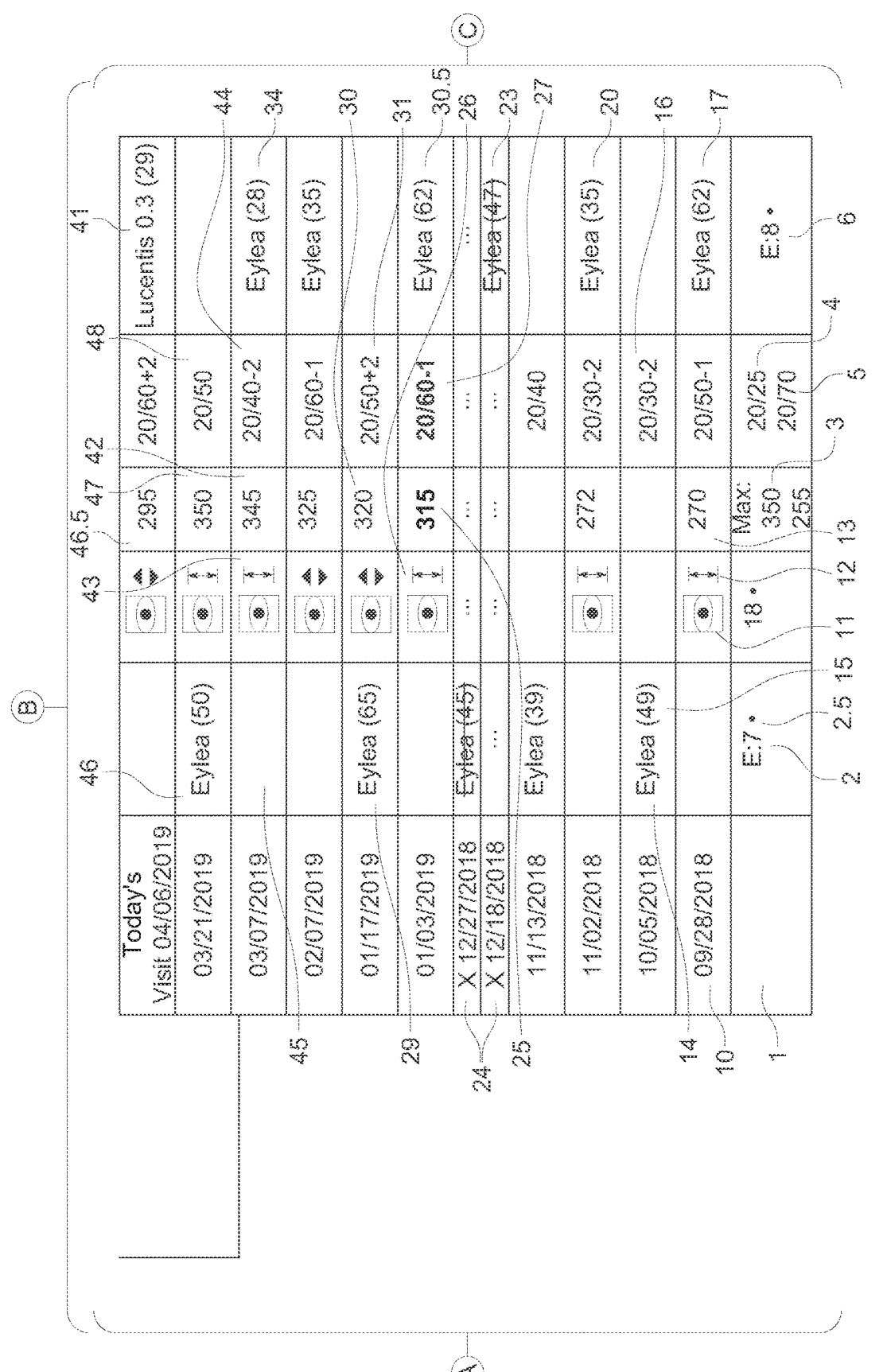
Figure 43D:
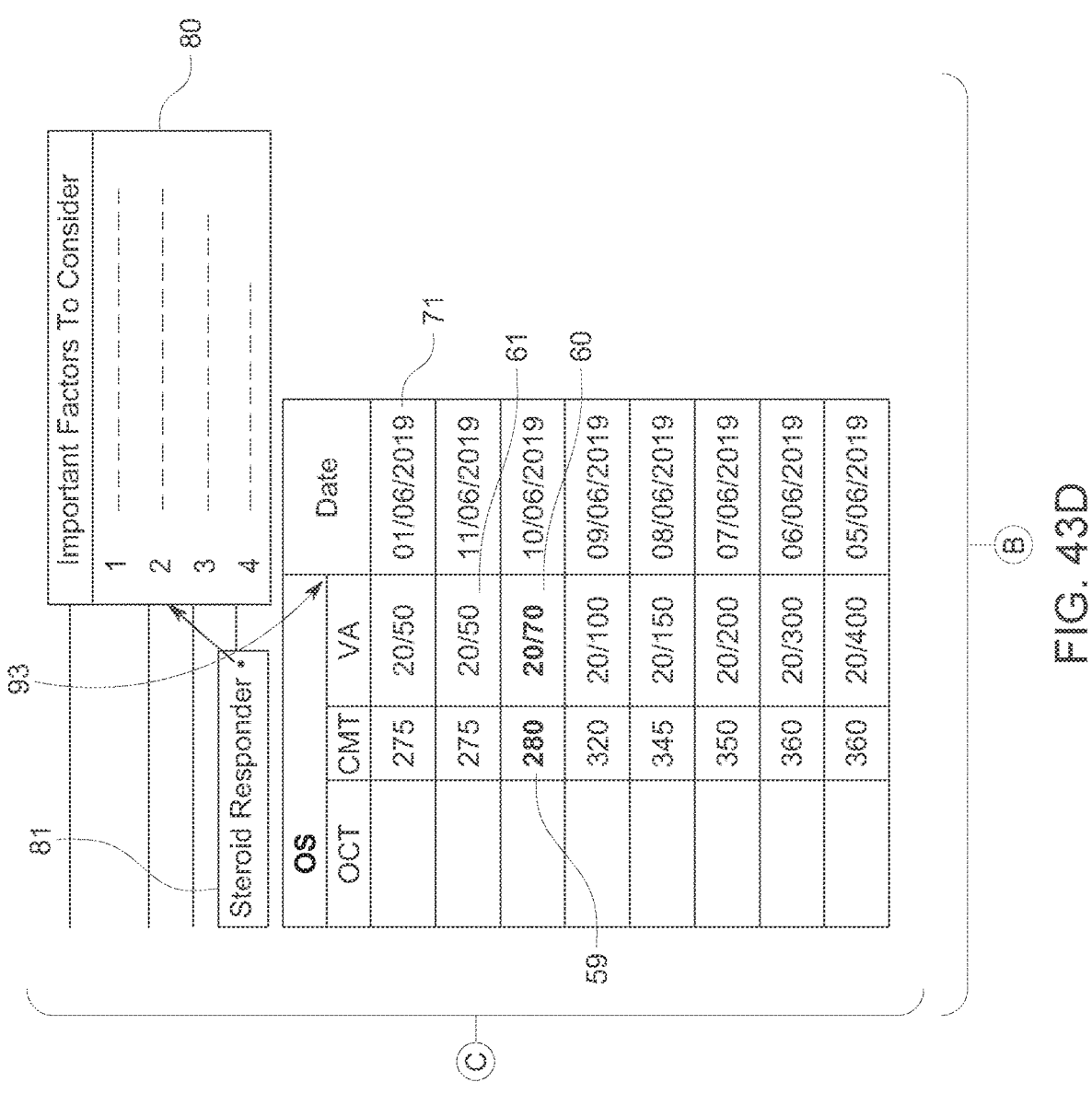
Figure 43E:
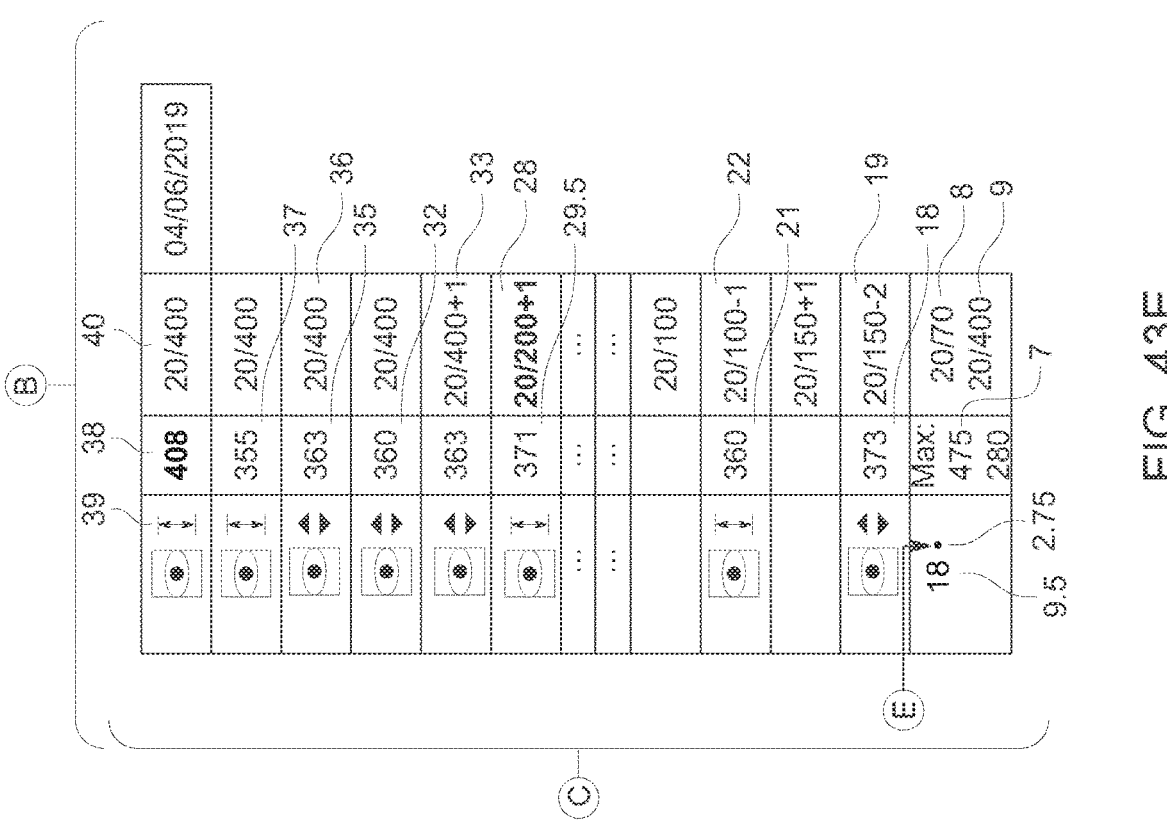

FIG. 42 illustrates a Flowsheet that can be used in predictive analytics in accordance with an embodiment of the present principles. In the embodiment of FIG. 42, 100 is the time of any medical service delivered. 101 is any medication or procedure, such as a laser, surgical intervention or any action taken at any time or date performed at a particular time 100. 102 is any diagnostic test, laboratory resting, imaging or other recording that can be measured to follow the efficacy of any action in 101. 104 is any clinical measurement of any date that can be recorded, such as any vital signs, blood pressure, symptoms, such as a level of pain indicator. Displayed is a measurement of the patient's vision. 103 is the measurement of the thickness of the retina at the center called central macular thickness (CMT). 101 shows the type of medicine that is injected in the eye. 104 represents clinical findings, 103 represents the result of a diagnostic tests, and 101 represents the type of procedure that a doctor would want to review over time. In this example, 101-105 are all right side of the body. 106 and 110-114 represent the same data as 101 to 105, but for the left side of body. It should be noted that other divisions than those shown can be used to correlate to locations on, for example, a patient's body. In FIG. 42, 118 depicts a mechanism for launching a different display, as depicted in FIG. 25 as 21080 and 1 represents a flowsheet summary row.

In FIG. 42, Element 2 is the summary data representation showing the number of injections, illustratively Eyleas. In the embodiment of FIG. 42 there are nine encounters and two cancelled encounters, which are displayed at 24. Since there were seven Eylea but only four are displaying on the nine encounters displayed, it is apparent the patient received three Eyleas before the Sep. 25, 2018 encounter row displayed 10. In the embodiment of FIG. 42, a user is able to scroll and find these other dates or click on the E7 at 2 and just those seven encounters can be shown. Element 6 depicts that a total of eight Eylea injections have been performed in the left eye.

In the embodiment of FIG. 42, 7 shows the worst retina swelling in the left eye in a first color (e.g., red) that measures 475 microns, and the least amount of thickness is 280 microns shown in a second color (e.g., green). It can be determined from FIG. 42 that since 280 is greater than the normal 250, the patient must have presented to the practice with some level of retinal swelling. In FIG. 42, 8 represents the clinical measurement of vision of the left eye and supports the fact that the patient must have presented with some edema because 9 shows the patient's worst vision was 20/400, but 8 shows the best was 20/70, which means on presentation the patient did not see well.

FIG. 43 illustrates a second Flowsheet that can be used in predictive analytics in accordance with an embodiment of the present principles. In the embodiment of FIG. 43,81 shows steroid responder in the Clinical Decision Support module and a user/medical care provider can utilize this to see an enlarge view 80. Embodiments of Data Command Center of the present principles are able to search data from all sources on a particular patient as described in FIG. 7.

For instance, social history, 5 described in greater detail below, displays information about the patient being a smoker and can impact how the patient can respond to the medicine. Knowing what stage diabetes, the patient is in, 6 of FIG. 44, and can be evaluated against diagnostic tests such as evaluating a photograph 6.5 of FIG. 44. The photo was 27 months ago, hence why in a photograph may be suggested for order 6.75 of FIG. 44. The fact that a patient missed seven appointments, 7 of FIG. 44, might explain why a particular appointment is not effective. 3 of FIG. 45 may represent insurance authorization is required, which is critical since each drug can be $2000.00 and insurance of that patient may require authorization before payment is approved.

In FIG. 42, 10 shows the first date of service and 11 is an icon for an image. By interacting with 11, the underlying image is displayed. If the presented data measuring the image 11 as seen in the next column 13, 270 microns, is not enough information for the user/medical care provider to come to a conclusion, the image can be further inspected. Each image of an OCT often has 18-30 slices. Slices can be evaluated for the best/worst thickness of that particular slice of the retina. There might be a particular slice that presents abnormal findings, and as such can be weighted to be alerted or to display as the first image in accordance with the present principles.

In FIG. 42, 12 is a symbol that can have many gradations. Ranking in any method the importance of the improvement, no improvement or worsening of an OCT. Such a scale can be utilized to display the underlying data as improving or worsening. 14 shows an Eylea injection was performed on this date of Oct. 5, 2018 and 15 shows the number of days since the last injection was given, which was 49 days. On Oct. 5, 2018 no OCT was performed. This makes sense because only seven days earlier on Sep. 28, 2018 11 an OCT was performed 11 so there was no need to repeat. There are governing rules for how often an insurance companies will pay for such a test. They usually will not pay under 4 weeks, which is 28 days, which also happens to be the earliest time period that insurance will pay for the specific type of injection associated with this disease. 16 shows that the patient's vision is 20/30, an improvement from the prior visit.

In FIG. 42, 17 shows that in the left eye, Eylea was injected, and it has been 62 days since the last one. 18 shows that the CMT is 373 microns, which is about the mid-point to what the minimum and maximum is as seen in 7. 19 shows that the patient's vision is 20/150. On September 28th, the doctor decided to inject the left eye 17. On October 5th, instead of waiting 62 days 17, since the patient's vision remains decreased at 20/150 19, but we know the best vision of the patient was at one time 20/70 8, the doctor decided to do it more frequently. Therefore, in 20 it is visible that the Eylea is repeated 35 days after the last injection.

In FIG. 42, 21 shows that there has been a little improvement to 360 microns from 18, 373 microns, and that the vision has also slightly improved to 20/100, as seen by comparing the value in 22 to the value in 19. It was then decided on Nov. 2, 2018 to repeat the injection in the right eye 20 and for the next visit, Nov. 13, 2018, which falls in a relatively safe parameter of just 39 days after the previous, to inject the right eye. Sometimes, if the patient does not worsen by spreading out the injections, perhaps stopping injections all together can occur. However, in the embodiment of FIG. 42, on Nov. 13, 2018, the patient is scheduled for an Eylea injection on December 18th for the left eye 23, which is 47 days after the previous left eye was injected.

Depicted in FIG. 42 is an example where on December 18th, the patient has a cancelled visit, 26. In such instances, embodiments of the present principles can now present a notification such as, "This patient has already fallen out of parameters of waiting too long. You must call them immediately to get them in ASAP." In FIG. 42, at 24, it can be seen that on December 27th the patient had previous scheduled to have Eylea in the right eye, which would have been 45 days after the previous injection of Nov. 13, 2018. 26 depicts that on January 26 an indicator that the OCT is worse. In FIG. 42, 25 depicts that the thickness is 315 microns. Compare that to the visit on Nov. 2, 2018, which was 272 microns and there is a dramatic change in thickness. This is why the alert is displayed. In some embodiments a trigger can be set at a specific percentage change between measurements to alert a display.

In FIG. 42, 27 depicts the 20/60-1 in color (e.g., orange). The reason, the patient has gone from 20/40 on 11/13/18 and has now decreased their vision by 50% to 20/60-1, is perhaps because of the two cancellations. In some embodiment, 24 can be highlighted (e.g., lit up) to help explain the conclusion. In FIG. 42, at 28 the patient is 20/200+1 OS, which is legal blindness. Such a result can be presented as a more critical alert because there has been a doubling of this patient's result.

In FIG. 42, 29.5 shows 371 microns of thickness compared to 21 at 360 microns. It is not highlighted because the 11 points, percentage wise, is not so much of a drop compared to the right eye that went from 272 to 315 at 25. 30.5 depicts that the doctor chose to do an Eylea injection in the left eye, which was 62 days from the last injection. From FIG. 42, it can be noted that 1/3/19 was 52 days from the last time an Eylea injection was done in the right eye. The cancelled visit on 12/27/18 shows if not cancelled, the Eylea injection would have been 45 days since the last time, and on 1/3/19 is seven days later. Therefore, if the Eylea injection was performed in the right eye, it would have already been 52 days since the last injection. In some embodiments, 52 days can be displayed at 26, reminding the doctor to take action. In the embodiment of FIG. 42, however, the doctor decided to treat the left eye perhaps, because it had been a significant amount of time since last injection, 62 days shown at 30.5.

From FIG. 42 it can be noted that this patient already had missed appointments, which might be an example of a circumstance in which embodiments of the present principles can suggest injections in both eyes, due to poor patient compliance. In FIG. 42, it can be noted that in 24 and 23, the Eylea was scheduled first in the left and on December 27th it was the right eye. In FIG. 42, at 29, it is noted that the patient returned on 1/17/2019. That is a full two weeks later. As is noted, that is already 65 days after the last injection 26. In FIG. 42, it can be noted that the patient's thickening is continuing to worsen at 320 microns 30.

In FIG. 42, at 31 it can be noted that the vision is slightly better, yet 28 shows legal blindness in the left eye. On 1/17/19, the doctor gets the patient scheduled in 20 days on 2/7/2019. In FIG. 42, because while 2/7/2019 represents 35 days since an injection in the right eye, and 32 shows 360 microns and 33 shows 20/40 vision, it is reasonably good that this left eye is being injected at 35 days. On February 7th, it has only been 20 days since the last injection of the right eye. Therefore, on February 7th, injecting both eyes could not have been performed as insurance payments require waiting at least 28 days. Since, in FIG. 42 it can be noted that it has now been 35 days since an injection occurred in the left eye and this is a more time appropriate injection cycle and there has been a slight improvement to 360 microns 32, a switch may not yet be recommended.

In FIG. 42, 34 in the example of 3/7/2019, it is noted that the patient has returned in the precise 28 days for a repeat injection and 35 shows that there is 363 microns of thickness. This is problematic. There is an increased thickening of 3 microns from 32 when there was 360 microns and the injection occurred only 28 days ago. In FIG. 42, 36 shows no improvement in vision and the patient is now twice as bad as legal blindness. In this instance, the Eylea is being injected and measured at 28 days, which is perfect timing and Eylea seems not to be working. In some embodiment, at 34, the medication could have been switched, but perhaps for this patient it was worth trying it one more time or insurance required Eylea injection instead of another drug as permission to switch may require advanced authorization.

In FIG. 42, 30.5 depicts that the Eylea was injected at 62 days. There was worsening from the previous visit of 20, but that could have been a time factor of a delay because of the cancelled visit depicted in 24. As noted from FIG. 42, the patient does return on 3/21/2019, 37, and the OCT is performed again. From FIG. 42 it can be noted that only two weeks after the injection, a maximum drug effect and the OCT indicates that the central macular thickness has improved to 355 (48) from 363, but the vision has remained 20/400. This is not a satisfactory result. Having an improvement of just eight microns, just two weeks after an injection, embodiments of the present principles can suggest that at the next visit on 4/6/19 there should be a switch from Eylea.

In FIG. 42, 41 shows that now there is a suggested switch to Lucentis, but 39 shows that there is even further worsening of the central macular thickness. In FIG. 42, 38 is highlighted and depicts that it is substantially worse than 355, and 40 depicts no improvement in vision. From FIG. 42, it is noticeably clear the Eylea is not working because it is only 29 days since the last time the Eylea had been injected. So, now two times in a row at 28 days and 29 days the Eylea has not only not improved the patient's condition, but the patient has been worsening. Therefore, in some embodiments a switch in medications can be automatically recommended.

In FIG. 42, 43 shows a colored (e.g., red) icon alert that the OCT is getting worse. 42 depicts that the thickness of the retina has increased to 345 microns from the previous visit of 325 microns. 44 depicts that the vision has not worsened. Nevertheless, on 3/7/2019, with this being the only good eye, FIG. 42 depicts that only the left eye was injected. As depicted in FIG. 42, when the patient returns on 3/21/2019, it had been 50 days and the retina has become more swollen to 350 microns. In FIG. 42,47 depicts a worsening of another 5 microns from the visit on 3/7/19 42 and the vision has slightly worsened to 20/50, 48.

Embodiments of the present principles described herein enable users/medical providers to visualize the impact of options for care on a patient with the assistance of the predictive analytics of the present principles. In accordance with the present principles, recommendations can be displayed in context with patient data as shown in 41 of FIG. 42 which automatically suggests Lucentis for the left eye on "todays visit." In some embodiments, pertinent information of why a recommendation is being made is also displayed. In some embodiment, a Data Command Center of the present principles can display a future likely scenario if the user/medical care provider chooses the suggested course of action or, if the user chooses another course of action.

In FIG. 42, 41 depicts an example of a suggestion that the left eye has a Lucentis injection and repeat it every 28 to 30 days and the right eye be treated with Eylea two weeks from "today's visit," 4/6/2019.

FIG. 43 illustrates a second Flowsheet that can be used in predictive analytics in accordance with an embodiment of the present principles. In the embodiment of FIG. 43, 50 enables a user with an option to display future predictions for different drugs. An option for Eylea in the right eye and Lucentis in the left eye is depicted in FIG. 43. Future encounter rows 50.5, can be added, showing what the results in the future could be. Reviewing past events for patient compliance can enable a determination of future compliance, and as such adjust projected outcomes accordingly, such as the two missed visits at 24. In FIG. 43, 41 depicts that the doctor treated with Lucentis in the left eye and Lucentis is repeated every 28 to 30 days all the way through to 11/6/2019, and as such, compliance weighting can increase. In the embodiment of FIG. 43, 62 depicts that the recommendation is to change from 30 to 60 day intervals for injections. Therefore, as depicted in FIG. 43, by 1/6/2019, 71 depicts that the left eye has greatly improved with vision now recorded as 20/50, which 8 in the summary row depicts that before this reading in 71, the best vision was 20/70. Therefore, the data of FIG. 43 predicts that continued use of Lucentis would result in better vision than the patient has ever had since vision measurements have been recorded.

65 displays that Eylea is injected that day, but now 9/6/2019 65 displays 500 microns, augmented in red, which could indicate another threshold of the patient's retina becoming especially thickened at 500 and the vision is now worse than 20/400 at count fingers also being displayed in red. A mandatory switch is displayed on 65, suggesting there is likely no good reason to consider Eylea any longer and therefore suggests switching to Lucentis. Now, on 9/6/2019 Lucentis has to be prescribed even though the doctor had initially chosen Eylea over Lucentis and rejected switching to Lucentis back in #41. The display shows the future visit with Lucentis finally a slow improvement.

Finally, on 12/6/2019, 67, after four injections of Lucentis, approximately every 28 days, the CMT 66 is 395 and the vision has improved to 20/150. However, compare that to FIG. 43, which can be toggled back and forth and displayed simultaneously or with transparency, and the doctor can visualize that the patient's vision is three times better in 71 of FIG. 43, the vision is 20/50 when using Lucentis as initially proposed starting 4/6/2019. The CMT 11/6/2019 is 275 when using Lucentis as suggested 4/6/2019 compared to on 12/6/2019 of 67, FIG. 45, CMT is 395 and vision is 20/150. It is clear, in this case, to the doctor that statistically the best route would be to follow the recommendation. Not doing so, it is shown the statistical probability even with optimal timing of a 3× improvement in vision with Lucentis versus Eylea 20/50 compared to 20/150.

In the embodiment of FIG. 43, 49 depicts a suggestion that Eylea be used in two weeks from 4/6/2019. This could be due to the fact that in FIG. 43, 46 shows that Eylea was used on March 21st. In the example of FIG. 43, the doctor confirms the suggestions and displayed is the statistical likelihood of clinical and diagnostic testing changes using the suggested method of treatment to continue Eylea injections. As such, in FIG. 43, 52 depicts that, Eylea, if used 29 days later, the CMT is predicted to be 305. In FIG. 43, on today's visit, 4/6/2019 the CMT is 295, at 46.5, which is a dramatic improvement in the right eye, which can be partly due to the fact that there is only 15 days from the last time 3/21/2019, an OCT and Eylea injection were performed, and 15 days perhaps happened to be the maximal effect of Eylea on CMT. With that improvement of 295, depicted at 46.5, the recommendation is made to continue to use Eylea and that is what is being displayed as being done on 4/21/2019 and each month until 57, 9/21/2019, when the injection is performed 60 days later.

In FIG. 43, 53 displays to the doctor that the CMT is predicted to be 255 on 7/21/2019, which in fact is back to normal which can be highlighted as 255 at 3 in the summary row. In the embodiment of FIG. 43, that was the patient's best vision and base line of 255, so the predictive scenario displayed can start on 7/21/2019 instead of every 30 days to every 60 days. In FIG. 43, 54 shows the CMT remains at 255 microns even with the injections spread out and it is highlighted because that is the best CMT even with injections now at 60 days instead of 30 days. 58 of FIG. 43 depicts that the injection being spread out to every 90 days, and the predicted values on 5/21/2020, which is 90 days later, are displayed. 55 shows a CMT of 255 and the VA for the first time is 20/25 in 56, which corresponds to 4, the best vision the patient ever had, and, in some embodiments, all can be highlighted to emphasize to the doctor the favorable outcome of following a suggested treatment. Row 72 of FIG. 43 depicts that the result of the suggested treatment is particularly good considering that by 5/21/2020 the patient is now only having injections of Eylea every 90 days and the patients CMT is normal and vision has returned to the best the patient has ever had.

One aspect of the whole life feature is its use as a health planning tool. With this tool, the physicians can visualize the past health status including but not limited to history of physiologic results, medications, procedures, and also visualize potential outcomes for the future under a chosen set of circumstances such as but not limited to effect of different medications.

In one aspect of the whole life feature, data representing potential future health outcomes is generated. This can be done in multiple ways including but not limited to statistical based techniques, machine learning, and artificial intelligence based techniques. In one implementation of data generation representing the future health outcomes, the DHR system may initially create a knowledge database. The knowledge database maybe created with expert knowledge or by gathering statistical data or both. As an example, expert opinions about which medication may work best for a patient with a certain type of disease within a certain type of demographic and with certain types of characteristics such as but not limited to age, sex, weight, height etc. may be collected and encoded. Expert opinions may also include more sophistication for example, it may include what may happen if the patient is a smoker and continued to smoke. The knowledge database may also be created using statistical based techniques. In the statistical based technique, patients with a similar disease may be classified using categories suggested by experts. Machine learning and AI technique may also be used to classify such patients. Over time as more data is collected, the effect of different medications or procedures or interventions may become evident for patients that are classified similarly. In a simple non-limiting example, patients with glaucoma may be classified by age, weight, sex, family history and occupation. The effect of different types of medications may be collected as the patient continues to visit the doctor. Over time, when a statistically significant amount of data has been collected the knowledge base may contain the underlying data representing potential future health outcomes for a given set of patient characteristics. Subsequently, the database may be queried with required inputs to determine such outcomes.

Figure 47:
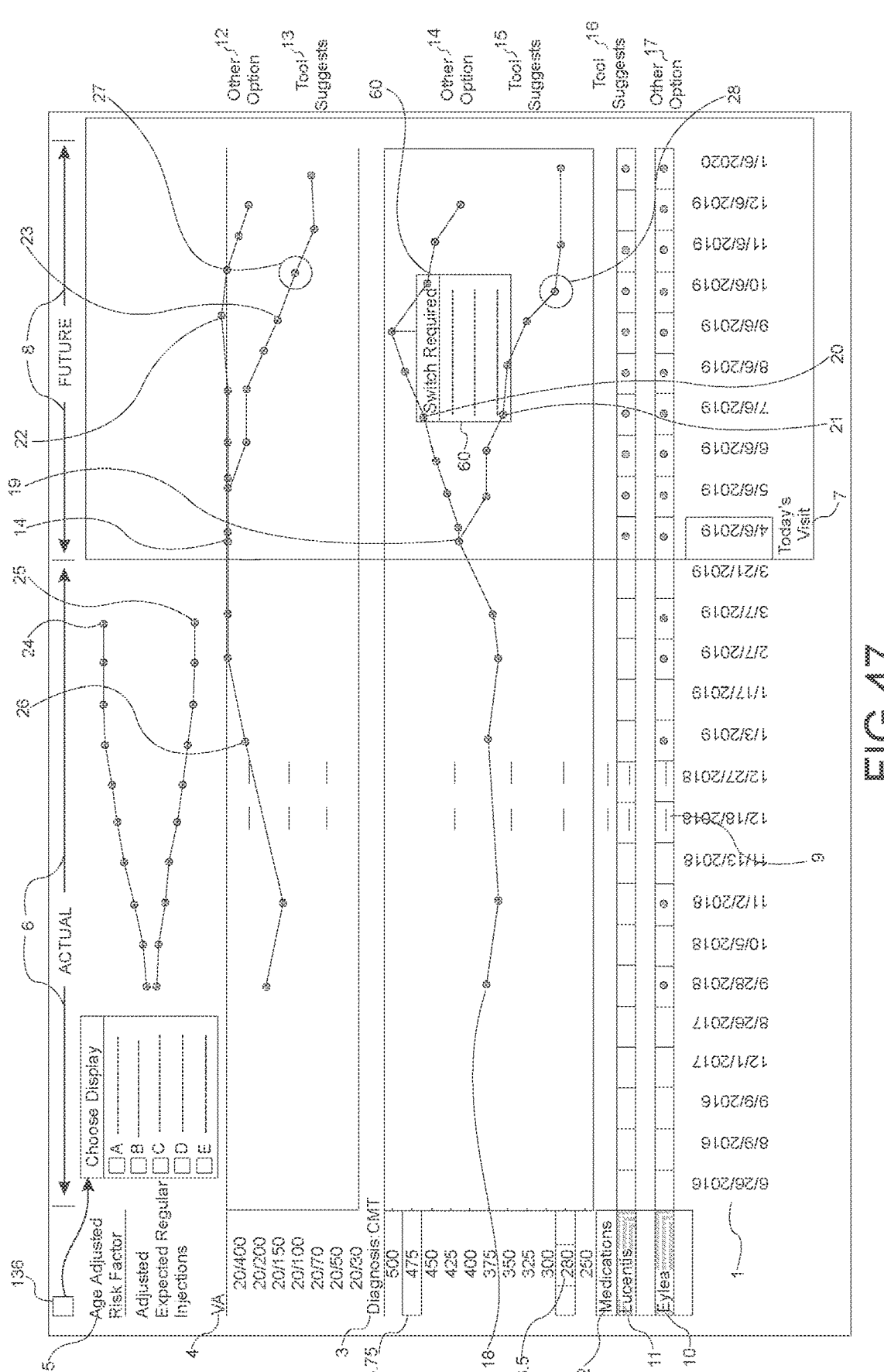
FIG. 47 illustrates predictive analytics in accordance with an embodiment of the present principles.

In another aspect of the whole life feature, the future health outcome data is displayed. FIG. 47 shows one example of how the future health outcome data may be displayed. In this example display configuration, the entire display is subdivided into several sections where different types of data are displayed. For example, section 6 shows the actual (past) data including physiologic parameters, medications prescribed and dates of service. Section 8 is a representation of the future as further explained below. Section 10 and 11 illustrate the different medications. Each medication may be color code or tagged uniquely as explained previously. Section 1 illustrates the dates. Section 3 and 4 illustrates two different physiologic parameters spanning the past, present and future. The number of physiologic parameters, the type of parameters to be displayed and analyzed, may be chosen by the physician once the whole life display is invoked. Once the physiologic parameters to be analyzed and displayed are chosen, the data in section 8 (or the future health outcome data) is generated as described previously. Specifically, the DHR tool can create one or multiple queries based on information about the patient and information about how the patients are classified in the knowledgebase. As an example, the knowledge base may contain the underlying data of how a particular medication typically performs for male patients between the ages 50 and 60 with BMI of above 25 for a particular disease. In this case, the query would be constructed by including the age of the patient, the BMI, the disease, and the suggested medication. Thus, if the patient has the characteristics of having that specific disease and is between 50 and 60 years of age and has a BMI of over 25, the knowledge database will provide a result. If the disease is glaucoma, an example result may be that the central macular thickness (CMT) decreases over a 12 month time frame with periodic injections of one type of medication. Another query may be formed for the same patient with the same conditions but with a different medication. Here a result may be that according to the data in the knowledge base, the second medication may not result in decreased CMT—it may in fact increase. Such results may be displayed on the display of FIG. 47.

In the example display illustrated in FIG. 47, the physiologic parameters are shown as a line graph (see element 18). In this example, line graph 18 illustrates the CMT values as measured in the previous visits in section 6 ("Actual values"). The physician has chosen to display the effect of medications Eylea and Lucentis with the patient currently on Eylea. Section 10 indicates when Eylea was administered. On the current visit ("Today's visit"), at least two queries were performed; one to determine the effect of Eylea for patients with similar characteristics and one to determine the effect of Lucentis also with similar characteristics. The underlying data in the knowledge base may show that patients with the particular set of characteristics do not respond well with Eylea but do respond well with Lucentis. The underlying data may also have a quantified value of how much the CMT is expected to increase or decrease over a period of time. If the increase or decrease is known quantitatively, then the line graph 18 may be extended from today's CMT value to a future value by adding or subtracting from the current value. The future health outcomes may also be displayed as a qualitative result. In other words, in section 8, the DHR can display a message. An example message may be "According to statistical data, this patient is expected to have a decrease of 3% over 1 year with Eylea".

Figure 46B:
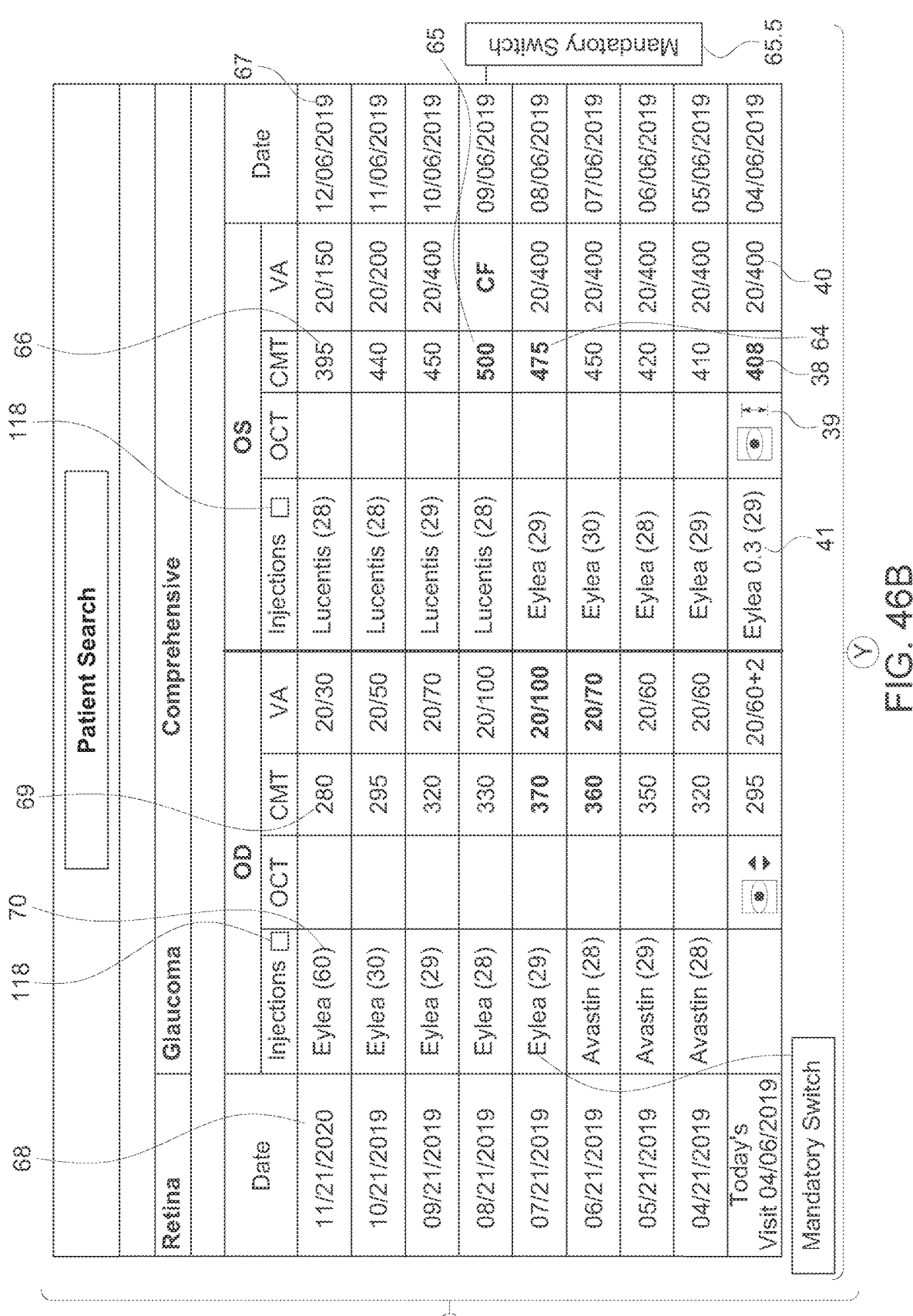
FIG. 46 illustrates predictive analytics in accordance with an embodiment of the present principles.
Figure 46C:
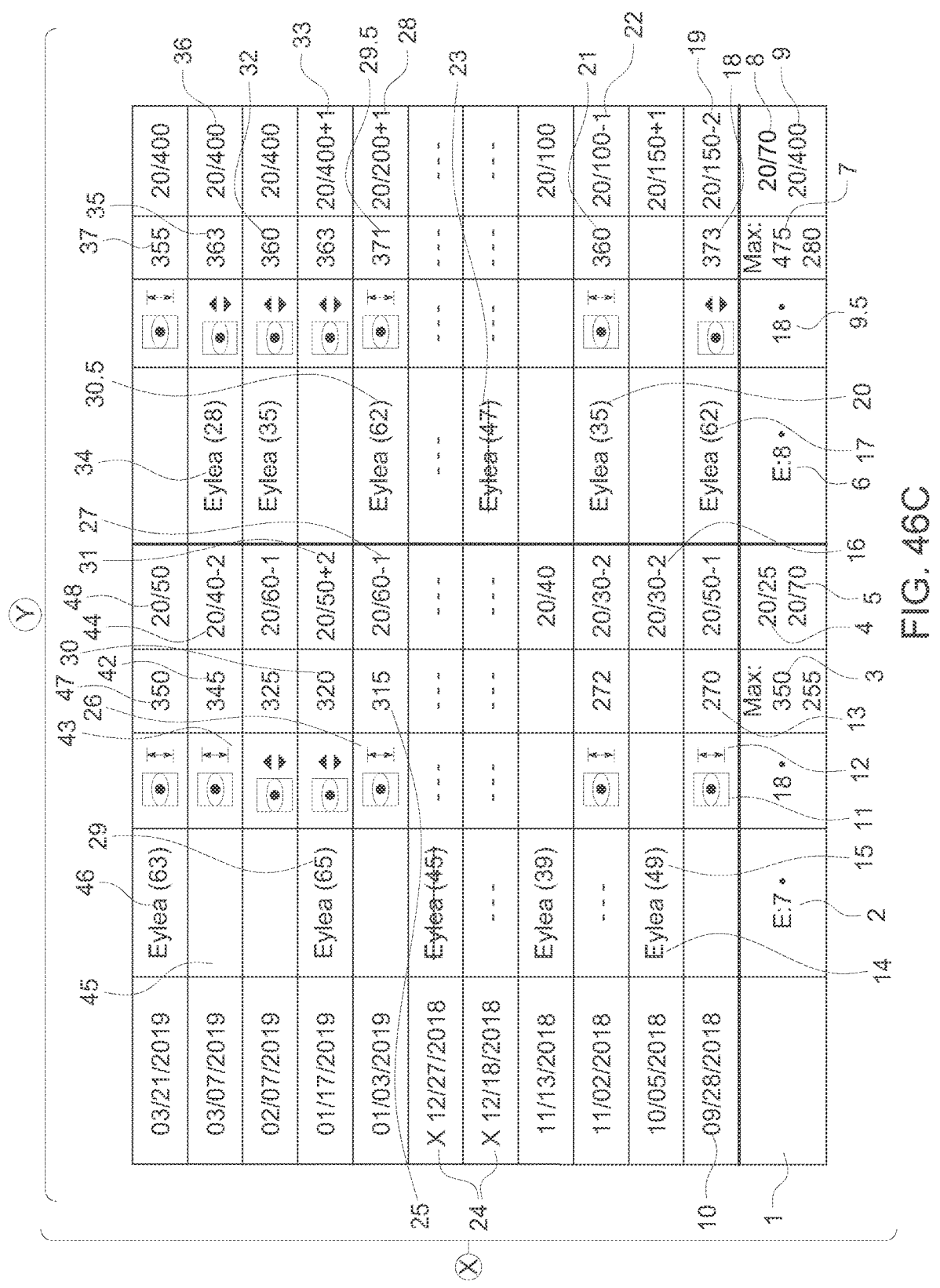

In another concept, representative images are displayed alongside the line graph in either the "Actual" section (Section 6) or the "Future" section (Section 8) as described below. FIG. 46 illustrates the concept. In this example, representations of the OCT images of the eye of the patient are displayed alongside the CMT values in the "Actual" section. The representations may be selected by the physician and the actual image associated with a data point may be displayed on another part of the display such as in the top of the display as illustrated by 37 and 38. The association of the data point to the image may have been done previously by a physician while examining the images and providing information to the patients. Alternatively, automated image analysis software that may include analysis packages based on various techniques such as but not limited to machine learning and AI may be used to choose the representative images.

In another concept, representative images for the "Future" section may also be displayed as described below. Here, of course no actual images of the patient exist because the date has not occurred yet. However, the knowledge database may include images from other patients who share the similar characteristics (or are similarly classified) with the specific patient being examined. Thus, in a prior step before the specific patient is being examined, images from other patients may be collected, classified using one or multiple categories and stored in the knowledge database. As the physician opens the record for a specific patient and activates the whole life feature, queries may be formed by the DHR system and sent to the knowledge database. These queries may then result in images from another one or multiple patients, representation of which may be displayed alongside the results of other queries. As an example, earlier the prediction of CMT was described as it related to which medication was prescribed. In the same manner two sets of images may be displayed from two different patients, both of whom have the same characteristics (or classified similarly) as the specific patient. One set of images may be of a patient on one medication (example Eylea) and another set of images may be of a patient on another medication (example Lucentis). These types of displays may be useful for various purposes including for the physician to rapidly make decisions about future orders including but not limited to medications or for the physician to educate the patient about his or her condition. In addition, as long as the underlying knowledge database supports it, the physician can investigate "what if" scenarios and visualize the results for analysis or communication.

Figures 44, 45:
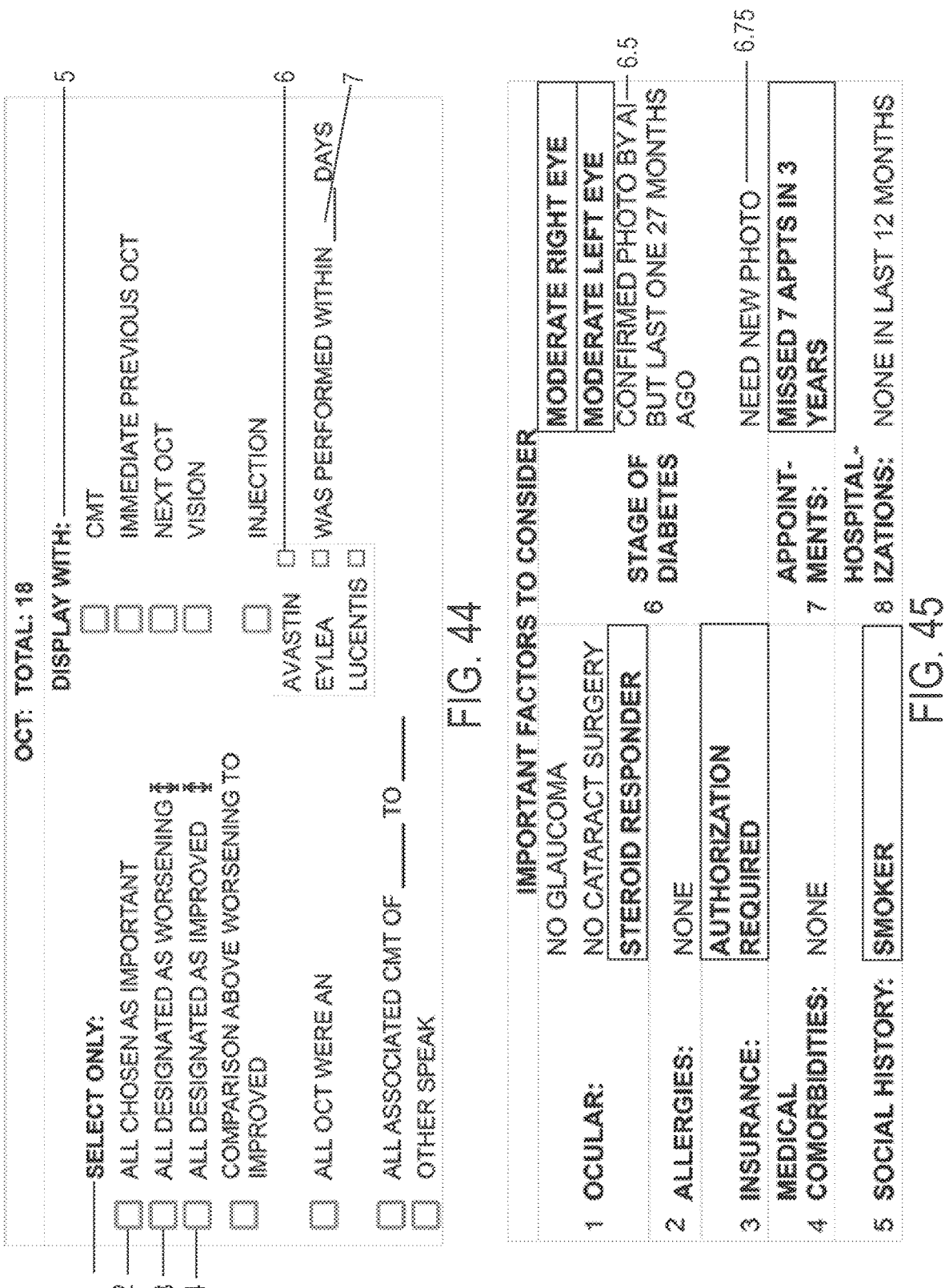
FIG. 44 illustrates predictive analytics in accordance with an embodiment of the present principles.
FIG. 45 illustrates predictive analytics in accordance with an embodiment of the present principles.

FIG. 46 illustrates predictive analytics in accordance with an embodiment of the present principles. In FIG. 45, the predicted analytics demonstrates to the doctor that the predicted outcome if the doctor chooses to save money and would treat the right eye on 4/21/2019 with Avastin instead of Eylea. In the embodiment of FIG. 46 CMT increases on 5/21/2019 to 350. By 6/21/2019, the CMT is now highlighted in color (e.g., yellow) because a threshold of worsening is predicted to be reached to an increase in CMT to 360 and the VA worsens to 20/70. In FIG. 46, in 3, the worst CMT was 350 and 360 is now augmented. The vision in 5 shows the worst it has been was 20/70 and now, with Avastin on Jun. 21, 2019, the vision has fallen to that poor level 20/70. When the patient comes in at the next visit on 7/21/2019, the prediction highlights the CMT for example in red because it is now significantly worse than even the worst it has ever been at 370 compared to 3 at 350 and the vision is 20/100 on 7/21/2019. Again, significantly worse than in 5. In FIG. 46, on 7/21/2019, with the vision the lowest ever and CMT also the worst, a mandatory switch to Eylea is suggested, because it has been determined from the data that continuing with Avastin would not be as effective. Therefore, in FIG. 45, displayed are the predicted results if Eylea is again started on 7/21/2019, and for the next four visits Eylea is repeated. As depicted in FIG. 45, by 11/11/2020 68, the patient's CMT is 280 at 69, which is returning to a more acceptable level, and the vision is predicted to substantially improve to 20/30, but still not the best it has been.

FIG. 44 and FIG. 45 depict a multiple panel display that can come up simultaneously with the displays in FIG. 42, FIG. 43, and FIG. 46 in accordance with an embodiment of the present principles. In some embodiments, generating a view of FIG. 47, FIG. 48, and FIG. 49 can include activating 118 in each of FIG. 42, FIG. 43, and FIG. 46. The reverse is also true of FIG. 47, FIG. 48, and FIG. 49 (described further below) by activating 136 either the display of FIG. 42, FIG. 43, or FIG. 46 can be generated or any other configured display can appear. Any number of panels displaying different data and correlating data can be generated on FIG. 47, FIG. 48, or FIG. 49 and in this whole life view, the panels can be moved around, and data can be zoomed into. However, utilizing 136 in FIG. 47, FIG. 48, and FIG. 49 enables a user to select what additional data to display.

In FIG. 47, 8 displays proposed dates of service in the future, 2 is a medication or a procedure panel, and 10 and 11 display two different color-coded medications, which shows how the patient responds to the treatment and can be compared over time. The effect of these different treatments can be measured in 3 of FIG. 47 where any diagnostic test or procedure can be followed and mapped out depending on what are the results. In FIG. 47, displayed is central macular thickness measured from 250 microns to 500 microns. In some embodiments and as depicted in FIG. 47, 280 can be highlighted or otherwise emphasized in a first color (e.g., green) at 3.5 and 475 microns can be highlighted in a second color (e.g., red) at 3.75 can be highlighted or otherwise emphasized as the best and worst CMT similar to the summary row described in 3 and 7 on FIG. 43 and FIG. 45.

In FIG. 47,4 depicts any clinical finding or symptom, illustratively a displayed vision, which is mapped from 20/30 to 20/400 and 5 can depict an age adjusted risk factor or adjusted expected results. In the embodiment of FIG. 47, patients can be shown how they compare to patients with similar demographics, conditions, and treatments. Visually, the doctor can see this as well as the patient, and it can help guide treatment. 24 of FIG. 47 shows how the patient is responding compared to patients shown in 25 with similar conditions and is age adjusted patients with similar issues, and how they would have responded under similar param-eters. In FIG. 47, 9 depicts an encounter, with cancelled or missed appointments. The user can now take into consider-ation if there is a change in the regular plan or resulting measurement that may occur because of a missed appoint-ment. The impact of the missed appointment can be directly visualized.

In FIGS. 47, 13, 15, and 16 are examples of suggestions made by embodiments of the present principles. FIG. 46 correlates to the findings seen in FIG. 42, for the left eye compared to FIG. 43 in the left eye. 18 of FIG. 47 shows the patient, who was injected with Eylea 10 on Sep. 25, 2018, and the CMT is 373 microns. This can be followed as Eylea injections occur, the CMT is mapped out. At 19 the CMT is shown to be 400 microns and is highlighted or otherwise emphasized in color (e.g., red). This can be set in many ways, but 400 microns is a worsening that can be pro-grammed to create an alert and be highlighted or otherwise emphasized when data represented by a number exceeds a certain threshold. It happens to be correlated by the sum-mary row in FIG. 43, at 7. As depicted in FIG. 47, the patient's vision is becoming the worst it has ever been. It can present a dramatic change between Mar. 7, 2019 to now, 408 microns. The CMT with 19. In some embodiments, this is where the decision tree can occur. Does the doctor follow 15, the application suggestion, or another option, 14? Note, a threshold line can be placed on any panel such as 3. If there is a number that a user or the tool feels an action is required if data crosses that threshold, then the user can see if the data is above or below that threshold line. In some embodiments, the user can drag the threshold line and set for an individual patient when actions should be taken.

In FIG. 46, at 21 an improving CMT using Lucentis is displayed in a first color (e.g., orange). 28 shows a continued improvement. In fact, it is highlighted or otherwise empha-sized in a second color (e.g., yellow) demonstrating that this patient has now returned to base-line. The CMT is the best it has ever been. In FIG. 46, at 27 it is depicted that the vision has also returned on Oct. 6, 2019 to the best that patient's vision has ever been. So, within each graph there can be great meaning. For instance, additional information about the vision can be obtained on 18. By utilizing 18 anywhere on any visit, the image or clinical data of any kind can appear, and information can be displayed showing the central macular thickness or clinical findings were derived or the actual diagnostic test itself can come up as seen on 35 and 36 of FIG. 48.

Figure 48:
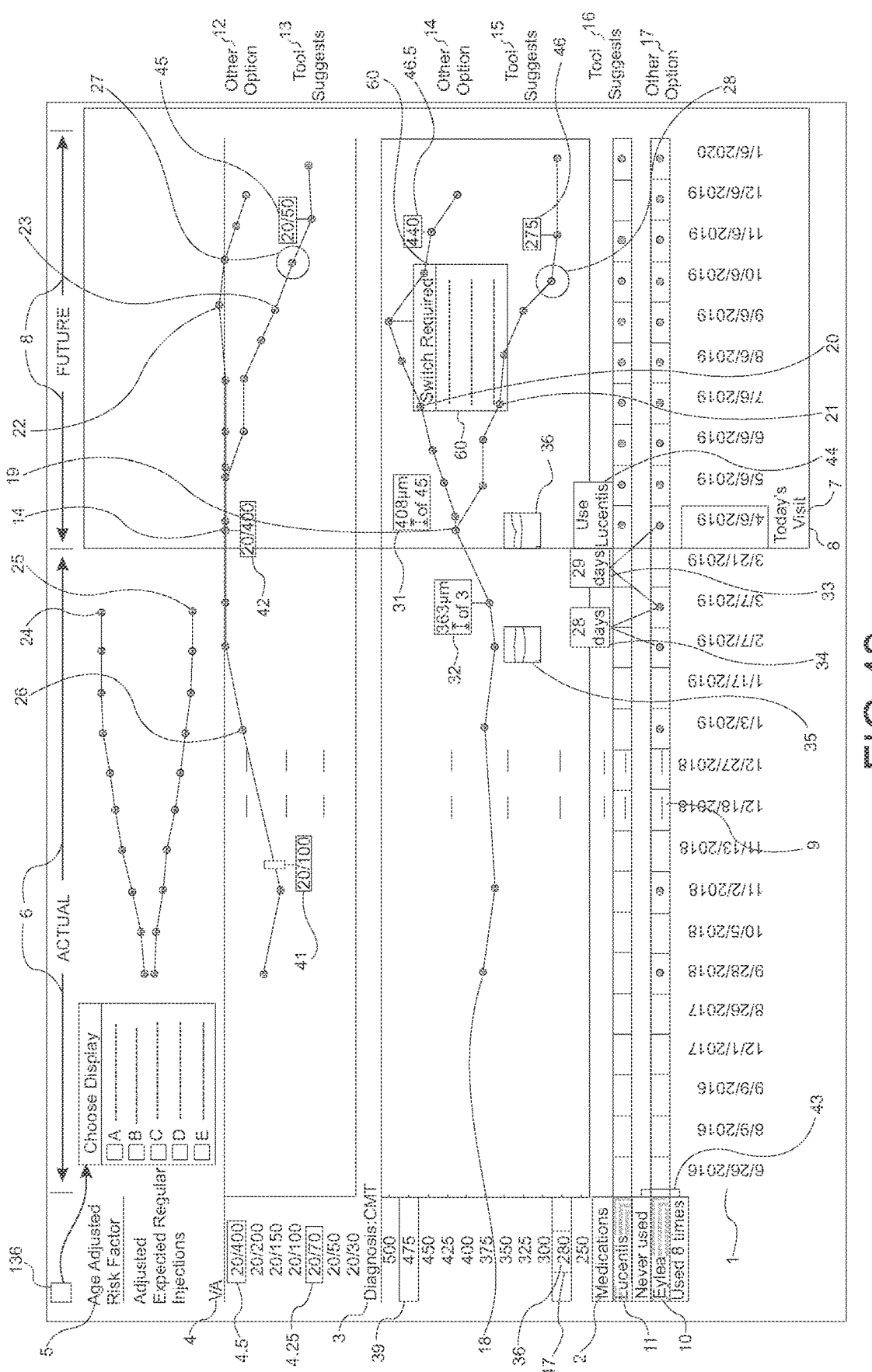
FIG. 48 illustrates predictive analytics in accordance with an embodiment of the present principles.

FIG. 48 depicts several elements suddenly popping up on the screen highlighted or otherwise emphasized by any method so the doctor can quickly understand the reasoning 31 shows that 19 was an increased thickening with a red arrow of 45 µm from the previous with it being 408 µm on 4/6/2019. simultaneously 32 shows the visit before was 363

µm and was a worsening with a red arrow of 3 microns from the previous OCT. That previous OCT is the one that chosen to display in a thumbnail on 35 and a thumbnail of the OCT which explain the changes seen on 19 and displayed with a thumbnail image of the OCT 36 showing the changes. These thumbnail images 35 and 36 are specifically chosen as the most important images for the doctor to consider. Each OCT image may have 19 slices but the one that's most important to compare is shown.

Figure 49:
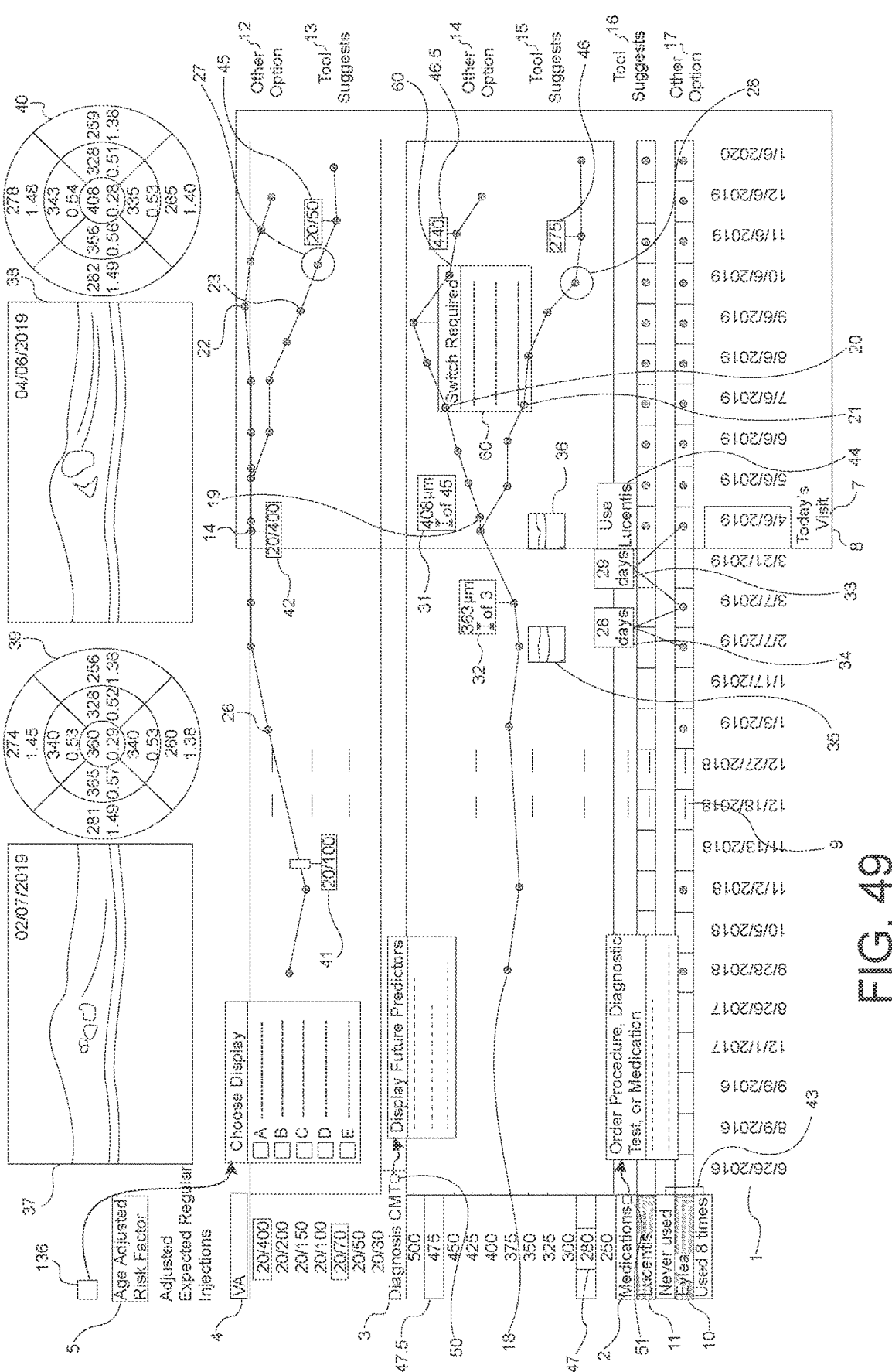
FIG. 49 illustrates predictive analytics in accordance with an embodiment of the present principles.
Figure 50A:
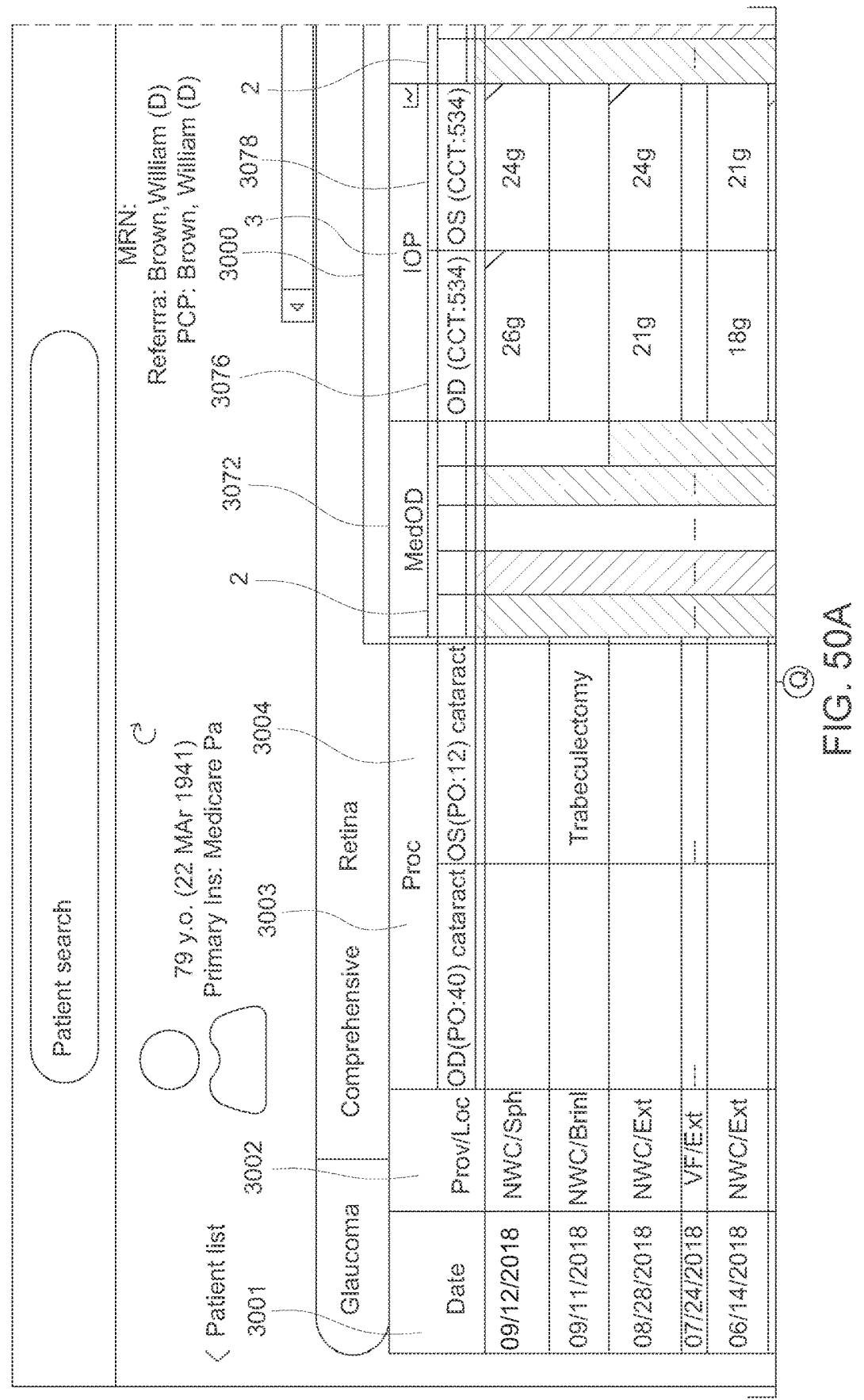
FIG. 50 depicts a first embodiment of a Medication Management chart that can be displayed in at least a portion of a medical records dashboard of the present principles in accordance with one embodiment.
Figure 50C:
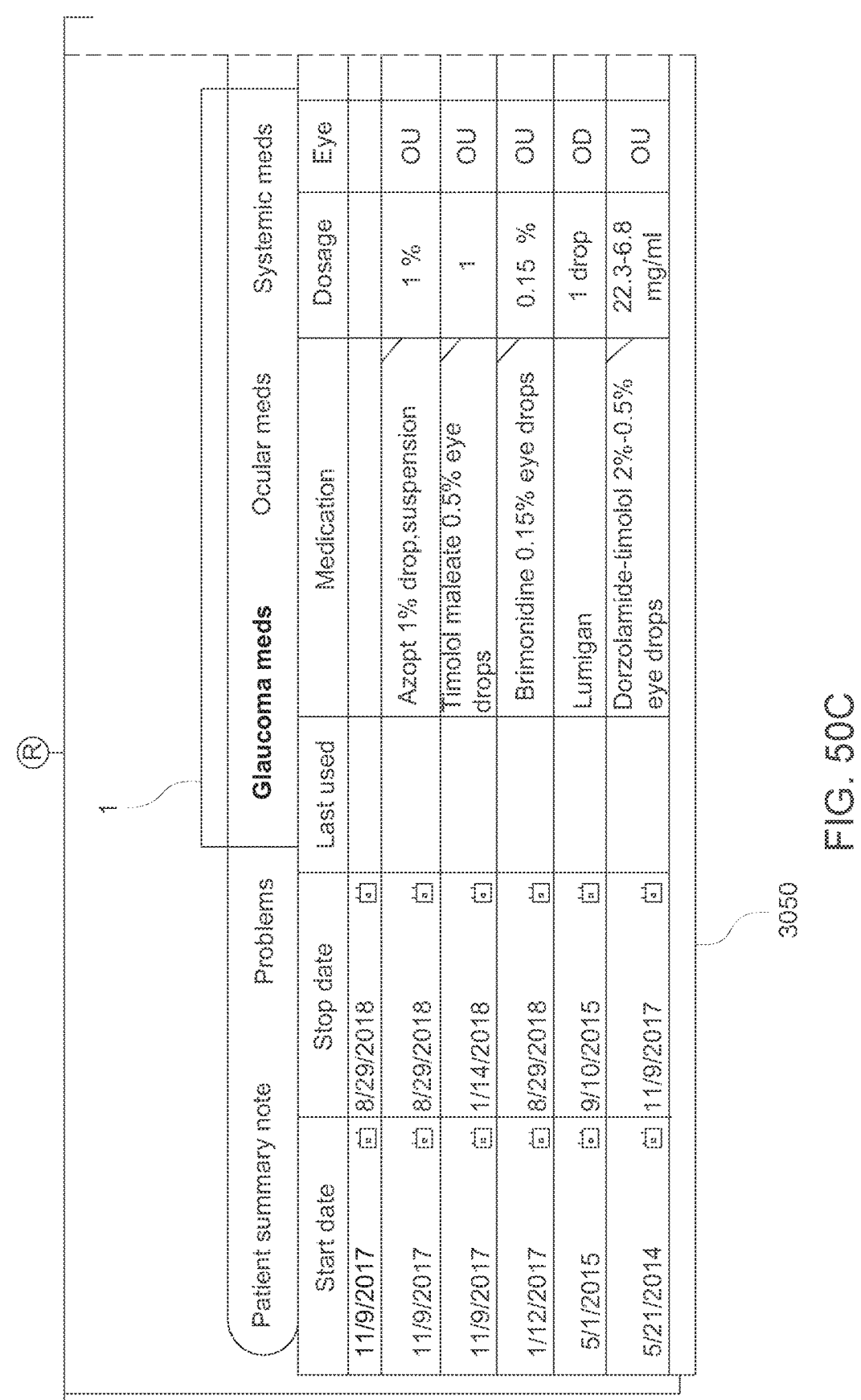
Figure 50D:
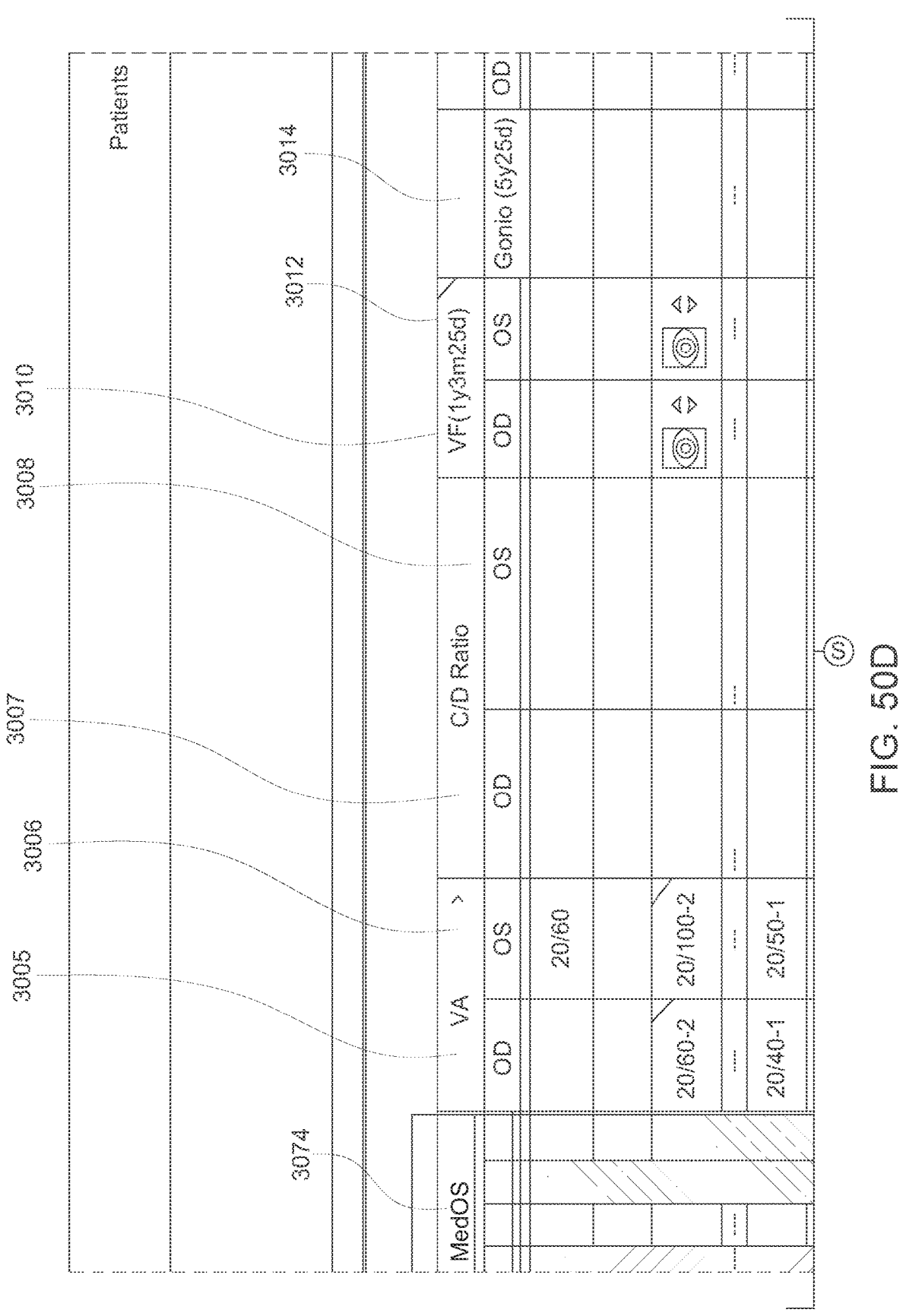
Figure 50F:
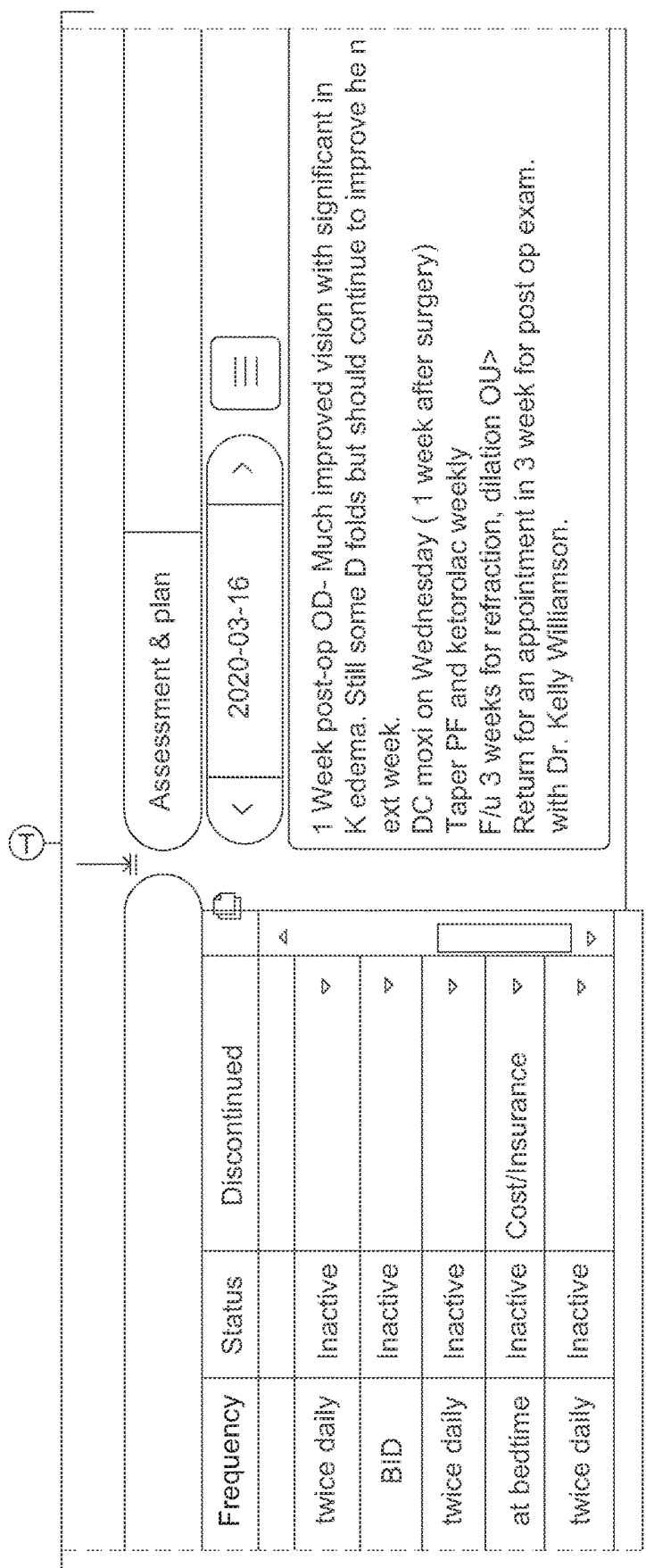
Figure 50G:
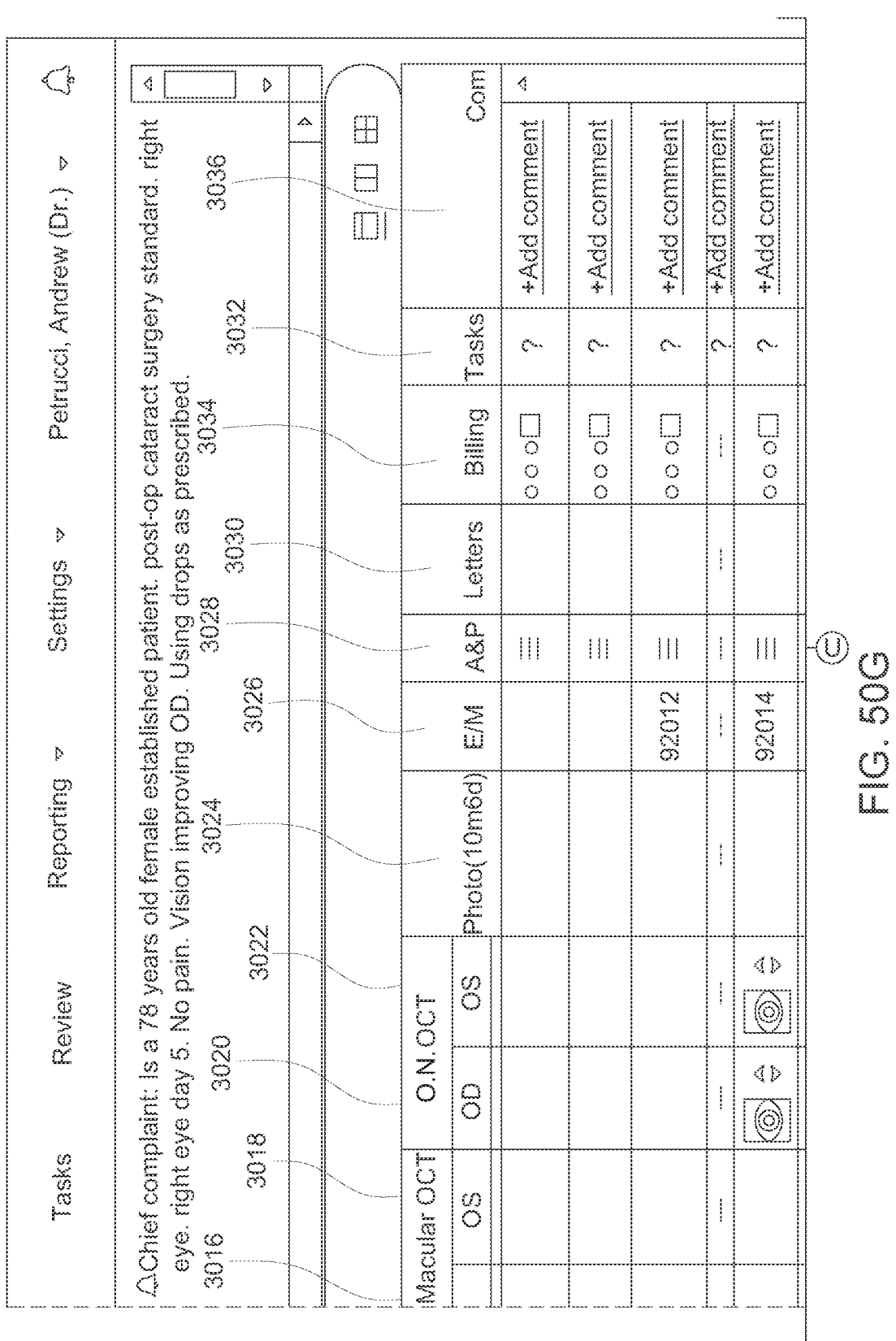
Figure 501:
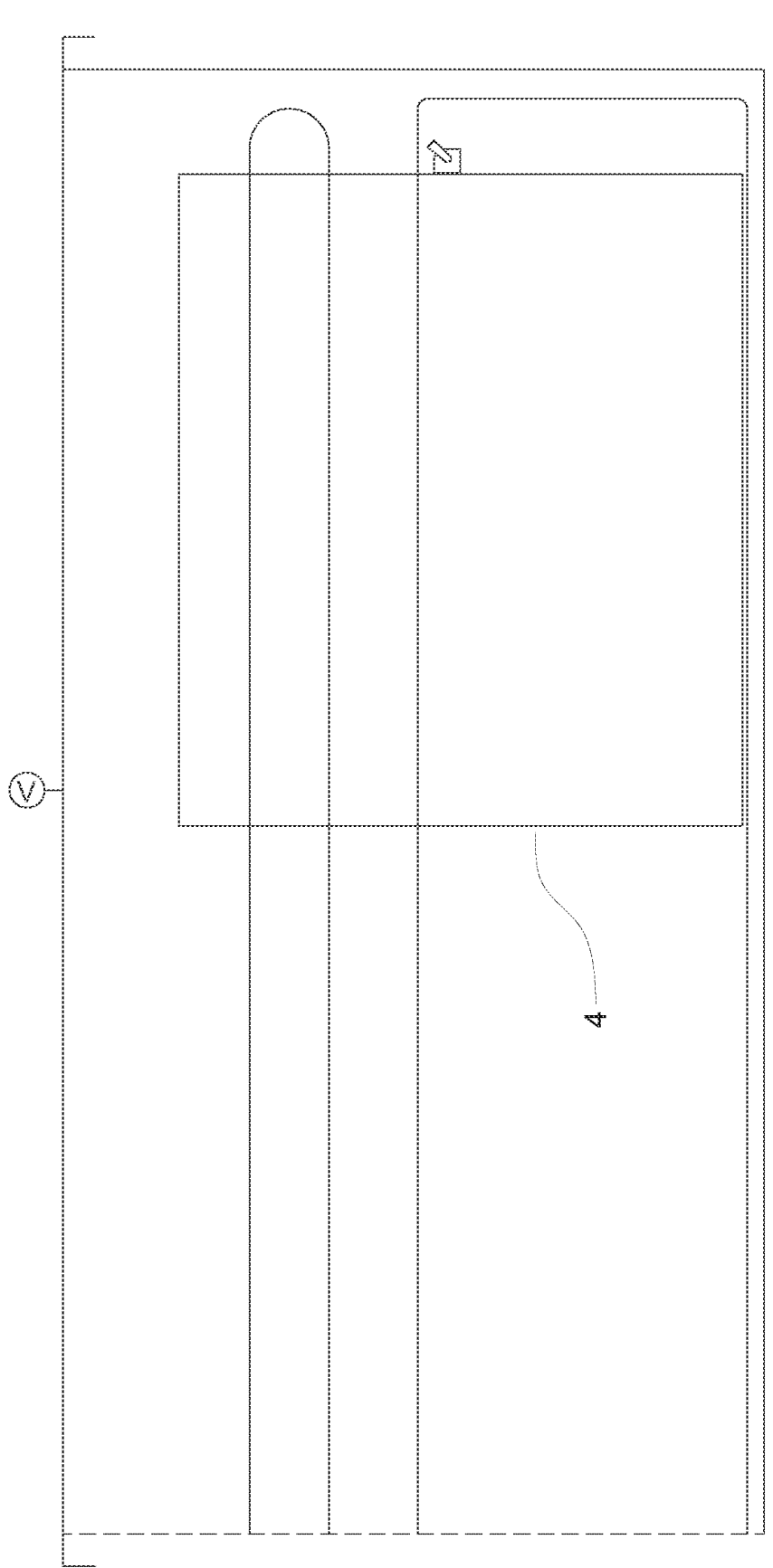

FIG. 49 shows the top panel number five collapsing to make room for the two images 35 and 36, so the doctor can see the enlargement of 35 in 37 shows Feb. 7, 2019° OCT 39 shows multiple measurements with the central measure-ment being the 360 µm that's most important. 39 shows the enlarged image from 4/6/2019 that was a thumbnail from 36 and again 40 shows the center of all of the different numbers being 408 µm which matches the 31. Now, the tool is able to show the exact images all in context with all other information so doctors can make a decision. Highlighted or otherwise emphasized in 43 is the fact that Eylea was used eight times in the past but Lucentis was never used. This supports the conclusion in 44 where the tool is recommend-ing using Lucentis. Now the tool goes one step further and displays the past compared to the future. 41 shows the vision is 20/100 on Nov. 2, 2018 and it shows an improvement at 20/50 in 45 if the switch is accepted by the doctor to Lucentis. The tool displays 46 and 46.5 comparing the result of predicted results using the different medicines 10 or 11 shown on the line graph of option (Eylea) 10 results in a CMT of 440 µm, 46.5 compared to 46 when the tools suggestion of Lucentis performed and improvement to 275 µm occurs. However, should the user choose not to follow the clinical decision support of the tool in 44 and chooses instead to continue to use Eylea, then when a threshold is reached is alerted and messages can be displayed as seen in 60 in FIG. 47-FIG. 49. Here the tool has been programmed as described in FIG. 44 and FIG. 45 to make the recom-mendation seen in 60, which states switch from current treatment mandated. 22 can display the clinical data why the invention has suggested this CDS recommendation. In one embodiment, the tool can display a predictive image in 38 that shows the tremendous worsening. The tool connects to or in one embodiment has a library of images of the patient's previous images or an archive of images that could represent what the system predicts what the image would look like if a different action is not taken.

Figure 51:
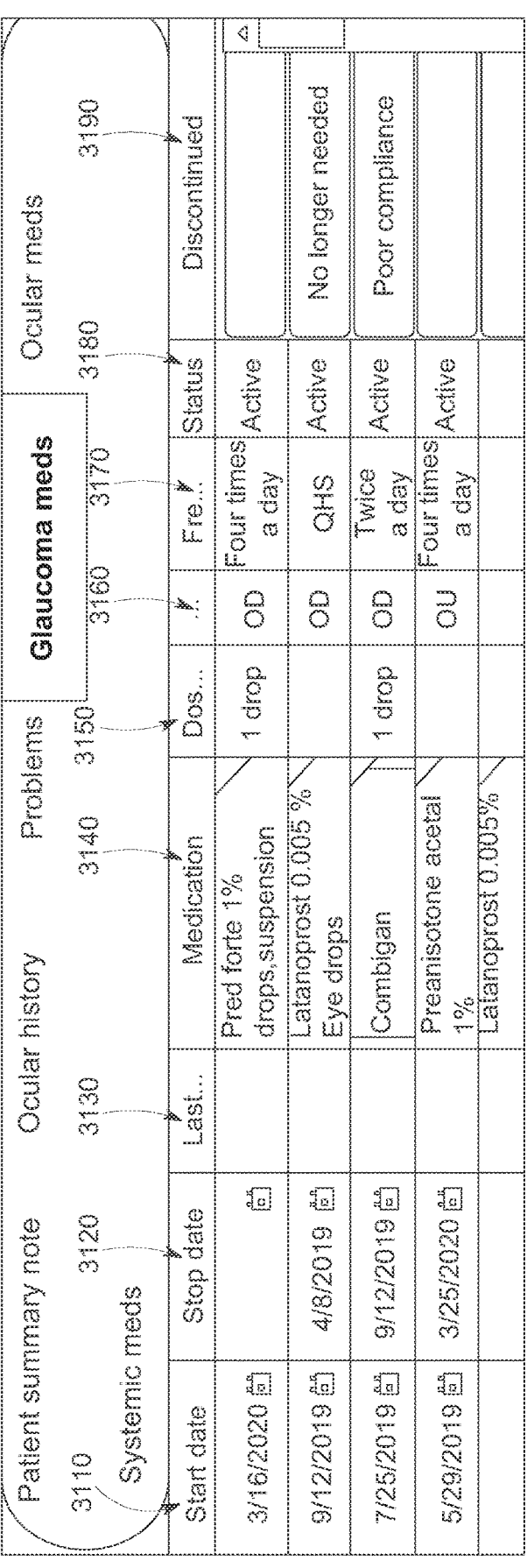
FIG. 51 depicts an embodiment of the control panel #1 of the Medication Management chart of FIG. 50 in accordance with an embodiment of the present principles.

In FIGS. 49, 50 and 51 enable a mechanism for a way to bring up onto the single view, a panel that centrals a way to display future predictions for procedures, medications or treatments of any kind as described and shown in 50 of FIG. 43, and the result through predictive analytics, AI or other means is displayed in 8 of FIG. 48-FIG. 49. An ordering panel to place orders and confirm orders as described in 90 of FIG. 43 can be similarly on the screen and an example of such a method is by utilizing 50 or 51 of FIG. 49. An ordering panel such as shown on 90, FIG. 43 can also come up on FIG. 49 display so while displaying everything that is relevant, doctors can now confirm their orders seeing the past as well as today's visit and the projected future. These results between two different medicines can also be dis-played to the patient to enhance understanding.

It is critical for a medical care provider to know what medications a patient has ever taken or is currently taking, what the frequency is, why the medication was taken or discontinued and reasons for switching to another medica-tion. There is currently no medication management tool that visually correlates the clinical parameters or disease state findings that the medication is prescribed to have an impact on. A Data Command Center of the present principles via at least one of a medical records dashboard and a Medications Management chart or tool in accordance with the present principles enables a user to correlate frequency, amount and types of medications taken to enable the user to visualize how that medication affects the parameters reviewing modulation such as blood pressure, eye pressure, weight, heart rate, etc. and corresponding it to when the medications were taken to see if there is a cause and effect. There is no system that can also correlate and display on a view surgical intervention, an injection or any other intervention and see how these additional factors correlate with timing of medication taken and how all this impacts clinical finding, measurements, disease progression and symptoms. A Data Command Center of the present principles enables a user to visually correlate diagnostic tests and images that may show how all these treatment modalities result in changes or lack thereof on lab results, imaging, etc. For example, and as enabled by embodiments of the present principles, if a patient is being treated for cancer and chemotherapeutic medication can be seen with direct access on one screen with x-rays taken over time showing changes in size of a tumor or mass along with the labs or clinical symptom changes all in context of when surgical or radiation therapy intervention was performed, enables medical care providers to efficiently and accurately make medical decisions.

Embodiments of a Data Command Center of the present principles can also be linked to a Pharmaceutical system or other provider of prescribed medication (i.e., E-prescribe or a similar system) such that a medical care provider is enabled to accurately track when medication was actually received by a patient. It can be very difficult if not impossible with current systems for a medical care provider to know when a medication was actually received by a patient. That is, medical care providers often rely on scribes to write prescriptions and when patients call to refill the medication, often it is not the medical care provider who prescribes the refills of medication but an assistant who does so. Even further, just because a medical care provider orders a drug for a patient that does not mean the patient actually went and got it filled or that the medication was taken as prescribed. To further complicate matter, patients can be given different medication than prescribed by the medical care provider because a generic drug instead of a brand drug could have been given.

Embodiments of a Data Command Center of the present principles can also be linked to home monitoring devices or system for being able to more accurately determine when medication was actually taken by a patient. That is, just because medications are prescribed and received by a patient does not mean that the patient has started taking the medication or even taking it as prescribed. A patient may also misunderstand what the doctor actually wants the patient to do and is actually taking the medication incorrectly. Embodiments of a Data Command Center via, for example, a medical records dashboard of the present principles enable medical care providers to more accurately track medications and how they are being taken by patients, which improves quality of care. More specifically, in accordance with the present principles, a medical care provider is enabled to visualize the medications, the start and stop dates, reasons for discontinuation, and is enabled to manage and change the display based on reality they confirm with the patient at point of care and via the pharmaceutical and home monitoring devices that can be linked into the Data Command Center of the present principles.

As described above, embodiments of a Data Command Center via, for example, at least one of a medical records dashboard and a Medication Management chart/tool of the present principles enables medical care providers to more accurately track medications and dates associated with the medications, for example in rows and columns. In some embodiments a Data Command Center via, for example, at least one of a medical records dashboard and a Medication Management chart/tool of the present principles can display tracked medication information in graph form. In some embodiments, each medication or class of medications associated with a patient can be represented by a bar graph or a linear graph or other visual method or means that in either the vertical direction or in a horizontal direction the doctor can visualize the actual start and stop dates of all relevant medications for a patient, which can all be seen simultaneously with any other relevant data that the medications can impact. More specifically, in some embodiments, a Data Command Center in accordance with the present principles, such as the Data Command center 001 of FIG. 1, can further include the ability to intelligently display medications in context (referred to by the inventors in some embodiments as Medication Management), by grouping, categorizing, expanding, contracting, displaying, hiding, and highlighting or flagging medications to visually present medications to a user of the Data Command Center (e.g., medical care provider) in a medical records dashboard in a manner that makes such medication more easily identifiable by the user. In one embodiment, Medication Management exists as a series of intelligent vertical columns representing individual medications, classes of medications, categories of medications, or logical groupings of medications, differentiating medications by color or combinations of colors, symbols, and/or text, graphing start and stop dates and times or individual doses correlated to relevant values and relevant events. In accordance with the present principles, graphical differentiation between medications can consist of individual colors for individual medications, combinations of colors for medications including more than one component, or complex graphical representations. In some embodiments, color standards, such as defined by the American Academy of Ophthalmology, can be used for color coding the medications and/or custom colors can be used. For example, in ophthalmology and with respect to eye care, medications have been assigned in the industry to have a certain color on the eye drop bottle or cap. In some embodiments, these colors can be displayed allowing recognition by the user of the class of medication. For instance, yellow is a beta blocker one of which is Timoptic. In accordance with the present principles, medical care providers who have memorized the color caps can instantly recognize, by viewing a medical records dashboard of the present principles, the class of medication without even seeing the name.

For example, FIG. 50 depicts a first embodiment of a Medication Management chart 3000 that can be displayed in at least a portion of a medical records dashboard of the present principles in accordance with one embodiment. The medical records dashboard of FIG. 50 illustratively comprises a patients Glaucoma chart including a date column 3001, a Provider/Location column 3000, a Procedures column for a right eye 3003 and for a left eye 3004, the Medications Management Chart 3000, a VA column for the right eye 3005 and for the left eye 3006, a C/D Ratio column for the right eye 3007 and for the left eye 3008, a VF column for the right eye 3010 and for the left eye 3012 including a Gonio column 3014, a Macular OCT column for the right eye 3016 and for the left eye 3018, an O.N. OCT column for the right eye 3020 and for the left eye 3022, a Photo column 3024, an E/M column 3026, an A&P column 3028, a Letters column 3030, a Tasks column 3032, a Billing column 3034, and a Comments column 3036 all arranged to depict information in rows of the medical records dashboard of FIG. 50 by date.

The Medications Management Chart 3000 of FIG. 50 includes a Medication column for the right eye 3072 and the left eye 3074, illustratively on either side of an IOP column for a right eye 3076 and the left eye 3078. all arranged to depict information in rows of the medical records dashboard by date. In the Medications Management Chart 300 of FIG. 50, the Medication column for the right eye 3072 and the left eye 3074 are illustratively separated into sections for separately displaying bars for each of a plurality of available medications. The embodiment of FIG. 50 depicts an example of a medical records dashboard including medication management in the field of eye care; however, embodiments of the present principles can be applied to substantially any medical specialty and the like.

In the embodiment of FIG. 50, the pressure of each eye of a patient is measured from 0 to 50. In addition, each of the medications taken associated with each respective eye of the patient are depicted in bar graph form and distinguished by color according to the dates taken. In the embodiment of the medical records dashboard of FIG. 50, the color bars representing the medications prescribed or administered to the patient are displayed adjacent to respective pressure data points for each eye according to a date administered to allow the user to directly correlate the effect of the medication on a respective eye. In the embodiment of FIG. 50, section #2 depicts the medication bar graphs, section #3 depicts clinical measurements of eye pressures that are affected by the medications, and window #4 depicts an ordering panel enabling the ordering of medication through, for example, E-prescribe, DoctorFirst, or other methods. In the embodiment of FIG. 50, window #1 depicts an embodiment and location of a control panel 3050 of the medical records dashboard, which identifies which medications are represented by which colors and identified a dosage, a frequency and a status of the medications being administered to a patient.

For example, FIG. 51 depicts an embodiment of the control panel #1 of the Medication Management chart of FIG. 50 in accordance with an embodiment of the present principles. The control panel of FIG. 51 illustratively includes a Start Date Column 3110 depicting a start date of a medication in a respective row, a Stop Date Column 3120 depicting a stop date (if any) of the medication in the respective row, a Last Column 3130 depicting a date when the medication in the respective row was last taken, a Medications Column 3140 depicting medications taken by the patient, a Dosage Column 3150 depicting a dosage amount of the medication taken by the patient, a Location Column 3160 indicating in what part of the patient's body the medication was applied, a Frequency Column 3170 indicating how often the medication is being applied, a Status Column 3180 depicting if the medications are or are not currently being applied, and a Discontinued Column 3190 depicting a reason for discontinuance of the medication (if a reasons exists). As depicted in FIG. 51, in accordance with some embodiments of the present principles, the Medications Column 3140 can be color coded such that each medication comprises a respective color.

Figure 52A:
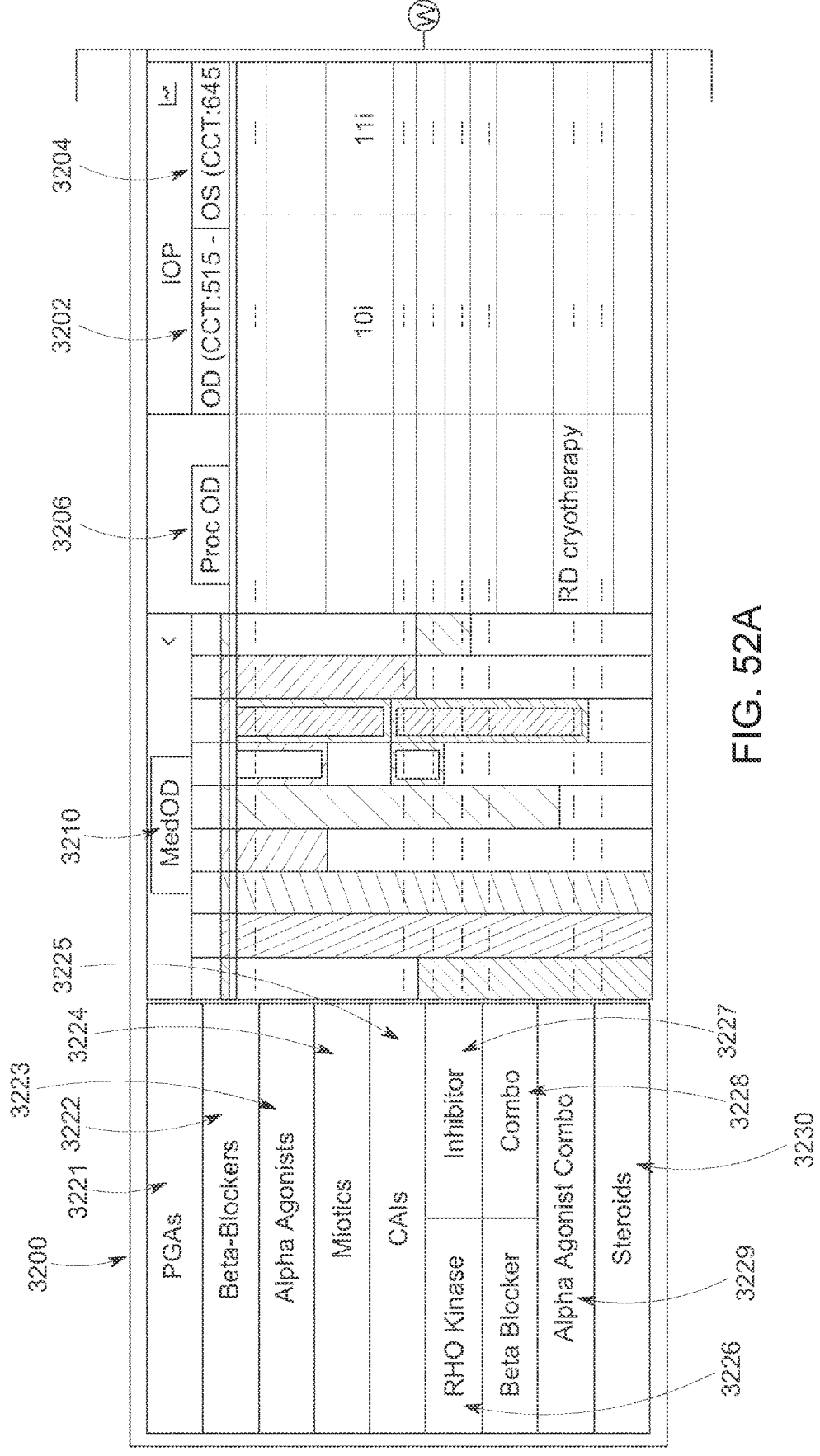
FIG. 52 depicts a Medication Management Chart that can be displayed as part of a medical records dashboard or as a stand-alone Medication Management tool in accordance with an embodiment of the present principles.
Figure 52B:
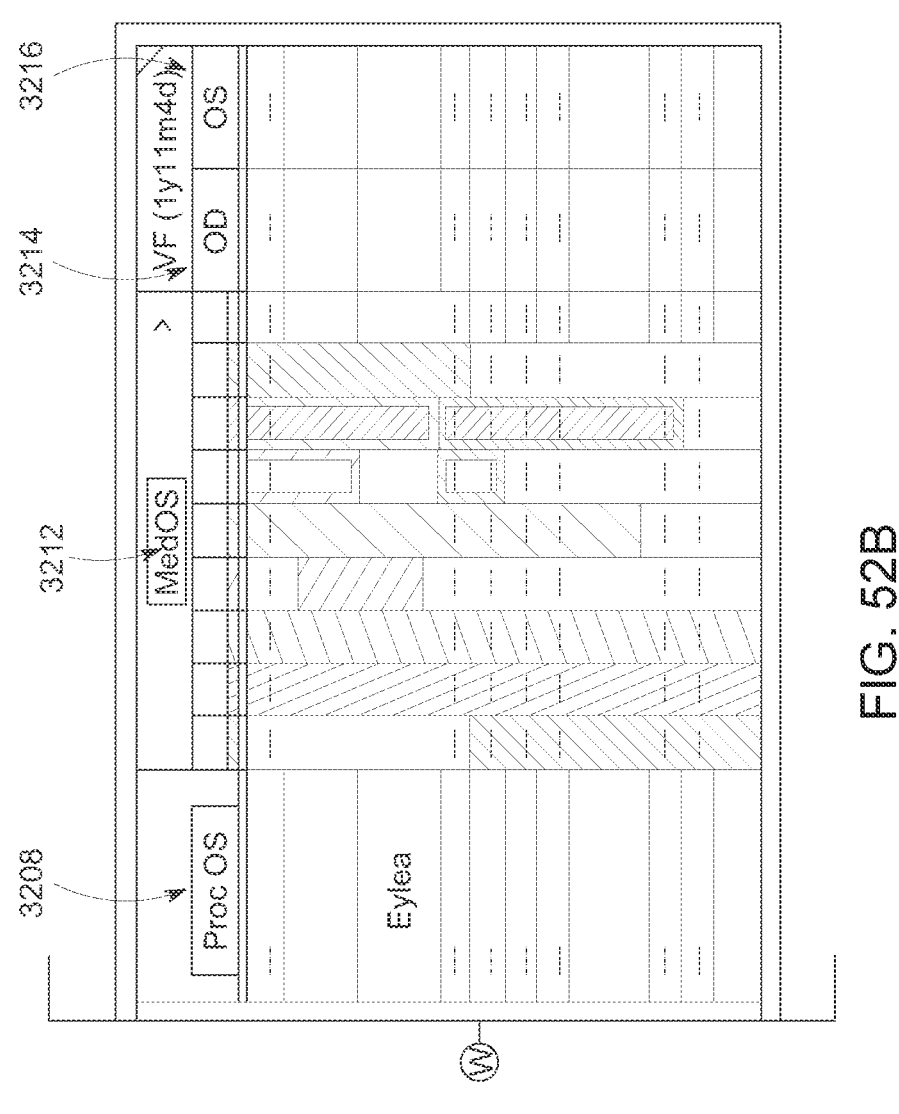

For example, FIG. 52 depicts a Medication Management Chart 3200 that can be displayed as part of a medical records dashboard or as a stand-alone Medication Management tool in accordance with an embodiment of the present principles. In the embodiment of FIG. 52, the Medication Management Chart 3200 includes a center section including respective columns depicting an intraocular pressure (IOP) for a patient's right eye 3202 and an intraocular pressure (IOP) for the patient's left eye 3204 on various different dates. In FIG. 52, next to the respective pressure columns for the patient's right eye 3202 and the patient's left eye are respective columns depicting respective procedures performed on the patient's right eye 3206 and the patient's left eye 3208 on the different dates. The Medication Management Chart 3200 of FIG. 52 further includes respective columns depicting respective medications prescribed or administered to the patient right eye 3210 and the patient's left eye 3212 on the different dates. The Medication Management Chart 3200 of FIG. 52 further includes a visual field (VF) column for the right eye 3214 and a VF column for the left eye 3216.

The Medication Management Chart 3200 of FIG. 52 further illustratively includes a color-coded key identifying medications present in the Medication Management Chart 3200. In the embodiment of FIG. 52, medications prescribed or administered to the patient's eyes include PGAs 3221, Beta-Blockers 3222, Alpha Agonists 3223, Miotics 3224, CAIs 3225, Rho Kinase 3226 and Inhibitor 3227, Beha-Blocker Combo 3228, Alpha Agonist Combo 3229, and Steroids 3230. As depicted in the Medication Management Chart 3200 of FIG. 52, in some embodiments, combinations of drugs can exist and can be depicted as a combination of the colors of the drugs that make-up the drug combination. Although in the embodiment of FIG. 52, the Medication Management Chart 3200 illustratively comprises a color-coded key for identifying the medications, in other embodiments of a Medication Management Chart of the present principles, a color-coded key does not have to be included. In addition, although in the embodiment of the present principles depicted in FIG. 52, the Medication Management Chart 3200 depicts a combination of drugs as a bar having one color representing a first drug and a box around the bar in a second color representing a second drug of the combination, in some embodiments a drug combination can be represented using a cross-hatch method, in which stripes in a bar are a first color representing a first drug and the rest of the bar is as second color representing the second drug of the combination. In accordance with the present principles, a drug combination can include more than two drugs and drugs and drug combinations can be represented by assigning a color to each drug and if a medication has more than one drug in it then all colors can be displayed by any means in, on or around the bar representing that medication.

FIG. 53A-FIG. 53I depict embodiments of a Medication Management Chart having different features in accordance with the present principles and will be described with reference to the medical records dashboard and the Medications Management Chart 3000 of FIG. 50. FIG. 53A depicts an example of how the Control Panel #1 of FIG. 50 can be implemented by a user to identify start and stop dates for the various medications taken by a user in accordance with an embodiment of the present principles. FIG. 53A further depicts how section 2 of the Control Panel #1 can be implemented to identify and assign colors for the medications and section 3 of the Control Panel #1 can be implemented to note reasons for a patient discontinuing a medication.

Figure 53B4:
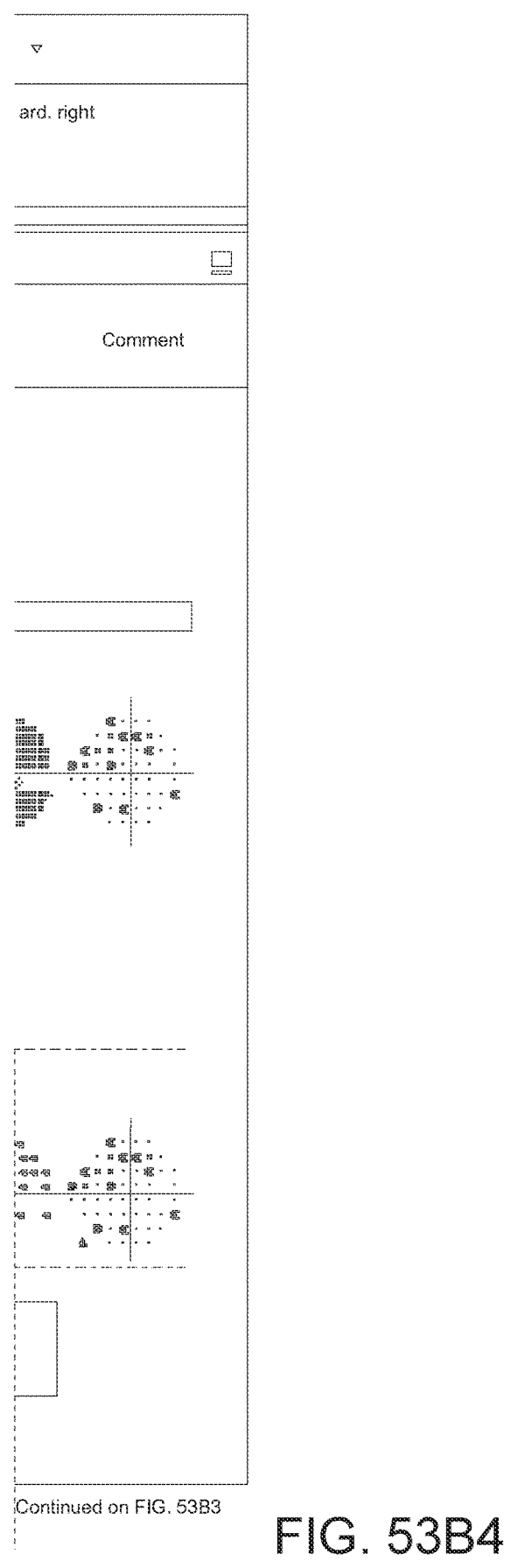

FIG. 53B depicts an embodiment of a Medication Management Chart in which icons can be activated to bring up additional information in accordance with an embodiment of the present principles. In FIG. 53B, element 1 depicts how by clicking on a column heading, information available under the column heading, such as a note inserted by a user, can be accessed, for example, in a pop-up window, element 3. In FIG. 53B, a note regarding a treatment plan for the patient was accessed via a pop-up window (element 3) when an icon under the column heading was activated. As depicted in the embodiment of FIG. 53B, the column heading can contain an icon indicating that a note exists. Element 2 of FIG. 53B depicts an icon in the OS column of the VF column that when activated can cause a display of a pop-up window (element 4), which displays a visual field image performed on the patient's left eye. Element 5 of FIG. 53B depicts how all of the medications being taken by a patient can be simultaneously displayed using bar graphs and color coding of the present principles.

FIG. 53C depicts another embodiment of a Medication Management Chart in which icons can be activated to bring up additional information in accordance with another embodiment of the present principles. In FIG. 53C, element 1 depicts how activating an icon in, for example, a column heading of the Medications Management chart can cause a display of a pop-up window (element 2), which in some embodiments can display another embodiment of a Medication Management chart which displays mediations using horizontal lines and correlates patient well-being data/information (i.e., intraocular pressure) with events that occurred to the patient that would affect the patient's well-being (i.e., the application of medications, surgery, etc.) and with a medication timeline (described in greater detail with respect to FIG. 54). As depicted in FIG. 53C, using such Medication Management charts of the present principles, a user can make a reasoned estimation of what caused a decline or an improvement in the patient's well-being. Element 4 of FIG. 53C depicts that an SILT was performed and element 5 depicts how a small drop in the IOP graph results. In FIG. 53C, element 6 depicts that a trabeculectomy surgery was performed and element 7 depicts how a large drop in IOP pressure results. From such results, a user can conclude that the surgery was successful since the goal of a trabeculectomy is to reduce pressure. Element 8 of FIG. 53C depicts a medication timeline) and element 9 depicts that the medications were stopped after surgery. As further depicted in FIG. 53C, a user can select to display information for one eye at a time as depicted in element 10 or for both eyes simultaneously. Element 11 of FIG. 53C depicts an alert to remind user to perform a visual field (VF).

FIG. 53D depicts an embodiment of the Medication Management Chart in which intraocular pressure, in addition to being listed by number, is also displayed as a vertical line graph, for example as depicted by element 1 in accordance with an embodiment of the present principles. In the embodiment of FIG. 53D, element 2 displays bar graphs of the medications being taken by the patient. element 3 of FIG. 53D depicts values of intraocular pressures of a right eye and element 4 displays the corresponding vertical line graphs of the values pointed out by element 3. In FIG. 53D, element 5 depicts how specific colors can correspond to an assigned medication, in this case orange.

FIG. 53E depicts an embodiment of the Medication Management Chart of FIG. 53D in which the control panel can be used to input a reason that a medication has been started or stopped in accordance with an embodiment of the present principles. In the embodiment of FIG. 53E, a drop down menu 33E1 can be used to enable a user to select a reason that a medication has been started or stopped.

FIG. 53F depicts an embodiment of the Medication Management Chart of FIG. 53D in which the correct start and stop dates for a medication in accordance with an embodiment of the present principles. The Medication Management Chart may have one or multiple panels, for example, 3314, 3317, 3320 which may be configured in various ways to display information and/or to accept input from the physician. In one concept of the Medication Management Chart, the Dynamic Health Records (DHP) system displays the medications prescribed to the patient. The start and stop data may be chosen manually by the physician or the DHR system may be able to parse the patient's prior records to obtain this data. A calendar tool such as illustrated as aspect 3340, may be provided by the DHR system as part of the Medication Management Chart to facilitate the manual entry of the dates. In another concept, each medication may be coded in or tagged in some manner such that a visual indication of the medication is provided. As a non-limiting example, each medication may be color coded. The tagging or the coding may be chosen by the physician. As a non-limiting example, the physician may choose different colors or other emphasis such as cross hatching for each medication. Further, the DHR system may also provide the capability to tag or color code different medications with the same tag or color. As an example, different medications belonging to the same type or class or family of medication may be color coded or tagged similarly. The color coding or tagging in some manner medications 3306 and 3310, provides for another concept. In this concept, similarly tagged or color-coded medication may be displayed and correlated along with diagnostic test 3317, clinical exam measurements 3304, 3308 and or any medical services including surgeries and procedures 3311. As a non-limiting example of correlating medications with one of the items mentioned, clinical measurements, the pressure in each eye may be displayed alongside the medication that was prescribed to that eye as a function of the date when the eye pressure was taken. This is illustrated for example by 3308 displaying the number. The numbers can also be converted into a line graph illustrating the intraocular pressure 3305 and 3309 also displayed alongside the medications that were given to the patient 3306 and 3310 as specifically shown by 3374 and 3370. For this part of the display, each type of medication that was similarly tagged or color coded is displayed in its own column with the start stop dates. A display such as this provides a rapid understanding of the effect of each medication on physiologic parameters as measured by a diagnostic test. For instance, 3366 can display a threshold or target line and the pressure can be seen to be higher 3369 or lower 3371 than the threshold and that can be directly visualized alongside the medications taken in 3310, allowing a user to formulate conclusions about the effectiveness of treatment. The color coding or tagging provides for yet another concept. In this concept because the duration of the medication is visually depicted with the length of the color-coded bars in panels 3306 and 3310, errors in medication orders-can be visually detected. As an example, bar graph 3374 can be seen starting with "today's visit" and can be seen extended through the future or next visit 3362 and 3362 can be expanded, for instance, in height to represent a specific time period. The actual length of time in, for instance, days, weeks, or months can be displayed in 3362. Errors in medication duration may be rapidly spotted. As an example, if the medication is supposed to be prescribed for 10 days but the order was entered incorrectly for 10 months, the length of the graph depicting the start and stop date of this medication will be unexpectedly long. Such errors can this be corrected before further processing. To facilitate the entry of the start and stop dates of any medication, the DHR system in addition to mechanism described in 3340, the dates can be set by the user clicking on the panels 3306 or 3309 and medication bar graphs dragged and anywhere along the column by clicking in different cells the medication can be stopped and started for as many times as needed. With this capability, any medication can be started and stopped multiple times to reflect accurately what may have happened in the past and display what the doctor is ordering or prescribing for medications today or in the future. In another concept, the DHR system allows the physician to insert an indicator for the target value of the physiologic parameter. In a non-limiting example, the physician may insert a line that indicates a target pressure in the panel that shows the intraocular pressure. This is illustrated by 3366. The measured pressure may be rapidly compared with the target pressure and conclusions about if the medication or medications is/are working as expected may be intuitively drawn. In a variation of this concept, the DHR system may allow one or multiple indicators to be inserted. In addition, the DHR system may allow the physician to choose the physiologic parameter to be displayed alongside the medications. For instance, by clicking 3315 a drop-down menu displaying a range 3368 can be chosen to set 3366 for a specific target value. 3366 can also in one embodiment be dragged along 3368 and set at the number that the user desires for a particular patient or group of patients. In another variation, multiple different physiologic or other parameters may be selected and displayed alongside each other In a non-limiting example, the blood pressure and the intraocular pressure may be displayed along with the medications the patient takes. The target value indicator leads to another variation of the concept. Here when the physiologic parameter exceeds the threshold value, then the DHR system may trigger one or multiple actions such as but not limited to creating and setting an alert, for instance, as displayed in 3370. In addition, in some embodiments, if a parameter exceeds the threshold value set, for instance, in 3366 a task, message, or alert can be sent to the physician or the care team, displaying a warning message on the screen, automatically scheduling further diagnostic tests, appointments, etc. The behavior when the physiologic or any measured parameter exceeds a threshold value or more generally if the parameter falls outside a preset range this may be programmed or determined by the rule's engine. In another concept, the Medication Management Chart may include a medication ordering panel 3350. In this panel, the physician may order one or multiple medications associated with current visit between the patient and the doctor. The medications may be tagged or color coded as described previously. In addition, the DHR system may also place one or multiple medication order for the future starting and stopping at specific dates. The display of the past, current and future medication orders may be displayed in the medication display panel 3320. This allows the physician to rapidly confirm the current and future orders based on the color coding or tagging. It is to be noted that for the future orders the physiologic parameters will not be shown. One other unique aspect of the system, allows a user to intermingle certain drugs that have similar actions but different active ingredients to even same active ingredients (generic) but different names given to them by drug companies (Brands). Patient's with complex multiple conditions and disease states may have so many different symptoms, and many dozens of drugs over their lifetime or even over a few years, it becomes virtually impossible for any one Doctor to keep track of them all, know when they were taken and correlate the drug with the problem the patient is having. Due to the extent of the number of drugs and symptoms and conditions, the system allows the doctor the option to group medications visually that normally would not be grouped together but if they have a similar action or are treating a certain condition, then perhaps in some cases groupings that the pharmaceutical world might not be grouped together either the system or the user could override the normal grouping to allow for proper decision making and following clinical or diagnostic measurements or symptoms to see how the medications impact those data elements the medications are being given for. To save space the medications can be grouped in ways not normally grouped but at any time the system allows for the Doctors to decouple the medications. Also, the specific medication and its normal active agent/class can be levered over or permanently seen on the bar graph even if it shares the same bar graph or column of medications not normally grouped together. To enhance understanding as a non-limiting example, if a patient has heart disease, and eye disease but also developed cancer and has pain, certain medications need to be visualized specifically within its normal active agent classification such as the agents treating the cancer, the heart disease and agents preventing blindness. However, to save room, since many agents can be given to control pain, in one display of the system all pain medicines can share a similar color or column just so visually the Doctor can differentiate all the medicines and the reasons for treatment. Pain medicines can include different brands such as Motrin, Al3eve, Advil with similar active agents. Then there are pain medications such as aspirin, Tylenol, codeine, morphine that all reduce pain but have very different active agents. To save space all could be highlighted or otherwise emphasized similarly and share a certain space on the system to allow other medications treating other disease states to be seen simultaneously when the doctor wants to see the global birds eye picture of the patient. Knowing wheat pain medications were taken when is critical and can be de3coupled when zoomed in and can be listed when desired by the user. No system prior to this allows the user to customize for the patient the presentation and allow true stop and start dates and actual usage more than one time but as many times as the medication may have been started or stopped. In one embodiment the system constantly monitors or connects to outside software E-RX systems and if there is cross reaction of the medications this is also displayed and warned to the Dr. visually showing the mismatch or if they order connected to the system and medications in the future that are being ordered have any issue the Doctor sees the order they are trying to enter and interaction problems with other drugs the patient is currently taking can be highlighted or otherwise emphasized on this display.

Displayed is an example of a user starting another brand of the same generic medication, Latanoprost, 3327. Not displayed is the option of, starting the same brand or another brand of same class or even the same drug listed in 3323. Note that 3327, Latanoprost and 3323, Lumigan are brands of the same generic, but are different medications within the same class of drugs called prostaglandin analogs, Lumigan being the branded form of bimatoprost and latanoprost the generic version of a similar medication. Therefore, the two drugs appear in the same column and both with the same color, representing the same generic or class or category of drug displayed. In this case, is the color teal, which happens to match the color cap of these two drugs sold by drug companies.

The same medication or class of medications can be started and stopped multiple times in a patient's life. Yet there is no EMR or prescription system that adequately manages and displays medications if they are started and/or stopped more than once. In addition, most start and stop dates in EMRs are generated by e-prescribing of medication. This does not necessarily correlate with when the medication was actually taken by the patient. This invention allows the doctor to efficiently view and display multiple medications, document when they were actually taken by the patient, and correlate with clinical findings and test results, even if they are in the same medication class or are started and stopped more than once. Although the specific example in FIG. 53F pertains to an eye disease glaucoma, the concepts and tool can apply to any disease state treated with medications.

Adding to the complexity is that there may be multiple medications within the same class as a non-limiting example specific to eye care but the system generalizes for all of medicine, (bimatoprost, latanoprost, and travoprost are all prostaglandin analogue class medications used to treat glaucoma), a medication may be available in branded or generic form (bimatoprost is the generic version of Lumigan, latanoprost is the generic version of Xylatan), there may be more than one brand of the same medication (Xelpros and Xylatan are both brand-names for latanoprost) and medications may come in different strengths for both the branded and generic version Whatever the reason, it is important for the doctor to know and be able to document when each medication was used and the reasons they were stopped. It is also important to be able to correlate the use of a medication with the clinical findings that the medication was intended to treat. In other words, does it seem to be working? Did the eye pressure drop when the glaucoma medication was started? Did the blood pressure go down when the anti-hypertensive meds were taken?

The tool provides the doctor with the ability, on this actionable display, to set the start and stop dates, as well as the reasons for starting and stopping medications. It then generates graphic displays and correlates and highlights relevant data. It can also provide an ordering/prescribing method without leaving the display.

Panel 3301 is an example of a group of panels being placed together in rows and columns, although each individual panel can be separated for different positioning on the display not in the same rows and columns dashboard. 3302 shows a panel of a column representing date of an encounter next to the provider that is associated with that date. Panel 3303 shows particular clinical measurements of the right side of the body associated with medications. 3304 shows an eye pressure being measured. 3305 displays a line graph of the measurements in 3304 for rapid recognition of variation of the changing measurement of the data. 3306 displays a number of bar graph columns with different classes of medications.

Similar information for the left eye (pressure readings 3308, pressure graph 3309, and medication bar graph 3310) appears on the other half of panel 3303. All the data in the tool is shown in rows over time with whatever data has been collected or generated at that particular encounter (office visit, diagnostic test, procedure).

3311 is a panel for procedures divided into right side of body displayed, 3312. Right eye (OD) has a light red background to differentiate 3313, which is the left eye (OS) shaded blue. 3314 is the overall panel with the particular modules within displayed together because of the relevant data to be displayed for this patient with a particular condition. In this case, glaucoma, the interrelationship of 3303, 3311 and 3307 allow for rapid correlated analysis.

3316 is a panel of physical examination data recorded overtime. 3317 are a number of columns that present diagnostic tests, imaging, laboratory testing or any other relevant testing. 3318 is a panel of assessment and plan, where whatever has been recorded in the doctor's plan on any particular encounter could be clicked upon and brought up in an image viewer 3350 and also edited or created while all relevant data that may impact the patient, the users views and, therefore, document more accurately in the plan, the findings, and recommended actions. 3319 is a column of financial data or any other data that might be necessary. Financial data of what medications cost or whether they are covered by insurance and properly authorized is critical for medication management and displayed in this column with additional underlying information able to be brought up onto the display.

3320 is a control panel that generates the display in 3301 described further in FIG. 51. A control panel can generate the display changes in any or all the panels described in 3301. A medication panel is shown in this FIG. 53A, which specifically controls sub-panels 3306 and 3310, but also relates to and controls the population and highlighting of other relevant data in any of the other modules interrelated to medications.

Panel 3330 can be activated with clicking 3325 is an example of a sub-panel that has a pop-down menu that can be implemented to note reasons for a patient starting or discontinuing a medication, which then generates a display of actions in the various other associated panels, such as 3306 and 3310.

FIG. 53A depicts an example of how control panel 3320 of FIG. 53A can be implemented by a user to identify start and stop dates for the various medications taken by a user in accordance with an embodiment of the present principles. Clicking, for instance, 3326 activates the start of a drug and 3326 activates the stop of the drug which can be conveniently chosen on a calendar seen in pop-up window 3340. Displayed is another way to stop and start drugs through an ERx panel, 3350. Which also allows for ordering and prescribing a medication. 3350 is also window/panel that is a viewer that will allow any data to be displayed without blocking other relevant data on the display. This can include, displaying images of diagnostic tests 3317 and the plans 3318. FIG. 53A further depicts how section 3390 can choose a category of drugs to be interacted within 3320 and selected to be displayed is the category of glaucoma medications. 3390 control panel can be implemented to identify and assign colors or other identifying features for the medications.

3320 generates the display of medications in 3306 for the right eye and 3310 in the left eye. Displayed are five different columns representing different classes, categories, generics, or any programmed comparison of medications in each column that have some defined feature, action, or ingredients. Any number of columns can be displayed, including just the columns representing certain medications the patient has ever had prescribed. In one embodiment, the actionable display modules can select the relevant columns of data that the patient should have on their individualized display. For instance, exclude or collapse columns that either have no data associated or are not relevant to the patient's condition, would be improper for the patient to have prescribed such as if the patient is allergic to a medication. Selecting only the relevant data and excluding certain data allows more information in less space. 3321 shows that a particular medication, 3323 Lumigan was started on 8/5/ 2017. Displayed in the bar graph is 3323, the start date of Lumigan that matches the start date in the control panel 3321. 3322 shows the stop date of 3323 was 11/4/18.

3330 depicts an embodiment of the medication management chart in which the control panel can document a reason that a medication has been started or stopped. The dropdown menu 3330 can enable a user to select a reason. Displayed as the reason 3323 was discontinued as "cost" and when placed in 3330, generates a display notation on the bar graph 3334, which also reflects the date the medication was stopped, matching 3322 stop date in module 3320. Note, the invention can auto populate this information initially from data in an EMR or generated by the Physician's ERx. One embodiment allows access to a drop-down menu from the columns themselves, for instance by clicking on 3316 or 3324. The tool provides the interconnection that no matter where the information is inputted on the display it will then be documented within the relevant location within the tool, in this case 3325 and 3329 as well as in one embodiment when there is full or two-way integration to allow for documentation in all relevant location with the EMR, PM and ERx systems as well.

One other unique aspect of the system allows a user to intermingle certain drugs that have similar actions but different active ingredients to even same active ingredients (generic) but different names given to them by drug companies (Brands). Patient's with complex multiple conditions and disease states may have so many different symptoms, and many dozens of drugs over their lifetime or even over a few years, it becomes virtually impossible for any one Doctor to keep track of them all, know when they were taken and correlate the drug with the problem the patient is having. Due to the extent of the number of drugs and symptoms and conditions, the system allows the doctor the option to group medications visually that normally would not be grouped together but if they have a similar action or are treating a certain condition, then perhaps in some cases groupings that the pharmaceutical world might not be grouped together either the system or the user could override the normal grouping to allow for proper decision making and following clinical or diagnostic measurements or symptoms to see how the medications impact those data elements the medications are being given for. To save space the medications can be grouped in ways not normally grouped but at any time the system allows for the Doctors to decouple the medications. Also, the specific medication and its normal active agent/ class can be levered over or permanently seen on the bar graph even if it shares the same bar graph or column of medications not normally grouped together. To enhance understanding as a non-limiting example, if a patient has heart disease, and eye disease but also developed cancer and has pain, certain medications need to be visualized specifically within its normal active agent classification such as the agents treating the cancer, the heart disease and agents preventing blindness. However, to save room, since many agents can be given to control pain, in one display of the system all pain medicines can share a similar color or column just so visually the Doctor can differentiate all the medicines and the reasons for treatment. Pain medicines can include different brands such as Motrin, Aleve, Advil with similar active agents. Then there are pain medications such as aspirin, Tylenol, codeine, morphine that all reduce pain but have very different active agents. To save space all could be highlighted or otherwise emphasized similarly and share a certain space on the system to allow other medications treating other disease states to be seen simultaneously when the doctor wants to see the global birds eye picture of the patient. Knowing wheat pain medications were taken when is critical and can be de3coupled when zoomed in and can be listed when desired by the user. No system prior to this allows the user to customize for the patient the presentation and allow true stop and start dates and actual usage more than one time but as many times as the medication may have been started or stopped. In one embodiment the system constantly monitors or connects to outside software E-RX systems and if there is cross reaction of the medications this is also displayed and warned to the Dr. visually showing the mismatch or if they order connected to the system and medications in the future that are being ordered have any issue the Doctor sees the order they are trying to enter and interaction problems with other drugs the patient is currently taking can be highlighted or otherwise emphasized on this display.

Unique to the invention is the ability for the doctor to start the same brand or generic medication, as well as all other medications in a way that correlates data on the display and allows the doctor to come to conclusions about cause and effect by visualizing the medications taken and comparing to clinical findings, surgical, and/or diagnostic test findings. Even if a medication had been prescribed, it does not mean it was actually taken. Therefore, upon questioning the patient, the tool allows the user to adjust the start and stop dates to reflect the patient's actual use of the medication.

FIG. 53A displays a calendar method for selecting start and stop times to generate the visual display. The doctor can select 3326, which then displays the calendar and the doctor, on the calendar, can click on the date to start a medication. For example, displayed on the calendar 5/6/19, for the medication 3327 to be displayed on 3306.

Other embodiments of this invention allow a user to speak the instructions by activating 3351. The tool understands the words and automatically sets the date that the doctor commands. Another embodiment allows the user to drag a bar graph or right click in any of the particular cells of the column that represents a particular date of service. For instance, left click to start a medication, in 3332, and another click to confirm it. Then, to stop the drug, the doctor can also click in a cell in the row or date the medication is to be stopped and the bar graph fills in between the two. The doctor could also have clicked on 3332 and dragged the bar to 3334. If the patient took multiple medications within the same class, a branded or generic version, or a different strength, the same process is repeated all appearing in the same column that is programmed to illustrate that class of medications.

FIG. 53A depicts an embodiment of the Medication Management Chart in which any numerical data, in this case displayed intraocular as intraocular pressure, in addition to being listed by number in 3304 right eye and 3308 left eye, 3305 and 3309 displays the corresponding vertical line graphs of the values pointed out by 3305 and 3309.

A critical feature of one embodiment allows the user to customize alerts and actions to be taken. The Vertical line graph noted can be mapped over any set of numbers 3368, a demarcation line 3366 can be placed within this range anywhere to mean whatever the user feels important to be able to visualize numerical data that is above or below this set demarcation line. The demarcation line could be automatically set for all patients with a common condition or can be customized per patient by the user. If the value in 3304 or 3308 is higher (to the left of the target) or lower (to the right of the displayed target) this can be a method of a user to, at a glance, draw conclusions of the success or failure of treatment whether it be medications displayed in 3306 and 3310 or procedures displayed in 3311.

Being able to set target data points and if exceeded to alert the doctor is critical because different values for one patient might be normal but abnormal for another. The user, when seeing an individual patient can determine what is the target or demonstrate a number when a decision needs to be made or to follow the effectiveness of a medication or procedure. The doctor can set the target which can set all columns to create an alert when a certain threshold is exceeded or the demarcation line 3366 can be set. The doctor can visualize that the medication 3370 had been prescribed for a significant period of time and the line graph 3369 was all high, to the left of the target pressure set at 3366. The medication 3370 was stopped and 3371 shows that it was stopped, and the line graph was to the right of 3366 which shows that the pressure was below the target pressure so perhaps medications were not needed hence the reason 3370 was discontinued. 3372 shows that the line graph has crossed 3366 and the pressure is now higher than it should be and indeed 3364 reflect that high number and 3367 Shows a red alert on 3372 illustrating the high pressure in 3364. Note, in 3374 the medication that had been stopped on 3370 has been restarted in row 3360 which represents today's visit and the medication 3374 is displayed into the next visit 3362. This depicts to the doctor that the medication is started today because the pressure is high and is continuing until the next visit and that is what they can show the patient visually and say to the patient and confirm that is what they want ordered.

By way of example, the doctor can set the target pressure or any data in any column, for instance 3304, 3308 that for a particular patient where data, in this case pressure, if it exceeds a target pressure that a recommendation can be displayed in 3350. An alert can also display 3348, 3364, 3367, 3370. An example how this can be set is the user can click on 3315 which activates a drop-down menu that lets the user set the particular pressure that is a demarcation target pressure 3366 for the patient. If the pressure exceeds the demarcation line of 3366, now the doctor can visualize whether the pressure recorded in 3308 is higher than it should be as displayed in 3369 or is below displayed in 3371. Additionally, 3364 can be set as extremely high by the user clicked 3315 and the doctor can choose a red alert as seen in 3364 and 3348 because the data in 3308 and 3304 has exceeded a certain threshold. All of this through rules engine can be tied to the need for diagnostic test. If the pressure exceeds a certain number in 3308 this may trigger the need for a diagnostic test and 3370 can have an alert over any of these diagnostic tests displayed, that this patient has not had a visual field and need one.

It should be noted that by clicking 3315 there's an option not just to set parameters but also display in a unique way converting the panels in any other format. Displayed in FIG. 53F is a vertical orientation for FIG. 33 but the same display can be presented in a horizontal whole life display described in FIG. 41.

Displayed is an example of why a medication is prescribed. In the pressure measurement column, 3308, the cell 3364 shows that the pressure is very high at 30, some embodiments are set to highlight when data exceeds a certain number alerting the user. 3367 shows that the alerted high pressure is displayed on the line graph. 3309 maps out the data shown as eye pressure readings between 5 to 40. 3366 is the measurement the user sets as a good goal target pressure, for that patient to have. The doctor can adjust 3366 by simply dragging 3366 to the left or right. 3315 can also activate a drop down menu that lets the doctor set the numbers for alerts to occur and that can move the target data line 3366 in one direction or the other as well as set alerts for diagnostic tests. FIG. 29 explains further how the data and alerts can be set by the user without leaving the display.

It is important to note that while FIG. 53F shows how medications can be displayed with relevant data for correlation and recognition by the user of patterns of changes that might require an action, this tool also allows for the setting of alerts that will trigger certain Highlighting that will help the doctor make decisions. FIG. 13 describes this further.

An example of why displaying relevant data simultaneously on the screen is important for a doctor to see, and then take action is illustrated in 3315 where a visual field with a red indicator, which can mean worsening, the doctor can directly access and view the worsening diagnostic test. When the doctor also has in view that the pressure is high, 27 in 3348, they may conclude a new medication needs to be started, 3336. The stop date of the drug can also be set and displayed by clicking 3328, and the doctor can as shown in 3328 set 7/6/19 on the calendar for when drug 3327 was stopped. Generated is the bar graph which in 3346 shows the stop date of medication for 3311, with the reason for stopping in 3329 and displayed "not needed" shown on 3346, shown by any method, for instance, hovering.

The doctor can instantly see, at a glance, why the medication is no longer needed, because 3338 shows that a surgery was performed and 3342 shows that the pressure is decreased to 8 the day after surgery 3338, reduced from what had been in the past as high of a pressure as 28, seen in the summary row, 3344. The summary row can display the maximum pressure over all the measurements recorded for this patient. Therefore, a user can instantly understand that the patient no longer needs that medication 3327, because a surgery that also controls pressure, 3338, was performed in the right eye. The Doctor can conclude surgery was effective and medication no longer needed. Therefore, the medication is stopped 3346.

The tool allows, in some embodiments, for the doctor to only interact with the tool itself without having to go to any other windows in the EMRs, when there is two-way integration, or the tool is embedded within the EMR itself. The actions that the doctor is placing by setting start and stop dates, can automatically be documented within the EMR in any section that is appropriate. For instance, information can be populated in the assessment and plan section by whatever is documented in this actionable display.

The doctor can also choose, after setting start and stop dates of all medications for the patient, instead of having it automatically be placed into the EMR plan, they can review first what has to be placed. For instance, clicking 3330, will convert into words, the exact start and stop dates as well as reasons for discontinuation or anything else inputted in 3300, 3340. The doctor can first view those words in a viewing panel, such as 3350. This panel 3350 can also serve to show images when clicked such as 3309, or previous plans, as well as connect to and display e-Rx. By clicking 3330, all interactions with the tool 3300 will now be transformed into words based on what the doctor has entered. Once the doctor confirms what is written in 3350, they can confirm, for instance, by clicking 3330 again, which then generates to action to place the documentation or orders into the EMR, plan or automatically anywhere else that is programmed for it to be placed. For instance, row 3305 would state "Lumigan 0.1% was started 8/5/2017, but was stopped 11/4/2018 because of cost." That information is derived from 3305, 3306, 3307 and 3308. The same translation of the actions taken in the tool would be repetitive for all of the medications that the doctor documents or orders within module 3340, 3300, and/or 3350.

In some embodiments, by clicking 3349 can generate a means for a doctor to actually place an order and prescribe medications either though panel 3330 that then links to the EMR or by connecting to e-Rx software in 3350. This means to create an order and prescribe medications can appear in 3350 and the doctor can interact with 3350 just as they would in an e-Rx prescribing system that pops-up in other locations of EMR systems. Unlike other systems, the inventions actionable display will show all of the relevant information, including relevant diagnostic tests 3309, procedures 3304, clinical findings 3301 and medications displayed in an accurate manner that the doctor can set to reflect reality with start and stop dates. For the first time, while prescribing medications, a doctor can see all the medications that are relevant in 3303, and can thereby draw conclusions on how the medications impact clinical findings, diagnostic tests, symptoms or how procedures impact the findings. Now, accurate ordering and prescribing for medications can occur.

Additionally, as the doctor prescribes a medication in 3350, unique to the system is relevant data is highlighted or otherwise emphasized. While some prescription modules linked to EMR might tell of an interaction of a medication or even make a recommendation, this system is the only one that would actually display, in one view, and show what the e-Rx system is referring to. For instance, if there is an interaction between one drug and the other, the entire column in 3303 of the drugs would have the interaction shown or an entirely new column, the tool will display with the medication of concern highlighted or otherwise emphasized. For instance, a bright red blinking color warning that this medication might interact with a drug that may be prescribed. Also, if one drug does not work as well, because it has been used in the past, the system can instantly display that medication in 3303 and highlight in the diagnostic test, columns such as 3309 or clinical findings in 3301 that are relevant. This tool allows for doctors to visually see clinical decision support recommendations, preferred practice patterns or interactions and not just see a pop-up alert out of context that other systems may have. As described elsewhere, all of the headers, summary rows and all of the cells through rules engine, predictive analytics and machine learning can show important information by highlighting relevant information, all without the doctors taking their eyes off the global picture of the patient.

FIG. 53F displays how a future order or a new prescription of a medication can appear on 3306 or 3310. Displayed is the new order 3374, so a doctor can confirm what they actually are prescribing and sending to the pharmacy is actually what they want. Once the doctor has decided to start the patient on a medicine, they can start the medication and order it in Panel 3350, or they can also order it through Panel 3320 and as previously described select the reason for starting through Panel 3330.

3320 and 3350 as Doctors interact with these panels, the tool can display the logical medications that could be ordered based on recommendations through preferred practice patterns, clinical decision support, rules engine that if the pressure is a certain high and 3308 and knowing what medications have been used in the past 3320 or 3350 can auto populate with suggestions to the doctor about what medicines would work. The doctor can except or reject any of them, but the important aspect of the invention is correlating important relevant data and then displaying it so a doctor at a glance can see trends and make some proper efficient decisions without leaving the display.

FIG. 53G depicts an embodiment of the Medication Management Chart of FIG. 53D in which both corrected start and stop dates for a medication taken by a patient and incorrect start and stop dates for a medication taken by a patient and listed for example by a 3$^{rd}$ party data provider such as an EMR can be displayed simultaneously in accordance with an embodiment of the present principles. In the embodiment of FIG. 53G, element 1 depicts a line depicting a start and stop date of a medication being taken by a patient as listed in an EMR. In FIG. 53G the line pointed out by element 1 is displayed within a bar pointed out by element 2, which depicts start and stop dates of a medication being taken by a patient as identified by a user. FIG. 53G also depicts an alternative embodiment. That is, FIG. 53G depicts an orange bar element 4 depicting a medication being taken by the patient. The orange bar depicts start and stop dates element 5 of the medication as listed in an EMR and a black line within the orange bar which depicts start and stop dates of the medication as determined by the user. Importantly and in accordance with the present principles, FIG. 53G depicts that more than one stop and stop date can be depicted for each medication in a Medication Management Chart of the present principles. In FIG. 53G, element 3 depicts the control module that can be used to adjust start and stop dates. In FIG. 53G, element 8 depicts how when the control module of element 3 is used to change a date, element 9 (5/5/17) the teal color bar graph starts the bar graph at that date.

FIG. 53H depicts an embodiment of the Medication Management Chart of FIG. 53D in which a user is alerted that a medication being taken by a patient has changed, even if medications are being listed by class and the new medication is of the same class as the old medication in accordance with an embodiment of the present principles. For example, in the embodiment of FIG. 53H, element 1 depicts a horizontal line in the bar of the medication that is being taken by the patient and that is being changed. element 2 of FIG. 53H depicts that before a change the medication being taken by the patient is Lumigan. The line pointed out by element 1 depicts a change in medication and element 3 depicts that the medication being taken after the change is Latanoprost, which is in the same class of medications as Lumigan.

FIG. 53I depicts an embodiment of the Medication Management Chart of FIG. 53H in which a user is able to select a portion of a graph to bring up additional information associated with the graph in accordance with an embodiment of the present principles. For example, in the embodiment of FIG. 53I, when a user hovers a selection tool (e.g., mouse) over a specific date portion of an IOP graph, a window 3311 appears displaying to the user information detailing, for example, when and/or where on that particular day an intraocular pressure was measured. Similarly, and as depicted in FIG. 53I, when a user hovers over a specific date portion of a medications graph, the window 3311 appears displaying to the user information detailing, for example, at what time or how long ago the medication was taken by the patient. In some embodiments, a time between the measurement in the office, for instance, a blood pressure or a pressure of the eye, and how long ago the patient actually took the medication can be measured and displayed, since some medications have a short duration of action and such information would be useful to the user.

In another embodiment and as briefly described above, Medication Management in a Data Command Center in accordance with the present principles exists as a series of intelligent horizontal rows within a correlative graph representing individual medications, classes of medications, categories of medications, or logical groupings of medications, differentiating medications by color or combinations of colors, symbols, and/or text, graphing start and stop dates and times or individual doses, correlated to relevant values and relevant events. In accordance with the present principles, graphical differentiation between medications can consist of individual colors for individual medications, combinations of colors for medications including more than one component, or complex graphical representations. In some embodiments, color standards, such as defined by the American Academy of Ophthalmology, can be used for color coding the medications and/or custom colors can be used. For example, in ophthalmology and with respect to eye care, medications have been assigned in the industry to have a certain color on the eye drop bottle or cap. In some embodiments, these colors can be displayed allowing recognition by the user of the class of medication. For instance, yellow is a beta blocker one of which is Timoptic. In accordance with the present principles, medical care providers who have memorized the color caps can instantly recognize, by viewing a medical records dashboard of the present principles, the class of medication without even seeing the name. Alternatively, or in addition, in some embodiments of the present principles a user can identify which generic or brand medication the patient is taking by any means including rolling over the graph and seeing the name of the medication pop up.

Figure 54:
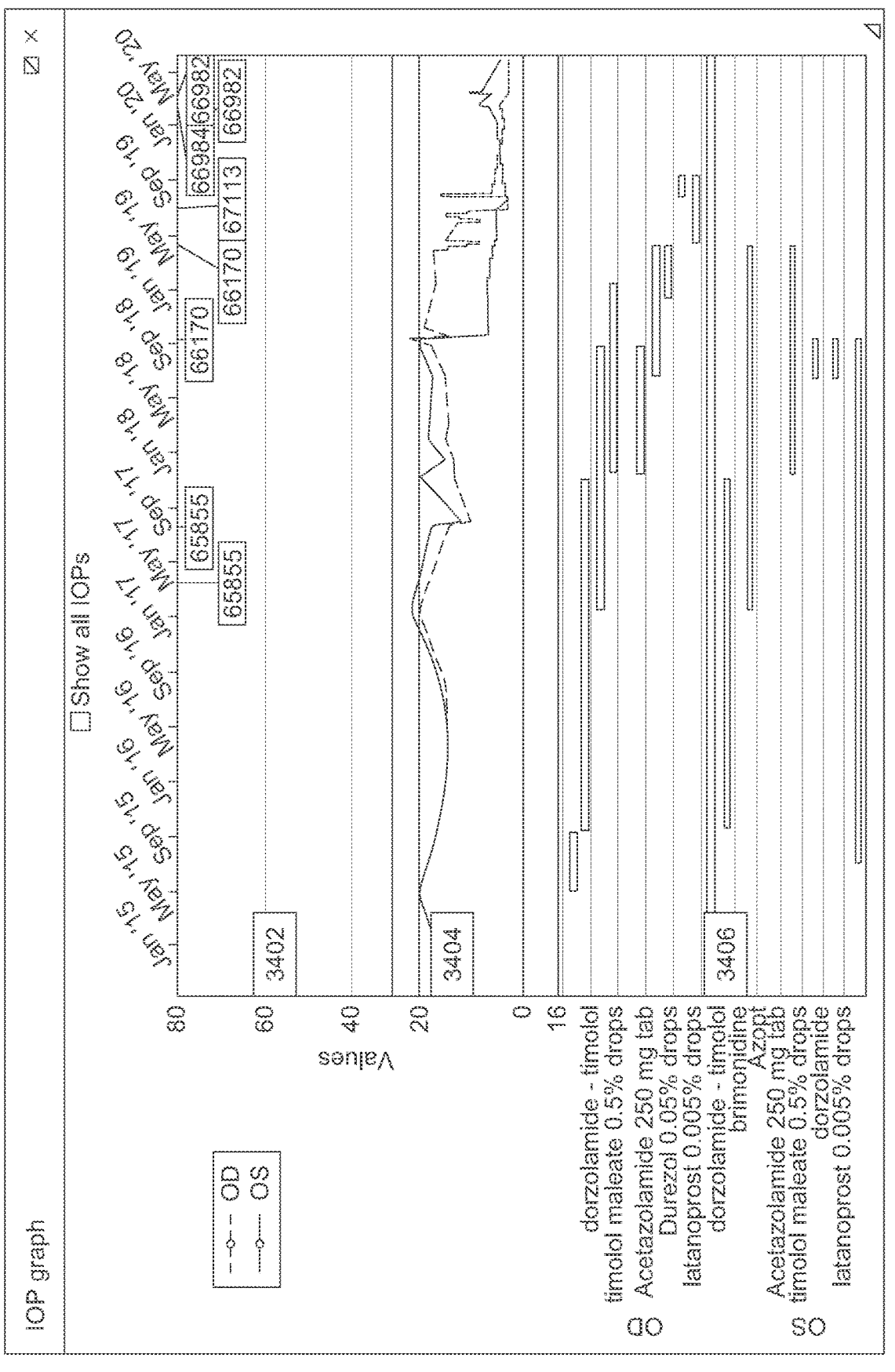
FIG. 54 depicts an illustration of a second embodiment of a Medication Management chart that can be displayed in at least a portion of the medical records dashboard of the present principles in accordance with one embodiment.

FIG. 54 depicts an illustration of a second embodiment of a Medication Management chart that can be displayed in at least a portion of the medical records dashboard of the present principles in accordance with one embodiment. In the embodiment of the present principles depicted in FIG. 54, the medications in the Medication Management chart are color-coded. Illustratively, in the Medication Management chart of FIG. 54, a top section 3402 illustrates dates of relevant events. In some embodiments, such events can include but are not limited to applied medications which can be taken by mouth (orally), given by injection into a vein (intravenously, IV), into a muscle (intramuscularly, IM), into the space around the spinal cord (intrathecally), or beneath the skin (subcutaneously, sc), placed under the tongue (sublingually) or between the gums and cheek (buccally), inserted in the rectum (rectally) or vagina (vaginally), placed in the eye (by the ocular route) or the ear (by the otic route), sprayed into the nose and absorbed through the nasal membranes (nasally), breathed into the lungs, usually through the mouth (by inhalation) or mouth and nose (by nebulization), applied to the skin (cutaneously) for a local (topical) or bodywide (systemic) effect, and/or delivered through the skin by a patch (transdermally) for a systemic effect, surgeries and any other procedures that can affect a patient's well-being.

A second, lower section 3404 of the Medication Management chart of the embodiment of FIG. 54 depicts a line graph correlating the relevant events that can affect a patient's well-being (i.e., the application of medications, surgery, etc.) of the top section 3402 to relevant values of patient well-being data/information (i.e., intraocular pressure) for each of a right eye and a left eye. In the Medication Management chart of FIG. 54, a third, lower section 3406 depicts a horizontal view of medications, which no longer spans a column of appointments, but denotes start/stop dates/times across a linear model. The linear model accounts for dates and key events in the top section of the diagram, such as the application of medications and major surgeries that may also have an effect on the results displayed in the middle section of the diagram. The third lower section 3406 displays an array of medications horizontally in context of the events and factors which can affect results, clearly showing the effect of medications and events on a single, or combination of multiple, tracked values.

Figure 55C:
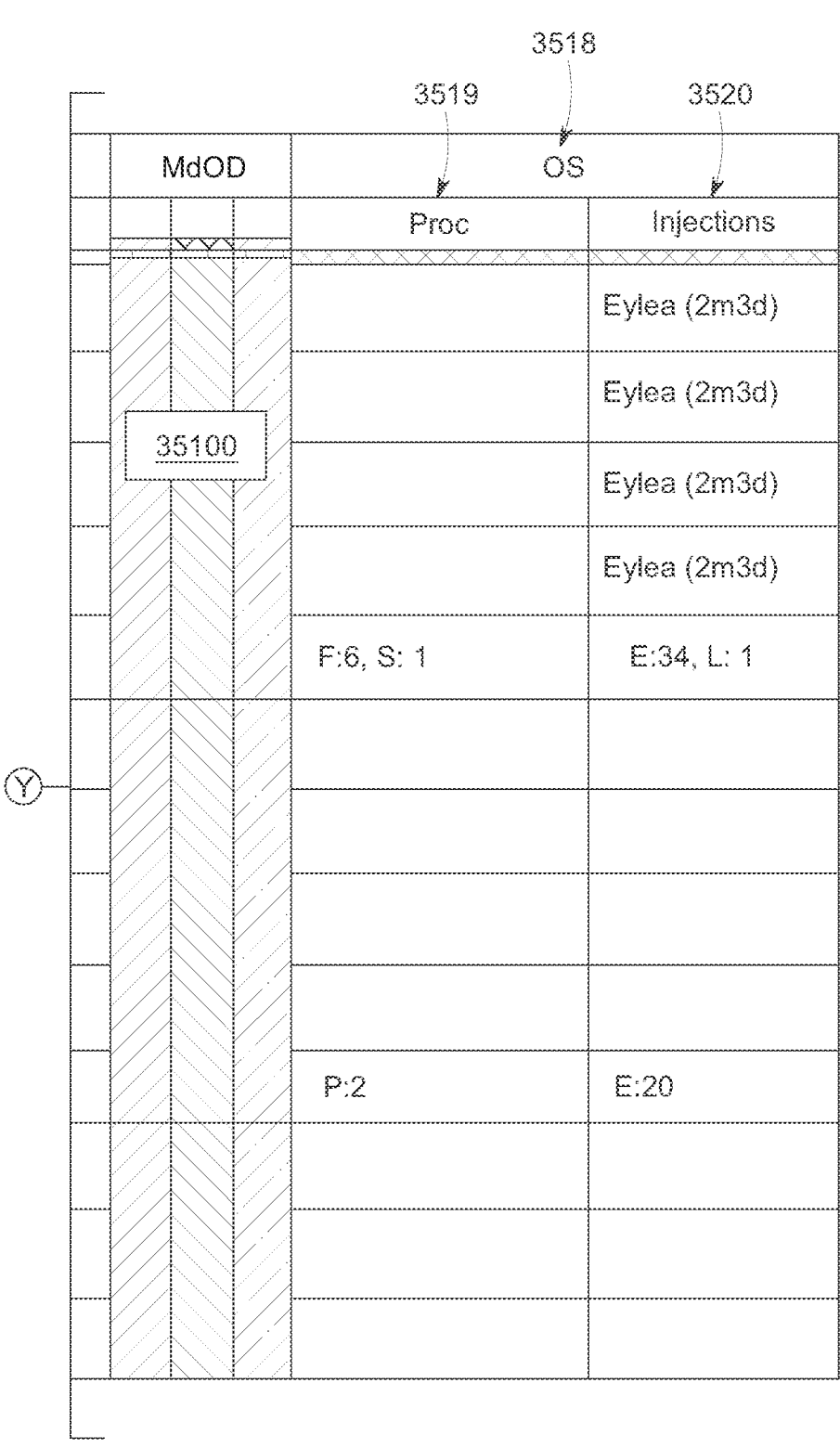
FIG. 55 depicts a medical records dashboard including a third embodiment of a Medication Management chart in accordance with an embodiment of the present principles.

In another embodiment, Medication Management in a Data Command Center in accordance with the present principles exists as a series of intelligent vertical columns representing individual medications, classes of medications, categories of medications, or logical groupings of medications, differentiating medications by color or combinations of colors, symbols, and/or text, graphing start and stop dates and times or individual doses. For example, FIG. 55 depicts a medical records dashboard including a third embodiment of a Medication Management chart in accordance with an embodiment of the present principles. That is, the medical records dashboard of FIG. 55 includes a report depicting three different patients within a plurality of rows and columns and a Medication Management chart 35100 in accordance with the present principles. In the embodiment of FIG. 55, the columns of the medical records dashboard include a VisitDate Column 3502 listing the visit date of a patient, a Provider/Location Column 3504, a NextVisit Column 3506 listing a next visit date for the patient, a Referring provider Column 3508 listing the name of, for example, a referring doctor, a Diagnosis Column 3510 including an OD column 3511 and an OS column 3512 including a diagnosis for each of a right and a left eye, a separate OD Column 3514 including a Procedure column 3515 listing procedures performed on a patient's right eye and an Injections column 3516 listing injections performed on the patient's right eye, and a separate OS Column 3518 including a Procedure column 3519 listing procedures performed on a patient's left eye and an Injections column 3520 listing injections performed on the patient's left eye.

In the medical records dashboard of FIG. 55, the Medication Management chart 35100 depicts a representation of color-coded vertical medication columns as described above with respect to the embodiments of FIG. 50, FIG. 52, and FIG. 53.

Figure 56:
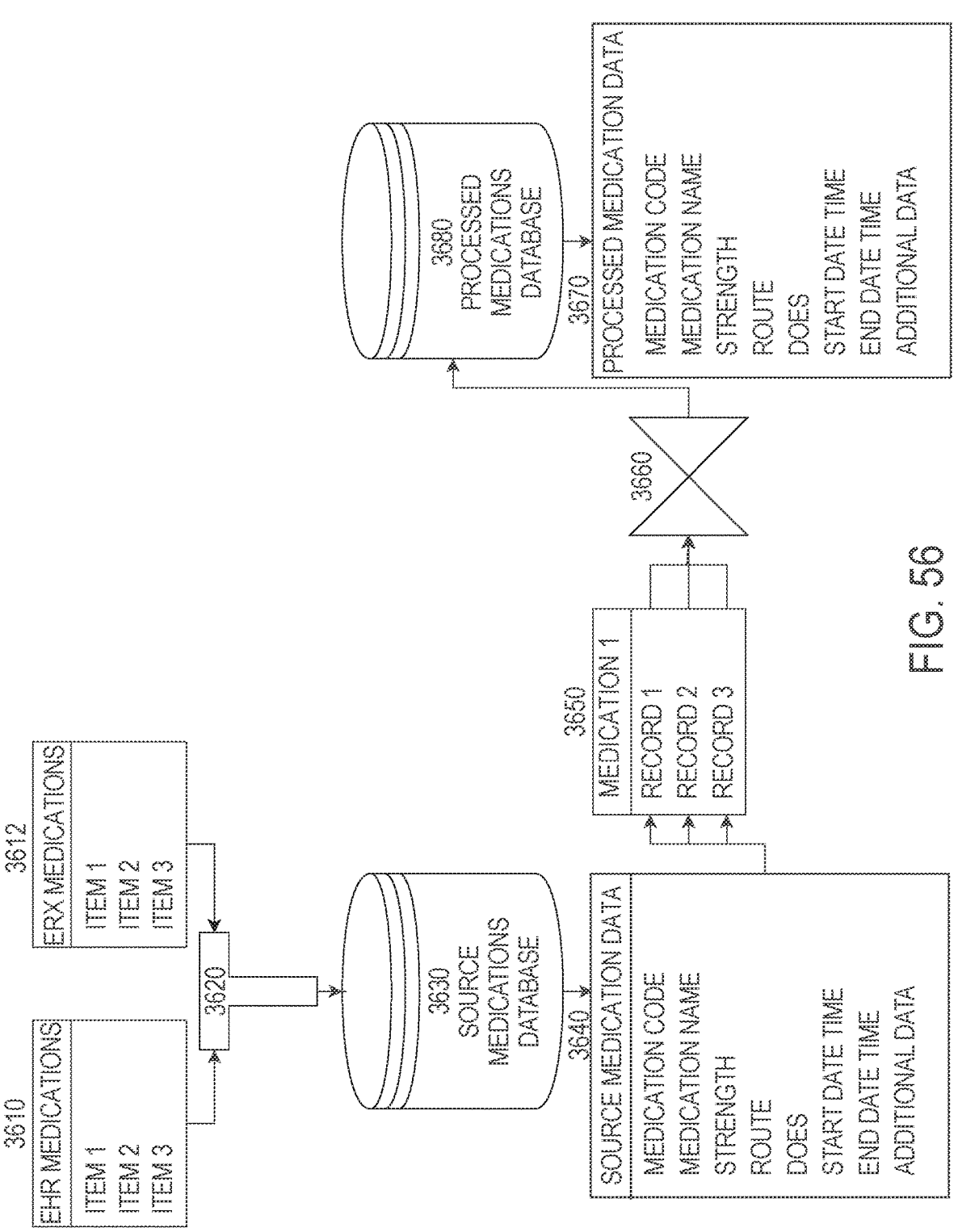
FIG. 56 depicts a high-level workflow diagram of an embodiment of Medication Management in a Data Command Center in accordance with an embodiment of the present principles.

FIG. 56 depicts a high-level workflow diagram of an embodiment of Medication Management in a Data Command Center in accordance with an embodiment of the present principles. In the embodiment of FIG. 56, Medication source data can be stored within an EHR 3610 or eRx platform 3612. In some embodiments, as depicted in FIG. 56, medication data can be imported by an API or other means of digital communication, for example in one embodiment by the integration module 002 of the Data Command center 001 of FIG. 1, and can be compiled into a table 3620 which can be stored in a database 3630. Data from a relevant source stored in the database 3630 can be extracted. Block 3640 depicts an accurate representation of extracted data from the relevant source. The data from the relevant source can then be isolated to at least one specific medication from the source data. Block 3650 of FIG. 56 represents records isolated for a specific medication from the source data. The isolated data can then be processed at 3660 through several intelligent algorithms to surmise a final representation of the view of the specific medication, in some embodiments a longitudinal view. For example, in some embodiments, source data disparities and variance of medication data between sources can be addressed by intelligent algorithms which acquire available data about the medications and data sources and process toward a desired result. Algorithms account for presence if codified data, non-codified data, null values, and other datatypes. Such algorithms can be directed to exporting consistent representations of source data. In some embodiments of the present principles, such algorithms can be applied by the Rules module 004 of the Data Command center 001 of FIG. 1 and can be stored in a means for storage accessible to at least the Rules module 004.

Each medication column or row in a medical records dashboard of the present principles can consist of one or more individual medications as depicted by processed medications data as listed in block 3670, which can be stored in the Processed Medications Database 3680.

In some embodiments, the Display module 006 of the Data Command center 001 of FIG. 1 in accordance with the present principles causes the display of the Medication Management data in a medical records dashboard of the present principles as described above, and specifically in at least one of the vertical, horizontal, and textual embodiments described above and in accordance with individual medications, classes of medications, categories of medications, or logical groupings of medications, differentiating medications by color and/or combinations of colors, symbols, and/or text, graphing start and stop dates and times or individual doses, correlated to relevant values and relevant events as described above.

In some embodiments of at least one of a medical records dashboard and a Medication Management chart in accordance with the present principles, Medication columns and rows can expand, contract, hide, or be display based on a medical care provider's specialty, the identity of a medical care provider and/or a patient, patient conditions, patient procedures, risk factors, diagnostic results, future orders, future appointments, values recorded, values not recorded, calculated values, and absolute values for display, unless otherwise disallowed in accordance with Dynamic Columns and/or Rows that can Collapse and Expand.

In some instances, medication data can be sourced from misleading, unreliable, or inconsistent records reflecting multiple start and stop dates and times for a single medication due to each individual reorder of a medication stopping a prior prescription and starting a new one, or not stopping but adding a new start date and time, and may not reflect actual patient usage of said medication. As such, in some embodiments a Data Command Center via at least of a medical records dashboard and a Medication Management chart in accordance with an embodiment of the present principles enables a user to manually override misleading, unreliable, or inconsistent records to accurately represent medication usage. In such embodiments, each instance of source medication data being altered can be recorded in an audit log to account for data integrity as well as data accuracy. In some embodiments, the source medication data itself is never altered, updated, added, or removed. In some embodiments, updating medication data in any instance of Medication Management in accordance with the present principles reflects in every instance of the Medication Management. For example, editing a stop date and time in a list view of a medical records dashboard can also update the stop date and time in all graphical views. In some embodiments, medication updates can be stored separately from source medication data.

In general, in accordance with the present principles, embodiments of a Data Command Center via at least one of a medical records dashboard and a Medication Management chart of the present principles enable medical care providers to visualize medications, respective start and stop dates, reasons for discontinuation, and enables medical care providers to manage and change a display based on facts able to be confirmed with a patient at a point of care and even with home monitoring devices that can be linked. As described above, in some embodiments each medication can be represented by a bar graph or a linear graph or other visual method or means that in either the vertical direction or in a horizontal direction, a medical care provider can visualize the actual start and stop dates of all relevant medications for their specialty or for that patient all seen simultaneously with any other relevant data that the medications can impact. The medications and any encounters or clinical services or measurements that the patient takes at home or home monitoring devices can all be automatically or manually inputted. The Medication Management chart/Medication Management tool of the present principles can initially be populated by information in the EMR, which may or may not be accurate, or from E-prescribe systems. A medical care provider using, for example a medical records dashboard, can make changes and through a linear bar graph or other means, each column or row can represent a particular medication or class of medication. With all of the patient's medications that are relevant to that medical care provider or the condition being treated, all medications that the patient is taking now or in the past, can be displayed so that medical care providers will know all the medications that the patient has ever taken.

Embodiments of the present principles provide access to whatever information is relevant to the treatment of a patient and is enabled to share this information with all other medical care providers. All medication that can be used to manage a particular condition can all be displayed on a single screen if there is room or collapsed so doctors can visualize other options. In some embodiments, just the columns and/or rows are automatically displayed, and other medication alternatives hidden until, through any means, a user accesses hidden patient-related information. In some embodiments, a Data Command Center via, for example at least one of a medical records dashboard and a Medication Management chart of the present principles, can offer clinical decision support in that if there is a set preferred treatment plan or the Data Command Center has programmed proper alternatives that a medical care provider should consider, the medical care provider can start the patient on a particular medication that can be suggested in a blank row or column next to other medications with the name of the suggested medicine.

In some embodiments, each user can move the columns and rows on which the medications are on to a particular section while being able to collapse and expand the entire history of every medication that the patient has taken. Each column or row, depending on whether a horizontal or vertical display is preferable, would be displayed from a start to a stop date and each corresponding date can be listed by office visit of encounter with different medical care providers and or by month, by day, by year, by hour or even minutes especially useful if the patient is hospitalized. In some embodiments of the present principles, a Data Command Center can receive inputs from a user via a user interface on how at least one of a medical records dashboard and a Medication Management chart should be configured to display patient related information from outside sources. For example, in some embodiments patient-related data/information from outside sources can be integrated into the Data Command center 001 via the Integration module 002 of the Data Command center 001 of FIG. 1. Once patient-related data/information is received by the Data Command center

001, the data can be compared to rules to be executed by the Rules module 004, which determine how and if received patient-related data should be displayed. As described above, in some embodiments, at least some of the rules for handling patient-related data/information can be provided to the Rules module 004 of the Data Command center 001 using a user interface. Patient-related data/information can then be caused to be displayed by the Display module 006 on at least the medical records dashboard of the present principles in accordance with the rules of the Rules module 004.

In some embodiments, multiple start and stop dates can exist for a medication based on when a patient admits that they really took the medication. As such, a medication bar graph might appear interrupted because, for example, the same medication might have been taken in 1993 and then re-started again in 2003 or the patient only took the medication for 10 months out of 12 months in a particular year. Such findings can be critical to patient care because if a patient does not take the medication as prescribed it can have an impact on a clinical finding or symptom or disease progression such as high blood pressure. Should a patient have blood pressure measured and suddenly the blood pressure is high, a medical care provider needs to know if it is not that the medication did not work, but perhaps that the patient did not take the medication.

An onset of other medical conditions or interventions such as surgeries or other life events like a death in the family can also be displayed in at least one of a medical records dashboard and a Medication Management chart of the present principles so a medical care provider can determine and take into all the information that can impact the well-being of a patient. As such in some embodiments, a medical records dashboard and a Medication Management chart of the present principles can display clinical findings, measurements, the laboratory findings, and/or whatever the medication impacts a patient's well-being such that a true change in a patient's well-being can be measured accurately and a medical care provider can see visualize the true effects of medications along with other medical services, interventions, and life events. By way of example, in the field of ophthalmology there are glaucoma medications, which are pressure medications for the eye. Sometimes just one eye drop will make the pressure go down, sometimes two, three and four different types of drops are needed. Usually, medical care providers add a medication if an eye pressure is not controlled to the level desired or if the medical care provider wants to replace one medication with another.

In some embodiments, at least one of a medical records dashboard and a Medication Management chart/tool of the present principles enables a medical care provider to document why a medication was started or stopped or if there has been a reaction to the medication. For instance, if the medication has been stopped because the patient is allergic or cannot afford it, or if it did not work. Such reasons can be input into the medical management tool by selecting the choice by any means such as a drop-down menu or through voice recognition software or any means. The information can then be displayed on a bar or line graph of that particular medication and either be permanently displayed or accessed via an icon or other access point.

In various embodiments of a medical records dashboard having a medication management tool (such as displayed in FIG. 50), in addition to a laboratory or clinical finding, there can be included an option to input information regarding procedures performed on a patient. For example, for a particular patient, a surgical procedure might be the reason there has been a sudden change in the well-being of the patient. For instance, there are some glaucoma pressure surgeries which will reduce the pressure and have the same effect as a medication or a laser surgery that might cause a pressure to be lower. It is important that a medical care provider have the option to view what procedure were performed on a patient to determine if a procedure might also have had an effect on the clinical finding, symptoms or disease progression on which the medication can also have an impact. Perhaps it is not the medication that is working, maybe it is the surgery.

Embodiments of the present principles are fully adjustable for all types of conditions, such as high blood pressure, diabetes, rheumatological diseases, and all types of cancer. All of these conditions have certain laboratories and clinical measurements that are taken either at the patient's home or from a testing center or on each visit with a medical care provider (i.e., doctors often record weight and blood pressure of the patient, etc.). In addition, a medical care provider can be enabled via at least one of a medical records dashboard and a Medication Management chart of the present principles to now E-prescribe or place an order for a new medication or cancel a drug. As such, by ordering a next medication, a medical care provider can instantly visualize what is being ordered as the new order can be displayed as a future medication. In such embodiments, a new column or row can appear with, for instance, a new bar graph because the medical care provider is now ordering a new medication.

A Data Command Center of the present principles enables a medical care provider to determine if incompatible medications or procedures have been ordered and/or scheduled. For example, in some embodiments, upon the visual display of ordered medications and/or procedures in at least one of a medical records dashboard and a Medication Management chart of the present principles, a medical care provider, by looking at the display, can visually determine through his/her experience and training that incompatible medications and/or procedures have been ordered or scheduled. Alternatively, or in addition, in some embodiments a Rules module, such as the Rules module 004 of the Data Command center 001 of FIG. 1, can be programmed to recognize incompatible medications and/or procedures. As such, when patient-related data/information containing incompatible medications and/or procedures is received or when incompatible medications or procedures have been ordered or scheduled by, for example, a medical care provider using for example at least one of a medical records dashboard and a Medication Management chart of the present principles, the Rules module 004 can cause an alert to be displayed by, for example, the Display module 006, the alert intended to bring to a user's attention that incompatible medications and/or procedures exist. In some embodiments, if such a condition exists, a pop-up can appear to enable a medical care provider to re-do their order and make sure the order is corrected.

In some embodiments, multiple medication graphs can be shown independently or on for example, at least one of a medical records dashboard and a Medication Management chart of the present principles, such that a user is able to compare different reporting of the same medications. For example, in some instances, patient-related data from an EMR can be inaccurate. However, it is advantageous for a medical care provider to know what has been documented, even if inaccurate. Embodiments of a medication management tool of the present principles can display two graphs, a first displaying what is actually documented in the EMR and a second displaying patient-related data that has been corrected by a medical care provider. In such embodiments, a medical care provider is enabled to check patient-related information from an EMR for accuracy.

In the medical field, medical care providers, such as doctors, use drug categories according to the affects they have on the human body. Many types of categories can be classified on the basis of chemical nature of the drug. The term of the drug or medication is used for diagnosing, curing, or treating a disease. Drugs classification can include but are not limited to a Chemical nature of the drug, Symptoms or diseases for which they are used (i.e., antihypertensive drugs), Organ system affected, Generations of drugs, such as antimicrobials or oral hypoglycemic agents, Receptor theory, Duration of action, and method of administration. Embodiments of a medical management tool in accordance with the present principles enable medical care providers to display all of a patient's medications by classification by, in some embodiments, selecting from a menu whatever classification method is most intuitive to the medical care provider as the medical care provider is treating the patient. By way of example, in the case of a subspecialist, like an ophthalmologist, the doctor might just want to know all medications of the eye, so the organ system affected is the eye. For instance, in the eyes category of disease can be glaucoma, which includes pressure control in the eyes. For glaucoma, there is a group of medications that control pressure in the eyes. Currently, there are eight classifications. In addition, there is macular degeneration disease or diabetic macular edema disease and there are classifications for those diseases as well. A medical care provider can decide to display, on a single display, either all of the ocular medications that the patient is taking singly or in categories. Alternatively, or in addition, a medical care provider can select to display medication by symptoms of the disease, such as the anti-hypertensive medications.

It can also be helpful to a medical care provider to know if a patient is taking an originally prescribed brand of the medication or if the patient is taking a generic medication. Embodiments of a medication management tool of the present principles provide a means for listing whether a patient is taking an originally prescribed brand of the medication or if the patient is taking a generic brand. A difference between the two brands of medication is that one might cost a significant amount more than the other and some can work a little differently and not be as affective. Medical care providers need to know whether the patient is taking a brand name or a generic. Some insurance companies will only pay for certain brands or generics, and mandate that medication be taken. Some medications will have a copay by the patient and the patient has to pay additional money. It can be critical that medical care providers also note cost to patients and to the insurance companies, so that medical care providers can control health care dollars.

In some embodiments of a Medication Management tool of a Data Command Center of the present principles, the Medication Management tool can make suggestions in regard to using a less expensive generic medication and in some embodiments can compare medication and procedure recommendations made by a user/medical care provider against what a patient's insurance will allow. For example, in some embodiments information regarding generic medications that can be substituted for brand name medications can be stored in a storage means accessible to, for example, the Rules module 004 of the Data Command center 001 of FIG. 1. As such, when a user/medical care provider prescribes a medication using the Medication Management tool and/or a medical records dashboard of the present principles, the Rules module 004, via for example the Display module 006, can cause a display of suggested generic medications, in some embodiments in a pop-up window, that can be prescribed to a patient in place of the brand name medication. Similarly, in some embodiments information regarding what medications and procedures can be authorized by a patient's insurance company can be stored in a storage means accessible by, for example, the Rules module 004 of the Data Command center 001 of FIG. 1. As such, when a user/medical care provider prescribes a medication or schedules a procedure using the Medication Management tool and/or a medical records dashboard of the present principles, the Rules module 004 can compare the information regarding what a patient's insurance company will allow and what medication the user/medical care provider has prescribed or what procedure was scheduled to determine if the patient's insurance company will allow the medication and/or procedure. If the Rules module 004 determines that a prescribed medication and/or scheduled procedure is not allowed by a patient's insurance company, the Rules module 004, via for example the Display module 006, can cause a display of an alert to the user/medical care provider to alert the user/medical care provider that a prescribed medication and/or scheduled procedure is not allowed by the patient's insurance company. In some embodiments, information regarding what medications and procedures can be authorized by a patient's insurance company can be stored in a storage means accessible to the Rules module 004 of the Data Command center 001 of FIG. 1.

In some embodiments, the Data Command Center of the present principles, such as the Data Command center 001 of FIG. 1, can provide, either via a medical records dashboard of the present principles or individually, a Medical Guidance tool to assist users/medical care providers to plan and schedule health services for patients. In some embodiments, the medical guidance tool of the present principles enables a scheduling of patients with automated methodology by, for example, prioritizing the risks of symptoms and diseases, and associating these with past procedures, diagnostic tests and other critical items that need to be evaluated. With such methodology, a medical guidance tool of the present principles guides users/medical care providers in determining, which patients needs the timeliest interventions, appointments and follow up. In some embodiment, the medical guidance tool is configured to examine patient records and information to determine if medications ordered, procedures ordered, follow up visits ordered and if a plan of treatment determined for the patient by a user/medical care provider are accurate or contain any errors.

Alternatively, or in addition, in some embodiments a medical guidance tool of the present principles can determine if a patient has missed an appointment and, in response, can alert a user/medical care provider to the fact that a patient has missed an appointment and/or can schedule a task for a user to at least contact the patient to schedule another appointment. In some embodiments, in addition to determining that the patient has missed an appointment, a medical guidance tool of the present principles can determine a level of risk presented to the patient's health by that patient missing the appointment. As such, patient's whose health is at a high risk by missing the appointment can be identified and contacted in an urgent manner to reschedule the missed appointment. In addition, the number of missed appointments can be tracked, whether the patient cancels or the practice cancels, and a pattern identified for the user/medical care provider.

In some embodiments of a medical guidance tool of the present principles, tasks can be generated for different users (e.g., doctors, staff, schedulers, etc.) and such tasks can be presented to different users depending on a determined level of risk or urgency to a patient. For example, doctors typically do no schedule follow up appointments for patients. Such task is usually performed by a scheduler. As such, typically scheduling tasks generated by a medical guidance tool of the present principles are generally directed to an identified scheduler. In some embodiments however, if a patient misses an appointment and the medical guidance tool of the present principles determines that missing the appointment presents an elevated risk to a patient's health, the medical guidance tool of the present principles can generate a rescheduling task that is now directed to the doctor. Alternatively, or in addition, the medical guidance tool of the present principles can generate an alert to be present to a user/medical care provider that the missed appointment presents an elevated risk to the health of the patient.

For example, in a scheduling embodiment, an integration module of the present principles, such as the integration module 002 of the Data Command Center 001 of FIG. 1, can collect patient data/information from outside sources (e.g., an EMR system). The patient data/information is made accessible, for example via a storage means, to a Rules module of the present principles, such as the Rules module 004 of the Data Command Center of FIG. 1. In addition to having access to the data/information collected by the Integration module 002, the Rules module 004 has access to all information input by a user/medical care provider via, for example, a medical records dashboard, such as the medical records dashboard 400. In some embodiments, the Rules module 004 is configured to further have access to patient related information and general medical knowledge including but not limited to medical information regarding health conditions and treatments, symptoms and side effects, procedures, images and diagnosis, and other related medical information. As such, in some embodiments, the Rules module 004 can monitor patient data/information and can be configured to monitor patient scheduling. As such, when a Rules module 004 determines that a patient has missed a scheduled appointment, by for example determining if a user/medical care provider has interacted with the patient that day or not by determining if any information has been entered into a medical records dashboard or other user system for that patient that day, a Rules module 004 can determine if a patient has missed a scheduled appointment. If the Rules module 004 determines that a patient has missed a scheduled appointment, the Rules module 004, via for example a Display module of the present principles, such as the Display module 006 of the Data Command center 001 of FIG. 1, can cause a display of an alert, to call to the attention of a user/medical care provider that the patient has missed a scheduled appointment. Alternatively, or in addition, the Rules module 004 can cause the scheduling of a task to be presented to a user/medical care provider such that a new appointment can be scheduled for the patient.

In some embodiments, having information regarding at least patient medical conditions, general and specific treatments and procedures, patient scheduling and other patient-related data/information, the Rules module 004 is able to determine if missing the scheduled appointment place the patient's health at an elevated risk. If so, the Rules module 004 can cause, for example via the Display module 006, a display of an alert, to call to the attention of a user/medical care provider that the patient's missed appointment results in an elevated risk to the patient's health. As described above, the determination of the elevated risk can cause the alert to be directed to a higher-level user such as a doctor instead of an administrator. In some embodiments of the present principles, the display of the alert itself can change and can be caused to be presented in a different color than usual or with other visual attributes, such as blinking or appear large on a display.

In some embodiments, a Medical Guidance tool of the present principles can assist in the scheduling of an appointment for a patient. For example, in an embodiment in which a scheduler is inputting patient data/information into an electronic system/spreadsheet/form, the Rules module 004 of the present principles can be configured to monitor such input patient data/information. Using the monitored input data/information and medical information known to the Rules module 004, the Rules module 004 can cause a display of a suggested appointment date to a user. For example, if a patient is known to have had a procedure performed and such procedure has a post-operative appointment typically scheduled for 30 days, the Rules module 004 can cause a display of a suggestion to a user that an appointment be scheduled for 30 days after the procedure was performed. In some embodiments, for suggesting an appointment, the Rules module 004 can further consider parameters such as time since a last procedure, symptoms since the last procedure, the doctor that performed the last procedure, medical history of the patient, the patient's disease state, and the like. In some embodiments, for new patients, the Rules module 004 can even take into account, who is referring the patient. If a patient referral comes from a doctor in a subspecialty that clearly would know what is an emergency, like another eye doctor, the Rules module 004 might suggest that an early appointment date must be made. In some embodiments, the Rules module 004 can create tasks for a user to make appointments on a suggested date or alternatively or in addition can schedule appointments without the need for a user intervention.

In some embodiments of the present principles, a Medical Guidance tool can assist in scheduling a patient to see a different doctor than the patient came to see. By way of example, in ophthalmology there may be in one office a general ophthalmologist, an optometrist, a retina surgeon and a glaucoma surgeon. A patient with diabetes and glaucoma may need to see the retina surgeon four times a year and the glaucoma surgeon three times a year. A scheduler for the practice or even the patient themselves can get confused as to which doctor to see. For instance, if the glaucoma doctor sees the patient and does not schedule the patient to return to the retina doctor, who handles another type of disease, not infrequently, patients can be totally lost, and the wrong provider is assigned to give care. While one provider may be taking care of one disease state, (i.e. glaucoma), the other states (i.e., diabetic eye disease or macular degeneration), can be inadvertently neglected. The same can be true in a multispecialty practice of internists, cardiologists, and pulmonologists. For example, an internist can have a good working relationship with the patient and sees the patient on a regular basis, however, the internist may not realize that the patient did not keep or ever get scheduled for an appointment with a cardiologist.

In some embodiments in accordance with the present principles, the Rules module 004, having knowledge of a patient's entire medical history, conditions, current procedures and treatments and having general knowledge of medicine and specifically the relationship between treatments and procedures of internists and cardiologists, can cause a display, for example via the display module 006, of at least one of an alert, suggestion and/or a task that causes the patient to be scheduled for an appointment with a cardiologist. A Medical Guidance tool of the present principles is able to determine when a patient is supposed to return for an appointment, what the high-risk scenarios exist, whether there was a procedure performed on a patient that requires a follow up with a particular doctor, whether a follow up appointment is kept by the patient, and is able to suggest or remind a user/medical care provider that they should consider sending a patient to another doctor. In some embodiments, not only are there indicators and alerts sent to the doctor who sees the patient, but indicator and alerts can be sent to an original doctor whose appointment has been missed, to a practice manager, or to anyone else in the practice to be able to determine whether a particular patient should be seeing a particular doctor or if the patient has been lost in the shuffle of so many visits. Such mistakes can happen in health systems and hospitals in which a patient who is not knowledgeable about medicine makes the assumption that each doctor talks to one another and shares records and therefore the patient assumes that if one doctor does not suggest that the patient sees another doctor, that the original doctor will be taking care of everything and the patient does not need follow-up care from a different doctor.

In some embodiments, a Medical Guidance tool of the present principles can monitor patient-related information intended to be reviewed by at least one user/medical care provider to determine if that information has been reviewed by the at least one user. For example, in some embodiments, the Medical Guidance tool, for example via the Rules module 004 can identify if results from tests ordered or notes from other medical care providers or any other "attachments" sent to for example a medical records dashboard, have been reviewed by all intended users/medical care providers for which they were intended. If the patient-related data/information intended for review by users/medical care providers has not been reviewed, the Medical Guidance tool can cause a display of an alert to the users/medical care providers that have not reviewed the patient-related data/information and for which the patient-related data/information was intended. Alternatively, or in addition, the Medical Guidance tool can create a task for at least one of users/medical care providers for which the patient-related data/information was intended and who have not reviewed the patient-related data.

For example, in a multispecialty practice, if the pathology results of a biopsy of a skin lesion was received and a family doctor sees the results, but the dermatologist who ordered the biopsy does not see the results, an alert can be sent out to either one or both of the doctors or alternatively or in addition, a task can be created for one or both of the doctors to view the results of the biopsy.

In some embodiments, a Medical Guidance tool of the present principles enables the pre-analysis of current and future patent visits. Such functionality enables users/medical care providers to prepare for patient visits and review scheduling of patients and test/procedures to determine if any errors exist. A user/medical care provider can review tests/procedures scheduled for a patient, when the patient last had similar tests, what patient's disease states are, what the likelihood is that the patient might need additional tests or another type of procedure, and even whether or not something might have been scheduled in error because information from the previous visit doesn't match up. For example, if a patient treatment plan indicates that an injection is to be done in the left eye, but the schedule says injection in the right eye, the Medical Guidance tool via, for example, the Rules module 004, can discover the discrepancy and cause an alert to be displayed to a user/medical care provider to warn of the discrepancy.

In some embodiments, a Medical Guidance tool of the present principles enables the post-analysis of patent visits. Such functionality enables users/medical care providers to pull up patient data/information related to visits of any past patients seen in any office or a particular patient seen with certain disease states or procedures or diagnostic tests and see what was done on any given time period or visit. Such functionality can be especially useful if a user/medical care provider references, for example, a medical records dashboard on the same day of a visit or shortly thereafter when the patients are fresh in their memory. During such review, a user/medical care provider can review to determine if their examinations were filled out correctly and that any diagnostic and/or procedural matters were performed and performed correctly and determine if any tests or orders were missed.

In some embodiments, a Medical Guidance tool of the present principles enables users/medical care providers to create a preferred practice method. For example, in some embodiments, a Rules module 004 is programmed with a preferred practice method of a user/medical care provider. The Rules module 004 can then provide services, such as assisting in the creation of appointments and determining if patients kept their scheduled appointments in accordance with the preferred practice method of the user/medical care provider.

In some embodiments, a Medical Guidance tool of the present principles enables a tracking of payments in accordance with the present principles. Current EMR systems require user driven reports to be run manually to identify items that have not been paid or are rejected by insurance carriers. Most insurance companies send payment for hundreds of separate patient claims on the same electronic check that is then posted automatically to many different patient accounts without inspection or review by a billing or staff member. This electronic process was developed to reduce workloads on staff who before were required to read the explanation of benefits and apply the payment manually to each individual claim item in the billing system, which allowed for greater oversight of incorrect payments and rejections.

In some embodiments of a Medical Guidance tool of the present principles, a Rules module, such as the Rules module 004 of the Data Command center 001 of FIG. 1, can be configured to monitor individual CPT codes in, for example in some embodiments, a medical records dashboard of the present principles, to identify when bills are not completely paid or are rejected. In some embodiments, if it is determined that a bill is not completely paid or rejected, the Rules module 004 can cause, for example via the Display module 006, a display of an alert to alert a user/medical care provider that a bill was not completely paid. Alternatively, or in addition, a task can be created for a user/medical care provider to correct the unpaid bill. In such embodiments, the Rules module 004 can have access to such information as specific insurance payors information, patients with high deductible plans, amount of billing, and the like. All pertinent data can be analyzed by, for example, the Rules module 004 and an indicator or a task can be created to alert the appropriate staff members and physicians enabling the users to make corrections rapidly. In some embodiments, based on user preferences, fully automated queries can generate indicators that can be viewed live while a patient is being treated.

In some embodiments of the present principles, a Medical Guidance tool of the present principles provides an electronic patient interface. For example, when a patient calls for an appointment or to ask questions or emails to schedule an appointment or ask questions, a user interface enables a patient to ask and answer questions, enter information, refill medications and the like. The reality is doctors often do not have the time to communicate with each and every single patient. In some embodiments, a Rules module of the present principles, such as the Rules module 004 of the Data Command center 001 of FIG. 1, having knowledge of all patient related data/information is also provided access to all information provided by a patient via the caller or email user interface. The Rules module 004 can evaluate every patient query in light of the information available to the Rules module 004. In some embodiments, the Rules module 004 determines if the patient is a current patient and if so, if the patient h had procedures or a risky diagnosis so that the Rules module 004 can present to a user/medical care provider a most complete picture of a patient as possible including which patients might be more problematic and urgent based on patient's symptoms, diagnosis, past procedures and other patient history In some embodiments the Rules module 004 can generate an alert directed to a user/medical care provider, the alert including the details of the patient developed by the Rules module 004. Alternatively, or in addition, the Rules module 004 can create a task for a user/medical care provider, the task including the details of the patient developed by the Rules module 004. If the alert/task is not responded to within a certain amount of time by the user/medical care provider, the Rules module 004 can generate another alert and/or task directed to another user/medical care provider to attempt to elicit a response for the patient.

Figure 57:
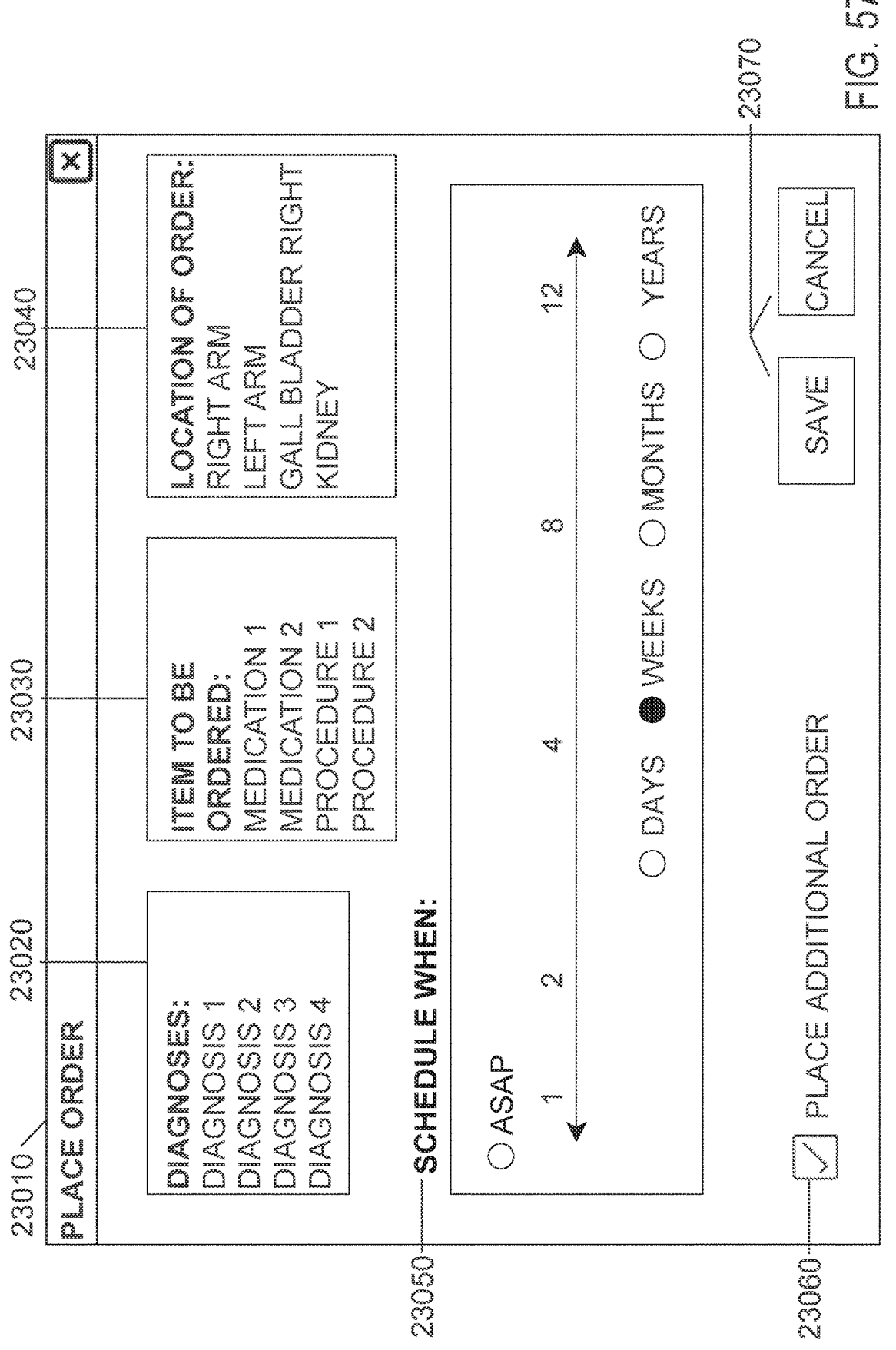
FIG. 57 illustrates an Ordering Panel with required Ordering Elements.

FIG. 57 depicts an example of an Ordering Panel of a Data Command Center of the present principles in accordance with an embodiment of the present principles. FIG. 57 illustrates the required elements for an Ordering Panel for the embodiment of FIG. 57. At 23010, an interface is available to place an order broken down into elements for placing a medical order in the context of Healthcare IT. Placing a medical order may include creating a medical order. Creating a medical order may also include reviewing or modifying a medical order. Diagnoses 23020 denote the condition or conditions of the patient requiring the ordered item. Codified in ICD-10 format or listed by common terminology, a healthcare professional can select one or more associated diagnoses for a patient. An item to be ordered 23030 can be a procedure, diagnostic test, medication, or other medical event for which an order is generally required. In addition to the event, a location can be required such as where on the body or which organ is to be the target of the order. This location can include specifications such as right or left side, which tooth, or other, more specific determinant than simply an arm or a leg. When placing an order, the date or duration can be specified 23050 to create an expectation of when the order is to be fulfilled. User Experience is also a factor in any technological solution, and as such, features can be included to enable easier use, access, or, in the case of 23060, the ability to place multiple orders without having to leave the order interface 23010. An order is completed, or placed, when a committal occurs, such as using the activation of the Save button, or ignored using the Cancel button 23070.

Figure 58:
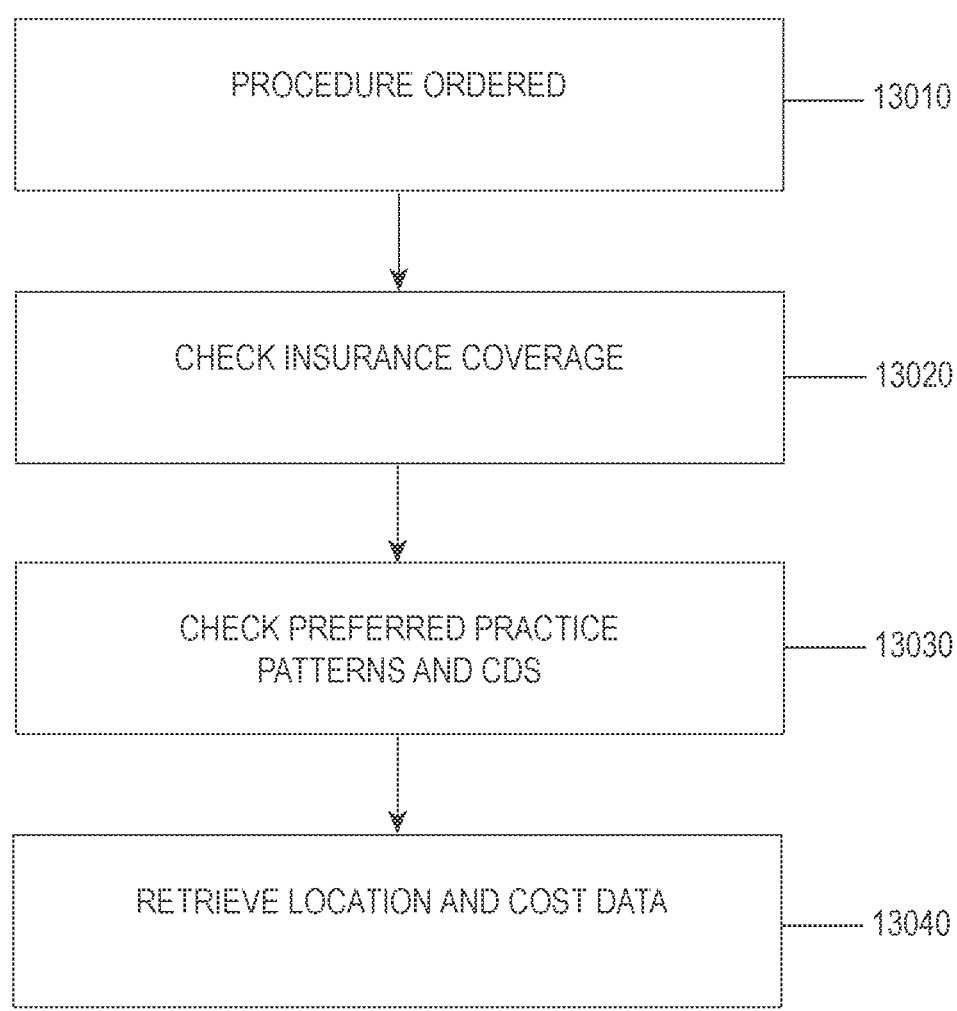
FIG. 58 illustrates generally the process for ordering a procedure in accordance with the tool described herein.

FIG. 58 depicts a flow diagram of an Order Processing method/algorithm in accordance with an embodiment of the present principles. For example, when a procedure is ordered at 13010, the Data Command Center of the present principles evaluates the insurance coverage at 13020. This process is described in greater detail below. Next, the Data Command Center evaluates the Preferred Practice Patterns and other clinical decision support rules at 13030. The last step in the process is to retrieve location, if applicable, and cost data 13040.

Figure 59:
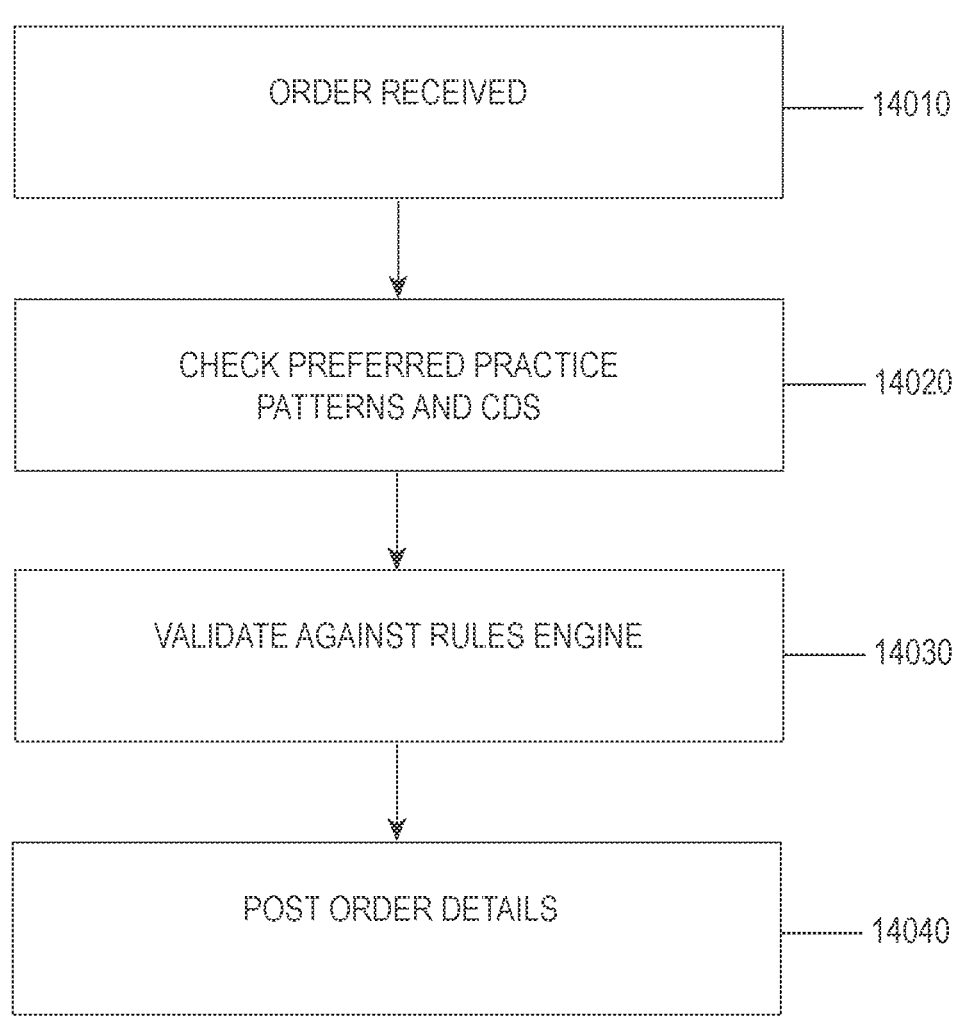
FIG. 59 illustrates generally the process for receiving an order in accordance with the tool described herein.

FIG. 59 depicts a flow diagram of an Order Receipt method/algorithm in accordance with an embodiment of the present principles. More specifically, FIG. 59 generally illustrates the process a Data Command Center of the present principles follows when order details are received from an external data source. When an order is received at 14010 the Data Command Center evaluates the Preferred Practice Patterns and other clinical decision support rules at 14020. Data gathered is then evaluated against the Rules Engine (for example 10180 of FIG. 3). Such processes are described in detail below with reference to FIG. 12. The last step in the process is to post and display relevant data to the user 14040.

Figure 60:
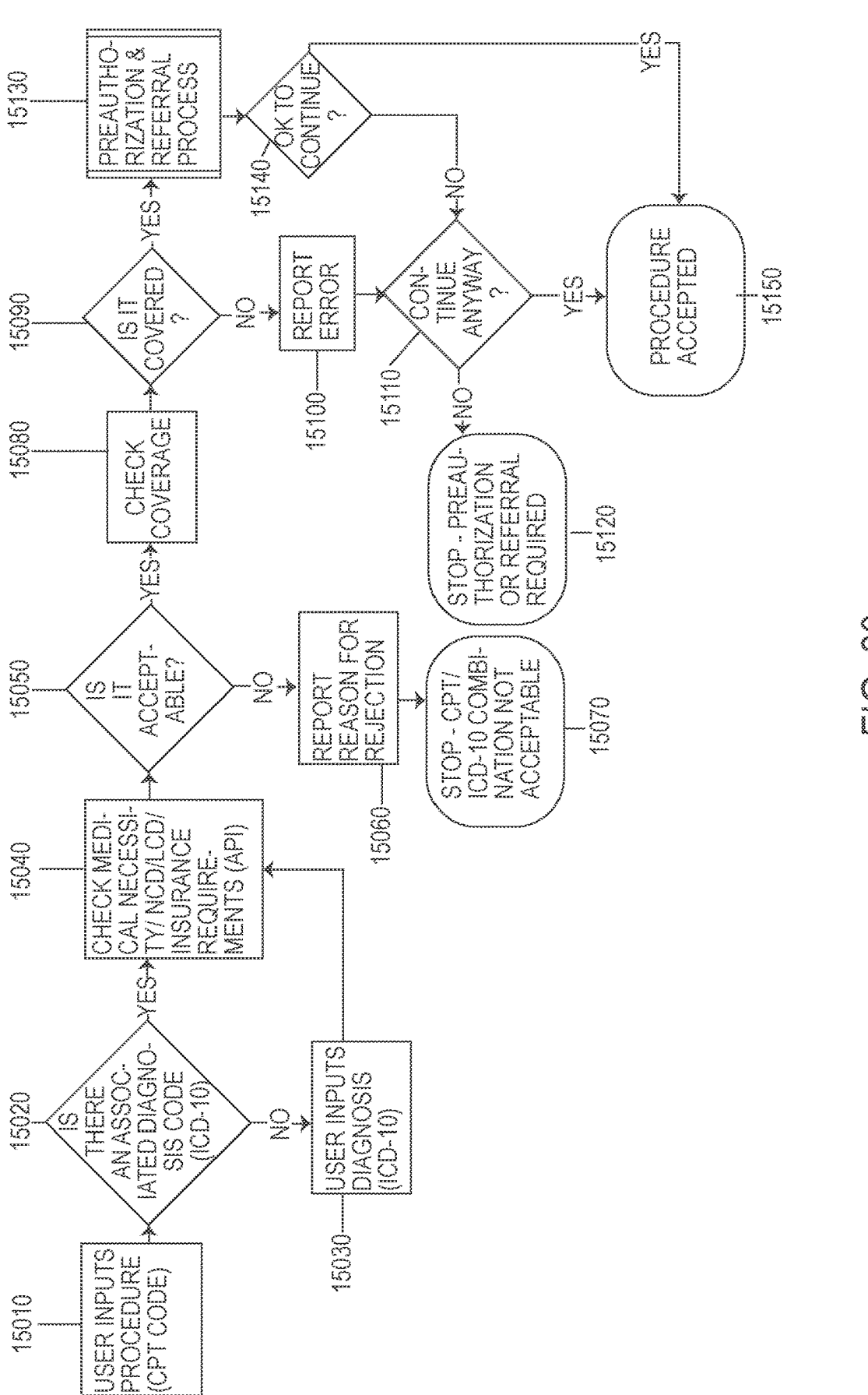
FIG. 60 illustrates the logic used to check for pre-authorization and/or a referral in accordance with the tool described herein.

FIG. 60 depicts a functional block diagram of the logic used to check for pre-authorization and/or a referral of an Ordering Process. As illustrated in FIG. 60, when a new procedure is ordered (15010), the Data Command Center reviews the input data (15020) for an associated ICD10 Diagnosis code. If no ICD10 Diagnosis code is found, the user is prompted to provide one (15030). Once the ICD10 Diagnosis code has been associated with the CPT procedure code, the Data Command Center evaluates the data against the applicable guidelines (15040) using a third-party API and determines if the combination of CPT and ICD10 codes is acceptable (15050). If the input is not acceptable (15040), the user is notified of the disposition and provided with a rejection reason (15060). A rejection will terminate the process (15070). On the other hand, if the input is acceptable (15050), the Data Command Center will review the patient's coverage (15080) for the procedure using a third-party API. If the procedure is not covered by the patient's insurance (15090), the system will provide the user with an error code (15100). The patient will then have the option (15110) to continue with the procedure (15150) (knowing it will be paid for out of pocket) or to decline the procedure (15120), which terminates the process. If the procedure is covered (15090), the preauthorization and referral process is invoked (15130). If the preauthorization and referral process (15130) does not approve the procedure (15140), the patient will again have the option (15110) to accept the procedure (15150) (knowing it will be paid for out of pocket) or to decline the procedure (15120), which will terminate the process. If the preauthorization and referral process (15130) approves the procedure (15140), the patient can move forward with the procedure knowing it is covered (15150).

Figure 61:
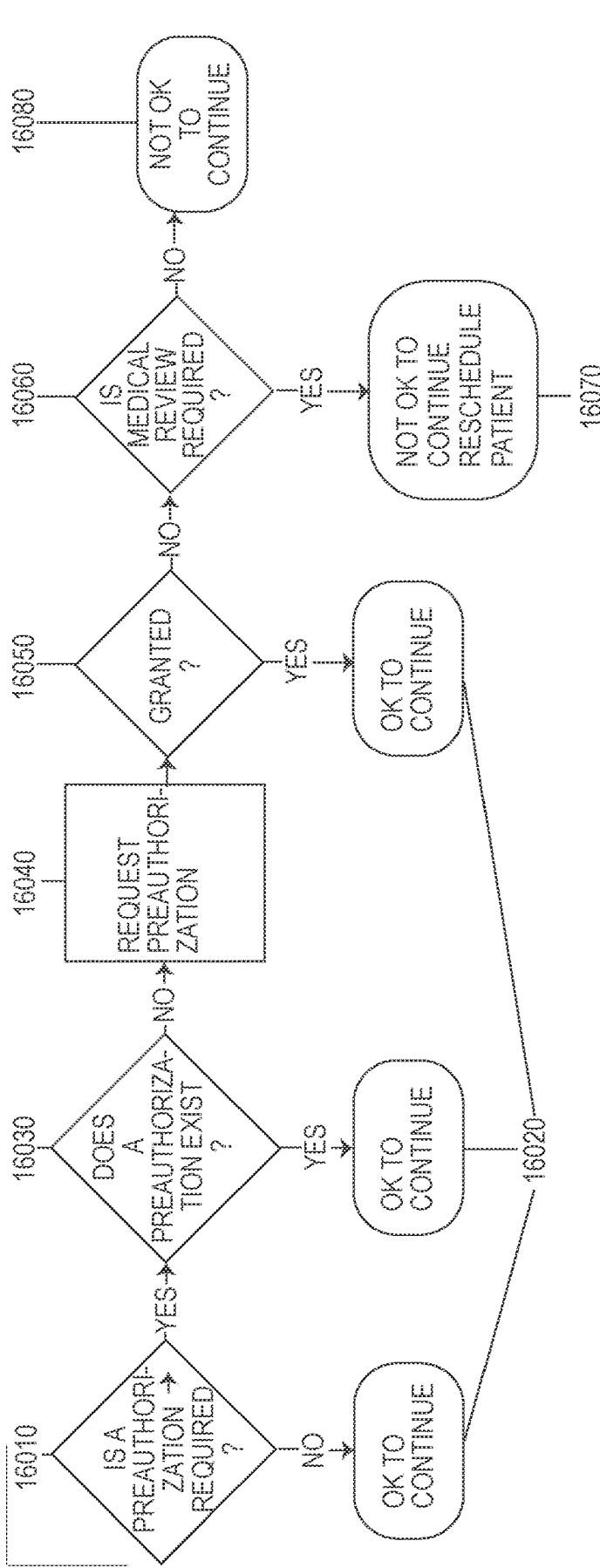
FIG. 61 Illustrates the precertification process that is invoked by presentation of a CPT Procedure code and an ICD10 Diagnosis code in accordance with the tool described herein.
Figure 62:
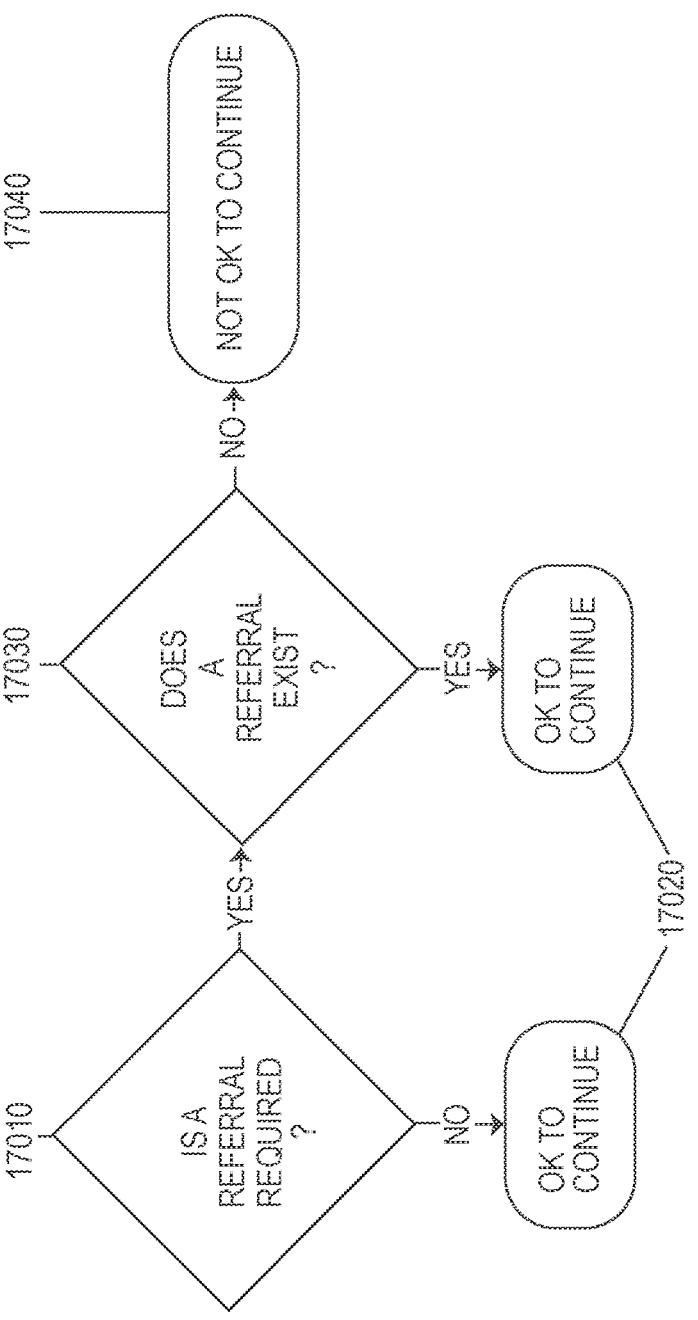
FIG. 62 Illustrates the referral process that is invoked by presentation of a CPT Procedure code and an ICD10 Diagnosis code in accordance with the tool described herein.

The preauthorization and referral process (15130) of the embodiment of FIG. 60 has two parallel processes, one which evaluates if the procedure requires preauthorization (FIG. 61) and another which evaluates if the procedure requires a referral (FIG. 62). The Precertification process described FIG. 61 is invoked by presentation of a CPT Procedure code and an ICD10 Diagnosis code. It is then determined using a third-party API whether or not a preauthorization is required (16010). If preauthorization (16010) is not required, then the process (16020) proceeds and the process returns an approval message (15140 from FIG. 60). If preauthorization 16010 is required, the system will then check for a pre-existing preauthorization (16030) using the third-party API. If a preauthorization exists, the authorization code is stored and the procedure can continue (16020)

and the process again returns an approval message (15140 from FIG. 60). If a preauthorization does not exist, the system will request a preauthorization (16040), again using the third-party API. If the request for preauthorization (16040) is granted (16050), then the process (16020) proceeds and the process returns an approval message (15140 from FIG. 60). If the request for preauthorization (16040) is not granted (16050), then the Data Command Center will evaluate if the request for preauthorization (16040) needs to go through medical review (16060). If the request for preauthorization (16040) needs to go through medical review (16060), then the process (16070) does not proceed and the process escapes to the negative path of 15140 in FIG. 60 to determine whether to continue anyway. If the request for preauthorization (15140) does not need to go through medical review (16060), then the process (16080) does not continue and the process escapes to the negative path of 15140 in FIG. 60 to determine whether to continue anyway.

The referral process illustrated in FIG. 62 is invoked by presentation of a CPT Procedure code and an ICD10 Diagnosis code. It is then determined using a third-party API whether or not a referral is required (17010). If a referral (17010) is not required, then the process (17020) proceeds and the process returns an approval message (15140 from FIG. 60). If a referral (17010) is required, the system will determine if a referral exists. If a referral exists (17030), then the process (17020) proceeds and the process an approval message (15140 from FIG. 60). If a referral does not exist, then the process (17040) does not continue and the process escapes to the negative path of 15140 in FIG. 60 to determine whether to continue anyway.

Figure 63A:
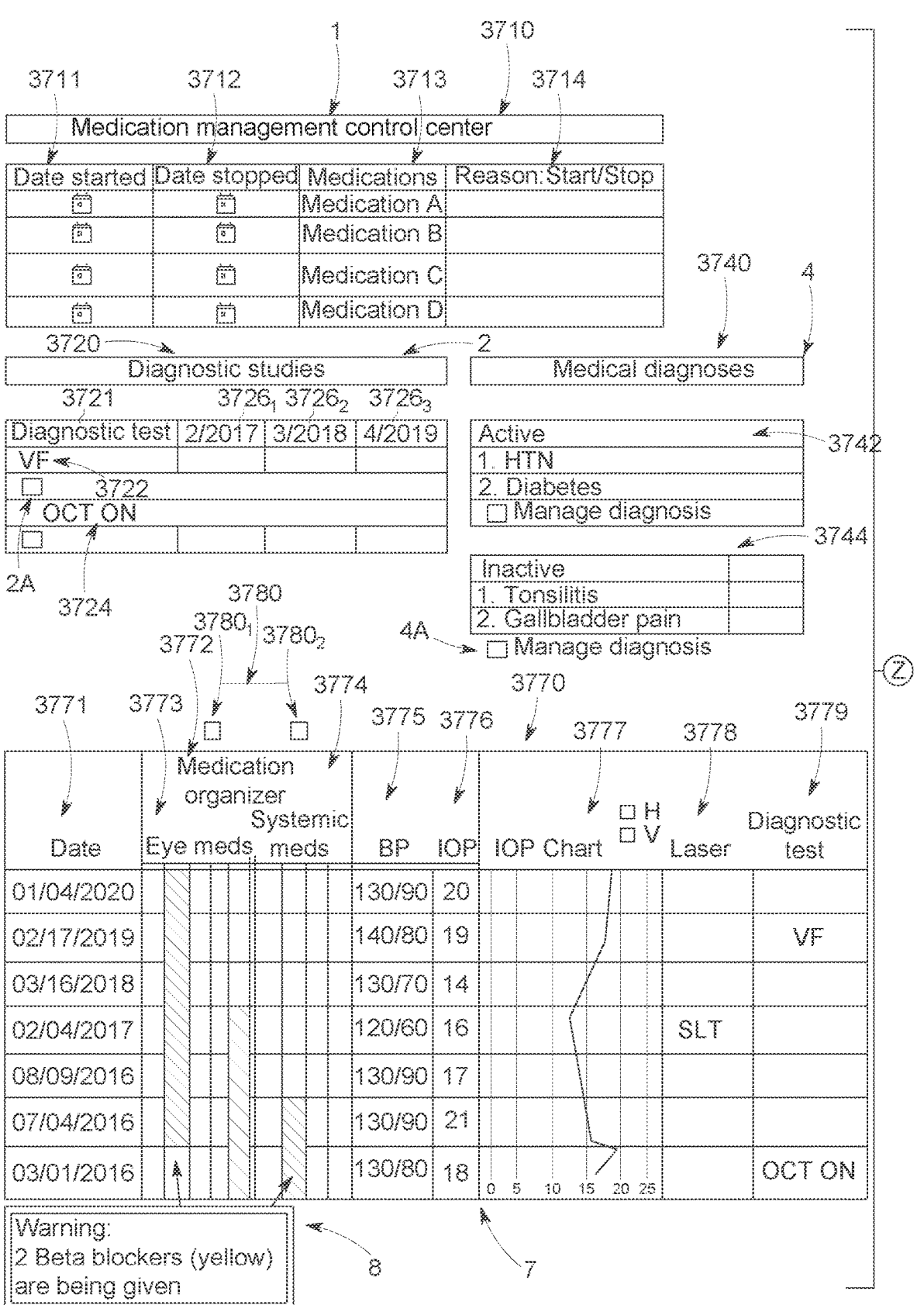
FIG. 63 depicts an exemplary embodiment of a Medications Management chart/tool which does not use rows or columns in accordance with an alternate embodiment of the present principles.
Figure 63B:
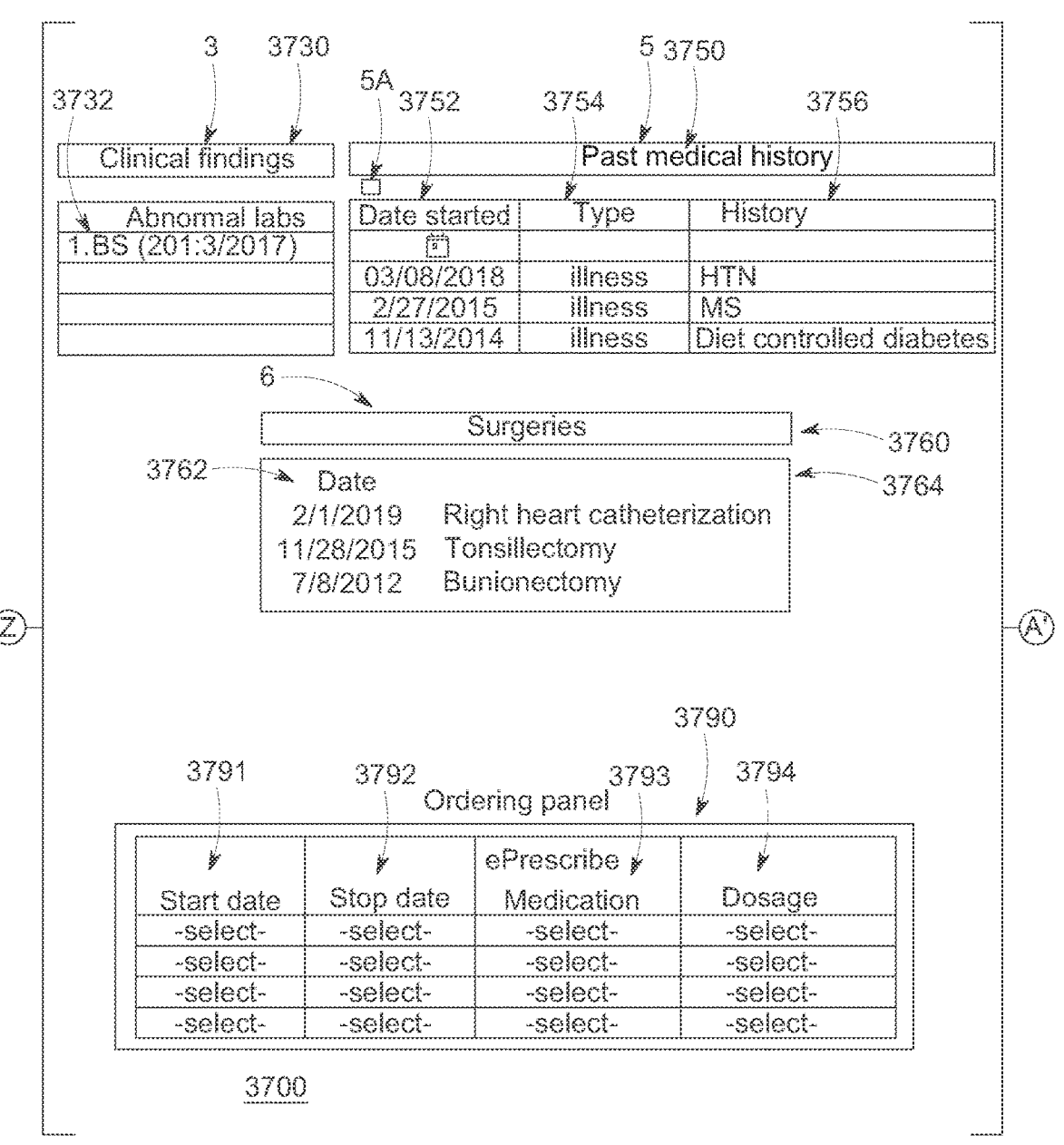

FIG. 63 depicts an exemplary embodiment of a Medications Management chart/tool 3700 which does not use rows or columns in accordance with an alternate embodiment of the present principles. Block 1 of the Medications Management chart/tool 3700 of FIG. 63 depicts a control panel 3710, which can be used to configure the bar graphs of block 7 and 8 described in greater detail below. The control panel 3710 of FIG. 63 illustratively comprises a date started column 3711, a date stopped column 3712, a medications column 3713 illustratively listing medicines A, B C and D, and a start/stop reasons column 3714.

Block 2 of the Medications Management chart/tool 3700 of FIG. 63 depicts a diagnostic studies menu 3720, which can be used to list diagnostic studies performed on a patient. The diagnostic studies menu 3720 of FIG. 63 illustratively comprises a diagnostic test column 3721, including a VF row 3722 and an OCT ON row 3724, and three date columns 3726₁, 3726₂ and 3726₃. In the diagnostic studies menu 3720 of FIG. 63, by hitting 2A, a user can pull up an individual test or get thumbnails of the tests performed on a patient. Block 3 of the Medications Management chart/tool 3700 of FIG. 63 depicts a clinical findings menu 3730, which can be used to list clinical findings on a patient. The clinical findings menu 3730 illustratively comprises an abnormal labs column 3732 for listing abnormal laboratory findings for a patient.

Block 4 of the Medications Management chart/tool 3700 of FIG. 63 depicts a medical diagnosis menu 3740, which can be used to list medical diagnosis made by a user for a patient. As depicted in the embodiment of FIG. 63, the medical diagnosis menu 3740 can be divided into active 3742 and inactive 3744 diseases. In the embodiment of FIG. 63, the various diagnoses or conditions of the patient can be managed on the screen by clicking 4A. Block 5 of the Medications Management chart/tool 3700 of FIG. 63 depicts a past medical history menu 3750, which can be used to list conditions that affect the well-being of a patient. As depicted in the embodiment of FIG. 63, the past medical history menu 3750 illustratively includes a date started column 3752, a type column 3754 and a history column 3756. In the embodiment of the past medical history menu 3750 of FIG. 63, by hitting 5A, a user is able to edit any of the information in the past medical history menu 3750.

Block 6 of the Medications Management chart/tool 3700 of FIG. 63 depicts a surgeries menu 3760, which can be used to list surgeries performed on a patient. As depicted in the embodiment of FIG. 63, the past medical history menu 3750 illustratively includes a date started column 3752, a type column 3754 and a history column 3756.

Block 7 of the Medications Management chart/tool 3700 of FIG. 63 depicts a dashboard 3770. The Dashboard 3770 of the Medications Management chart/tool 3700 of FIG. 63 illustratively comprises a date column 3771, a medication organizer column 3772 including an eye medications column 3773 and a systemic medications column 3774, a blood pressure (BP) column 3775, an intraocular pressure (IOP) column 3776, an IOP chart/graph column 3777, a laser column 3778, and a Diagnostic test column 3779. The Dashboard 3770 of the Medications Management chart/tool 3700 of FIG. 63 illustratively further comprises a respective ordering panel selection block 3780₁, 3780₂ for each of the eye medication column 3773 and the systemic medications column 3774. When a user selects either of the ordering panel selection blocks 3780₁, 3780₂, an ordering panel 3790 such as an E-prescribed panel is displayed that enables the user to place an order, which can include prescribing a medicine, and comes up in a way that does not block the entire view. The ordering panel 3790 illustratively comprises a start date column 3791, a stop date column 3792, a medication column 3793, and a dosage column 3794.

In the Dashboard 3770 of the Medications Management chart/tool 3700 of FIG. 63, the eye medication column 3773 and the systemic medications column 3774 include bar graph representations of medications associated with the treatment of a patient's eye. Illustratively, in the Medications Management chart/tool 3700 of FIG. 63, a user is being warned in block 8 that two beta blockers, depicted as yellow bars, are being given to the patient. Since there is a relationship between the two, the user needs to know.

Figure 64D:
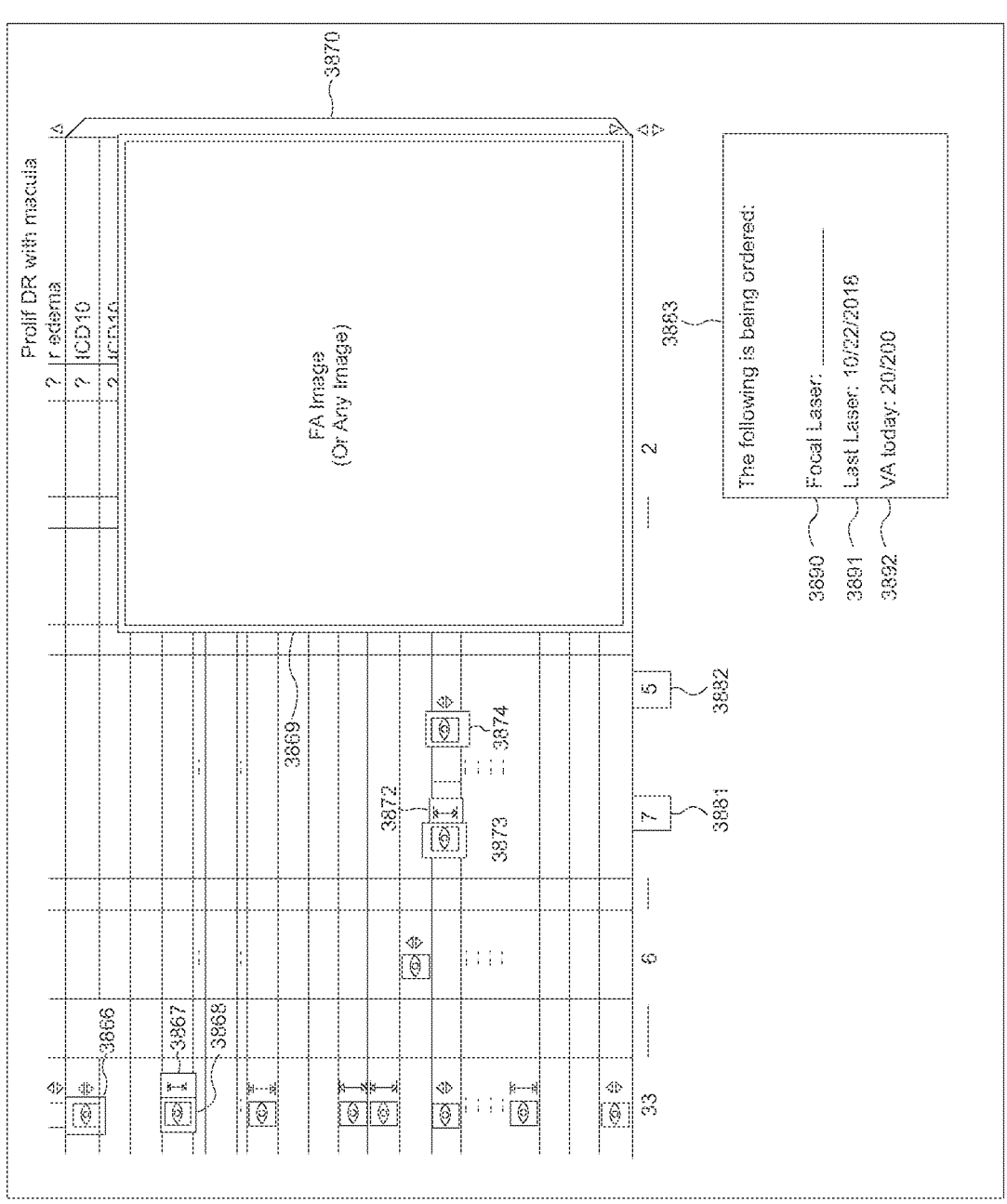
FIG. 64D depicts a fourth enlarged portion of the Data Command Center of FIG. 64.

FIG. 64 depicts an embodiment of a medical records dashboard of a Data Command Center in which a user/ medical care provider is enabled to place orders in context with other relevant patient data/information, so as to enable the user/medical care provider to see the future orders in context and confirm that the orders submitted are in fact what the user/medical care provider intends in accordance with the present principles. The details of FIG. 64 are being presented as FIG. 64A-FIG. 64D (collectively referred to as FIG. 64 below) to enable more clear visualization of the features of the embodiment of FIG. 64. In some embodiments, a column of the medical records dashboard can be expanded by selecting the column. For example, in FIG. 64, the column 3801 is expanded as depicted by window 3818 to allow for room for placing an order. In some embodiments, the window 3818 can comprise a pop-up panel for placing orders. In FIG. 64 cells 3804, 3818, and 3839 depict examples of cells displayed in the medical records dashboard that are in the line and above corresponding columns that identify that orders have been made and/or enable the placement of new orders. For example, cell 3804, as depicted in expanded FIG. 64A corresponds to a panel that can be used for placing orders for a right eye (OD) 3803 and is located directly above procedures 3877 performed in the past for the right eye (OD). Another example is the ordering panel 3839 which is above the FA column. Illustratively, in the FA column, a user can identify when the last time something was performed, enabling a user/medical care provider to determine if it is time to order a new procedure. From the medical records dashboard of FIG. 64 it can be determined from row 3871 that the last FA 3873 was done (3/7/19) and the FA in the header cell 3839 depicts that the last FA, was 195 days ago as depicted in cell 3840. In the embodiment of the medical records dashboard of FIG. 64, a user is enabled place an order while visualizing a particular CPT codes (diagnostic test, procedures, office visit, etc.) ordered in the past and can visualize how often it was performed, when the last time it was performed. In FIG. 64, an illustrated FA 3839 in row 3876 reports the total number of times the item to be re-ordered was previously performed. In the example of an FA shown in cell 3881 of FIG. 64 an FA was performed seven times, in the right eye. In FIG. 64, cell 3882 depicts that an FA was performed five times in the past in the left eye.

As described above, in the embodiment of FIG. 64, expansion of an ordering panel can occur in both in height and in width. In some embodiments, to enable the expansion of an ordering panel, columns that are considered by a user/medical care provider as unnecessary can be collapsed to enable viewing expanded ordering panels in context with information deemed necessary. For example, a clinical measurement, such as vision measurements in columns 3810, 3809, 3811 can be collapsed if a user determines such information is not currently needed, enabling horizontal expansion of ordering panels. In some embodiments, the ordering panels 3839, 3813, 3804 can widen when the user/medical care provider clicks on them to then place an order to enable a user/medical care provider to simultaneously visualize, using a single display, data relevant to the newly placed orders. In accordance with embodiments of the present principles, the display 3830 remains interactive during the display of the ordering panels to enable a user to scroll down to see past FA performed, for example, prior to the 10/18/18 row 3830 of FIG. 64 depicts a search mechanism enabling the user to type in or ask any questions and whatever rows with the relevant data would be the rows visualized with other rows collapsed or hidden. For instance, Cell 3881 depicts that seven FA were done yet only the FA done 03/07/19 3871 is displayed in this single view but all seven dates of service when 3839 were performed, the tool would display those rows for instance clicking on cell 3881 to display may be important as a user is ordering a new FA. In this way, as the user orders, for example, an FA, the user is able to visualize what was done in the past.

In the embodiment of FIG. 64, an FA can be ordered by activating ordering panel 3839 to expand the panel. The user could then decide if what the users want displayed in hat column, 3839 is just the most recent FAs, in FIG. 64 depicted by cells 3874 and 3873 in row 3871. A user, alternatively, could scroll down and find the other FAs for the earlier dates or by clicking on cells 3881 for the right eye or 3882 for the left eye or the tool can be programmed to show all the past dates that the particular test or procedure was performed. Embodiments of the present principles enable a user to search as depicted in cell 3830 or to scroll to display the seven FA rows. In some embodiments, all of the rows and dates of service can be collapsed to make room to display today's visit in, for example, cell 3848. That is, because an action is being performed by a user, a current row can remain visible. A next visit then can be displayed in a follow up cell 3847 and a future order cell 3846 can become visible, as the user places orders for different future dates of service with row popping-up as user places orders for each future visit. Alternatively, in the embodiment of FIG. 64, a user can prioritize the visualization of rows/cells depicting when FA was performed and collapse other rows/cells by clicking on icon 3852, which enables a collapsing of all rows except the rows when an FA was performed.

In the embodiment of the medical records dashboard of FIG. 64, if a user/medical care provider wants to double check if an order placed is proper and wants to see a related study itself, the user/medical care provider can select cells 3874 and a respective image can be displayed in 3869 so the ordered study can be interpreted in context of all other information being presented in the medical records dashboard. The user/medical care provider can view directly, an image or even choose multiple icon images of, for example, the FA. The ordering panels that are displayed when selected (i.e., 3801 or 3839) can be customized by specialty, for example in FIG. 64 for a retina specialist. In the embodiment of FIG. 64, a retina specialist can perform injections on a patient, as such in accordance with some embodiments of the present principles, the retina specialist can be presented with an option to perform the FA before an injection, 3843. In such embodiments, the injections are not hidden and can be seen in column 3807. The scheduling for the test (e.g., FA 3839) can then be accomplished by activating cell 3861, at which point an option for selection can be displayed (i.e., 3837) and the user can select form a pull down menu how far in the future (illustratively one month 3836) to order the study.

In some embodiments, a Rules module, such as the Rules module 004 of the Data Command center 001 of the embodiment of FIG. 1, can be configured to determine if a patient's insurance company will disapprove of ordered studies and can further be programmed to determine if a patient has an aversion to an ordered study and can cause a display, for example via the Display module 006, of an alert or information window on the medical records dashboard to inform a user/medical care provider of such instances.

In the embodiment of FIG. 64, cell 3813 can be used to order an OCT test. For example, cell 3814 can be selected by a user to select a left eye then OCT (OS), cell 3826 selects a next visit, and cell 3827 can be selected for choosing a time period. In some embodiments, a Rules module, such as the Rules module 004 of the Data Command center 001 of the embodiment of FIG. 1, can have access to a storage means containing rules for scheduling tests (i.e., certain tests have rules for how often the tests can be performed on a patient) and the Rules module 004 be configured to determine if tests/studies have been improperly ordered. In such instances, the Rules module 004 can cause a display, for example via the Display module 006, of an alert or information window on the medical records dashboard to inform a user/medical care provider that perhaps a test/study has been improperly ordered via, for example, a pop-up window 3831.

In the embodiment of FIG. 64, a user/medical care provider is enabled by the medical records dashboard to select a reason for ordering a test or procedure. In the embodiment of FIG. 64, cell 3859 can provide a menu providing options for a user to select for inputting reasons for ordering a test or procedure. In some embodiments, such options provided to a user in cell 3859 can be pre-programmed. Alternatively or in addition, a Rules module, such as the Rules module 004 of the Data Command center 001 of FIG. 1, can be programmed to monitor data/information related to a patient including, but not limited to, previous diagnosis made, previous tests ordered, previous procedures ordered and respective reasons for ordering the tests and procedures, and the Rules module 004 can be configured to learn, for example, through machine learning and/or artificial intelligence means to determine at least a best reason for ordering tests and procedures depending on relevant patient information. In such embodiments, the Rules module 004 can cause the display, for example via the Display module 006, of most logical reasons for ordering a test or procedure in, for example, a drop down menu provided by cell 3859 of the medical records dashboard of FIG. 64. For example, the Rules module 004 can be aware of what CPT codes can be associated with ICDs for a particular patient for which test and/or procedures are being ordered and the most logical diagnostic codes can be presented, for example in cells 3833, 3834, and 3835. In the embodiment of FIG. 64, if a user/medical care provider is unsatisfied with the reasons for ordering provided in, for example, a drop down menu provided by cell 3859, the user/medical care provider can select cell 3832 to see more options or to insert a reason for ordering.

In the embodiment of the medical records dashboard of FIG. 64, a user/medical care provider can select using for example cell 3814, for which eye a test/study/procedure is to be ordered. A diagnosis and information regarding what is ordered is displayed in rows 3848, 3847, 3846, 3845, and 3844, collectively 3817 depending on when the order is scheduled. The user can visualize the order, then by any means, confirm it is correct, by selecting cell 3814. The user/medical care provider is able to confirm everything in a row displayed is correct as visualized and confirm the order for that entire future date of service by selecting cell 3819. In the embodiment of FIG. 64, a user can be informed of what is being ordered by displaying in a corresponding row, an empty icon or empty box, for example 3960 of 3846. If the doctor wants to also order an OCT in the right eye, cell 3812 can be selected and the process repeated.

In the embodiment of the medical records dashboard of FIG. 64, cell 3870 shows all past encounters of relevance in which a user can view all of the information by scrolling or viewing on a single display. Cell 3870 keeps track of every encounter and a date and/or time of the encounter, any medical service, ICD 10 with diagnosis or clinical information or procedural information. Cell 3876 includes a summary of how often orders have been placed in any period of time. Row 3848 depicts information regarding "today's visit." Today's visit can be live and in real time in some embodiments. Clinical information, i.e. in this example vision (1A), can be displayed as it is input in corresponding columns 3810, 3809, 3811. Column 3807 depicts what is to be done today and in the embodiment of FIG. 64 depicts an injection with medication 3853, "Eylea sample." Cell 3854 of FIG. 64 depicts that the procedure was to be performed 28 days ago, which, as described above, can be checked by the medical records dashboard for compliance.

In the embodiment of FIG. 64, row 3848 shows under column 3814 an OCT and an empty box 3858. Such configuration can indicate to a user/medical care provider that the ordered procedure/test/study has not yet been performed because in the embodiment of FIG. 64 the order was scheduled in "today's visit," meaning that the user/medical care provider placed the order today. In comparison, cell 3866 is filled in because on the last visit the test had been performed.

In some embodiment of the present principles, an appearance of the cells of the medical records dashboard can be altered to distinguish/highlight the information in the cells.

For example, in the embodiment of FIG. 64, cells 3860, 3862, 3863, 3850, 3851, 3849, 3852 are examples of cells containing future orders. In some embodiments, cells can be made lighter or darker to differentiate past versus future actions/orders. In addition, and for example, row 3848 of "today's visit" can be made blue. Even further, in some embodiments of the present principles, icons or markers can be included in cells/rows/columns of the medical records dashboard to enable a user to make a determination of the information included in a cell just by looking at the icon/marker. In some embodiments, the icons/markers can also include color to further distinguish between information represented by the icon/marker. For example, icons 3865, 3880 can be shown as colored indicators to indicate a status of the condition of a user's eye described in cell 3867 and 3872.

In the embodiment of the medical records dashboard of FIG. 64, related cells can be highlighted or otherwise emphasized to call a user's attention to relevant patient data when placing an order. For example, cell 3822 enables a user to order a laser. Cell 3850 depicts that a focal laser is to be ordered in the future. In conjunction, cell 3877 can be highlighted or otherwise emphasized to alert the user/medical care provider of the last time a similar focal laser was done. In addition, cell 3879 can be highlighted or otherwise emphasized to alert a user what the vision of the patient was at the time of the last laser performed Oct. 22, 2018. As such, a user/medical care provider can take into account related patient data as they place an order for a focal laser in cell 3803 as displayed in cell 3850 for a follow up row 3846, as scheduled by any means, byway of example, within the pop-up window 3803. By noting a previous condition of the vision of a patient in accordance with the present principles, a user can identify if a patient's condition is getting better, worse or remaining the same. For example, in the embodiment of FIG. 64, icons 3865 and 3897 show red indicators to indicate a worsening of a condition of a patient's eye.

In another example of placing orders, as described above a medical records dashboard of the present principles, via for example a Rules module, can be aware of what the most common ICD10 might be (i.e., via cell 3832) when ordering. Cell 3842 depicts a user selecting a box and an order can be directly linked to the box the user selects, which can be displayed in a pop-up window as depicted in cell 3827, 3861, and 3836. The future encounter can be selected and confirmed in cell 3828 and the next encounter ordered in cell 3829, which in this embodiment means another date of service in the future is to be ordered and displayed, and the process starts again. This functionality enables users/medical care providers to confirm future orders by reviewing available patient related data being simultaneously displayed in the medical records dashboard.

As depicted in the embodiment of FIG. 64, the medical records dashboard can include panel 3878 for assisting a user/medical care provider in placing an order. That is, in some embodiments, when a user/medical care provider is placing an order, panel 3878 can be presented to the user/medical care provider to present to the user/medical care provider a list of things that the user/medical care provider should take into considerations when placing an order. In the embodiment of FIG. 64, the panel 3878 includes considerations such as 3884 a diagnostic test that was done today or on a previous visit, 3885 clinical findings found today, 3886 a last time the same or similar test/study/procedure was done, 3887 insurance issues, 3888 allergy concerns, and 3889 possible interactions with other tests and/or medications. A Rules module, such as the Rules module 004 of the Data Command center 001 of FIG. 1, can be configured to monitor such considerations and alert a user/medical care provider if a problem is determined. Although the panel 3878 of FIG. 64 depicts a specific listing of considerations in panel 3878, in alternate embodiments, the considerations listed in panel 3878 can change dependent upon what is being ordered.

As depicted in the embodiment of FIG. 64, the medical records dashboard can include panel 3893 for assisting a user/medical care provider in placing orders. That is, in some embodiments, when a user/medical care provider is placing an order, panel 3883 can be presented to the user/ medical care provider to present to the user/medical care provider an order summary. In the embodiment of FIG. 64, the panel 3883 includes a listing of 3890 what is being ordered, 3891 a last date the same procedure was performed on the patient, and 3892 any relevant clinical information. Although the panel 3883 of FIG. 64 depicts a specific listing of related order information in panel 3883, in alternate embodiments, the order related information listed in panel 3883 can change dependent upon what is being ordered.

Figure 65A:
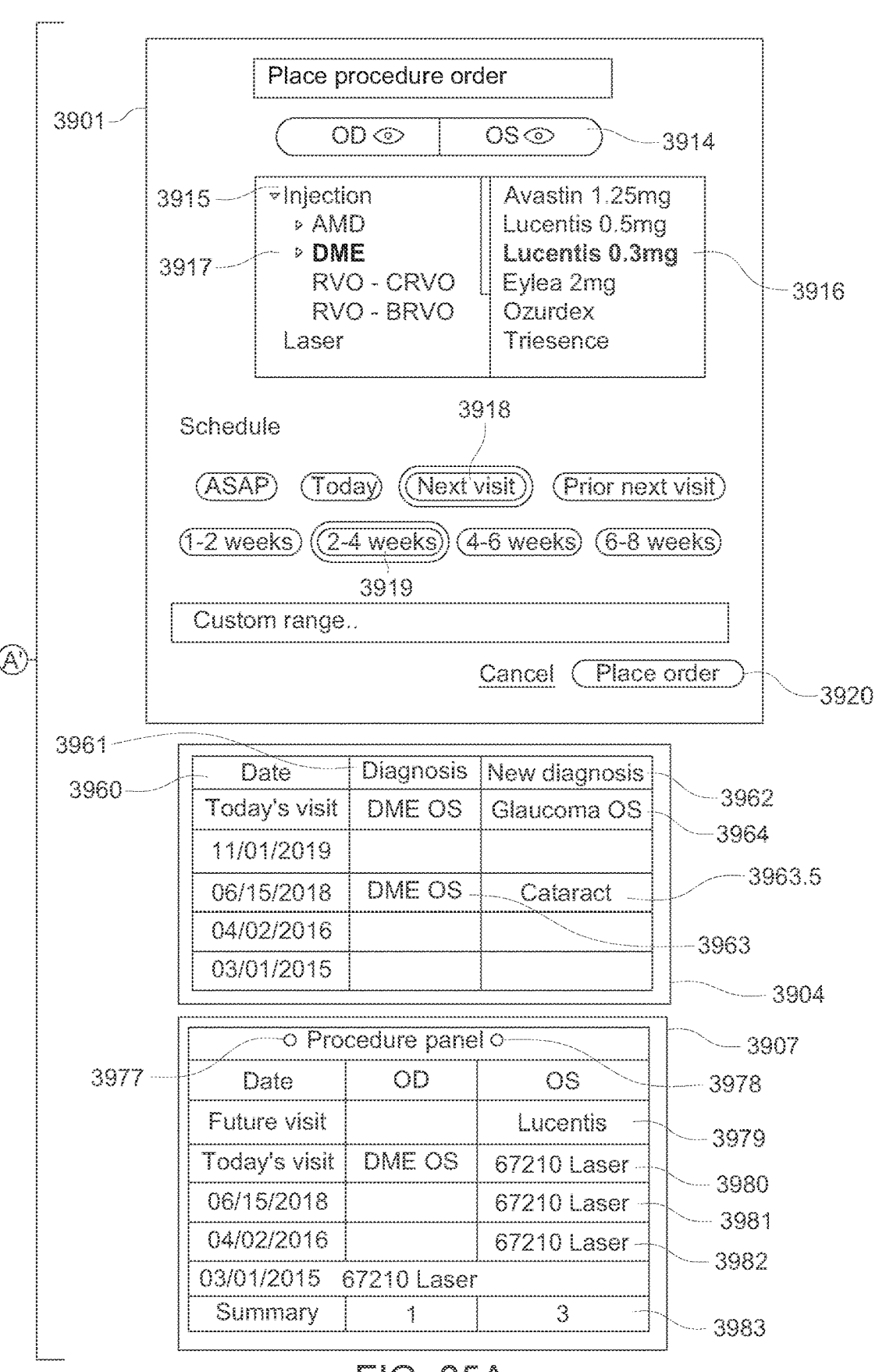
FIG. 65 depicts an embodiment of a medical records dashboard of a Data Command Center in which a user/medical care provider is enabled to place orders in context with other relevant patient data/information, so as to enable the user/medical care provider to see the future orders in context in an embodiment not using rows and columns in accordance with the present principles.
Figure 65B:
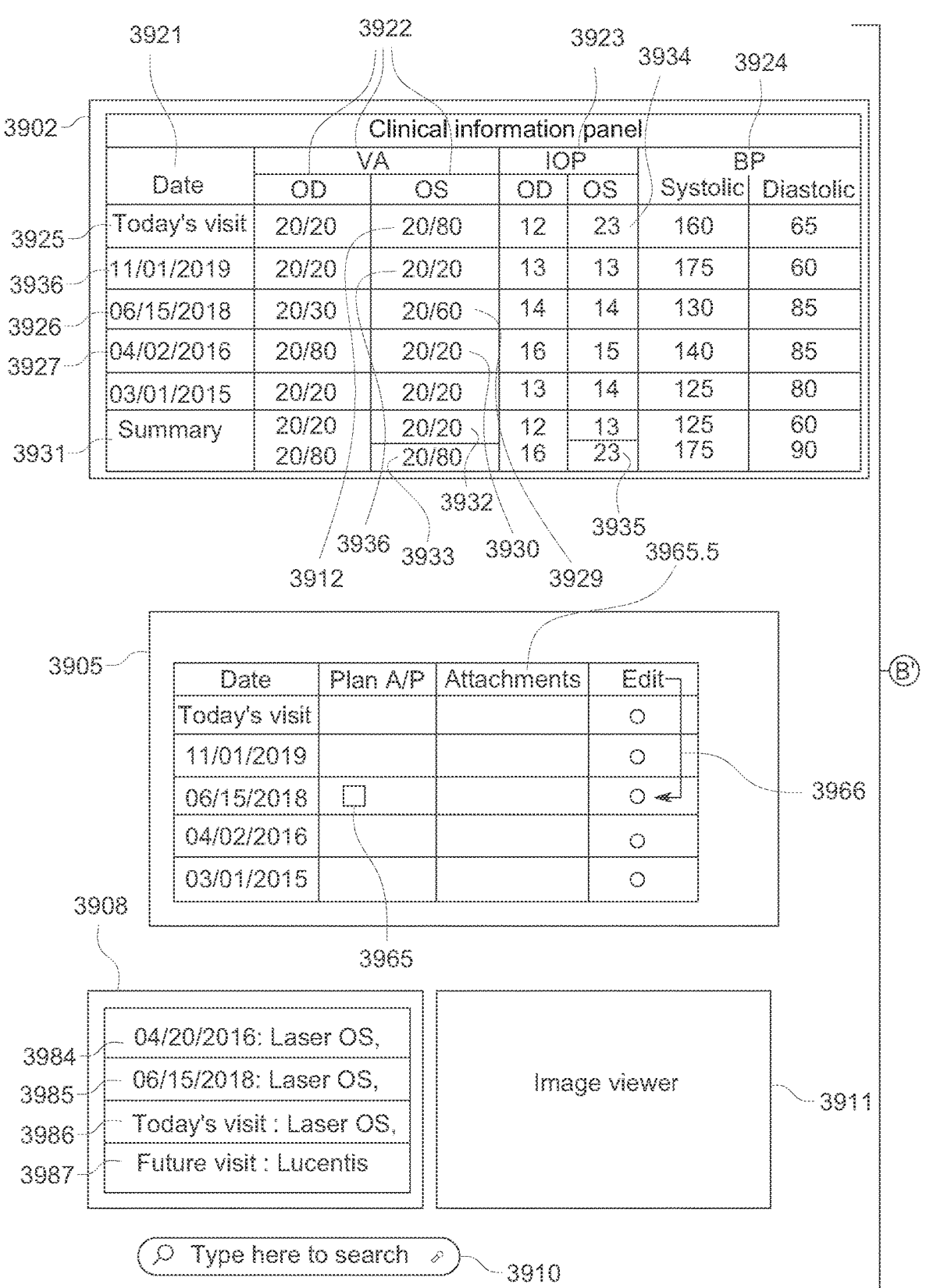
Figure 65C:
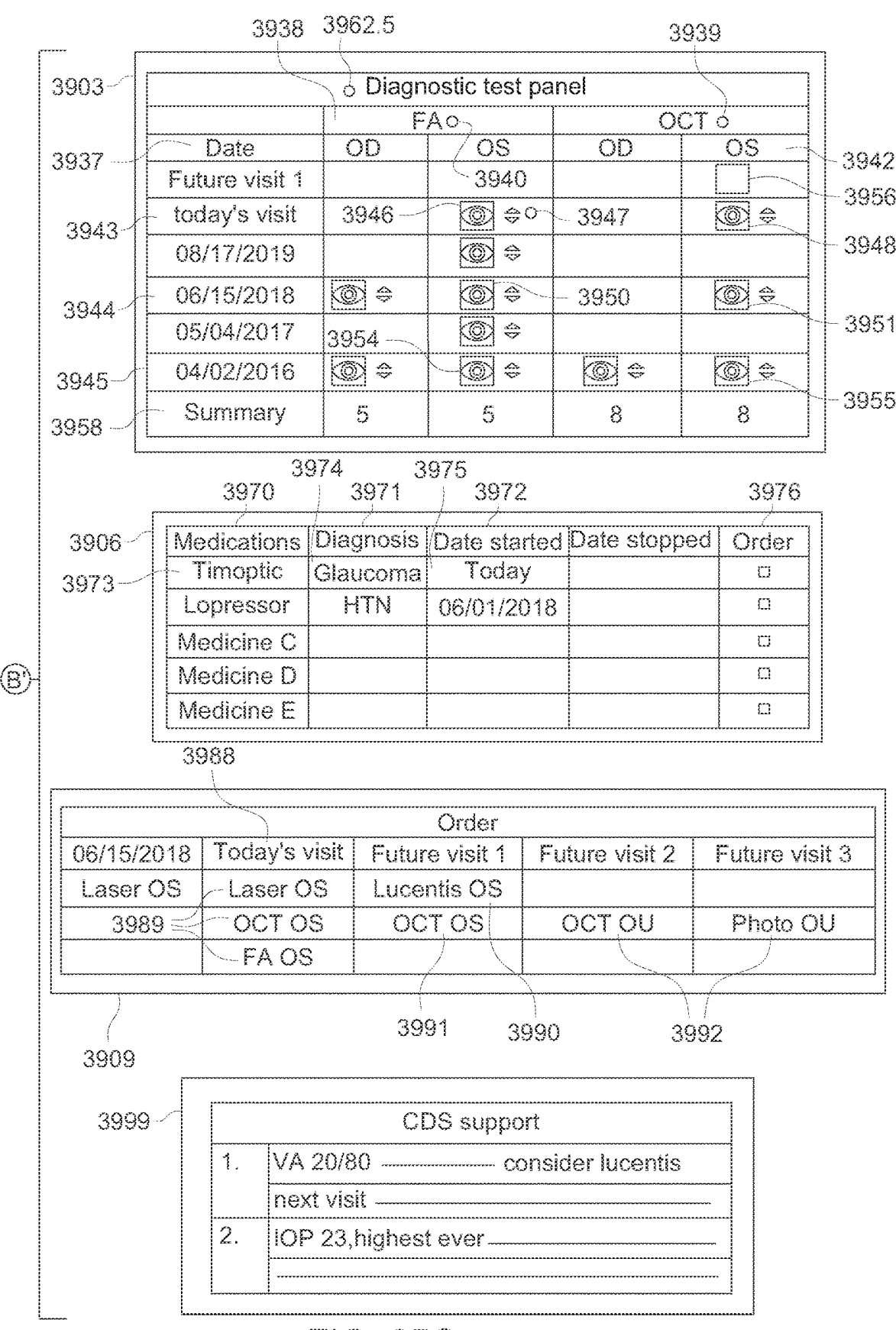

FIG. 65 depicts an embodiment of a medical records dashboard in which a medical care provider is able to place orders in context, so as to enable the user to order as well as visualize orders placed, today or in the future with relevant data displayed. Clinical data, diagnostic tests and procedures are correlated, so at a glance doctors can determine what orders are needed, and then the orders are inserted in sequence, allowing for confirmation of the accuracy of the order placed. EMR companies have data dispersed throughout the EMR on separate windows. When EMR companies do present data on the same view, the information is difficult to compare and only are the same category of medical services correlated to each other. One embodiment of the invention compiles relevant data across categories of medical services as an order is placed on a dashboard in rows and columns. This new embodiment displayed in FIG. 65 allows for ready identification and tracking of relevant data of different medical services i.e. clinical data, examination data, procedures performed, diagnostic tests and even billing information, in separate modules or panels all uniquely correlated. This invention allows the options for multiple areas to be displayed with different data sets grouped into multiple panels or modules with related data generated and configured and highlighted or otherwise emphasized to allow for efficient correlation by the user. Zooming, scrolling, and searching functions are enabled so user can see information that they want to see. Some embodiments where EMR systems require opening multiple windows or separate displays, the invention will highlight the relevant information no matter where the data is located.

FIG. 65 illustrates the modules all on one display with one user interface allowing the user a bird's eye view while highlighting relevant related information. Element module 3901 displays one means for an order for a medical service to be created by the doctor during today's visit or for a future visit. This ordering panel does not always have to be displayed. In fact, its contents and options for ordering change based on the context. There are many different ways to access and generate this overlay, element 3901. It can occur, for instance, by clicking on 3939 or, 3940 in element 3903, which is diagnostic testing module. So, accessing the ordering mechanism panel through particular panel specific data, would change the context for generating the overlay in panel 3901, and the information contained and input and output from element 3901 would be different. If instead of accessing 3901 from elements 3939 or 3940 within the diagnostic test module 3903 was instead generated from 3978 in element 3907, which is a panel displaying data for procedures, 3901 would generate an entirely different overlay or window with different information, rules, and analytics specific to ordering procedures. In fact, displayed in 3901 is an example of ordering mechanism for a particular type of procedure, an injection of a medication called Lucentis, 3916. Another example where the context of the ordering mechanism of 3901 would generate entirely different set of orders and rules is if 3976 were clicked in the module 3906 which is dedicated to data on medications.

Panels 3902-3906 can display relevant data related to the order being placed in 3901 so that doctors can make efficient and accurate medical decisions for a patient. In addition to displaying relevant data, the order created in 3901, can be displayed in the correct logical location, so the doctors can confirm the orders they are placing are correct. The orders can be displayed, in a variety of formats with panels generated to display the order with other relevant past, present or future orders such as seen in panels 3907, 3908 and 3909. Relevant data is displayed in 3902-3906 to allow for the orders to be placed in context with the doctor visualizing relevant data.

In FIG. 65, element 3902 depicts where clinical data of any kind can be displayed with relevant data over a period of time. 3921 shows the time of the measurement of the clinical or examination data. 3922 illustrates a vision (VA) measurement with vision results separated into right (OD) and left (OS) eyes. 3923 is a pressure of the eye (IOP) column that can also be separated into right and left eye. 3924 is an example of another clinical measurement BP (blood pressure). Element 3903 shows a diagnostic testing panel, which can include any type of medical service most commonly represented by a CPT code. Displayed are examples of diagnostic tests. In the medical field examples include pathology results, chemistries, photographs, radiological procedures. The diagnostic tests displayed are 3938, an FA (Fluorescein Angiography) separated into OD (right) and OS (left). 3942 shows an example of a diagnostic test column of the left eye for a diagnostic test called OCT (Optical Coherence Tomography). By clicking any of the icons, for instance 3946 or 3950 the underlying data or images of diagnostic tests can be viewed, displayed, and compared in the image viewer 3911. An interpretation of the test can be viewed or entered by the doctor by clicking on 3947. These icons, 3957, in addition to providing a mechanism to pull up directly the image or test, can demonstrate that a test was done, but also in limited space convey additional information such as a worsening highlighted or otherwise emphasized for instance in red or improving test highlighted for instance in green. 3958 is a summary that can display the total number of a particular test performed in a patient. 3954 shows a total of 8 of test 3957 were performed over time for this patient. Displayed however is just one such test, 3957 because other tests are not relevant to issue being displayed to the doctor. However, the doctor can have access to the other 7 of 3957 by clicking in some embodiment on 3959.

An order for a particular diagnostic test today's or for a future visit can be ordered by any means, but displayed is one example by clicking 3940 or 3939 and either a means to order that test is accessed in 3901 or in 3903, through a mechanism described in FIG. 64, for instance, Element 3818. 3942.5 shows an area the doctor can click if they want to know financial information about any diagnostic test. A column next to each diagnostic test can be displayed which shows cost and payments which may help a doctor in deciding what to order in the future as perhaps some insurance will not pay for certain tests. 3904 shows a panel that displays patient's diagnosis or problem list or other data. 3960 is the date a diagnosis was recorded. 3961 is the diagnosis and 3962 is a column if the diagnosis is new and not recorded for this patient before.

3905 displays a panel that shows a means that a doctor's assessment and plans can be seen and directly accessed by clicking 3965. The plan can come up anywhere on the screen for instance over 3905 or 3911. All panels can be moved in some embodiments by the doctor. Doctor can view from 3905 any or all past or present plans and can also view attachments which may be scanned into the EMR, column 3965.5. The plans can be created, edited, or modified by, for instance, clicking 3966 and in some embodiments populated elsewhere into the chart 3906 shows a panel that displays the various medication a patient is on. 3970 is a column that displays a listing of the medications the patient is on. 3971 displays the diagnosis or condition that the medication is treating. 3972 displays the date the medication is started. Other columns can be added to display any information that is needed. Medications can also be ordered from this panel, with the ability to access an outside medication ordering platform. For instance, medications can be ordered by clicking in the columns 3976, which can activate a mechanism that generates an overlay to pull up software that can place medication orders. This invention allows these medication orders to be placed, even if connected from industry standard shared medication platforms. Unique to this invention, while a medication is ordered, relevant clinical, procedural, or diagnostic data is visible to the user. This provides efficient, accurate medication orders to be placed. Bar graphs of the medications can also be displayed.

Window/panel 3907 displays relevant procedures performed on a patient. If finances are relevant, for instance, choosing a less expensive medication for an injection, clicking 3977 adds a column next to the procedure column showing financial information. Module 3911 shows a panel image viewer where diagnostic and images can be enlarged after directly accessing the data, by for instance, clicking on icons in the diagnostic Panel 3903 for example 3957. If the user wants more information shown in the panels with direct one click access or hovering the underlying data and images can be displayed. For instance, clicking on 3946 or any of the diagnostic icons, allows for the actual study to come up and be evaluated in 3911, with relevant data displayed in all the panels to enhance interpretation. Panels that may not be needed when 3911 is displaying an image can collapse to allow for more room. For instance, collapsing 3908, 3905, 3910 and 3912 would allow 3911 to expand to enlarge the image associated with, for instance, 3946.

The panel 3912 displays a clinical decision support area where advice can be offered to the doctor. When a CDS message is offered to the doctor instead of just a pop up message as seen in some systems that offer advice or show a warning to a doctor, the system can display the relevant data that explains and supports CDS advice, so a doctor can quickly determine if the advice or warning is accurate. Similarly, just as when an order is placed, relevant data is displayed, so too the same display of relevant supporting data to the CDS can be displayed. Each module 3901-3909 and 3911 is a smart module. With each module able to display conclusions that help the doctor understand orders to place and visualize, the supporting data behind the CDS recommendations.

In element 3910, searches can be typed or through voice recognition a search of all the data in the invention, EMR and or PM system, the invention can display and correlate by highlighting information in each of the relevant panels, the answer that the search question asked. Suggestions of care known as clinical decision support, can be displayed in 3912.

Displayed in FIG. 65 is an example of a retina doctor determining how to treat a patient with a certain medical condition and then placing an order. In panel 3904, a patient is shown to have diabetic macular edema, DME 3963 in the left eye on Jun. 15, 2018 and Panel 3902 displays the same date also highlighted in blue in 3926. The vision (VA) is decreased to a level of 20/60, #3929. On that same day, Jun. 15, 2018, in module 3903, two diagnostic tests were performed, 3950 and 3951 also highlighted in blue. Panel 3907 and 3908 are two ways of demonstrating in #3981 and #3985 that on Jun. 15, 2018 a laser was performed also highlighted in blue. The doctor can then understand on that visit, what the patient's vision was, the diagnostic tests and that a laser was performed. The doctor also has displayed the immediate previous visit when the last laser in the left eye was performed, which the invention has determined is relevant to a laser being done on the same eye. The previous visit, where a laser was performed is yellow on 4/2/16 #3982. This is one of many methods the invention uses to differentiate all relevant information 6/15/18 laser date (blue) from the last laser date of 4/2/16 (yellow). Also highlighted in yellow are other medical services on 4/2/16, 3927, 3930, 3945, 3554, 3955, 3984. Element #3936 shows that on 11/1/19 the visit after 6/15/18 that patients vision improved from 20/60 (3929) to 20/20 (#3936), which is normal vision. The patient does not have any treatment such as laser on that day.

The patient, when they return on "today's visit," all relevant data is displayed in each module. Once measurements on "today's visit" are entered, the invention can evaluate the data and if the rules engine, or through predictive analytics, or machine learning, suggestions for care or the modules detect data that needs to be brought to the doctor's attention, data can be highlighted or otherwise emphasized, and alerts created. Also, the CDS module can make suggestions and module 3912 displays, in FIG. 65, a message that says: "1. VA 20/80 worst it has ever been. Confirm with OCT (3948) that it is worsening therefore, consider laser now and Lucentis within one month. 2. IOP 23 today (3954), highest ever. Consider starting glaucoma medicine." The invention allows the CDS message to display the evidence behind its suggestion by highlighting clinical findings shown in 3902 by any method i.e. highlighting #3912, since the vision has greatly decreased to 20/80 and 3934 can also blink and be orange, alerting the doctor the IOP is also the worst at 23. In a summary row, the worst vision ever 3933, also is highlighted in orange and can blink, showing the doctors that 3912 is in fact the worst vision the patient ever had, and the best vision #3932 the patient has ever had is also shown on the summary row 3931. Displayed in 3902 is 3912 and 3933 are both orange, but any means can be used to illustrate to the doctor the connection of today's vision being the worst ever. This allows the doctor to quickly correlate what the vision was today compared to the past. Panel 3903 shows that today's visit ordered was a 3946 FA and a 3948 OCT. Element 3947 allows the doctor to either interpret or discover how good or bad that diagnostic test was and confirm the CDS claim of worsening. The doctor can see these clinical findings and the diagnostic findings and confirm that the CDS suggestion of a laser is correct.

In one example embodiment, a computer implemented method of creating medical orders includes generating a dashboard display comprising one or multiple visible panels having data corresponding to different respective medical services. A request to create an order is received in response to user interaction with a first one of the multiple panels. First medical information is retrieved as a function of information associated with the panel from which the request was received, and a place order panel is populated with the retrieved first medical information. In one example, order information is received via the place order panel and second medical information is received in response to the order information. Selected multiple panels are then populated with the retrieved second medical information that is helpful in the ordering process. In one embodiment, the first and second medical information comprise multiple of clinical data, examination data, procedures performed, diagnostic tests and billing information provided in respective ones of the multiple visible panels. The first one of the multiple panels may comprise a procedure panel corresponding to a first procedure, and the second medical information may include diagnostic information correlated to the first procedure for display in a diagnostic panel and prior procedures performed correlated to the first procedure for display in the procedure panel. The second medical information may include examination data correlated to the first procedure for display in a clinical information panel. The second medical information may include medication data correlated to the first procedure for display in a medication information panel. In one embodiment, the second medical information that is displayed in the respective panels is highlighted or otherwise emphasized. The first medical information may include data covering a selected period of time such as past, present and future times. The method may also include receiving user input corresponding to a diagnostic test icon in a diagnostic panel, retrieving an image corresponding to the diagnostic test, and displaying the image in an image viewer panel. In one embodiment, the first one of the multiple panels comprises a medication panel, and wherein selection of an order icon from the medication panel generates an overlay for ordering medications. in a further embodiment, one of the multiple panels comprises a clinical decision support panel that includes clinical decision support information that includes supporting data. One of the multiple panels comprises a diagnostic panel populated with retrieved first medical information comprising historical diagnoses data.

The doctor then on 3901 places a procedural order. One way of ordering a procedure is by clicking #3978, which is within a module that generate and displays relevant procedures. The tool understanding the context is accessing the procedure panel from 3907 to order a procedure such as a laser, this generates an overlay layer or window seen in 3901 with information that receives input to allow the doctor to place an order for a procedure, but also as the doctor places the order, so a confirmation of the proper order can be visualized. The user visualizes that the order they are placing for a laser is a repeat of a previous laser because when the laser is populated in "todays visit" in Element #3980 it is lined up with the other lasers performed in the left eye in the past 3981, 3982. The doctor can see this is a repeat laser and can visualize that this and is the third laser that is going to be done in this left eye. The summary row number 3 is displayed 3983 and confirms that fact and the 3 is also orange confirming the laser today 3980 is the third time the laser has been done in the left eye. Panel 3908 also displays #3986 a laser is to be done today. Panel 3909 shows that today's visit, #3988 that a laser is to be performed as well as an OCT and FA 3989. The FA and OCT are also displayed in panel 3903 as 3946 and 3948. The doctor has now determined what action to take and what to do today, i.e., order, a laser to be done today and can visualize it is being properly ordered and to be billed in the left eye today with all of the diagnostic tests 3946 and 3948. Sometimes an accidental click can cause the order to be placed in the wrong part of the body but by visualizing the order in context with the past, the doctor can confirm that the order is in the correct part and side of the body. In this case, the left not the right eye and can confirm the order by clicking for instance, #3920. Now, the doctor turns their attention to the future visit, and what they plan to do in the future. In this particular example CDS suggested a Lucentis injection was needed in the future. The doctor is shown since the patient's vision today was the worst it has ever been, in #3912, and the diagnostic test performed 3946 and 3948 the doctor can confirm the need for this Lucentis by displaying the image in 3911, the doctor can confirm, with all of this relevant information present, to now on the next visit, injection in the eye with a medication that can help the retina improve and by performing both the laser "today" displayed in 3980 as well as in a future visit an injection of medication in the eye, displayed as Lucentis as, this may be the best medication for the patient, which CDS suggested. Once again, the doctor turns to procedural panel 3901 by clicking 3978 or activating 3901 by any other means and places an order. Displayed, is the doctor choosing on 3914 the left eye. 3915 chooses an injection. 3916, the injection that the doctor selects is a medication called Lucentis. 3917 shows the doctor explaining why they are doing the injection by selecting an ICD-10 diagnostic code illustrated as DME, which stands for diabetic macular edema, also displayed in 3963. The tool knows the reason and could automatically populate the reason or diagnosis. 3918 shows the doctor wants to inject Lucentis at the next visit. 3919 shows that the next visit the doctor orders to be in two to four weeks. Now in panel 3907, 3979 shows the future visit, and that the doctor is ordering Lucentis and populates that cell. Now the doctor can see, in context, what this future visit looks like and that the previous procedures in 3980 (todays visit) 3981 6/15/18 visit and 3982 4/2/16 visit performed in the left eye and the doctor can re-confirm that this is exactly what they want to do. #3987 is another mechanism to show the future visit of Lucentis displayed. Now with the doctor seeing this and also being able to have direct access to any of the diagnostic tests displayed in 3903 and could, for instance, look at 3946 or 3948 to confirm the Lucentis injection is needed. Once the decision is clear, and what they are ordering is proper, they can then click 3920 confirming the order.

The doctor may decide that another diagnostic test should be performed on this future visit, so clicking 3939, which is the OCT column or going back to 3901 and choosing, instead of procedures, the diagnostic tests, can order an OCT for the next visit. That OCT or whatever diagnostic test that the doctor might want to order, the same methods described for ordering the Lucentis injection displayed in 3901 can be repeated to order an OCT in the left eye on the future visit. Once ordered the OCT is displayed in 3956 future visit, as well as 3989, which would become a permanent order once 3920 is clicked. It is a square, empty box 3956 because the OCT has not yet been performed. Whereas in 3948, it is a filled in square or icon because the OCT has been performed. There is also a new diagnosis seen, glaucoma, on 3964 which explains why a new medication also in blue was started that day in 3906, Timoptic 3973. CDS suggested that IOP was the highest ever at 23 and 3934 is orange and 3535 is orange alerting the doctor this is the highest pressure ever.

Now the doctor if they agree with the CDS can click on 3976 and the process is repeated, and they order a glaucoma drug 3973 and 3975 shows the medicine starting today.

Through this mechanism, the doctor can place orders, see all relevant information, and make certain their orders are correct and confirm if the CDS messages and alerts are accurate at a glance seeing the data that supports the recommendations. Finally, the orders placed appear in the panels in row displaying today's visit. For example, 3943, 3980 and the future visit, for example 3956, 3979, and the doctor can visualize the orders that they placed are exactly as they meant to order in the correct part of the body in the time period the doctor wants and by clicking 3920 confirms the orders.

For example, in some embodiments in accordance with the present principles, Rules and Configurations can be predetermined and stored, for example, in the Rules module 004, for determining which data of a Flowsheet and, as such, which portions of the medical records dashboard to display or hide. Alternatively, or in addition, in some embodiments, a user can self-configure the medical records dashboard to display only certain portions or to hide certain data of a Flowsheet and, as such, which portions of the medical records dashboard to display or to hide using, for example, a user interface (not shown) associated with the medical records dashboard. Alternatively, or in addition, data of the Flowsheet can contain an indicator (e.g., a flag) that can be identified by, for example, the Rules module 004, for determining when and if a piece of data should be displayed or hidden.

In some embodiments, the Data Command center 001 enables the medical records dashboard to intelligently expand, collapse, display, and/or hide columns, rows and/or any other portion of the medical records dashboard to show precisely what a user wishes to display. For example, in one embodiment, a Flowsheet including patient treatment and health information can be accessed from an EHR system using, in some embodiments, an icon/button, keystroke, or series of keystrokes associated with at least one of the Data Command center 001 and the medical records dashboard. Upon accessing the Flowsheet, a set of Rules and Configurations associated with, for example, the Rules module 004 of the Data Command center 001, can be evaluated to determine which data from the Flowsheet is to be displayed in the medical records dashboard. For example, in some embodiments, the Rules module 004 can include information on what data to display, and in turn what portions of the medical records dashboard to display, based on, including but not limited to, at least one of an identity of a medical care provider, an identity of a patient, a medical care provider's specialty, conditions of a patient, patient procedures, risk factors, diagnostic results, future orders, future appointments, values recorded, values not recorded, calculated values, and absolute values for display.

For example, in some embodiments in accordance with the present principles, Rules and Configurations can be predetermined and stored, for example, in the Rules module 004, for determining which data of a Flowsheet and, as such, which portions of the medical records dashboard to display or hide. Alternatively, or in addition, in some embodiments, a user can self-configure the medical records dashboard to display only certain portions or to hide certain data of a Flowsheet and, as such, which portions of the medical records dashboard to display or to hide using, for example, a user interface (not shown) associated with the medical records dashboard. Alternatively, or in addition, data of the Flowsheet can contain an indicator (e.g., a flag) that can be identified by, for example, the Rules module 004, for determining when and if a piece of data should be displayed or hidden.

As described above, a Data Command Center of the present principles is able to intelligently aggregate and display data through a variety of means. In many embodiments described within this patent, a Rules Engine 10180 of FIG. 3 determines which data to show, hide, highlight, send auto-tasks on, and other key functionality of the Data Command Center such as those laid out in Dynamic Data Representations as described above. In further embodiments of FIG. 19 described above, aggregated and filtered data can be displayed in text or graphical manner utilizing various configurations which can be stored in a table or generated during processing. Displayed data can also be aggregated into a correlative line graph (FIG. 33) aligning multiple modules within a single interface, correlated along a common timeline.

Figure 66:
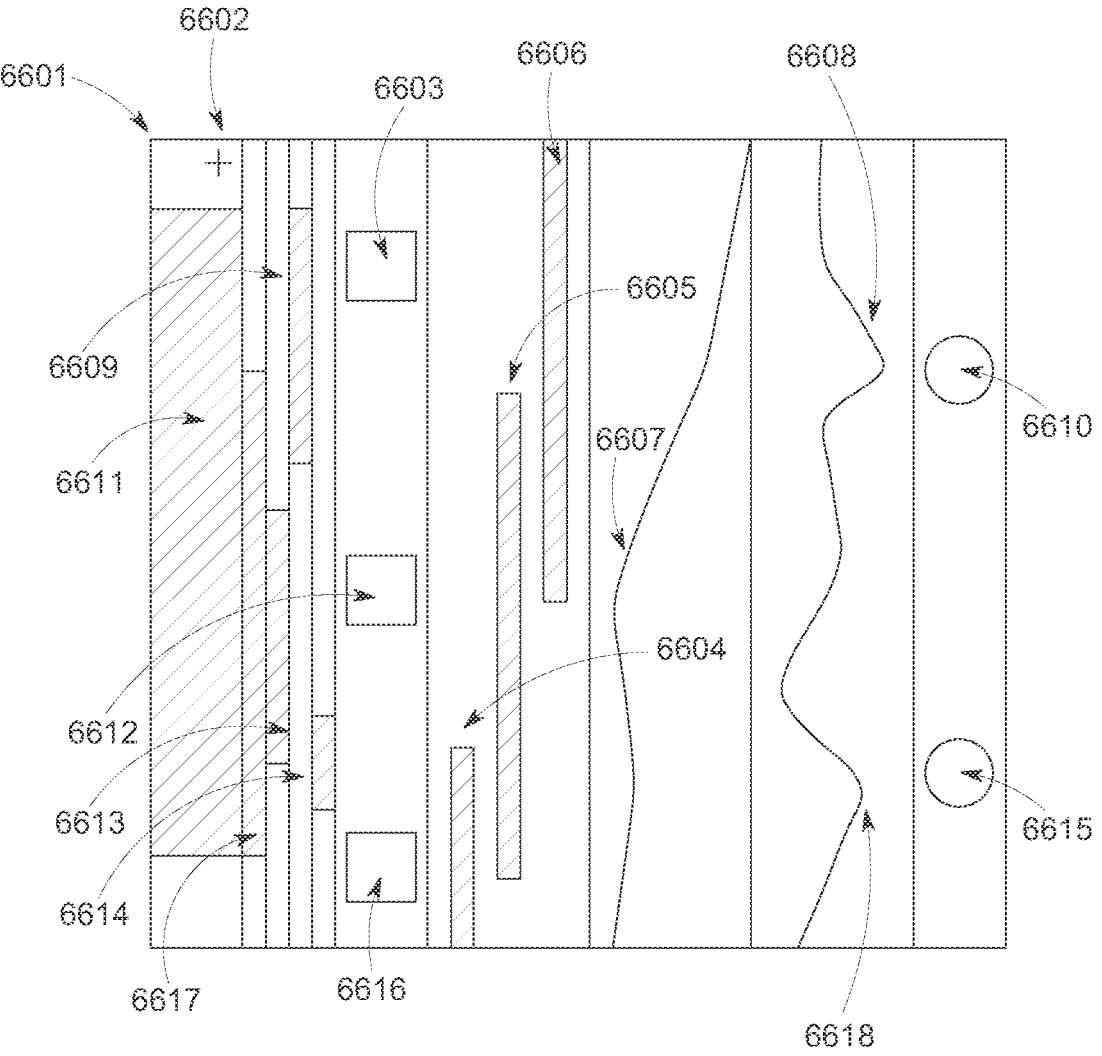
FIG. 66 depicts multiple embodiments of this invention correlated with each other.

As seen in FIG. 66, several embodiments and correlations may coexist within the same, or multiple, panels. A panel such as this may be generated by selecting an icon, such as 21085 of FIG. 25, or invoked as the result of a trigger or triggers. At 6601, we see multiple, correlated panels aligned. 6611 denotes a logical grouping of medications, and may exist as a summary representation of all medications within the logical group. Employing an icon such as seen at 6602, a user may expand to show the individual medications. 6611 may represent medications for a condition, such as diabetes. 6617 may represent one diabetes medication, while 6609 may represent another, and 6609 may represent a third. It may only be important for a doctor to know the patient is being treated for diabetes, yet the option exists to drill down into the specific medications. 6603, 6612, and 6616 may represent procedures. These procedures do not necessarily require a logical grouping and may represent a heart attack at 6603, broken leg at 6612, and kidney stones at 6616. A summary representation of all procedures may be employed outside of a doctor's specialty to make them aware of the larger health of a patient. When correlated in context of diabetes medications, it may instruct a different plan of treatment. 6604-6606 may represent conditions. In the case of 6604 and 6605, conditions may start and stop, yet at 6606, a condition may be ongoing, or may represent a condition for which there is no end. Each of these conditions are correlated with medications and procedures. At 6607, we see a line graph representing results, perhaps blood sugar for a diabetic, and we specifically see a rise correlated with the onset of the condition at 6606. At 6608 and 6618, we see another line graph, perhaps representing blood pressure. The spikes in pressure correlated with life events, represented by 6610 and 6615. A death in the family at 6610 may be responsible for the spike at 6608, and 6615 may represent a marriage, with a slower rise in pressure building up to the event at 6618. The ability to correlate disparate information, otherwise not seen, correlated, or even present, in existing systems allows an overview as to the full health of a patient and continuity of care. Those skill in the art will appreciate that each module or section of each module is a dynamic data representation, and as such, may be reordered, hidden, expanded, collapsed, augmented, or otherwise altered in accordance with present principles.

The methods and processes described herein may be implemented in software, hardware, or a combination thereof, in different embodiments. In addition, the order of methods can be changed, and various elements can be added, reordered, combined, omitted, or otherwise modified. All examples described herein are presented in a non-limiting manner. Various modifications and changes can be made as would be obvious to a person skilled in the art having benefit of this disclosure. Realizations in accordance with embodiments have been described in the context of particular embodiments. These embodiments are meant to be illustrative and not limiting. Many variations, modifications, additions, and improvements are possible. Accordingly, plural instances can be provided for components described herein as a single instance. Boundaries between various components, operations and data stores are somewhat arbitrary, and particular operations are illustrated in the context of specific illustrative configurations. Other allocations of functionality are envisioned and can fall within the scope of claims that follow. Structures and functionality presented as discrete components in the example configurations can be implemented as a combined structure or component. These and other variations, modifications, additions, and improvements can fall within the scope of embodiments as defined in the claims that follow.

In the foregoing description, numerous specific details, examples, and scenarios are set forth in order to provide a more thorough understanding of the present disclosure. It will be appreciated, however, that embodiments of the disclosure can be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described can include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated.

Embodiments in accordance with the disclosure can be implemented in hardware, firmware, software, or any combination thereof. Embodiments can also be implemented as instructions stored using one or more machine-readable media, which may be read and executed by one or more processors. A machine-readable medium can include any mechanism for storing or transmitting information in a form readable by a machine (e.g., a computing device or a "virtual machine" running on one or more computing devices). For example, a machine-readable medium can include any suitable form of volatile or non-volatile memory.

Modules, data structures, and the like defined herein are defined as such for ease of discussion and are not intended to imply that any specific implementation details are required. For example, any of the described modules and/or data structures can be combined or divided into sub-modules, sub-processes or other units of computer code or data as can be required by a particular design or implementation.

In the drawings, specific arrangements or orderings of schematic elements can be shown for ease of description. However, the specific ordering or arrangement of such elements is not meant to imply that a particular order or sequence of processing, or separation of processes, is required in all embodiments. In general, schematic elements used to represent instruction blocks or modules can be implemented using any suitable form of machine-readable instruction, and each such instruction can be implemented using any suitable programming language, library, application-programming interface (API), and/or other software development tools or frameworks. Similarly, schematic elements used to represent data or information can be implemented using any suitable electronic arrangement or data structure. Further, some connections, relationships or associations between elements can be simplified or not shown in the drawings so as not to obscure the disclosure.

The following are examples for multiple different aspects of the present inventive subject matter.

Order Examples:

1. A computer implemented method of creating medical orders, the method comprising:
   generating a dashboard display comprising one or multiple visible panels having data corresponding to medical information;
   receiving a request to create an order in response to user interaction with a first one of the multiple panels;
   displaying an order panel;
   identifying first medical information as a function of user interaction with the order panel; and emphasizing the first medical information in the multiple visible panels.

2. The method of example 1 and further comprising adding additional medical information in one of the multiple panels.

3. The method of any of examples 1-2 and further comprising adding an additional panel to display additional medical information.

4. The method of any of examples 1-3 and further comprising displaying information in the order panel as a function of information from one or more panels of the multiple panels.

5. The method of any of examples 1-4 wherein the first information and information from one or more panels of the multiple panels comprise multiple of clinical data, examination data, procedures performed, diagnostic tests and billing information provided in respective ones of the multiple visible panels.

6. The method of any of examples 1-5 wherein the first one of the multiple panels comprise a procedure panel corresponding to a first procedure, and wherein the and information from one or more panels of the multiple panels comprises:
   diagnostic information correlated to the first procedure for display in a diagnostic panel; and
   prior procedures performed correlated to the first procedure for display in the procedure panel.

7. The method of any of examples 1-6 wherein the information from one or more panels of the multiple panels comprises examination data associated with the first procedure for display in a clinical information panel.

8. The method of any of examples 1-7 wherein the information from one or more panels of the multiple panels comprises medication data correlated to the first procedure for display in a medication information panel.

9. The method of any of examples 1-8 and further comprising emphasizing the information from one or more panels of the multiple panels that is displayed in the respective panels including the order panel.

10. The method of any of examples 1-9 wherein the order panel displays medical order information.

11. The method of example 10 wherein the selected period of time comprises past, present and future times.

12. The method of any of examples 10-11 wherein one of more of the multiple panels displays future predicted values of medical information.

13. The method of any of examples 1-12 and further comprising:

receiving user input corresponding to a diagnostic test icon in a diagnostic panel;

retrieving an image corresponding to the diagnostic test; and displaying the image in an image viewer panel.

14. The method of any of examples 1-14 wherein the first one of the multiple panels comprises a medication panel, and wherein selection of an order icon from the medication panel generates an overlay for ordering medications.

15. The method of any of examples 1-14 wherein one of the multiple panels comprises a clinical decision support panel that include clinical decision support information that includes supporting data.

16. The method of any of examples 1-15 wherein one of the multiple panels comprises a diagnostic panel populated with identified first medical information comprising historical diagnoses data.

17. The method of any of examples 1-16 wherein the first one of the multiple panels comprises a list of patients, and wherein the request to create an order creates an order for each patient selected in the list, each order being individually modifiable.

18. A machine-readable storage device having instructions for execution by a processor of a machine to cause the processor to perform operations to perform a method, the operations comprising:

generating a dashboard display comprising one or multiple visible panels having data corresponding to medical services;

receiving a request to create an order in response to user interaction with a first one of the multiple panels;

displaying an order panel;

identifying first medical information as a function of user interaction with the order panel; and emphasizing the first medical information in the multiple panels.

19. The device of example 18, the operations further comprising adding additional medical information in one of the multiple panels.

20. The method of any of examples 18-19 and further comprising:

populating the order panel as a function of information from one or more panels of the multiple panels:

receiving order information via the place order panel;

retrieving second medical information in response to the order information; and populating selected multiple panels with the retrieved second medical information.

21. The device of any of examples 18-20 wherein the first information and information from one or more panels of the multiple panels comprise multiple of clinical data, examination data, procedures performed, diagnostic tests and billing information provided in respective ones of the multiple visible panels.

22. The device of any of examples 18-21 wherein the first one of the multiple panels comprise a procedure panel corresponding to a first procedure, and wherein the and information from one or more panels of the multiple panels comprises:

diagnostic information correlated to the first procedure for display in a diagnostic panel; and prior procedures performed correlated to the first procedure for display in the procedure panel.

23. A device comprising:

a processor; and a memory device coupled to the processor and having a program stored thereon for execution by the processor to perform operations comprising:

generating a dashboard display comprising one or multiple visible panels having data corresponding to medical services;

receiving a request to create an order in response to user interaction with a first one of the multiple panels;

displaying an order panel;

identifying first medical information as a function of user interactions with the order panel; and emphasizing the first medical information in the multiple panels.

24. The device of example 23, the operations further comprising adding additional medical information in one of the multiple panels.

25. The method of example 24 and further comprising populating the order panel as a function of information from one or more panels of the multiple panels.

26. A computer implemented method of displaying patient medications over time, the method comprising:

accessing event data representative of patient medication events, the event data including an event date and a medication identifier for each patient medication event;

generating a display including a list of medication events in chronological order in a first axis of the display;

associating the medication event dates and a corresponding medication family to identify time periods corresponding to one or more medications; and representing the medication families in the display along a second axis transverse to the first axis and having an attribute spanning the time period along the first axis corresponding to the patient medication events that include the one or more medications, wherein the attribute for each of the medication families is different and spans the time period corresponding to each of the respective one or more medications.

27. The method of example 26 wherein the attribute is indicative of a type of drug.

28. The method of example 27 wherein the attribute is a color assignable by a user.

29. The method of any of examples 26-28 wherein the event data includes description of treatments selected from at least one of a procedure and a measured parameter.

30. The method of any of examples 26-29 wherein the first axis includes a row for each of the one or more medication events and the second axis includes a column for each of the one or more medications.

31. The method of any of examples 26-30 wherein at least one of the time periods corresponding to one or more medications includes multiple non-contiguous time periods.

32. A method for medication management and display in a data command center comprising one or more windows for display and including information from at least one database, the data command center displaying on a screen, using the one or more windows, at least one of medical services, clinical data, examination findings, diagnostic tests, and procedures performed on one or more patients, the one or more windows comprising a plurality of data fields for displaying the information received or derived from the at least one database, wherein the at least one of the medical services, the clinical data, the examination findings, the diagnostic tests, and the procedures are arranged in on the screen according to at least one of a time and a date that the medical services, the clinical data, the examination findings, the diagnostic tests and the procedures were performed on the one or more patients, the method comprising:

determining, from the at least one database and the at least one of the medical services, the clinical data, the examination findings, the diagnostic tests, and the procedures, medications administered to the one or more patients;

generating a respective graphical representation for each of the determined medications administered to the one or more patients; and displaying at least one generated, respective graphical representation of at least one medication administered to a patient in the at least one or more windows in context with at least the information from the at least one patient database and the at least one of the medical services, the clinical data, the examination findings, the diagnostic tests, and the procedures, wherein the at least one generated, respective graphical representation of the at least one medication administered to the patient is arranged in on the screen according to at least one of the times and the dates that the at least one medication was being administered to the patient;

wherein the at least one or more windows displaying the graphical representations are dynamically collapsible and expandable.

33. The method of example 32, wherein the at least one generated, respective graphical representation enables a user to immediately identify on sight a respective medication without having to read a name of the medication.

34. The method of any of examples 32-34, wherein the generated, respective graphical representations represent at least one of individual medications, classes of medications, combinations of medications, or logical groupings of medications.

35. The method of any one of examples 32-34, wherein the generated, respective graphical representations differentiate medications by at least one of color, combinations of colors, or symbols.

36. The method of example 35, wherein the colors are colors standardized by the American Academy of Ophthalmology.

37. The method of any of examples 32-36, wherein respective graphical representations are generated for and separately listed by each condition of a patient for which medications are being administered.

38. The method of any of examples 32-37, further comprising: generating and displaying an alert if a medication associated with a respective one of the one or more patients has changed since a last visit.

39. A data command center visual display system that displays data on a display screen, comprising:

a computing device comprising at least one processor;

a non-transitory computer-readable medium, having stored thereon, software instructions that when executed by the at least one processor of the computing device, cause the computing device to perform operations comprising at least:

linking to and receiving patient related medical records including patient data from at least one patient data source, wherein the patient data includes at least one of medical services, clinical data, examination findings, diagnostic tests, and procedures performed on one or more patients;

determining, from at least one of the patient data and the at least one of the medical services, the clinical data, the examination findings, the diagnostic tests, and the procedures, medications administered to each of the one or more patients;

generating a respective graphical representation for each of the determined medications administered to each of the one or more patients; and displaying using the one or more windows, at least one of medical services, clinical data, examination findings, diagnostic tests, and procedures performed on one or more patients and at least one generated, respective graphical representation of at least one medication administered to a patient in context with at least one of the patient data and the at least one of the medical services, the clinical data, the examination findings, the diagnostic tests, and the procedures;

wherein the at least one of the medical services, the clinical data, the examination findings, the diagnostic tests, and the procedures are arranged on the screen according to at least one of a time and a date that the medical services, the clinical data, the examination findings, the diagnostic tests and the procedures were performed on the one or more patients;

wherein the at least one generated, respective graphical representation of the at least one medication administered to the patient is arranged on the screen according to at least one of the times and the dates that the at least one medication was being administered to the patient; and wherein the at least one or more windows displaying the graphical representations and the graphical representations are dynamically collapsible and expandable.

40. The data command center visual data system of example 39, wherein the at least one generated, respective graphical representation enables a user to immediately identify on sight a respective medication without having to read a name of the medication.

41. The data command center visual display system of any of examples 39-40, wherein the generated, respective graphical representations represent at least one of individual medications, classes of medications, combinations of medications, or logical groupings of medications.

42. The data command center visual display system of any of examples 39-41, wherein the generated, respective graphical representations differentiate medications by at least one of color, combinations of colors, or symbols.

43. The data command center visual display system of example 42, wherein the colors are colors standardized by the American Academy of Ophthalmology.

44. The data command center visual display system of any of examples 39-43, wherein respective graphical representations are generated for and separately listed by each condition of a patient for which medications are being administered.

45. The data command center visual display system of any of examples 39-44, wherein the computing device is further configured to:

generate and display an alert if a medication being administered to the one or more patients has changed since a last visit.

46. A method for dynamic data display in a data command center comprising a medical records dashboard including one or more windows including information received or derived from at least one patient database, the medical records dashboard comprising a display on a screen, using the one or more windows, of at least one of medical services, clinical data, examination findings, diagnostic tests, and the procedures performed on one or more patients, the one or more windows comprising a plurality of data fields, including at least one adjustable data field, for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, the method comprising:

receiving patient-related data from the at least one patient database;

displaying patient-related data in selected, respective ones of the data fields;

in response to an entry or change of patent-related data in at least one of the respective ones of the data fields, making a change to the displayed data in at least one other of the respective ones of the data fields.

47. The method of example 46, wherein the change to the displayed data in the at least one other of the respective ones of the data fields includes at least one of expanding the data representation, truncating the data representation, adding an alert to the data representation, highlighting the data representation, adding a representation to the data field indicating that data is missing, adding a graphical representation indicating access to underlying information, adding a thumbnail representation, adding a text link data representation, or including a Summary Data Representation, which illustrates a single data representation comprised of multiple data sources.

48. The method of any of examples 46-47, wherein data fields are expanded or truncated depending on user specialty or interests.

49. The method of any of examples 46-48 wherein the one or window include multiple windows, the method further comprising:

receiving a representation of a user action to modify a size of one of the multiple windows;

modifying the size of the one of the multiple windows in accordance with the representation of the user action; and modifying the size of at least one of the other of the multiple windows in accordance with one or more window resizing rules.

50. A data command center visual display system that displays data on a display screen, comprising:

a computing device comprising at least one processor;

a non-transitory computer-readable medium, having stored thereon, software instructions that when executed by the at least one processor of the computing device, cause the computing device to perform operations comprising at least:

linking to and receiving patient related medical records including patient data from at least one patient data source; and displaying a medical records dashboard including one or more windows, the medical record dashboard capable of displaying, using the one or more windows, patient data from at least one patient data source including at least one of medical services, clinical data, examination findings, diagnostic tests, and the procedures performed on one or more patients, the one or more windows comprising a plurality of data fields, including at least one adjustable data field, for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients;

wherein a display of patient data in the medical records dashboard includes dynamic data fields in which:

in response to an entry or change of patent-related data in at least one of the respective ones of the data fields, a change is made to the data in at least one other of the respective ones of the data fields.

51. The data command center visual display system of example 50, wherein the change to the data in the at least one other of the respective ones of the data fields includes at least one of expanding the data representation, truncating the data representation, adding an alert to the data representation, highlighting the data representation, adding a representation to the data field indicating that data is missing, adding a graphical representation indicating access to underlying information, adding a thumbnail representation, adding a text link data representation, or including a Summary Data Representation, which illustrates a single data representation comprised of multiple data sources.

52. The data command center visual display system of any of examples 50-51 wherein data fields are expanded or truncated depending on user specialty or interests.

53. A computer implemented method comprising:

determining a timeline for a whole life view of data associated with multiple selected parameters for which medical data corresponding to the patient is available;

accessing medical data, including a patient's medical data corresponding to the multiple selected parameters;

conforming the accessed medical data to the timeline; and displaying each of the selected parameters adjacent to each other along the timeline, wherein the display is zoomable along the timeline.

54. The method of example 53 and further comprising:

predicting future values for the selected parameters; and displaying predicted future values along the timeline.

55. The method of example 54 wherein the predicted future values are selected based on machine learning rules trained on data from multiple patients.

56. The method of any one of examples 53-55 wherein the selected parameters include data related to procedures, labs, diagnoses, and medications.

57. The method of one of examples 53-55 wherein the multiple selected parameters are selected as a function of a first parameter selected by a user from one of multiple panels displaying different sets of data.

58. The method of one of examples 53-55 wherein the timeline is selected based on rules, including a first record in time corresponding to at least one of the selected parameters.

59. The method of one of examples 53-55 wherein the display is temporally zoomable to alter the timeline to show more or less information.

60. The method of one of examples 53-55 wherein the display comprises graphical representations of the selected parameters including links to images.

61. The method of example 60 wherein the graphical representations of data include procedure codes that operate as links to procedure details.

62. The method of one of examples 53-55 wherein the medical data includes non-patient data and the non-patient data comprises life expectancy data of patients having a disease that is similar to a disease of the patient.

63. The method of any one of examples 53-55 wherein the medical data includes non-patient data and the non-patient data comprises data corresponding to how a cohort of other patients react to a selected drug.

64. The method of any one of examples 53-55 wherein the different periods of time along the timeline are zoomable at different scales.

This disclosure is to be considered as exemplary and not restrictive in character, and all changes and modifications that come within the guidelines of the disclosure are desired to be protected.

What is claimed is:

1. A computer implemented method for presenting patient information on a medical record dashboard display, the information obtained from at least one data source, the method comprising:

receiving a patient identifier;

accessing the at least one data source using the patient identifier to obtain first medication information including times the first medication was prescribed, ordered, taken or administered to a patient for treating a medical condition;

executing rules by parsing first medication information via a rules engine to identify and access at least one of cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data, or health care associated statistics corresponding to the first medication of the patient;

executing rules by parsing first medication information via the rules engine to identify and access the at least one data source to identify and obtain medical condition treatment effectiveness information related to an effect by the medication; and the medical condition treatment effectiveness information comprising at least one of examination findings, clinical data, structured clinical data, symptoms, diagnosis, diagnostic tests, diagnostic test results, diagnostic images or diagnostic image measurements displayed over time;

executing rules by parsing the first medication information via the rules engine to display the first medication information visually correlated in time with the related medical condition treatment effectiveness information from which medical condition treatment effectiveness is observable to track medical condition treatment effectiveness over time; and displaying the at least one of the identified cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication via the display such that the at least one of the cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics are visible on the display concurrently with the first medication information and the related medical condition treatment effectiveness information that remain visible.

2. The method of claim 1 wherein medication information comprises injection information.

3. The method of claim 1 and further comprising generating a graphical representation of the at least one of medication information and medical condition treatment effectiveness information over time wherein displaying the obtained medication information and medical condition treatment effectiveness information comprises displaying the graphical representation.

4. The method of claim 3 wherein the graphical representation of at least one of the medication information and the medication treatment effectiveness information are displayed in one or more windows and are dynamically emphasized, added, removed or updated based on a change in medication information, medication treatment effectiveness information, new patient symptoms, patient actual usage, or medical information.

5. The method of claim 1 wherein the data source comprises multiple data sources from at least three of an electronic health records system, a health information exchange, patient portal, home health monitoring system, shared care system, telemedicine system, laboratory system, an image management system, inventory management system, healthcare information technology system, picture archiving and communication system, claims-based system, insurance company system, artificial intelligence system, practice management system, or prescription data source.

6. The method of claim 5 wherein the at least one data source comprises an inventory management system, patient portal, home health monitoring system, telemedicine system, or shared care system.

7. The method of claim 1 and further comprising displaying a selectable icon or visual indicator for displaying a means for placing an order for administering, performing, or prescribing a medication, injection, procedure, diagnostic test, image, or medical service or scheduling an order to administer, or perform a medication, injection, procedure, diagnostic test, image, or medical service.

8. The method of claim 1 wherein the display includes rows and columns of at least one of medication information, medical condition treatment effectiveness information, cost data, authorizations, insurance coverage determinations, or insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics.

9. The method of claim 1, further comprising:

generating and displaying an alert if a medication associated with the patient has changed since a last visit, or a potential interaction between medications is detected, or a patient has a clinical finding that suggests an adverse reaction to a medication or a change in patient usage of the medication occurs.

10. The method of claim 9, further comprising an automatic message is sent to at least one of a provider, shared care doctor, patient, administrative staff, and clinical staff.

11. The method of claim 1 wherein one or more medical condition treatment effectiveness information are emphasized, added, removed, or updated, based on a threshold.

12. The method of claim 1 wherein displaying at least one of the medical condition treatment effectiveness information, cost data, claims data, authorizations, insurance coverage determinations, er insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics information comprise an icon, graphical marker, graphical representation, indicator, or displayed visual representation.

13. The method of claim 12 wherein at least one of the icon, graphical marker, indicator, or displayed visual representation comprises a link to accesses underlying information for display on the medical record dashboard display.

14. The method of claim 12 wherein the icon, graphical marker, indicator, or displayed visual representation comprises a change in appearance based on a status of an underlying claim, authorization, inventory data, actual patient usage, clinical trial protocol, clinical research data or medical condition treatment effectiveness information changing which is automatically or manually set.

15. The method of claim 12, wherein at least one of the icon, graphical marker, indicator, or displayed visual representation identifies at least one of a claim not yet made, incorrect claim, a claim being made, a claim being paid, a payment being pending, a payment being denied, an authorization pending, authorization received, and authorization denied.

16. The method of claim 1 wherein the at least one of cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical research data or health care associated statistics includes alternative treatment options.

17. The method of claim 16 wherein medical condition treatment effectiveness of alternative treatments or predicted results is also displayed.

18. The method of claim 1, further comprising executing rules using a natural language processing engine and an artificial intelligence engine to analyze at least one of insurance guidelines, medication contraindications, medical research, clinical decision support frameworks, messages received from the patient, evaluating orders or scheduling of a patient, evaluating severity of a missed appointment, medical coding standards, and insurance audit procedures, to validate treatment plans and medical coding, correlate diagnoses to medical necessity criteria, identify inconsistencies or discrepancies in coding, and support insurance submission and audit compliance procedures.

19. The method of claim 1, further comprising executing rules using natural language processing and artificial intelligence to dynamically generate and present, in response to a patient's medical condition and treatment, a patient's inquiry, one or more of relevant examination findings, structured clinical data, symptoms, diagnoses, diagnostic tests, and diagnostic images, based on correlation with at least one of medication use, patient's symptoms, insurance rules, or clinical guidelines.

20. The method of claim 1, wherein executing rules includes:
preprocessing patient-related information from the at least one patient data source; and
generating an object optimized for displaying at least one of the cost data, claims data, authorizations, inventory data insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics.

21. The method of claim 20 wherein displaying at least one of the cost data, claims data, authorizations, inventory data insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics uses the generated object.

22. The method of claim 1 wherein executing the display rules to generate a medical record dashboard display can be modified based on a specified medical specialty.

23. The method of claim 1 wherein an alert is generated by the rules engine or a natural language processing or artificial intelligence system based on local or national guidelines, local or national coverage determinations, compliance with regulations, incorrect claim submitted, preferred practice patterns, prescription medication software, actual patient usage, clinical trial protocol, clinical research data, insurance requirements, clinical research study, clinical decision support information, comanagement system, information from a patient portal, home health monitoring system, shared care system, telemedicine system, laboratory system, or artificial intelligence engines and the alert comprises at least one of highlighting displayed information selected from the group consisting of medical services, clinical data, examination data, symptoms, medicine, diagnostic test, images, injections, procedure, claim information, insurance regulations, and authorizations.

24. The method of claim 23 wherein the alert includes information corresponding to at least one of missed appointments, incorrectly scheduled follow up appointments or future appointments, diagnostic test not performed in a certain period of time, an injection or procedure performed or scheduled in an incorrect period of time on a wrong part of a body, or a drug, injection or procedure not authorized, a change in patient insurance, a change in insurance of clinical guidelines, clinical research study, unfulfilled prescription, actual patient usage, or discrepancy in data.

25. The method of claim 24, further comprising an automatic message is sent to at least one of a provider, shared care doctor, patient, administrative staff, and clinical staff.

26. The method of claim 1 and further comprising:
accessing a plurality of clinical guidelines from disparate sources;
applying natural language processing and rules-based parsing to align guideline content by at least one of condition, treatment, and timing attributes; and
generating a summary outlining similarities and discrepancies among the guidelines.

27. The method of claim 1 wherein the rules engine comprises a natural language processing model trained on at least one of clinical guidelines, clinical decision support guidelines, financial guidelines, clinical data, and clinical documentation interpreting guidelines, clinical data, and clinical documentation and wherein detecting an inconsistency between at least one of patient history, patient symptom, examination findings, medications, actual patient usage of a medication, or orders, flag potential problems with the medication, or the actual usage of the medication, insurance submission issues or authorization mismatches and generating an alert compromises:

processing interpreted data though an inference engine comparing clinical data, orders, medications, and clinical notes to guidelines;

identifying potential diagnostic codes, or procedural codes not present in existing structured data or problem with a medication or the actual usage of the medication or reaction to medication or symptom;

identifying commonalities and discrepancies between patient information and guidelines, plan or order that is inconsistent with at least one of clinical guidelines, clinical decision support guidelines, financial guidelines, clinical data, and clinical documentation interpreting guidelines, clinical data, expected medication effects or usage and clinical documentation; and generating alerts or alternative orders based on the commonalities and discrepancies.

28. The method of claim 1, further compromising evaluating and weighting treatment options, procedures, diagnostic tests, clinical data, symptoms, clinical data research and diagnostic imagery based on their effectiveness over time, and executing artificial intelligence rules to recommend alternative treatments, predicted results, diagnostic approaches, or medications based on at least one of cost effectiveness, payer authorization status, insurance regulations, insurance related information, guidelines, local or national guidelines, local or national coverage determinations, inventory data, clinical decision support, preferred practice patterns, actual patient usage, medication contraindications, health care associated statistics, or correlation with treatment efficacy.

29. A data visual display system that displays data on a display, comprising:

a computing device comprising at least one processor; and a non-transitory computer-readable medium, having stored thereon, software instructions that when executed by the at least one processor of the computing device, cause the computing device to perform operations comprising:

receiving a patient identifier;

accessing at least one data source using the patient identifier to obtain first medication information including times the first medication was prescribed, ordered, taken or administered to a patient for treating a medical condition;

executing rules by parsing first medication information via a rules engine to identify and access at least one of cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication of the patient;

executing rules by parsing first medication information via the rules engine to identify and access the at least one data source to identify and obtain medical condition treatment effectiveness information related to an effect by the medication, the medical condition treatment effectiveness information comprising at least one of examination findings, clinical data, symptoms, diagnosis, diagnostic tests, diagnosis test results, diagnostic images, or diagnostic image measurements displayed over time;

executing rules by parsing the first medication information via the rules engine to display the first medication information visually correlated in time with the related medical condition treatment effectiveness information from which medical condition treatment effectiveness is observable to track medical condition treatment effectiveness over time; and displaying the at least one of the identified cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication via the display such that the at least one of the cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics are visible on the display concurrently with the first medication information and the related medical condition treatment effectiveness information that remain visible.

30. The system of claim 29, wherein medication information comprises injection information.

31. The system of claim 29 and further comprising displaying a selectable icon or visual indicator for displaying a means for placing an order for administering, performing or prescribing a medication, injection, a procedure, diagnostic test, image or medical service or scheduling an order to administer, or perform a medication, injection, procedure, diagnostic test, image, or medical service.

32. A non-transitory computer readable storage device having instructions for execution by a computer to perform operations comprising:

executing rules by a rules engine based on a patient identifier to access at least one data source to obtain first medication information including times the first medication was prescribed, ordered, taken or administered to a patient for treating a medical condition;

executing rules by parsing first medication information via the rules engine to identify and access at least one of cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication of the patient;

executing rules by parsing first medication information via the rules engine to identify and access the at least one data source to identify and obtain medical condition treatment effectiveness information related to an effect by the medication, the medical condition treatment effectiveness information comprising at least one of examination findings, clinical data, symptoms, diagnosis, diagnostic tests, diagnostic test results, diagnostic images, or diagnostic image measurements over time;

executing rules by parsing the first medication information via the rules engine to display the first medication information visually correlated in time with the information from which related medical condition treatment effectiveness information is observable to track medical condition treatment effectiveness over time; and displaying the at least one of the identified cost data, claims data, authorizations, insurance coverage determinations, er-insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication via the display such that the at least one of the cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics are visible on the display concurrently with the first medication information and the related medical condition treatment effectiveness information that remain visible.

33. A method for presenting patient information on a medical record dashboard display, the information obtained from at least one data source, the method comprising:

selecting a first medication related to treating a patient medical condition;

executing rules via a rules engine based on one or more patient identifiers to access the at least one data source to obtain first medication information including times the first medication was prescribed, ordered, taken or administered;

executing rules by parsing first medication information via the rules engine to identify and access the at least one data source to identify and obtain medical condition treatment effectiveness information related to an effect by the medication, the medical condition treatment effectiveness information comprising at least one of examination findings, clinical data, symptoms, diagnosis, diagnostic tests, diagnostic test results diagnostic images, or diagnostic image measurements over time from which medical condition treatment effectiveness is observable by a user of the medical record dashboard display;

executing rules by parsing the first medication information via the rules engine to display the first medication information visually correlated in time with the information from which related medical condition treatment effectiveness is observable to track medical condition treatment effectiveness over time;

executing rules by parsing first medication information via the rules engine to identify and access the at least one data source to obtain at least one of cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication; and displaying at least one of the cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics corresponding to the first medication via the display such that the at least one of the cost data, claims data, authorizations, insurance coverall determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics are visible on the display concurrently with the first medication information and the related medical condition treatment effectiveness information that remain visible.

34. The method of claim 33 wherein at least one of the medical condition treatment effectiveness information, cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics is represented by an icon, graphical marker, indicator, or displayed visual representation that is connected to underlying information which can be directly accessed from the display by hovering, or clicking or using a pointing device or any other method to cause the underlying information to be displayed.

35. The method of claim 33 wherein at least one of the medication information, medication treatment effectiveness information, authorizations, insurance coverage determinations, and insurance guidelines, insurance regulations, insurance related information, guidelines, local or national guidelines, local or national coverage determinations, inventory data, clinical decision support, preferred practice patterns, actual patient usage, clinical trial protocol, clinical research data or health care associated statistics are displayed in one or more windows and are dynamically emphasized, added, removed or updated based on a change in medication information, medication treatment effectiveness information, authorizations, insurance coverage determinations, er-insurance guidelines, insurance regulations, insurance related information, guidelines, local or national guidelines, local or national coverage determinations, inventory data, clinical decision support, preferred practice patterns, actual patient usage, clinical trial protocol, clinical research data, health care associated statistics or medical information.

36. The method of claim 33 wherein the data source comprises multiple data sources from at least two of an electronic health records system, a health information exchange, patient portal, home health monitoring system, shared care system, telemedicine system, an image management system, inventory management system, healthcare information technology system, picture archiving and communication system, claims-based system, insurance companies, practice management system, or prescription data source.

37. The method of claim 33 wherein an alert is generated by the rules engine or a natural language processing or artificial intelligence system based on local or national guidelines, local or national coverage determinations, compliance with regulations, preferred practice patterns, prescription medication software, actual patient usage, clinical trial protocol, clinical research data, insurance requirements, clinical research study, clinical decision support information, comanagement system, information from a patient portal, home health monitoring system, shared care system, telemedicine system, laboratory system, or artificial intelligence engines and the alert comprises at least one of highlighting displayed information selected from the group consisting of medical services, clinical data, examination data, symptoms, medicine, diagnostic test, images, injections, procedure, claim information, insurance regulations, and authorizations.

38. The method of claim 33 wherein the at least one of cost data, claims data, authorizations, insurance coverage determinations, insurance guidelines, insurance regulations, insurance related information, guidelines, local or national guidelines, local or national coverage determinations, inventory data, clinical decision support, preferred practice patterns, actual patient usage or health care associated statistics includes alternative treatment options.

39. The method of claim 33, further comprising:

generating and displaying an alert if a medication associated with the one or more patients has changed since a last visit, or a potential interaction between medications is detected, or a patient has a clinical finding that suggests an adverse reaction to a medication or a change in usage of the medication occurs.

40. The method of claim 33, further compromising evaluating and weighting treatment options, procedures, diagnostic tests, clinical data symptoms, and diagnostic imagery based on their effectiveness over time, and executing artificial intelligence rules to recommend alternative treatments, predicted results, diagnostic approaches, or medications based on at least one of cost effectiveness, payer authorization status, insurance regulations, insurance related information, guidelines, local or national guidelines, local or national coverage determinations, inventory data, clinical decision support, preferred practice patterns, actual patient usage, medication contraindications health care associated statistics, or correlation with treatment efficacy.

\*    \*    \*    \*    \*